United States Patent
Glunz et al.

(10) Patent No.: US 9,926,282 B2
(45) Date of Patent: Mar. 27, 2018

(54) PHTHALAZINONES AND ISOQUINOLINONES AS ROCK INHIBITORS

(71) Applicant: BRISTOL-MYERS SQUIBB COMPANY, Princeton, NJ (US)

(72) Inventors: Peter W. Glunz, Yardley, PA (US); Yan Zou, Jamison, PA (US); Mimi L. Quan, Yardley, PA (US); Vladimir Ladziata, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/759,495

(22) PCT Filed: Jan. 17, 2014

(86) PCT No.: PCT/US2014/011957
§ 371 (c)(1),
(2) Date: Jul. 7, 2015

(87) PCT Pub. No.: WO2014/113620
PCT Pub. Date: Jul. 24, 2014

(65) Prior Publication Data
US 2015/0353505 A1    Dec. 10, 2015

Related U.S. Application Data

(60) Provisional application No. 61/754,007, filed on Jan. 18, 2013.

(51) Int. Cl.
| | |
|---|---|
| C07D 237/32 | (2006.01) |
| C07D 401/10 | (2006.01) |
| C07D 401/12 | (2006.01) |
| C07D 403/10 | (2006.01) |
| C07D 403/12 | (2006.01) |
| C07D 405/12 | (2006.01) |
| C07D 413/12 | (2006.01) |
| C07D 417/12 | (2006.01) |
| C07D 417/14 | (2006.01) |
| C07D 513/04 | (2006.01) |
| C07D 405/10 | (2006.01) |
| C07D 217/24 | (2006.01) |
| C07D 413/10 | (2006.01) |
| C07D 417/10 | (2006.01) |
| C07D 471/04 | (2006.01) |
| C07D 487/04 | (2006.01) |
| C07D 491/048 | (2006.01) |

(52) U.S. Cl.
CPC ......... *C07D 237/32* (2013.01); *C07D 217/24* (2013.01); *C07D 401/10* (2013.01); *C07D 401/12* (2013.01); *C07D 403/10* (2013.01); *C07D 403/12* (2013.01); *C07D 405/10* (2013.01); *C07D 405/12* (2013.01); *C07D 413/10* (2013.01); *C07D 413/12* (2013.01); *C07D 417/10* (2013.01); *C07D 417/12* (2013.01); *C07D 417/14* (2013.01); *C07D 471/04* (2013.01); *C07D 487/04* (2013.01); *C07D 491/048* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 2012/0122842 A1* | 5/2012 | Curtin | C07D 209/44 514/210.21 |
| 2014/0206686 A1 | 7/2014 | Glunz et al. | |

FOREIGN PATENT DOCUMENTS

| | | |
|---|---|---|
| CN | 102180909 A | 9/2011 |
| CN | 103242647 A | 8/2013 |
| DE | 25 31 776 A1 | 2/1977 |
| DE | 198 04 085 A1 | 8/1999 |

(Continued)

OTHER PUBLICATIONS

McMahon et al. (2000).*
Pinedo et al. (2000).*
CAS Registry No. 401646-88-6, Entered STN: Mar. 18, 2002.
CAS Registry No. 674337-79-2, Entered STN: Apr. 12, 2004.
CAS Registry No. 692279-56-4, Entered STN: Jun. 13, 2004.
CAS Registry No. 700349-58-2, Entered STN: Jun. 28, 2004.

(Continued)

*Primary Examiner* — Paul V Ward
(74) *Attorney, Agent, or Firm* — Hong Liu

(57) ABSTRACT

The present invention provides compounds of Formula (I) or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

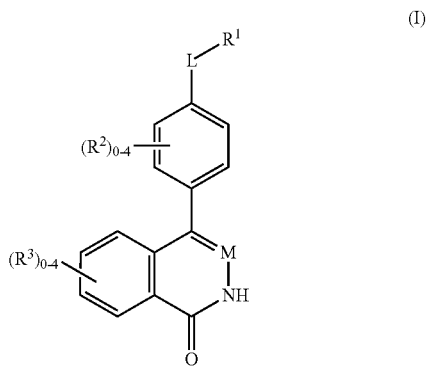

17 Claims, No Drawings

(56) References Cited

FOREIGN PATENT DOCUMENTS

| EP | 0 475 527 A2 | | 3/1992 |
|---|---|---|---|
| EP | 0 481 383 A1 | | 4/1992 |
| EP | 0 634 402 A1 | | 1/1995 |
| JP | 2000-72675 A | | 3/2000 |
| JP | 20040434582/2004 | * | 2/2004 |
| WO | WO 98/38168 A1 | | 9/1998 |
| WO | WO 99/40072 A1 | | 8/1999 |
| WO | WO 00/44726 A1 | | 8/2000 |
| WO | WO 00/50419 A1 | | 8/2000 |
| WO | WO 02/36576 A1 | | 5/2002 |
| WO | WO 03/068750 A1 | | 8/2003 |
| WO | WO 2004/024694 A1 | | 3/2004 |
| WO | WO2004024694 | * | 3/2004 |
| WO | WO 2005/097750 A1 | | 10/2005 |
| WO | WO 2006/036981 A2 | | 4/2006 |
| WO | WO 2006/124874 A2 | | 11/2006 |
| WO | WO 2008/086014 A2 | | 7/2008 |
| WO | WO 2009/064422 A2 | | 5/2009 |
| WO | WO 2011/019400 A2 | | 2/2011 |
| WO | WO 2012/072033 A1 | | 6/2012 |

OTHER PUBLICATIONS

CAS Registry No. 939750-00-2, Entered STN: Jun. 28, 2007.
CAS Registry No. 1180660-61-0, Entered STN: Sep. 4, 2009.
Kiselyov, A.S. et al., "1-(Azolyl)-4-(aryl)-phthalazines: Novel Potent Inhibitors of VEGF Receptors I and II", Chem. Biol. Drug. Des., vol. 68, pp. 250-255 (2006).
Mei, Q. et al., "Highly efficient red iridium(III) complexes based on phthalazine derivatives for organic light-emitting diodes", Dyes and Pigments, vol. 97, pp. 43-51 (2013).
REAXYS® PubChem Report generated Dec. 23, 2013.

* cited by examiner

PHTHALAZINONES AND ISOQUINOLINONES AS ROCK INHIBITORS

CROSS REFERENCES TO RELATED APPLICATIONS

This application is a 371 of International Application No. PCT/US2014/011957, filed on Jan. 17, 2014, which claims the benefit of U.S. Provisional Application Ser. No. 61/754,007 filed on Jan. 18, 2013 which is incorporated herein by reference.

FIELD OF THE INVENTION

The present invention relates generally to novel phthalazinone and isoquinolinone compounds, and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley, D. et al., *Cancer Res.*, 65:3788-

3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005)), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel phthalazinone and isoquinolinone compounds, their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

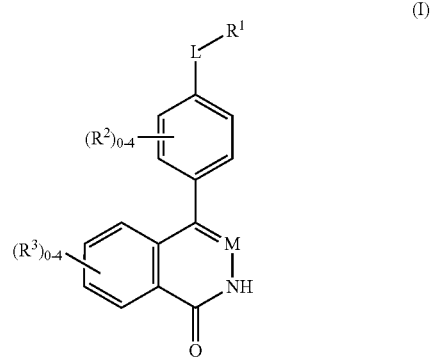

or stereoisomers, tautomers, pharmaceutically acceptable salts, solvates, or prodrugs thereof, wherein:

M is selected from N and $CR^{10}$;

L is selected from $-CR^4R^4C(O)-$, $-OC(O)-$, $-NR^6C(O)-$, and $-NR^6-$;

$R^1$ is selected from $NR^5R^5$, $C_{3-10}$ carbocycle and 4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, $-OH$, $-CH_2OH$, $-OCH_2F$, $-OCHF_2$, $-OCF_3$, CN, $-NH_2$, $-NH(C_{1-4}$ alkyl), $-N(C_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, carbocycle, and heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$— 4-10 membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form 4- to 15-membered heterocycle substituted with 1-4 R$^7$;

R$^6$, at each occurrence, is independently selected from H and C$_{1-4}$ alkyl;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C$_{2-4}$ alkenyl, C$_{2-4}$ alkynyl, —(CH$_2$)$_n$—C(O)C$_{1-4}$ alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—C(O)O-alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$ SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form 4- to 10-membered heterocycle substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CH$_2$)$_n$NR$^a$R$^a$, —(CH$_2$)$_n$CONR$^a$R$^a$, —O(CH$_2$)$_n$carbocycle, —O(CH$_2$)$_n$heterocycle, —O(CH$_2$)$_n$NR$^a$R$^a$, —(CR$^{10}$R$^{10}$)$_n$— 4-10 membered heterocycle, wherein said alkyl, alkoxyl, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —Re, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4;

p, at each occurrence, is independently selected from 0, 1, and 2; provided 1) when L is NHC(O), R$^1$ is other than

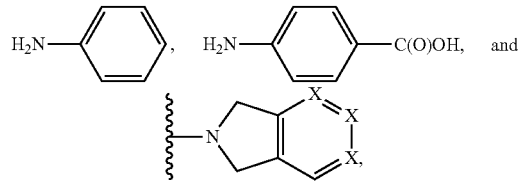

wherein X is N or a substituted or unsubstituted carbon atom;

2) when L is NR$^6$, R$^1$ is heterocycle substituted with 1-4 R$^7$.

In another aspect, the present invention provides compounds of Formula (I) or stereoisomers, tautomers, pharmaceutically acceptable salts, solvates, or prodrugs thereof, wherein:

M is CR$^{10}$;

L is selected from —CR$^4$R$^4$C(O)—, —OC(O)—, and —NR$^6$C(O)—;

R$^1$ is selected from NR$^5$R$^5$, C$_{3-10}$ carbocycle and 4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^3$, at each occurrence, is independently selected from halogen, $C_{1-6}$ alkyl, $C_{1-4}$ alkoxy;

$R^4$ is H;

$R^5$, at each occurrence, is independently selected from H, $C_{1-4}$ alkyl, $-(CR^6R^6)_n-C_{3-10}$ carbocycle and 4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form 4- to 15-membered heterocycle substituted with 1-4 $R^7$;

$R^7$, at each occurrence, is independently selected from H, $C_{1-4}$ alkyl, $C_{1-4}$ alkoxy, $-NR^8R^8$, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H and $C_{1-4}$ alkyl;

$R^9$, at each occurrence, is independently selected from halogen, OH, $C_{1-4}$ alkyl, $C_{1-4}$ alkoxy;

$R^{10}$ is selected from H and $C_{1-4}$ alkyl;

n, at each occurrence, is independently selected from 0, 1, 2, 3, and 4; and p, at each occurrence, is independently selected from 0, 1, and 2;

other variables are as defined in Formula (I) above.

In another aspect, the present invention provides compounds of Formula (II):

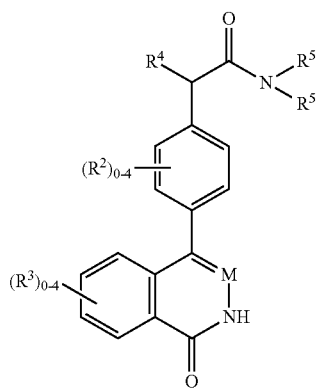

(II)

or stereoisomers, tautomers, pharmaceutically acceptable salts, solvates, or prodrugs thereof, wherein:

M is selected from N and $CR^{10}$;

$R^5$, at each occurrence, is independently selected from H, $C_{1-4}$ alkyl, $-(CR^6R^6)_n-C_{3-10}$ carbocycle, and $-(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n$ $-NR^8R^8$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$ alkyl, C(O)carbocycle, C(O)heterocycle, $-(CH_2)_n$ $C(O)NR^aR^a$, C(O)O-alkyl, C(O)O-carbocycle, C(O)O-heterocycle, $SO_2$alkyl, $SO_2$carbocycle, $SO_2$heterocycle, $SO_2NR^aR^a$, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-(CH_2)_nNR^aR^a$, $-(CH_2)_nCONR^aR^a$, $-O(CH_2)_n$heterocycle, $-O(CH_2)_{(2-4)}NR^aR^a$, $-(CR^{10}R^{10})_n-$ 4-10 membered heterocycle, wherein said alkyl, alkoxyl, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$N(C_{1-4}$ alkyl)$_2$, $-CONH-C_{1-4}$ alkylene-N $(C_{1-4}$ alkyl)$_2$, $-C_{1-4}$ alkylene-O—P(O)(OH)$_2$, $-NHCO_2(C_{1-4}$ alkyl), $-R^c$, $COR^c$, $CO_2R^c$, and $CONHR^c$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

other variables are as defined in Formula (I) above.

In another aspect, the present invention provides compounds of Formula (II) or stereoisomers, tautomers, pharmaceutically acceptable salts, solvates, or prodrugs thereof, wherein:

$R^5$ is selected from H, $C_{1-4}$ alkyl, —$(CH_2)_n$—$C_{3-10}$ carbocycle, —$(CH_2)_n$-aryl, —$(CH_2)_n$-4-10 membered heterocycle selected from

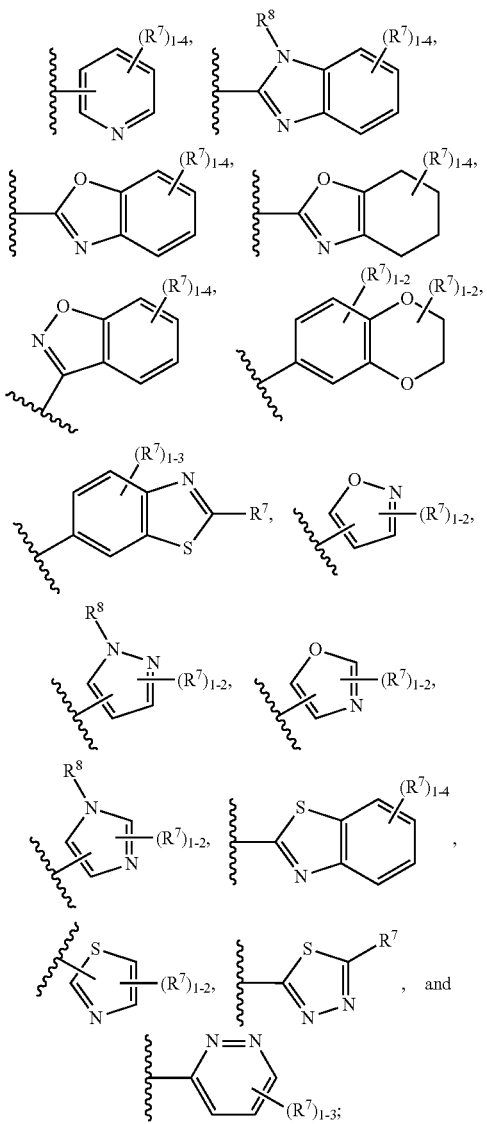

wherein said alkyl, cycloalkyl, aryl are substituted with 1-4 $R^7$; and other variables are as defined in Formula (II) above.

In another aspect, the present invention provides compounds of Formula (II) or stereoisomers, tautomers, pharmaceutically acceptable salts, solvates, or prodrugs thereof, wherein:

$R^5$ and $R^5$ are taken together with the nitrogen atom to which they are attached to form a heterocycle selected from

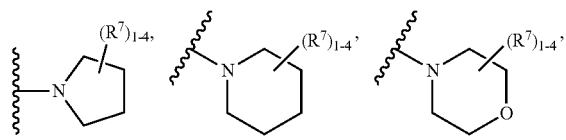

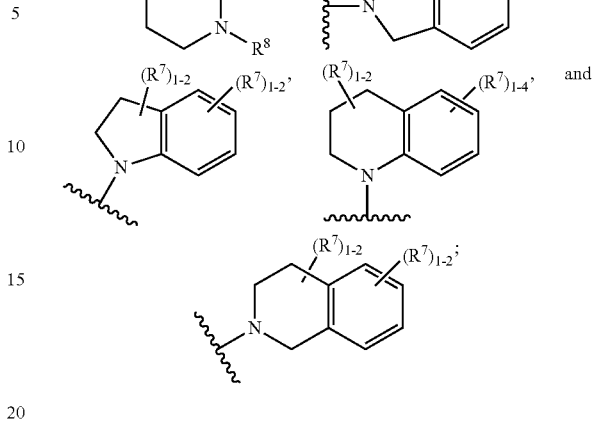

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$CH_2NH_2$, —NHCO($C_{1-4}$ alkyl), —$NHCOCF_3$, —$NHCO_2(C_{1-4}$ alkyl), —NHC(O)$NH_2$, —NHC(O)NH($C_{1-4}$ alkyl), —NHC(O)N($C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, —$(CH_2)_n$—$C(O)NR^aR^a$, C(O)O-alkyl, C(O)O-carbocycle, C(O)O-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$; and $R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$— 4-10 membered heterocycle, wherein said alkyl, alkoxyl, carbocycle, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N (C_{1-4} alkyl)_2, —C_{1-4} alkylene-O—P(O)(OH)_2, —NHCO_2(C_{1-4} alkyl), —R^c, COR^c, CO_2R^c, and CONHR^c;

R^c, at each occurrence, is independently selected from —(CH_2)_n—C_{3-6} cycloalkyl, —(CH_2)_n-phenyl, and —(CH_2)_n-5- to 6-membered heterocycle containing carbon atoms and 1-4 heteroatoms selected from the group consisting of: N, NH, N(C_{1-4} alkyl), O, and S(O)_p; wherein each ring moiety is substituted with 0-2 R^d; and R^d, at each occurrence, is independently selected from =O, halogen, —OH, C_{1-4} alkyl, NH_2, NH(C_{1-4} alkyl), N(C_{1-4} alkyl)_2, C_{1-4} alkoxy, and —NHCO(C_{1-4} alkyl), and heterocycle containing carbon atoms and 1-4 heteroatoms selected from the group consisting of: N, NH, N(C_{1-4} alkyl), O, and S(O)_p;

other variables are as defined in Formula (II) above.

In another aspect, the present invention provides compounds of Formula (III):

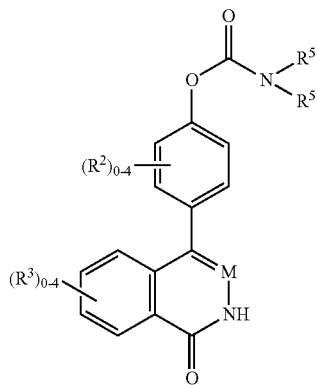

(III)

or stereoisomers, tautomers, pharmaceutically acceptable salts, solvates, or prodrugs thereof, wherein:

M is selected from N and CR^{10};

R^5, at each occurrence, is independently selected from H, C_{1-4} alkyl, —(CR^6R^6)_n—C_{3-10} carbocycle, and —(CR^6R^6)_n-4-10 membered heterocycle comprising carbon atoms and 1-4 heteroatoms selected from N, NR^8, O, and S(O)_p, wherein said alkyl, carbocycle, and heterocycle are substituted with 1-4 R^7;

alternatively, R^5 and R^5 are taken together with the nitrogen atom to which they are attached to form 4- to 10-membered heterocycle substituted with 1-4 R^7;

R^6, at each occurrence, is independently selected from H and C_{1-4} alkyl;

R^7, at each occurrence, is independently selected from H, =O, NO_2, halogen, C_{1-4} alkyl, C_{1-4} alkoxy, CN, OH, CF_3, —(CH_2)_n—CO_2H, —(CH_2)_n—CO_2(C_{1-4} alkyl), —(CH_2)_n—NR^8R^8, —NHCO(C_{1-4} alkyl), —NHCOCF_3, —NHCO_2(C_{1-4} alkyl), —NHCO_2(CH_2)_2O(C_{1-4} alkyl), —NHCO_2(CH_2)_3O(C_{1-4} alkyl), —NHCO_2(CH_2)_2OH, —NHCO_2(CH_2)_2NH_2, —NHCO_2(CH_2)_2N(C_{1-4} alkyl)_2, —NHCO_2CH_2CO_2H, —CH_2NHCO_2(C_{1-4} alkyl), —NHC(O)NR^8R^8, —NHSO_2(C_{1-4} alkyl), —SO_2NH_2, —SO_2NH(C_{1-4} alkyl), —SO_2N(C_{1-4} alkyl)_2, —SO_2NH(CH_2)_2OH, —SO_2NH(CH_2)_2O(C_{1-4} alkyl), —(CH_2)_n—CONR^8R^8, —O(CH_2)_n-carbocycle, —O(CH_2)_n-heterocycle, —NHCO-carbocycle, —NHCO-heterocycle, —(CH_2)_n-carbocycle, and —(CH_2)_n-heterocycle comprising carbon atoms and 1-4 heteroatoms selected from N, NR^8, O, and S(O)_p, wherein said alkyl, alkenyl, alkynyl, alkoxyl, carbocycle, and heterocycle are substituted with 0-4 R^9;

R^8, at each occurrence, is independently selected from H, C_{1-4} alkyl, C(O)C_{1-4}alkyl, C(O)carbocycle, C(O)heterocycle, —(CH_2)_n—C(O)NR^aR^a, C(O)O-alkyl, C(O)O-carbocycle, C(O)O-heterocycle, SO_2alkyl, SO_2carbocycle, SO_2heterocycle, SO_2NR^aR^a, —(CH_2)_n-carbocycle, and —(CH_2)_n-heterocycle, wherein said alkyl, carbocycle, and heterocycle are substituted with 0-4 R^9;

R^9, at each occurrence, is independently selected from halogen, OH, NO_2, CHF_2, CF_3, C_{1-4} alkyl, C_{1-4} alkoxy, CH_2OH, CO_2H, CO_2(C_{1-4} alkyl), CONH_2, —(CH_2)_nNR^aR^a, —(CH_2)_nCONR^aR^a, —O(CH_2)_nheterocycle, —O(CH_2)_{(2-4)}NR^aR^a, —(CR^{10}R^{10})_n— 4-10 membered heterocycle, wherein said alkyl, alkoxyl, carbocycle, and heterocycle are substituted with 0-4 R^b;

n, at each occurrence, is independently selected from 0, 1, 2, 3, and 4; and p, at each occurrence, is independently selected from 0, 1, and 2;

other variables are as defined in Formula (I) above.

In another aspect, the present invention provides compounds of Formula (I) or stereoisomers, tautomers, pharmaceutically acceptable salts, solvates, or prodrugs thereof, wherein:

L is —NR^6—;

R^1 is heteroaryl substituted with 1-4 R^7;

R^7, at each occurrence, is independently selected from H, halogen, C_{1-4} alkyl, C_{1-4} alkoxy, CN, OH, —(CH_2)_n-carbocycle, and —(CH_2)_n-heterocycle, wherein said alkyl, alkoxyl, carbocycle, and heterocycle are substituted with 0-4 R^9;

other variables are as defined in Formula (I) above.

In another aspect, the present invention provides compounds of Formula (I) or stereoisomers, tautomers, pharmaceutically acceptable salts, solvates, or prodrugs thereof, wherein:

L is —NR^6—;

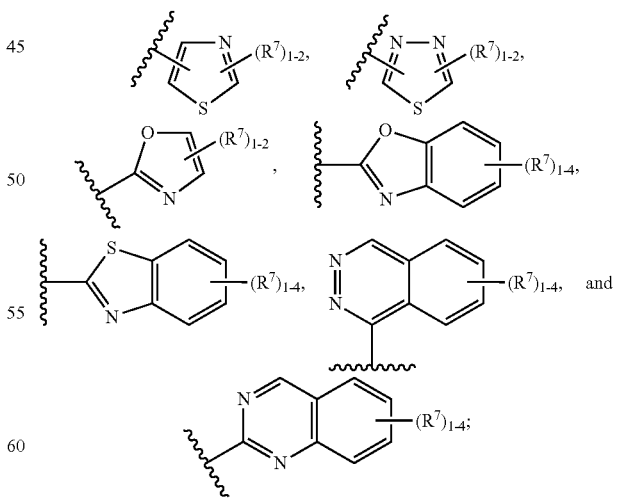

other variables are as defined in Formula (I) above.

In still another aspect, the present invention provides compounds of Formula (IV):

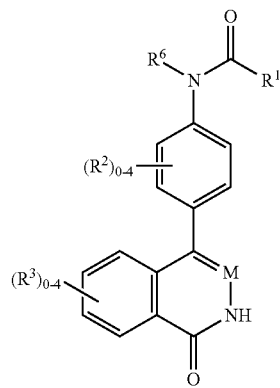

(IV)

or stereoisomers, tautomers, pharmaceutically acceptable salts, solvates, or prodrugs thereof, wherein:

$R^1$ is selected from $NR^5R^5$, $C_{3-10}$ carbocycle, and 5- to 10-membered heterocycle, wherein said carbocycle and heterocycle are substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C(O)C_{1-4}$alkyl, $C(O)$carbocycle, $C(O)$heterocycle, —$(CH_2)_n$—$C(O)NR^aR^a$, $C(O)O$-alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, alkenyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$— 4-10 membered heterocycle, wherein said alkyl, alkoxyl, carbocycle, and heterocycle are substituted with 0-4 $R^b$;

n, at each occurrence, is independently selected from 0, 1, 2, 3, and 4;

p, at each occurrence, is independently selected from 0, 1, and 2;

other variables are as defined in Formula (I) above.

In still another aspect, the present invention provides compounds of Formula (IV), or stereoisomers, tautomers, pharmaceutically acceptable salts, solvates, or prodrugs thereof, wherein:

$R^1$ is selected from

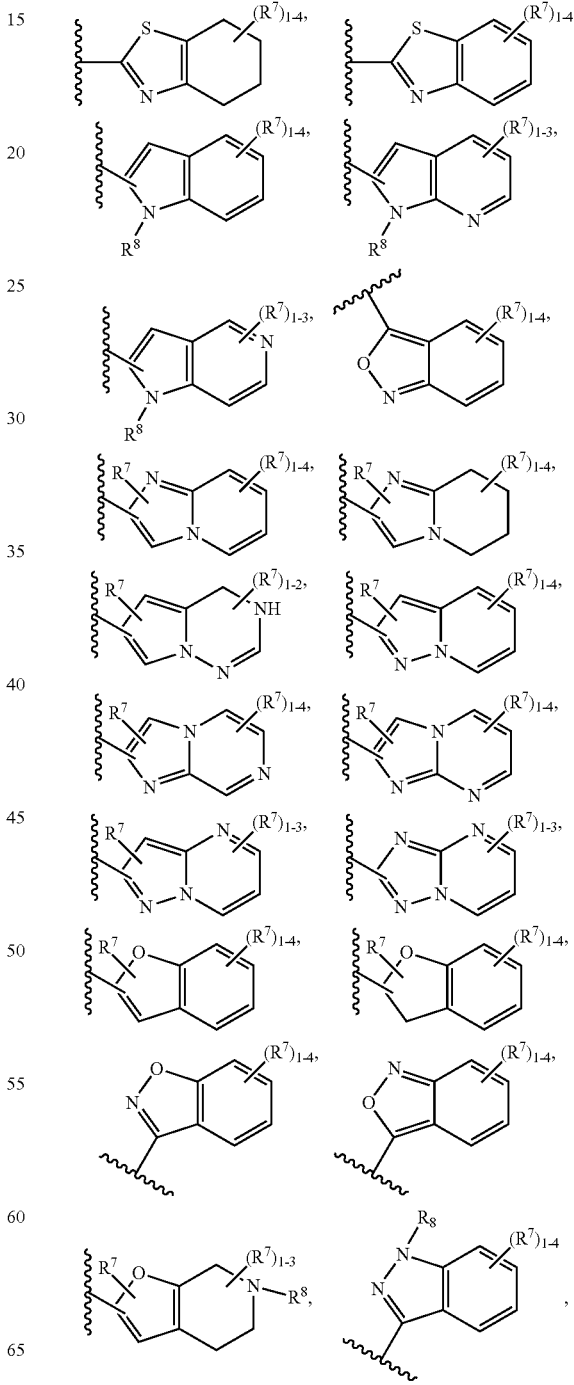

-continued

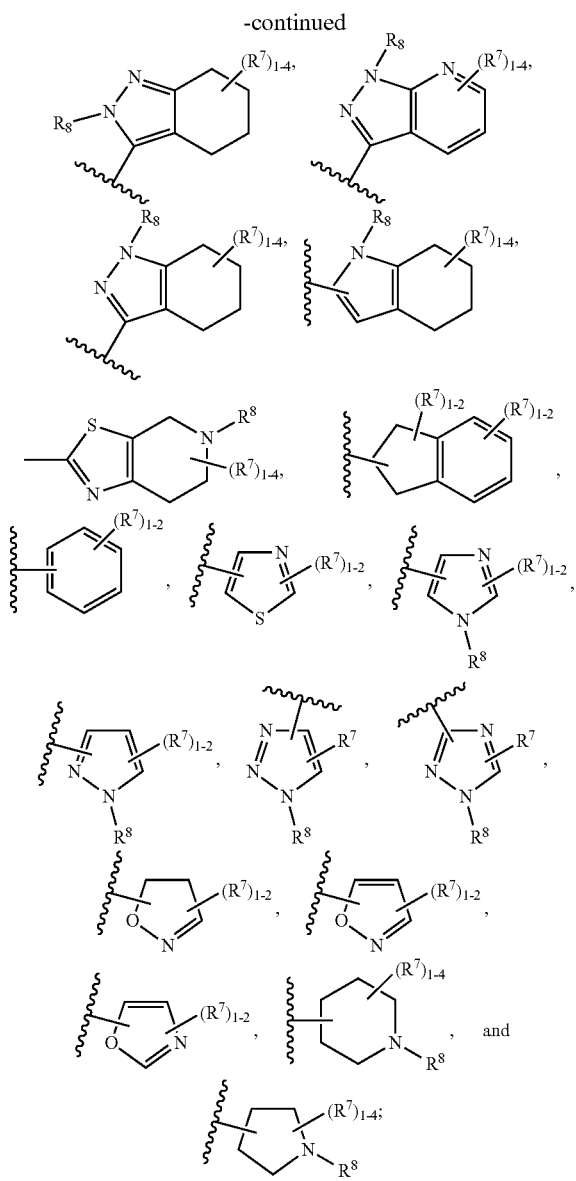

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)$—$NR^8R^8$, —$NHCO(C_{1-4}$ alkyl), —$NHCOCF_3$, —$NHCO_2$ $(C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC $(O)NR^8R^8$, —$NHSO_2(C_{1-4}$ alkyl), —$SO_2NH_2$, —$SO_2NH$ $(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)O$-alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$; and $R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}$ $NR^aR^a$, —$(CR^{10}R^{10})_n$— 4-10 membered heterocycle, wherein said alkyl, alkoxyl, carbocycle, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2$ $(C_{1-4}$ alkyl), $CONH_2$, —$CONH(C_{1-4}$ alkyl), —$CON(C_{1-4}$ alkyl$)_2$, —CONH—$C_{1-4}$ alkylene-$O(C_{1-4}$ alkyl), —CONH—$C_{1-4}$ alkylene-$N(C_{1-4}$ alkyl$)_2$, —CONH—$C_{1-4}$ alkylene-N $(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$; and $R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

other variables are as defined in Formula (IV) above.

In still another aspect, the present invention provides compounds of Formula (IV), or stereoisomers, tautomers, pharmaceutically acceptable salts, solvates, or prodrugs thereof, wherein:

$R^1$ is $NR^5R^5$;

$R^5$ and $R^5$ are taken together with the nitrogen atom to which they are attached to form 4- to 10-membered heterocycle substituted with 1-4 $R^7$;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2$ $(C_{1-4}$ alkyl), —$NHC(O)NH_2$, —$NHC(O)NH(C_{1-4}$ alkyl), —$NHC(O)N(C_{1-4}$ alkyl$)_2$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl$)_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)O$-alkyl, $C(O)O$-carbocycle, C(O)O-heterocycle, $SO_2$alkyl, $SO_2$carbocycle, $SO_2$heterocycle, $SO_2NR^aR^a$, —$(CH_2)_n$-cycloalkyl, —$(CH_2)_n$-phenyl, and —$(CH_2)_n$-heterocycle, wherein said alkyl, carbocycle, and heterocycle are substituted with 0-4 $R^9$; and $R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$— 4-10 membered heterocycle, wherein said alkyl, alkoxyl, carbocycle, and heterocycle are substituted with 0-4 $R^b$; and other variables are as defined in Formula (IV) above.

In another aspect, the present invention provides compounds of Formula (I) or stereoisomers, tautomers, pharmaceutically acceptable salts, solvates, or prodrugs thereof, wherein:

M is selected from N and $CR^{10}$;

L is selected from $C_{1-2}$ alkylene substituted with 1-2 $R^4$, wherein one or both carbon atoms and the groups attached thereto are replaced by O, $NR^6$, and C(O);

$R^1$ is selected from $NR^5R^5$, $C_{3-10}$ carbocycle and 4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl$)_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, carbocycle, and heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$— 4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form 4- to 15-membered heterocycle substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2$($C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)C_{1-4}$ alkyl, —$(CH_2)_n$—C(O)carbocycle, —$(CH_2)_n$—C(O)heterocycle, —$(CH_2)_n$—$C(O)NR^aR^a$, —$(CH_2)_n$—C(O)O-alkyl, —$(CH_2)_n$—C(O)O-carbocycle, —$(CH_2)_n$—C(O)O-heterocycle, —$(CH_2)_n$—$SO_2$alkyl, —$(CH_2)_n SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CH_2)_n NR^aR^a$, —$(CH_2)_n CONR^aR^a$, —$O(CH_2)_n$carbocycle, —$O(CH_2)_n$heterocycle, —$O(CH_2)_n NR^aR^a$, —$(CR^{10}R^{10})_n$— 4-10 membered heterocycle, wherein said alkyl, alkoxyl, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —$CONH$—$C_{1-4}$ alkylene-$O(C_{1-4}$ alkyl), —$CONH$—$C_{1-4}$ alkylene-$N(C_{1-4}$ alkyl$)_2$, —$CONH$—$C_{1-4}$ alkylene-N $(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;
provided
(1) when L is NHC(O), $R^1$ is other than

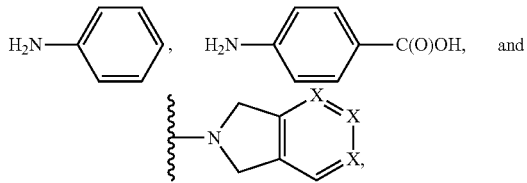

wherein X is N or a substituted or unsubstituted carbon atom;
(2) when L is NH, $R^1$ is other than

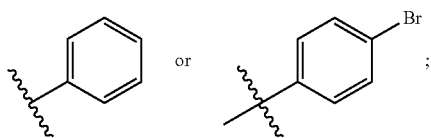 [SMILES: *c1ccccc1 ; *c1ccc(Br)cc1]

(3) when L is O, $R^1$ is other than

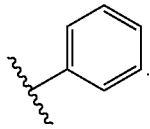

In another aspect, the present invention provides compounds of Formula (V):

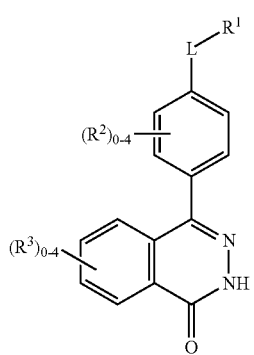

(V)

or stereoisomers, tautomers, pharmaceutically acceptable salts, solvates, or prodrugs thereof, wherein:
L is selected from —$CR^4R^4C(O)$—, —OC(O)—, —$NR^6C(O)$—, and —$NR^6$—;
$R^1$ is selected from $NR^5R^5$, $C_{3-10}$ carbocycle and 4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;
$R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl$)_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, carbocycle, and heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$— 4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$;
alternatively, $R^5$ and $R^5$ are taken together with the nitrogen atom to which they are attached to form 4- to 15-membered heterocycle substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—C(O)O-alkyl, —$(CH_2)_n$—C(O)O-carbocycle, —$(CH_2)_n$—C(O)O-heterocycle, —$(CH_2)_n$—$SO_2$alkyl, —$(CH_2)_n$$SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;
alternatively, $R^8$ and $R^8$ are taken together with the nitrogen atom to which they are attached to form 4- to 10-membered heterocycle substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), $—(CH_2)_n NR^a R^a$, $—(CH_2)_n CONR^a R^a$, $—O(CH_2)_n$carbocycle, $—O(CH_2)_n$heterocycle, $—O(CH_2)_n NR^a R^a$, $—(CR^{10} R^{10})_n$— 4-10 membered heterocycle, wherein said alkyl, alkoxyl, carbocycle, and heterocycle are substituted with 0-4 $R^b$;

$R^a$, at each occurrence, is independently selected from H, $C_{1-4}$ alkyl, $—(CH_2)_n OH$, $CO(C_{1-4}$ alkyl), $COCF_3$, $CO_2(C_{1-4}$ alkyl), $—CONH_2$, $—CONH—C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $—CONH(C_{1-4}$ alkyl), $—CON(C_{1-4}$ alkyl)$_2$, $—CONH—C_{1-4}$ alkylene-$O(C_{1-4}$ alkyl), $—CONH—C_{1-4}$ alkylene-$N(C_{1-4}$ alkyl)$_2$, $—CONH—C_{1-4}$ alkylene-N ($C_{1-4}$ alkyl)$_2$, $—C_{1-4}$ alkylene-O—P(O)(OH)$_2$, $—NHCO_2(C_{1-4}$ alkyl), $—R^c$, $COR^c$, $CO_2R^c$, and $CONHR^c$;

$R^c$, at each occurrence, is independently selected from $—(CH_2)_n—C_{3-6}$ cycloalkyl, $—(CH_2)_n$-phenyl, and $—(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and $—NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

provided (1) when L is NHC(O), $R^1$ is other than

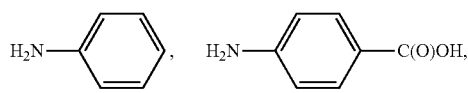

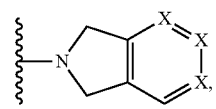

wherein X is N or a substituted or unsubstituted carbon atom;

(2) when L is $NR^6$, $R^1$ is heteroaryl substituted with 1-4 $R^7$.

In another aspect, the present invention provides compounds of Formula (VI):

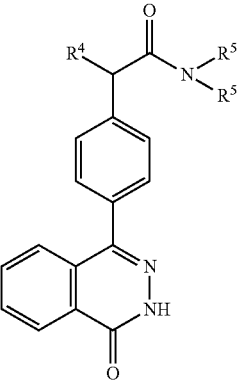

(VI)

or stereoisomers, tautomers, pharmaceutically acceptable salts, solvates, or prodrugs thereof, wherein:

$R^5$, at each occurrence, is independently selected from H, $C_{1-4}$ alkyl, $—(CR^6R^6)_n—C_{3-10}$ carbocycle, and $—(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, $—(CH_2)_n—CO_2H$, $—(CH_2)_n—CO_2(C_{1-4}$ alkyl), $—(CH_2)_n—NR^8R^8$, $—NHCO(C_{1-4}$ alkyl), $—NHCOCF_3$, $—NHCO_2(C_{1-4}$ alkyl), $—NHCO_2(CH_2)_2O(C_{1-4}$ alkyl), $—NHCO_2(CH_2)_3O(C_{1-4}$ alkyl), $—NHCO_2(CH_2)_2OH$, $—NHCO_2(CH_2)_2NH_2$, $—NHCO_2(CH_2)_2N(C_{1-4}$ alkyl)$_2$, $—NHCO_2CH_2CO_2H$, $—CH_2NHCO_2(C_{1-4}$ alkyl), $—NHC(O)NR^8R^8$, $—NHSO_2(C_{1-4}$ alkyl), $—SO_2NH_2$, $—SO_2NH(C_{1-4}$ alkyl), $—SO_2N(C_{1-4}$ alkyl)$_2$, $—SO_2NH(CH_2)_2OH$, $—SO_2NH(CH_2)_2O(C_{1-4}$ alkyl), $—(CH_2)_n—CONR^8R^8$, $—O(CH_2)_n$-carbocycle, $—O(CH_2)_n$-heterocycle, $—NHCO$-carbocycle, $—NHCO$-heterocycle, $—(CH_2)_n$-carbocycle, and $—(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, $—(CH_2)_n C(O)NR^aR^a$, C(O)O-alkyl, C(O)O-carbocycle, C(O)O-heterocycle, $SO_2$alkyl, $SO_2$carbocycle, $SO_2$heterocycle, $SO_2NR^aR^a$, $—(CH_2)_n$-carbocycle, and $—(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $—(CH_2)_n NR^aR^a$, $—(CH_2)_n CONR^aR^a$, $—O(CH_2)_n$heterocycle, $—O(CH_2)_{(2-4)} NR^aR^a$, $—(CR^{10}R^{10})_n$— 4-10 membered heterocycle, wherein said alkyl, alkoxyl, carbocycle, and heterocycle are substituted with 0-4 $R^b$;

$R^a$, at each occurrence, is independently selected from H, $C_{1-4}$ alkyl, $—(CH_2)_n OH$, $CO(C_{1-4}$ alkyl), $COCF_3$, $CO_2(C_{1-4}$ alkyl), $—CONH_2$, $—CONH—C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —$CONH$—$C_{1-4}$ alkylene-$O(C_{1-4}$ alkyl), —$CONH$—$C_{1-4}$ alkylene-$N(C_{1-4}$ alkyl$)_2$, —$CONH$—$C_{1-4}$ alkylene-N $(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

other variables are as defined in Formula (V) above.

In another aspect, the present invention provides compounds of Formula (VI) or stereoisomers, tautomers, pharmaceutically acceptable salts, solvates, or prodrugs thereof, wherein:

$R^5$ is selected from H, $C_{1-4}$ alkyl, —$(CH_2)_n$—$C_{3-10}$ carbocycle, —$(CH_2)_n$-aryl, —$(CH_2)_n$-4-10 membered heterocycle selected from

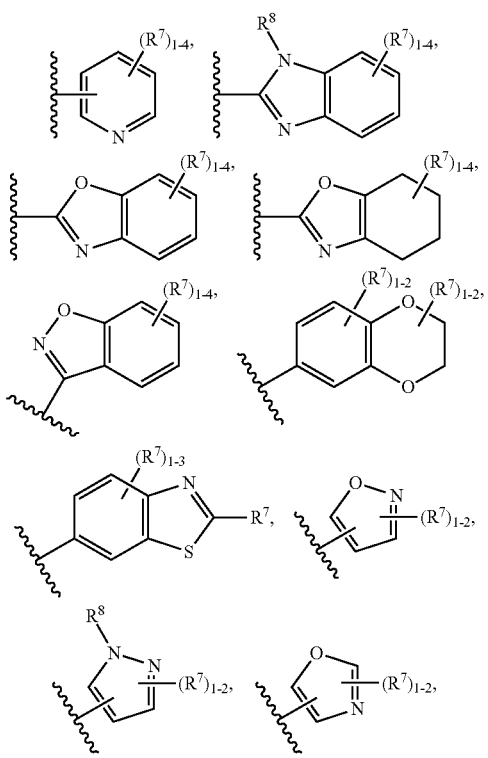

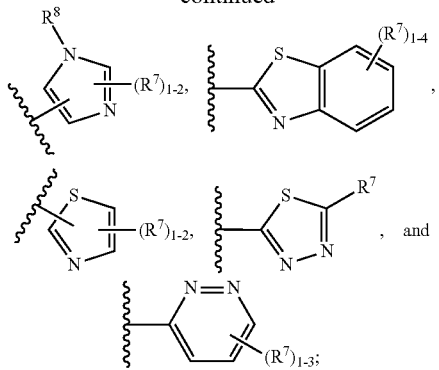

wherein said alkyl, cycloalkyl, aryl are substituted with 1-4 $R^7$; and other variables are as defined in Formula (V) above.

In another aspect, the present invention provides compounds of Formula (VI) or stereoisomers, tautomers, pharmaceutically acceptable salts, solvates, or prodrugs thereof, wherein:

$R^5$ and $R^5$ are taken together with the nitrogen atom to which they are attached to form a heterocycle selected from

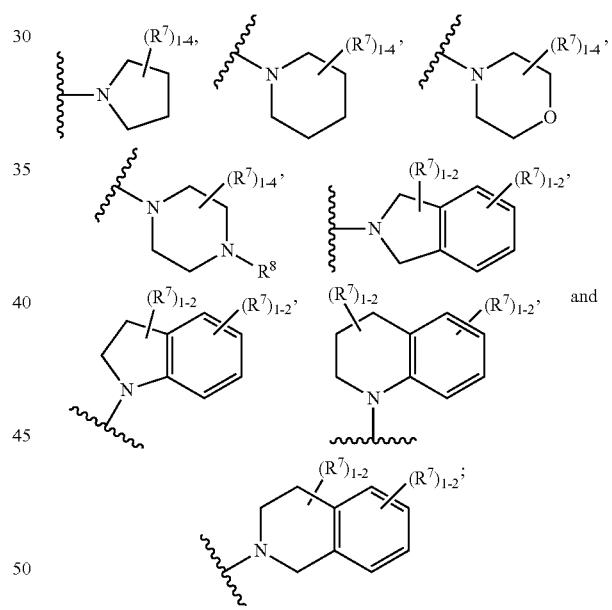

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$CH_2NH_2$, —$NHCO(C_{1-4}$ alkyl), —$NHCOCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl$)_2$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —O$(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

R⁸, at each occurrence, is independently selected from H, C₁₋₄ alkyl, C(O)C₁₋₄alkyl, C(O)carbocycle, C(O)heterocycle, —(CH₂)ₙ—C(O)NRᵃRᵃ, C(O)O-alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, carbocycle, and heterocycle are substituted with 0-4 R⁹;

alternatively, R⁸ and R⁸ are taken together with the nitrogen atom to which they are attached to form 4- to 10-membered heterocycle substituted with 0-4 R⁹; and R⁹, at each occurrence, is independently selected from halogen, OH, NO₂, CHF₂, CF₃, C₁₋₄ alkyl, C₁₋₄ alkoxy, CH₂OH, CO₂H, CO₂(C₁₋₄ alkyl), CONH₂, —(CH₂)ₙNRᵃRᵃ, —(CH₂)ₙCONRᵃRᵃ, —O(CH₂)ₙheterocycle, —O(CH₂)₍₂₋₄₎NRᵃRᵃ, —(CR¹⁰R¹⁰)ₙ— 4-10 membered heterocycle, wherein said alkyl, alkoxyl, carbocycle, and heterocycle are substituted with 0-4 Rᵇ;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form 4- to 10-membered heterocycle, wherein said alkyl, alkylene, and heterocycle are substituted with 0-4 Rᵇ;

Rᵇ, at each occurrence, is independently selected from =O, halogen, C₁₋₄ alkyl, C₁₋₄ alkoxy, OCF₃, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N (C₁₋₄ alkyl)₂, —C₁₋₄ alkylene-O—P(O)(OH)₂, —NHCO₂(C₁₋₄ alkyl), —Rᶜ, CORᶜ, CO₂Rᶜ, and CONHRᶜ;

Rᶜ, at each occurrence, is independently selected from —(CH₂)ₙ—C₃₋₆ cycloalkyl, —(CH₂)ₙ-phenyl, and —(CH₂)ₙ-5- to 6-membered heterocycle containing carbon atoms and 1-4 heteroatoms selected from the group consisting of: N, NH, N(C₁₋₄ alkyl), O, and S(O)ₚ; wherein each ring moiety is substituted with 0-2 Rᵈ; and Rᵈ, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and heterocycle containing carbon atoms and 1-4 heteroatoms selected from the group consisting of: N, NH, N(C₁₋₄ alkyl), O, and S(O)ₚ;

other variables are as defined in Formula (VI) above.

In another aspect, the present invention provides compounds of Formula (VII):

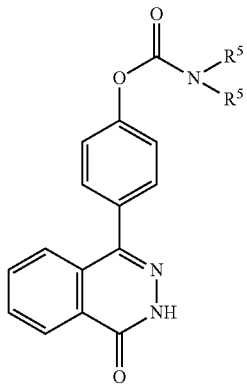

(VII)

or stereoisomers, tautomers, pharmaceutically acceptable salts, solvates, or prodrugs thereof, wherein:

R⁵, at each occurrence, is independently selected from H, C₁₋₄ alkyl, —(CR⁶R⁶)ₙ—C₃₋₁₀ carbocycle, and —(CR⁶R⁶)ₙ-4-10 membered heterocycle comprising carbon atoms and 1-4 heteroatoms selected from N, NR⁸, O, and S(O)ₚ, wherein said alkyl, carbocycle, and heterocycle are substituted with 1-4 R⁷;

alternatively, R⁵ and R⁵ are taken together with the nitrogen atom to which they are attached to form 4- to 10-membered heterocycle substituted with 1-4 R⁷;

R⁶, at each occurrence, is independently selected from H and C₁₋₄ alkyl;

R⁷, at each occurrence, is independently selected from H, =O, NO₂, halogen, C₁₋₄ alkyl, C₁₋₄ alkoxy, CN, OH, CF₃, —(CH₂)ₙ—CO₂H, —(CH₂)ₙ—CO₂(C₁₋₄ alkyl), —(CH₂)ₙ—NR⁸R⁸, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, C(O)C₁₋₄alkyl, C(O)carbocycle, C(O)heterocycle, —(CH₂)ₙ—C(O)NRᵃRᵃ, C(O)O-alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, carbocycle, and heterocycle are substituted with 0-4 R⁹;

R⁹, at each occurrence, is independently selected from halogen, OH, NO₂, CHF₂, CF₃, C₁₋₄ alkyl, C₁₋₄ alkoxy, CH₂OH, CO₂H, CO₂(C₁₋₄ alkyl), CONH₂, —(CH₂)ₙNRᵃRᵃ, —(CH₂)ₙCONRᵃRᵃ, —O(CH₂)ₙheterocycle, —O(CH₂)₍₂₋₄₎NRᵃRᵃ, —(CR¹⁰R¹⁰)ₙ— 4-10 membered heterocycle, wherein said alkyl, alkoxyl, carbocycle, and heterocycle are substituted with 0-4 Rᵇ;

n, at each occurrence, is independently selected from 0, 1, 2, 3, and 4; and p, at each occurrence, is independently selected from 0, 1, and 2;

other variables are as defined in Formula (V) above.

In another aspect, the present invention provides compounds of Formula (V) or stereoisomers, tautomers, pharmaceutically acceptable salts, solvates, or prodrugs thereof, wherein:

L is —NR⁶—;

R⁷, at each occurrence, is independently selected from H, halogen, C₁₋₄ alkyl, C₁₋₄ alkoxy, CN, OH, —(CH₂)ₙ-carbocycle, and —(CH₂)ₙ-heterocycle, wherein said alkyl, alkoxyl, carbocycle, and heterocycle are substituted with 0-4 R⁹;

other variables are as defined in Formula (V) above.

In another aspect, the present invention provides compounds of Formula (V) or stereoisomers, tautomers, pharmaceutically acceptable salts, solvates, or prodrugs thereof, wherein:

L is —NR⁶—; and
R¹ is selected from

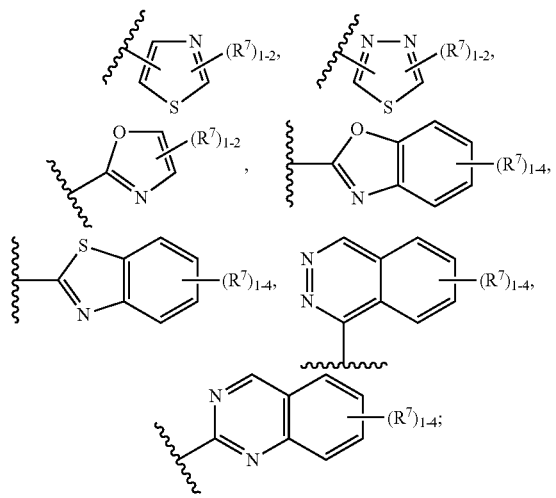

other variables are as defined in Formula (V) above.

In still another aspect, the present invention provides compounds of Formula (VIII):

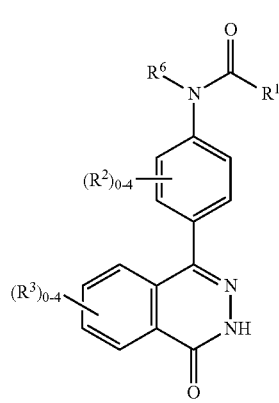

(VIII)

or stereoisomers, tautomers, pharmaceutically acceptable salts, solvates, or prodrugs thereof, wherein:

R¹ is selected from NR⁵R⁵, C$_{3-10}$ carbocycle, and 5- to 10-membered heterocycle, wherein said carbocycle and heterocycle are substituted with 1-4 R⁷;

R⁵, at each occurrence, is independently selected from H, C$_{1-4}$ alkyl, —(CR⁶R⁶)$_n$—C$_{3-10}$ carbocycle, and —(CR⁶R⁶)$_n$-4-10 membered heterocycle comprising carbon atoms and 1-4 heteroatoms selected from N, NR⁸, O, and S(O)$_p$, wherein said alkyl, carbocycle, and heterocycle are substituted with 1-4 R⁷;

alternatively, R⁵ and R⁵ are taken together with the nitrogen atom to which they are attached to form 4- to 10-membered heterocycle substituted with 1-4 R⁷;

R⁶, at each occurrence, is independently selected from H and C$_{1-4}$ alkyl;

R⁷, at each occurrence, is independently selected from H, =O, NO₂, halogen, C$_{1-4}$ alkyl, C$_{1-4}$ alkoxy, CN, OH, CF₃, —(CH₂)$_n$—CO₂H, —(CH₂)$_n$—CO₂(C$_{1-4}$ alkyl), —(CH₂)$_n$—NR⁸R⁸, —NHCO(C$_{1-4}$ alkyl), —NHCOCF₃, —NHCO₂(C$_{1-4}$ alkyl), —NHCO₂(CH₂)₂O(C$_{1-4}$ alkyl), —NHCO₂(CH₂)₃O(C$_{1-4}$ alkyl), —NHCO₂(CH₂)₂OH, —NHCO₂(CH₂)₂NH₂, —NHCO₂(CH₂)₂N(C$_{1-4}$ alkyl)₂, —NHCO₂CH₂CO₂H, —CH₂NHCO₂(C$_{1-4}$ alkyl), —NHC(O)NR⁸R⁸, —NHSO₂(C$_{1-4}$ alkyl), —SO₂NH₂, —SO₂NH(C$_{1-4}$ alkyl), —SO₂N(C$_{1-4}$ alkyl)₂, —SO₂NH(CH₂)₂OH, —SO₂NH(CH₂)₂O(C$_{1-4}$ alkyl), —(CH₂)$_n$—CONR⁸R⁸, —O(CH₂)$_n$-carbocycle, —O(CH₂)$_n$-heterocycle, —NHCO-carbocycle, —NHCO-heterocycle, —(CH₂)$_n$-carbocycle, and —(CH₂)$_n$-heterocycle comprising carbon atoms and 1-4 heteroatoms selected from N, NR⁸, O, and S(O)$_p$, wherein said alkyl, alkenyl, alkynyl, alkoxyl, carbocycle, and heterocycle are substituted with 0-4 R⁹;

R⁸, at each occurrence, is independently selected from H, C$_{1-4}$ alkyl, C$_{2-4}$ alkenyl, C(O)C$_{1-4}$alkyl, C(O)carbocycle, C(O)heterocycle, —(CH₂)$_n$—C(O)NR$^a$R$^a$, C(O)O-alkyl, C(O)O-carbocycle, C(O)O-heterocycle, SO₂alkyl, SO₂carbocycle, SO₂heterocycle, SO₂NR$^a$R$^a$, —(CH₂)$_n$-carbocycle, and —(CH₂)$_n$-heterocycle, wherein said alkyl, alkenyl, carbocycle, and heterocycle are substituted with 0-4 R⁹;

R⁹, at each occurrence, is independently selected from halogen, OH, NO₂, CHF₂, CF₃, C$_{1-4}$ alkyl, C$_{1-4}$ alkoxy, CH₂OH, CO₂H, CO₂(C$_{1-4}$ alkyl), CONH₂, —(CH₂)$_n$NR$^a$R$^a$, —(CH₂)$_n$CONR$^a$R$^a$, —O(CH₂)$_n$heterocycle, —O(CH₂)$_{(2-4)}$NR$^a$R$^a$, —(CR¹⁰R¹⁰)$_n$— 4-10 membered heterocycle, wherein said alkyl, alkoxyl, carbocycle, and heterocycle are substituted with 0-4 R$^b$;

n, at each occurrence, is independently selected from 0, 1, 2, 3, and 4;

p, at each occurrence, is independently selected from 0, 1, and 2;

other variables are as defined in Formula (V) above.

In still another aspect, the present invention provides compounds of Formula (VIII), or stereoisomers, tautomers, pharmaceutically acceptable salts, solvates, or prodrugs thereof, wherein:

R¹ is selected from

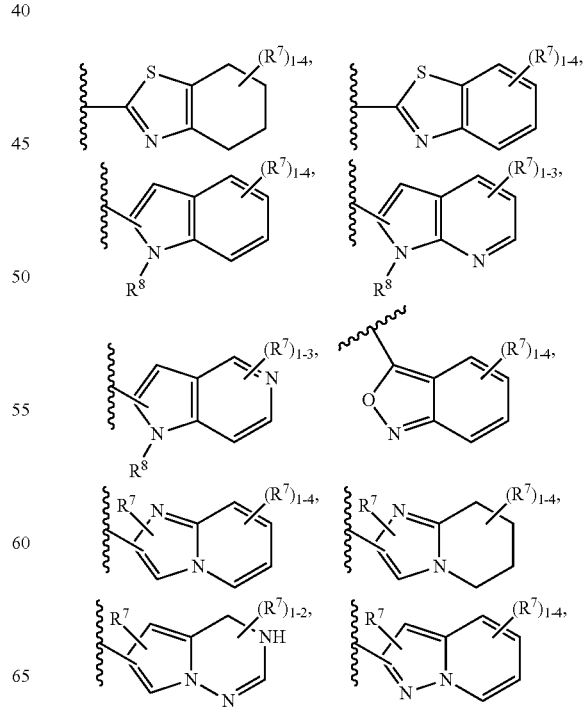

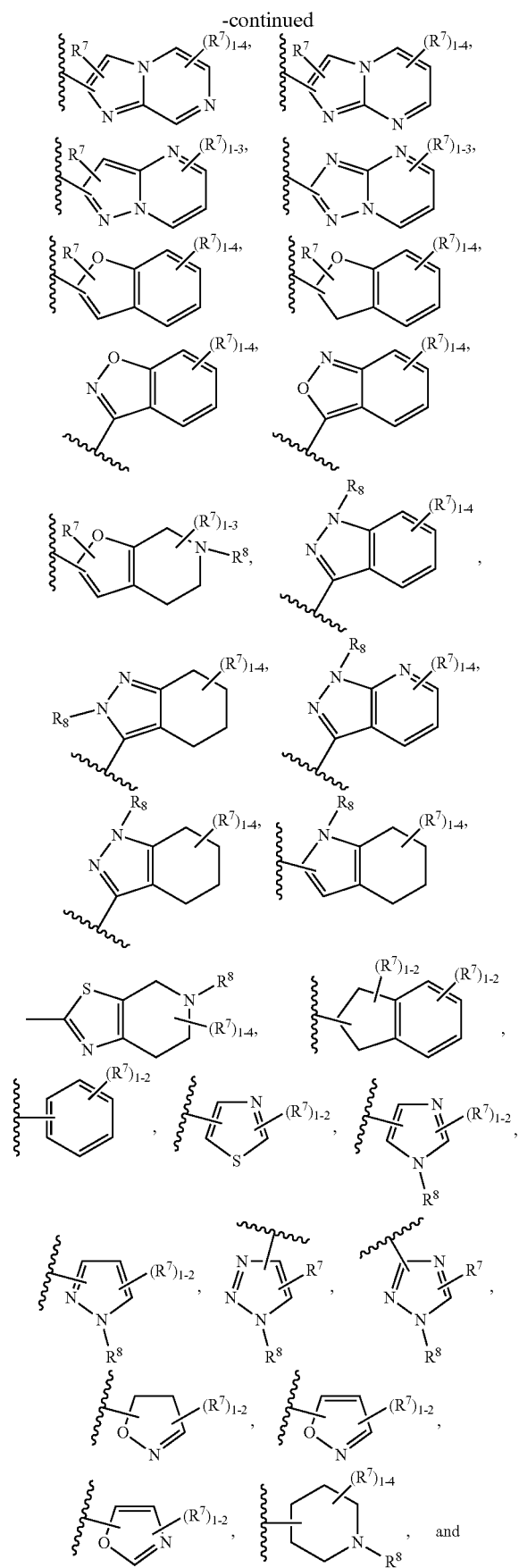

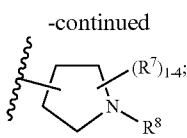

R[7], at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR[8]R[8], —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR[8]R[8], —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR[8]R[8], —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR[8], O, and S(O)$_p$, wherein said alkyl, alkenyl, alkynyl, alkoxyl, carbocycle, and heterocycle are substituted with 0-4 R[9];

R[8], at each occurrence, is independently selected from H, C$_{1-4}$ alkyl, C(O)C$_{1-4}$alkyl, C(O)carbocycle, C(O)heterocycle, —(CH$_2$)$_n$—C(O)NR$^a$R$^a$, C(O)O-alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R[9];

alternatively, R[8] and R[8] are taken together with the nitrogen atom to which they are attached to form 4- to 10-membered heterocycle substituted with 0-4 R[9]; and R[9], at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR[10]R[10])$_n$— 4-10 membered heterocycle, wherein said alkyl, alkoxyl, carbocycle, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$; and R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

other variables are as defined in Formula (VIII) above.

In still another aspect, the present invention provides compounds of Formula (VIII), or stereoisomers, tautomers, pharmaceutically acceptable salts, solvates, or prodrugs thereof, wherein:

R$^1$ is NR$^5$R$^5$;

R$^5$ and R$^5$ are taken together with the nitrogen atom to which they are attached to form 4- to 10-membered heterocycle substituted with 1-4 R$^7$;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, —(CH$_2$)$_n$—C(O)NR$^a$R$^a$, C(O)O-alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-cycloalkyl, —(CH$_2$)$_n$-phenyl, and —(CH$_2$)$_n$-heterocycle, wherein said alkyl, carbocycle, and heterocycle are substituted with 0-4 R$^9$; and R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$— 4-10 membered heterocycle, wherein said alkyl, alkoxyl, carbocycle, and heterocycle are substituted with 0-4 R$^b$; and other variables are as defined in Formula (VIII) above.

In one embodiment, the present invention provides compounds of Formulae (I), (II), (III), and (IV), or stereoisomers, tautomers, pharmaceutically acceptable salts, solvates, or prodrugs thereof, wherein M is N or CR$^{10}$; L is selected from —CR$^4$R$^4$C(O)—, —OC(O)—, and —NR$^6$C(O—; R$^1$ is selected from NR$^5$R$^5$, C$_{3-10}$ carbocycle and 4- to 12-membered heterocycle comprising carbon atoms and 1-4 heteroatoms selected from N, NR$^8$, O, and S(O)$_p$; wherein said alkyl, carbocycle and heterocycle are substituted with 1-4 R$^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, and —NR$^6$C(O)—; R$^1$ is selected from NR$^5$R$^5$, C$_{3-10}$ carbocycle and 4- to 12-membered heterocycle comprising carbon atoms and 1-4 heteroatoms selected from N, NR$^8$, O, and S(O)$_p$; wherein said alkyl, carbocycle and heterocycle are substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—, and —NR$^6$—; R$^1$ is 4- to 12-membered heterocycle comprising carbon atoms and 1-4 heteroatoms selected from N, NR$^8$, O, and S(O)$_p$ and substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)— or NR$^6$—; R$^1$ is selected from

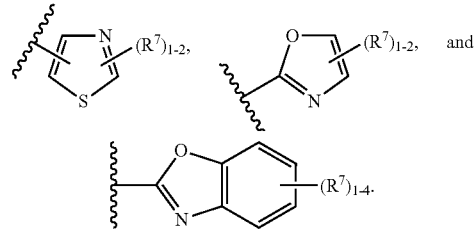

In one embodiment, the present invention provides compounds of Formulae (I), (IV), (V), and (VIII), or stereoisomers, tautomers, pharmaceutically acceptable salts, solvates, or prodrugs thereof, wherein L is —NR$^6$C(O)—; R$^1$ is C$_{3-10}$ carbocycle substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—; R$^1$ is C$_{3-6}$ cycloalkyl substituted with 1-4 R$^7$ or aryl substituted with 1-4 R$^7$; R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—; R$^1$ is cyclopropyl, cyclobutyl, cyclopentyl, cyclohexyl or phenyl, each substituted with 1-4 R$^7$; R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$- carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, and —NR$^6$C(O)—; R$^1$ is NR$^5$R$^5$; R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said carbocycle and heterocycle are substituted with 1-4 R$^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, and —NR$^6$C(O)—; R$^1$ is NR$^5$R$^5$; R$^5$, at each occurrence, is independently selected from H, C$_{1-4}$ alkyl, —(CH$_2$)$_n$—C$_{3-10}$ carbocycle, —(CH$_2$)$_n$-aryl, —(CH$_2$)$_n$-4-10 membered heterocycle selected from

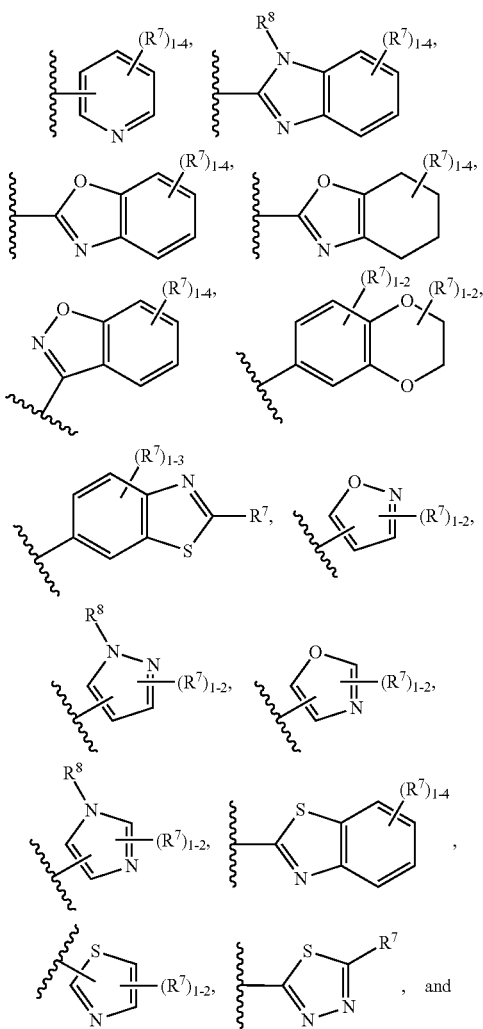

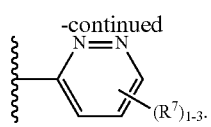

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, and —NR$^6$C(O)—; R$^1$ is NR$^5$R$^5$; R$^5$ and R$^5$ are taken together with the nitrogen atom to which they are attached to form 4- to 10-membered heterocycle comprising carbon atoms and 1-4 heteroatoms selected from N, NR$^8$, O, and S(O)$_p$, wherein said heterocycle is substituted with 1-4 R$^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, and —NR$^6$C(O)—; R$^1$ is NR$^5$R$^5$; R$^5$ and R$^5$ are taken together with the nitrogen atom to which they are attached to form a heterocycle selected from

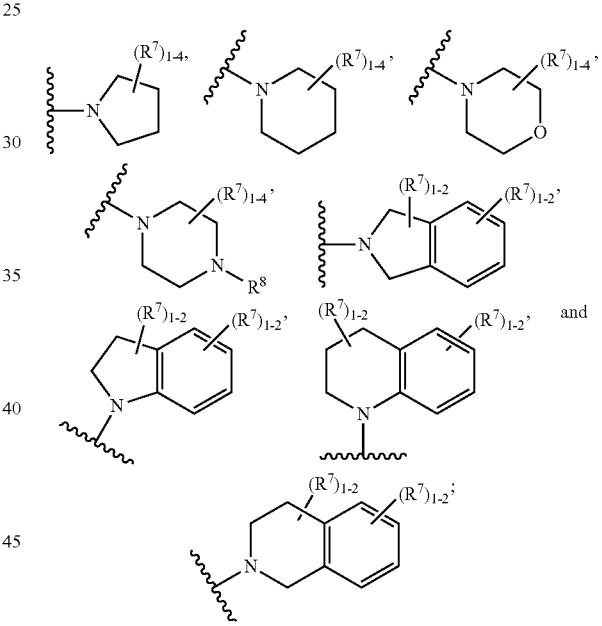

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR⁴R⁴C(O)—, —OC(O)—, and —NR⁶C(O)—; R¹ is selected from

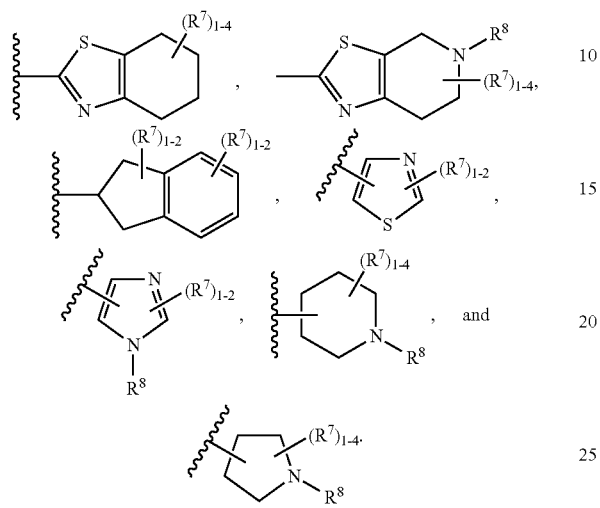

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR⁴R⁴C(O)—, —OC(O)—, and —NR⁶C(O)—; R¹ is selected from NR⁵R⁵, $C_{3-10}$ carbocycle and 4- to 12-membered heterocycle comprising carbon atoms and 1-4 heteroatoms selected from N, NR⁸, O, and $S(O)_p$; wherein said alkyl, carbocycle and heterocycle are substituted with 1-4 R⁷; R⁵, at each occurrence, is independently selected from H, $C_{1-4}$ alkyl, —(CR⁶R⁶)$_n$—$C_{3-10}$ carbocycle, and —(CR⁶R⁶)$_n$-4-10 membered heterocycle comprising carbon atoms and 1-4 heteroatoms selected from N, NR⁸, O, and $S(O)_p$, wherein said alkyl, carbocycle and heterocycle are substituted with 1-4 R⁷; alternatively, R⁵ and R⁵ are taken together with the nitrogen atom to which they are attached to form 4- to 10-membered heterocycle substituted with 1-4 R⁷.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR⁴R⁴C(O)—, —OC(O)—, and —NR⁶C(O)—; R¹ is selected from $C_{3-10}$ carbocycle and 4- to 12-membered heterocycle comprising carbon atoms and 1-4 heteroatoms selected from N, NR⁸, O, and $S(O)_p$; wherein said carbocycle and heterocycle are substituted with 1-4 R⁷; R⁵, at each occurrence, is independently selected from H, $C_{1-4}$ alkyl, —(CR⁶R⁶)$_n$—$C_{3-10}$ carbocycle substituted with 1-4 R⁷, and —(CR⁶R⁶)$_n$-4-10 membered heterocycle selected from

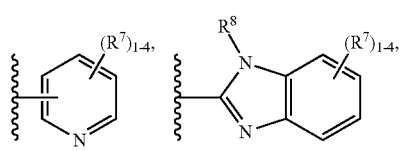

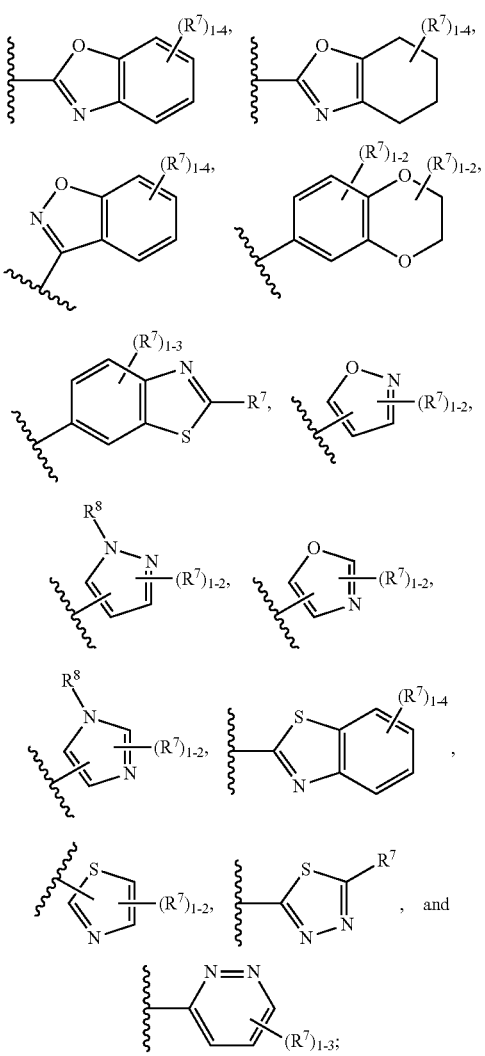

alternatively, R⁵ and R⁵ are taken together with the nitrogen atom to which they are attached to form a heterocycle selected from

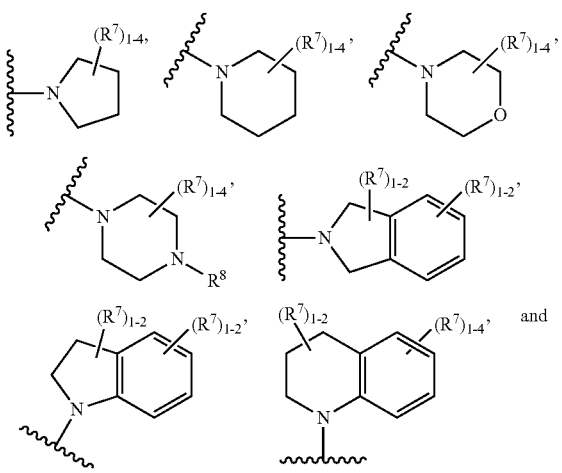

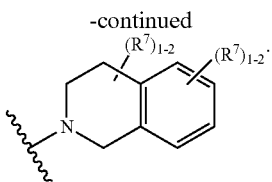

In another aspect, the present invention provides a compound selected from any subset list of compounds exemplified in the present application.

In another embodiment, the compounds of the present invention have ROCK $IC_{50}$ values ≤10 µM.

In another embodiment, the compounds of the present invention have ROCK $IC_{50}$ values ≤1 µM.

In another embodiment, the compounds of the present invention have ROCK $IC_{50}$ values ≤0.1 µM.

In another embodiment, the compounds of the present invention have ROCK $IC_{50}$ values ≤0.05 µM.

In another embodiment, the compounds of the present invention have ROCK $IC_{50}$ values ≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

II. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_2$-6 alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
CH$_2$Cl$_2$ Dichloromethane
CH$_3$CN or ACN Acetonitrile
CDCl$_3$ deutero-chloroform
CHCl$_3$ Chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimethylaminopropyl)-N-ethylcarbodiimide
EDCI N-(3-dimethylaminopropyl)-N-ethylcarbodiimide hydrochloride EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
SEM-Cl 2-(trimethylsilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 µL assay containing 20 mM HEPES, pH 7.5, 20 mM $MgCl_2$, 0.015% Brij-35, 4 mM DTT, 5 µM ATP and 1.5 µM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK assay described above and found having ROCK inhibitory activity. A range of ROCK inhibitory activity ($IC_{50}$ values) of ≤50 µM (50000 nM) was observed. Table A below lists the ROCK $IC_{50}$ values measured for the following examples. $IC_{50}$ ranges against ROCKs are as follows: +++=0.1-100 nM; ++=101-1000 nM; +=1001-50000 nM.

TABLE A

| Example No. | ROCK1 $IC_{50}$ (nM) | ROCK2 $IC_{50}$ (nM) |
| --- | --- | --- |
| 1 | − | +++ |
| 2 | ++ | +++ |
| 3 | ++ | +++ |
| 4 | − | ++ |
| 5 | − | ++ |
| 6 | − | ++ |
| 7 | − | +++ |
| 8 | − | + |
| 9 | + | +++ |
| 10 | ++ | +++ |
| 11 | + | ++ |
| 12 | + | + |
| 13 | + | + |
| 14 | + | + |
| 15 | + | + |
| 16 | + | + |
| 17 | + | +++ |
| 18 | + | + |
| 19 | + | + |
| 20 | + | ++ |
| 21 | ++ | +++ |
| 22 | + | + |
| 23 | ++ | +++ |
| 24 | ++ | +++ |
| 25 | ++ | +++ |
| 26 | + | +++ |
| 27 | + | +++ |
| 28 | + | ++ |
| 29 | + | +++ |
| 30 | − | − |
| 31 | + | +++ |
| 32 | − | − |
| 33 | +++ | +++ |
| 34 | + | ++ |
| 35 | ++ | +++ |
| 36 | + | +++ |
| 37 | ++ | +++ |
| 38 | ++ | +++ |
| 39 | ++ | +++ |

TABLE A-continued

| Example No. | ROCK1 IC$_{50}$ (nM) | ROCK2 IC$_{50}$ (nM) |
|---|---|---|
| 40 | ++ | +++ |
| 41 | +++ | +++ |
| 42 | + | +++ |
| 43 | + | ++ |
| 44 | + | +++ |
| 45 | − | +++ |
| 46 | + | +++ |
| 47 | ++ | +++ |
| 48 | ++ | +++ |
| 49 | − | +++ |
| 50 | +++ | +++ |
| 51 | + | +++ |
| 52 | ++ | ++ |
| 53 | +++ | +++ |
| 54 | ++ | +++ |
| 55 | + | + |
| 56 | + | + |
| 57 | + | + |
| 58 | +++ | +++ |
| 59 | + | + |
| 60 | +++ | +++ |
| 61 | +++ | +++ |
| 62 | +++ | +++ |
| 63 | ++ | +++ |
| 64 | ++ | +++ |
| 65 | +++ | +++ |
| 66 | +++ | +++ |
| 67 | ++ | +++ |
| 68 | − | +++ |
| 69 | + | ++ |
| 70 | + | +++ |
| 71 | + | +++ |
| 72 | ++ | +++ |
| 73 | ++ | +++ |
| 73 | − | − |
| 74 | + | +++ |
| 75 | +++ | +++ |
| 76 | +++ | +++ |
| 77 | +++ | +++ |
| 78 | ++ | +++ |
| 79 | +++ | +++ |
| 80 | +++ | +++ |
| 81 | + | ++ |
| 82 | + | ++ |
| 83 | +++ | +++ |
| 84 | ++ | +++ |
| 85 | +++ | +++ |
| 86 | ++ | +++ |
| 87 | ++ | +++ |
| 88 | + | +++ |
| 89 | ++ | +++ |
| 90 | ++ | +++ |
| 91 | + | +++ |
| 92 | ++ | +++ |
| 93 | +++ | +++ |
| 94 | +++ | +++ |
| 95 | +++ | +++ |
| 96 | ++ | +++ |
| 97 | ++ | ++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | ++ | +++ |
| 106 | + | +++ |
| 107 | +++ | +++ |
| 108 | ++ | +++ |
| 109 | +++ | +++ |
| 110 | +++ | +++ |
| 111 | ++ | ++ |
| 112 | + | ++ |
| 113 | ++ | ++ |
| 114 | ++ | +++ |
| 115 | +++ | +++ |
| 116 | +++ | +++ |
| 117 | +++ | +++ |
| 118 | ++ | +++ |
| 119 | ++ | +++ |
| 120 | +++ | +++ |
| 121 | ++ | +++ |
| 122 | +++ | +++ |
| 123 | ++ | +++ |
| 124 | ++ | +++ |
| 125 | +++ | +++ |
| 126 | ++ | +++ |
| 127 | +++ | +++ |
| 128 | +++ | +++ |
| 129 | +++ | +++ |
| 130 | +++ | +++ |
| 131 | +++ | +++ |
| 132 | +++ | +++ |
| 133 | ++ | +++ |
| 134 | ++ | +++ |
| 135 | ++ | +++ |
| 136 | + | +++ |
| 137 | +++ | +++ |
| 138 | +++ | +++ |
| 139 | +++ | +++ |
| 140 | +++ | +++ |
| 141 | +++ | +++ |
| 142 | +++ | +++ |
| 143 | + | + |
| 144 | +++ | +++ |
| 145 | +++ | +++ |
| 146 | +++ | +++ |
| 147 | +++ | +++ |
| 148 | +++ | +++ |
| 149 | +++ | +++ |
| 150 | +++ | +++ |
| 151 | +++ | +++ |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | +++ |
| 159 | +++ | +++ |
| 160 | +++ | +++ |
| 161 | +++ | +++ |
| 162 | +++ | +++ |
| 163 | +++ | +++ |
| 164 | +++ | +++ |
| 165 | +++ | +++ |
| 166 | ++ | +++ |
| 167 | +++ | +++ |
| 168 | +++ | +++ |
| 169 | +++ | +++ |
| 170 | +++ | +++ |
| 171 | +++ | +++ |
| 172 | +++ | +++ |
| 173 | +++ | +++ |
| 174 | +++ | +++ |
| 175 | +++ | +++ |
| 176 | +++ | +++ |
| 177 | +++ | +++ |
| 178 | ++ | +++ |
| 179 | +++ | +++ |
| 180 | +++ | +++ |
| 181 | ++ | +++ |
| 182 | +++ | +++ |
| 183 | +++ | +++ |
| 184 | +++ | +++ |
| 185 | +++ | +++ |
| 186 | ++ | +++ |
| 187 | +++ | +++ |
| 188 | +++ | +++ |
| 189 | +++ | +++ |
| 190 | +++ | +++ |
| 191 | +++ | +++ |
| 192 | ++ | +++ |
| 193 | + | ++ |
| 194 | ++ | +++ |

TABLE A-continued

| Example No. | ROCK1 IC$_{50}$ (nM) | ROCK2 IC$_{50}$ (nM) |
|---|---|---|
| 195 | +++ | +++ |
| 196 | + | ++ |
| 197 | +++ | +++ |
| 198 | +++ | +++ |
| 199 | +++ | +++ |
| 200 | +++ | +++ |
| 201 | +++ | +++ |
| 202 | +++ | +++ |
| 203 | ++ | +++ |
| 204 | ++ | +++ |
| 205 | ++ | +++ |
| 206 | +++ | +++ |
| 207 | +++ | +++ |
| 208 | +++ | +++ |
| 209 | ++ | ++ |
| 210 | ++ | ++ |
| 211 | + | ++ |
| 212 | ++ | +++ |
| 213 | +++ | +++ |
| 214 | +++ | +++ |
| 215 | ++ | ++ |
| 216 | + | ++ |
| 217 | + | ++ |
| 218 | + | ++ |
| 219 | +++ | +++ |
| 220 | +++ | +++ |
| 221 | ++ | ++ |
| 222 | +++ | +++ |
| 223 | +++ | +++ |
| 224 | +++ | +++ |
| 225 | +++ | +++ |
| 226 | +++ | +++ |
| 227 | ++ | +++ |
| 228 | +++ | +++ |
| 229 | +++ | +++ |
| 230 | +++ | +++ |
| 231 | ++ | +++ |
| 232 | ++ | +++ |
| 233 | ++ | ++ |
| 234 | ++ | +++ |
| 235 | +++ | +++ |
| 236 | ++ | +++ |
| 237 | ++ | +++ |
| 238 | ++ | +++ |
| 239 | ++ | +++ |
| 240 | ++ | +++ |
| 241 | +++ | +++ |
| 242 | ++ | +++ |
| 243 | − | − |
| 244 | +++ | +++ |
| 245 | +++ | +++ |
| 246 | +++ | +++ |
| 247 | +++ | +++ |
| 248 | ++ | +++ |
| 249 | +++ | +++ |
| 250 | ++ | +++ |
| 251 | ++ | +++ |
| 252 | + | ++ |
| 253 | + | ++ |
| 254 | ++ | +++ |
| 255 | + | ++ |
| 256 | ++ | +++ |
| 257 | + | +++ |
| 258 | +++ | +++ |
| 259 | ++ | +++ |
| 260 | ++ | +++ |
| 261 | +++ | +++ |
| 262 | ++ | +++ |
| 263 | ++ | +++ |
| 264 | +++ | +++ |
| 265 | +++ | +++ |
| 266 | +++ | +++ |
| 267 | ++ | +++ |
| 268 | +++ | +++ |
| 269 | + | +++ |
| 270 | +++ | +++ |
| 271 | +++ | +++ |
| 272 | +++ | +++ |
| 273 | ++ | +++ |
| 274 | +++ | +++ |
| 275 | +++ | +++ |
| 276 | + | +++ |
| 277 | ++ | +++ |
| 278 | ++ | +++ |
| 279 | ++ | +++ |
| 280 | ++ | +++ |
| 281 | ++ | +++ |
| 282 | ++ | +++ |
| 283 | +++ | +++ |
| 284 | +++ | +++ |
| 285 | +++ | +++ |
| 286 | ++ | +++ |
| 287 | +++ | +++ |
| 288 | +++ | +++ |
| 289 | +++ | +++ |
| 290 | +++ | +++ |
| 291 | ++ | +++ |
| 292 | ++ | +++ |
| 293 | ++ | +++ |
| 294 | ++ | +++ |
| 295 | ++ | +++ |
| 296 | ++ | +++ |
| 297 | +++ | +++ |
| 298 | +++ | +++ |
| 299 | ++ | +++ |
| 300 | +++ | +++ |
| 301 | +++ | +++ |
| 302 | +++ | +++ |
| 303 | ++ | +++ |
| 304 | ++ | +++ |
| 305 | + | + |
| 306 | ++ | +++ |
| 307 | ++ | +++ |
| 308 | +++ | +++ |
| 309 | +++ | +++ |
| 310 | ++ | +++ |
| 311 | +++ | +++ |
| 312 | ++ | +++ |
| 313 | +++ | +++ |
| 314 | +++ | +++ |
| 315 | +++ | +++ |
| 316 | ++ | +++ |
| 317 | +++ | +++ |
| 318 | +++ | +++ |
| 319 | +++ | +++ |
| 320 | +++ | +++ |
| 321 | +++ | ++ |
| 322 | +++ | ++ |
| 323 | +++ | +++ |
| 324 | +++ | +++ |
| 325 | ++ | +++ |
| 326 | +++ | ++ |
| 327 | +++ | +++ |
| 328 | ++ | +++ |
| 329 | +++ | +++ |
| 330 | +++ | ++ |
| 331 | ++ | +++ |
| 332 | +++ | +++ |
| 333 | +++ | +++ |
| 334 | +++ | +++ |
| 335 | +++ | +++ |
| 336 | +++ | +++ |
| 337 | +++ | +++ |
| 338 | +++ | ++ |
| 339 | +++ | +++ |
| 340 | +++ | +++ |
| 341 | +++ | +++ |
| 342 | +++ | +++ |
| 343 | +++ | +++ |
| 344 | +++ | +++ |
| 345 | ++ | +++ |
| 346 | + | ++ |
| 347 | + | ++ |
| 348 | ++ | +++ |
| 349 | +++ | +++ |
| 350 | +++ | +++ |

TABLE A-continued

| Example No. | ROCK1 IC$_{50}$ (nM) | ROCK2 IC$_{50}$ (nM) |
| --- | --- | --- |
| 351 | +++ | +++ |
| 352 | + | ++ |
| 353 | ++ | +++ |
| 354 | +++ | +++ |
| 355 | + | +++ |
| 356 | +++ | ++ |
| 357 | + | ++ |
| 358 | ++ | +++ |
| 359 | + | +++ |
| 360 | + | +++ |
| 361 | ++ | +++ |
| 362 | + | +++ |
| 363 | + | +++ |
| 364 | ++ | +++ |
| 365 | + | 221.80 |
| 366 | ++ | +++ |
| 367 | + | +++ |
| 368 | + | +++ |
| 369 | ++ | +++ |
| 370 | + | +++ |
| 371 | ++ | ++ |
| 372 | ++ | ++ |
| 373 | +++ | +++ |
| 374 | +++ | +++ |
| 375 | +++ | +++ |
| 376 | ++ | +++ |
| 377 | + | +++ |
| 378 | +++ | +++ |
| 379 | ++ | +++ |
| 380 | ++ | +++ |
| 381 | +++ | +++ |
| 382 | +++ | +++ |
| 383 | ++ | +++ |
| 384 | ++ | +++ |
| 385 | +++ | +++ |
| 386 | ++ | +++ |
| 387 | + | +++ |
| 388 | ++ | +++ |
| 389 | ++ | +++ |
| 390 | ++ | +++ |
| 391 | ++ | +++ |
| 392 | +++ | +++ |
| 393 | +++ | +++ |
| 394 | ++ | +++ |
| 395 | +++ | +++ |
| 396 | ++ | +++ |
| 397 | + | ++ |
| 398 | ++ | +++ |
| 399 | ++ | ++ |
| 400 | +++ | +++ |
| 401 | +++ | +++ |
| 402 | ++ | +++ |
| 403 | +++ | +++ |
| 404 | +++ | +++ |
| 405 | +++ | +++ |
| 406 | +++ | +++ |
| 407 | +++ | +++ |
| 408 | ++ | +++ |
| 409 | – | – |
| 410 | – | – |
| 411 | – | – |
| 412 | – | – |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously). When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

Scheme 1

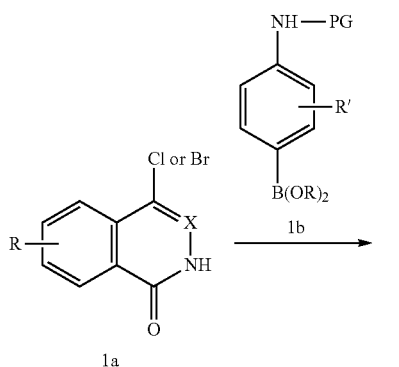

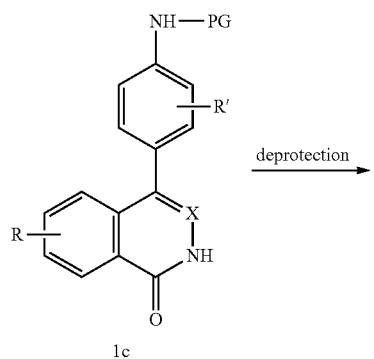

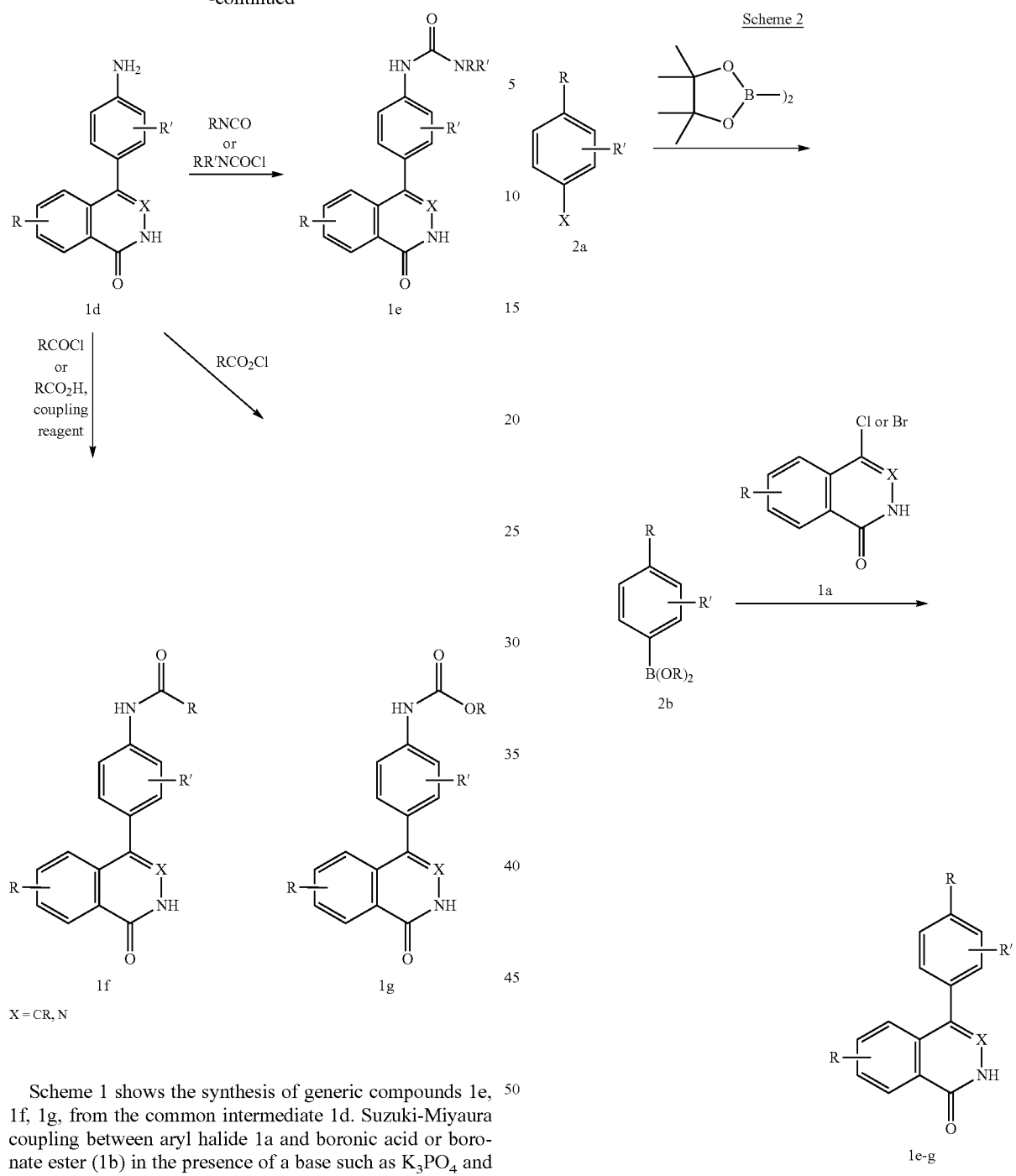

Scheme 1 shows the synthesis of generic compounds 1e, 1f, 1g, from the common intermediate 1d. Suzuki-Miyaura coupling between aryl halide 1a and boronic acid or boronate ester (1b) in the presence of a base such as $K_3PO_4$ and a catalyst such as $Pd(PPh_3)_4$ affords intermediate 1c. Cleavage of the protecting group, such as using TFA or HCl in dioxane when PG=Boc, affords the arylamine intermediate 1d. Intermediate 1d is converted to the urea target 1e by treatment with an isocyanate or a carbamic chloride. Intermediate 1d is converted to the amide target 1f by treatment with an acid chloride in the presence of a base such as pyridine or DIEA. Alternatively, Target 1f is prepared by coupling of intermediate 1d with a carboxylic acid in the presence of a coupling reagent, such as HATU or BOP, and a base such as DIEA. Intermediate 1d is converted to the carbamate target 1g by treatment with a chloroformate in the presence of a base such as DIEA or TEA.

Alternatively, targets 1e-g can be prepared as shown in Scheme 2. Aryl halide 2a (commercially available or prepared by literature methods) is converted to the aryl boronic acid or boronate ester 2b by coupling with bis(pinacolato)diboron in the presence of a base such a potassium acetate and a catalyst such as $PdCl_2(dppf)$ in dioxane or DMSO. Suzuki-Miyaura coupling between aryl halide 1a and boronic acid or boronate ester (2b) in the presence of a base such as $K_3PO_4$ and a catalyst such as $Pd(PPh_3)_4$ affords target compounds 1e-g.

Scheme 3

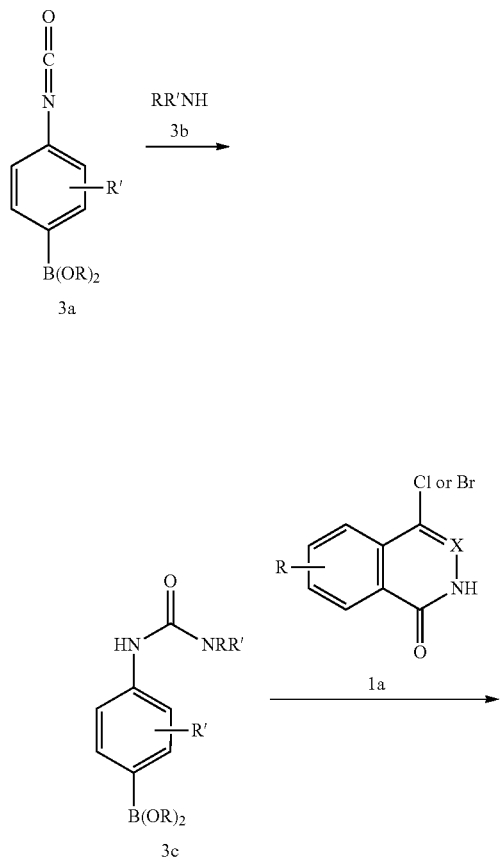

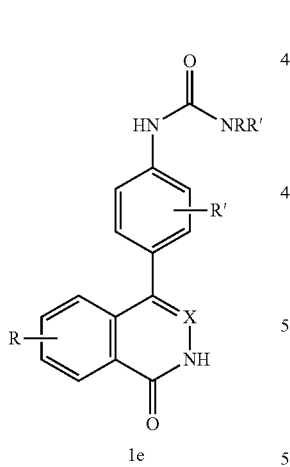

X = N, CR

Scheme 4

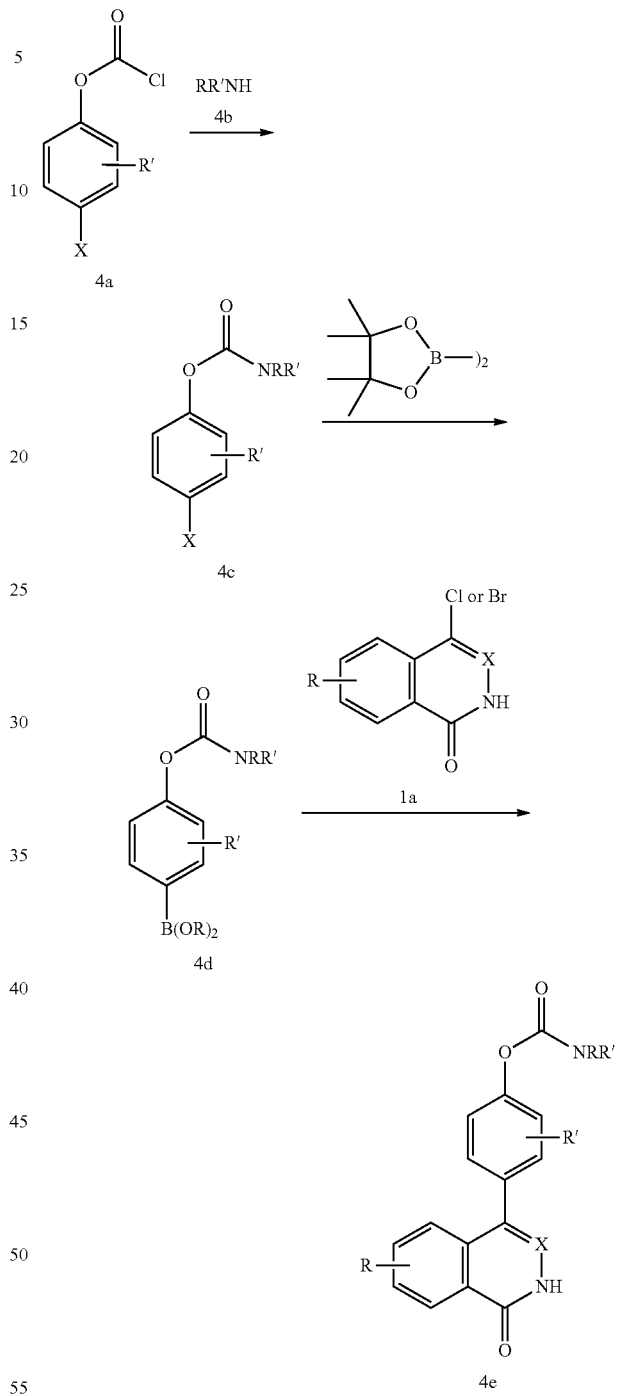

X = N, CR

Alternatively, target 1e can be prepared as shown in Scheme 3 beginning from isocyanate 3a, which is either commercially available or can be prepared from the aniline precursor upon treatment with phosgene (or equivalent) and an appropriate base such as TEA. Intermediate 3a is reacted with amine (3b) to afford urea 3c. Suzuki-Miyaura coupling between aryl halide 1a and boronic acid or boronate ester (3c) in the presence of a base such as $K_3PO_4$ and a catalyst such as $Pd(PPh_3)_4$ affords target compounds 1e.

Scheme 4 shows the synthesis of carbamate target 4e, beginning from chloroformate 4a (either commercially available or prepared by treatment of an appropriate halophenol with phosgene or a phosgene equivalent). Intermediate 4a is reacted with an amine (4b) in the presence of a base such as TEA to afford carbamate 4c. Aryl halide 4c is converted to the aryl boronic acid or boronate ester 4d by coupling with bis(pinacolato)diboron in the presence of a base such a potassium acetate and a catalyst such as $PdCl_2$ (dppf) in dioxane or DMSO. Suzuki-Miyaura coupling between aryl halide 1a and boronic acid or boronate ester (4d) in the presence of a base such as $K_3PO_4$ and a catalyst such as $Pd(PPh_3)_4$ affords target compound 4e.

Scheme 5 shows the synthesis of amide target 5e, beginning with boronic acid/ester 5a, which is either commercially available or is prepared from the aryl halide precursor. Suzuki-Miyaura coupling between aryl halide 1a and boronic acid or boronate ester (5a) in the presence of a base such as $K_3PO_4$ and a catalyst such as $Pd(PPh_3)_4$ affords intermediate 5b. Cleavage of the protecting group (PG) by alkaline hydrolysis (or other reagents as appropriate) affords carboxylic acid 5c. Coupling of intermediate 5c with amine 5d in the presence of a coupling reagent, such as HATU or BOP, and a base such as DIEA affords target 5e.

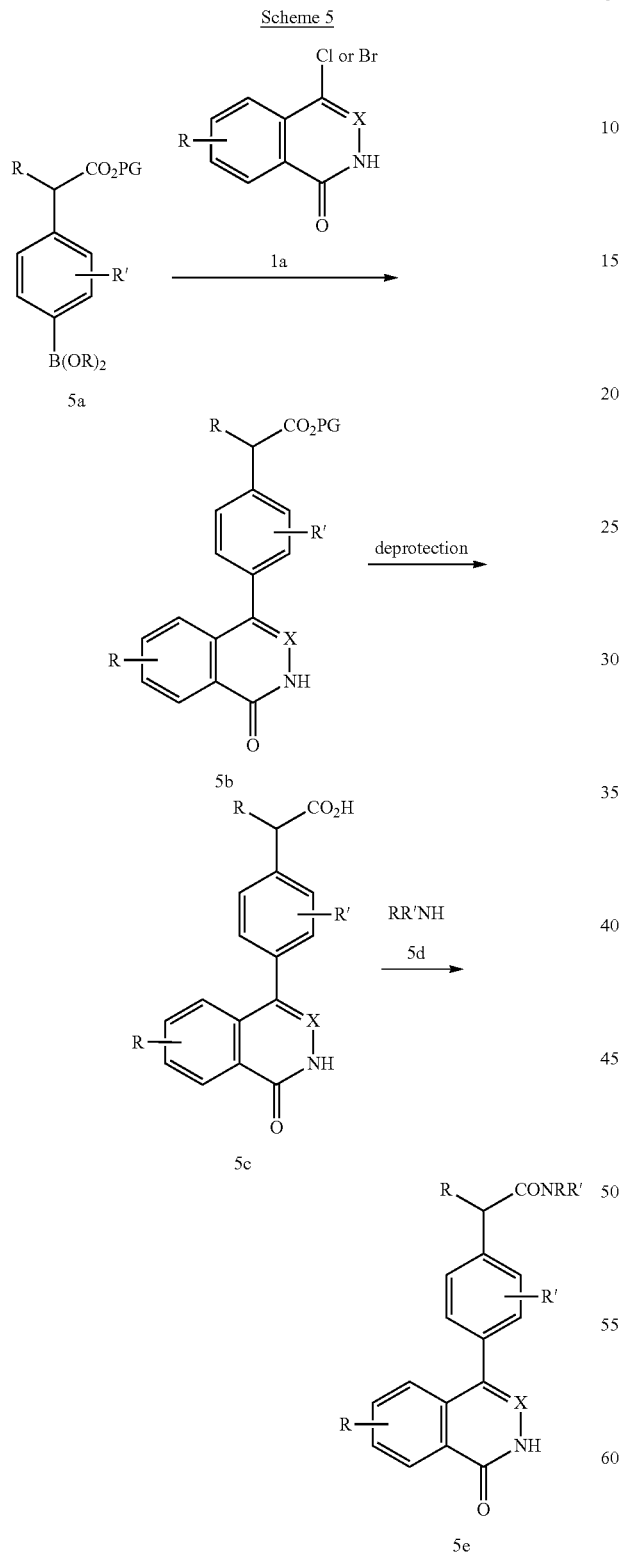

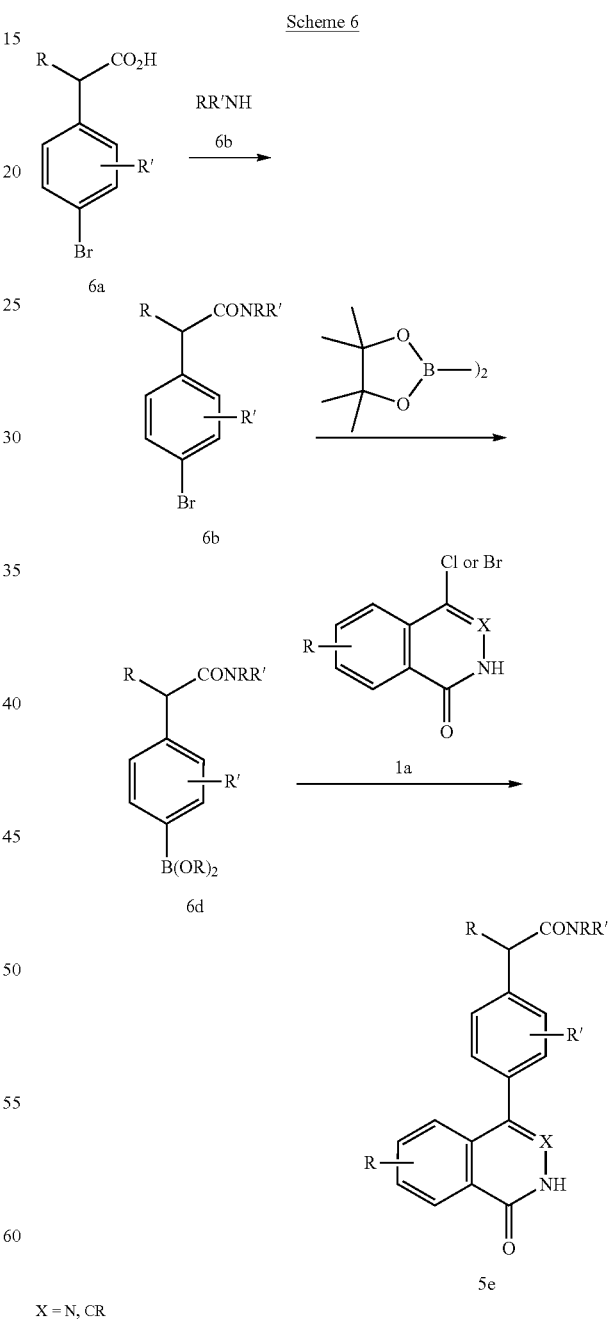

Scheme 6 shows an alternate synthesis to target 5e beginning from acid 6a. Coupling of intermediate 6a with amine 6b in the presence of a coupling reagent, such as HATU or BOP, and a base such as DIEA affords intermediate amide 6c. Aryl halide 6c is converted to the aryl boronic acid or boronate ester 6d by coupling with bis(pinacolato)diboron in the presence of a base such a potassium acetate and a catalyst such as PdCl$_2$(dppf) in dioxane or DMSO. Suzuki-Miyaura coupling between aryl halide 1a and boronic acid or boronate ester (6d) in the presence of a base such as K$_3$PO$_4$ and a catalyst such as Pd(PPh$_3$)$_4$ affords target compound 5e.

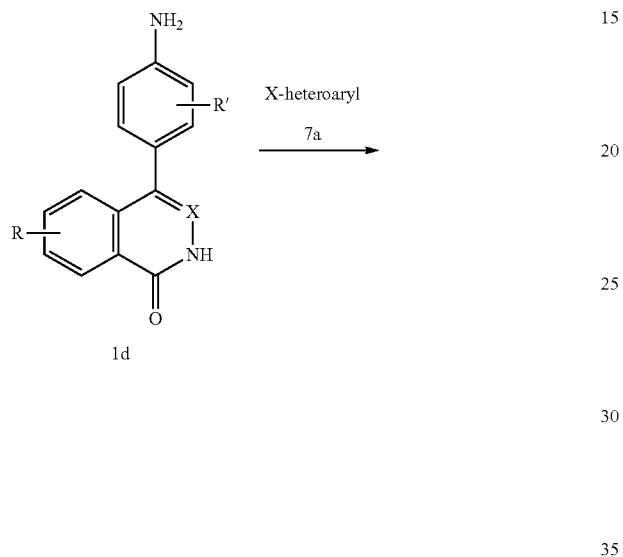

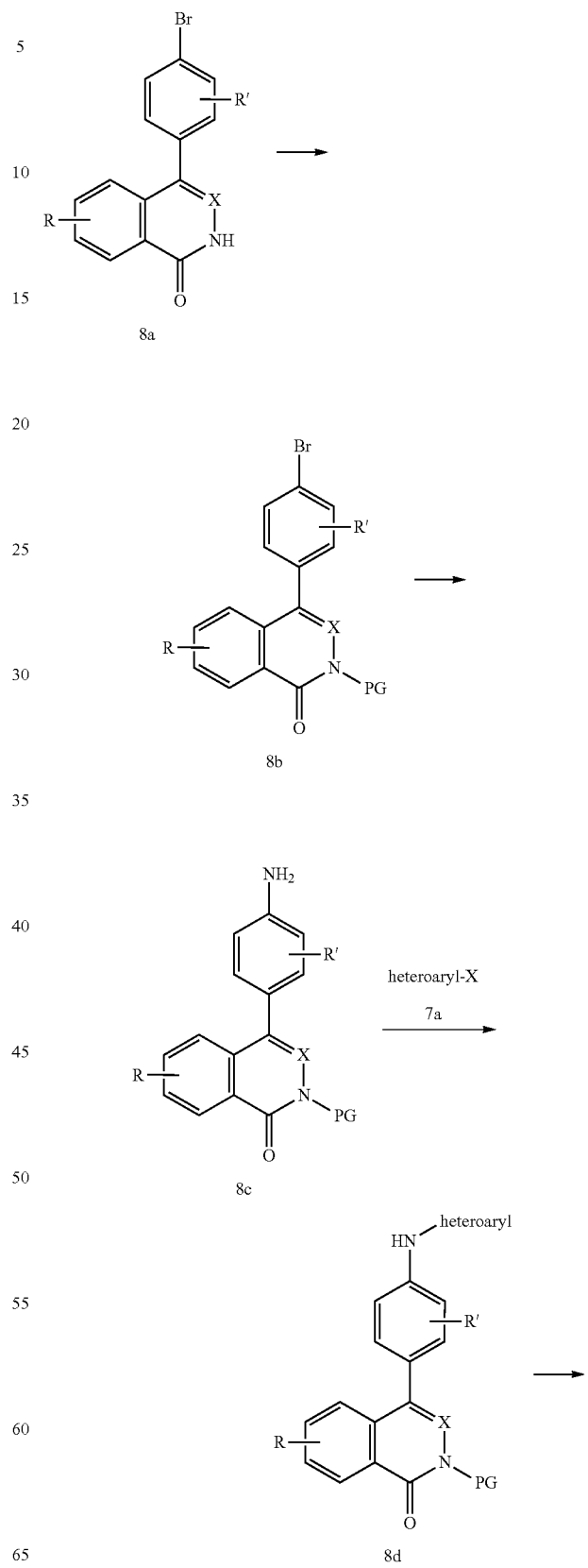

Scheme 7 shows the synthesis of target 7b beginning with intermediate aniline 1d. Aniline 1d is coupled with heteroaryl halide 7a under thermal S$_N$Ar conditions in the presence of a base such as DIEA in a solvent such as DMF to afford 7b. Alternatively, 1d and 7a may be coupled under Buchwald-Hartwig N-arylation conditions using a base such as Cs$_2$CO$_3$, a catalyst such as Pd$_2$(dba)$_3$ and an appropriate ligand to afford 7b.

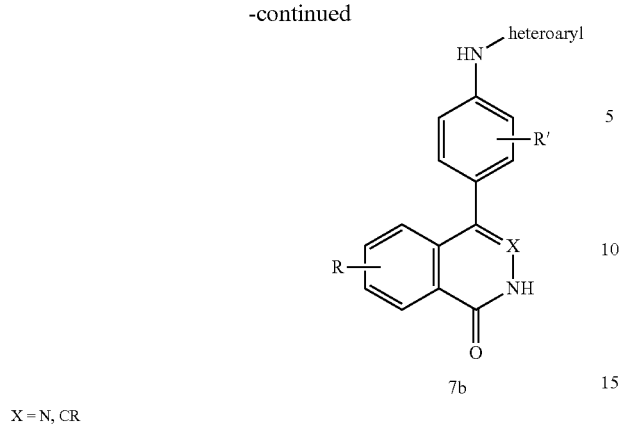

7b

X = N, CR

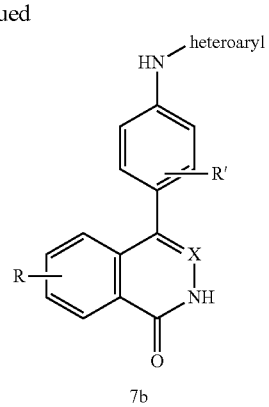

7b

X = N, CR

Scheme 8 shows an alternative synthesis of target 7b, beginning from intermediate 8a, which is either commercially available or can be prepared by literature methods. An appropriate protecting group is introduced by treatment with a base such as potassium carbonate and a protecting group reagent such as para-methoxybenzyl chloride to afford 8b. Treatment of aryl bromide 8b with sodium azide, Cu$_2$O and a ligand such as proline affords aniline 8c. Aniline 8c is coupled with heteroaryl halide 7a under thermal S$_N$Ar conditions in the presence of a base such as DIEA in a solvent such as DMF to afford intermediate 8d. Alternatively, 8c and 7a may be coupled under Buchwald-Hartwig N-arylation conditions using a base such as Cs$_2$CO$_3$, a catalyst such as Pd$_2$(dba)$_3$ and an appropriate ligand to afford intermediate 8d. Cleavage of the protecting group under appropriate conditions (TFA in the case of a para-methoxybenzyl protecting group) affords target 7b.

Scheme 9 shows an alternative synthesis of target 7b, starting from aryl bromide 8b. Coupling of intermediate 8b with heteroaryl amine 9a under Buchwald-Hartwig N-arylation conditions using a base such as Cs$_2$CO$_3$, a catalyst such as Pd$_2$(dba)$_3$ and an appropriate ligand affords intermediate 8d. Cleavage of the protecting group under appropriate conditions (TFA in the case of a para-methoxybenzyl protecting group) affords target 7b.

Scheme 10

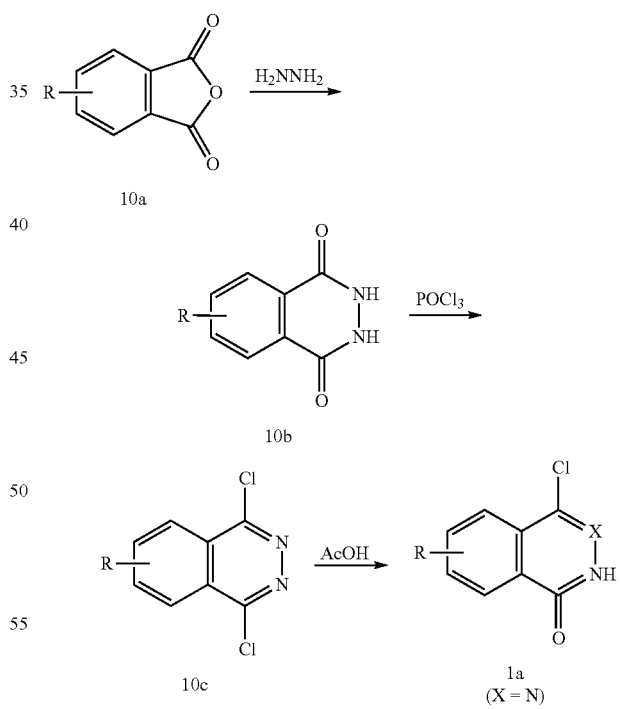

Scheme 9

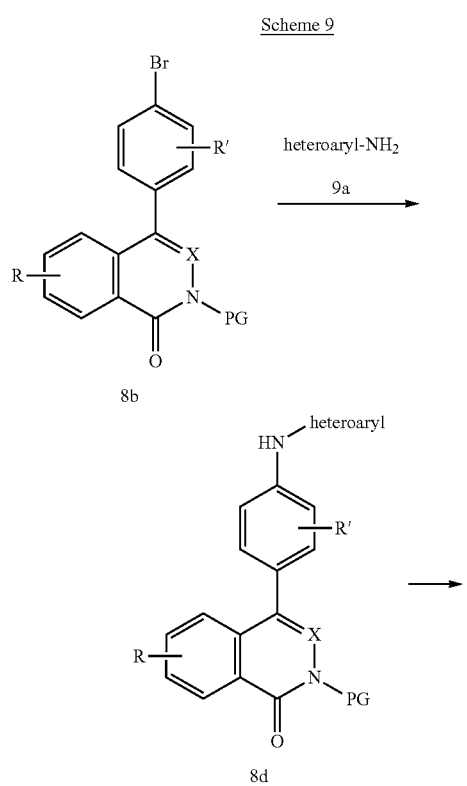

Scheme 10 shows the synthesis of intermediate 1a, where X=N. Furan-2,5-dione 10a can be converted to intermediate 10b by treatment with a reagent such as hydrazine. Intermediate 10b is chlorinated by treatment with a reagent such as POCl$_3$ to afford dichloro intermediate 10c. Partial hydrolysis of 10c with a reagent such as AcOH affords intermediate 1a.

Scheme 11

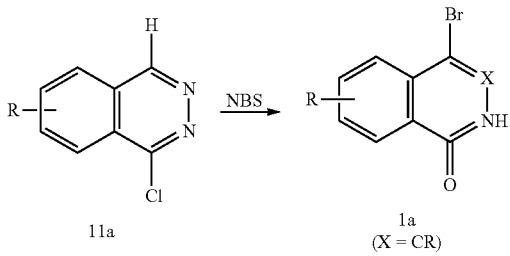

Scheme 11 shows the synthesis of intermediate 1a, where X=CR. Intermediate 11a is brominated with a reagent such as NBS to afford intermediate 1a.

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (90% $H_2O$, 10% MeOH, 0.1% TFA) and Solvent B (10% $H_2O$, 90% MeOH, 0.1% TFA, UV 220 nm) or with gradients of Solvent A (90% $H_2O$, 10% ACN, 0.1% TFA) and Solvent B (10% $H_2O$, 90% ACN, 0.1% TFA, UV 220 nm) or with gradients of Solvent A (98% $H_2O$, 2% ACN, 0.05% TFA) and Solvent B (98% ACN, 2% $H_2O$, 0.05% TFA, UV 220 nm) (or) SunFire Prep C18 OBD 5µ 30×100 mm, 25 min gradient from 0-100% B. A=$H_2O$/ACN/TFA 90:10:0.1. B=ACN/$H_2O$/TFA 90:10:0.1 (or) Waters XBridge C18, 19×200 mm, 5-µm particles; Guard Column: Waters XBridge C18, 19×10 mm, 5-µm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A:
SunFire C18 column (3.5 µm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B:
XBridge Phenyl column (3.5 µm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C:
Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method D:
Waters BEH C18, 2.1×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E:
Waters BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F:
Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Intermediate 1: 2-(4-(4-Oxo-3,4-dihydrophthalazin-1-yl)phenyl)acetic Acid

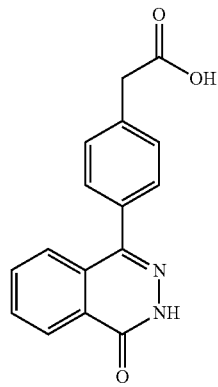 [SMILES: O=C(O)Cc1ccc(-c2n[nH]c(=O)c3ccccc23)cc1]

Intermediate 1A: Ethyl 2-(4-(4,4,5,5-tetramethyl-1,3,2-dioxaborolan-2-yl)phenyl)acetate

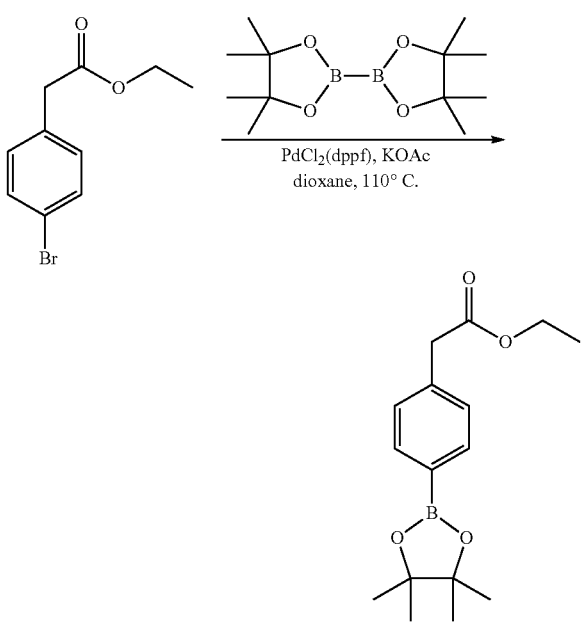

To a vial containing a degassed (3× vacuum/Ar) mixture of ethyl 2-(4-bromophenyl)acetate (1 g, 4.11 mmol), bis(pinacolato)diboron (1.25 g, 4.94 mmol), and potassium acetate (1.21 g, 12.3 mmol) in dioxane (10 mL), was added PdCl$_2$(dppf) CH$_2$Cl$_2$ adduct (0.090 g, 0.123 mmol). The reaction mixture was degassed, sealed and heated at 110° C. for 16 h. The mixture was diluted with water, then extracted with EtOAc. The organic phase was concentrated and purified via flash chromatography (EtOAc/hexane) to afford 1.1 g (92%) of Intermediate 1A. MS(ESI) m/z: 291.2 (M+H)$^+$; $^1$H NMR (500 MHz, CDCl$_3$) δ 7.84-7.71 (m, 2H), 7.34-7.28 (m, J=8.0 Hz, 2H), 4.15 (q, J=7.0 Hz, 2H), 3.63 (s, 2H), 1.27 (s, 12H), 1.26-1.22 (m, 3H).

Intermediate 1B: Ethyl 2-(4-(4-oxo-3,4-dihydrophthalazin-1-yl)phenyl)acetate

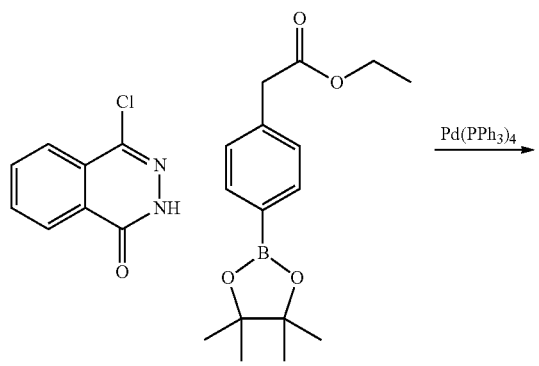

To 4-chlorophthalazin-1(2H)-one (200 mg, 1.11 mmol), Intermediate 1A (386 mg, 1.33 mmol) and K$_3$PO$_4$ (588 mg, 2.77 mmol), were added dioxane (9 mL) and water (1 mL). The mixture was degassed (evacuated and flushed with Ar (5×)). Pd(PPh$_3$)$_4$ (64.0 mg, 0.055 mmol) was added, then the mixture was degassed (2×). The reaction vial was sealed and heated in a microwave reactor at 150° C. for 30 min. The reaction mixture was concentrated and purified via flash chromatography (EtOAc/hexane) to afford 218 mg (46%) of Intermediate 1B. MS(ESI) m/z: 309.1 (M+H)$^+$; $^1$H NMR (500 MHz, DMSO-d$_6$) δ 12.84 (s, 1H), 8.46-8.28 (m, 1H), 7.99-7.82 (m, 2H), 7.69 (d, J=7.2 Hz, 1H), 7.59-7.54 (m, 2H), 7.45 (d, J=6.6 Hz, 2H), 4.12 (qd, J=7.1, 1.8 Hz, 2H), 3.79 (s, 2H), 1.22 (td, J=7.0, 1.9 Hz, 3H).

Intermediate 1

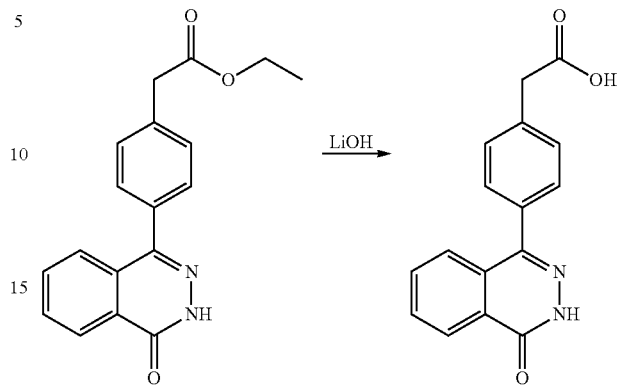

To a solution of Intermediate 1B (210 mg, 0.681 mmol) in MeOH (5 mL) and THF (5 mL), was added 1M aq. lithium hydroxide (3.41 mL, 3.41 mmol). The mixture was stirred rt overnight, then was concentrated. The residue was acidified with TFA, then was dissolved in DMSO/MeOH, and purified preparative HPLC to afford 170 mg (89%) of Intermediate 1. MS(ESI) m/z: 281.0 (M+H)$^+$; $^1$H NMR (500 MHz, DMSO-d$_6$) δ 12.83 (s, 1H), 8.42-8.21 (m, 1H), 7.99-7.82 (m, 2H), 7.77-7.62 (m, 1H), 7.59-7.50 (m, 2H), 7.49-7.37 (m, J=8.3 Hz, 2H), 3.69 (s, 2H).

Intermediate 2: 5-((4-Methylpiperazin-1-yl)methyl)isoindoline, 3 TFA

Intermediate 2A: tert-Butyl di(prop-2-yn-1-yl)carbamate

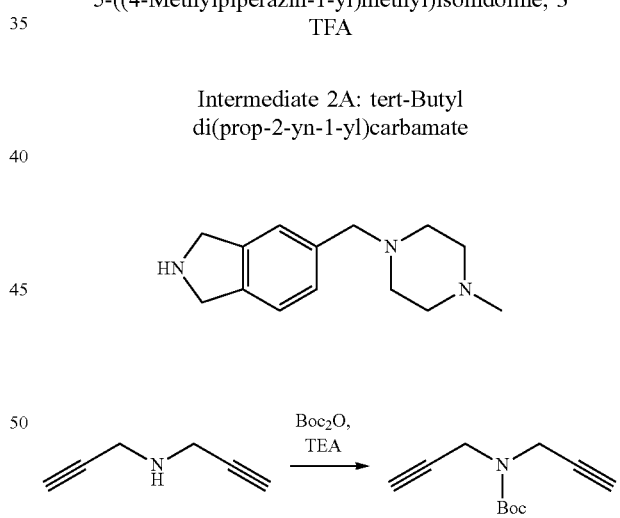

To a solution of 2-propyn-1-amine and N-2-propynyl-(1.110 mL, 10.74 mmol) in THF (20 mL) at rt, was added BOC$_2$O (2.58 g, 11.81 mmol). To this mixture was added TEA (0.150 mL, 1.074 mmol). The mixture was stirred at rt for 14 h. The reaction mixture was concentrated to an oil. The oil was partitioned between 0.2 N HCl and EtOAc. The organic phase was washed with H$_2$O, sat. NaHCO$_3$ and brine, dried (Na$_2$SO$_4$), filtered through a 1" pad of SiO$_2$ and concentrated to afford 2.40 g (100%) of Intermediate 2A as a yellow oil. MS(ESI) m/z: 216.1 (M+H)$^+$; $^1$H NMR (400 MHz, CDCl$_3$) δ 4.17 (br. s., 4H), 2.22 (t, J=2.4 Hz, 2H), 1.48 (s, 9H).

Intermediate 2B: tert-Butyl 5-(hydroxymethyl)isoindoline-2-carboxylate

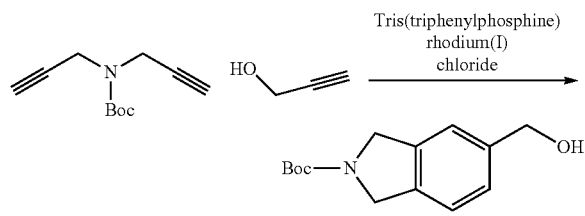

To a degassed (evacuated and flushed with Ar (5×)) solution of prop-2-yn-1-ol (0.961 mL, 16.11 mmol) in toluene (5 mL) at 50° C., were added in 5 portions at 10 minute intervals Intermediate 2A (1.20 g, 5.37 mmol) in degassed toluene (5 mL) and Tris(triphenylphosphine)rhodium(I) chloride (0.124 g, 0.134 mmol). Following the last addition, the brown mixture was stirred at 50° C. for 1.25 h. The reaction mixture was concentrated, then was co-evaporated with CHCl$_3$ (2×). The crude product was purified by flash chromatography (0 to 100% ethyl acetate/hexanes, eluted at 75% EtOAc) to afford 1.15 g (86% yield) of Intermediate 2B as a white solid. MS(ESI) m/z: 521.3 (M+H)$^+$; $^1$H NMR (400 MHz, CD$_3$OD) δ 7.33-7.21 (m, 3H), 4.63 (dd, J=5.6, 3.2 Hz, 4H), 4.60 (s, 2H), 1.52 (s, 9H).

Intermediate 2C: tert-Butyl 5-(((methylsulfonyl)oxy)methyl)isoindoline-2-carboxylate

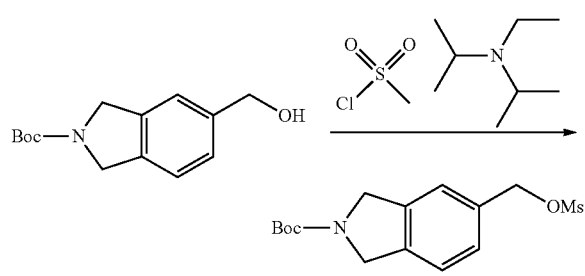

To a solution of Intermediate 2B (500 mg, 2.006 mmol) in DCM (10 mL) at 0° C., were added DIEA (0.420 mL, 2.407 mmol) and Ms-Cl (0.172 mL, 2.206 mmol). The mixture was stirred at 0° C. for 1.5 h. The mixture was diluted with DCM, then was washed with half sat. NH$_4$Cl and brine. The organic phase was dried (Na$_2$SO$_4$) and concentrated to afford 655 mg (100%) of Intermediate 2C as a brown oil. The material was used in the following step without further purification. MS(ESI) m/z: 272.0 (M-t-Bu+2H)$^+$.

Intermediate 2D: tert-Butyl 5-((4-methylpiperazin-1-yl)methyl)isoindoline-2-carboxylate

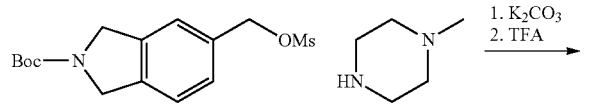

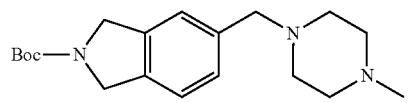

To a solution of Intermediate 2C (657 mg, 2.007 mmol) in acetone (10 mL) at rt, were added K$_2$CO$_3$ (416 mg, 3.01 mmol) and 1-methyl piperazine (0.556 mL, 5.02 mmol). The mixture was stirred at rt for 2.5 h, then 1 h at 50° C. The mixture was concentrated, then was partitioned between EtOAc and H$_2$O. The aqueous phase was extracted with EtOAc (2×). The combined organic phase was dried (Na$_2$SO$_4$) and concentrated to afford Intermediate 2D as a brown oil. MS(ESI) m/z: 332.2 (M+H)$^+$; $^1$H NMR (400 MHz, CD$_3$OD) δ 7.30-7.21 (m, 3H), 4.63 (dd, J=5.5, 2.0 Hz, 4H), 3.53 (s, 2H), 2.50 (br. s., 8H), 2.27 (s, 3H), 1.52 (s, 9H).

Intermediate 2

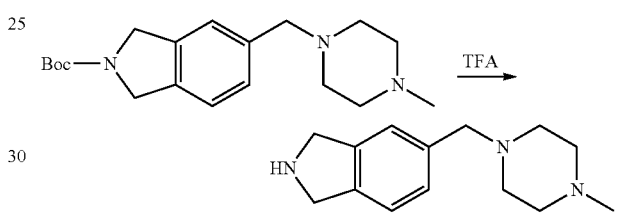

Intermediate 2D was treated with 4N HCl in dioxane (5 mL, 20.00 mmol) and the resultant suspension was stirred for 1 h, then was concentrated. The mixture was redissolved in TFA (10 mL) and was stirred at rt for 20 min. The mixture was concentrated. The brown oil was coevaporated with DCM (2×), ether, MeOH and CH$_3$CN to afford 1.36 g (100% yield, ~85% purity) of Intermediate 2 as a brown semisolid, which was used as is without further purification. MS(ESI) m/z: 232.2 (M+H)$^+$; $^1$H NMR (400 MHz, CD$_3$OD) δ 7.49-7.40 (m, 3H), 4.62 (s, 4H), 3.82 (s, 2H), 3.34 (br. s., 4H), 2.89 (s, 3H), 2.90 (br. s, 4H).

Intermediate 3: 4-(4-Aminophenyl)phthalazin-1(2H)-one, TFA Salt

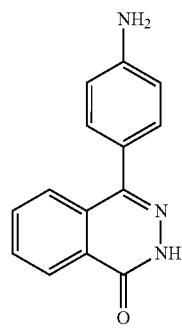 [SMILES: Nc1ccc(-c2n[nH]c(=O)c3ccccc23)cc1]

Intermediate 3A: tert-Butyl (4-(4-oxo-3,4-dihydrophthalazin-1-yl)phenyl)carbamate

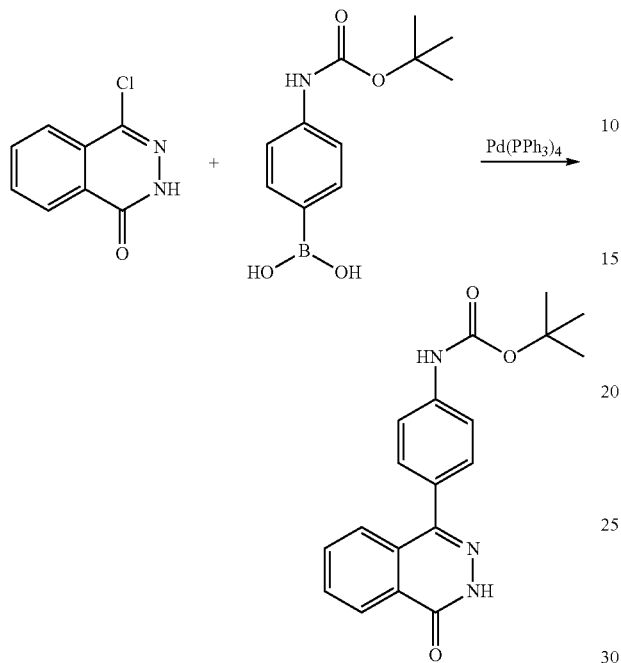

To 4-chlorophthalazin-1(2H)-one (118 mg, 0.653 mmol), (4-((tert-butoxycarbonyl)amino)phenyl)boronic acid (170 mg, 0.719 mmol) and potassium phosphate (347 mg, 1.634 mmol), were added dioxane (9 mL) and water (1 mL). The mixture was degassed (evacuated and flushed with Ar (5×)). Pd(PPh$_3$)$_4$ (37.8 mg, 0.033 mmol) was added, then the mixture was degassed (2×). The reaction vial was sealed and heated in a microwave reactor at 150° C. for 35 min. The reaction mixture was concentrated and purified via flash chromatography to afford 150 mg (68%) of Intermediate 3A. MS(ESI) m/z: 338.1 (M+H)$^+$.

Intermediate 3

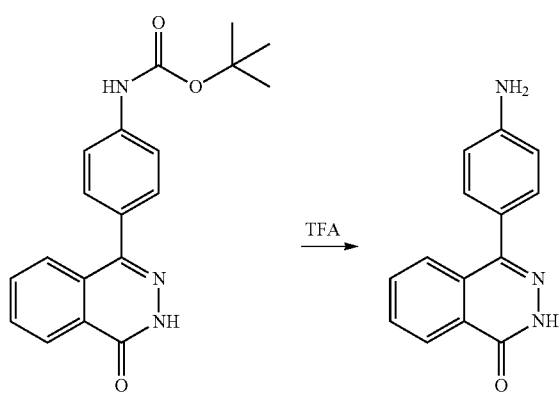

To Intermediate 3A (150 mg, 0.445 mmol) in CH$_2$Cl$_2$ (3 mL), was added TFA (2 mL). The mixture was stirred rt for 2 h, then was concentrated. The crude product was purified via flash chromatography, then preparative HPLC to afford 62 mg (59%) of Intermediate 3. MS(ESI) m/z: 238.1 (M+H)$^+$; $^1$H NMR (500 MHz, CD$_3$OD) δ 8.44 (dt, J=4.7, 2.3 Hz, 1H), 7.97-7.87 (m, 2H), 7.81-7.75 (m, 1H), 7.71-7.61 (m, 2H), 7.41-7.30 (m, 2H).

Intermediate 4: 2-(2-Fluoro-4-(4,4,5,5-tetramethyl-1,3,2-dioxaborolan-2-yl)phenyl)-1-(isoindolin-2-yl)ethanone

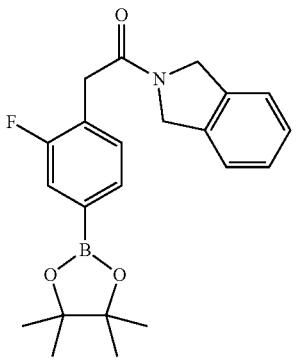 [SMILES: CC1(C)OB(c2ccc(CC(=O)N3Cc4ccccc4C3)c(F)c2)OC1(C)C]

Intermediate 4A: 2-(4-Bromo-2-fluorophenyl)-1-(isoindolin-2-yl)ethanone

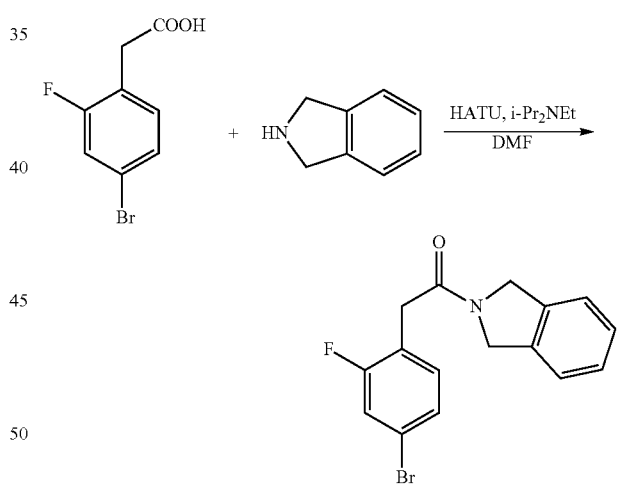

To 2-(4-bromo-2-fluorophenyl)acetic acid (300 mg, 1.287 mmol), isoindoline (0.161 mL, 1.416 mmol), and HATU (587 mg, 1.545 mmol) in DMF (5 mL), was added DIEA (0.450 mL, 2.57 mmol). The mixture was stirred at rt for 1 h. The resultant heterogeneous mixture was diluted with EtOAc, then was washed with H$_2$O, 1 N HCl, H$_2$O, sat. NaHCO$_3$ and brine. The organic phase was dried (Na$_2$SO$_4$), filtered and concentrated. The crude product was purified by flash chromatography (gradient from 0 to 100% ethyl acetate/hexanes) to afford 147 mg (34%) of Intermediate 4A as a white solid. MS(ESI) m/z: 333.9 (M+H)$^+$; $^1$H NMR (400 MHz, CDCl$_3$) δ 7.34-7.30 (m, 3H), 7.30-7.22 (m, 4H), 4.89 (s, 2H), 4.83 (s, 2H), 3.73 (s, 2H)

77
Intermediate 4

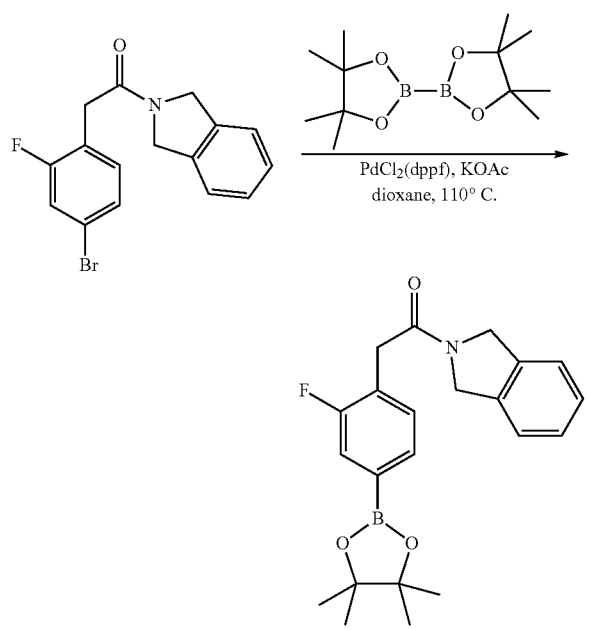

To a mixture of Intermediate 4A (146 mg, 0.437 mmol), bis(pinacolato)diboron (133 mg, 0.524 mmol), and potassium acetate (129 mg, 1.31 mmol) in a reaction vial, was added dioxane (3 mL). The mixture was degassed (evacuated and flushed with Ar (3×)). PdCl$_2$(dppf) CH$_2$Cl$_2$ adduct (9.6 mg, 0.013 mmol) was added, then reaction mixture was degassed (3× vacuum/Ar). The vial was sealed, then was heated at 110° C. for 2 h. The reaction mixture was diluted with EtOAc, then was washed with H$_2$O and brine. The organic phase was dried (Na$_2$SO$_4$) and concentrated. The crude product was purified by flash chromatography (gradient from 0 to 50% ethyl acetate/hexanes) to afford 120 mg (72%) of Intermediate 4 as a yellow solid. MS(ESI) m/z: 386.1 (M+H)$^+$; $^1$H NMR (400 MHz, CDCl$_3$) δ 7.55 (dd, J=7.5, 0.9 Hz, 1H), 7.50 (d, J=10.1 Hz, 1H), 7.39 (t, J=7.4 Hz, 1H), 7.32-7.22 (m, 4H), 4.84 (s, 4H), 3.80 (s, 2H), 1.33 (s, 12H).

Intermediate 5: 2-(3-Fluoro-4-(4,4,5,5-tetramethyl-1,3,2-dioxaborolan-2-yl)phenyl)-1-(isoindolin-2-yl)ethanone

78
Intermediate 5A: 2-(4-Bromo-3-fluorophenyl)-1-(isoindolin-2-yl)ethanone

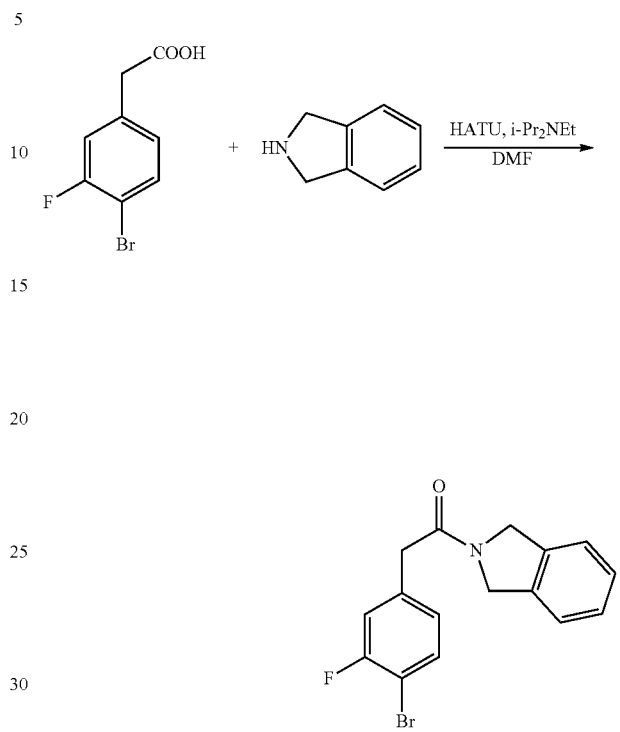

To a mixture of 2-(4-bromo-3-fluorophenyl)acetic acid (300 mg, 1.287 mmol), isoindoline (0.161 mL, 1.416 mmol), and HATU (734 mg, 1.931 mmol) in DMF (5 mL), was add DIEA (0.450 mL, 2.6 mmol). The mixture was stirred rt for 18 h. The reaction mixture was diluted with EtOAc, then was washed with H$_2$O, 1 N HCl, H$_2$O, sat. Na$_2$CO$_3$ and brine. The organic phase was dried (Na$_2$SO$_4$), filtered through a 1" pad of SiO$_2$ and concentrated. The crude product was purified by flash chromatography (gradient from 0 to 100% ethyl acetate/hexanes) to afford 379 mg (88%) of Intermediate 5A as an off-white solid. MS(ESI) m/z: 333.9 (M+H)$^+$; $^1$H NMR (400 MHz, CDCl$_3$) δ 7.50 (dd, J=8.0, 7.4 Hz, 1H), 7.33-7.22 (m, 4H), 7.14 (dd, J=9.2, 2.0 Hz, 1H), 7.01 (dd, J=8.5, 1.9 Hz, 1H), 4.83 (s, 4H), 3.72 (s, 2H).

Intermediate 5

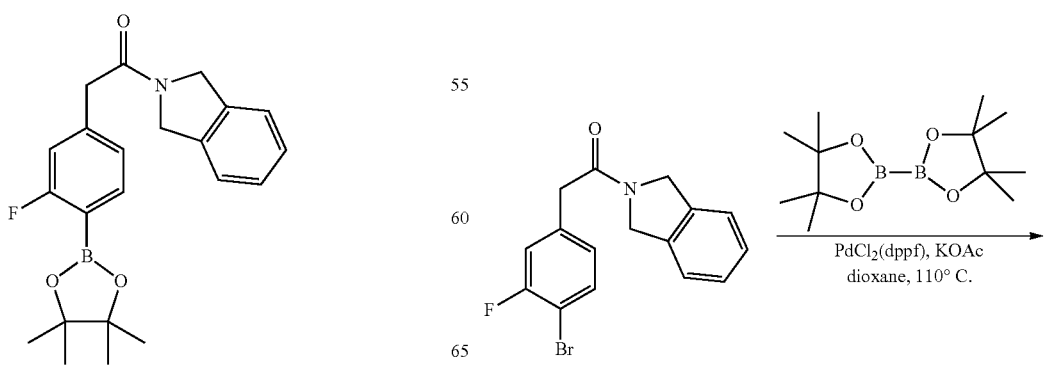

-continued

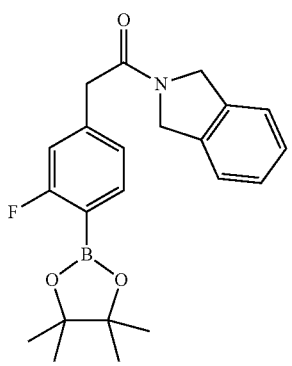 [SMILES: CC1(C)OB(c2ccc(CC(=O)N3Cc4ccccc4C3)cc2F)OC1(C)C]

To a mixture of Intermediate 5A (200 mg, 0.598 mmol), bis(pinacolato)diboron (182 mg, 0.718 mmol), and potassium acetate (176 mg, 1.80 mmol) in a reaction vial, was added dioxane (5 mL). The mixture was degassed (evacuated and flushed with Ar (3×)). PdCl$_2$(dppf) CH$_2$Cl$_2$ adduct (13 mg, 0.018 mmol) was added, then the reaction mixture was degassed (3× vacuum/Ar). The vial was sealed, then was heated at 110° C. for 2 h. Additional catalyst (13 mg) was added and the reaction mixture was stirred at 110° C. for 2 more hours. The reaction mixture was cooled to room temperature, then was filtered and concentrated. The crude product was purified by flash chromatography (gradient from 0 to 100% ethyl acetate/hexanes) to afford 208 mg (91%) of Intermediate 5 as a yellow solid. MS(ESI) m/z: 386.1 (M+H)$^+$; $^1$H NMR (400 MHz, CDCl$_3$) δ 7.71 (t, J=6.9 Hz, 1H), 7.35-7.20 (m, 4H), 7.13 (d, J=7.5 Hz, 1H), 7.04 (d, J=10.1 Hz, 1H), 4.83 (s, 2H), 4.77 (s, 2H), 3.78 (s, 2H), 1.35 (s, 12H).

Intermediate 6: 4-Bromoisoquinolin-1(2H)-one

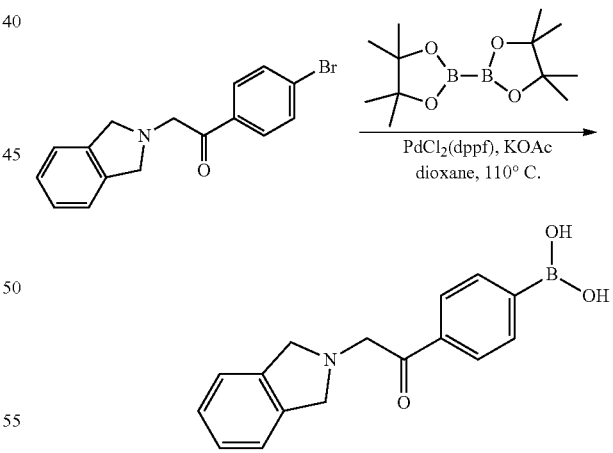

To a solution of isoquinolin-1(2H)-one (105 mg, 0.723 mmol) in DMF (2 mL), was added NBS (142 mg, 0.796 mmol). The mixture was stirred at rt for 2 h, then was concentrated. The crude product was purified via preparative HPLC to afford 110 mg (68%) of Intermediate 6. MS(ESI) m/z: 223.9 (M+H)$^+$; $^1$H NMR (500 MHz, DMSO-d$_6$) δ 11.57 (br. s., 1H), 8.24 (dd, J=8.0, 0.8 Hz, 1H), 7.88-7.83 (m, 1H), 7.79-7.75 (m, 1H), 7.61 (ddd, J=8.0, 7.1, 1.1 Hz, 1H), 7.55 (s, 1H).

Intermediate 7:
2-(4-Bromophenyl)-1-(isoindolin-2-yl)ethanone

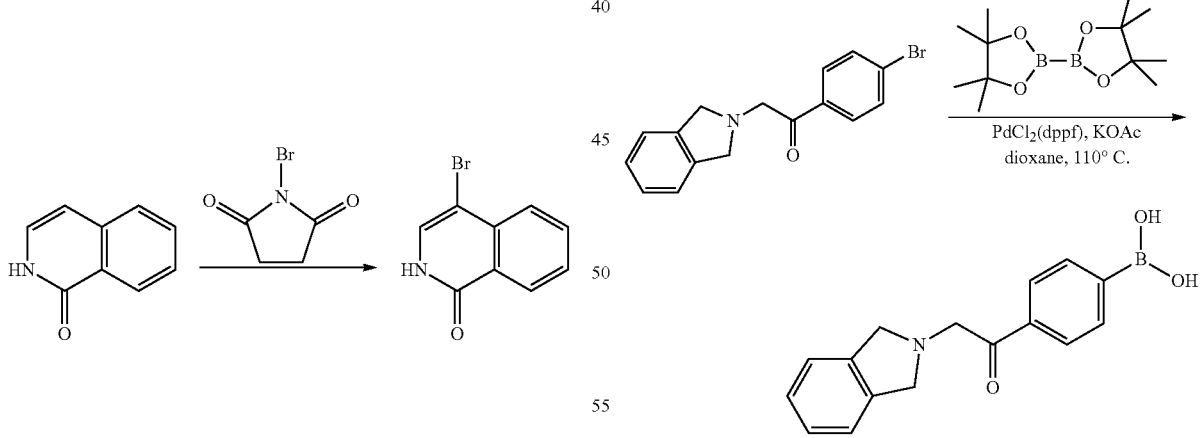

To a mixture of 2-(4-bromophenyl)acetic acid (300 mg, 1.395 mmol), isoindoline (183 mg, 1.535 mmol), and HATU (796 mg, 2.093 mmol) in DMF (5 mL), was add DIEA (0.487 mL, 2.79 mmol). The mixture was stirred at rt overnight. The reaction mixture was quenched with water, then extracted with EtOAc. The organic phase was washed with 10% LiCl, brine, and concentrated. The residue was purified via flash chromatography (EtOAc/hexane) to afford 390 mg (88%) of Intermediate 7. MS(ESI) m/z: 316.0 (M+H)$^+$.

Intermediate 8:
(4-(2-(Isoindolin-2-yl)acetyl)phenyl)boronic acid

A mixture of Intermediate 7 (30 mg, 0.095 mmol), bis(pinacolato)diboron (24 mg, 0.095 mmol), and potassium acetate (27.9 mg, 0.285 mmol) in dioxane (1 mL) was degassed (3× vacuum/Ar). Then PdCl$_2$(dppf) CH$_2$Cl$_2$ adduct (2.083 mg, 2.85 mol) was added, the reaction mixture was degassed again (3× vacuum/Ar), sealed in a vial and heated at 110° C. for 2 h. The reaction was purified via preparative HPLC to afford 14 mg (53%) of Intermediate 8. MS(ESI) m/z: 282.1 (M+H)$^+$.

Intermediate 9: 1-(Isoindolin-2-yl)-2-(4-(4,4,5,5-tetramethyl-1,3,2-dioxaborolan-2-yl)phenyl)ethanone

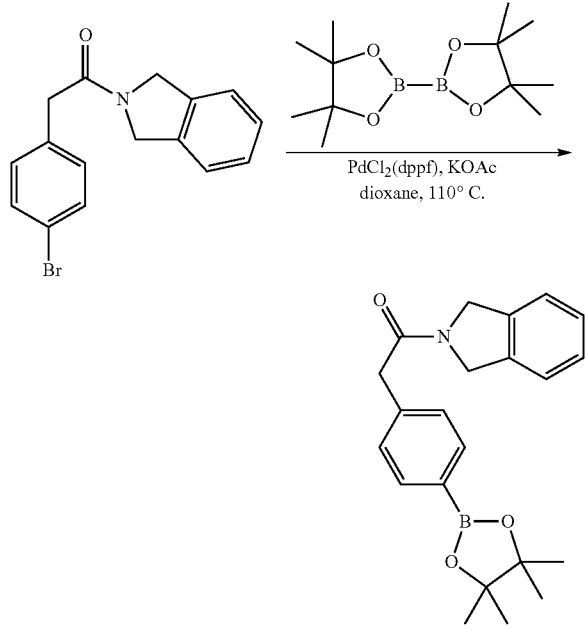

According to a procedure similar to the preparation of Intermediate 8, Intermediate 7 (400 mg, 1.27 mmol) afforded after flash chromatography (0 to 60% EtOAc/hexane gradient) 406 mg (88%) of Intermediate 9. MS(ESI) m/z: 364.1 (M+H)+; 1H NMR (500 MHz, CDCl3) δ 7.82-7.77 (m, J=8.3 Hz, 2H), 7.39-7.33 (m, J=8.0 Hz, 2H), 7.27 (d, J=0.6 Hz, 3H), 7.27-7.24 (m, 1H), 7.20 (d, J=6.6 Hz, 1H), 4.84 (s, 2H), 4.77 (s, 2H), 3.81 (s, 2H), 1.38-1.31 (m, 12H).

Intermediate 10: N-(4-(4,4,5,5-Tetramethyl-1,3,2-dioxaborolan-2-yl)phenyl)indoline-1-carboxamide

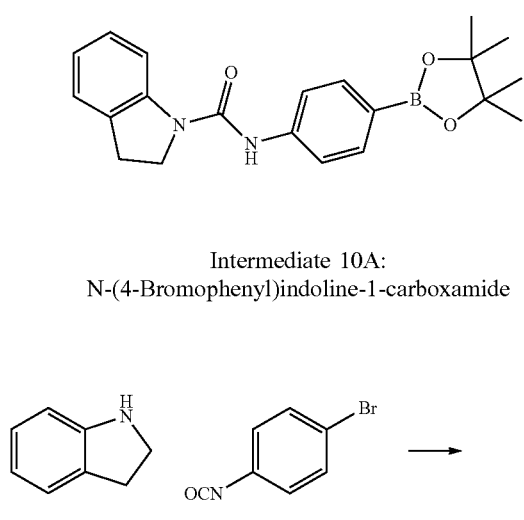

Intermediate 10A: N-(4-Bromophenyl)indoline-1-carboxamide

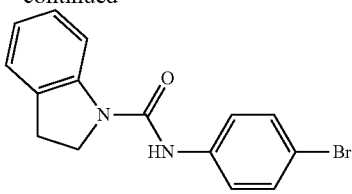

A mixture of 1-bromo-4-isocyanatobenzene (300 mg, 1.515 mmol) and indoline (199 mg, 1.667 mmol) in CH2Cl2 (5 mL) was stirred at rt 1 h. The reaction mixture was diluted with EtOAc (100 mL), then was washed with 1 N HCl, sat. Na2CO3, and brine. The organic phase was dried over Na2SO4, then concentrated. The residue was purified by flash chromatography (0-60% EtOAc/hexane gradient) to afford 470 mg (98%) of Intermediate 10A as a yellow foam. MS(ESI) m/z: 317.0 (M+H)+; 1H NMR (500 MHz, CDCl3) δ 7.88 (d, J=8.0 Hz, 1H), 7.49-7.42 (m, 2H), 7.41-7.35 (m, 2H), 7.22-7.17 (m, 2H), 6.99 (td, J=7.4, 1.1 Hz, 1H), 6.47 (br. s., 1H), 4.15-4.05 (m, 2H), 3.25 (t, J=8.5 Hz, 2H).

Intermediate 10

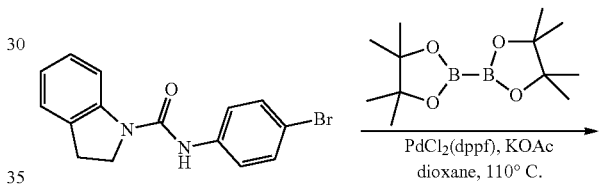

To a mixture of Intermediate 10A (470 mg, 1.482 mmol), bis(pinacolato)diboron (452 mg, 1.778 mmol), and potassium acetate (436 mg, 4.45 mmol) in dioxane (20 mL), was added PdCl2(dppf) CH2Cl2 adduct (32.5 mg, 0.044 mmol). The reaction mixture was degassed (3× vacuum/Ar), sealed in a vial and heated at 110° C. for 3 h. The reaction was quenched with water, extracted with EtOAc (2×30 mL). The combined organic layer was washed with brine, dried (Na2SO4) and concentrated. The residue was purified by flash chromatography (0-60% EtOAc/hexane gradient) to afford 430 mg (80%) of Intermediate 10 as a white solid. MS(ESI) m/z: 365.1 (M+H)+; 1H NMR (500 MHz, CDCl3) δ 7.89 (d, J=8.0 Hz, 1H), 7.81-7.77 (m, J=8.3 Hz, 2H), 7.52-7.48 (m, 2H), 7.23-7.18 (m, 2H), 7.01-6.94 (m, 1H), 6.56 (s, 1H), 4.17-4.04 (m, 2H), 3.25 (t, J=8.5 Hz, 2H), 1.39-1.32 (m, 12H).

Intermediate 11: 2-(4-(4-Oxo-3,4-dihydrophthalazin-1-yl)phenyl)propanoic acid

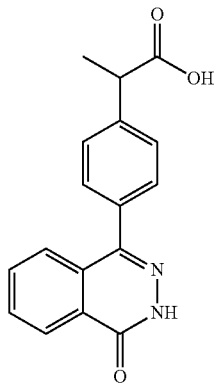 [SMILES: CC(C(=O)O)c1ccc(-c2n[nH]c(=O)c3ccccc23)cc1]

Intermediate 11A: Ethyl 2-(4-bromophenyl)propanoate

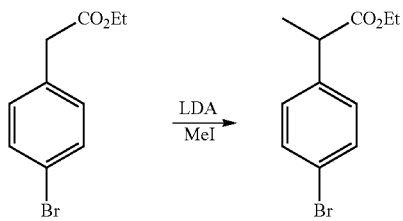

To a solution of ethyl 2-(4-bromophenyl)acetate (150 mg, 0.617 mmol) in THF (3 mL) at −78° C., was added 1.5M LDA (0.514 mL, 0.926 mmol). The mixture was stirred at −78° C. for 20 min, then iodomethane (175 mg, 1.23 mmol) was added. The solution was allowed to warm to rt and stirred overnight. The reaction mixture was concentrated and the residue was purified by flash chromatography (0-20% EtOAc/hexane gradient) to afford 120 mg (76%) of Intermediate 11A as a yellow oil. MS(ESI) m/z: 257.0 (M+H)$^+$; $^1$H NMR (500 MHz, CDCl$_3$) δ 7.47-7.42 (m, 2H), 7.21-7.16 (m, 2H), 4.12 (dddd, J=17.6, 10.4, 7.1, 3.7 Hz, 2H), 3.67 (q, J=7.3 Hz, 1H), 1.48 (d, J=7.2 Hz, 3H), 1.21 (t, J=7.2 Hz, 3H).

Intermediate 11B: Ethyl 2-(4-(4,4,5,5-tetramethyl-1,3,2-dioxaborolan-2-yl)phenyl)propanoate

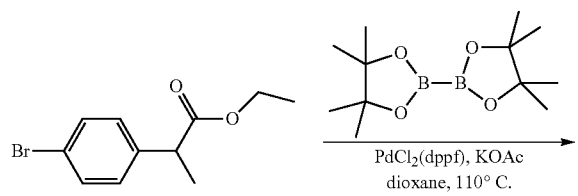

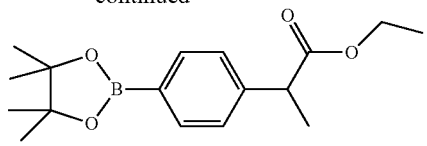

To a mixture of Intermediate 11A (120 mg, 0.467 mmol), bis(pinacolato)diboron (142 mg, 0.56 mmol), and potassium acetate (137 mg, 1.40 mmol) in dioxane (4 mL), was added PdCl$_2$(dppf) CH$_2$Cl$_2$ adduct (10 mg, 0.014 mmol). The reaction mixture was degassed (3× vacuum/Ar), sealed and heated at 110° C. for 16 h. The reaction mixture was concentrated and the residue was purified by flash chromatography (0-30% EtOAc/hexane gradient) to afford 120 mg (85%) of Intermediate 11B as a yellow oil. MS(ESI) m/z: 327.2 (M+H)$^+$; $^1$H NMR (500 MHz, CDCl$_3$) δ 7.81-7.75 (m, J=8.3 Hz, 2H), 7.35-7.29 (m, J=8.0 Hz, 2H), 4.11 (dddd, J=17.8, 10.6, 7.1, 3.6 Hz, 2H), 3.77-3.66 (m, 1H), 1.49 (d, J=7.2 Hz, 3H), 1.37-1.30 (m, 12H), 1.19 (t, J=7.2 Hz, 3H).

Intermediate 11C: Ethyl 2-(4-(4-oxo-3,4-dihydrophthalazin-1-yl)phenyl)propanoate

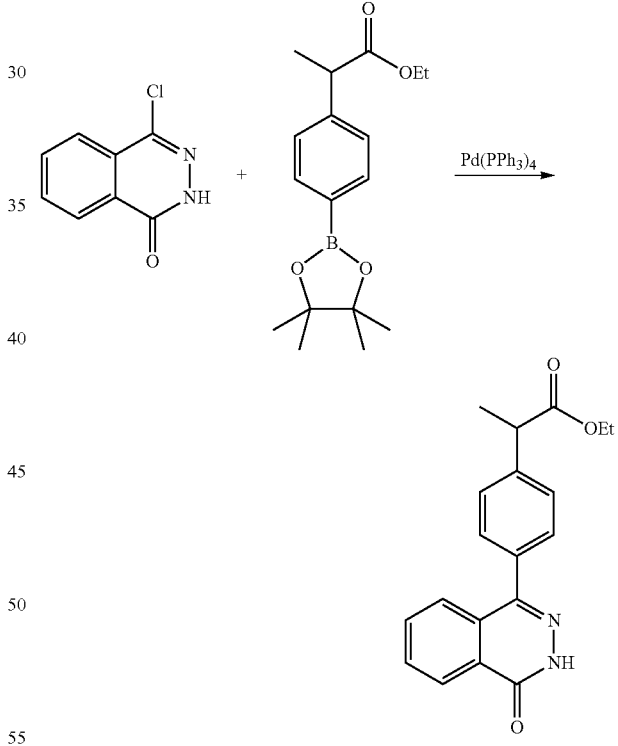

To 4-chlorophthalazin-1(2H)-one (70 mg, 0.388 mmol), Intermediate 11B (118 mg, 0.388 mmol) and potassium phosphate (206 mg, 0.969 mmol), were added dioxane (3 mL) and water (0.333 mL). The mixture was degassed (evacuated and flushed with Ar (5×)). Pd(PPh$_3$)$_4$ (22.40 mg, 0.019 mmol) was added, then the mixture was degassed (2×). The reaction vial was sealed and heated in a microwave reactor at 150° C. for 30 min. The reaction mixture was concentrated and the residue was purified by flash chromatography (0-80% EtOAc/hexane gradient) to afford 100 mg (80%) of Intermediate 11C as a yellow foam. MS(ESI) m/z:

323.1 (M+H)+; 1H NMR (500 MHz, DMSO-d6) δ 12.84 (s, 1H), 8.41-8.31 (m, 1H), 7.98-7.84 (m, 2H), 7.70 (d, J=7.7 Hz, 1H), 7.57 (d, J=8.3 Hz, 2H), 7.47 (d, J=8.0 Hz, 2H), 4.20-4.02 (m, 2H), 3.91 (d, J=6.9 Hz, 1H), 1.46 (d, J=7.2 Hz, 3H), 1.17 (t, J=7.0 Hz, 3H).

Intermediate 11

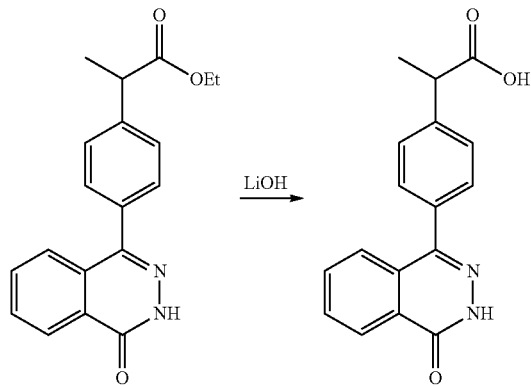 [SMILES: CCOC(=O)C(C)c1ccc(-c2n[nH]c(=O)c3ccccc23)cc1 ; "LiOH" ; CC(C(=O)O)c1ccc(-c2n[nH]c(=O)c3ccccc23)cc1]

To a solution of Intermediate 11C (100 mg, 0.310 mmol) in THF (3 mL), was added 1M LiOH (0.620 mL, 0.620 mmol). The mixture was stirred at rt for 3 h, then was concentrated. The residue was purified via preparative HPLC to afford 90 mg (99%) of Intermediate 11 as a white solid. MS(ESI) m/z: 295.1 (M+H)+; 1H NMR (500 MHz, DMSO-d6) δ 12.83 (s, 1H), 8.42-8.23 (m, 1H), 7.99-7.82 (m, 2H), 7.78-7.66 (m, 1H), 7.61-7.52 (m, J=8.0 Hz, 2H), 7.50-7.40 (m, J=8.0 Hz, 2H), 3.80 (q, J=7.2 Hz, 1H), 1.44 (d, J=6.9 Hz, 3H).

Intermediate 12: 6-Methoxy-N-(4-(4,4,5,5-tetramethyl-1,3,2-dioxaborolan-2-yl)phenyl)indoline-1-carboxamide

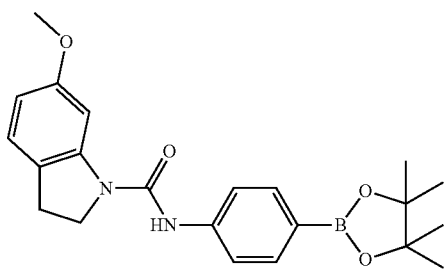 [SMILES: COc1ccc2c(c1)N(C(=O)Nc1ccc(B3OC(C)(C)C(C)(C)O3)cc1)CC2]

Intermediate 12A:
N-(4-Bromophenyl)-6-methoxyindoline-1-carboxamide

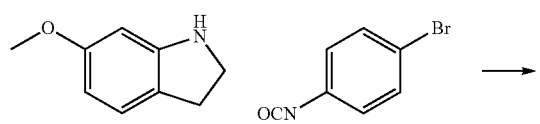

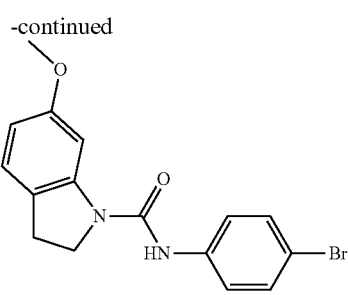

1-Bromo-4-isocyanatobenzene (146 mg, 0.737 mmol) was mixed with 6-methoxyindoline (110 mg, 0.737 mmol) in DCM (3 mL), and stirred rt 2 h. The reaction mixture was diluted with EtOAc (100 mL), then was washed with 1 N HCl, sat Na2CO3, and brine, dried (Na2SO4), and concentrated. The residue was purified by flash chromatography (gradient 0-50% EtOAc/Hex) to afford Intermediate 12A (230 mg, 0.662 mmol, 90% yield) as a purple solid. MS(ESI) m/z: 346.9 (M+H)+; 1H NMR (500 MHz, chloroform-d) δ 7.58 (d, J=2.2 Hz, 1H), 7.43-7.34 (m, 2H), 7.34-7.28 (m, 2H), 7.02 (d, J=8.3 Hz, 1H), 6.60 (br. s., 1H), 6.50 (dd, J=8.1, 2.3 Hz, 1H), 3.98 (t, J=8.5 Hz, 2H), 3.82-3.72 (m, 3H), 3.07 (t, J=8.4 Hz, 2H).

Intermediate 12

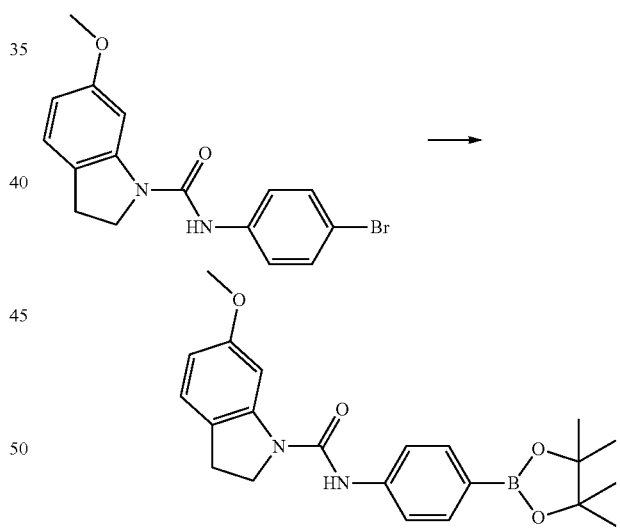

To a mixture of Intermediate 12A (230 mg, 0.662 mmol), 4,4,4',4',5,5,5',5'-octamethyl-2,2'-bi(1,3,2-dioxaborolane) (202 mg, 0.795 mmol), and potassium acetate (195 mg, 1.99 mmol) in dioxane (20 mL), was added PdCl2(dppf) CH2Cl2 adduct (14.5 mg, 0.020 mmol). The reaction mixture was degassed (3× vacuum/Ar), sealed in a vial and heated at 110° C. for 3 h. The mixture was diluted with water, extracted with EtOAc (2×30 mL). The combined organic layer was washed with brine, dried (Na2SO4) and concentrated. The residue was by flash chromatography (gradient 0-60% EtOAc/Hex) to afford Intermediate 12 (230 mg, 88% yield) as a white solid. MS(ESI) m/z: 395.1 (M+H)+.

Intermediate 13: 4-(4-Bromophenyl)-2-(4-methoxybenzyl)phthalazin-1(2H)-one

Intermediate 14: 4-(4-Aminophenyl)-2-(4-methoxybenzyl)phthalazin-1(2H)-one

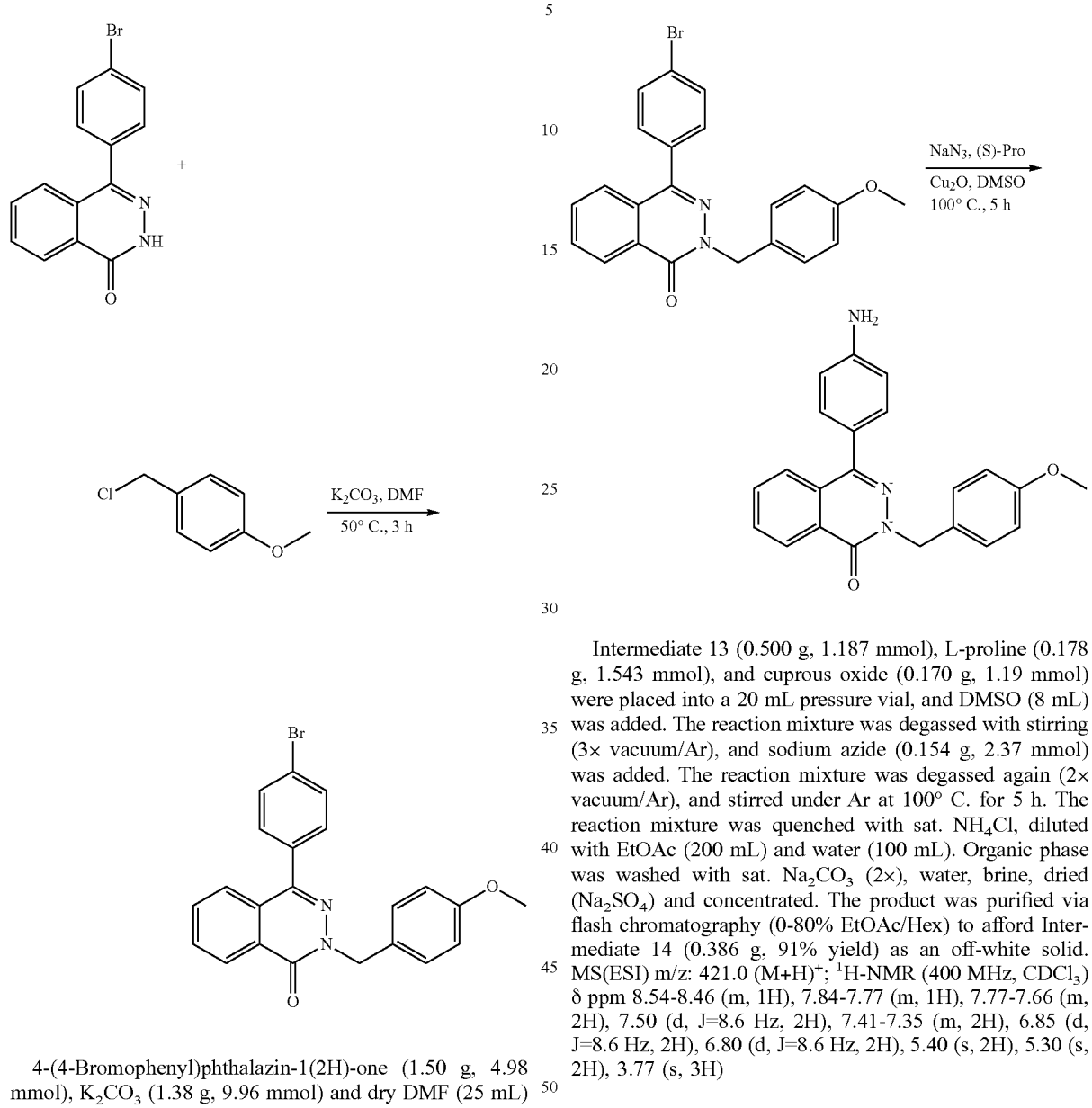

4-(4-Bromophenyl)phthalazin-1(2H)-one (1.50 g, 4.98 mmol), K$_2$CO$_3$ (1.38 g, 9.96 mmol) and dry DMF (25 mL) were added into a round bottom flask. To the above mixture, 1-(chloromethyl)-4-methoxybenzene (1.35 mL, 9.96 mmol) was added dropwise with stirring at rt over 5 min. Then, the reaction mixture was stirred at 50° C. for 2 h. The reaction mixture was cooled to rt, diluted with water (150 mL) and EtOAc (250 mL). The organic phase was separated, washed with water (3×100 mL), brine (1×50 mL), and dried (Na$_2$SO$_4$). EtOAc was removed under reduced pressure and the residue was purified by flash chromatography (0-50% EtOAc/Hex). The material was recrystallized from hexanes/EtOAc (7:3; ~100 mL), washed with hexanes and dried to afford Intermediate 13 (1.39 g, 66.2% yield) as a white solid. MS(ESI) m/z: 421.0 (M+H)$^+$; $^1$H-NMR (400 MHz, CDCl$_3$) δ ppm 8.56-8.49 (m, 1H), 7.75 (quind, J=7.4, 1.3 Hz, 2H), 7.69-7.62 (m, 3H), 7.47 (t, J=7.9 Hz, 4H), 6.85 (d, J=8.6 Hz, 2H), 5.39 (s, 2H), 3.77 (s, 3H).

Intermediate 13 (0.500 g, 1.187 mmol), L-proline (0.178 g, 1.543 mmol), and cuprous oxide (0.170 g, 1.19 mmol) were placed into a 20 mL pressure vial, and DMSO (8 mL) was added. The reaction mixture was degassed with stirring (3× vacuum/Ar), and sodium azide (0.154 g, 2.37 mmol) was added. The reaction mixture was degassed again (2× vacuum/Ar), and stirred under Ar at 100° C. for 5 h. The reaction mixture was quenched with sat. NH$_4$Cl, diluted with EtOAc (200 mL) and water (100 mL). Organic phase was washed with sat. Na$_2$CO$_3$ (2×), water, brine, dried (Na$_2$SO$_4$) and concentrated. The product was purified via flash chromatography (0-80% EtOAc/Hex) to afford Intermediate 14 (0.386 g, 91% yield) as an off-white solid. MS(ESI) m/z: 421.0 (M+H)$^+$; $^1$H-NMR (400 MHz, CDCl$_3$) δ ppm 8.54-8.46 (m, 1H), 7.84-7.77 (m, 1H), 7.77-7.66 (m, 2H), 7.50 (d, J=8.6 Hz, 2H), 7.41-7.35 (m, 2H), 6.85 (d, J=8.6 Hz, 2H), 6.80 (d, J=8.6 Hz, 2H), 5.40 (s, 2H), 5.30 (s, 2H), 3.77 (s, 3H)

Intermediate 15: 1-(2-Hydroxy-2-methylpropyl)-1H-indazole-3-carboxylic Acid

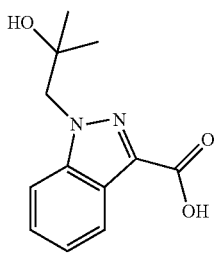

Intermediate 15A: Ethyl 1-(2-hydroxy-2-methylpropyl)-1H-indazole-3-carboxylate

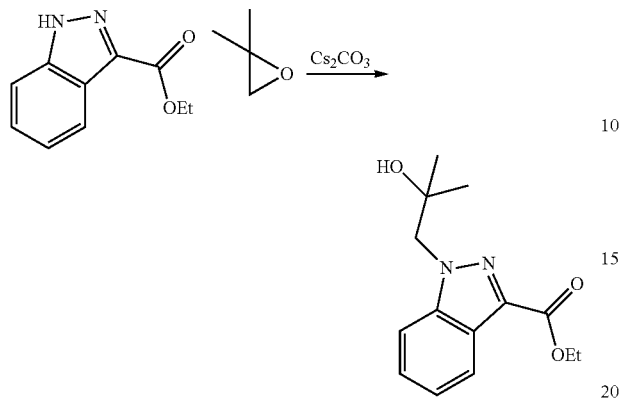

To a vial containing ethyl 1H-indazole-3-carboxylate (75 mg, 0.39 mmol) and 2,2-dimethyloxirane (0.088 mL, 0.99 mmol), was added acetonitrile (1.5 mL). To this mixture was added Cs$_2$CO$_3$ (193 mg, 0.591 mmol). The vial was sealed and the mixture was stirred at 90° C. for 2.5 h. The reaction mixture was partitioned between EtOAc and H$_2$O. The aqueous phase was extracted with EtOAc. The combined organic phase was washed with brine, dried (Na$_2$SO$_4$) and concentrated. The crude product was purified by flash chromatography (gradient from 0 to 100% ethyl acetate/hexanes) to afford Intermediate 15A (45 mg, 43.5% yield) as a colorless oil. MS(ESI) m/z: 263.1 (M+H)$^+$; $^1$H NMR (400 MHz, chloroform-d) δ 8.24 (dt, J=8.3, 0.9 Hz, 1H), 7.58-7.52 (m, 1H), 7.50-7.43 (m, 1H), 7.32 (ddd, J=8.0, 6.9, 0.9 Hz, 1H), 4.52 (q, J=7.2 Hz, 2H), 4.45 (s, 2H), 2.73 (s, 1H), 1.48 (t, J=7.2 Hz, 3H), 1.26 (s, 6H).

Intermediate 15

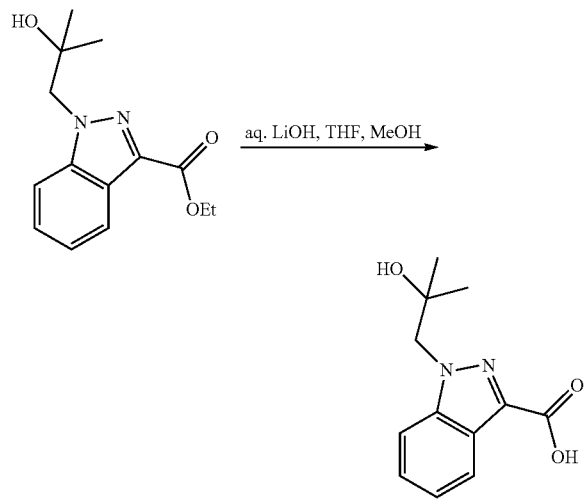

To a solution of Intermediate 15A (45 mg, 0.17 mmol) in THF (1 mL), was added 1M aq. LiOH (0.20 mL, 0.20 mmol), followed by MeOH (0.3 mL). The homogeneous mixture was stirred at rt for 1.5 h. Additional 1M aq. LiOH (0.1 mL, 0.1 mmol) was added and the mixture was stirred at rt for 14 h. The reaction mixture was partially evaporated to remove volatile solvents. The solution was diluted with H$_2$O, then was acidified with 1 N HCl (~0.3 mL). The aqueous phase was extracted with EtOAc (3×). The combined organic phase was washed with brine, dried (Na$_2$SO$_4$) and concentrated to afford Intermediate 15 (40 mg, 100% yield) as an off-white solid. MS(ESI) m/z: 235.1 (M+H)$^+$; $^1$H NMR (400 MHz, chloroform-d) δ 8.27 (d, J=8.1 Hz, 1H), 7.59 (d, J=8.4 Hz, 1H), 7.48 (t, J=7.6 Hz, 1H), 7.41-7.31 (m, 1H), 4.48 (s, 2H), 1.30 (s, 6H).

Intermediate 16: 1-(2-Hydroxy-2-methylpropyl)-1H-indole-3-carboxylic Acid

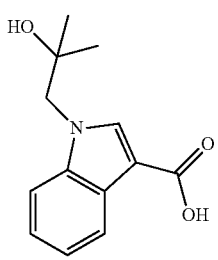

Intermediate 16A: Methyl 1-(2-hydroxy-2-methylpropyl)-1H-indole-3-carboxylate

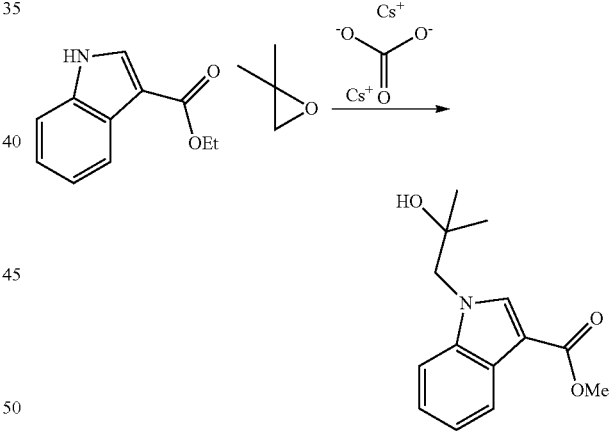

To a vial containing methyl 1H-indole-3-carboxylate (200 mg, 1.14 mmol) and 2,2-dimethyloxirane (0.254 mL, 2.85 mmol), was added acetonitrile (3 mL). To this mixture was added Cs$_2$CO$_3$ (558 mg, 1.71 mmol). The vial was sealed and the mixture was stirred at 90° C. for 2.5 h. The reaction mixture was partitioned between EtOAc and H$_2$O. The aqueous phase was extracted with EtOAc. The combined organic phase was washed with brine, dried (Na$_2$SO$_4$) and concentrated. The crude product was purified by flash chromatography (gradient from 0 to 100% ethyl acetate/hexanes) to afford Intermediate 16A (274 mg, 1.108 mmol, 97% yield) white solid. MS(ESI) m/z: 248.1 (M+H)$^+$; $^1$H NMR (400 MHz, chloroform-d) δ 8.26-8.11 (m, 1H), 7.91 (s, 1H), 7.49-7.38 (m, 1H), 7.31-7.23 (m, 2H), 4.13 (s, 2H), 3.91 (s, 3H), 1.48 (s, 1H), 1.29 (s, 6H).

91

Intermediate 16

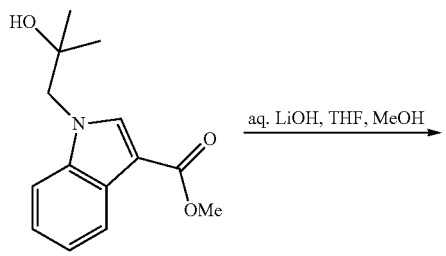

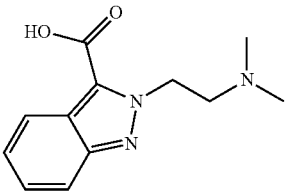

To a solution of Intermediate 16A (272 mg, 1.10 mmol) in THF (5 mL), was added 1M aq. LiOH (1.2 mL, 1.2 mmol), followed by MeOH (1 mL). The homogeneous mixture was stirred at rt for 1.5 h. Additional 1M aq. LiOH (1.0 mL, 1.0 mmol) was added and the mixture was stirred at rt for 14 h. The reaction mixture was heated at 50° C. for 24 h, then at 60° C. for 9 h. The reaction mixture was partially concentrated to remove the organic solvent. The partially insoluble mixture was diluted with H$_2$O and was washed with Et$_2$O. The organic phase was extracted with H$_2$O (2×). The combined aqueous phase was acidified to pH 3 with 1 N HCl, then was extracted with EtOAc (3×). The combined organic phase was washed with brine, dried (Na$_2$SO$_4$) and concentrated to afford Intermediate 16 (255 mg, 99% yield) as an off-white solid. MS(ESI) m/z: 234.1 (M+H)$^+$; $^1$H NMR (400 MHz, chloroform-d) δ 8.27-8.20 (m, 1H), 8.01 (s, 1H), 7.49-7.42 (m, 1H), 7.34-7.26 (m, 2H), 4.15 (s, 2H), 1.30 (s, 6H).

Intermediate 17: 1-(2-(Dimethylamino)ethyl)-1H-indazole-3-carboxylic Acid

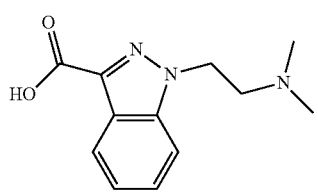

92

Intermediate 18: 2-(2-(Dimethylamino)ethyl)-2H-indazole-3-carboxylic Acid

Intermediate 17A: Methyl 1-(2-(dimethylamino)ethyl)-1H-indazole-3-carboxylate

Intermediate 17B: Methyl 2-(2-(dimethylamino)ethyl)-2H-indazole-3-carboxylate

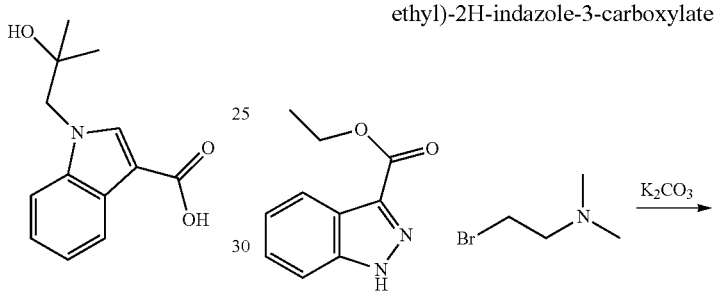

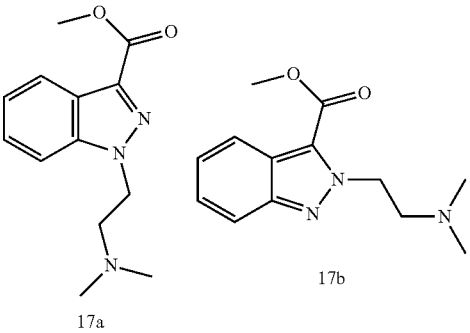

In a sealed tube, ethyl 1H-indazole-3-carboxylate (50 mg, 0.263 mmol) mixed with 2-bromo-N,N-dimethylethanamine (120 mg, 0.789 mmol), K$_2$CO$_3$ (182 mg, 1.314 mmol) in DMF (5 mL), stirred 80° C. o/n. Concentrated and purified by prep HPLC. Two fractions were collected, 1st fraction concentrated to afford Intermediate 17A (29 mg, 45% yield) as a white solid. MS(ESI) m/z: 248.1 (M+H)$^+$; $^1$H NMR (400 MHz, chloroform-d) δ 8.21 (d, J=8.4 Hz, 1H), 7.65-7.59 (m, 1H), 7.58-7.52 (m, 1H), 7.43-7.36 (m, 1H), 4.96 (t, J=6.4 Hz, 2H), 4.06 (s, 3H), 3.81 (t, J=6.4 Hz, 2H), 2.88 (s, 6H).

2nd fraction concentrated to afford Intermediate 17B (19 mg, 29% yield) as a white solid. MS(ESI) m/z: 248.1 (M+H)$^+$; $^1$H NMR (400 MHz, chloroform-d) δ 8.00 (d, J=8.4 Hz, 1H), 7.74 (d, J=8.8 Hz, 1H), 7.44-7.38 (m, 1H), 7.38-7.29 (m, 1H), 5.35 (t, J=6.1 Hz, 2H), 4.06 (s, 3H), 3.80 (t, J=6.1 Hz, 2H), 3.00 (s, 6H).

Intermediate 17

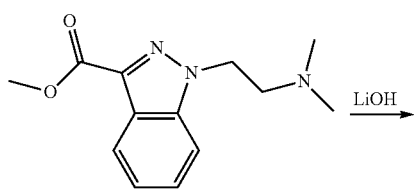

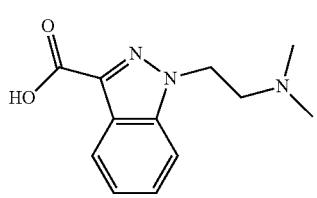 [SMILES: CN(C)CCn1nc(C(=O)O)c2ccccc21]

Intermediate 17A (28 mg, 0.113 mmol), dissolved in THF (2 mL), add 1M lithium hydroxide (0.283 mL, 0.283 mmol), stirred rt o/n. Concentrated and acidified with TFA, dissolved in ACN, purified via prep HPLC to afford Intermediate 17 (23 mg, 87% yield). MS(ESI) m/z: 234.1 (M+H)$^+$; $^1$H NMR (400 MHz, methanol-$d_4$) δ 8.20 (dt, J=8.3, 0.9 Hz, 1H), 7.79-7.73 (m, 1H), 7.57 (ddd, J=8.5, 7.2, 1.1 Hz, 1H), 7.40 (ddd, J=8.1, 7.1, 0.9 Hz, 1H), 4.97-4.91 (m, 2H), 3.89-3.81 (m, 2H), 3.04 (s, 6H).

Intermediate 18

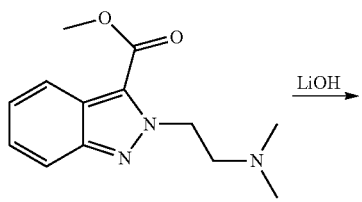

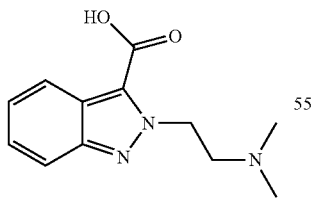

According to the procedure for preparation of Intermediate 17, saponification of Intermediate 17b (19 mg) with lithium hydroxide afforded Intermediate 18 (16 mg, 89%). MS(ESI) m/z: 234.1; $^1$H NMR (400 MHz, methanol-$d_4$) δ 8.10 (dt, J=8.5, 1.0 Hz, 1H), 7.76 (dt, J=8.7, 0.9 Hz, 1H), 7.41 (ddd, J=8.6, 6.7, 1.2 Hz, 1H), 7.34-7.28 (m, 1H), 5.38-5.32 (m, 2H), 3.89-3.81 (m, 2H), 3.02 (s, 6H).

Intermediate 19: 2-(Oxetan-3-ylmethyl)-2H-indazole-3-carboxylic Acid

Intermediate 20: 1-(Oxetan-3-ylmethyl)-1H-indazole-3-carboxylic Acid

Intermediate 19A: Ethyl 2-(oxetan-3-ylmethyl)-2H-indazole-3-carboxylate

Intermediate 19B: Ethyl 1-(oxetan-3-ylmethyl)-1H-indazole-3-carboxylate

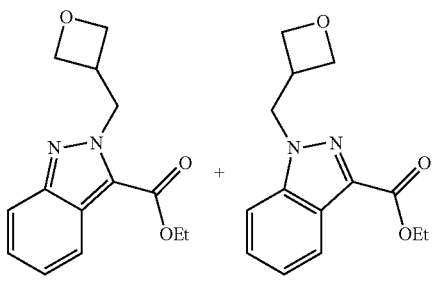

19a     19b

To a vial containing ethyl 1H-indazole-3-carboxylate (50 mg, 0.263 mmol) in acetonitrile (2 mL), were added 3-(bromomethyl)oxetane (59.5 mg, 0.394 mmol) and Cs$_2$CO$_3$ (128 mg, 0.394 mmol). The vial was sealed and the mixture was stirred at 90° C. for 3 h. Add DCM, filtered, concentrated and the residue was loaded onto 10 g column, eluted with EtOAc/Hex (0-60%); collected 1st peak at 20% EtOAc, concentrated to afford Intermediate 19A (27 mg, 40% yield). MS(ESI) m/z: 261.1 (M+H)$^+$; $^1$H NMR (400 MHz, chloroform-d) δ 8.03 (dt, J=8.4, 1.2 Hz, 1H), 7.77 (dt, J=8.5, 1.0 Hz, 1H), 7.40-7.33 (m, 1H), 7.33-7.28 (m, 1H), 5.24 (d, J=7.3 Hz, 2H), 4.81 (dd, J=7.9, 6.4 Hz, 2H), 4.67 (t, J=6.3 Hz, 2H), 4.50 (q, J=7.0 Hz, 2H), 3.80-3.64 (m, 1H), 1.51 (t, J=7.0 Hz, 3H).

Collected 2nd peak at 35% EtOAc was concentrated to afford Intermediate 19B. (30 mg, 44% yield). MS(ESI) 261.1 (M+H)$^+$; $^1$H NMR (400 MHz, chloroform-d) δ 8.23 (dt, J=8.3, 0.9 Hz, 1H), 7.54-7.44 (m, 2H), 7.33 (ddd, J=8.1, 6.7, 1.2 Hz, 1H), 4.85-4.76 (m, 4H), 4.59-4.55 (m, 2H), 4.54-4.48 (m, 2H), 3.70 (tt, J=7.5, 5.8 Hz, 1H), 1.48 (t, J=7.2 Hz, 3H).

Intermediate 19

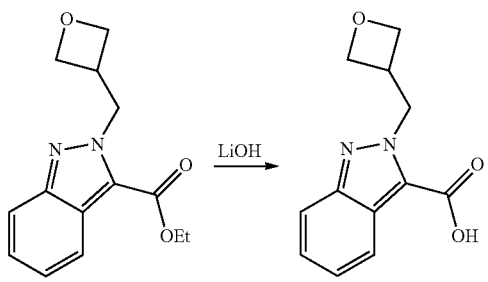

According to the procedure for preparation of Intermediate 17, saponification of Intermediate 19a (27 mg) with lithium hydroxide afforded Intermediate 19 (24 mg, 99%). MS(ESI) 233.1 (M+H)$^+$; $^1$H NMR (400 MHz, methanol-d$_4$) d 8.39 (dt, J=8.6, 1.0 Hz, 1H), 7.91-7.87 (m, 2H), 7.65 (ddd, J=8.5, 5.4, 2.3 Hz, 1H), 5.18 (dd, J=14.1, 8.4 Hz, 1H), 4.97 (dd, J=13.9, 5.3 Hz, 1H), 4.90 (dd, J=11.6, 8.3 Hz, 1H), 4.69 (dd, J=11.6, 5.2 Hz, 1H), 3.86 (d, J=5.3 Hz, 2H), 3.69 (tt, J=8.3, 5.3 Hz, 1H).

Intermediate 20

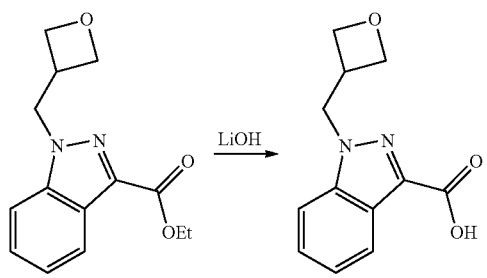

According to the procedure for preparation of Intermediate 17, saponification of Intermediate 19b (30 mg) with lithium hydroxide afforded Intermediate 20 (22 mg, 82%). MS(ESI) 233.1 (M+H)$^+$; $^1$H NMR (400 MHz, methanol-d$_4$) δ 8.15 (dt, J=8.2, 1.0 Hz, 1H), 7.71 (dt, J=8.5, 0.8 Hz, 1H), 7.49 (ddd, J=8.5, 7.2, 1.1 Hz, 1H), 7.32 (ddd, J=8.1, 7.1, 0.9 Hz, 1H), 4.93-4.85 (m, 2H), 4.61 (t, J=6.2 Hz, 2H), 3.76-3.60 (m, 1H).

Intermediate 21: 1-((1-((Benzyloxy)carbonyl)piperidin-4-yl)methyl)-1H-indazole-3-carboxylic Acid

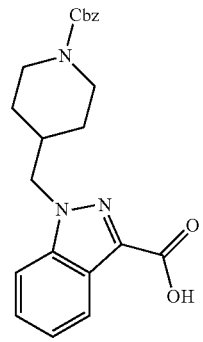 [SMILES: O=C(O)c1nn(CC2CCN(C(=O)OCc3ccccc3)CC2)c2ccccc12]

Intermediate 21A: Methyl 1-((1-((benzyloxy)carbonyl)piperidin-4-yl)methyl)-1H-indazole-3-carboxylate

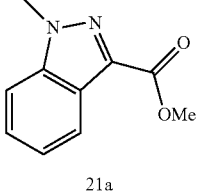

21a

To a vial containing ethyl 1H-indazole-3-carboxylate (100 mg, 0.526 mmol) in acetonitrile (5 mL), were added benzyl 4-(bromomethyl)piperidine-1-carboxylate (246 mg, 0.789 mmol) and Cs$_2$CO$_3$ (257 mg, 0.789 mmol). The vial was sealed and the mixture was stirred at 90° C. for 12 h. Concentrated and purified by prep HPLC. Two fractions were collected, 1st fraction concentrated to afford Intermediate 21a (80 mg, 37% yield) as a white solid. MS(ESI) 408.1 (M+H)$^+$; $^1$H NMR (400 MHz, chloroform-d) δ 9.62 (br. s., 1H), 8.24 (dt, J=8.1, 0.9 Hz, 1H), 7.51-7.43 (m, 2H), 7.40-7.30 (m, 6H), 5.17-5.10 (m, 2H), 4.36 (d, J=7.3 Hz, 2H), 4.30-4.15 (m, 2H), 4.06 (s, 3H), 2.86-2.66 (m, 2H), 2.30 (ddt, J=15.4, 7.8, 3.8 Hz, 1H), 1.67-1.50 (m, 2H), 1.30 (qd, J=12.4, 4.1 Hz, 2H).

Intermediate 21

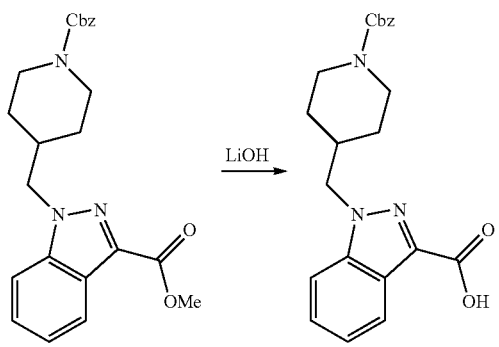 [SMILES: COC(=O)c1nn(CC2CCN(C(=O)OCc3ccccc3)CC2)c2ccccc12 ; "LiOH" ; O=C(O)c1nn(CC2CCN(C(=O)OCc3ccccc3)CC2)c2ccccc12]

According to the procedure for preparation of Intermediate 17, saponification of Intermediate 21A (80 mg) with lithium hydroxide afforded Intermediate 21 (46 mg, 60%). MS(ESI) 394.1 (M+H)$^+$; $^1$H NMR (400 MHz, methanol-$d_4$) δ 8.15 (dt, J=8.2, 1.0 Hz, 1H), 7.65 (d, J=8.6 Hz, 1H), 7.46 (ddd, J=8.4, 7.0, 1.1 Hz, 1H), 7.34-7.24 (m, 6H), 4.87 (br. s., 2H), 4.38 (d, J=7.3 Hz, 2H), 4.11 (d, J=13.6 Hz, 2H), 2.76 (br. s., 2H), 2.25 (ddt, J=15.2, 7.7, 3.9 Hz, 1H), 1.52 (d, J=11.4 Hz, 2H), 1.25 (qd, J=12.4, 4.4 Hz, 2H).

Intermediate 22: 1-((Tetrahydro-2H-pyran-4-yl)methyl)-1H-indazole-3-carboxylic Acid

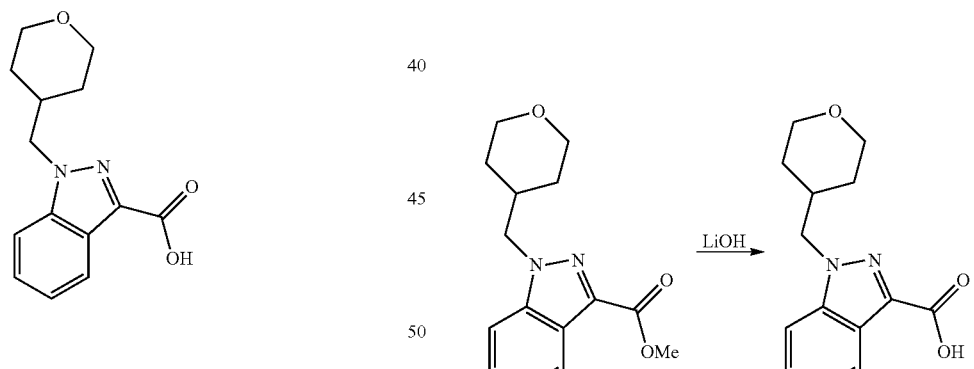

To a vial containing ethyl 1H-indazole-3-carboxylate (150 mg, 0.789 mmol) in DMF (2 mL), were added 4-(bromomethyl)tetrahydro-2H-pyran (212 mg, 1.18 mmol) and Cs$_2$CO$_3$ (385 mg, 1.18 mmol). The vial was sealed and the mixture was stirred at 90° C. for 3 h. The reaction mixture was concentrated and purified by prep HPLC. Two fractions were collected, 1st fraction was concentrated to afford Intermediate 22A (76 mg, 35% yield) as a white solid. MS(ESI) 275.1 (M+H)$^+$; $^1$H NMR (400 MHz, chloroform-d) δ 8.23 (dt, J=8.3, 0.9 Hz, 1H), 7.50-7.47 (m, 2H), 7.34 (ddd, J=8.1, 4.6, 3.2 Hz, 1H), 4.37 (d, J=7.5 Hz, 2H), 4.09-3.99 (m, 5H), 3.47-3.33 (m, 2H), 2.46-2.30 (m, 1H), 1.55-1.45 (m, 4H).

Intermediate 22

Intermediate 22A: Methyl 1-((tetrahydro-2H-pyran-4-yl)methyl)-1H-indazole-3-carboxylate

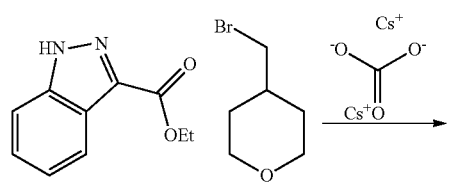

According to the procedure for preparation of Intermediate 17, saponification of Intermediate 22A (78 mg) with lithium hydroxide afforded Intermediate 22 (66 mg, 89%). MS(ESI) 261.1 (M+H)$^+$; $^1$H NMR (400 MHz, methanol-$d_4$) δ 8.21-8.11 (m, 1H), 7.66 (d, J=8.6 Hz, 1H), 7.46 (td, J=7.7, 0.9 Hz, 1H), 7.30 (ddd, J=8.1, 7.1, 0.7 Hz, 1H), 4.37 (d, J=7.3 Hz, 2H), 3.88 (dt, J=11.3, 3.2 Hz, 2H), 3.39-3.33 (m, 2H), 2.29 (dt, J=15.1, 7.6 Hz, 1H), 1.48-1.36 (m, 4H).

Intermediate 23: 1-((3-Methyloxetan-3-yl)methyl)-1H-indazole-3-carboxylic Acid

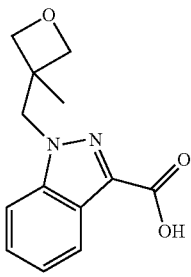 [SMILES: CC1(Cn2nc(C(=O)O)c3ccccc32)COC1]

Intermediate 23A: Ethyl 1-((3-methyloxetan-3-yl)methyl)-1H-indazole-3-carboxylate

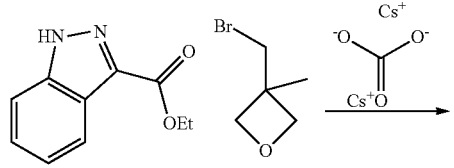

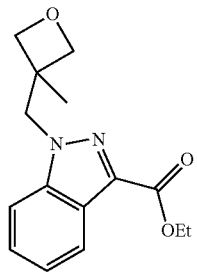

According to the procedure for preparation of Intermediate 19B, alkylation of ethyl 1H-indazole-3-carboxylate (200 mg) with 3-(bromomethyl)-3-methyloxetane afforded Intermediate 23A (183 mg, 63%). MS(ESI) 275.1 (M+H)$^+$; $^1$H NMR (400 MHz, chloroform-d) δ 8.26-8.20 (m, 1H), 7.49-7.44 (m, 2H), 7.35-7.28 (m, 1H), 4.80 (d, J=6.2 Hz, 2H), 4.65 (s, 2H), 4.56-4.47 (m, 2H), 4.45-4.36 (m, 2H), 1.48 (t, J=7.2 Hz, 3H), 1.30 (s, 3H).

Intermediate 23

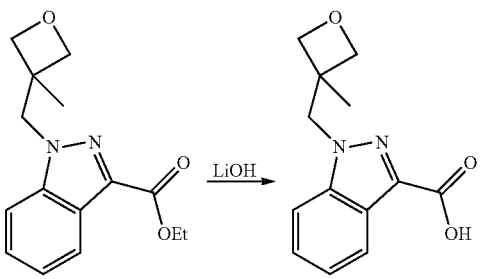

According to the procedure for preparation of Intermediate 17, saponification of Intermediate 23A (183 mg) with lithium hydroxide to afforded Intermediate 23 (145 mg, 88%). MS(ESI) 247.1 (M+H)$^+$; $^1$H NMR (400 MHz, methanol-d$_4$) δ 8.16 (dt, J=8.3, 1.0 Hz, 1H), 7.66 (d, J=8.6 Hz, 1H), 7.46 (ddd, J=8.4, 7.1, 1.0 Hz, 1H), 7.30 (ddd, J=8.1, 7.1, 0.9 Hz, 1H), 4.83 (d, J=6.2 Hz, 2H), 4.69 (s, 2H), 4.38 (d, J=6.2 Hz, 2H), 1.22 (s, 3H).

Intermediate 24: 1-((Tetrahydrofuran-3-yl)methyl)-1H-indazole-3-carboxylic Acid

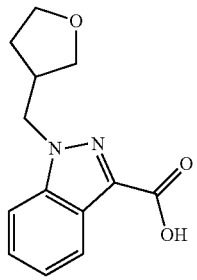 [SMILES: O=C(O)c1nn(CC2CCOC2)c2ccccc12]

Intermediate 24A: Ethyl 1-((tetrahydrofuran-3-yl)methyl)-1H-indazole-3-carboxylate

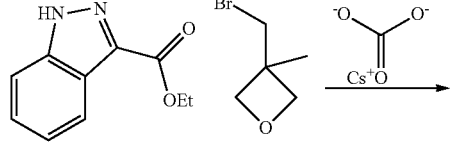

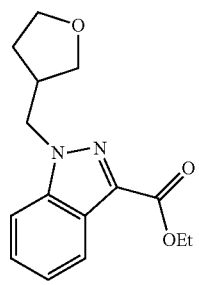

According to the procedure for preparation of Intermediate 19B, alkylation of ethyl 1H-indazole-3-carboxylate (200 mg) 3-(bromomethyl)tetrahydrofuran afforded Intermediate 24A (140 mg, 49%). MS(ESI) 275.2 (M+H)$^+$; $^1$H NMR (400 MHz, chloroform-d) δ 8.23 (dt, J=8.2, 1.0 Hz, 1H), 7.52-7.41 (m, 2H), 7.35-7.28 (m, 1H), 4.53 (q, J=7.1 Hz, 2H), 4.45 (d, J=7.7 Hz, 2H), 3.97 (td, J=8.4, 5.5 Hz, 1H), 3.80-3.70 (m, 2H), 3.67-3.58 (m, 1H), 3.14-3.00 (m, 1H), 2.01 (dtd, J=12.9, 7.9, 5.6 Hz, 1H), 1.80-1.67 (m, 1H), 1.49 (t, J=7.2 Hz, 3H).

Intermediate 24

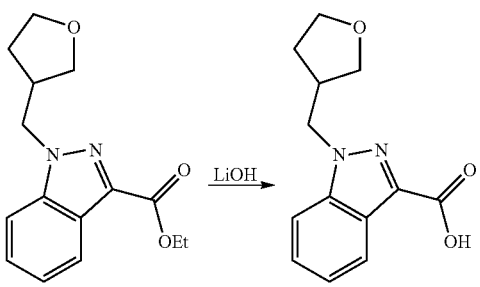

According to the procedure for preparation of Intermediate 17, saponification of Intermediate 24A (140 mg) with lithium hydroxide afforded Intermediate 24 (120 mg, 95%). MS(ESI) 247.1 (M+H)$^+$; $^1$H NMR (400 MHz, methanol-d$_4$) δ 8.11 (d, J=8.4 Hz, 1H), 7.57 (d, J=8.6 Hz, 1H), 7.39 (ddd, J=8.4, 7.0, 1.1 Hz, 1H), 7.28-7.19 (m, 1H), 4.40 (d, J=7.5 Hz, 2H), 3.86 (td, J=8.1, 5.5 Hz, 1H), 3.70-3.61 (m, 2H), 3.56 (dd, J=8.9, 5.4 Hz, 1H), 2.94-2.82 (m, 1H), 2.00-1.84 (m, 1H), 1.75-1.58 (m, 1H).

Intermediate 25: 1-((Tetrahydrofuran-3-yl)methyl)-1H-indazole-3-carboxylic Acid (Enantiomer 1)

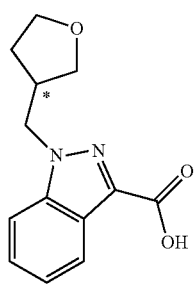 [SMILES: O=C(O)c1nn(CC2CCOC2)c2ccccc12]

Intermediate 26: 1-((Tetrahydrofuran-3-yl)methyl)-1H-indazole-3-carboxylic Acid (Enantiomer 2)

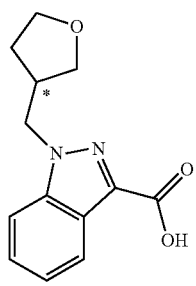 [SMILES: O=C(O)c1nn(CC2CCOC2)c2ccccc12]

The enantiomers of Intermediate 24 (64 mg) were separated via the following conditions:
Column: CHIRALPAK® AD-H, 4.6×250 mm, 5
Mobile Phase: 15% MeOH/85% CO$_2$
Flow Conditions: 2.0 mL/min, 150 Bar, 35° C.
Detector Wavelength: 220 nm
Injection Details: 10 μL of ~1 mg/mL in MeOH 1st isomer: Intermediate 25 (24 mg, 38%). MS(ESI) 247.2 (M+H)$^+$; $^1$H NMR (400 MHz, methanol-d$_4$) δ 8.16 (d, J=8.1 Hz, 1H), 7.68 (d, J=8.6 Hz, 1H), 7.48 (t, J=7.5 Hz, 1H), 7.32 (t, J=7.4 Hz, 1H), 4.49 (d, J=7.7 Hz, 2H), 3.93 (td, J=8.1, 5.5 Hz, 1H), 3.82-3.71 (m, 2H), 3.62 (dd, J=8.9, 5.2 Hz, 1H), 3.05-2.86 (m, 1H), 2.12-1.90 (m, 1H), 1.87-1.66 (m, 1H).

2nd isomer: Intermediate 26 (25 mg, 39%). MS(ESI) 247.2 (M+H)$^+$; $^1$H NMR (400 MHz, methanol-d$_4$) δ 8.16 (d, J=8.1 Hz, 1H), 7.68 (d, J=8.6 Hz, 1H), 7.48 (t, J=7.5 Hz, 1H), 7.32 (t, J=7.4 Hz, 1H), 4.49 (d, J=7.7 Hz, 2H), 3.93 (td, J=8.1, 5.5 Hz, 1H), 3.82-3.71 (m, 2H), 3.62 (dd, J=8.9, 5.2 Hz, 1H), 3.05-2.86 (m, 1H), 2.12-1.90 (m, 1H), 1.87-1.66 (m, 1H).

Intermediate 27: 1-(Oxetan-2-ylmethyl)-1H-indazole-3-carboxylic Acid

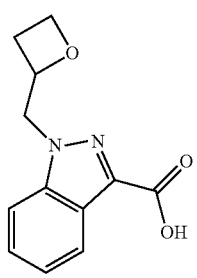

Intermediate 27A: Ethyl 1-(oxetan-2-ylmethyl)-1H-indazole-3-carboxylate

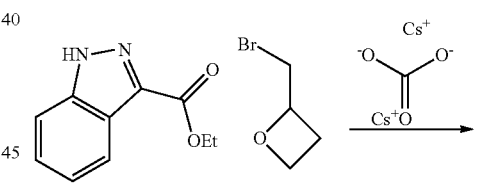

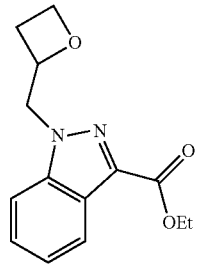 [SMILES: O=C(O)c1nn(CC2CCO2)c2ccccc12]

According to the procedure for preparation of Intermediate 19B, alkylation of ethyl 1H-indazole-3-carboxylate (160 mg) with 2-(bromomethyl)oxetane afforded Intermediate 27A (100 mg, 46%). MS(ESI) 247.2 (M+H)$^+$; $^1$H NMR (400 MHz, chloroform-d) δ 8.21 (dt, J=8.3, 0.9 Hz, 1H), 7.66 (dt, J=8.5, 0.8 Hz, 1H), 7.43 (ddd, J=8.4, 7.0, 1.1 Hz, 1H), 7.36-7.27 (m, 1H), 5.33-5.21 (m, 1H), 4.82-4.66 (m, 2H), 4.64-4.48 (m, 3H), 4.23 (dt, J=9.1, 6.0 Hz, 1H), 2.80-2.64 (m, 1H), 2.64-2.46 (m, 1H), 1.48 (t, J=7.2 Hz, 3H).

Intermediate 27

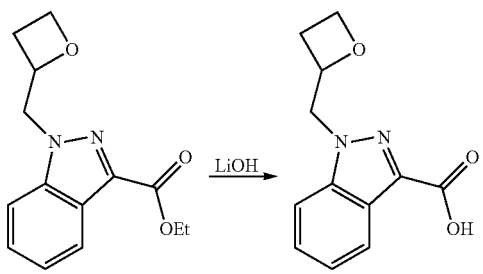

According to the procedure for preparation of Intermediate 17, saponification of Intermediate 27A (100 mg) with lithium hydroxide afforded Intermediate 27 (90 mg, 99%). MS(ESI) 233.1 (M+H)$^+$; $^1$H NMR (400 MHz, methanol-d$_4$) δ 8.14 (dt, J=8.3, 1.0 Hz, 1H), 7.80-7.69 (m, 1H), 7.44 (ddd, J=8.4, 7.0, 1.1 Hz, 1H), 7.37-7.25 (m, 1H), 5.25 (dtd, J=7.7, 6.4, 3.7 Hz, 1H), 4.81-4.64 (m, 2H), 4.55 (ddd, J=8.6, 7.3, 5.7 Hz, 1H), 4.28 (dt, J=9.1, 6.0 Hz, 1H), 2.74 (dtd, J=11.4, 8.2, 6.3 Hz, 1H), 2.61-2.51 (m, 1H).

Intermediate 28: 1-(2-Methoxyethyl)-1H-indazole-3-carboxylic Acid

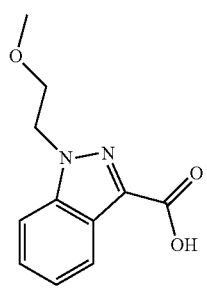 [SMILES: COCCn1nc(C(=O)O)c2ccccc21]

Intermediate 28A: Ethyl 1-(2-methoxyethyl)-1H-indazole-3-carboxylate

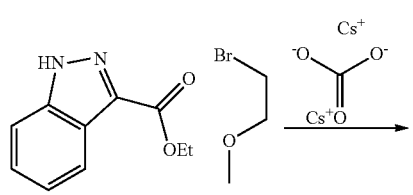

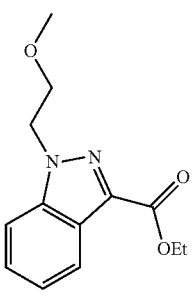

According to the procedure for preparation of Intermediate 19B, alkylation of ethyl 1H-indazole-3-carboxylate (150 mg) with 1-bromo-2-methoxyethane afforded Intermediate 28A (104 mg, 53%). MS(ESI) 249.1 (M+H)$^+$; $^1$H NMR (400 MHz, chloroform-d) δ 8.20 (dt, J=8.2, 1.0 Hz, 1H), 7.55 (d, J=8.6 Hz, 1H), 7.42 (ddd, J=8.4, 7.0, 1.1 Hz, 1H), 7.29 (ddd, J=8.0, 7.0, 0.8 Hz, 1H), 4.63 (t, J=5.5 Hz, 2H), 4.52 (q, J=7.0 Hz, 2H), 3.85 (t, J=5.4 Hz, 2H), 3.26 (s, 3H), 1.48 (t, J=7.0 Hz, 3H).

Intermediate 28

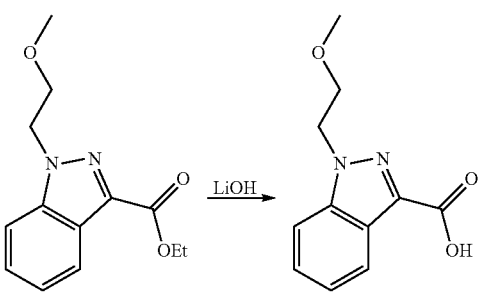

According to the procedure for preparation of Intermediate 17, saponification of Intermediate 28A (104 mg) with lithium hydroxide afforded Intermediate 28 (90 mg, 98%). MS(ESI) 221.1 (M+H)$^+$; $^1$H NMR (400 MHz, methanol-d$_4$) δ 8.14 (dt, J=8.3, 0.9 Hz, 1H), 7.67 (dt, J=8.6, 0.9 Hz, 1H), 7.45 (ddd, J=8.5, 7.2, 1.1 Hz, 1H), 7.30 (ddd, J=8.1, 7.0, 0.8 Hz, 1H), 4.64 (t, J=5.2 Hz, 2H), 3.85 (t, J=5.3 Hz, 2H), 3.27-3.20 (m, 3H).

Intermediate 29: 1-(2-Hydroxypropyl)-1H-indazole-3-carboxylic Acid

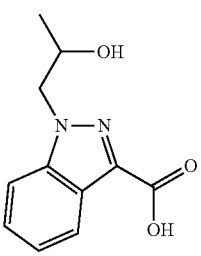 [SMILES: CC(O)Cn1nc(C(=O)O)c2ccccc21]

Intermediate 29A: Methyl 1-(2-hydroxypropyl)-1H-indazole-3-carboxylate

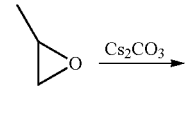

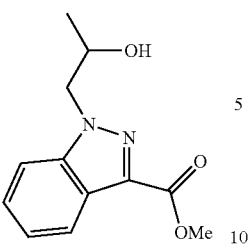

To a vial containing ethyl 1H-indazole-3-carboxylate (200 mg, 1.052 mmol) in DMF (3 mL), was added 2-methyloxirane (122 mg, 2.103 mmol) and $Cs_2CO_3$ (411 mg, 1.262 mmol). The vial was sealed and the mixture was stirred at 80° C. o/n. LC/MS showed reaction completed. Quenched with water, extracted with EtOAc, washed organic layer with 10% LiCl, brine, concentrated and the residue was purified by prep HPLC to afford Intermediate 29A (35 mg, 14%). MS(ESI) 235.1 (M+H)$^+$; $^1$H NMR (400 MHz, chloroform-d) δ 8.19 (dt, J=8.2, 1.0 Hz, 1H), 7.95 (s, 1H), 7.58-7.52 (m, 1H), 7.43 (ddd, J=8.4, 7.0, 1.1 Hz, 1H), 7.30 (ddd, J=8.0, 6.9, 0.9 Hz, 1H), 4.50-4.35 (m, 3H), 4.03-3.94 (m, 3H), 2.93 (s, 2H), 2.85 (d, J=0.4 Hz, 2H), 1.37-1.24 (m, 3H).

Intermediate 29

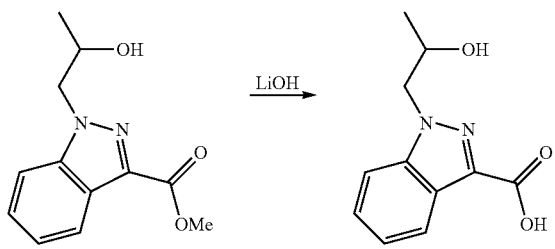 [SMILES: COC(=O)c1nn(CC(C)O)c2ccccc12 ; "LiOH" ; CC(O)Cn1nc(C(=O)O)c2ccccc21]

According to the procedure for preparation of Intermediate 17, saponification of Intermediate 29A (35 mg) with lithium hydroxide afforded Intermediate 29 (25 mg, 81%). MS(ESI) 221.1 (M+H)$^+$; $^1$H NMR (400 MHz, methanol-d$_4$) δ 8.15 (dt, J=8.2, 1.0 Hz, 1H), 7.73-7.65 (m, 1H), 7.46 (ddd, J=8.4, 7.0, 1.1 Hz, 1H), 7.30 (ddd, J=8.1, 7.0, 0.8 Hz, 1H), 4.48-4.42 (m, 2H), 4.29 (td, J=6.4, 5.4 Hz, 1H), 1.28-1.18 (m, 3H).

Intermediate 30: 1-(3-(Benzyloxy)-2-hydroxypropyl)-1H-indazole-3-carboxylic Acid

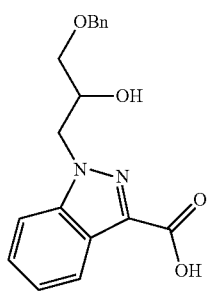

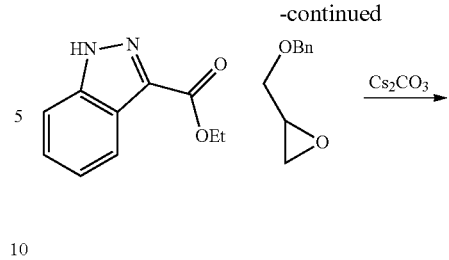

To a vial containing ethyl 1H-indazole-3-carboxylate (200 mg, 1.052 mmol) in DMF (3 mL), was added 2-((benzyloxy)methyl)oxirane (345 mg, 2.103 mmol) and $Cs_2CO_3$ (514 mg, 1.577 mmol). The vial was sealed and the mixture was stirred at 80° C. o/n. LC/MS showed reaction completed. Quenched with water, extracted with EtOAc, washed organic layer with 10% LiCl, brine, concentrated and the residue was purified by prep HPLC. 1st fraction concentrated to afford Intermediate 30 (120 mg, 35% yield) as a white solid. MS(ESI) 327.1 (M+H)$^+$; $^1$H NMR (400 MHz, chloroform-d) δ 8.19 (d, J=8.1 Hz, 1H), 7.55 (d, J=8.4 Hz, 1H), 7.46-7.37 (m, 1H), 7.36-7.27 (m, 6H), 4.63-4.57 (m, 2H), 4.51-4.48 (m, 2H), 4.45-4.36 (m, 1H), 3.59-3.41 (m, 4H).

Intermediate 31: 1-(2,3-Dihydroxypropyl)-1H-indazole-3-carboxylic Acid

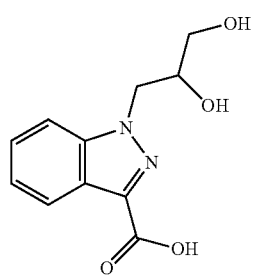

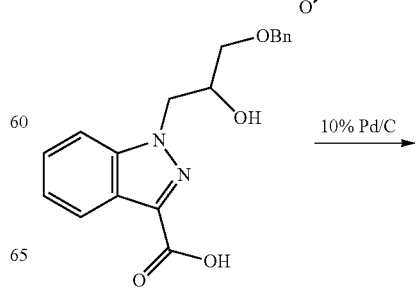

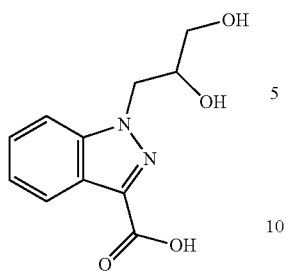

Intermediate 30 (90 mg, 0.276 mmol) was dissolved in MeOH (3 mL), degassed and add 10% Pd/C (20 mg). Stirred under $H_2$ balloon for 3 h, filtered and concentrated under vacuum to afford Intermediate 31 as a colorless oil (58 mg, 89%). MS(ESI) 237.1 (M+H)$^+$; $^1$H NMR (400 MHz, methanol-$d_4$) δ 8.17-8.10 (m, 1H), 7.70 (d, J=8.6 Hz, 1H), 7.45 (ddd, J=8.4, 7.1, 1.0 Hz, 1H), 7.29 (ddd, J=8.0, 7.0, 0.8 Hz, 1H), 4.62 (dd, J=14.3, 4.4 Hz, 1H), 4.51 (dd, J=14.3, 7.3 Hz, 1H), 4.16 (dq, J=7.3, 5.0 Hz, 1H), 3.66-3.53 (m, 2H).

Intermediate 32: 1-(2-(2-Methoxyethoxyl)ethyl)-1H-indazole-3-carboxylic Acid

According to the procedure for preparation of Intermediate 19B, alkylation of ethyl 1H-indazole-3-carboxylate (150 mg) with 1-bromo-2-(2-methoxyethoxyl)ethane afforded Intermediate 32A (105 mg, 46%). MS(ESI) 293.2 (M+H)$^+$; $^1$H NMR (400 MHz, chloroform-d) δ 8.20 (dt, J=8.2, 1.0 Hz, 1H), 7.63-7.57 (m, 1H), 7.42 (ddd, J=8.4, 7.0, 1.1 Hz, 1H), 7.30 (ddd, J=8.1, 7.0, 0.9 Hz, 1H), 4.67 (t, J=5.6 Hz, 2H), 4.53 (q, J=7.3 Hz, 2H), 3.97 (t, J=5.7 Hz, 2H), 3.56-3.48 (m, 2H), 3.43-3.37 (m, 2H), 3.28 (s, 3H), 1.48 (t, J=7.2 Hz, 3H).

Intermediate 32

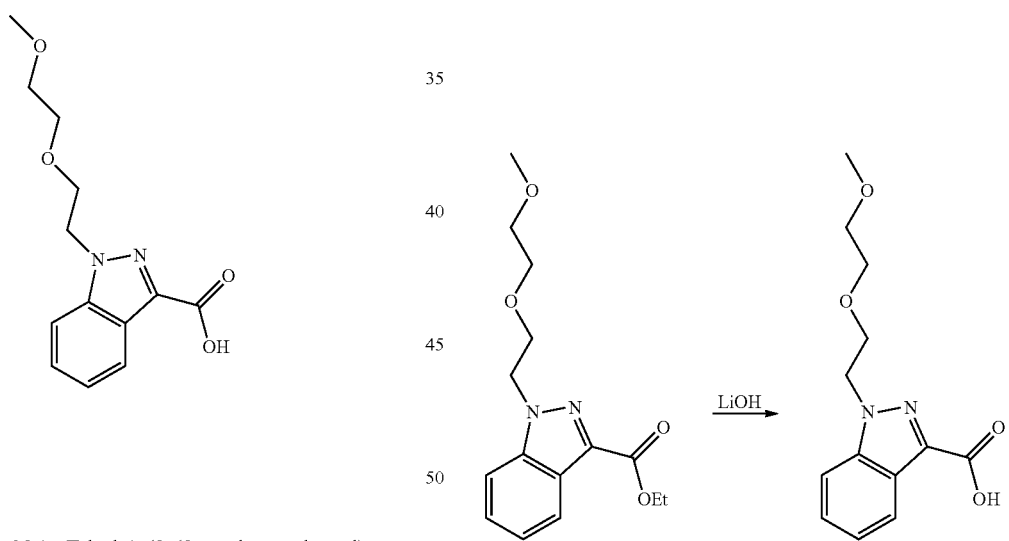

Intermediate 32A: Ethyl 1-(2-(2-methoxyethoxyl)ethyl)-1H-indazole-3-carboxylate

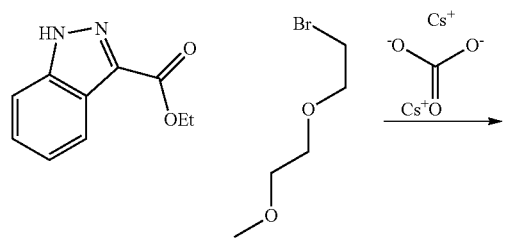

According to the procedure for preparation of Intermediate 17, saponification of Intermediate 32A (105 mg)) with lithium hydroxide afforded Intermediate 32 (93 mg, 98%). MS(ESI) 265.1 (M+H)$^+$; $^1$H NMR (500 MHz, methanol-$d_4$) δ 8.12 (dt, J=8.2, 0.9 Hz, 1H), 7.72-7.62 (m, 1H), 7.42 (ddd, J=8.4, 7.0, 1.1 Hz, 1H), 7.27 (ddd, J=8.1, 7.0, 0.8 Hz, 1H), 4.62 (t, J=5.4 Hz, 2H), 3.93 (t, J=5.4 Hz, 2H), 3.49-3.43 (m, 2H), 3.37-3.32 (m, 2H), 3.17 (s, 3H).

Intermediate 33: 1-((1-(tert-Butoxycarbonyl)azetidin-3-yl)methyl)-1H-indazole-3-carboxylic Acid

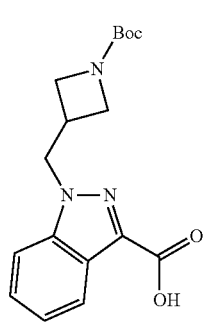 [SMILES: CC(C)(C)OC(=O)N1CC(Cn2nc(C(=O)O)c3ccccc32)C1]

Intermediate 33

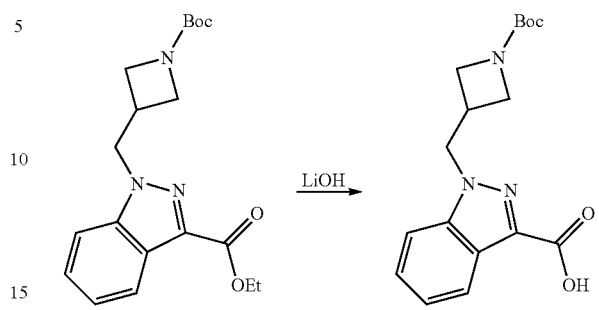

According to the procedure for preparation of Intermediate 17, saponification of Intermediate 33A (180 mg) with lithium hydroxide afforded Intermediate 33 (155 mg, 93%). MS(ESI) 332.1 (M+H)$^+$; $^1$H NMR (400 MHz, methanol-d$_4$) δ 8.16 (dt, J=8.2, 1.0 Hz, 1H), 7.73 (d, J=8.6 Hz, 1H), 7.50 (ddd, J=8.5, 7.2, 1.1 Hz, 1H), 7.33 (ddd, J=8.0, 7.0, 0.8 Hz, 1H), 4.72 (d, J=7.3 Hz, 2H), 4.06-3.96 (m, 2H), 3.84 (br. s., 2H), 3.27-3.17 (m, 1H), 1.41 (s, 9H).

Intermediate 34: 1-(2-(Benzyloxy)ethyl)-1H-indazole-3-carboxylic Acid

Intermediate 33A: Ethyl 1-((1-(tert-butoxycarbonyl)azetidin-3-yl)methyl)-1H-indazole-3-carboxylate

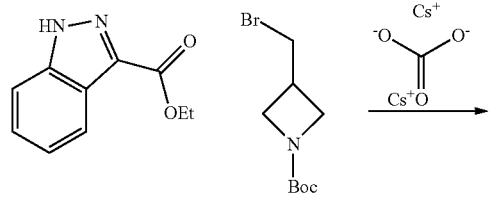

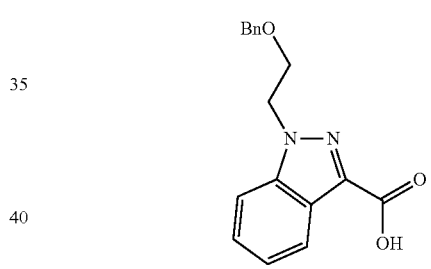

Intermediate 34A: Ethyl 1-(2-(benzyloxy)ethyl)-1H-indazole-3-carboxylate

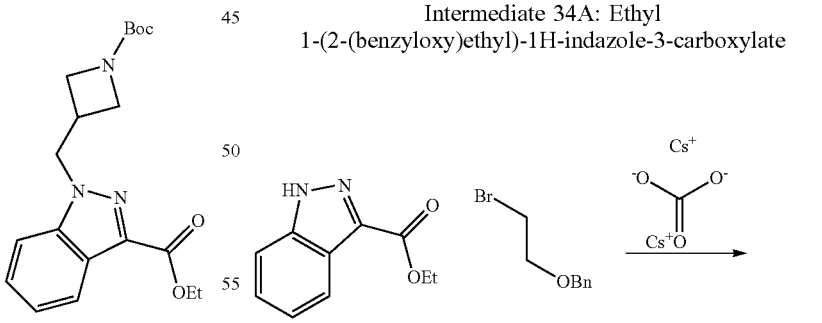

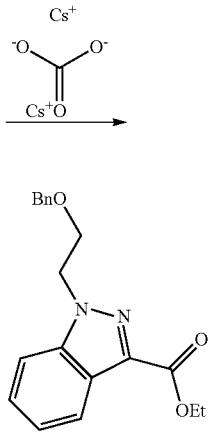

According to the procedure for preparation of Intermediate 19B, alkylation of ethyl 1H-indazole-3-carboxylate (150 mg) with tert-butyl 3-(bromomethyl)azetidine-1-carboxylate afforded Intermediate 33A (180 mg, 48%). MS(ESI) 360.1 (M+H)$^+$; $^1$H NMR (400 MHz, chloroform-d) δ 8.22 (d, J=8.4 Hz, 1H), 7.56-7.43 (m, 2H), 7.32 (ddd, J=8.0, 6.8, 1.1 Hz, 1H), 4.67 (d, J=7.7 Hz, 2H), 4.57-4.44 (m, 2H), 4.02 (t, J=8.5 Hz, 2H), 3.80 (dd, J=8.9, 5.2 Hz, 2H), 3.24 (ddd, J=7.9, 5.1, 2.6 Hz, 1H), 1.48 (t, J=7.0 Hz, 3H), 1.44 (s, 9H).

According to the procedure for preparation of Intermediate 19B, alkylation of ethyl 1H-indazole-3-carboxylate (120 mg) with ((2-bromoethoxy)methyl)benzene afforded Intermediate 34A (120 mg, 59%). MS(ESI) 325.2 (M+H)$^+$; $^1$H NMR (500 MHz, chloroform-d) δ 8.21 (d, J=8.3 Hz, 1H), 7.56 (d, J=8.5 Hz, 1H), 7.40 (d, J=1.4 Hz, 1H), 7.32-7.27 (m, 1H), 7.25-7.20 (m, 3H), 7.11-7.06 (m, 2H), 4.66 (t, J=5.5 Hz, 2H), 4.52 (q, J=7.2 Hz, 2H), 4.40 (s, 2H), 3.93 (t, J=5.4 Hz, 2H), 1.47 (t, J=7.0 Hz, 3H).

Intermediate 34

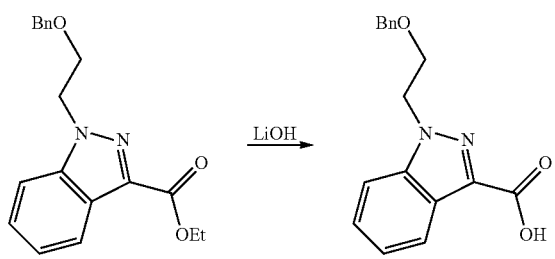

According to the procedure for preparation of Intermediate 17, saponification of Intermediate 34A (120 mg) with lithium hydroxide afforded Intermediate 34 (100 mg, 91%). MS(ESI) 297.2 (M+H)$^+$; $^1$H NMR (500 MHz, methanol-d$_4$) d 8.15 (dt, J=8.1, 1.0 Hz, 1H), 7.65 (d, J=8.5 Hz, 1H), 7.42 (ddd, J=8.5, 7.1, 1.0 Hz, 1H), 7.33-7.25 (m, 1H), 7.20-7.13 (m, 3H), 7.05-6.90 (m, 2H), 4.65 (t, J=5.2 Hz, 2H), 4.37 (s, 2H), 3.91 (t, J=5.1 Hz, 2H).

Intermediate 35:
1-(2-Hydroxyethyl)-1H-indazole-3-carboxylic Acid

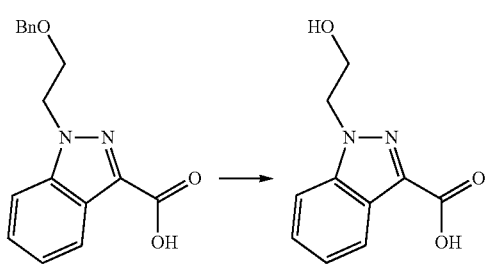 [SMILES: O=C(O)c1nn(CCOCc2ccccc2)c2ccccc12 ; O=C(O)c1nn(CCO)c2ccccc12]

Intermediate 34 (84 mg, 0.283 mmol) was dissolved in MeOH (2 mL), degassed and add 10% Pd/C (15 mg), stirred under H$_2$ balloon for 2 h. Filtered and concentrated to afford Intermediate 35 (55 mg, 94%) as a white solid. MS(ESI) 207.1 (M+H)$^+$; $^1$H NMR (400 MHz, methanol-d$_4$) d 8.14 (dt, J=8.3, 1.0 Hz, 1H), 7.72-7.62 (m, 1H), 7.45 (ddd, J=8.4, 7.0, 1.1 Hz, 1H), 7.29 (ddd, J=8.1, 7.1, 0.9 Hz, 1H), 4.64-4.53 (m, 2H), 4.07-3.97 (m, 2H).

Intermediate 36: 1-(2-(Tetrahydro-2H-pyran-4-yl) ethyl)-1H-indazole-3-carboxylic Acid

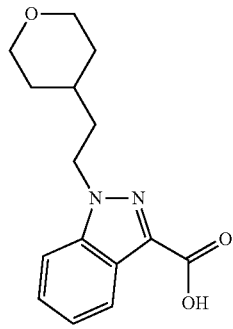 [SMILES: O=C(O)c1nn(CCC2CCOCC2)c2ccccc12]

Intermediate 36A: Ethyl 1-(2-(tetrahydro-2H-pyran-4-yl)ethyl)-1H-indazole-3-carboxylate

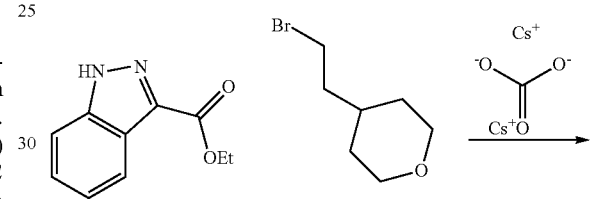

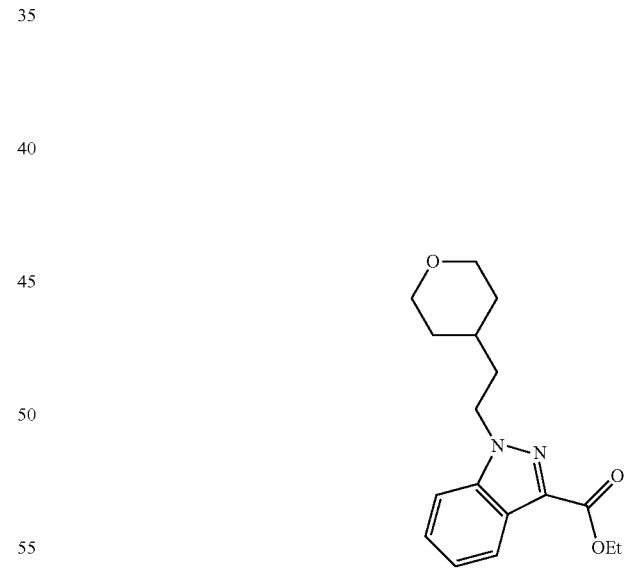

According to the procedure for preparation of Intermediate 19B, alkylation of ethyl 1H-indazole-3-carboxylate (120 mg) with 4-(2-bromoethyl)tetrahydro-2H-pyran afforded Intermediate 36A (90 mg, 47%). MS(ESI) 303.2 (M+H)$^+$; $^1$H NMR (500 MHz, chloroform-d) δ 8.23 (dt, J=8.3, 1.0 Hz, 1H), 7.54-7.42 (m, 2H), 7.31 (ddd, J=8.0, 5.9, 1.8 Hz, 1H), 4.62-4.43 (m, 4H), 4.01-3.87 (m, 2H), 3.34 (td, J=11.8, 2.1 Hz, 2H), 1.98-1.85 (m, 2H), 1.65 (dd, J=12.9, 1.9 Hz, 2H), 1.54 (dd, J=7.4, 3.6 Hz, 1H), 1.48 (t, J=7.2 Hz, 3H), 1.41-1.29 (m, 2H).

Intermediate 36

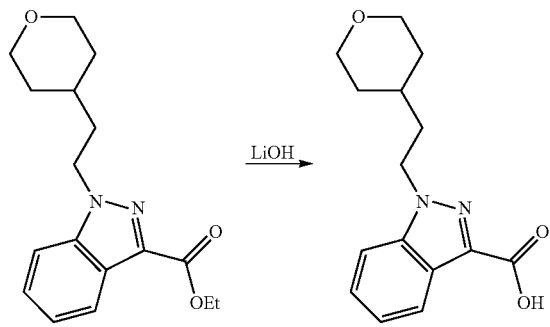 [SMILES: CCOC(=O)c1nn(CCC2CCOCC2)c2ccccc12 ; "LiOH" ; O=C(O)c1nn(CCC2CCOCC2)c2ccccc12]

According to the procedure for preparation of Intermediate 17, saponification of Intermediate 36A (90 mg) with lithium hydroxide afforded Intermediate 36 (80 mg, 98%). MS(ESI) 275.2 (M+H)+; $^1$H NMR (400 MHz, methanol-$d_4$) d 8.22-8.12 (m, 1H), 7.62 (d, J=8.6 Hz, 1H), 7.45 (ddd, J=8.4, 7.0, 0.9 Hz, 1H), 7.30 (ddd, J=8.1, 7.1, 0.7 Hz, 1H), 4.51 (t, J=7.3 Hz, 2H), 3.96-3.81 (m, 2H), 3.38-3.24 (m, 2H), 1.86 (q, J=7.0 Hz, 2H), 1.72-1.60 (m, 2H), 1.54-1.42 (m, 1H), 1.37-1.24 (m, 2H).

Intermediate 37: 1-(3-(Benzyloxy)propyl)-1H-indazole-3-carboxylic Acid

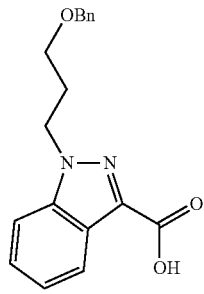 [SMILES: O=C(O)c1nn(CCCOCc2ccccc2)c2ccccc12]

Intermediate 37A: Ethyl 1-(3-(benzyloxy)propyl)-1H-indazole-3-carboxylate

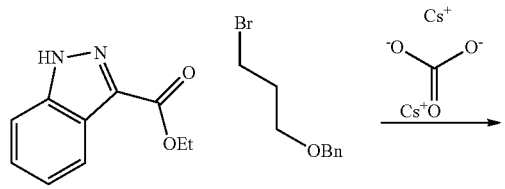

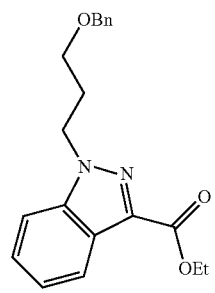

According to the procedure for preparation of Intermediate 19B, alkylation of ethyl 1H-indazole-3-carboxylate (120 mg) with ((3-bromopropoxy)methyl)benzene afforded Intermediate 37A (105 mg, 49%). MS(ESI) 339.2 (M+H)+; $^1$H NMR (400 MHz, chloroform-d) δ 8.22 (dt, J=8.1, 1.0 Hz, 1H), 7.53-7.47 (m, 1H), 7.43-7.37 (m, 1H), 7.37-7.25 (m, 6H), 4.66-4.60 (m, 2H), 4.56-4.48 (m, 2H), 4.43 (s, 2H), 3.40 (t, J=5.7 Hz, 2H), 2.35-2.21 (m, 2H), 1.48 (t, J=7.2 Hz, 3H).

Intermediate 37

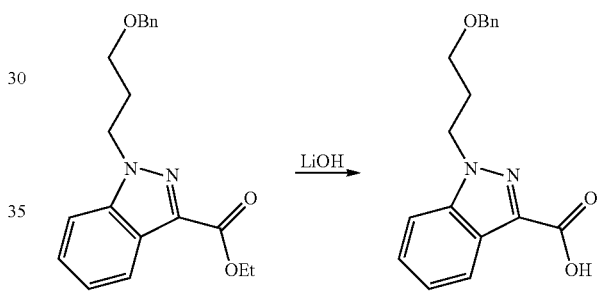

According to the procedure for preparation of Intermediate 17, saponification of Intermediate 37A (105 mg) with lithium hydroxide afforded Intermediate 37 (88 mg, 91%). MS(ESI) 339.2 (M+H)+; $^1$H NMR (400 MHz, methanol-$d_4$) d 8.15 (d, J=8.4 Hz, 1H), 7.54 (d, J=8.6 Hz, 1H), 7.38 (ddd, J=8.4, 7.0, 1.1 Hz, 1H), 7.31-7.20 (m, 7H), 4.54 (t, J=6.7 Hz, 2H), 4.34 (s, 2H), 3.41-3.36 (m, 2H), 2.25-2.10 (m, 2H).

Intermediate 38: 1-(3-Hydroxypropyl)-1H-indazole-3-carboxylic Acid

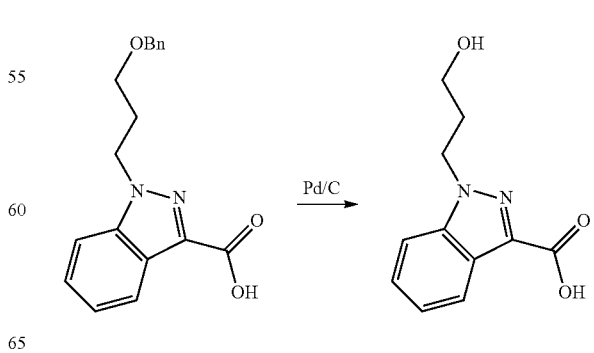

Intermediate 37 (80 mg, 0.258 mmol) was dissolved in MeOH (3 mL), degassed and add 10% Pd/C (20 mg). Stirred under H₂ balloon for 3 h, filtered and concentrated under vacuum to afford Intermediate 38 as a colorless oil (50 mg, 75%). MS(ESI) 221.1 (M+H)⁺; ¹H NMR (500 MHz, methanol-d₄) d 8.17-8.13 (m, 1H), 7.68 (d, J=8.5 Hz, 1H), 7.46 (ddd, J=8.4, 7.0, 1.1 Hz, 1H), 7.30 (ddd, J=8.0, 7.1, 0.8 Hz, 1H), 4.60 (t, J=6.9 Hz, 2H), 3.55 (t, J=6.1 Hz, 2H), 2.14 (t, J=6.3 Hz, 2H).

Intermediate 39: 1-(3-Methoxypropyl)-1H-indazole-3-carboxylic Acid

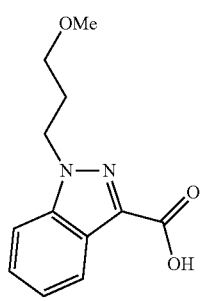 [SMILES: COCCCn1nc(C(=O)O)c2ccccc21]

Intermediate 39

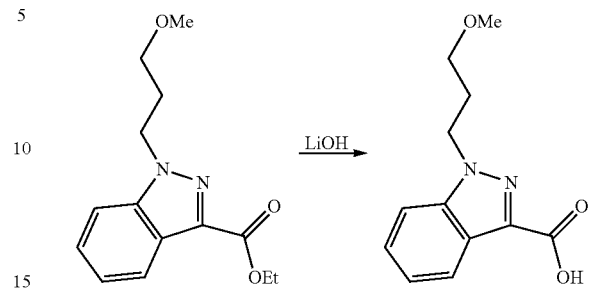

According to the procedure for preparation of Intermediate 17, saponification of Intermediate 39A (50 mg) with lithium hydroxide afforded Intermediate 39 (44 mg, 99%). MS(ESI) 235.1 (M+H)⁺; ¹H NMR (400 MHz, methanol-d₄) d 8.14 (dt, J=8.3, 0.9 Hz, 1H), 7.62 (d, J=8.6 Hz, 1H), 7.49-7.41 (m, 1H), 7.29 (ddd, J=8.1, 7.0, 0.8 Hz, 1H), 4.61-4.54 (m, 2H), 3.28 (t, J=5.9 Hz, 2H), 3.25 (s, 3H), 2.16 (t, J=6.1 Hz, 2H).

Intermediate 40: 1-(Pyridin-4-ylmethyl)-1H-indazole-3-carboxylic Acid

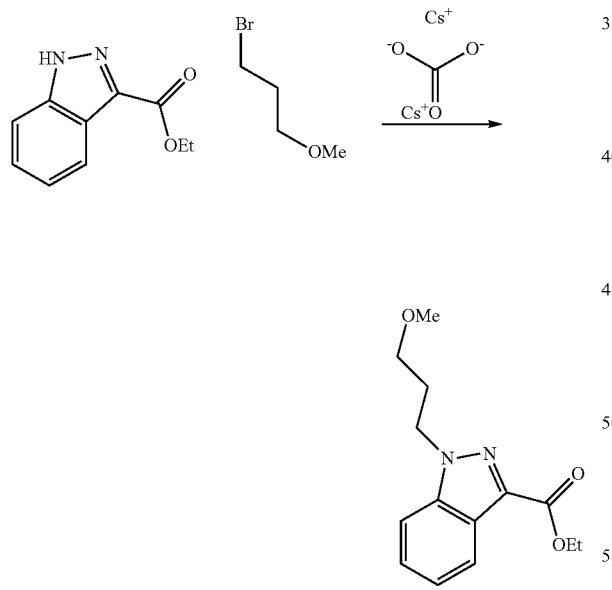

Intermediate 39A: Ethyl 1-(3-methoxypropyl)-1H-indazole-3-carboxylate

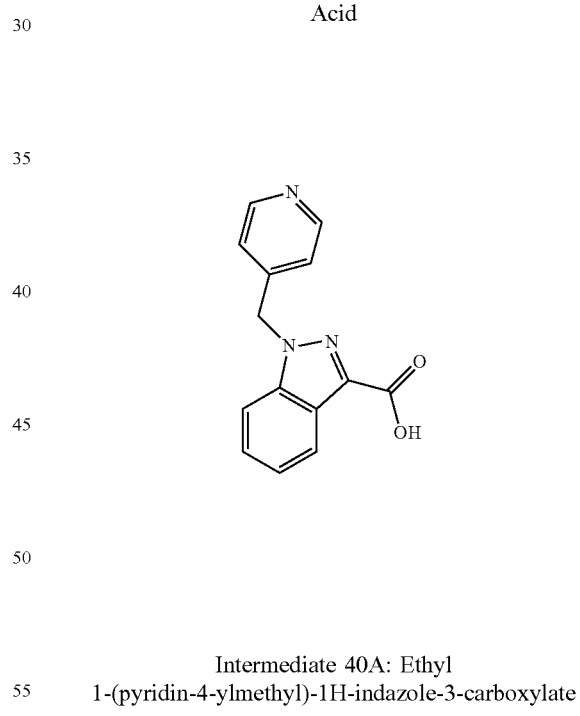

Intermediate 40A: Ethyl 1-(pyridin-4-ylmethyl)-1H-indazole-3-carboxylate

According to the procedure for preparation of Intermediate 19B, alkylation of ethyl 1H-indazole-3-carboxylate (80 mg) with 1-bromo-3-methoxypropane afforded Intermediate 39A (50 mg, 45%). MS(ESI) 263.2 (M+H)⁺; ¹H NMR (500 MHz, chloroform-d) δ 8.21 (d, J=8.3 Hz, 1H), 7.56 (d, J=8.5 Hz, 1H), 7.40 (d, J=1.4 Hz, 1H), 7.32-7.27 (m, 1H), 7.25-7.20 (m, 3H), 7.11-7.06 (m, 2H), 4.66 (t, J=5.5 Hz, 2H), 4.52 (q, J=7.2 Hz, 2H), 4.40 (s, 2H), 3.93 (t, J=5.4 Hz, 2H), 1.47 (t, J=7.0 Hz, 3H).

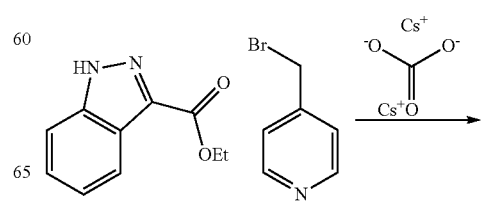

117
-continued

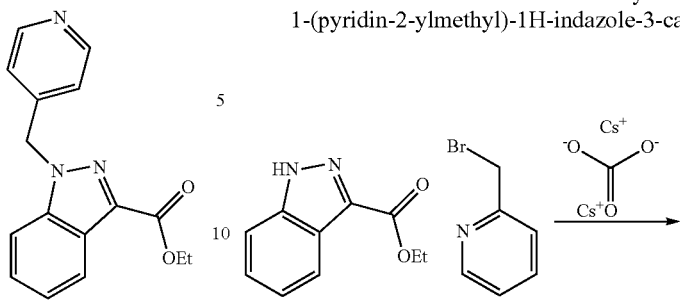

According to the procedure for preparation of Intermediate 19B, alkylation of ethyl 1H-indazole-3-carboxylate (70 mg) with 4-(bromomethyl)pyridine afforded Intermediate 40A (50 mg, 48%). MS(ESI) 282.1 (M+H)+; 1H NMR (400 MHz, chloroform-d) δ 8.61-8.42 (m, 2H), 8.26 (dt, J=8.2, 1.1 Hz, 1H), 7.47-7.37 (m, 1H), 7.35-7.31 (m, 1H), 7.31 (d, J=0.7 Hz, 1H), 7.06-6.99 (m, 2H), 5.70 (s, 2H), 4.54 (q, J=7.3 Hz, 2H), 1.48 (t, J=7.2 Hz, 3H).

Intermediate 40

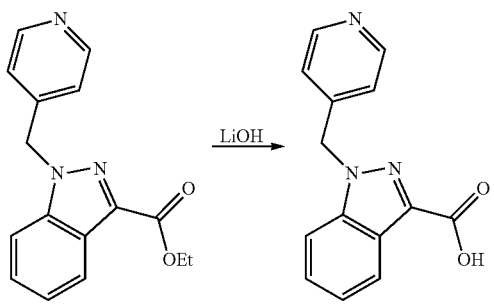 [SMILES: CCOC(=O)c1nn(Cc2ccncc2)c2ccccc12 ; "LiOH" ; O=C(O)c1nn(Cc2ccncc2)c2ccccc12]

According to the procedure for preparation of Intermediate 17, saponification of Intermediate 40A (50 mg) with lithium hydroxide afforded Intermediate 40 (45 mg, 95%). MS(ESI) 254.1 (M+H)+; 1H NMR (400 MHz, methanol-d4) d 8.56-8.44 (m, 2H), 8.28-8.13 (m, 1H), 7.70-7.57 (m, 1H), 7.48 (d, J=1.3 Hz, 1H), 7.36 (dd, J=8.3, 1.0 Hz, 1H), 7.26-7.15 (m, 2H), 5.84 (s, 2H).

Intermediate 41:
1-(Pyridin-2-ylmethyl)-1H-indazole-3-carboxylic Acid

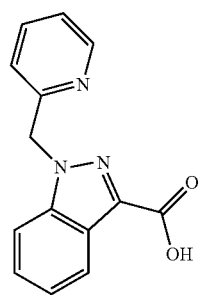

118
Intermediate 41A: Ethyl
1-(pyridin-2-ylmethyl)-1H-indazole-3-carboxylate

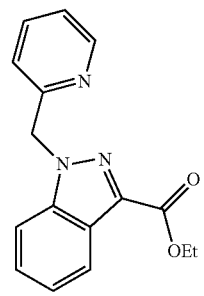 [SMILES: O=C(O)c1nn(Cc2ccccn2)c2ccccc12]

According to the procedure for preparation of Intermediate 19B, alkylation of ethyl 1H-indazole-3-carboxylate (70 mg) with 2-(bromomethyl)pyridine afforded Intermediate 41A (88 mg, 85%). MS(ESI) 282.1 (M+H)+; 1H NMR (400 MHz, chloroform-d) δ 8.61-8.54 (m, 1H), 8.24 (dt, J=8.1, 1.0 Hz, 1H), 7.55 (td, J=7.7, 1.8 Hz, 1H), 7.45 (dt, J=8.5, 0.9 Hz, 1H), 7.38 (ddd, J=8.4, 6.9, 1.2 Hz, 1H), 7.35-7.29 (m, 1H), 7.20-7.14 (m, 1H), 6.92 (d, J=7.9 Hz, 1H), 5.84 (s, 2H), 4.54 (q, J=7.3 Hz, 2H), 1.49 (t, J=7.2 Hz, 3H).

Intermediate 41

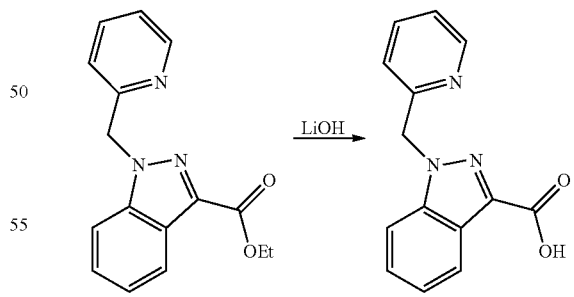

According to the procedure for preparation of Intermediate 17, saponification of Intermediate 41A (88 mg) with lithium hydroxide afforded Intermediate 41 (105 mg, 91%). MS(ESI) 254.1 (M+H)+; 1H NMR (400 MHz, methanol-d4) d 8.67 (dd, J=5.4, 0.8 Hz, 1H), 8.21 (dt, J=8.1, 1.0 Hz, 1H), 8.12 (td, J=7.8, 1.8 Hz, 1H), 7.74-7.61 (m, 2H), 7.51 (ddd, J=8.4, 7.1, 1.0 Hz, 1H), 7.42 (d, J=7.9 Hz, 1H), 7.37 (ddd, J=8.1, 7.1, 0.9 Hz, 1H), 5.99 (s, 2H).

Intermediate 42: 1-(Pyridin-3-ylmethyl)-1H-indazole-3-carboxylic Acid

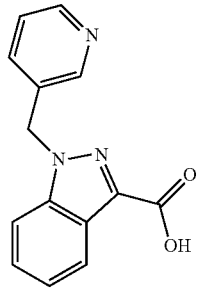 [SMILES: O=C(O)c1nn(Cc2cccnc2)c2ccccc12]

Intermediate 42A: Ethyl 1-(pyridin-3-ylmethyl)-1H-indazole-3-carboxylate

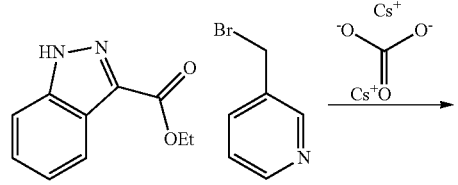

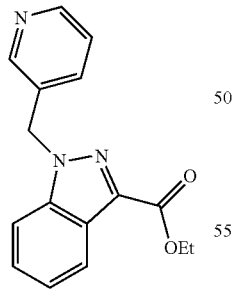

According to the procedure for preparation of Intermediate 19B, alkylation of ethyl 1H-indazole-3-carboxylate (70 mg) with 3-(bromomethyl)pyridine afforded Intermediate 42A (18 mg, 18%). MS(ESI) 282.1 (M+H)+; 1H NMR (400 MHz, chloroform-d) δ 8.61 (d, J=1.8 Hz, 1H), 8.54 (dd, J=4.8, 1.5 Hz, 1H), 8.25 (dt, J=8.1, 1.0 Hz, 1H), 7.54-7.47 (m, 1H), 7.45-7.30 (m, 3H), 7.22 (ddd, J=7.9, 4.8, 0.8 Hz, 1H), 5.73 (s, 2H), 4.55 (q, J=7.0 Hz, 2H), 1.50 (t, J=7.2 Hz, 3H).

Intermediate 42

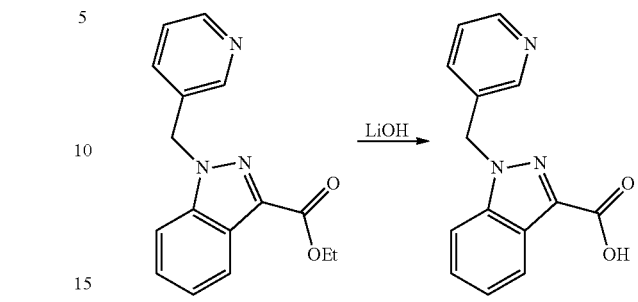

According to the procedure for preparation of Intermediate 17, saponification of Intermediate 42A (18 mg) with lithium hydroxide afforded Intermediate 42 (23 mg, 98%). MS(ESI) 254.1 (M+H)+; 1H NMR (500 MHz, methanol-d4) d 8.94-8.84 (m, 1H), 8.78 (d, J=5.5 Hz, 1H), 8.49-8.37 (m, 1H), 8.18 (dt, J=8.3, 0.8 Hz, 1H), 8.02-7.92 (m, 1H), 7.77 (d, J=8.5 Hz, 1H), 7.52 (ddd, J=8.4, 7.0, 1.1 Hz, 1H), 7.36 (ddd, J=8.1, 7.2, 0.7 Hz, 1H), 5.98 (s, 2H).

Intermediate 43: 6-Fluoro-1-(2-methylprop-1-en-1-yl)-1H-indazole-3-carboxylic Acid

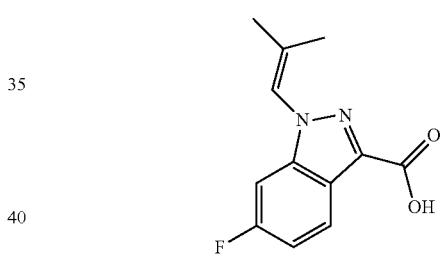

Intermediate 44: 6-Fluoro-1-(2-hydroxy-2-methylpropyl)-1H-indazole-3-carboxylic Acid

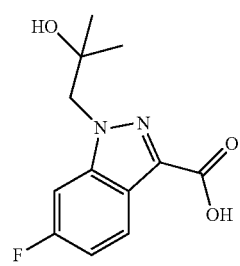

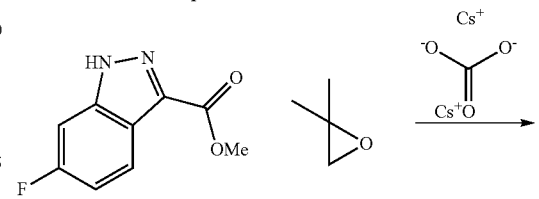

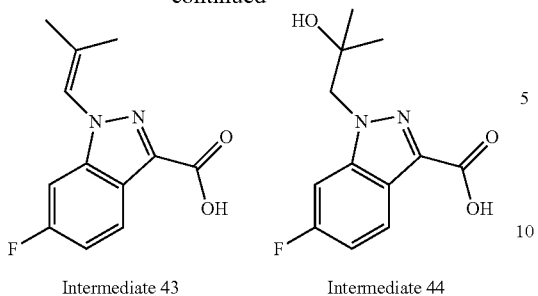

Intermediate 43                Intermediate 44

To a vial containing methyl 6-fluoro-1H-indazole-3-carboxylate (200 mg, 1.030 mmol) in DMF (3 mL), were added 2,2-dimethyloxirane (0.458 mL, 5.15 mmol) and $Cs_2CO_3$ (403 mg, 1.236 mmol). The vial was sealed and the mixture was stirred at 80° C. for 3 h. Quenched with water, acidified with 1 N HCl. Extracted with EtOAc, the organic layer was concentrated and loaded on 10 g column, eluted with MeOH/DCM. Collected two fractions: 1st fraction: 5% MeOH; 2nd fraction: 8% MeOH.

1st fraction afforded Intermediate 43 (26 mg, 11%). MS(ESI) 235.1 $(M+H)^+$; $^1H$ NMR (500 MHz, DMSO-$d_6$) δ 13.78 (br. s., 1H), 8.05 (dd, J=9.1, 5.5 Hz, 1H), 7.55 (dt, J=9.9, 1.1 Hz, 1H), 7.44-7.32 (m, 1H), 7.21 (td, J=9.3, 2.3 Hz, 1H), 1.93 (d, J=1.1 Hz, 3H), 1.79 (d, J=1.4 Hz, 3H).

2nd fraction afforded Intermediate 44 (90 mg, 36%). MS(ESI) 253.1 $(M+H)^+$; $^1H$ NMR (400 MHz, methanol-$d_4$) δ 8.10 (dd, J=9.0, 5.3 Hz, 1H), 7.44 (dd, J=9.5, 2.0 Hz, 1H), 7.08 (td, J=9.1, 2.1 Hz, 1H), 4.39 (s, 2H), 1.24 (s, 6H).

Intermediate 45: 5-Fluoro-1-(2-methylprop-1-en-1-yl)-1H-indazole-3-carboxylic Acid

Intermediate 46: 5-Fluoro-1-(2-hydroxy-2-methylpropyl)-1H-indazole-3-carboxylic Acid

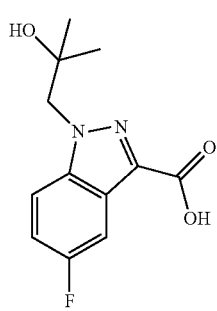

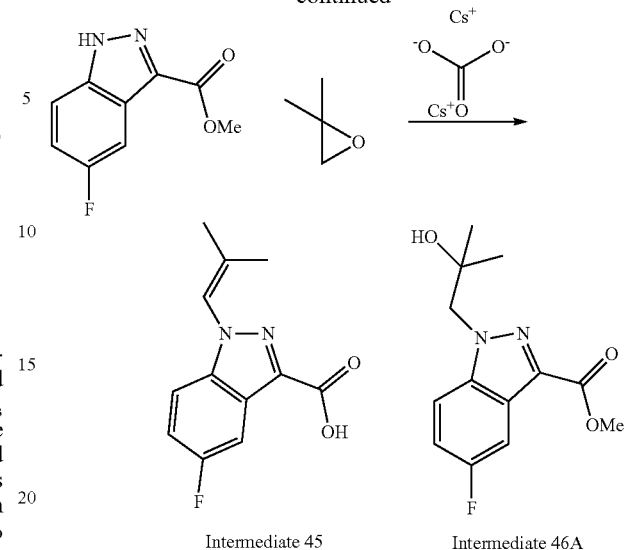

Intermediate 45                Intermediate 46A

To a vial containing methyl 5-fluoro-1H-indazole-3-carboxylate (200 mg, 1.03 mmol) in ACN (3 mL), were added 2,2-dimethyloxirane (0.458 mL, 5.15 mmol) and $Cs_2CO_3$ (403 mg, 1.24 mmol). The vial was sealed and the mixture was stirred at 80° C. for 3 h. Filtered, concentrated and the residue was loaded onto 10 g column, eluted with EtOAc/Hex (0-60%); collected a 1st fraction at 40% EtOAc. Then eluted with MeOH/DCM (0-10%); collected a 2nd fraction at 10% MeOH.

2nd fraction concentrated to afford Intermediate 45 (20 mg, 8%). MS(ESI) 235.1 $(M+H)^+$; $^1H$ NMR (400 MHz, methanol-$d_4$) δ 7.84-7.70 (m, 1H), 7.63 (ddd, J=9.4, 2.5, 0.7 Hz, 1H), 7.29 (dt, J=3.1, 1.5 Hz, 1H), 7.21 (td, J=9.2, 2.4 Hz, 1H), 1.98 (d, J=1.3 Hz, 3H), 1.76 (d, J=1.3 Hz, 3H).

1st fraction concentrated to afford Intermediate 46A (130 mg, 48%). MS(ESI) 267.1 $(M+H)^+$; $^1H$ NMR (400 MHz, chloroform-d) δ 7.81-7.76 (m, 1H), 7.58-7.52 (m, 1H), 7.18 (td, J=8.9, 2.4 Hz, 1H), 4.42 (s, 2H), 4.02-3.97 (m, 3H), 1.26 (s, 6H).

Intermediate 46

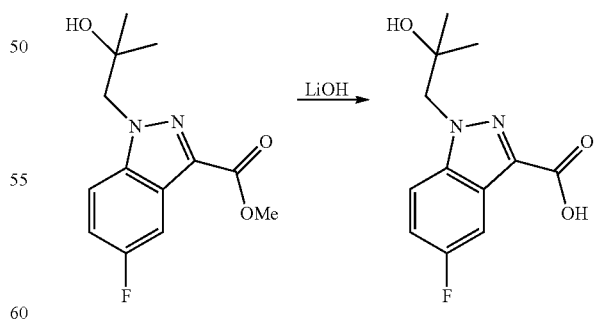

According to the procedure for preparation of Intermediate 17, saponification of Intermediate 46A (130 mg) with lithium hydroxide afforded Intermediate 46 (115 mg, 93%) as a white solid. MS(ESI) 253.1 $(M+H)^+$; $^1H$ NMR (500 MHz, methanol-$d_4$) δ 7.77-7.68 (m, 2H), 7.32-7.20 (m, 1H), 4.43 (s, 2H), 1.30-1.21 (m, 6H).

Intermediate 47: 1-((Tetrahydro-2H-pyran-2-yl)methyl)-1H-indazole-3-carboxylic Acid

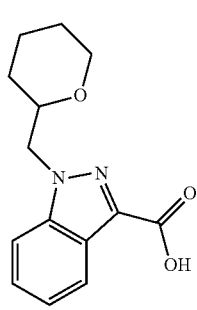 [SMILES: O=C(O)c1nn(CC2CCCCO2)c2ccccc12]

Intermediate 47A: Ethyl 1-((tetrahydro-2H-pyran-2-yl)methyl)-1H-indazole-3-carboxylate

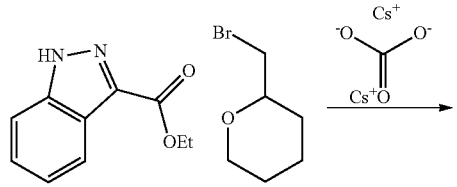

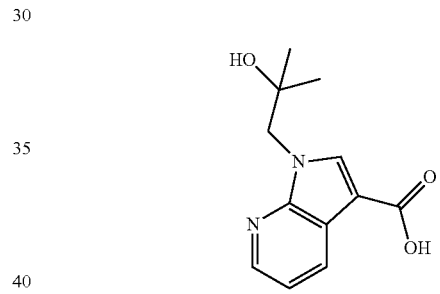

According to the procedure for preparation of Intermediate 19B, alkylation of ethyl 1H-indazole-3-carboxylate (150 mg) with 2-(bromomethyl)tetrahydro-2H-pyran afforded Intermediate 47A (163 mg, 72%). MS(ESI) 267.1 (M+H)$^+$; $^1$H NMR (400 MHz, chloroform-d) δ 8.20 (dt, J=8.2, 1.0 Hz, 1H), 7.63-7.57 (m, 1H), 7.43 (ddd, J=8.4, 7.1, 1.2 Hz, 1H), 7.31 (ddd, J=8.0, 6.9, 0.9 Hz, 1H), 4.62-4.45 (m, 4H), 4.00-3.81 (m, 2H), 3.33 (td, J=11.6, 2.5 Hz, 1H), 1.91-1.80 (m, 1H), 1.68-1.59 (m, 1H), 1.57-1.44 (m, 6H), 1.42-1.28 (m, 1H).

Intermediate 47

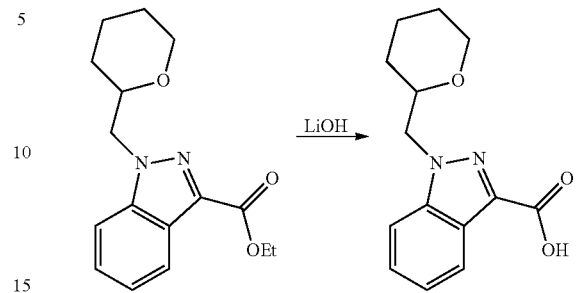

According to the procedure for preparation of Intermediate 17, saponification of Intermediate 47A (46 mg) with lithium hydroxide afforded Intermediate 47 (30 mg, 72%) as a white solid. MS(ESI) 261.2 (M+H)$^+$; $^1$H NMR (400 MHz, methanol-d$_4$) d 8.13 (dd, J=8.1, 0.9 Hz, 1H), 7.75-7.62 (m, 1H), 7.52-7.40 (m, 1H), 7.40-7.25 (m, 1H), 4.59-4.41 (m, 2H), 3.94-3.80 (m, 2H), 1.93-1.78 (m, 1H), 1.65 (d, J=11.7 Hz, 1H), 1.59-1.42 (m, 3H), 1.41-1.26 (m, 1H).

Intermediate 48: 1-(2-Hydroxy-2-methylpropyl)-1H-pyrrolo[2,3-b]pyridine-3-carboxylic Acid Intermediate 48A: Methyl 1-(2-hydroxy-2-methylpropyl)-1H-pyrrolo[2,3-b]pyridine-3-carboxylate

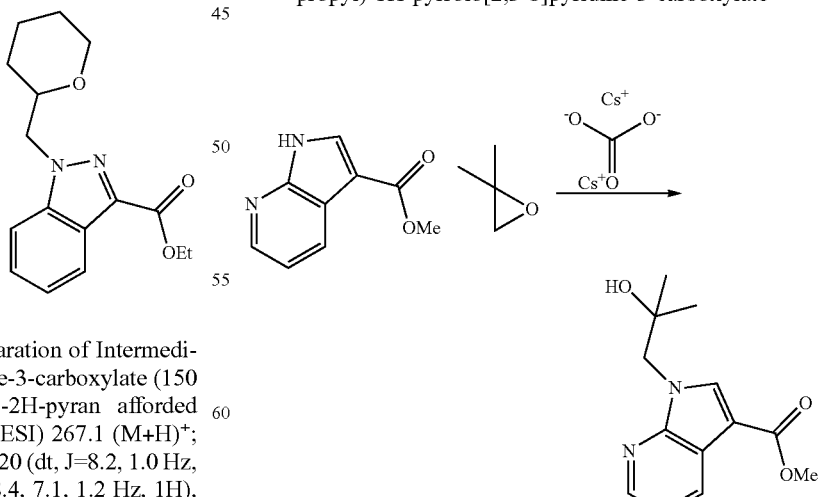

To a vial containing methyl 1H-pyrrolo[2,3-b]pyridine-3-carboxylate (120 mg, 0.681 mmol) in DMF (3 mL), were added 2,2-dimethyloxirane (0.303 mL, 3.41 mmol) and Cs₂CO₃ (266 mg, 0.817 mmol). The vial was sealed and the mixture was stirred at 80° C. for 3 h. Quenched with water, extracted with EtOAc, concentrated and the residue was loaded onto 10 g column, eluted with EtOAc/Hex (0-60%); collected a fraction at 40% EtOAc. Concentrated to afford Intermediate 48A (134 mg, 79%). MS(ESI) 249.1 (M+H)⁺; ¹H NMR (400 MHz, chloroform-d) δ 8.45 (dd, J=7.9, 1.5 Hz, 1H), 8.33 (dd, J=4.7, 1.7 Hz, 1H), 7.99 (s, 1H), 7.24 (dd, J=7.9, 4.6 Hz, 1H), 4.44 (s, 1H), 4.33 (s, 2H), 3.92 (s, 3H), 1.24 (s, 6H).

Intermediate 48

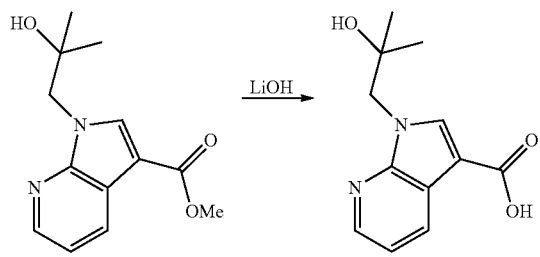 [SMILES: COC(=O)c1cn(CC(C)(C)O)c2ncccc12 ; "LiOH" ; CC(C)(O)Cn1cc(C(=O)O)c2cccnc21]

According to the procedure for preparation of Intermediate 17, saponification of Intermediate 48A (134 mg) with lithium hydroxide afforded Intermediate 48 (127 mg, 99%) as a white solid. MS(ESI) 235.2 (M+H)⁺; ¹H NMR (400 MHz, methanol-d₄) d 8.47 (dd, J=7.9, 1.5 Hz, 1H), 8.29 (d, J=4.0 Hz, 1H), 8.14 (s, 1H), 7.23 (dd, J=7.9, 4.8 Hz, 1H), 4.33 (s, 2H), 1.17 (s, 6H).

Intermediate 49: 5-Fluoro-1-((tetrahydrofuran-3-yl)methyl)-1H-indazole-3-carboxylic Acid

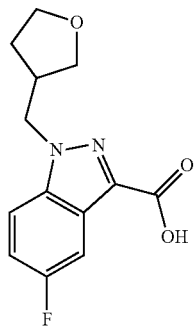 [SMILES: O=C(O)c1nn(CC2CCOC2)c2ccc(F)cc12]

Intermediate 49A: Methyl 5-fluoro-1-((tetrahydrofuran-3-yl)methyl)-1H-indazole-3-carboxylate

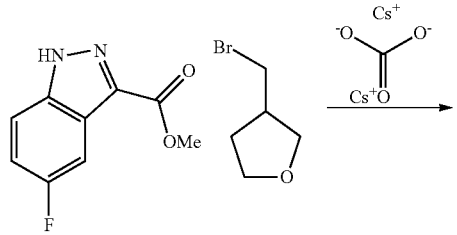

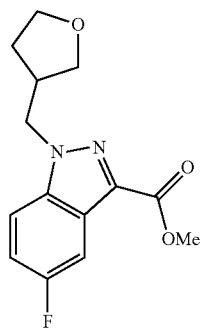

According to the procedure for preparation of Intermediate 19B, alkylation of ethyl 1H-indazole-3-carboxylate (100 mg) with 3-(bromomethyl)tetrahydrofuran afforded Intermediate 49A (66 mg, 46%). MS(ESI) 279.2 (M+H)⁺; ¹H NMR (400 MHz, chloroform-d) δ 7.87-7.81 (m, 1H), 7.46-7.41 (m, 1H), 7.22 (td, J=8.9, 2.4 Hz, 1H), 4.41 (d, J=7.7 Hz, 2H), 4.06-4.00 (m, 3H), 3.97-3.92 (m, 1H), 3.80-3.67 (m, 2H), 3.60 (dd, J=9.1, 4.7 Hz, 1H), 3.11-2.95 (m, 1H), 2.08-1.96 (m, 1H), 1.74-1.64 (m, 1H).

Intermediate 49

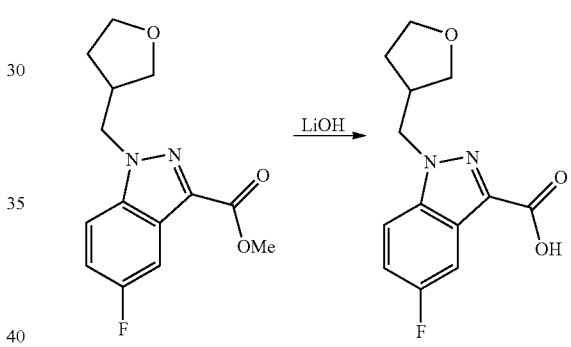

According to the procedure for preparation of Intermediate 17, saponification of Intermediate 49A (68 mg) with lithium hydroxide afforded Intermediate 49 (63 mg, 98%) as a white solid. MS(ESI) 265.2 (M+H)⁺; ¹H NMR (500 MHz, methanol-d₄) d 7.74-7.67 (m, 2H), 7.26 (td, J=8.9, 2.5 Hz, 1H), 4.47 (d, J=7.7 Hz, 2H), 3.92 (td, J=8.3, 5.5 Hz, 1H), 3.77-3.69 (m, 2H), 3.60 (dd, J=8.8, 5.2 Hz, 1H), 3.01-2.87 (m, 1H), 2.08-1.95 (m, 1H), 1.80-1.69 (m, 1H).

Intermediate 50: 6-Fluoro-1-((tetrahydrofuran-3-yl)methyl)-1H-indazole-3-carboxylic Acid

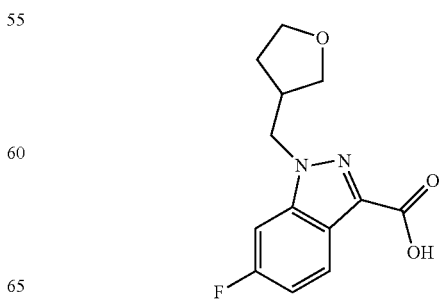

Intermediate 50A: Methyl 6-fluoro-1-((tetrahydrofuran-3-yl)methyl)-1H-indazole-3-carboxylate

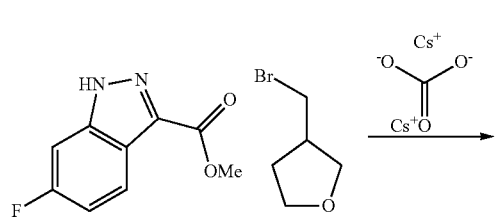

According to the procedure for preparation of Intermediate 19B, alkylation of ethyl 1H-indazole-3-carboxylate (100 mg) with 3-(bromomethyl)tetrahydrofuran afforded Intermediate 50A (68 mg, 47%). MS(ESI) 279.2 (M+H)$^+$; $^1$H NMR (400 MHz, chloroform-d) δ 8.22-8.15 (m, 1H), 7.18-7.04 (m, 2H), 4.37 (d, J=7.7 Hz, 2H), 4.03 (s, 3H), 3.96 (td, J=8.3, 5.4 Hz, 2H), 3.82-3.72 (m, 2H), 3.61 (dd, J=9.0, 4.8 Hz, 1H), 3.09-2.95 (m, 1H), 2.02 (dtd, J=12.9, 8.0, 5.5 Hz, 1H), 1.74-1.63 (m, 1H).

Intermediate 50

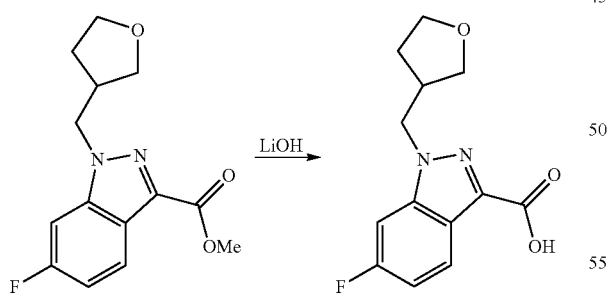

According to the procedure for preparation of Intermediate 17, saponification of Intermediate 50A (68 mg) with lithium hydroxide afforded Intermediate 50 (50 mg, 77%) as a white solid. MS(ESI) 265.2 (M+H)$^+$; $^1$H NMR (500 MHz, methanol-d$_4$) δ 8.12 (dd, J=8.7, 5.1 Hz, 1H), 7.44 (dd, J=9.4, 1.9 Hz, 1H), 7.10 (td, J=9.1, 2.2 Hz, 1H), 4.43 (d, J=7.7 Hz, 2H), 3.93 (td, J=8.2, 5.4 Hz, 1H), 3.84-3.71 (m, 2H), 3.61 (dd, J=8.8, 5.5 Hz, 1H), 3.04-2.83 (m, 1H), 2.12-1.93 (m, 1H), 1.84-1.65 (m, 1H).

Intermediate 51: 6-(2-Hydroxy-2-methylpropoxy)pyrazolo[1,5-a]pyridine-3-carboxylic Acid

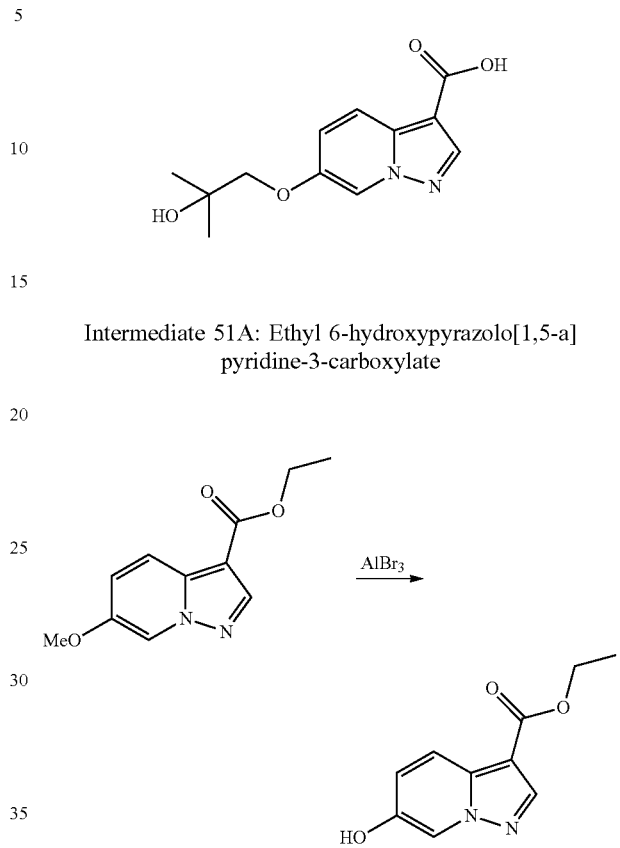

Intermediate 51A: Ethyl 6-hydroxypyrazolo[1,5-a]pyridine-3-carboxylate

Ethyl 6-methoxypyrazolo[1,5-a]pyridine-3-carboxylate (130 mg, 0.59 mmol) was mixed with aluminum tribromide (787 mg, 2.95 mmol) in EtSH (2 ml) and stirred at rt for 2 h. Cooled to 0° C., add MeOH dropwise, concentrated, and the residue was loaded onto 10 g column, eluted with EtOAc/Hex (0-40%); collected fraction at 30% EtOAc, concentrated to afford Intermediate 51A (50 mg, 41%). MS(ESI) 207.1 (M+H)$^+$; $^1$H NMR (400 MHz, methanol-d$_4$) d 8.25 (s, 1H), 8.15 (dd, J=2.1, 0.8 Hz, 1H), 7.99 (dd, J=9.5, 0.7 Hz, 1H), 7.27 (dd, J=9.6, 2.1 Hz, 1H), 4.35 (q, J=7.3 Hz, 2H), 1.40 (t, J=7.2 Hz, 3H).

Intermediate 51B: Ethyl 6-(2-hydroxy-2-methylpropoxy)pyrazolo[1,5-a]pyridine-3-carboxylate

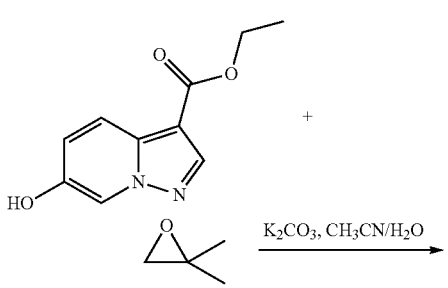

-continued

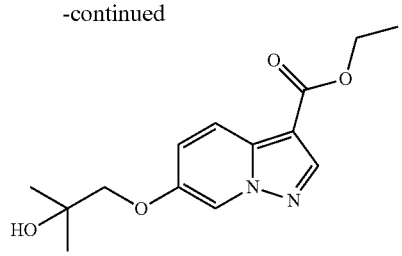

To a solution of Intermediate 51A (50 mg, 0.24 mmol) in acetonitrile (3 ml) and water (0.2 ml) was added $K_2CO_3$ (134 mg, 0.970 mmol) and 2,2-dimethyloxirane (0.646 ml, 7.27 mmol). The reaction mixture was heated to 120° C. by MW for 35 min, LCMS shows the reaction was completed with formation of desired product. Filtered and purified through prep HPLC to afford Intermediate 51B (51 mg, 76%). MS(ESI) 279.2 (M+H)$^+$; $^1$H NMR (400 MHz, chloroform-d) δ 8.35 (s, 1H), 8.34-8.31 (m, 1H), 8.11-8.04 (m, 1H), 7.29 (dd, J=9.6, 2.1 Hz, 1H), 4.39 (q, J=7.2 Hz, 2H), 3.86 (s, 2H), 1.45-1.39 (m, 9H)

Intermediate 51

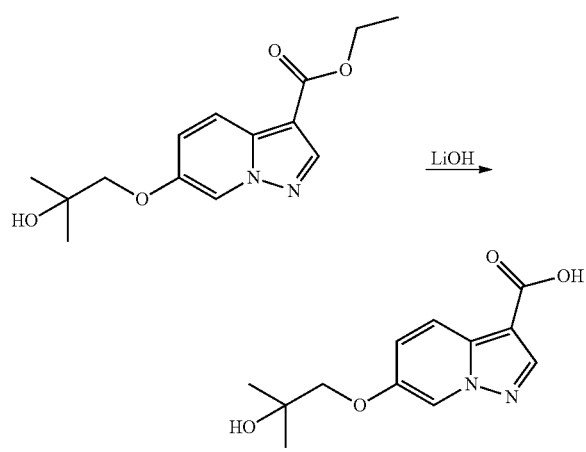

According to the procedure for preparation of Intermediate 17, saponification of Intermediate 51B (51 mg) with lithium hydroxide afforded Intermediate 51 (25 mg, 55%) as a white solid. MS(ESI) 251.2 (M+H)$^+$; $^1$H NMR (500 MHz, methanol-d$_4$) d 8.33 (dd, J=2.2, 0.6 Hz, 1H), 8.28 (s, 1H), 8.03 (dd, J=9.6, 0.6 Hz, 1H), 7.37 (dd, J=9.6, 1.9 Hz, 1H), 3.86 (s, 2H), 1.35 (s, 6H)

Intermediate 52: 6-(2-Methoxyethoxyl)pyrazolo[1,5-a]pyridine-3-carboxylic Acid

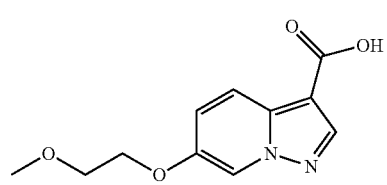 [SMILES: COCCOc1ccc2c(C(=O)O)cnn2c1]

Intermediate 52A: Ethyl 6-(2-methoxyethoxy)pyrazolo[1,5-a]pyridine-3-carboxylate

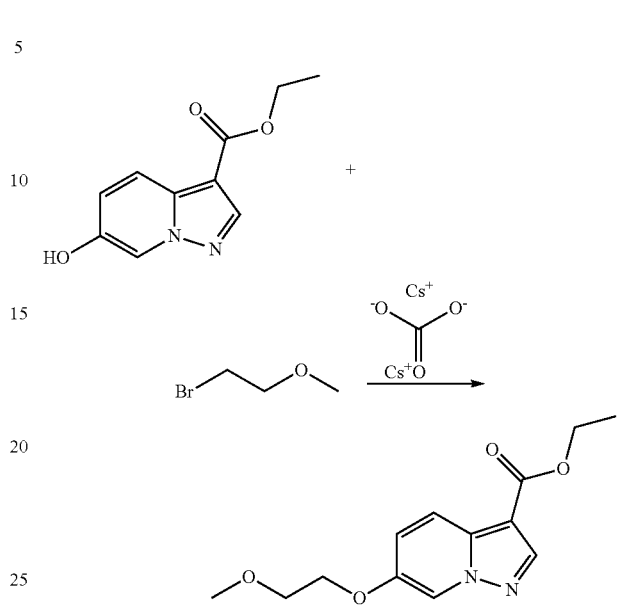

To a vial containing Intermediate 51A (30 mg, 0.145 mmol) in $CH_3CN$ (3 mL), were added 1-bromo-2-methoxyethane (30.3 mg, 0.218 mmol) and $Cs_2CO_3$ (95 mg, 0.29 mmol). The vial was sealed and the mixture was stirred at 70° C. for 3 h. LC/MS showed reaction completed. Filtered and concentrated. The residue was loaded onto 10 g column, eluted with EtOAc/Hex (0-50%); collected fraction at 30% EtOAc, concentrated to afford Intermediate 52A (25 mg, 65%). MS(ESI) 265.2 (M+H)$^+$; $^1$H NMR (500 MHz, methanol-d$_4$) d 8.35 (dd, J=2.2, 0.5 Hz, 1H), 8.27 (s, 1H), 8.03-7.99 (m, 1H), 7.34 (dd, J=9.6, 2.2 Hz, 1H), 4.35 (q, J=7.2 Hz, 2H), 4.22-4.15 (m, 2H), 3.82-3.74 (m, 2H), 3.50-3.41 (m, 3H), 1.40 (t, J=7.2 Hz, 3H).

Intermediate 52

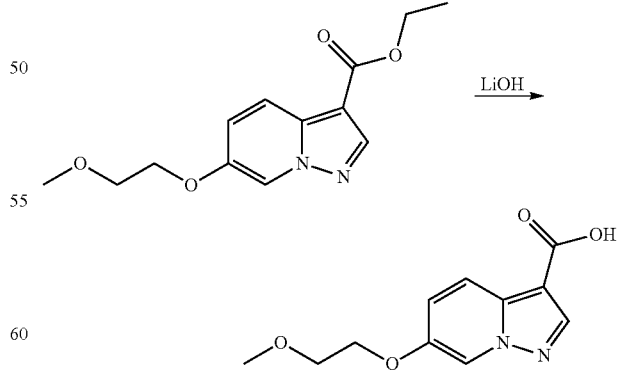

According to the procedure for preparation of Intermediate 17, saponification of Intermediate 52A (25 mg) with lithium hydroxide afforded Intermediate 52 (12 mg, 54%) as a white solid. MS(ESI) 237.1 (M+H)$^+$.

Intermediate 53: 6-(2-(Pyrrolidin-1-yl)ethoxy)pyrazolo[1,5-a]pyridine-3-carboxylic Acid

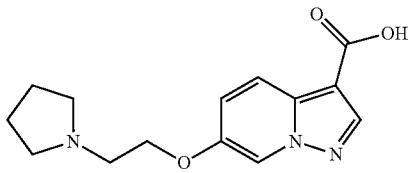 [SMILES: O=C(O)c1cnn2cc(OCCN3CCCC3)ccc12]

Intermediate 53A: Ethyl 6-(2-(pyrrolidin-1-yl)ethoxy)pyrazolo[1,5-a]pyridine-3-carboxylate

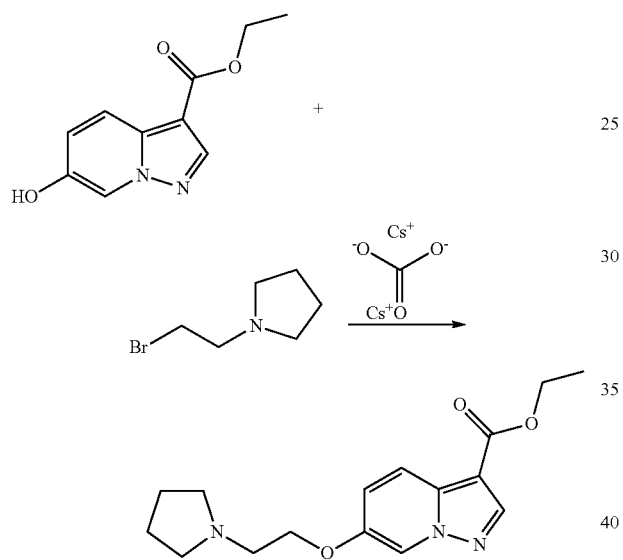

According to the procedure for preparation of Intermediate 52A, alkylation of Intermediate 51A (36 mg) with 1-(2-bromoethyl)pyrrolidine afforded Intermediate 53A (29 mg, 55%) as a white solid. MS(ESI) 304.2 (M+H)⁺; ¹H NMR (400 MHz, chloroform-d) d 8.39-8.25 (m, 3H), 8.07 (d, J=9.5 Hz, 1H), 7.21 (dd, J=9.7, 2.2 Hz, 1H), 4.44-4.38 (m, 3H), 4.38-4.33 (m, 1H), 4.06-3.94 (m, 2H), 3.69-3.62 (m, 2H), 3.05 (d, J=9.7 Hz, 2H), 2.17 (d, J=4.0 Hz, 4H), 1.41 (t, J=7.2 Hz, 3H).

Intermediate 53

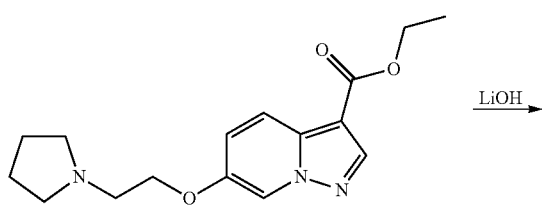

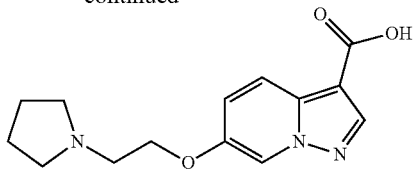

According to the procedure for preparation of Intermediate 17, saponification of Intermediate 53A (29 mg) with lithium hydroxide afforded Intermediate 53 (16 mg, 61%) as a white solid. MS(ESI) 276.2 (M+H)⁺; ¹H NMR (400 MHz, methanol-d₄) d 8.41 (d, J=1.5 Hz, 1H), 8.30 (s, 1H), 8.04 (d, J=9.5 Hz, 1H), 7.39 (dd, J=9.6, 2.1 Hz, 1H), 4.47-4.40 (m, 2H), 3.80 (d, J=7.5 Hz, 2H), 3.76-3.68 (m, 2H), 3.25 (br. s., 2H), 2.21-2.12 (m, 2H), 2.09 (br. s., 2H).

Intermediate 54: 6-(2-(Dimethylamino)ethoxy)pyrazolo[1,5-a]pyridine-3-carboxylic Acid

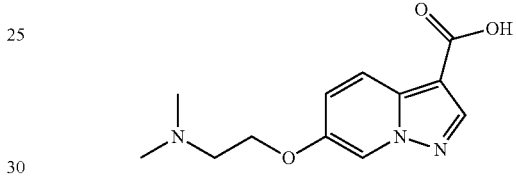

Intermediate 54A: Ethyl 6-(2-(dimethylamino)ethoxy)pyrazolo[1,5-a]pyridine-3-carboxylate

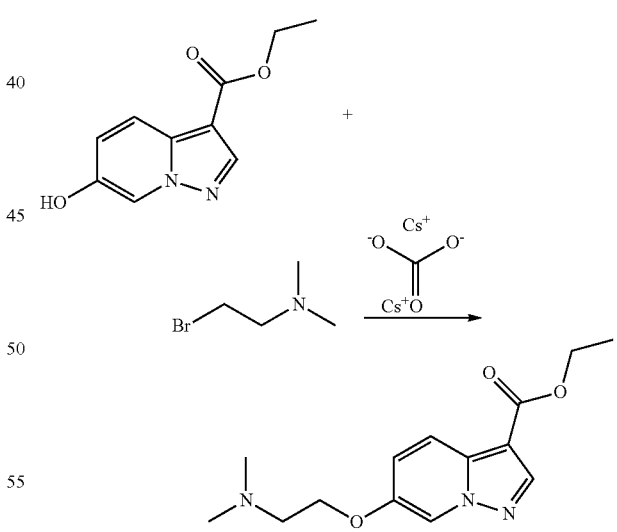

According to the procedure for preparation of Intermediate 52A, alkylation of Intermediate 51A (35 mg) with 2-bromo-N,N-dimethylethanamine afforded Intermediate 54A (20 mg, 43%) as a white solid. MS(ESI) 278.2 (M+H)⁺; ¹H NMR (500 MHz, methanol-d₄) d 8.47 (dd, J=2.2, 0.8 Hz, 1H), 8.32 (s, 1H), 8.07 (dd, J=9.6, 0.5 Hz, 1H), 7.42 (dd, J=9.6, 2.2 Hz, 1H), 4.52-4.42 (m, 2H), 4.36 (q, J=7.2 Hz, 2H), 3.70-3.61 (m, 2H), 3.06-2.99 (m, 6H), 1.45-1.35 (m, 3H).

Intermediate 54

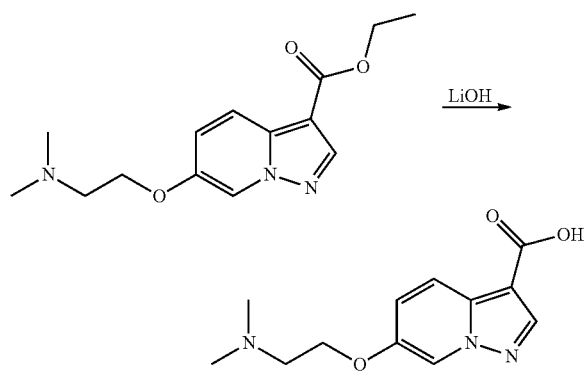

According to the procedure for preparation of Intermediate 17, saponification of Intermediate 54A (18 mg) with lithium hydroxide afforded Intermediate 54 (8 mg, 61%) as a white solid. MS(ESI) 250.2 (M+H)$^+$; $^1$H NMR (500 MHz, methanol-d$_4$) δ 8.47 (dd, J=2.2, 0.6 Hz, 1H), 8.32 (s, 1H), 8.11-8.07 (m, 1H), 7.41 (dd, J=9.6, 2.2 Hz, 1H), 4.49-4.40 (m, 2H), 3.71-3.60 (m, 2H), 3.02 (s, 6H).

Intermediate 55: 6-(2-Morpholinoethoxy)pyrazolo[1,5-a]pyridine-3-carboxylic Acid

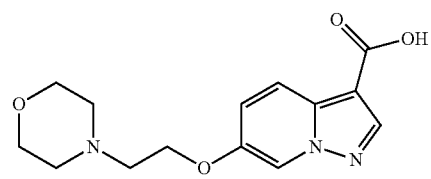 [SMILES: O=C(O)c1cnn2cc(OCCN3CCOCC3)ccc12]

Intermediate 55A: Ethyl 6-(2-morpholinoethoxyl)pyrazolo[1,5-a]pyridine-3-carboxylate

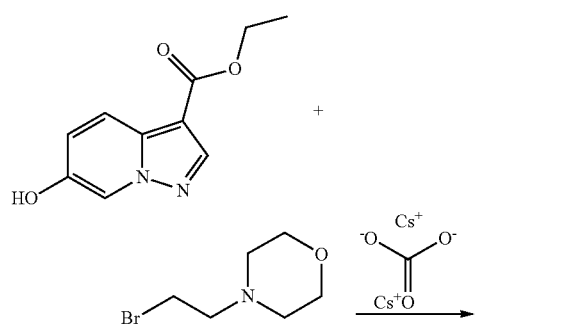

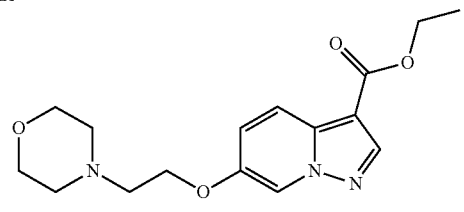

According to the procedure for preparation of Intermediate 52A, alkylation of Intermediate 51A (40 mg) with 4-(2-bromoethyl)morpholine afforded Intermediate 55A (47 mg, 76%) as a white solid. MS(ESI) 320.3 (M+H)$^+$; $^1$H NMR (400 MHz, chloroform-d) δ 8.30 (s, 1H), 8.13-8.10 (m, 1H), 8.02 (dd, J=9.7, 0.7 Hz, 1H), 7.20 (dd, J=9.7, 2.2 Hz, 1H), 4.36 (q, J=7.2 Hz, 2H), 4.11 (t, J=5.6 Hz, 2H), 3.77-3.69 (m, 4H), 2.83 (t, J=5.6 Hz, 2H), 2.61-2.53 (m, 4H), 1.40 (t, J=7.2 Hz, 3H).

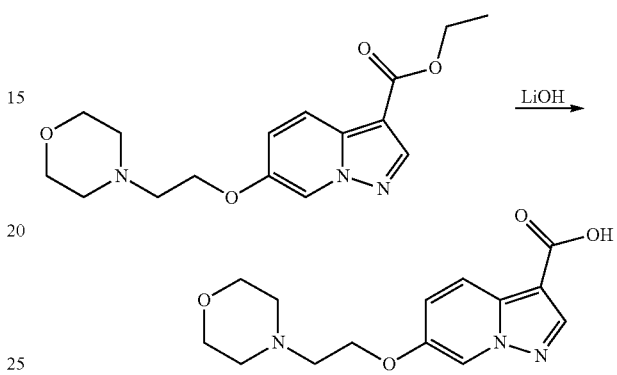

Intermediate 55

According to the procedure for preparation of Intermediate 17, saponification of Intermediate 55A (47 mg) with lithium hydroxide afforded Intermediate 55 (58 mg, 97%) as a white solid. MS(ESI) 320.3 (M+H)$^+$; $^1$H NMR (400 MHz, methanol-d$_4$) δ 8.38 (dd, J=2.2, 0.7 Hz, 1H), 8.32 (s, 1H), 8.09 (dd, J=9.7, 0.7 Hz, 1H), 7.36 (dd, J=9.7, 2.2 Hz, 1H), 4.51-4.43 (m, 2H), 3.97 (br. s., 4H), 3.72-3.64 (m, 2H), 3.61-3.35 (m, 4H).

Intermediate 56: 5-(2-Hydroxy-2-methylpropoxy)pyrazolo[1,5-a]pyridine-3-carboxylic Acid

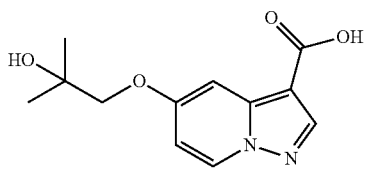 [SMILES: CC(C)(O)COc1ccn2ncc(C(=O)O)c2c1]

Intermediate 56A: Ethyl 5-hydroxypyrazolo[1,5-a]pyridine-3-carboxylate

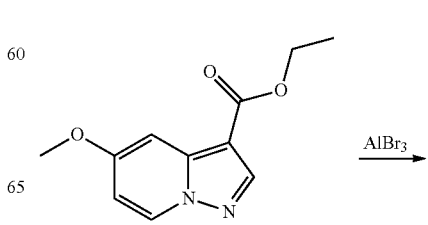

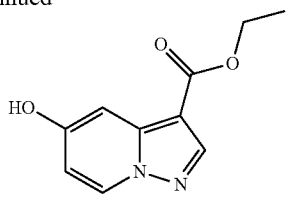

Ethyl 5-methoxypyrazolo[1,5-a]pyridine-3-carboxylate (300 mg, 1.36 mmol) was mixed with aluminum tribromide (1817 mg, 6.81 mmol) in EtSH (5 ml) and stirred at rt for 3 h. Cooled to 0° C., add MeOH dropwise, then water. Extracted with EtOAc. Concentrated and the residue was loaded onto 24 g column, eluted with EtOAc/Hex (0-40%); collected fraction at 30% EtOAc, concentrated to afford Intermediate 56A (90 mg, 32%). MS(ESI) 207.2 (M+H)$^+$; $^1$H NMR (400 MHz, methanol-$d_4$) d 8.42 (dd, J=7.5, 0.4 Hz, 1H), 8.21 (s, 1H), 7.41-7.27 (m, 1H), 6.67 (dd, J=7.5, 2.6 Hz, 1H), 4.32 (q, J=7.0 Hz, 2H), 1.39 (t, J=7.2 Hz, 3H).

Intermediate 56B: Ethyl 5-(2-hydroxy-2-methyl-propoxy)pyrazolo[1,5-a]pyridine-3-carboxylate

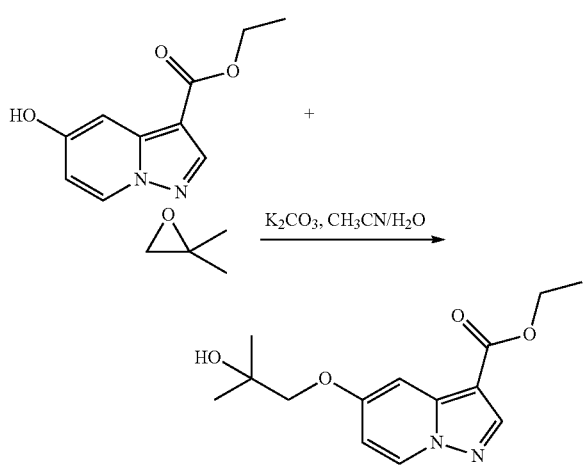

To a solution of Intermediate 56A (22 mg, 0.107 mmol) in acetonitrile (3 ml) and water (0.2 ml) was added K$_2$CO$_3$ (59.0 mg, 0.427 mmol) and 2,2-dimethyloxirane (0.142 ml, 1.600 mmol). The reaction mixture was heated to 120° C. by microwave for 30 min. Additional 2,2-dimethyloxirane (0.142 ml, 1.60 mmol) was added, and the mixture was stirred at 120° C. for 30 min. The mixture was concentrated and the residue was loaded onto 10 g column, eluted with EtOAc/Hex (0-40%); collected product at 30% EtOAc, concentrated to afford Intermediate 56B (27 mg, 91%). MS(ESI) 279.3 (M+H)$^+$.

Intermediate 56

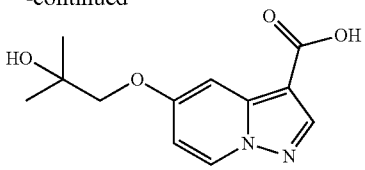

According to the procedure for preparation of Intermediate 17, saponification of Intermediate 56B (27 mg) with lithium hydroxide afforded Intermediate 56 (19 mg, 78%) as a white solid. MS(ESI) 251.1 (M+H)$^+$; $^1$H NMR (400 MHz, methanol-$d_4$) d 8.54-8.42 (m, 1H), 8.25 (s, 1H), 7.42 (d, J=2.6 Hz, 1H), 6.82 (dd, J=7.5, 2.6 Hz, 1H), 3.92 (s, 2H), 1.35 (s, 6H).

Intermediate 57: 5-Methoxypyrazolo[1,5-a]pyridine-3-carboxylic Acid

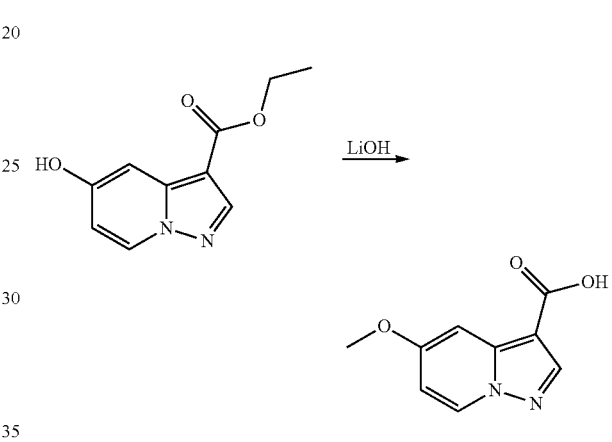

According to the procedure for preparation of Intermediate 17, saponification of ethyl 5-methoxypyrazolo[1,5-a]pyridine-3-carboxylate (19 mg) with lithium hydroxide afforded Intermediate 57 (16 mg, 97%) as a white solid. MS(ESI) 193.1 (M+H)$^+$.

Intermediate 58: 5-(2-(Pyrrolidin-1-yl)ethoxy)pyrazolo[1,5-a]pyridine-3-carboxylic Acid

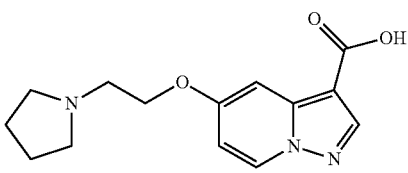 [SMILES: O=C(O)c1cnn2ccc(OCCN3CCCC3)cc12]

Intermediate 58A: Ethyl 5-(2-(pyrrolidin-1-yl)ethoxy)pyrazolo[1,5-a]pyridine-3-carboxylate

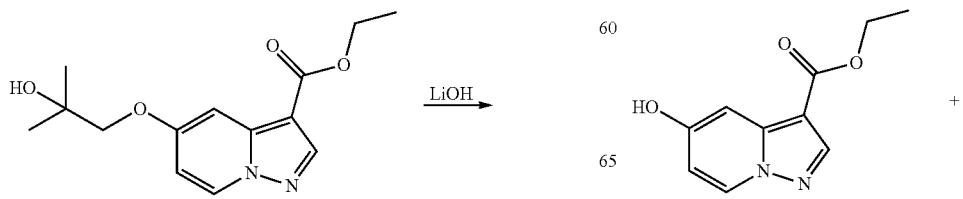

-continued

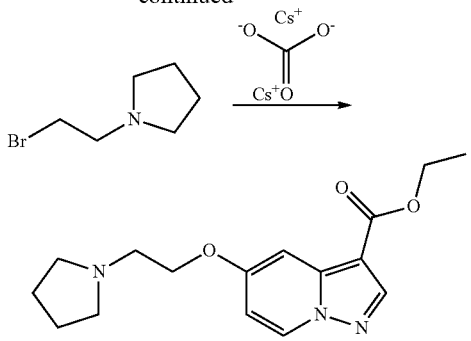

To a vial containing Intermediate 56A (45 mg, 0.22 mmol) in DMF (3 mL), were added 1-(2-bromoethyl)pyrrolidine, hydrobromide (85 mg, 0.33 mmol) and $Cs_2CO_3$ (213 mg, 0.655 mmol). The vial was sealed and the mixture was stirred at 70° C. for 16 h. LC/MS showed reaction completed. Filtered and concentrated. Purified through prep HPLC to afford Intermediate 58A (48 mg, 73%). MS(ESI) 304.3 $(M+H)^+$; $^1$H NMR (500 MHz, methanol-$d_4$) d 8.55 (dd, J=7.4, 0.6 Hz, 1H), 8.30 (s, 1H), 7.52 (d, J=2.8 Hz, 1H), 6.86 (dd, J=7.7, 2.8 Hz, 1H), 4.55-4.47 (m, 2H), 4.36 (q, J=7.0 Hz, 2H), 3.84-3.73 (m, 4H), 3.29-3.19 (m, 2H), 2.21 (br. s., 2H), 2.08 (br. s., 2H), 1.46-1.33 (m, 3H).

Intermediate 58

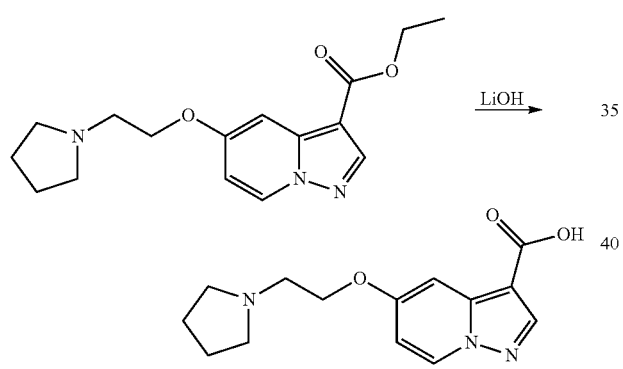

According to the procedure for preparation of Intermediate 17, saponification of Intermediate 58A (48 mg) with lithium hydroxide afforded Intermediate 58 (34 mg, 55%) as a white solid. MS(ESI) 276.3 $(M+H)^+$; $^1$H NMR (500 MHz, methanol-$d_4$) d ppm 8.54 (1H, dd, J=7.57, 0.69 Hz), 8.29 (1H, s), 7.5 (1H, d, J=2.75 Hz), 6.85 (1H, dd, J=7.43, 2.75 Hz), 4.44-4.56 (2H, m), 3.71-3.84 (4H, m), 3.26-3.28 (2H, m), 2.21 (2H, br. s.), 2.07 (2H, br. s.).

Intermediate 59: 5-(2-Methoxyethoxyl)pyrazolo[1,5-a]pyridine-3-carboxylic Acid

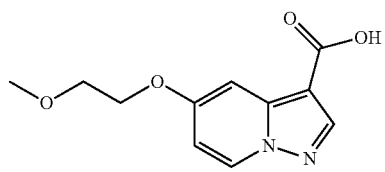 [SMILES: COCCOc1ccn2ncc(C(=O)O)c2c1]

Intermediate 59A: Ethyl 5-(2-methoxyethoxyl)pyrazolo[1,5-a]pyridine-3-carboxylate

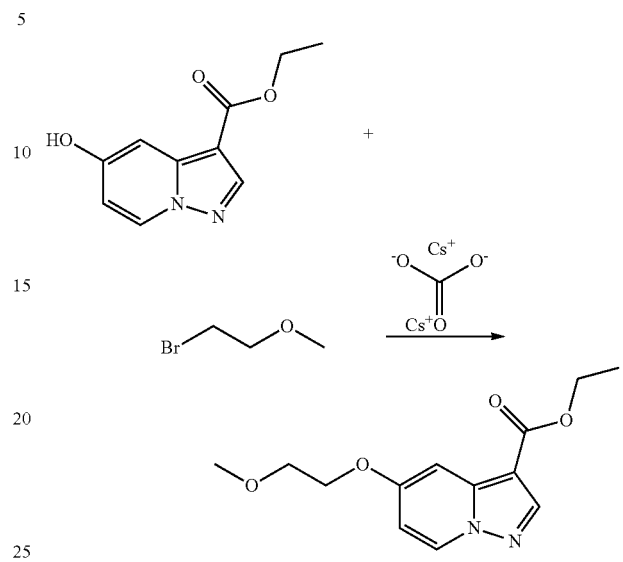

According to the procedure for preparation of Intermediate 58A, alkylation of Intermediate 56A (35 mg) with 1-bromo-2-methoxyethane afforded Intermediate 59A (37 mg, 82%) as a white solid. MS(ESI) 265.3 $(M+H)^+$; $^1$H NMR (500 MHz, chloroform-d) d 8.31 (dd, J=7.4, 0.5 Hz, 1H), 8.27 (s, 1H), 7.42 (d, J=2.8 Hz, 1H), 6.66 (dd, J=7.4, 2.8 Hz, 1H), 4.35 (q, J=7.0 Hz, 2H), 4.28-4.17 (m, 2H), 3.85-3.74 (m, 2H), 3.51-3.42 (m, 3H), 1.39 (t, J=7.2 Hz, 3H).

Intermediate 59

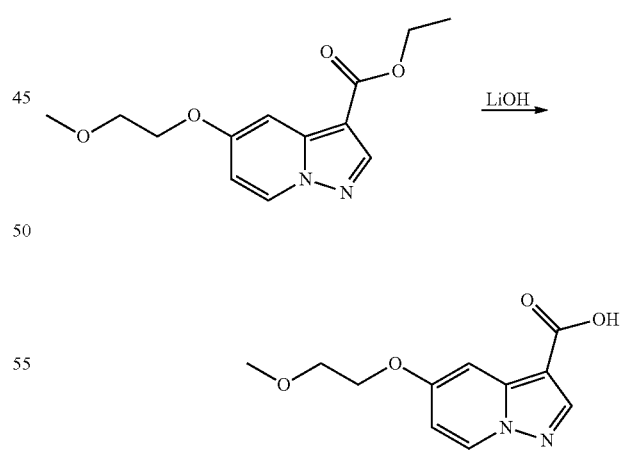

According to the procedure for preparation of Intermediate 17, saponification of Intermediate 59A (37 mg) with lithium hydroxide afforded Intermediate 59 (28 mg, 85%) as a white solid. MS(ESI) 237.3 $(M+H)^+$; $^1$H NMR (400 MHz, methanol-$d_4$) d 8.47 (dd, J=7.6, 0.5 Hz, 1H), 8.26 (s, 1H), 7.44 (d, J=2.6 Hz, 1H), 6.77 (dd, J=7.5, 2.6 Hz, 1H), 4.31-4.19 (m, 2H), 3.90-3.75 (m, 2H), 3.47-3.39 (m, 3H).

Intermediate 60: 5-(2-Morpholinoethoxy)pyrazolo[1,5-a]pyridine-3-carboxylic Acid

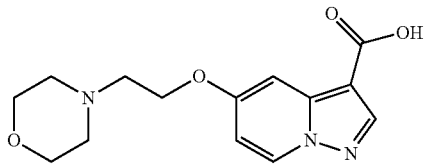

Intermediate 60A: Ethyl 5-(2-morpholinoethoxyl)pyrazolo[1,5-a]pyridine-3-carboxylate

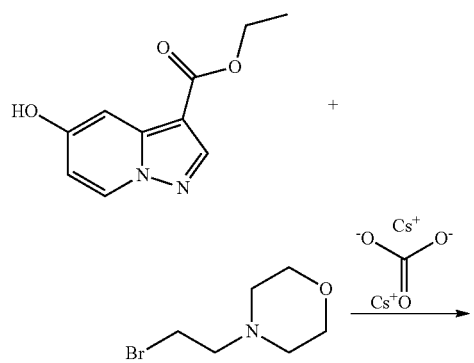

According to the procedure for preparation of Intermediate 58A, alkylation of Intermediate 56A (40 mg) with 4-(2-bromoethyl)morpholine afforded Intermediate 60A (51 mg, 82%) as a white solid. MS(ESI) 320.3 (M+H)$^+$; $^1$H NMR (400 MHz, chloroform-d) δ 8.30 (dd, J=7.5, 0.7 Hz, 1H), 8.25 (s, 1H), 7.40 (d, J=2.6 Hz, 1H), 6.60 (dd, J=7.5, 2.6 Hz, 1H), 4.33 (q, J=7.0 Hz, 2H), 4.19 (t, J=5.6 Hz, 2H), 3.78-3.67 (m, 4H), 2.83 (t, J=5.6 Hz, 2H), 2.61-2.53 (m, 4H), 1.37 (t, J=7.2 Hz, 3H).

Intermediate 60

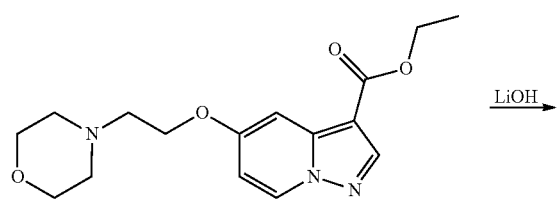

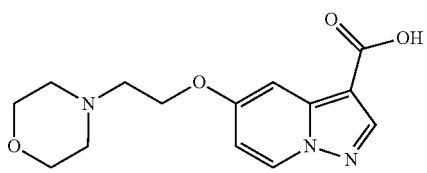 [SMILES: O=C(O)c1cnn2ccc(OCCN3CCOCC3)cc12]

According to the procedure for preparation of Intermediate 17, saponification of Intermediate 60A (51 mg) with lithium hydroxide afforded Intermediate 60 (60 mg, 93%) as a white solid. MS(ESI) 292.3 (M+H)$^+$; $^1$H NMR (400 MHz, methanol-d$_4$) d 8.53 (dd, J=7.6, 0.5 Hz, 1H), 8.29 (s, 1H), 7.50 (d, J=2.6 Hz, 1H), 6.83 (dd, J=7.5, 2.6 Hz, 1H), 4.58-4.51 (m, 2H), 4.05 (br. s., 2H), 3.88 (br. s., 2H), 3.78-3.70 (m, 2H), 3.65-3.48 (m, 2H), 3.45-3.34 (m, 2H).

Intermediate 61: 5-(2-Hydroxypropoxy)pyrazolo[1,5-a]pyridine-3-carboxylic Acid

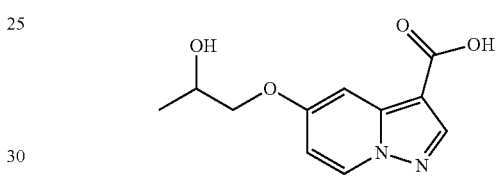

Intermediate 61A: Ethyl 5-(2-hydroxypropoxy)pyrazolo[1-5-a]pyridine-3-carboxylate

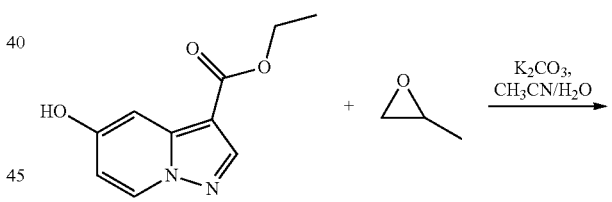

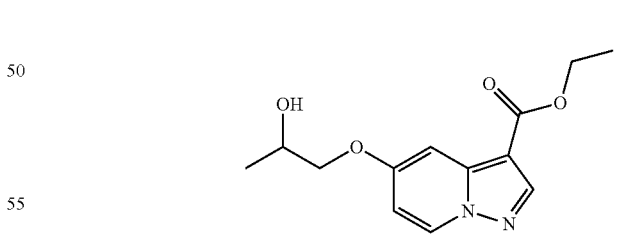

To a solution of Intermediate 56A (41 mg, 0.20 mmol) in acetonitrile (3 ml) and water (0.2 ml) was added K$_2$CO$_3$ (137 mg, 0.994 mmol) and 2-methyloxirane (0.417 ml, 5.97 mmol). The reaction mixture was heated to 120° C. on MW for 30 min. Reaction is completed. Concentrated and the residue was loaded onto 10 g column, eluted with EtOAc/Hex (0-50%); collected fraction at 30% EtOAc, concentrated to afford Intermediate 61A (26 mg, 50%). MS(ESI) 265.2 (M+H)$^+$.

Intermediate 61

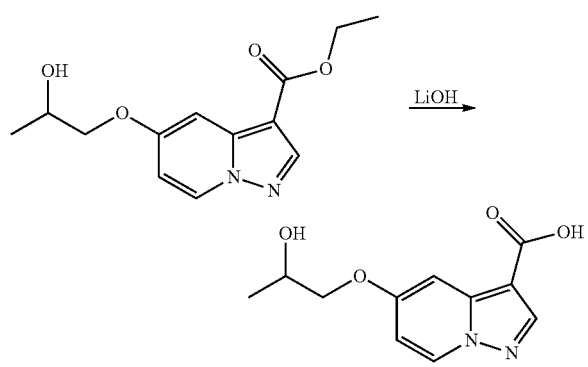

According to the procedure for preparation of Intermediate 17, saponification of Intermediate 61A (26 mg) with lithium hydroxide afforded Intermediate 61 (21 mg, 82%) as a white solid. MS(ESI) 265.2 (M+H)$^+$; $^1$H NMR (400 MHz, methanol-$d_4$) d 8.46 (dd, J=7.6, 0.6 Hz, 1H), 8.27-8.23 (m, 1H), 7.41 (d, J=2.6 Hz, 1H), 6.84-6.75 (m, 1H), 4.17 (td, J=6.5, 4.0 Hz, 1H), 4.08-3.90 (m, 2H), 1.38-1.23 (m, 3H).

Intermediate 62: 5-(2-Hydroxyethoxyl)pyrazolo[1,5-a]pyridine-3-carboxylic Acid

Intermediate 62A: Methyl 5-(2-(benzyloxy)ethoxy)pyrazolo[1,5-a]pyridine-3-carboxylate

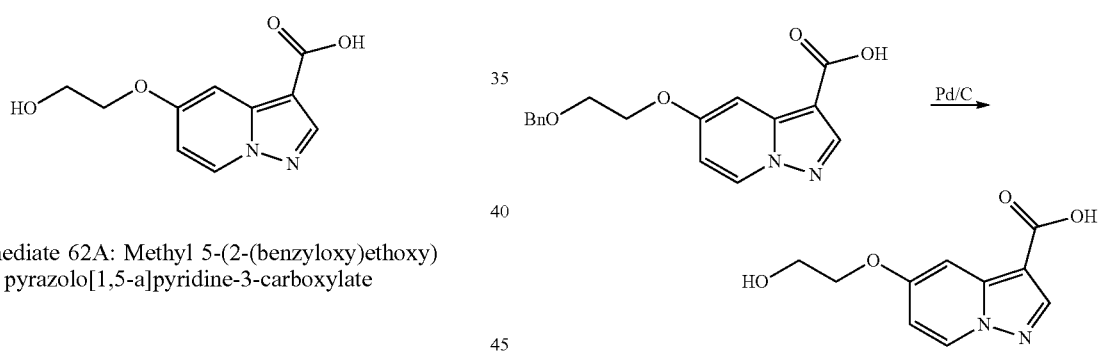

According to the procedure for preparation of Intermediate 58A, alkylation of methyl 5-hydroxypyrazolo[1,5-a]pyridine-3-carboxylate (43 mg) with ((2-bromoethoxy)methyl)benzene afforded Intermediate 62A (71 mg, 99%). MS(ESI) 327.3 (M+H)$^+$.

Intermediate 62B: 5-(2-(Benzyloxy)ethoxy)pyrazolo[1,5-a]pyridine-3-carboxylic Acid

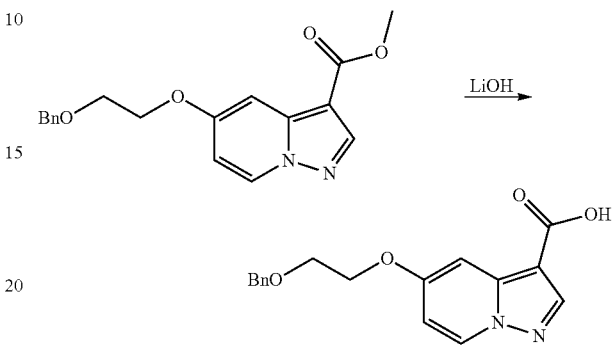

According to the procedure for preparation of Intermediate 17, saponification of Intermediate 62A (75 mg) with lithium hydroxide afforded Intermediate 62B (46 mg, 64%) as a white solid. MS(ESI) 313.2 (M+H)$^+$.

Intermediate 62

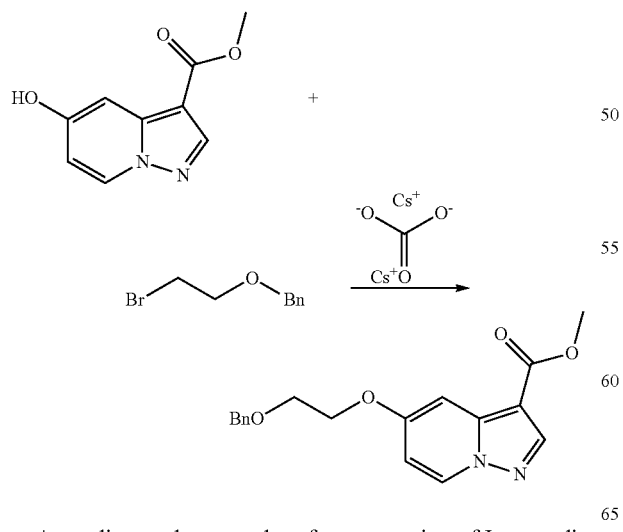

Intermediate 62B (43 mg, 0.138 mmol) was mixed with MeOH (5 mL), degassed, add 10% Pd/C (ca. 20 mg), stirred under H$_2$ balloon o/n for 16 h. Filtered and concentrated to afford Intermediate 62 (26 mg, 85%). MS(ESI) 223.2 (M+H)$^+$; $^1$H NMR (400 MHz, methanol-$d_4$) d 8.46 (d, J=7.7 Hz, 1H), 8.25 (s, 1H), 7.42 (d, J=2.6 Hz, 1H), 6.78 (dd, J=7.6, 2.8 Hz, 1H), 4.25-4.14 (m, 2H), 3.97-3.87 (m, 2H).

Intermediate 63: 5-(2-Hydroxy-3-methoxypropoxy)pyrazolo[1,5-a]pyridine-3-carboxylic Acid

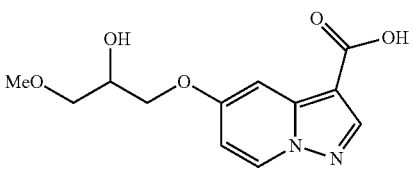 [SMILES: COCC(O)COc1ccn2ncc(C(=O)O)c2c1]

Intermediate 63A: Ethyl 5-(2-hydroxy-3-methoxy-propoxy)pyrazolo[1,5-a]pyridine-3-carboxylate

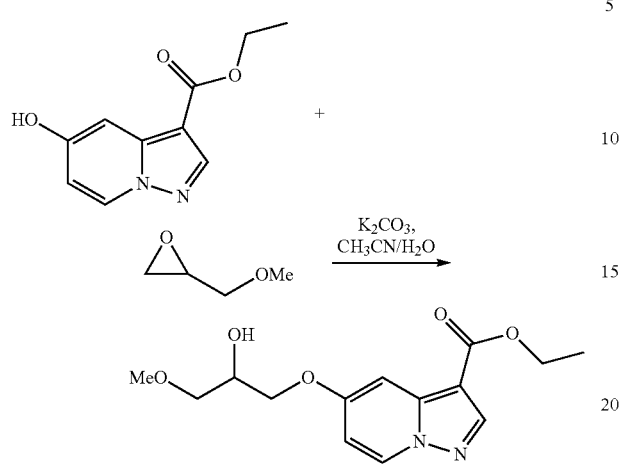

To a solution of Intermediate 56A (38 mg, 0.184 mmol) in acetonitrile (3 ml) and water (0.2 ml) was added K$_2$CO$_3$ (102 mg, 0.737 mmol) and 2-(methoxymethyl)oxirane (487 mg, 5.53 mmol). The reaction mixture was heated to 120° C. on MW for 35 min, LCMS shows the reaction was complete with formation of desired product. Filtered and purified through prep HPLC to afford Intermediate 63A (30 mg, 55%). MS(ESI) 295.2 (M+H)$^+$.

Intermediate 63

According to the procedure for preparation of Intermediate 17, saponification of Intermediate 63A (60 mg) with lithium hydroxide afford Intermediate 63 (47 mg, 87%) as a white solid. MS(ESI) 267.1 (M+H)$^+$; $^1$H NMR (500 MHz, methanol-d$_4$) δ 8.48-8.45 (m, 1H), 8.26 (s, 1H), 7.43 (d, J=2.8 Hz, 1H), 6.78 (dd, J=7.4, 2.8 Hz, 1H), 4.24-4.06 (m, 3H), 3.60-3.53 (m, 2H), 3.46-3.38 (m, 3H).

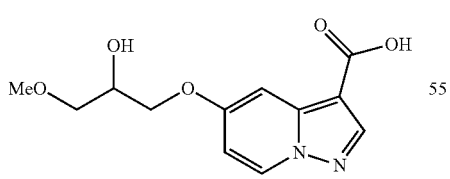

Intermediate 66: 4-(4-Aminophenyl)isoquinolin-1(2H)-one, TFA

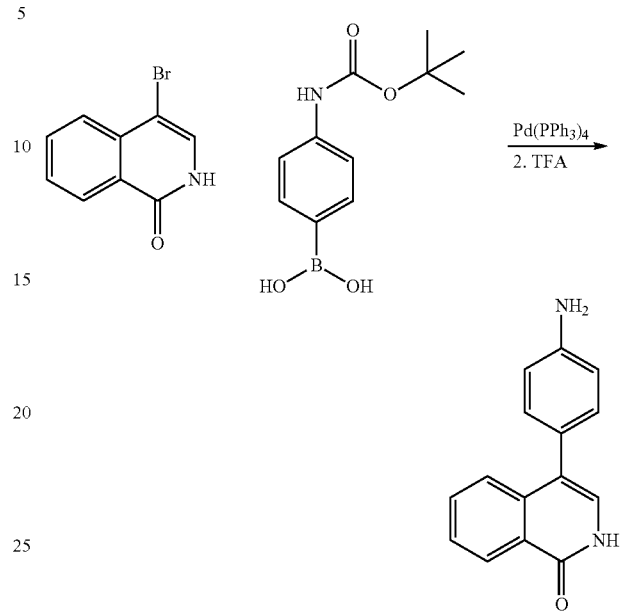

To 4-bromoisoquinolin-1(2H)-one (166 mg, 0.741 mmol), (4-((tert-butoxycarbonyl)amino)phenyl)boronic acid (176 mg, 0.741 mmol) and K$_3$PO$_4$ (393 mg, 1.85 mmol), were added dioxane (9 mL) and water (1 mL). The mixture was degassed (evacuated and flushed with Ar (5×)). Pd(PPh$_3$)$_4$ (43 mg, 0.037 mmol) was added, then the mixture was degassed (2×). The reaction vial was sealed and heated in a microwave reactor at 150° C. for 40 min. The reaction mixture was concentrated, then the residue was purified by flash chromatography (0-100% EtOAc/Hex). The product was dissolved in DCM (2 mL), then was treated with TFA (1 mL). The mixture was stirred rt for 1 h, concentrated and purified via preparative HPLC to afford Intermediate 66 (117 mg, 45% yield). MS(ESI) m/z: 237.1 (M+H)$^+$; $^1$H NMR (500 MHz, methanol-d$_4$) δ 8.41 (dd, J=8.0, 0.8 Hz, 1H), 7.70 (ddd, J=8.3, 7.0, 1.5 Hz, 1H), 7.61-7.50 (m, 5H), 7.49-7.42 (m, 2H), 7.14 (s, 1H), 3.35 (s, 1H).

Intermediate 67: 2-(4-(1-Oxo-1,2-dihydroisoquinolin-4-yl)phenyl)acetic Acid

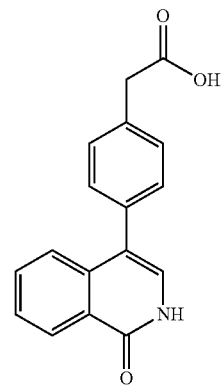

Intermediate 67A: Ethyl 2-(4-(1-oxo-1,2-dihydroisoquinolin-4-yl)phenyl)acetate

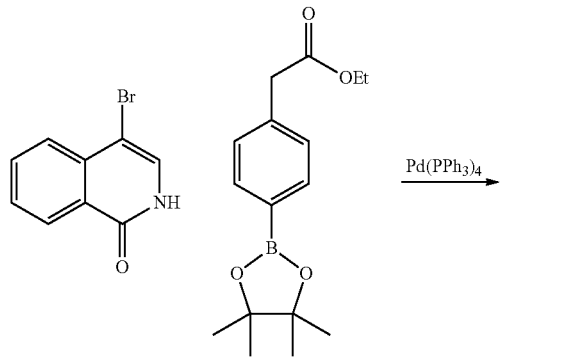

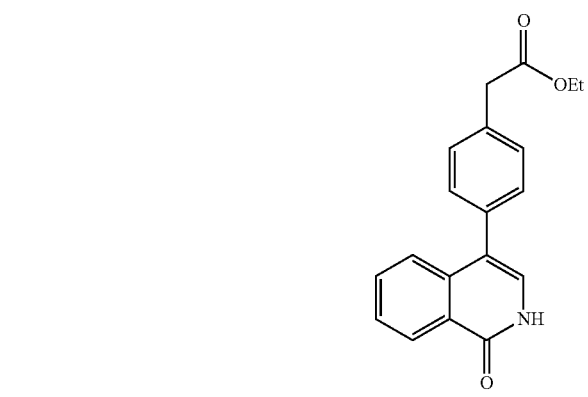

To 4-bromoisoquinolin-1(2H)-one (166 mg, 0.741 mmol), Intermediate 1A (215 mg, 0.741 mmol) and K₃PO₄ (393 mg, 1.85 mmol), were added dioxane (9 mL) and water (1 mL). The mixture was degassed (evacuated and flushed with Ar (5×)). Pd(PPh₃)₄ (43 mg, 0.037 mmol) was added, then the mixture was degassed (2×). The reaction vial was sealed and heated in a microwave reactor at 150° C. for 40 min. The reaction mixture was concentrated, then was purified via prep HPLC to afford Intermediate 67A (21 mg, 9.2% yield). MS(ESI) m/z: 308.1 (M+H)⁺.

Intermediate 67

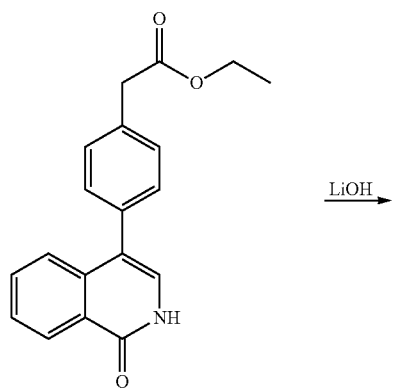

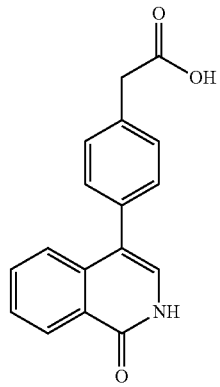 [SMILES: O=C(O)Cc1ccc(-c2c[nH]c(=O)c3ccccc23)cc1]

A solution of Intermediate 67A (21 mg, 0.068 mmol) in THF, was treated with 1M lithium hydroxide (0.2 ml, 0.200 mmol). The mixture was stirred rt for 16 h, then was concentrated. The residue was purified via preparative HPLC to afford Intermediate 67 (13 mg, 68% yield). MS(ESI) m/z: 280.1 (M+H)⁺; ¹H NMR (500 MHz, DMSO-d₆) δ 12.40 (br. s., 1H), 11.43 (d, J=5.2 Hz, 1H), 8.30 (dd, J=7.8, 1.0 Hz, 1H), 7.69 (ddd, J=8.1, 7.0, 1.4 Hz, 1H), 7.57-7.49 (m, 2H), 7.42-7.33 (m, 5H), 7.08 (d, J=5.8 Hz, 1H), 3.31 (br. s., 2H).

Intermediate 68: 4-Bromo-6,7-dimethoxyisoquinolin-1(2H)-one

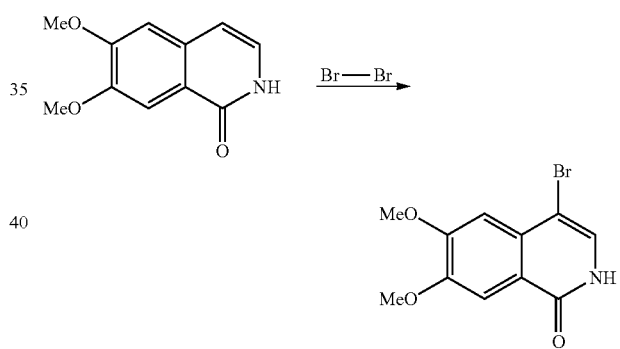

To a solution of 6,7-dimethoxyisoquinolin-1(2H)-one (205 mg, 1.00 mmol) in AcOH (2 mL), was add bromine (192 mg, 1.199 mmol) in AcOH (1 mL). The mixture was stirred rt for 1 h, then poured onto ice and extracted with EtOAc. The organic phase was washed with brine, then was concentrated. The product was purified by flash chromatography (0-80% EtOAc/Hex) to afford Intermediate 68 (230 mg, 0.81 mmol, 81% yield) as white form. MS(ESI) m/z: 283.9 (M+H)⁺; ¹H NMR (500 MHz, DMSO-d₆) δ 11.42 (br. s., 1H), 7.62 (s, 1H), 7.44 (br. s., 1H), 7.13 (s, 1H), 3.94 (s, 3H), 3.89 (s, 3H).

Intermediate 69: 6-Isopropoxyindoline

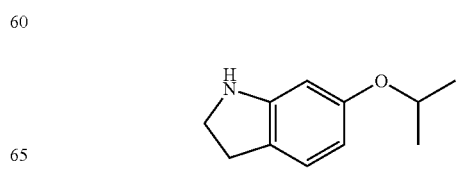

Intermediate 69A: 6-(Benzyloxy)indoline

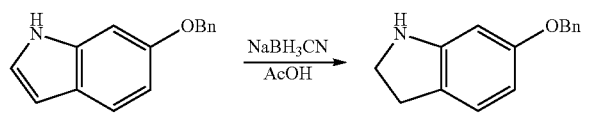 [SMILES: "AcOH" ; c1ccc(COc2ccc3cc[nH]c3c2)cc1 ; "NaBH3CN" ; c1ccc(COc2ccc3c(c2)NCC3)cc1]

To a solution of 6-(benzyloxy)-1H-indole (580 mg, 2.60 mmol) in EtOH (5 mL) at 0° C., was added Sodium cyanoborohydride (326 mg, 5.20 mmol). The mixture was stirred rt for 16 h then was concentrated. The residue was purified via prep HPLC to afford Example 69A (280 mg; 32% yield) as a yellow oil. MS(ESI) m/z: 226.1 (M+H)$^+$; $^1$H NMR (500 MHz, chloroform-d) δ 10.54 (br. s., 2H), 7.46-7.32 (m, 5H), 7.26 (d, J=8.5 Hz, 1H), 7.13 (d, J=2.2 Hz, 1H), 6.99 (dd, J=8.5, 2.2 Hz, 1H), 4.99 (s, 2H), 3.97-3.84 (m, 2H), 3.23 (t, J=7.6 Hz, 2H).

Intermediate 69B: tert-Butyl 6-(benzyloxy)indoline-1-carboxylate

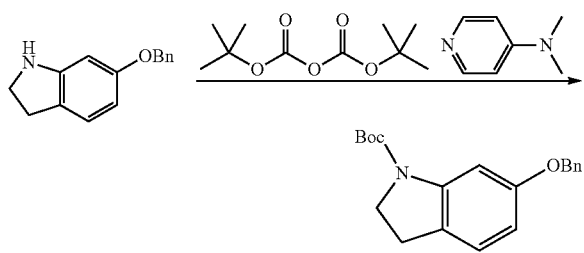

To a mixture of Intermediate 69A (270 mg, 1.20 mmol) and Boc$_2$O (0.334 mL, 1.44 mmol) in THF at rt, was added cat. DMAP. The resulting mixture was stirred rt for 16 h, then was concentrated and. The residue was purified via flash chromatography (0-50% EtOAc/Hex) to afford Intermediate 69B (150 mg; 39% yield). MS(ESI) m/z: 326.1 (M+H)$^+$; $^1$H NMR (500 MHz, chloroform-d) δ 7.54-7.46 (m, 2H), 7.45-7.37 (m, 2H), 7.36-7.31 (m, 1H), 7.04 (d, J=8.0 Hz, 1H), 6.60 (dd, J=8.1, 2.3 Hz, 1H), 5.10 (s, 2H), 4.10-3.91 (m, 2H), 3.04 (t, J=8.7 Hz, 2H), 1.71-1.55 (m, 9H).

Intermediate 69C: tert-Butyl 6-hydroxyindoline-1-carboxylate

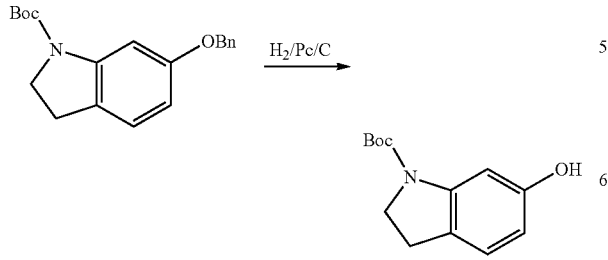

To a degassed solution of Intermediate 69B (140 mg, 0.43 mmol) in MeOH (5 mL) was added 10% Pd/C (30 mg). The mixture was stirred under H$_2$ (balloon) for 4 h. The mixture was filtered and concentrated to afford Intermediate 69C (90 mg; 89% yield) as white solid. MS(ESI) m/z: 236.1 (M+H)$^+$; $^1$H NMR (500 MHz, methanol-d$_4$) δ 7.32-7.12 (m, 1H), 6.93-6.85 (m, 1H), 6.41-6.30 (m, 1H), 3.95-3.85 (m, 2H), 3.01-2.88 (m, 2H), 1.54 (br. s., 9H).

Intermediate 69D: tert-Butyl 6-isopropoxyindoline-1-carboxylate

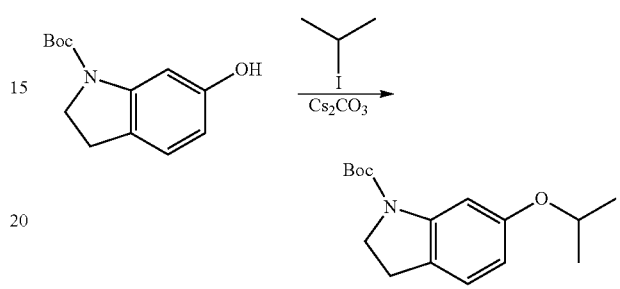

Intermediate 69C (45 mg, 0.19 mmol) was mixed with 2-iodopropane (163 mg, 0.956 mmol), Cs$_2$CO$_3$ (93 mg, 0.287 mmol) in DMF (3 mL). The mixture was stirred at 80° C. for 16 h, then was concentrated. The residue was purified via flash chromatography (0-40% EtOAc/Hex) to afford Intermediate 69D (35 mg; 66% yield) as colorless foam. MS(ESI) m/z: 277.9 (M+H)$^+$; $^1$H NMR (500 MHz, methanol-d$_4$) δ 7.50-7.26 (m, 1H), 7.01-6.95 (m, 1H), 6.46 (dd, J=8.3, 2.5 Hz, 1H), 4.50 (dt, J=11.9, 6.0 Hz, 1H), 3.99-3.83 (m, 2H), 3.03-2.92 (m, 2H), 1.64-1.48 (m, 9H), 1.32-1.25 (m, 6H).

Intermediate 69

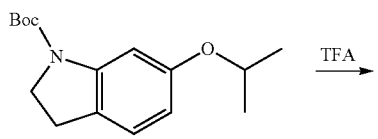

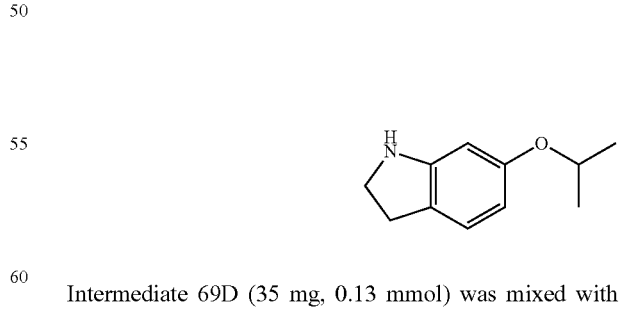

Intermediate 69D (35 mg, 0.13 mmol) was mixed with TFA (0.5 mL) and DCM (1 mL), and stirred rt for 20 min. The mixture was concentrated to afford Intermediate 69 (36 mg; 99% yield) as a colorless foam. MS(ESI) m/z: 177.9 (M+H)$^+$; $^1$H NMR (500 MHz, methanol-d$_4$) δ 7.40-7.31 (m, 1H), 7.05-6.95 (m, 2H), 4.61 (dt, J=12.1, 6.1 Hz, 1H), 3.86 (t, J=7.7 Hz, 2H), 3.24 (t, J=7.7 Hz, 2H), 1.34-1.27 (m, 6H).

Intermediate 70: 1-(Isoindolin-2-yl)-2-(3-methyl-4-(4,4,5,5-tetramethyl-1,3,2-dioxaborolan-2-yl)phenyl)ethanone

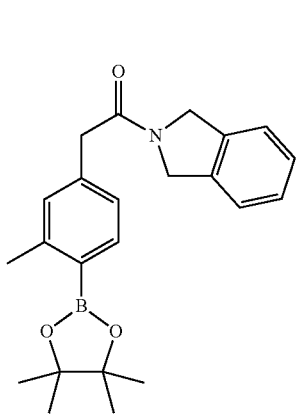 [SMILES: Cc1cc(CC(=O)N2Cc3ccccc3C2)ccc1B1OC(C)(C)C(C)(C)O1]

Intermediate 70A: 2-(4-Bromo-3-methylphenyl)-1-(isoindolin-2-yl)ethanone

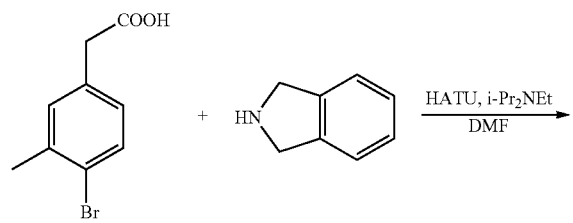

To a solution of 2-(4-bromo-3-methylphenyl)acetic acid (200 mg, 0.87 mmol), isoindoline (0.109 mL, 0.96 mmol), and DIEA (0.305 mL, 1.75 mmol) in DMF (3 mL), was add HATU (398 mg, 1.05 mmol). The mixture was stirred at rt for 19 h. The reaction mixture was diluted with EtOAc, then was washed with H$_2$O, sat. Na$_2$CO$_3$ and brine. The organic phase was dried (Na$_2$SO$_4$) and concentrated. The crude product was purified by flash chromatography to afford Intermediate 70A (128 mg, 44% yield) as an off-white solid. MS(ESI) 329.9 (M+H)$^+$; $^1$H NMR (400 MHz, chloroform-d) δ 7.48 (d, J=8.1 Hz, 1H), 7.32-7.27 (m, 3H), 7.25-7.20 (m, 2H), 7.01 (dd, J=8.1, 1.8 Hz, 1H), 4.82 (d, J=5.3 Hz, 4H), 3.69 (s, 2H), 2.38 (s, 3H).

Intermediate 70

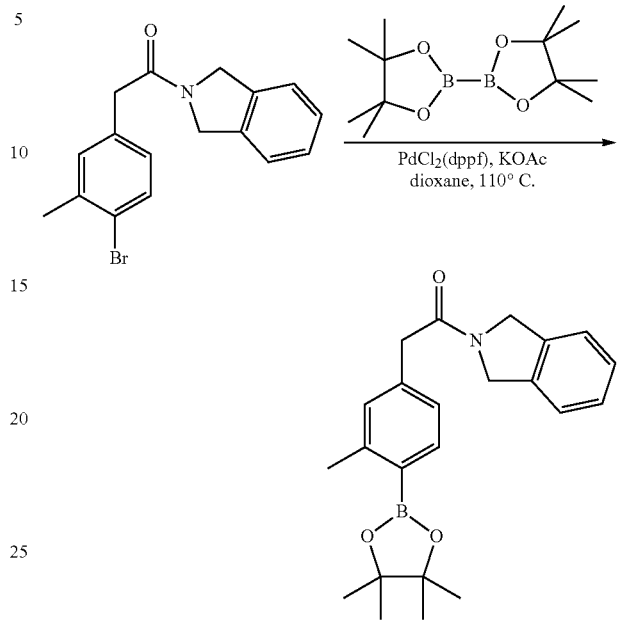

To a degassed (evacuated and flushed with Ar (3×)) mixture of Intermediate 70A (128 mg, 0.388 mmol), 4,4,4',4',5,5,5',5'-octamethyl-2,2'-bi(1,3,2-dioxaborolane) (118 mg, 0.465 mmol) and potassium acetate (114 mg, 1.16 mmol) in dioxane (2 mL), was added PdCl$_2$(dppf) CH$_2$Cl$_2$ adduct (15.8 mg, 0.019 mmol). The mixture was degassed (2×), then the vial was sealed and stirred at 110° C. for 2.5 h. The reaction mixture was diluted with EtOAc and was washed with H$_2$O and brine. The organic phase was dried (Na$_2$SO$_4$), filtered through a 1" pad of SiO$_2$ and concentrated. The crude product was purified by flash chromatography (gradient from 0 to 100% ethyl acetate/hexanes) to afford Intermediate 70 (126 mg, 86% yield) as a yellow solid. MS(ESI) 378.1 (M+H)$^+$; $^1$H NMR (400 MHz, chloroform-d) δ 7.73 (d, J=7.7 Hz, 1H), 7.32-7.23 (m, 3H), 7.21-7.10 (m, 3H), 4.82 (s, 2H), 4.75 (s, 2H), 3.75 (s, 2H), 2.52 (s, 3H), 1.32 (s, 12H).

Intermediate 71: 1-(Indolin-1-yl)-2-(3-methyl-4-(4,4,5,5-tetramethyl-1,3,2-dioxaborolan-2-yl)phenyl)ethanone

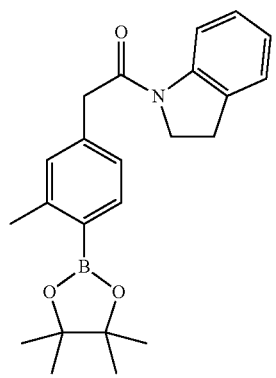 [SMILES: Cc1cc(CC(=O)N2CCc3ccccc32)ccc1B1OC(C)(C)C(C)(C)O1]

According to the procedure the preparation of Intermediate 70, substituting indoline for isoindoline afforded Intermediate 71. MS(ESI) 378.1 (M+H)⁺; ¹H NMR (400 MHz, chloroform-d) δ 8.26 (d, J=7.9 Hz, 1H), 7.73 (d, J=7.5 Hz, 1H), 7.23-7.07 (m, 4H), 7.04-6.96 (m, 1H), 4.01 (t, J=8.5 Hz, 2H), 3.78 (s, 2H), 3.13 (t, J=8.5 Hz, 2H), 2.52 (s, 3H), 1.33 (s, 12H).

Intermediate 72: 2-(3-Fluoro-4-(4,4,5,5-tetramethyl-1,3,2-dioxaborolan-2-yl)phenyl)-1-(indolin-1-yl)ethanone

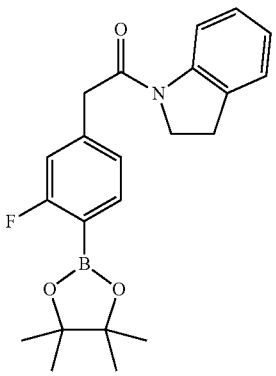 [SMILES: CC1(C)OB(c2ccc(CC(=O)N3CCc4ccccc43)cc2F)OC1(C)C]

According to the procedure the preparation of Intermediate 5, substituting indoline for isoindoline afforded Intermediate 72. MS(ESI) 382.1 (M+H)⁺; ¹H NMR (400 MHz, chloroform-d) δ 8.24 (d, J=8.1 Hz, 1H), 7.71 (dd, J=7.5, 6.6 Hz, 1H), 7.23-7.13 (m, 2H), 7.11 (d, J=7.7 Hz, 1H), 7.06-6.99 (m, 2H), 4.03 (t, J=8.5 Hz, 2H), 3.82 (s, 2H), 3.16 (t, J=8.5 Hz, 2H), 1.35 (s, 12H).

Intermediate 73: 4-Bromo-6-methoxyisoquinolin-1(2H)-one

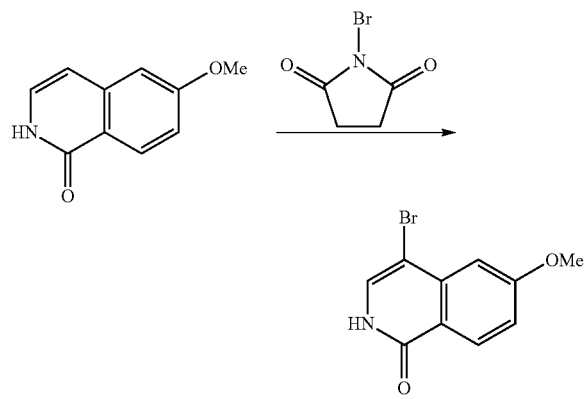

To a solution of 6-methoxyisoquinolin-1(2H)-one (112 mg, 0.639 mmol) in DMF (2 mL), was added NBS (137 mg, 0.767 mmol). The mixture was stirred at rt overnight, then was concentrated. The residue was purified via prep HPLC to afford Intermediate 73 (120 mg, 74% yield) as white solid. MS(ESI) m/z: 253.9 (M+H)⁺; ¹H NMR (400 MHz, DMSO-d₆) δ 11.41 (br. s., 1H), 8.16 (d, J=8.8 Hz, 1H), 7.53 (d, J=4.4 Hz, 1H), 7.18 (dd, J=8.8, 2.4 Hz, 1H), 7.11 (d, J=2.4 Hz, 1H), 3.99-3.87 (m, 3H).

Intermediate 74: 1-(Indolin-6-yloxy)-2-methylpropan-2-ol, TFA

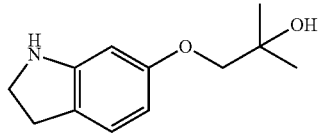

Intermediate 74A: tert-Butyl 6-(2-hydroxy-2-methylpropoxy)indoline-1-carboxylate

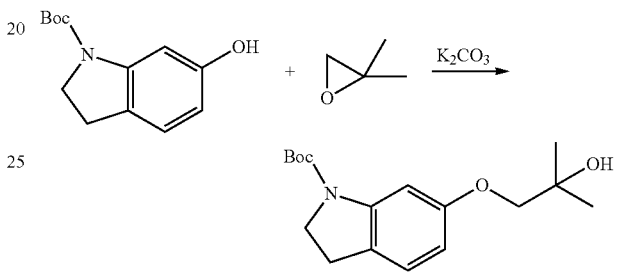

To a mixture of Intermediate 69C (12 mg, 0.051 mmol) and 2,2-dimethyloxirane (37 mg, 0.51 mmol) in acetonitrile (1 mL), was added K₂CO₃ (35 mg, 0.26 mmol) in water (0.1 mL). The mixture was stirred in a sealed tube at 100° C. for 3 h, then was concentrated. The residue was purified via flash chromatography (0-40% EtOAc/Hex) to afford Intermediate 74A (12 mg, 64% yield). MS(ESI) m/z: 308.2 (M+H). ¹H NMR (500 MHz, chloroform-d) δ 7.61-7.46 (m, 1H), 7.02 (d, J=8.0 Hz, 1H), 6.50 (dd, J=8.1, 2.3 Hz, 1H), 3.99 (t, J=8.3 Hz, 2H), 3.80 (s, 2H), 3.07-2.96 (m, 2H), 1.59 (d, J=18.4 Hz, 9H), 1.33 (s, 6H).

Intermediate 74

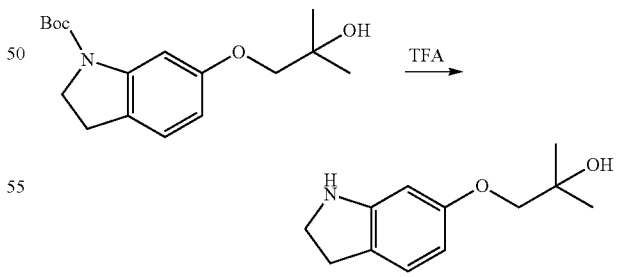

Intermediate 74A (12 mg, 0.039 mmol) was stirred with TFA (0.5 mL) and DCM (0.5 mL) for 20 min, then was concentrated to afford Intermediate 74 (12 mg, 96% yield). MS(ESI) m/z: 208.2 (M+H)⁺; ¹H NMR (500 MHz, methanol-d₄) δ 7.41-7.32 (m, 1H), 7.07-6.97 (m, 2H), 3.84 (t, J=7.7 Hz, 2H), 3.81 (s, 2H), 3.24 (t, J=7.7 Hz, 2H), 1.32 (s, 6H).

Intermediate 75: 6-(Pyridin-3-ylmethoxy)indoline, 2TFA

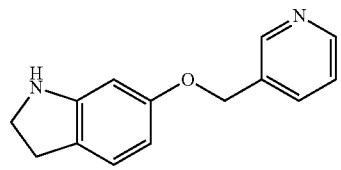 [SMILES: c1cncc(COc2ccc3c(c2)NCC3)c1]

Intermediate 75A: tert-Butyl 6-(pyridin-3-ylmethoxy)indoline-1-carboxylate

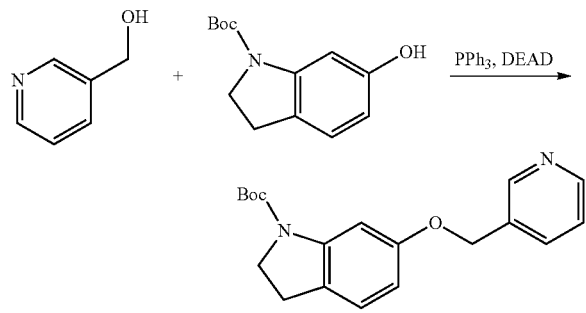

To a solution of pyridin-3-ylmethanol (26.4 mg, 0.242 mmol), Intermediate 69C (38 mg, 0.162 mmol), and triphenylphosphine (106 mg, 0.404 mmol) in THF (3 mL), was added DEAD (0.064 mL, 0.404 mmol). The reaction was stirred at rt overnight. The mixture was purified by preparative HPLC to afford Intermediate 75A (42 mg, 59% yield) as a white solid. MS(ESI) m/z: 327.1 (M+H)$^+$; $^1$H NMR (500 MHz, chloroform-d) δ 15.42 (br. s., 1H), 8.91 (s, 1H), 8.81 (d, J=5.2 Hz, 1H), 8.35 (d, J=8.0 Hz, 1H), 7.82 (dd, J=8.0, 5.5 Hz, 1H), 7.63 (br. s., 1H), 7.05 (d, J=8.3 Hz, 1H), 6.54 (d, J=7.2 Hz, 1H), 5.23 (s, 2H), 4.00 (t, J=8.5 Hz, 2H), 3.04 (t, J=8.5 Hz, 2H), 1.56 (br. s., 9H).

Intermediate 75

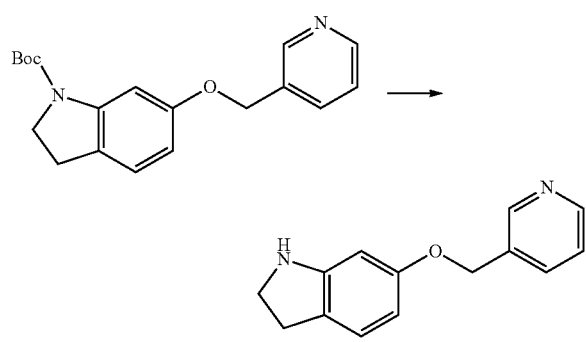

Intermediate 75A (45 mg, 0.102 mmol) was stirred with TFA (1 mL) and DCM (2 mL) at rt for 20 min, then was concentrated to afford Intermediate 75 (47 mg, 100% yield) as a yellow oil. MS(ESI) m/z: 227.1 (M+H)$^+$; $^1$H NMR (500 MHz, methanol-d$_4$) δ 9.01 (s, 1H), 8.85 (d, J=5.5 Hz, 1H), 8.70 (d, J=8.5 Hz, 1H), 8.10 (dd, J=8.0, 5.8 Hz, 1H), 7.45 (d, J=8.5 Hz, 1H), 7.24 (d, J=2.2 Hz, 1H), 7.21 (dd, J=8.5, 2.5 Hz, 1H), 5.40 (s, 2H), 3.94-3.85 (m, 2H), 3.28 (t, J=7.7 Hz, 2H).

Intermediate 76: 6-(Pyridin-2-ylmethoxy)indoline, 2TFA

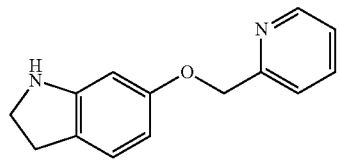 [SMILES: c1ccc(COc2ccc3c(c2)NCC3)nc1]

According to the procedure for the preparation of Intermediate 75, substituting pyridin-2-ylmethanol for pyridin-3-ylmethanol afforded Intermediate 76. MS(ESI) m/z: 227.1 (M+H)$^+$; $^1$H NMR (500 MHz, methanol-d$_4$) δ 8.82 (dd, J=5.5, 0.8 Hz, 1H), 8.48 (td, J=7.8, 1.7 Hz, 1H), 8.07 (d, J=7.7 Hz, 1H), 7.98-7.82 (m, 1H), 7.46 (d, J=8.5 Hz, 1H), 7.35-7.14 (m, 2H), 5.56-5.39 (m, 2H), 3.93-3.82 (m, 2H), 3.30-3.25 (m, 2H).

Intermediate 77: 6-(Pyridin-4-ylmethoxy)indoline, 2TFA

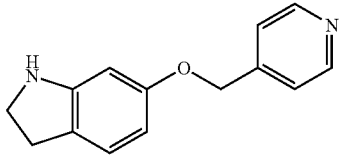 [SMILES: c1cc(COc2ccc3c(c2)NCC3)ccn1]

According to the procedure for the preparation of Intermediate 75, substituting pyridin-4-ylmethanol for pyridin-3-ylmethanol afforded Intermediate 77. MS(ESI) m/z: 227.1 (M+H)$^+$; $^1$H NMR (500 MHz, methanol-d$_4$) δ 8.94-8.84 (m, 2H), 8.22-8.15 (m, 2H), 7.48-7.41 (m, 1H), 7.25 (d, J=2.2 Hz, 1H), 7.21 (dd, J=8.5, 2.5 Hz, 1H), 5.51 (s, 2H), 3.93-3.87 (m, 2H), 3.28 (t, J=7.7 Hz, 2H).

Intermediate 78: (R)-6-((Tetrahydrofuran-3-yl)oxy)indoline, TFA

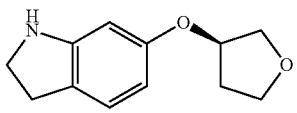 [SMILES: c1cc2c(cc1O[C@@H]1CCOC1)NCC2]

According to the procedure for the preparation of Intermediate 75, substituting (S)-tetrahydrofuran-3-ol for pyridin-3-ylmethanol afforded Intermediate 78. MS(ESI) m/z: 206.1 (M+H)$^+$; $^1$H NMR (500 MHz, methanol-d$_4$) δ 7.38 (d, J=8.3 Hz, 1H), 7.05 (d, J=2.2 Hz, 1H), 7.01 (dd, J=8.5, 2.2 Hz, 1H), 5.03 (qd, J=4.0, 1.5 Hz, 1H), 4.02-3.79 (m, 6H), 3.25 (t, J=7.7 Hz, 2H), 2.32-2.21 (m, 1H), 2.12-2.04 (m, 1H).

Intermediate 79:
(S)-6-((Tetrahydrofuran-3-yl)oxy)indoline, TFA

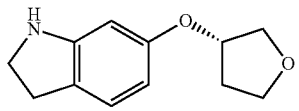 [SMILES: c1cc2c(cc1O[C@H]1CCOC1)NCC2]

According to the procedure for the preparation of Intermediate 75, substituting (R)-tetrahydrofuran-3-ol for pyridin-3-ylmethanol afforded Intermediate 79. MS(ESI) m/z: 206.1 (M+H)$^+$; $^1$H NMR (500 MHz, methanol-$d_4$) δ 7.40-7.35 (m, 1H), 7.08-6.97 (m, 2H), 4.05-3.81 (m, 6H), 3.25 (t, J=7.7 Hz, 2H), 2.38-2.23 (m, 1H), 2.17-2.03 (m, 1H).

Intermediate 80: (R)-6-((1-Methylpyrrolidin-3-yl)oxy)indoline, 2TFA

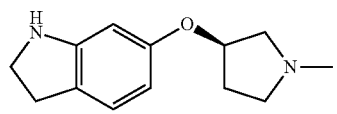 [SMILES: CN1CC[C@@H](Oc2ccc3c(c2)NCC3)C1]

According to the procedure for the preparation of Intermediate 75, substituting (S)-1-methylpyrrolidin-3-ol for pyridin-3-ylmethanol afforded Intermediate 80. MS(ESI) m/z: 219.1 (M+H)$^+$; $^1$H NMR (500 MHz, methanol-$d_4$) δ 7.46-7.39 (m, 1H), 7.17-7.11 (m, 1H), 7.10-7.03 (m, 1H), 5.24 (br. s., 1H), 3.98-3.79 (m, 4H), 3.50-3.35 (m, 1H), 3.27 (t, J=7.7 Hz, 2H), 3.01 (br. s., 3H), 2.68 (br. s., 1H), 2.49-2.33 (m, 1H), 2.27 (br. s., 1H).

Intermediate 81: (S)-6-((1-Methylpyrrolidin-3-yl)oxy)indoline, 2TFA

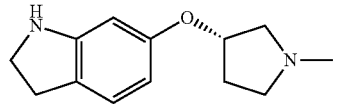 [SMILES: CN1CC[C@H](Oc2ccc3c(c2)NCC3)C1]

According to the procedure for the preparation of Intermediate 75, substituting (R)-1-methylpyrrolidin-3-ol for pyridin-3-ylmethanol afforded Intermediate 81. MS(ESI) m/z: 219.1 (M+H)$^+$.

Intermediate 82:
2-(Indolin-6-yloxy)-N,N-dimethylethanamine, 2TFA

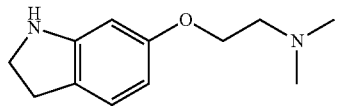

According to the procedure for the preparation of Intermediate 75, substituting 2-(dimethylamino)ethanol for pyridin-3-ylmethanol afforded Intermediate 82. MS(ESI) m/z: 207.2 (M+H)$^+$.

Intermediate 83:
6-((1-Methylpiperidin-4-yl)oxy)indoline, 2TFA

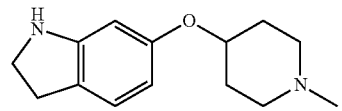 [SMILES: CN1CCC(Oc2ccc3c(c2)NCC3)CC1]

According to the procedure for the preparation of Intermediate 75, substituting 1-methylpiperidin-4-ol for pyridin-3-ylmethanol afforded Intermediate 83. MS(ESI) m/z: 233.2 (M+H)$^+$.

Intermediate 84: Methyl 2-(indolin-6-yloxy)acetate

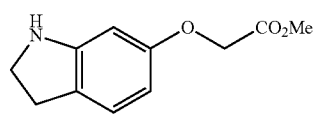 [SMILES: COC(=O)COc1ccc2c(c1)NCC2]

According to the procedure for the preparation of Intermediate 69, substituting methyl 2-bromoacetate for 2-iodopropane afforded Intermediate 84. MS(ESI) m/z: 208.1 (M+H)$^+$; $^1$H NMR (500 MHz, methanol-$d_4$) δ 7.38 (d, J=8.5 Hz, 1H), 7.05 (d, J=2.2 Hz, 1H), 7.02 (dd, J=8.4, 2.3 Hz, 1H), 4.77 (s, 2H), 3.86 (t, J=7.7 Hz, 2H), 3.78-3.75 (m, 3H), 3.24 (t, J=7.7 Hz, 2H).

Intermediate 85: 6-(Oxetan-3-ylmethoxy)indoline, TFA

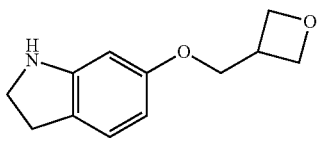 [SMILES: c1cc2c(cc1OCC1COC1)NCC2]

According to the procedure for the preparation of Intermediate 75, substituting 3-(bromomethyl)oxetane for pyridin-3-ylmethanol afforded Intermediate 85. MS(ESI) m/z: 206.1 (M+H)$^+$.

Intermediate 86:
6-(2-(Pyrrolidin-1-yl)ethoxy)indoline, 2TFA

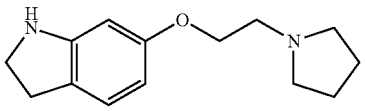 [SMILES: c1cc2c(cc1OCCN1CCCC1)NCC2]

According to the procedure for the preparation of Intermediate 69, substituting methyl 1-(2-bromoethyl)pyrrolidine, hydrobromide for 2-iodopropane afforded Intermediate 86. MS(ESI) m/z: 233.1 (M+H)$^+$.

Intermediate 87: 1-(6-(2-Hydroxy-2-methylpropoxy) indolin-1-yl)-2-(4-(4,4,5,5-tetramethyl-1,3,2-dioxaborolan-2-yl)phenyl)ethanone Intermediate 87

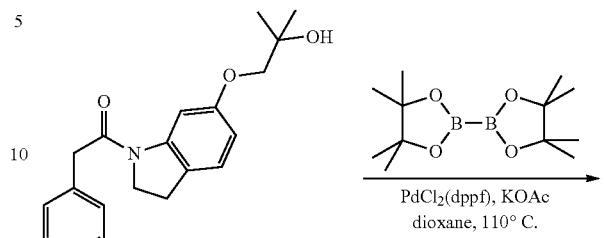

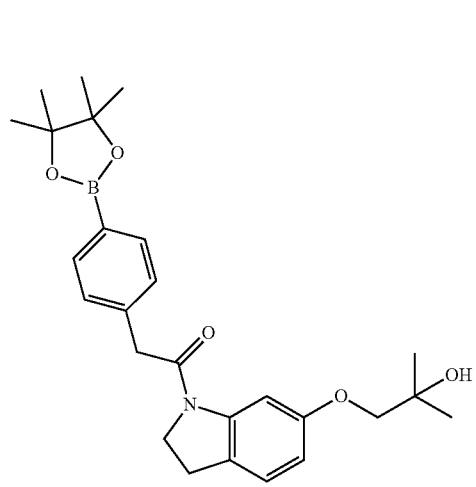 [SMILES: CC(C)(O)COc1ccc2c(c1)N(C(=O)Cc1ccc(B3OC(C)(C)C(C)(C)O3)cc1)CC2]

Intermediate 87A: 2-(4-Bromophenyl)-1-(6-(2-hydroxy-2-methylpropoxy)indolin-1-yl)ethanone

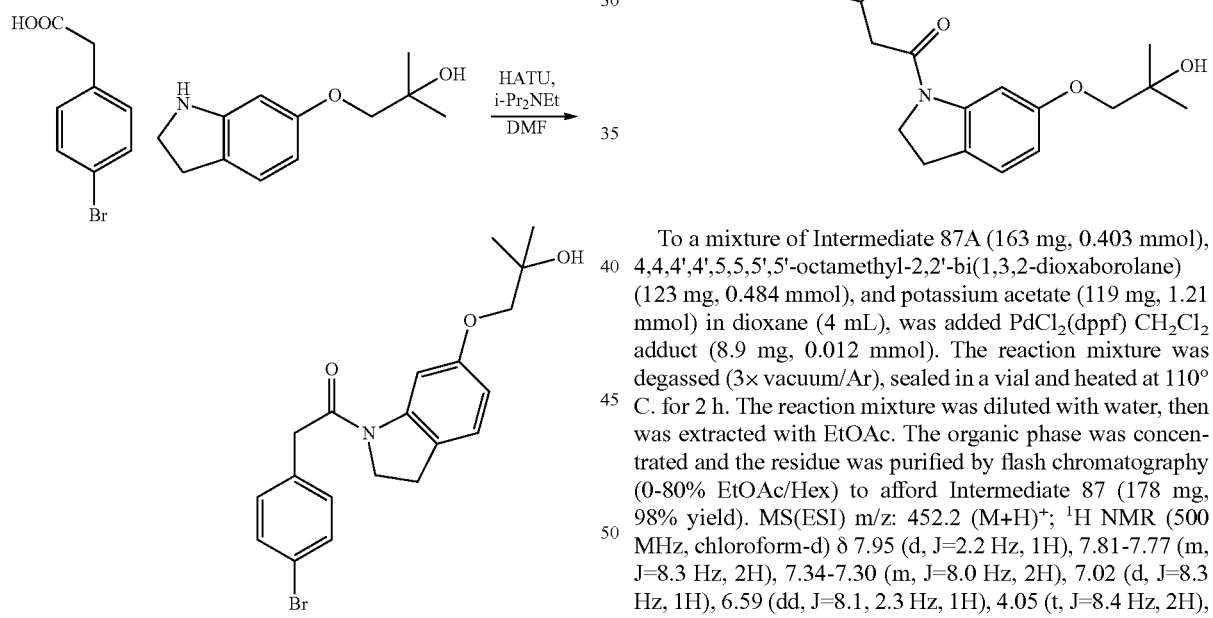

To a mixture of Intermediate 87A (163 mg, 0.403 mmol), 4,4,4',4',5,5,5',5'-octamethyl-2,2'-bi(1,3,2-dioxaborolane) (123 mg, 0.484 mmol), and potassium acetate (119 mg, 1.21 mmol) in dioxane (4 mL), was added PdCl$_2$(dppf) CH$_2$Cl$_2$ adduct (8.9 mg, 0.012 mmol). The reaction mixture was degassed (3× vacuum/Ar), sealed in a vial and heated at 110° C. for 2 h. The reaction mixture was diluted with water, then was extracted with EtOAc. The organic phase was concentrated and the residue was purified by flash chromatography (0-80% EtOAc/Hex) to afford Intermediate 87 (178 mg, 98% yield). MS(ESI) m/z: 452.2 (M+H)$^+$; $^1$H NMR (500 MHz, chloroform-d) δ 7.95 (d, J=2.2 Hz, 1H), 7.81-7.77 (m, J=8.3 Hz, 2H), 7.34-7.30 (m, J=8.0 Hz, 2H), 7.02 (d, J=8.3 Hz, 1H), 6.59 (dd, J=8.1, 2.3 Hz, 1H), 4.05 (t, J=8.4 Hz, 2H), 3.80 (d, J=13.2 Hz, 4H), 3.07 (t, J=8.3 Hz, 2H), 1.34 (s, 12H), 1.24-1.22 (m, 6H).

To a mixture of 2-(4-bromophenyl)acetic acid (92 mg, 0.43 mmol), Intermediate 74 (138 mg, 0.43 mmol), and HATU (245 mg, 0.644 mmol) in DMF (5 mL), was add DIEA (0.375 mL, 2.15 mmol). The mixture was stirred rt for 16 h. The reaction mixture was concentrated and the residue was purified by flash chromatography (0-80% EtOAc/Hex) to afford Intermediate 87A (162 mg, 93% yield) as a colorless foam. MS(ESI) m/z: 404.0 (M+H)$^+$; $^1$H NMR (500 MHz, chloroform-d) δ 7.93 (d, J=2.2 Hz, 1H), 7.49-7.44 (m, 2H), 7.20-7.14 (m, J=8.3 Hz, 2H), 7.04 (d, J=8.3 Hz, 1H), 6.60 (dd, J=8.3, 2.2 Hz, 1H), 4.11-4.02 (m, 2H), 3.77 (s, 2H), 3.72 (s, 2H), 3.10 (t, J=8.4 Hz, 2H), 1.36-1.28 (m, 6H).

Intermediate 88:
N,N-Dimethylindoline-6-carboxamide, TFA

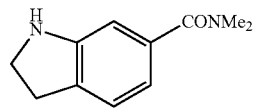

Intermediate 88A: N,N-Dimethyl-1H-indole-6-carboxamide

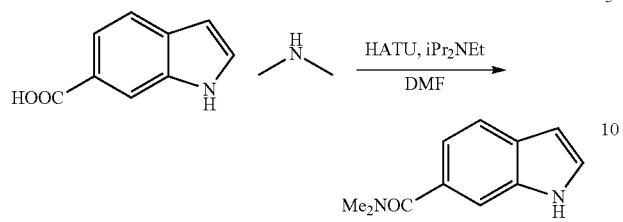

To a mixture of 1H-indole-6-carboxylic acid (110 mg, 0.683 mmol), dimethylamine, HCl (83 mg, 1.024 mmol), and HATU (389 mg, 1.024 mmol) in DMF (3 mL), was added DIEA (0.596 mL, 3.41 mmol). The mixture was stirred rt for 2 h, then was concentrated. The mixture was purified by prep HPLC to afford Intermediate 88A (125 mg, 97% yield). MS(ESI) m/z: 189.0 (M+H)$^+$; $^1$H NMR (500 MHz, chloroform-d) δ 9.56 (br. s., 1H), 7.61 (d, J=8.0 Hz, 1H), 7.38-7.34 (m, 1H), 7.24-7.19 (m, 1H), 7.12 (dd, J=8.1, 1.5 Hz, 1H), 6.53-6.48 (m, 1H), 3.27-3.05 (m, 3H), 2.99 (br. s., 3H).

Intermediate 88

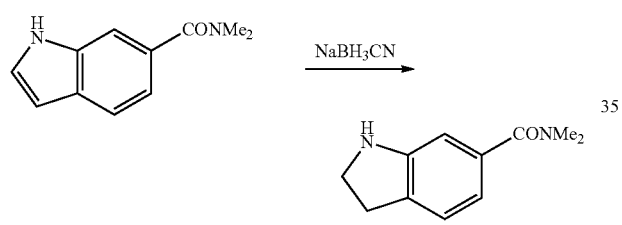

To a solution of Intermediate 88A (125 mg, 0.664 mmol) in AcOH (3 mL) at 0° C. was added Sodium cyanoborohydride (83 mg, 1.328 mmol). The mixture was stirred at 0° C. for 5 min, warmed to rt and stirred for 5 h. The reaction mixture was made basic with 20% NaOH at 0° C., then was extracted with DCM (3×70 mL). The organic layer was washed with brine, dried over Na$_2$SO$_4$, concentrated and purified via preparative HPLC to afford Intermediate 88 (155 mg, 0.509 mmol, 77% yield) as a yellow oil. MS(ESI) m/z: 191.1 (M+H)$^+$; $^1$H NMR (500 MHz, methanol-d$_4$) δ 7.60-7.53 (m, 1H), 7.52-7.46 (m, 2H), 3.89 (t, J=7.8 Hz, 2H), 3.36 (t, J=7.8 Hz, 2H), 3.11 (s, 3H), 3.00 (s, 3H).

Intermediate 89: Indolin-6-yl(4-methylpiperazin-1-yl)methanone, 2TFA

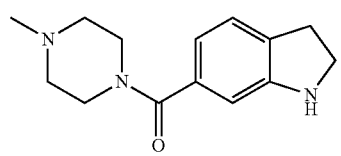 [SMILES: CN1CCN(C(=O)c2ccc3c(c2)NCC3)CC1]

According to the procedure for the preparation of Intermediate 88, substituting 1-methylpiperazine for dimethylamine, HCl afforded Intermediate 89. MS(ESI) m/z: 246.1 (M+H)$^+$.

Intermediate 90: (4-Hydroxypiperidin-1-yl)(indolin-5-yl)methanone

According to the procedure for the preparation of Intermediate 88, substituting piperidin-4-ol for dimethylamine, HCl and 1H-indole-5-carboxylic acid for 1H-indole-6-carboxylic acid afforded Intermediate 90. MS(ESI) m/z: 247.1 (M+H)$^+$; $^1$H NMR (400 MHz, chloroform-d) δ 7.16-7.12 (m, 1H), 7.03 (dd, J=8.0, 1.7 Hz, 1H), 6.51 (d, J=7.9 Hz, 1H), 3.93 (br. s., 1H), 3.84 (tt, J=8.3, 4.0 Hz, 2H), 3.64-3.41 (m, 4H), 3.19 (ddd, J=13.2, 9.5, 3.3 Hz, 2H), 2.99 (t, J=8.5 Hz, 2H), 1.88-1.73 (m, 2H), 1.57-1.41 (m, 2H).

Intermediate 91: (4-Hydroxypiperidin-1-yl)(indolin-6-yl)methanone, TFA

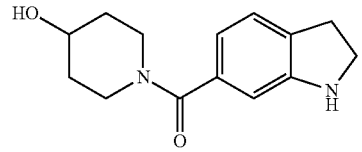 [SMILES: O=C(c1ccc2c(c1)NCC2)N1CCC(O)CC1]

According to the procedure for the preparation of Intermediate 88, substituting piperidin-4-ol for dimethylamine, HCl afforded Intermediate 91. MS(ESI) m/z: 247.1 (M+H)$^+$; $^1$H NMR (500 MHz, methanol-d$_4$) δ 7.57 (dd, J=7.7, 0.8 Hz, 1H), 7.51-7.47 (m, 2H), 4.16 (br. s., 1H), 3.95-3.88 (m, 3H), 3.60 (br. s., 1H), 3.37 (t, J=7.8 Hz, 3H), 3.28-3.17 (m, 1H), 2.02-1.88 (m, 1H), 1.82 (br. s., 1H), 1.57 (br. s., 1H), 1.46 (br. s., 1H).

Intermediate 92: Indolin-6-yl(morpholino)methanone, TFA

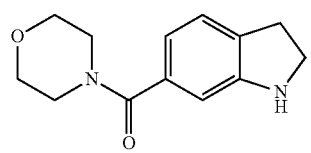 [SMILES: O=C(c1ccc2c(c1)NCC2)N1CCOCC1]

According to the procedure for the preparation of Intermediate 88, substituting morpholine for dimethylamine, HCl afforded Intermediate 92. MS(ESI) m/z: 233.1 (M+H)$^+$; $^1$H NMR (400 MHz, chloroform-d) δ 12.19 (br. s., 3H), 7.42 (d, J=7.9 Hz, 1H), 7.35 (dd, J=7.8, 1.2 Hz, 1H), 7.20 (s, 1H), 3.93 (t, J=7.8 Hz, 2H), 3.77 (br. s., 4H), 3.60 (br. s., 2H), 3.42-3.24 (m, 4H).

Intermediate 93:
Indolin-5-yl(morpholino)methanone

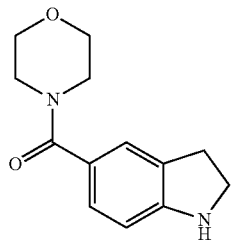 [SMILES: O=C(c1ccc2c(c1)CCN2)N1CCOCC1]

According to the procedure for the preparation of Intermediate 88, substituting morpholine for dimethylamine, HCl and 1H-indole-5-carboxylic acid for 1H-indole-6-carboxylic acid afforded Intermediate 93. MS(ESI) m/z: 233.1 (M+H)$^+$; $^1$H NMR (400 MHz, chloroform-d) δ 7.19 (d, J=1.1 Hz, 1H), 7.11-7.06 (m, 1H), 6.53 (d, J=8.1 Hz, 1H), 4.04 (br. s., 1H), 3.76-3.54 (m, 10H), 3.02 (t, J=8.6 Hz, 2H).

Intermediate 94:
4-(4-Amino-2-methylphenyl)phthalazin-1(2H)-one, TFA

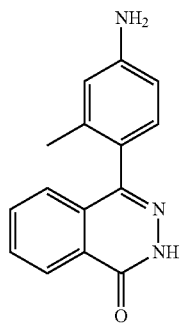 [SMILES: Cc1cc(N)ccc1-c1n[nH]c(=O)c2ccccc12]

Intermediate 94A: tert-Butyl (4-bromo-3-methylphenyl)carbamate

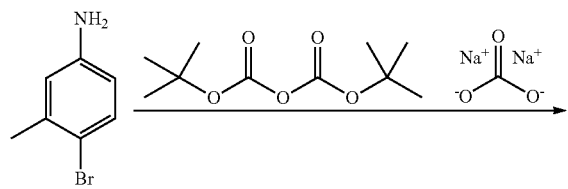

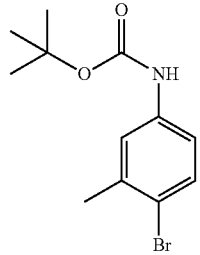

To a solution of 4-bromo-3-methylaniline (2.0 g, 10.8 mmol) and Boc$_2$O (2.82 g, 12.9 mmol) in MeOH (20 mL), was added sodium carbonate (2.51 g, 23.7 mmol). The mixture was stirred at rt for 5 h. Additional Boc$_2$O (0.28 g, 1.3 mmol) was added and the mixture was stirred at rt for 20 h. The reaction mixture was filtered to remove inorganic salt. The filtrate was concentrated to give a white solid, which was suspended in EtOAc (~100 mL). The suspension was filtered through a 1" pad of SiO2. The filtrate was concentrated to afford Intermediate 94A (3.03 g, 98% yield) as a white solid. MS(ESI) m/z: 307.9 (M+Na)$^+$; $^1$H NMR (400 MHz, chloroform-d) δ 7.40 (d, J=8.6 Hz, 1H), 7.32 (d, J=1.8 Hz, 1H), 7.02 (dd, J=8.6, 2.6 Hz, 1H), 6.38 (br. s., 1H), 2.36 (s, 3H), 1.51 (s, 9H).

Intermediate 94B: tert-Butyl (4-(5,5-dimethyl-1,3,2-dioxaborinan-2-yl)-3-methylphenyl)carbamate

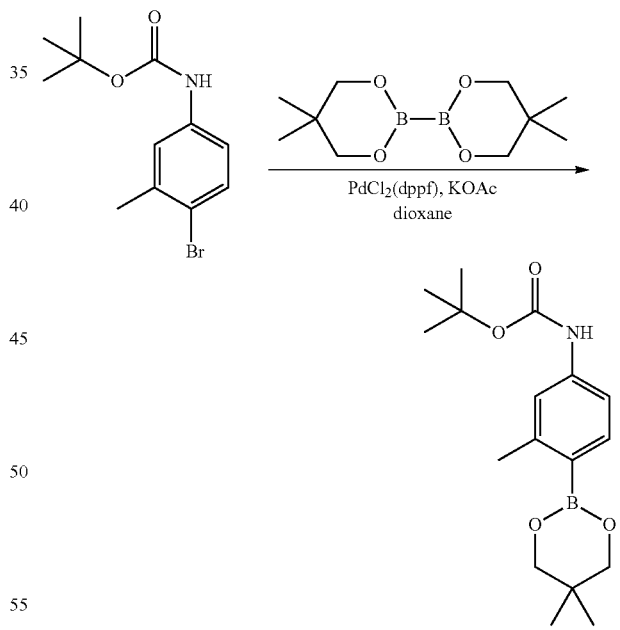

To a vial containing Intermediate 94A (1.5 g, 5.24 mmol), 5,5,5',5'-tetramethyl-2,2'-bi(1,3,2-dioxaborinane) (1.30 g, 5.77 mmol) and potassium acetate (1.54 g, 15.7 mmol), was added dioxane (15 ml). The mixture was degassed (evacuated and flushed with Ar (3×)), then PdCl$_2$(dppf) CH$_2$Cl$_2$ adduct (0.214 g, 0.262 mmol) was added. The mixture was degassed (3×), then the vial was sealed and heated at 110° C. for 2.5 h. The reaction mixture was partitioned between EtOAc and H$_2$O. The organic phase was washed with H$_2$O and brine, dried (Na$_2$SO$_4$), filtered through a 1" pad of SiO$_2$ and concentrated. The crude product was purified by flash chromatography (gradient from 0 to 50% ethyl acetate/hexanes) to afford Intermediate 94B (1.545 g, 4.84 mmol, 92% yield) as an orange foam. MS(ESI) m/z: 250.2 (M(boronic acid)-H)⁻; ¹H NMR (400 MHz, chloroform-d) δ 7.67 (d, J=8.1 Hz, 1H), 7.17 (s, 1H), 7.11 (dd, J=8.1, 2.0 Hz, 1H), 6.41 (br. s., 1H), 3.75 (s, 4H), 2.49 (s, 3H), 1.51 (s, 9H), 1.02 (s, 6H).

Intermediate 94C: tert-Butyl (3-methyl-4-(4-oxo-3,4-dihydrophthalazin-1-yl)phenyl)carbamate

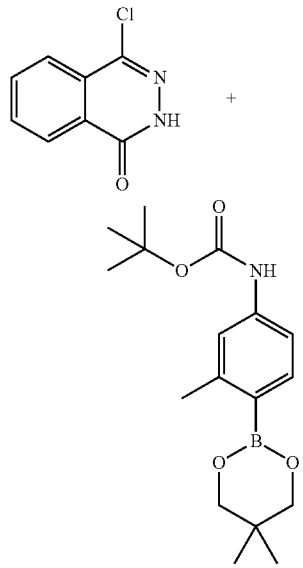

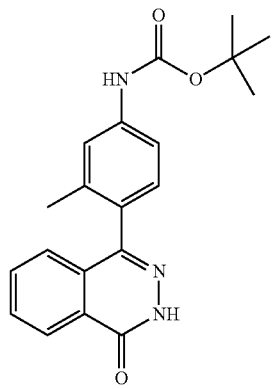

To 4-chlorophthalazin-1(2H)-one (400 mg, 2.22 mmol), Intermediate 94B (778 mg, 2.44 mmol) and phosphoric acid, potassium salt (1175 mg, 5.54 mmol), were added dioxane (6 mL) and water (0.667 mL). The mixture was degassed (evacuated and flushed with Ar (5×)). Pd(PPh₃)₄ (128 mg, 0.111 mmol) was added, then the mixture was degassed (2×). The reaction vial was sealed and heated in a microwave reactor at 150° C. for 40 min. The reaction mixture was partitioned between EtOAc and H₂O. The organic phase was washed with H₂O and brine, dried (Na₂SO₄) and concentrated. The crude product was purified by flash chromatography (gradient from 0 to 100% ethyl acetate/hexanes) to afford Intermediate 94C (540 mg, 1.54 mmol, 69% yield) as a white solid. MS(ESI) m/z: 352.0 (M+H)⁺; ¹H NMR (400 MHz, methanol-d₄) δ 8.46-8.40 (m, 1H), 7.91-7.80 (m, 2H), 7.47-7.35 (m, 3H), 7.20 (d, J=8.1 Hz, 1H), 2.09 (s, 3H), 1.54 (s, 9H).

Intermediate 94

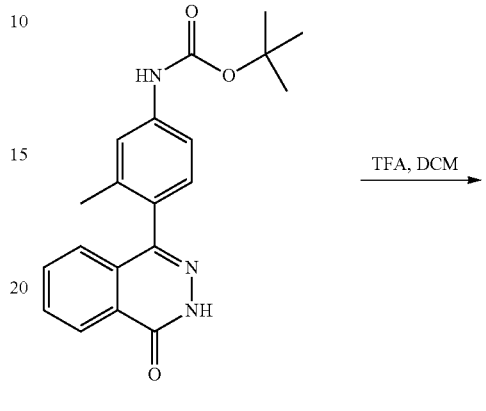

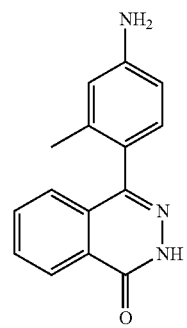

To a suspension of Intermediate 94C (540 mg, 1.54 mmol) in DCM (5 mL), was added TFA (2 mL). The mixture was stirred at rt for 2 h. The reaction mixture was concentrated, then was co-evaporated with DCM (3×) to afford Intermediate 94 (723 mg, 98% yield) as a solid. MS(ESI) m/z: 252.1 (M+H)⁺; ¹H NMR (400 MHz, methanol-d₄) δ 8.45 (dd, J=7.9, 1.1 Hz, 1H), 7.93-7.82 (m, 2H), 7.48 (d, J=8.1 Hz, 1H), 7.38-7.27 (m, 3H), 2.19 (s, 3H)

Intermediate 95:
4-(Dimethylamino)-N-(indolin-6-yl)benzamide, 2TFA

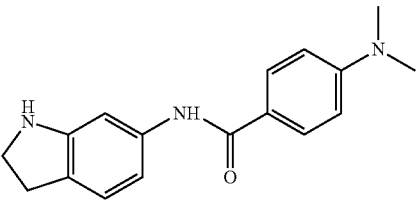 [SMILES: CN(C)c1ccc(C(=O)Nc2ccc3c(c2)NCC3)cc1]

Intermediate 95A: tert-Butyl 6-nitroindoline-1-carboxylate

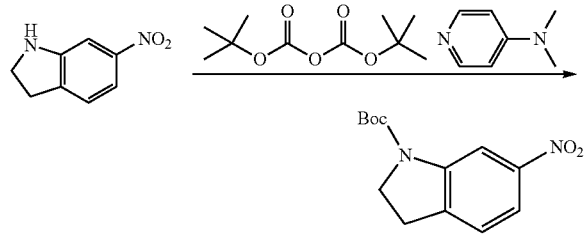

To a mixture of 6-nitroindoline (300 mg, 1.83 mmol) and Boc$_2$O (0.509 mL, 2.19 mmol) in THF at rt, was added cat. DMAP. The resulting mixture was stirred rt o/n. The reaction mixture was concentrated and the residue was purified by flash chromatography (0-20% EtOAc/Hex) to afford Intermediate 95A (480 mg, 99% yield). MS(ESI) m/z: 287.0 (M+Na)$^+$; $^1$H NMR (500 MHz, methanol-d$_4$) δ 8.51 (br. s., 1H), 7.81 (dd, J=8.3, 2.2 Hz, 1H), 7.33 (d, J=8.3 Hz, 1H), 4.12-4.02 (m, 2H), 3.25-3.16 (m, 2H), 1.67-1.49 (m, 9H).

Intermediate 95B: tert-Butyl 6-Aminoindoline-1-carboxylate

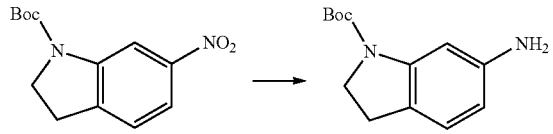 [SMILES: CC(C)(C)OC(=O)N1CCc2ccc([N+](=O)[O-])cc21 ; CC(C)(C)OC(=O)N1CCc2ccc(N)cc21]

To a degassed mixture of Intermediate 95A (450 mg, 1.70 mmol) in MeOH (10 mL), was add 10% Pd/C. The mixture was stirred rt for 2 h under H$_2$ (balloon). The reaction mixture was filtered and concentrated. The residue was purified by flash chromatography (0-40% EtOAc/Hex) to afford Intermediate 95B (300 mg, 75% yield). MS(ESI) m/z: 235.1 (M+H)$^+$; $^1$H NMR (500 MHz, chloroform-d) δ 7.78-7.14 (m, 1H), 6.54-6.42 (m, 2H), 3.90 (br. s., 2H), 3.61-3.40 (m, 2H), 2.96 (t, J=8.5 Hz, 2H), 1.71-1.46 (m, 9H).

Intermediate 95C: tert-Butyl 6-(4-(dimethylamino)benzamido)indoline-1-carboxylate

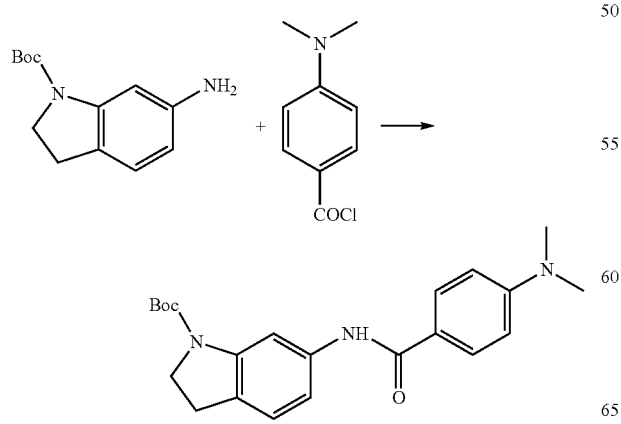

To a mixture of 4-(dimethylamino)benzoyl chloride (22 mg, 0.12 mmol) and Intermediate 95B (23 mg, 0.098 mmol) in DCM (2 mL) at 0° C., was added DIEA (0.051 mL, 0.30 mmol). The mixture was stirred rt for 1 h, then was concentrated. The residue was purified by flash chromatography (0-60% EtOAc/Hex) to afford Intermediate 95C (17 mg, 45.4% yield). MS(ESI) m/z: 382.2 (M+H)$^+$; $^1$H NMR (400 MHz, chloroform-d) δ 8.17-8.02 (m, 1H), 7.91-7.82 (m, 2H), 7.60 (br. s., 1H), 7.15 (d, J=8.6 Hz, 2H), 4.07-3.97 (m, 2H), 3.19-3.14 (m, 6H), 3.12-3.05 (m, 2H), 1.58 (br. s., 9H)

Intermediate 95

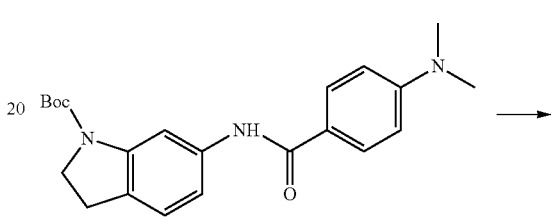

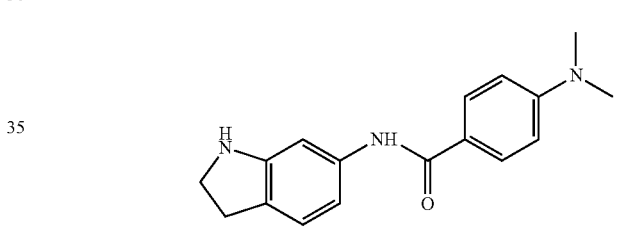

Intermediate 95C (17 mg, 0.045 mmol) stirred with TFA and DCM for 20 min, then was concentrated to afford Intermediate 95 (19 mg). MS(ESI) m/z: 282.1 (M+H)$^+$; $^1$H NMR (400 MHz, methanol-d$_4$) δ 7.94-7.85 (m, 3H), 7.76-7.67 (m, 1H), 7.44 (d, J=8.6 Hz, 1H), 6.90-6.81 (m, 2H), 3.93-3.87 (m, 2H), 3.35 (t, J=7.7 Hz, 2H), 3.07 (s, 6H).

Intermediate 96: 4-(4-Amino-2-chlorophenyl)phthalazin-1(2H)-one

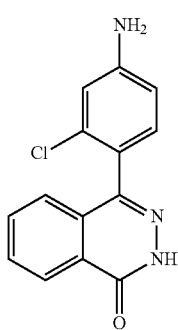 [SMILES: Nc1ccc(-c2n[nH]c(=O)c3ccccc23)c(Cl)c1]

Intermediate 96A: tert-Butyl (4-bromo-3-chlorophenyl)carbamate

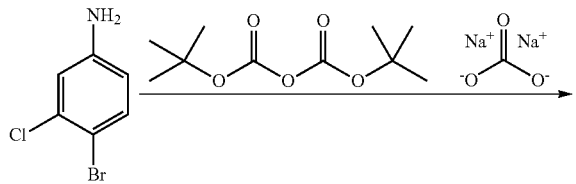

To a solution of 4-bromo-3-chloroaniline (1.5 g, 7.3 mmol) and Boc$_2$O (2.38 g, 10.9 mmol) in MeOH (20 mL), was added sodium carbonate (1.694 g, 15.98 mmol). The mixture was stirred at rt for 16 h. The reaction mixture was concentrated. The residue was suspended in water, then extracted with DCM. The organic phase was concentrated and the residue was purified by flash chromatography (0-20% EtOAc/Hex) to afford Intermediate 96A (2.0 g, 6.52 mmol, 90% yield). $^1$H NMR (400 MHz, chloroform-d) δ 7.64 (d, J=2.4 Hz, 1H), 7.49 (d, J=8.8 Hz, 1H), 7.08 (dd, J=8.7, 2.5 Hz, 1H), 6.46 (br. s., 1H), 1.53-1.51 (m, 9H).

Intermediate 96B: tert-Butyl (3-chloro-4-(4,4,5,5-tetramethyl-1,3,2-dioxaborolan-2-yl)phenyl)carbamate

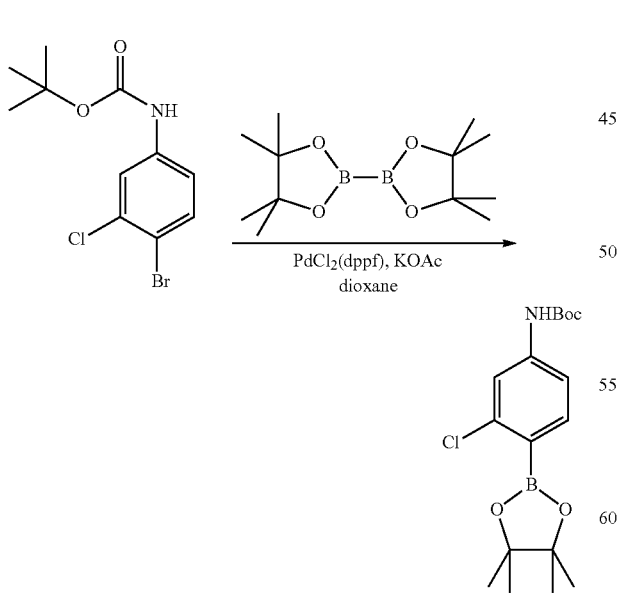

A mixture of Intermediate 96A (1.96 g, 6.39 mmol), 4,4,4',4',5,5,5',5'-octamethyl-2,2'-bi(1,3,2-dioxaborolane) (1.79 g, 7.03 mmol), and potassium acetate (1.88 g, 19.2 mmol) in dioxane (10 mL). Then PdCl$_2$(dppf) CH$_2$Cl$_2$ adduct (0.14 g, 0.19 mmol) was added, the reaction mixture was degassed (3× vacuum/Ar), sealed in a vial and heated at 110° C. for 16 h. The reaction was quenched with water, extracted with EtOAc, concentrated and purified through via flash chromatography (0-40% EtOAc/Hex) to Intermediate 96B (1.40 g, 62% yield). MS(ESI) m/z: 298.1 (M-(t-Bu)+2H)$^+$; $^1$H NMR (400 MHz, chloroform-d) δ 7.63 (d, J=8.1 Hz, 1H), 7.49 (d, J=2.0 Hz, 1H), 7.18 (dd, J=8.1, 2.0 Hz, 1H), 6.50 (s, 1H), 1.52 (s, 9H), 1.40-1.33 (m, 12H).

Intermediate 96C: tert-Butyl (3-chloro-4-(4-oxo-3,4-dihydrophthalazin-1-yl)phenyl)carbamate

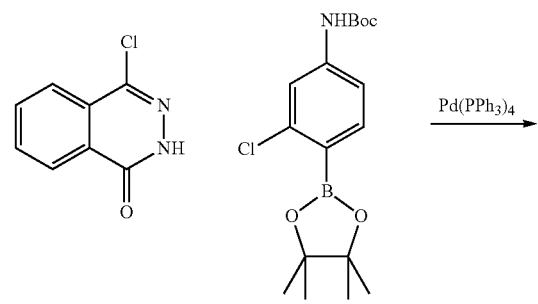

To 4-chlorophthalazin-1(2H)-one (100 mg, 0.554 mmol), Intermediate 96B (206 mg, 0.581 mmol) and phosphoric acid, potassium salt (294 mg, 1.38 mmol), were added dioxane (5 mL) and water (0.556 mL). The mixture was degassed (evacuated and flushed with Ar (5×)). Pd(PPh$_3$)$_4$ (32 mg, 0.028 mmol) was added, then the mixture was degassed (2×). The reaction vial was sealed and heated in a microwave reactor at 150° C. for 30 min. The reaction mixture was concentrated, then purified by flash chromatography (0-80% EtOAc/Hex) to afford Intermediate 96C (200 mg, 97% yield). (ESI) m/z: 372.0 (M+H)$^+$.

Intermediate 96

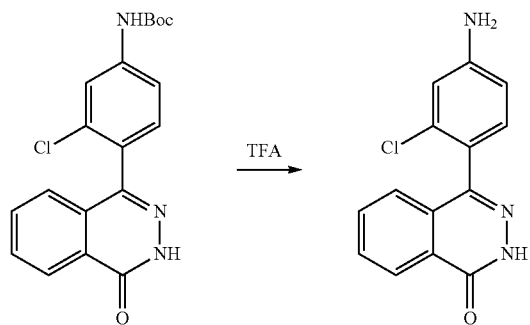 [SMILES: CC(C)(C)OC(=O)Nc1ccc(-c2n[nH]c(=O)c3ccccc23)c(Cl)c1 ; Nc1ccc(-c2n[nH]c(=O)c3ccccc23)c(Cl)c1]

Intermediate 96C (200 mg, 0.538 mmol) was stirred with TFA (2 mL) and DCM (3 ml) at rt for 30 min. The reaction mixture was concentrated and the residue was purified by flash chromatography (0-100% EtOAc/Hex) to afford Intermediate 96 (120 mg, 82% yield). MS(ESI) m/z 272.0 (M+H)$^+$; $^1$H NMR (400 MHz, DMSO-d$_6$) δ 12.73 (s, 1H), 8.36-8.22 (m, 1H), 7.93-7.78 (m, 2H), 7.41-7.24 (m, 1H), 7.13 (d, J=8.4 Hz, 1H), 6.76 (d, J=2.2 Hz, 1H), 6.64 (dd, J=8.4, 2.2 Hz, 1H), 5.75 (s, 1H).

Intermediate 97: N-(3-Methyl-4-(4,4,5,5-tetramethyl-1,3,2-dioxaborolan-2-yl)phenyl)indoline-1-carboxamide

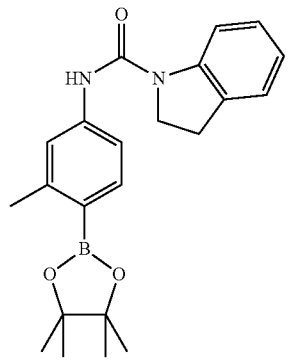 [SMILES: Cc1cc(NC(=O)N2CCc3ccccc32)ccc1B1OC(C)(C)C(C)(C)O1]

Intermediate 97A: N-(4-Bromo-3-methylphenyl)indoline-1-carboxamide

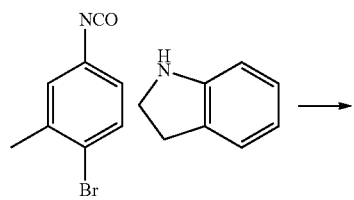

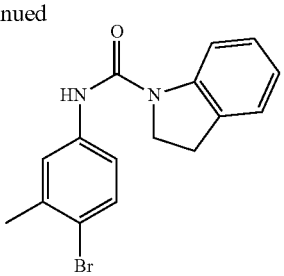

To a solution of 1-bromo-4-isocyanato-2-methylbenzene (111 mg, 0.523 mmol) in CH$_2$Cl$_2$ (1 mL), was added indoline (68.6 mg, 0.576 mmol) in CH$_2$Cl$_2$ (1 mL). The mixture was stirred at rt for 1 h, then was concentrated. The residue was purified by flash chromatography (0-50% EtOAc/Hex) to afford Intermediate 97A (170 mg, 0.513 mmol, 98% yield) as a white solid. MS(ESI) m/z: 331.0 (M+H)$^+$.

Intermediate 97

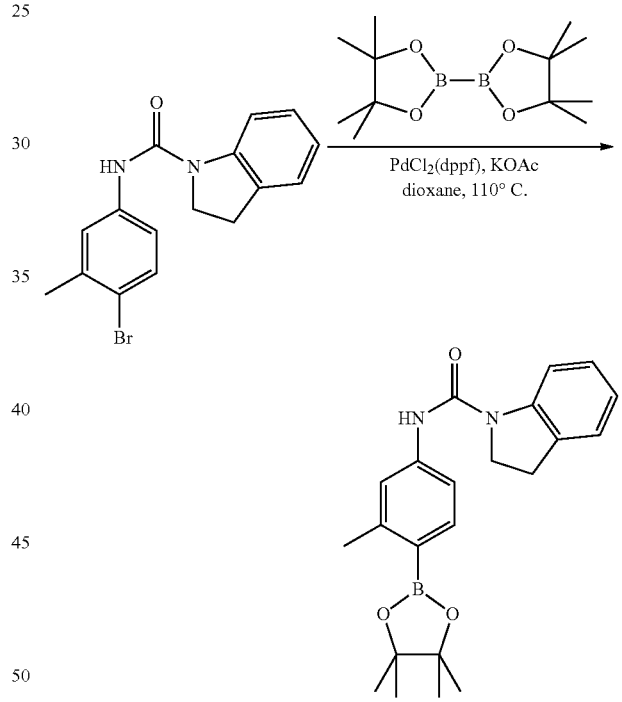

A mixture of Intermediate 97A (170 mg, 0.513 mmol), 4,4,4',4',5,5,5',5'-octamethyl-2,2'-bi(1,3,2-dioxaborolane) (143 mg, 0.565 mmol), and potassium acetate (151 mg, 1.54 mmol) in dioxane (10 mL). PdCl$_2$ (dppf) CH$_2$Cl$_2$ adduct (11.27 mg, 0.015 mmol) was added, the reaction mixture was degassed (3× vacuum/Ar), sealed in a vial and heated at 110° C. for 3 h. The reaction was quenched with water and extracted with EtOAc. The organic phase was concentrated and the residue was purified via flash chromatography (0-40% EtOAc/Hex) to afford Intermediate 97 (100 mg, 0.264 mmol, 51.5% yield). MS(ESI) m/z: 379.1 (M+H)$^+$; $^1$H NMR (400 MHz, chloroform-d) δ 7.89 (d, J=7.9 Hz, 1H), 7.74 (d, J=8.1 Hz, 1H), 7.33 (d, J=2.0 Hz, 1H), 7.26-7.16 (m, 3H), 7.01-6.93 (m, 1H), 6.50 (s, 1H), 4.08 (t, J=8.5 Hz, 2H), 3.23 (t, J=8.6 Hz, 2H), 2.54 (s, 3H), 1.35 (s, 12H).

Intermediate 98: Methyl 2-(3-((4-(4,4,5,5-tetramethyl-1,3,2-dioxaborolan-2-yl)phenyl)carbamoyl)-H-indazol-1-yl)acetate

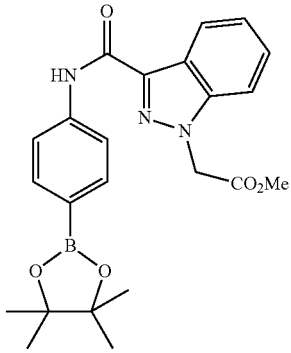 [SMILES: COC(=O)Cn1nc(C(=O)Nc2ccc(B3OC(C)(C)C(C)(C)O3)cc2)c2ccccc21]

Intermediate 98A: tert-Butyl 3-((4-bromophenyl)carbamoyl)-1H-indazole-1-carboxylate

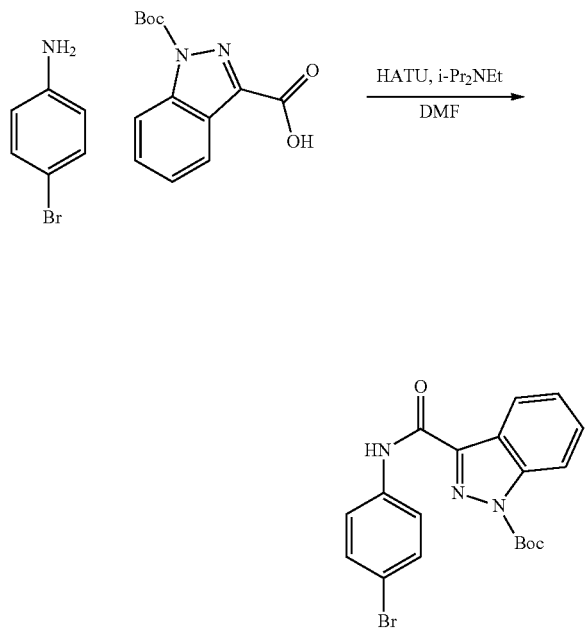

To a solution of 4-bromoaniline (63.0 mg, 0.366 mmol), 1-(I-butoxycarbonyl)-1H-indazole-3-carboxylic acid (96 mg, 0.366 mmol), and HATU (146 mg, 0.384 mmol) in DMF (3 mL), was added DIEA (0.32 mL, 1.83 mmol). The reaction mixture was stirred at rt for 16 h, then was diluted with water. The mixture was extracted with EtOAc. The organic phase was washed with 10% LiCl and brine, then concentrated. The residue was purified by flash chromatography (0-20% EtOAc/Hex) to afford Intermediate 98A (118 mg, 77% yield). MS(ESI) m/z: 416.1 (M+H)$^+$; $^1$H NMR (400 MHz, chloroform-d) δ 8.98 (s, 1H), 8.48 (dt, J=8.0, 0.9 Hz, 1H), 8.12 (d, J=8.6 Hz, 1H), 7.72-7.65 (m, 2H), 7.63-7.56 (m, 1H), 7.54-7.48 (m, 2H), 7.45 (ddd, J=8.1, 7.1, 0.9 Hz, 1H), 1.78 (s, 9H).

Intermediate 98B: N-(4-Bromophenyl)-1H-indazole-3-carboxamide

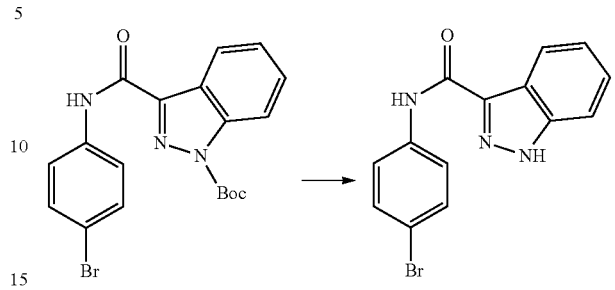

Intermediate 98A (118 mg, 0.283 mmol) was stirred with TFA (1 mL) and DCM (2 mL) for 30 min at rt, then was concentrated. The residue was purified by flash chromatography (0-50% EtOAc/Hex) to afford Intermediate 98B (65 mg, 0.206 mmol, 72.5% yield) as a yellow solid. MS(ESI) m/z: 316.0 (M+H)$^+$; $^1$H NMR (400 MHz, DMSO-d$_6$) δ 13.80 (br. s., 1H), 10.49 (s, 1H), 8.22 (d, J=8.1 Hz, 1H), 7.99-7.84 (m, 2H), 7.67 (d, J=8.4 Hz, 1H), 7.57-7.49 (m, 2H), 7.46 (ddd, J=8.3, 7.0, 1.0 Hz, 1H), 7.34-7.24 (m, 1H).

Intermediate 98C: Methyl 2-(3-((4-bromophenyl)carbamoyl)-1H-indazol-1-yl)acetate

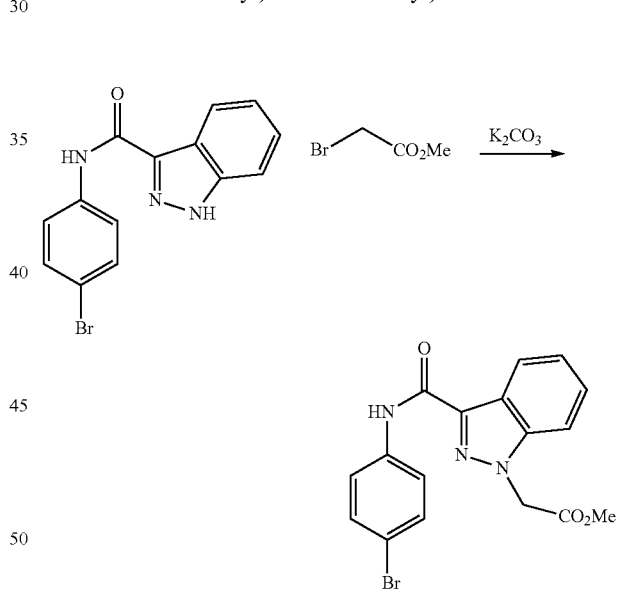

To a vial containing Intermediate 98B (65 mg, 0.21 mmol) in DMF (3 mL), were added methyl 2-bromoacetate (38 mg, 0.25 mmol) and K$_2$CO$_3$ (43 mg, 0.31 mmol). The vial was sealed and the mixture was stirred at rt for 3 h. The reaction mixture was concentrated, then the residue was diluted with water and extracted with EtOAc. The organic phase was dried over Na$_2$SO$_4$ and concentrated. The residue was purified by flash chromatography (0-50% EtOAc/Hex) to afford Intermediate 98C (70 mg, 88% yield) as a yellow solid. MS(ESI) m/z: 388.0 (M+H)$^+$; $^1$H NMR (400 MHz, chloroform-d) δ 8.80 (s, 1H), 8.44 (dt, J=8.1, 1.0 Hz, 1H), 7.70-7.60 (m, 2H), 7.55-7.45 (m, 3H), 7.41-7.32 (m, 2H), 5.20 (s, 2H), 3.79 (s, 3H).

Intermediate 98

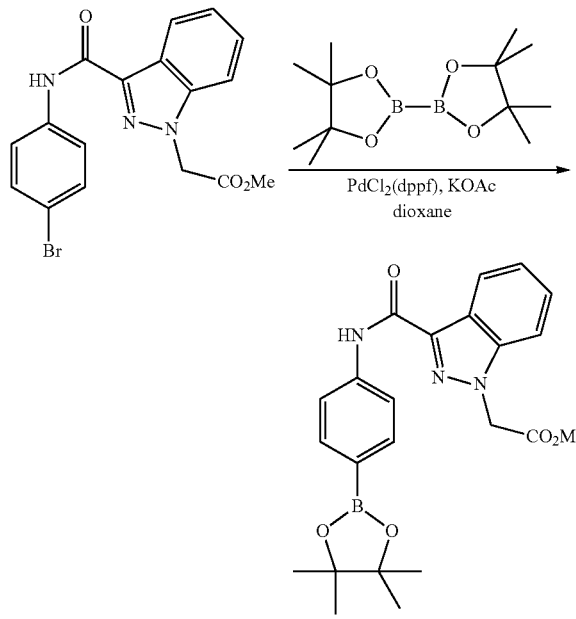

To a mixture of Intermediate 98C (72 mg, 0.19 mmol), 4,4,4',4',5,5,5',5'-octamethyl-2,2'-bi(1,3,2-dioxaborolane) (51.8 mg, 0.204 mmol), and potassium acetate (54.6 mg, 0.556 mmol) in dioxane (10 mL), was added PdCl$_2$(dppf) CH$_2$Cl$_2$ adduct (4.1 mg, 5.6 mol). The reaction mixture was degassed (3× vacuum/Ar), sealed in a vial and heated at 110° C. for 3 h. The reaction was diluted with water, then was extracted with EtOAc. The organic phase was concentrated, then the product was purified by flash chromatography (0-50% EtOAc/Hex) to afford Intermediate 98 (80 mg, 99% yield) as a colorless oil. MS(ESI) m/z: 388.0 (M+H)$^+$; $^1$H NMR (400 MHz, chloroform-d) δ 8.89 (s, 1H), 8.46 (dt, J=8.1, 1.0 Hz, 1H), 7.89-7.82 (m, 2H), 7.81-7.73 (m, 2H), 7.53-7.43 (m, 1H), 7.35 (td, J=8.1, 1.0 Hz, 2H), 5.21 (s, 2H), 3.78 (s, 3H), 1.36 (s, 12H).

Intermediate 99: Methyl 3-(3-((4-(4,4,5,5-tetramethyl-1,3,2-dioxaborolan-2-yl)phenyl)carbamoyl)-1H-indazol-1-yl)propanoate

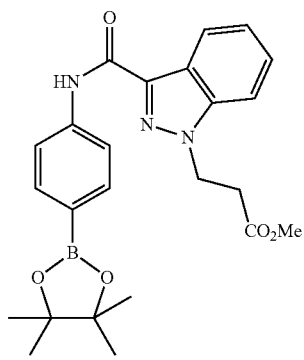 [SMILES: COC(=O)CCn1nc(C(=O)Nc2ccc(B3OC(C)(C)C(C)(C)O3)cc2)c2ccccc21]

According to the procedure for the preparation of Intermediate 98, substituting methyl 3-bromopropanoate for methyl 2-bromoacetate afforded Intermediate 99. MS(ESI) m/z: 450.3 (M+H)$^+$.

Intermediate 100: 1-(3-Hydroxy-3-methylbutyl)-N-(4-(4,4,5,5-tetramethyl-1,3,2-dioxaborolan-2-yl)phenyl)-1H-indazole-3-carboxamide

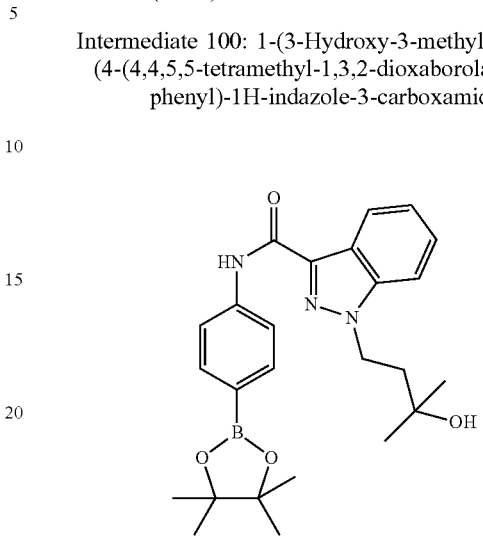

Intermediate 100A: Methyl 3-(3-((4-bromophenyl)carbamoyl)-1H-indazol-1-yl)propanoate

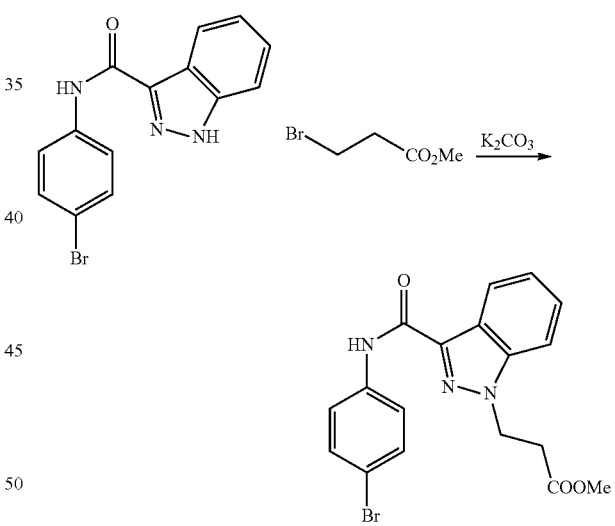

To a vial containing Intermediate 98B (150 mg, 0.474 mmol) in DMF (3 mL), were added methyl 3-bromopropanoate (95 mg, 0.569 mmol) and K$_2$CO$_3$ (98 mg, 0.712 mmol). The vial was sealed and the mixture was stirred at rt for 3 h. The reaction mixture was concentrated, and the residue was diluted with water and extracted with EtOAc. The organic phase was dried over Na$_2$SO$_4$ and concentrated. The residue was purified by flash chromatography (0-50% EtOAc/Hex) to afford Intermediate 100A (180 mg, 94% yield). MS(ESI) m/z: 402.2 (M+H)$^+$; $^1$H NMR (500 MHz, chloroform-d) δ 8.80 (s, 1H), 8.39 (d, J=8.3 Hz, 1H), 7.68-7.63 (m, 2H), 7.56-7.44 (m, 4H), 7.32 (ddd, J=8.0, 6.9, 0.8 Hz, 1H), 4.71 (t, J=6.9 Hz, 2H), 3.73-3.66 (m, 3H), 3.05 (t, J=6.7 Hz, 2H).

Intermediate 100B: N-(4-Bromophenyl)-1-(3-hydroxy-3-methylbutyl)-1H-indazole-3-carboxamide

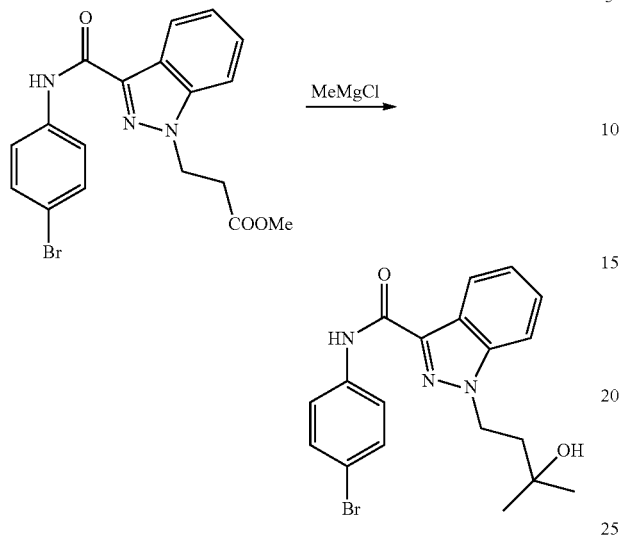

Intermediate 100A (85 mg, 0.211 mmol) was treated with 3M methylmagnesium chloride (0.704 mL, 2.11 mmol) at 0° C. to afford Intermediate 100B (68 mg, 80% yield) as a colorless oil. MS(ESI) m/z: 402.1 (M+H)⁺; ¹H NMR (400 MHz, chloroform-d) δ 8.84 (s, 1H), 8.40 (dt, J=8.2, 1.0 Hz, 1H), 7.71-7.63 (m, 2H), 7.52-7.40 (m, 4H), 7.31 (ddd, J=8.1, 6.7, 1.1 Hz, 1H), 4.64-4.52 (m, 2H), 2.20-2.09 (m, 2H), 1.34 (s, 6H).

Intermediate 100

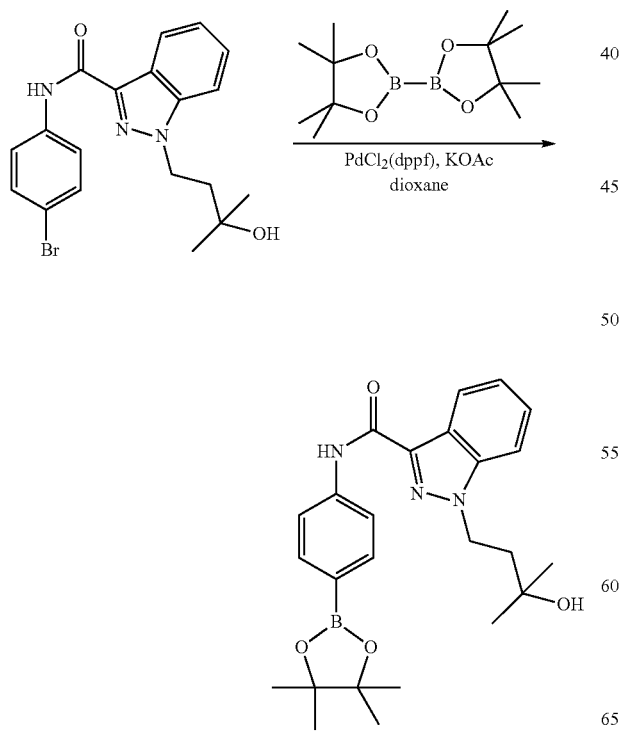

A mixture of Intermediate 100B (70 mg, 0.17 mmol), 4,4,4',4',5,5,5',5'-octamethyl-2,2'-bi(1,3,2-dioxaborolane) (49 mg, 0.191 mmol), and potassium acetate (51 mg, 0.52 mmol) in dioxane (10 mL). Then PdCl₂(dppf) CH₂Cl₂ adduct (3.8 mg, 5.22 mol) was added, the reaction mixture was degassed (3× vacuum/Ar), sealed in a vial and heated at 110° C. for 3 h. The reaction progress was quenched with water, extracted with EtOAc. The organic phase was concentrated and was purified by flash chromatography (0-50% EtOAc/Hex) to afford Intermediate 100 (78 mg, 100% yield). MS(ESI) m/z: 450.3.

Intermediate 101: 1-((1-(tert-Butoxycarbonyl)piperidin-4-yl)methyl)-1H-indazole-3-carboxylic Acid

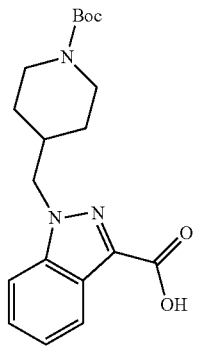 [SMILES: CC(C)(C)OC(=O)N1CCC(Cn2nc(C(=O)O)c3ccccc32)CC1]

According to the procedure for the preparation of Intermediate 21, substituting tert-butyl 4-(bromomethyl)piperidine-1-carboxylate, hydrobromide for benzyl 4-(bromomethyl)piperidine-1-carboxylate afforded Intermediate 101. MS(ESI) m/z: 360.3 (M+H)⁺; ¹H NMR (500 MHz, methanol-d₄) δ 8.14 (d, J=8.0 Hz, 1H), 7.64 (d, J=8.5 Hz, 1H), 7.47-7.40 (m, 1H), 7.31-7.25 (m, 1H), 4.36 (d, J=7.2 Hz, 2H), 4.06-3.97 (m, 2H), 2.66 (br. s., 2H), 2.21 (ddt, J=11.2, 7.5, 3.8 Hz, 1H), 1.53-1.45 (m, 2H), 1.44-1.35 (m, 9H), 1.26-1.17 (m, 2H).

Intermediate 102: 4-(4-Amino-2-methoxyphenyl)phthalazin-1(2H)-one, TFA

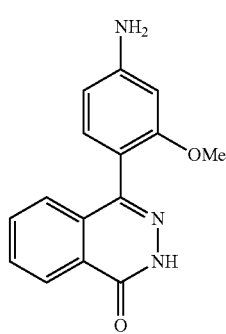 [SMILES: COc1cc(N)ccc1-c1n[nH]c(=O)c2ccccc12]

Intermediate 102A: tert-Butyl (4-bromo-3-methoxyphenyl)carbamate

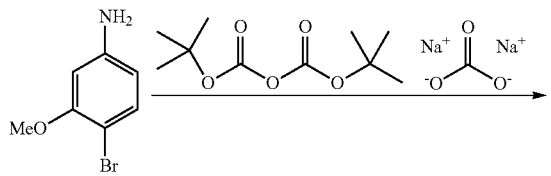

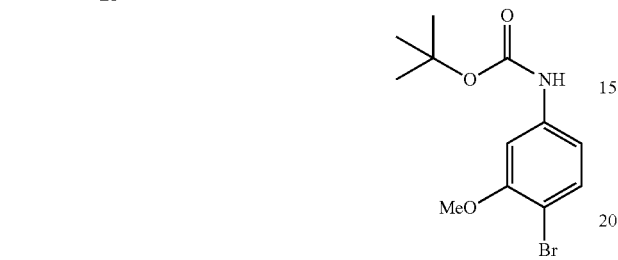

To a solution of 4-bromo-3-methoxyaniline, HCl (0.6 g, 2.5 mmol) and Boc$_2$O (0.824 g, 3.77 mmol) in MeOH (10 mL), was added sodium carbonate (0.80 g, 7.55 mmol). The mixture was stirred at rt for 3 h. The reaction mixture was concentrated and the residue was purified by flash chromatography (0-20% EtOAc/Hex) to afford Intermediate 102A (550 mg, 72% yield). MS(ESI) m/z: 302.2 (M+H)$^+$; $^1$H NMR (400 MHz, chloroform-d) δ 7.39 (d, J=8.4 Hz, 1H), 7.32 (s, 1H), 6.63 (dd, J=8.5, 2.3 Hz, 1H), 6.49 (br. s., 1H), 3.91 (s, 3H), 1.55-1.48 (m, 9H).

Intermediate 102B: tert-Butyl (3-methoxy-4-(4,4,5,5-tetramethyl-1,3,2-dioxaborolan-2-yl)phenyl)carbamate

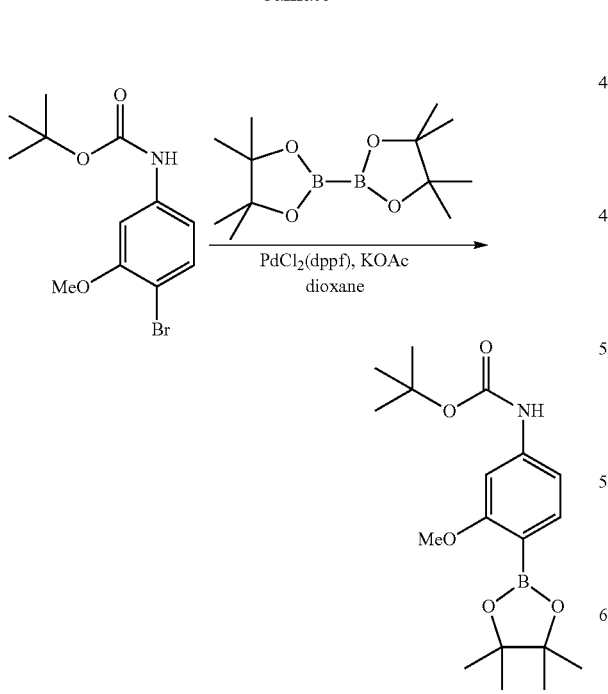

To a mixture of Intermediate 102A (340 mg, 1.13 mmol), 4,4,4',4',5,5,5',5'-octamethyl-2,2'-bi(1,3,2-dioxaborolane) (314 mg, 1.24 mmol), and potassium acetate (331 mg, 3.38 mmol) in dioxane (8 mL), was added PdCl$_2$(dppf) CH$_2$Cl$_2$ adduct (24.7 mg, 0.034 mmol). The reaction mixture was degassed (3× vacuum/Ar), sealed in a vial and heated at 110° C. for 3 h. The reaction was diluted with water and extracted with EtOAc. The organic phase was concentrated and the residue was purified by flash chromatography (0-50% EtOAc/Hex) to afford Intermediate 102B (200 mg, 51% yield) as a colorless foam. MS(ESI) m/z: 350.3 (M+H)$^+$; $^1$H NMR (500 MHz, chloroform-d) δ 7.59 (d, J=8.0 Hz, 1H), 7.18 (br. s., 1H), 6.81 (br. s., 1H), 6.75 (dd, J=8.1, 1.8 Hz, 1H), 3.81 (s, 3H), 1.54-1.48 (m, 9H), 1.36-1.31 (m, 12H).

Intermediate 102C: tert-Butyl (3-methoxy-4-(4-oxo-3,4-dihydrophthalazin-1-yl)phenyl)carbamate

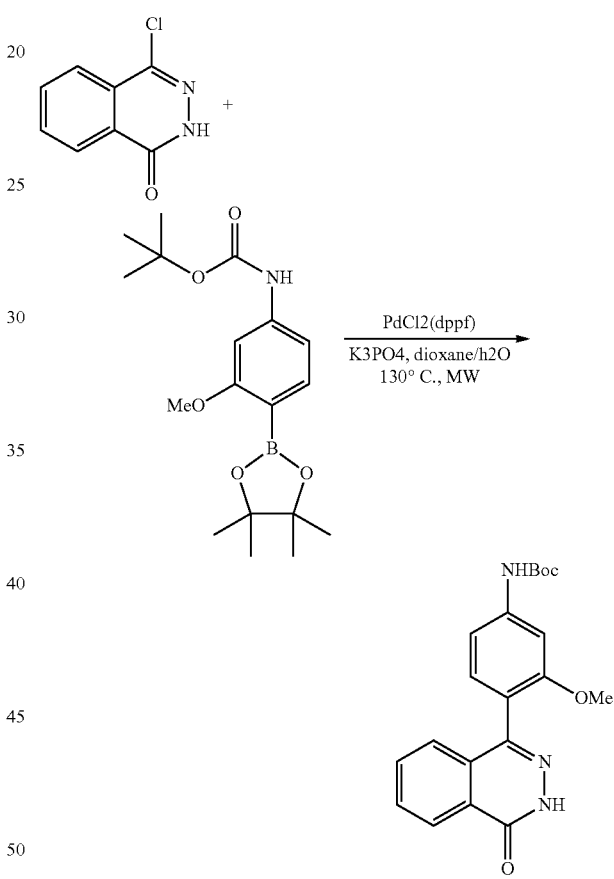

To a 5 mL of microwave vial containing solution of Intermediate 102B (155 mg, 0.443 mmol) in dioxane (3 mL) were added potassium phosphate tribasic (235 mg, 1.107 mmol), dioxane (3 mL), water (0.3 mL) and PdCl$_2$(dppf) CH$_2$Cl$_2$ adduct (36.2 mg, 0.044 mmol) at RT. The reaction was purged with nitrogen and then was heated with microwave at 130° C. for 15 min. The reaction mixture was concentrated and the residue was purified by flash chromatography (0-80% EtOAc/Hex) to afford Intermediate 102C (88 mg, 54% yield). MS(ESI) m/z: 368.2 (M+H)$^+$; $^1$H NMR (400 MHz, chloroform-d) δ 9.83 (s, 1H), 8.47 (dd, J=7.6, 1.2 Hz, 1H), 7.84-7.63 (m, 2H), 7.48 (s, 1H), 7.45-7.34 (m, 1H), 6.84 (dd, J=8.1, 2.0 Hz, 1H), 6.64 (s, 1H), 3.76 (s, 3H), 1.57 (s, 9H).

Intermediate 102

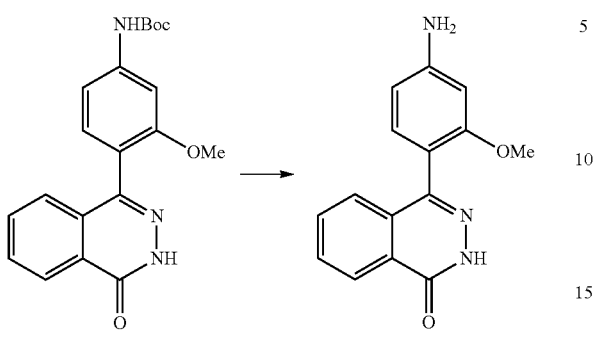

Intermediate 102C (85 mg, 0.231 mmol) was stirred with TFA (1 ml) and DCM (2 ml) at rt for 30 min, concentrated to give Intermediate 102 (78 mg, 88% yield). MS(ESI) m/z: 268.2 (M+H)$^+$; $^1$H NMR (500 MHz, methanol-d$_4$) δ 8.42-8.37 (m, 1H), 7.83 (quind, J=7.3, 1.5 Hz, 2H), 7.50 (d, J=8.0 Hz, 1H), 7.37-7.33 (m, 1H), 7.17 (d, J=1.9 Hz, 1H), 7.14 (dd, J=8.0, 1.9 Hz, 1H), 3.82-3.76 (m, 3H).

Intermediate 103:
4-(4-Amino-2-ethoxyphenyl)phthalazin-1(2H)-one

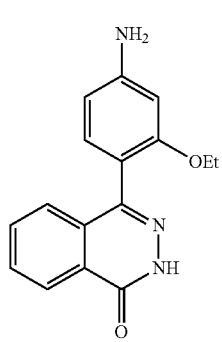 [SMILES: CCOc1cc(N)ccc1-c1n[nH]c(=O)c2ccccc12]

According to the procedure for the preparation of Intermediate 102, substituting 4-bromo-3-ethoxyaniline for 4-bromo-3-methoxyaniline, HCl afforded after flash chromatography (0-90% EtOAc/Hex) Intermediate 103. MS(ESI) m/z: 282.2 (M+H)$^+$; $^1$H NMR (400 MHz, DMSO-d$_6$) δ 12.57 (s, 1H), 8.33-8.13 (m, 1H), 7.90-7.72 (m, 2H), 7.44-7.33 (m, 1H), 6.95 (d, J=8.1 Hz, 1H), 6.34 (d, J=1.8 Hz, 1H), 6.26 (dd, J=7.9, 2.0 Hz, 1H), 5.38 (s, 2H), 3.97-3.81 (m, 2H), 0.97 (t, J=7.0 Hz, 3H).

Intermediate 104:
4-(4-Amino-3-methoxyphenyl)phthalazin-1(2H)-one

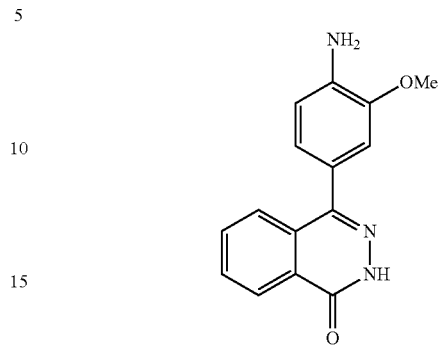

According to the procedure for the preparation of Intermediate 102, substituting 4-bromo-2-methoxyaniline, HCl for 4-bromo-3-methoxyaniline, HCl afforded after flash chromatography (0-100% EtOAc/Hex) Intermediate 104. MS(ESI) m/z: 268.2 (M+H)$^+$; $^1$H NMR (400 MHz, THF) δ 11.64 (br. s., 1H), 8.43-8.34 (m, 1H), 7.87-7.81 (m, 1H), 7.77-7.69 (m, 2H), 7.01 (d, J=1.8 Hz, 1H), 6.91 (dd, J=7.9, 2.0 Hz, 1H), 6.71 (d, J=7.9 Hz, 1H), 3.84 (s, 3H).

Intermediate 105:
4-(4-Amino-3-hydroxyphenyl)phthalazin-1(2H)-one

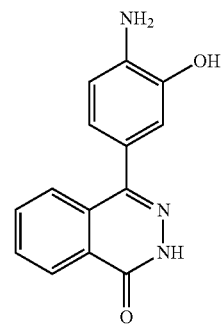 [SMILES: Nc1ccc(-c2n[nH]c(=O)c3ccccc23)cc1O]

Intermediate 105A: tert-Butyl (2-methoxy-4-(4-oxo-3,4-dihydrophthalazin-1-yl)phenyl)carbamate

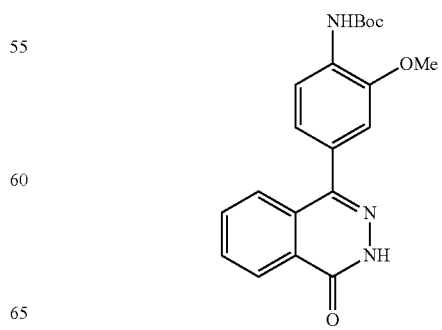

According to the procedure for the preparation of Intermediate 102C, substituting 4-bromo-2-methoxyaniline, HCl for 4-bromo-3-methoxyaniline, HCl afforded Intermediate 105A.

Intermediate 105

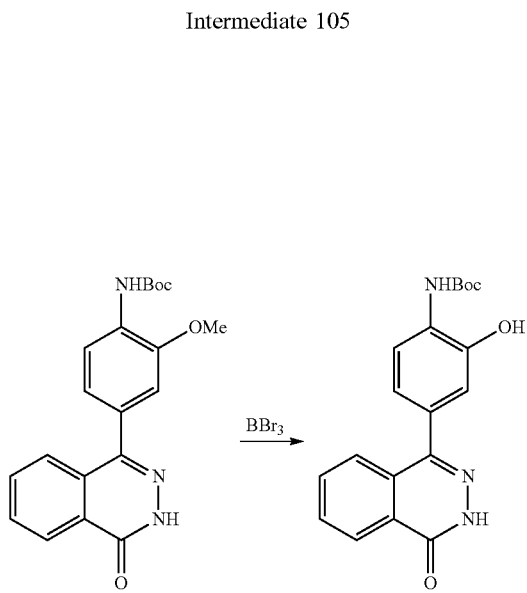

To a solution of Intermediate 105A (25 mg, 0.068 mmol) in DCM (2 mL), was add boron tribromide (0.34 mL, 0.34 mmol). The mixture was stirred at rt o/n, then was diluted with water and made basic with Na$_2$CO$_3$. The mixture was extracted with EtOAc, then the organic phase was concentrated. The residue was purified by flash chromatography (0-100% EtOAc/Hex) to afford Intermediate 105 (8 mg, 46% yield). MS(ESI) m/z: 254.1 (M+H)$^+$; $^1$H NMR (400 MHz, methanol-d$_4$) δ 7.21-7.15 (m, 1H), 6.72-6.65 (m, 1H), 6.64-6.57 (m, 2H), 5.72 (d, J=1.8 Hz, 1H), 5.70-5.58 (m, 2H).

Intermediate 106: Methyl 5-amino-2-(4-oxo-3,4-dihydrophthalazin-1-yl)benzoate

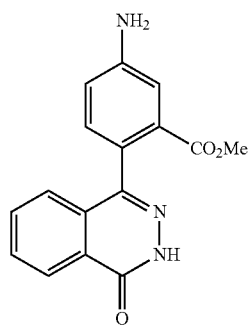 [SMILES: COC(=O)c1cc(N)ccc1-c1n[nH]c(=O)c2ccccc12]

Intermediate 106A: Methyl 2-bromo-5-((tert-butoxycarbonyl)amino)benzoate

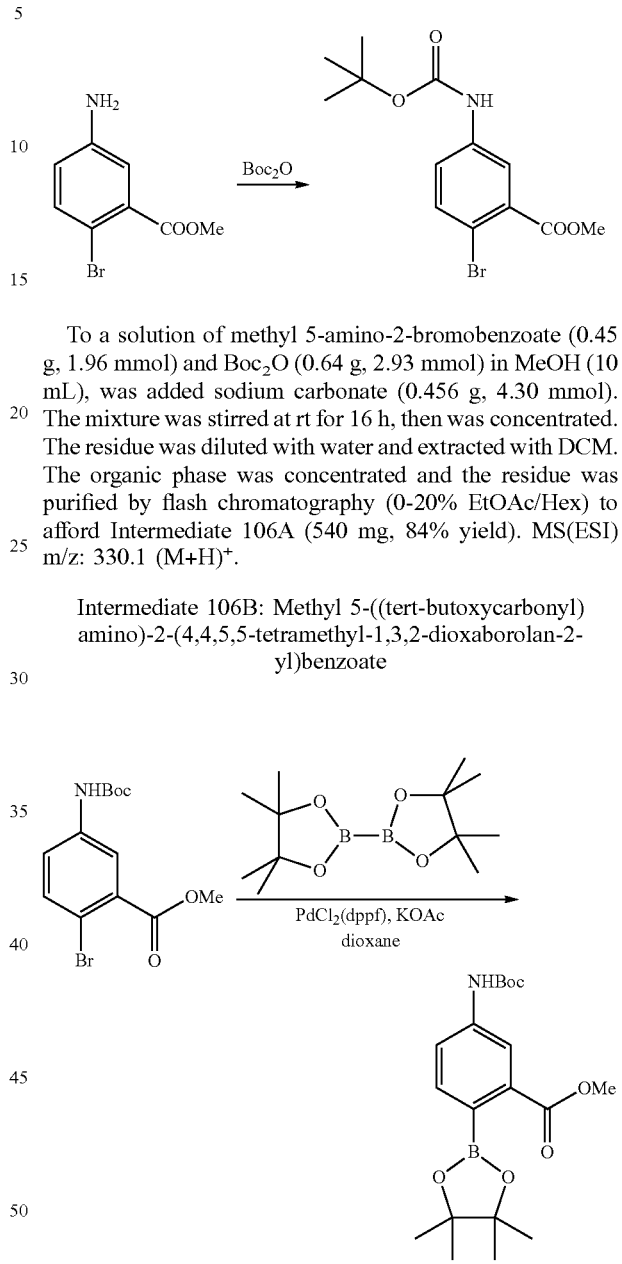

To a solution of methyl 5-amino-2-bromobenzoate (0.45 g, 1.96 mmol) and Boc$_2$O (0.64 g, 2.93 mmol) in MeOH (10 mL), was added sodium carbonate (0.456 g, 4.30 mmol). The mixture was stirred at rt for 16 h, then was concentrated. The residue was diluted with water and extracted with DCM. The organic phase was concentrated and the residue was purified by flash chromatography (0-20% EtOAc/Hex) to afford Intermediate 106A (540 mg, 84% yield). MS(ESI) m/z: 330.1 (M+H)$^+$.

Intermediate 106B: Methyl 5-((tert-butoxycarbonyl)amino)-2-(4,4,5,5-tetramethyl-1,3,2-dioxaborolan-2-yl)benzoate To a mixture of Intermediate 106A (360 mg, 1.09 mmol), 4,4,4',4',5,5,5',5'-octamethyl-2,2'-bi(1,3,2-dioxaborolane) (305 mg, 1.20 mmol), and potassium acetate (321 mg, 3.27 mmol) in dioxane (3 mL), was added PdCl$_2$(dppf) CH$_2$Cl$_2$ adduct (24 mg, 0.033 mmol). The reaction mixture was degassed (3× vacuum/Ar), sealed in a vial and heated at 110° C. for 3 h. The reaction mixture was diluted with water, then extracted with EtOAc. The organic phase was concentrated and the residue was purified by flash chromatography (0-40% EtOAc/Hex) to afford Intermediate 106B (310 mg, 75% yield) as a yellow oil. MS(ESI) m/z: 376.3 (M+H)$^+$; $^1$H NMR (400 MHz, chloroform-d) δ ppm 7.95 (1H, d, J=1.98 Hz), 7.54 (1H, dd, J=8.14, 1.76 Hz), 7.40 (1H, d, J=7.92 Hz), 7.03 (1H, s), 3.87 (3H, s), 1.50 (9H, s), 1.39 (12H, s).

Intermediate 106C: Methyl 5-((tert-butoxycarbonyl)amino)-2-(4-oxo-3,4-dihydrophthalazin-1-yl)benzoate

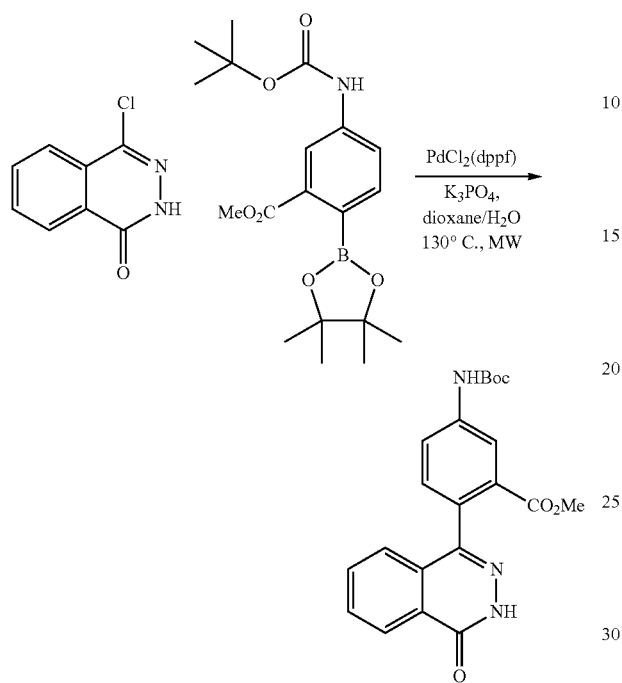

To a 5 mL of microwave vial containing a solution of Intermediate 106B (92 mg, 0.24 mmol) in dioxane (3 mL) were added 4-chlorophthalazin-1(2H)-one (40 mg, 0.22 mmol), potassium phosphate tribasic (118 mg, 0.554 mmol), water (0.3 mL) and PdCl$_2$(dppf) CH$_2$Cl$_2$ adduct (18.09 mg, 0.022 mmol) at RT. The reaction was purged with nitrogen, sealed and then heated in a microwave reactor at 130° C. for 15 min. The reaction mixture was diluted with water, then was extracted with EtOAc. The organic phase was concentrated and the residue was purified by flash chromatography (0-80% EtOAc/Hex) to afford Intermediate 106C (38 mg, 43% yield) as a white solid. MS(ESI) m/z: 396.3 (M+H)$^+$; $^1$H NMR (400 MHz, methanol-d$_4$) δ 8.44-8.38 (m, 1H), 8.22 (d, J=2.4 Hz, 1H), 7.88-7.76 (m, 3H), 7.42 (d, J=8.4 Hz, 1H), 7.37-7.31 (m, 1H), 3.55 (s, 3H), 1.56 (s, 9H).

Intermediate 106

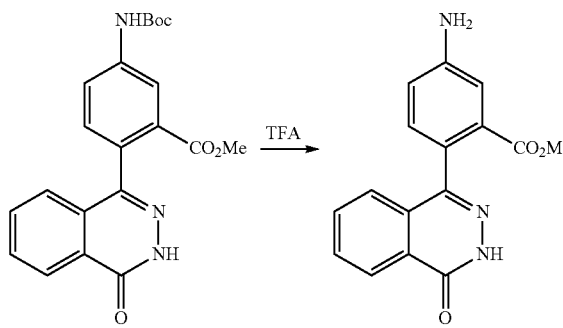

Intermediate 106C (66 mg, 0.17 mmol) was stirred with TFA (1 mL) and DCM (1 mL) at rt for 30 min, then was concentrated. The residue was purified by flash chromatography (0-90% EtOAc/Hex) to afford Intermediate 106 (47 mg, 95% yield). MS(ESI) m/z: 296.2 (M+H)$^+$; $^1$H NMR (400 MHz, methanol-d$_4$) δ 8.48-8.36 (m, 1H), 7.87-7.75 (m, 2H), 7.46-7.38 (m, 1H), 7.36 (d, J=2.4 Hz, 1H), 7.19 (d, J=8.1 Hz, 1H), 6.96 (dd, J=8.1, 2.4 Hz, 1H), 3.49 (s, 3H).

Intermediate 107: 4-(4-Amino-3-fluorophenyl)phthalazin-1(2H)-one, TFA

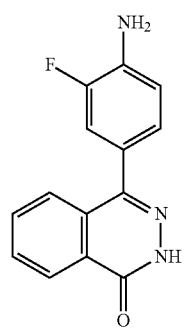 [SMILES: Nc1ccc(-c2n[nH]c(=O)c3ccccc23)cc1F]

Intermediate 107A: tert-Butyl (2-fluoro-4-(4-oxo-3,4-dihydrophthalazin-1-yl)phenyl)carbamate

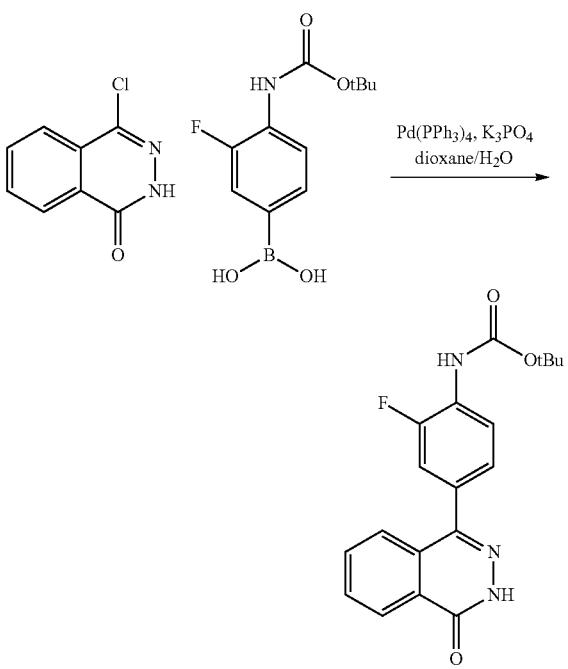

To a vial containing 4-chlorophthalazin-1(2H)-one (100 mg, 0.554 mmol), (4-((tert-butoxycarbonyl)amino)-3-fluorophenyl)boronic acid (155 mg, 0.609 mmol) and potassium phosphate tribasic (294 mg, 1.38 mmol), were added dioxane (1.8 mL) and water (0.2 mL). The mixture was degassed (evacuated and flushed with Ar (3×)), then was treated with Pd(Ph₃P)₄ (32 mg, 0.028 mmol). The mixture was degassed (3×), then the vial was sealed and heated in a microwave reactor at 150° C. for 30 min. The mixture was partitioned between EtOAc and H₂O. The aqueous phase was extracted with EtOAc. The combined organic phase was washed with brine, dried (Na₂SO₄) and concentrated. The crude product was purified by flash chromatography (gradient from 0 to 100% ethyl acetate/hexanes) to afford Intermediate 107A as a white solid (124 mg, 63% yield). MS(ESI) m/z: 356.1 (M+H)⁺; ¹H NMR (400 MHz, methanol-d₄) δ 8.40-8.48 (m, 1H), 8.06 (t, J=8.36 Hz, 1H), 7.86-7.96 (m, 2H), 7.81-7.86 (m, 1H), 7.35-7.43 (m, 2H), 1.56 (s, 9H); ¹⁹F NMR (376 MHz, methanol-d₄) δ −129.38 (s, 1F).

Intermediate 107

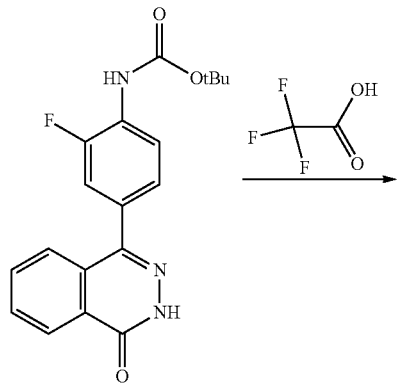

To a suspension of Intermediate 107A (123 mg, 0.346 mmol) in DCM (2 mL), was added TFA (2 mL). The resultant yellow solution was stirred at rt for 1.25 h, then was concentrated to afford Intermediate 107 (128 mg, 100% yield) as a white solid. MS(ESI) m/z: 256.1 (M+H)⁺; ¹H NMR (400 MHz, methanol-d₄) δ 8.39-8.46 (m, 1H), 7.82-7.96 (m, 3H), 7.25 (dd, J=1.98, 11.88 Hz, 1H), 7.19 (dd, J=1.98, 8.14 Hz, 1H), 6.94-7.04 (m, 1H).

Intermediate 108: 4-(4-Amino-2-(hydroxymethyl)phenyl)phthalazin-1(2H)-one

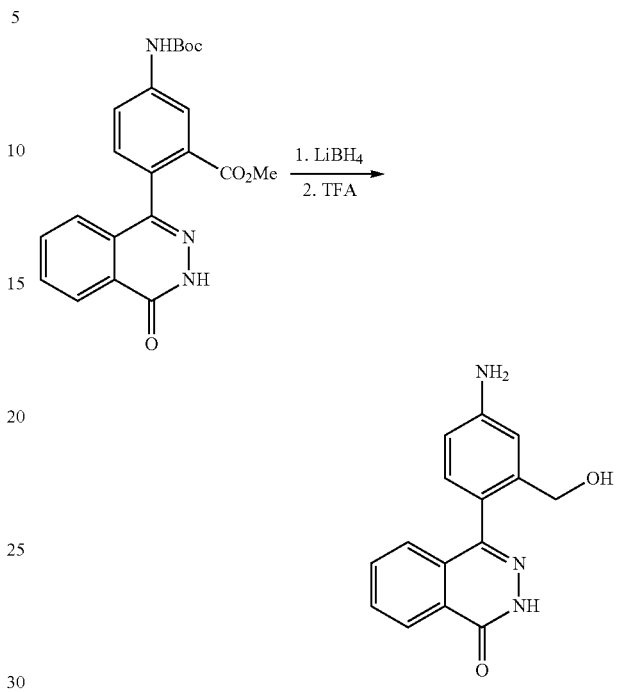

To a solution of Intermediate 106C (220 mg, 0.556 mmol) in THF (1 mL) was added 2.0 M (in THF) lithium borohydride (0.684 mL, 1.37 mmol) at room temperature. The reaction mixture was stirred at room temperature for 16 h, then was quenched with MeOH and concentrated. The residue was purified by flash chromatography (0-90% EtOAc/Hex) to afford tert-butyl (3-(hydroxymethyl)-4-(4-oxo-3,4-dihydrophthalazin-1-yl)phenyl)carbamate (88 mg, 59% yield). The material was stirred with TFA (1 mL) and DCM (1 mL) for 30 min, then was concentrated. The residue was purified by flash chromatography (0-20% MeOH/DCM) to afford Intermediate 108 (88 mg, 59% yield). MS(ESI) m/z: 268.2 (M+H)⁺; ¹H NMR (400 MHz, methanol-d₄) δ 8.48-8.36 (m, 1H), 7.83 (quind, J=7.3, 1.5 Hz, 2H), 7.54-7.41 (m, 1H), 7.23-7.15 (m, 2H), 6.93 (dd, J=7.9, 2.6 Hz, 1H), 4.42 (br. s., 2H).

Intermediate 109: 1-((Tetrahydrofuran-2-yl)methyl)-1H-indazole-3-carboxylic Acid

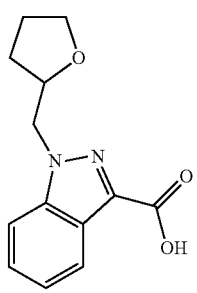 [SMILES: O=C(O)c1nn(CC2CCCO2)c2ccccc12]

Intermediate 109A: Ethyl 1-((tetrahydrofuran-2-yl)methyl)-1H-indazole-3-carboxylate

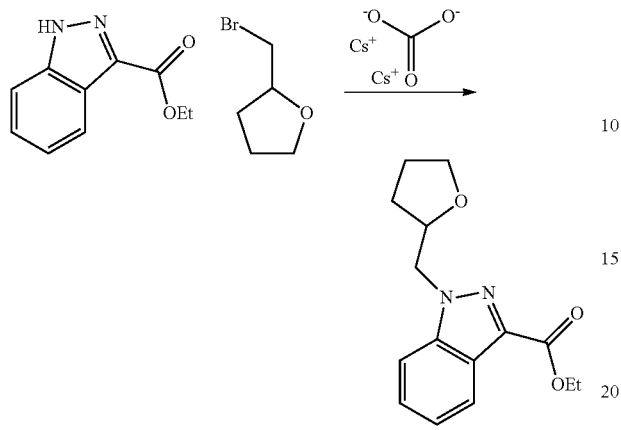

To a vial containing ethyl 1H-indazole-3-carboxylate (200 mg, 1.05 mmol) in acetonitrile (3 mL), were added 2-(bromomethyl)tetrahydrofuran (226 mg, 1.37 mmol) and $Cs_2CO_3$ (514 mg, 1.58 mmol). The vial was sealed and the mixture was stirred at 70° C. overnight. The reaction mixture was diluted with water, then was extracted with EtOAc. The organic phase was with 10% LiCl and brine, then was concentrated. The residue was purified by flash chromatography (0-60% EtOAc/Hex) to afford Intermediate 109A (199 mg, 69% yield). MS(ESI) m/z: 275.2 $(M+H)^+$; $^1H$ NMR (400 MHz, chloroform-d) δ 8.19 (dt, J=8.1, 1.0 Hz, 1H), 7.63-7.57 (m, 1H), 7.41 (ddd, J=8.4, 7.0, 1.1 Hz, 1H), 7.29 (ddd, J=8.1, 7.0, 0.9 Hz, 1H), 4.64-4.47 (m, 4H), 4.40 (qd, J=6.3, 4.5 Hz, 1H), 3.81-3.63 (m, 2H), 2.05-1.94 (m, 1H), 1.88-1.64 (m, 3H), 1.48 (t, J=7.2 Hz, 3H).

Intermediate 109

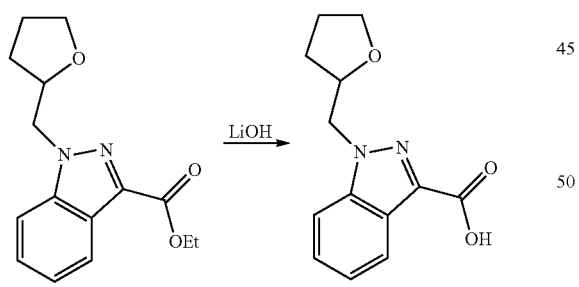

To a solution of Intermediate 109A (205 mg, 0.747 mmol) in THF (3 mL), was added 1M lithium hydroxide (2.242 mL, 2.242 mmol), stirred at rt overnight. The reaction mixture was concentrated, then the residue was taken up in water and EtOAc, then acidified with 1 N HCl. The phases were separated, then the aqueous phase was extracted with EtOAc (3×). The combined organic phase was washed with brine, dried ($Na_2SO_4$) and concentrated to afford Intermediate 109 (175 mg, 95% yield) as a colorless oil. MS(ESI) m/z: 247.1 $(M+H)^+$; $^1H$ NMR (400 MHz, methanol-$d_4$) δ 8.15 (dt, J=8.1, 1.0 Hz, 1H), 7.72 (dt, J=8.6, 0.9 Hz, 1H), 7.47 (ddd, J=8.4, 7.0, 1.1 Hz, 1H), 7.31 (ddd, J=8.1, 7.0, 0.9 Hz, 1H), 4.65-4.52 (m, 2H), 4.46-4.33 (m, 1H), 3.87-3.62 (m, 2H), 2.16-1.94 (m, 1H), 1.93-1.65 (m, 3H).

Intermediate 110: 4-(4-Aminophenyl)-7-methoxyphthalazin-1(2H)-one, TFA

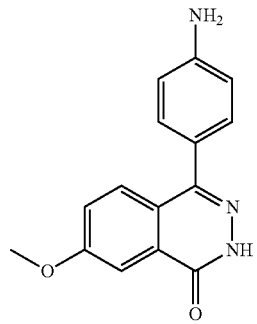 [SMILES: COc1ccc2c(-c3ccc(N)cc3)n[nH]c(=O)c2c1]

Intermediate 110A: Ethyl 2-(4-((tert-butoxycarbonyl)amino)benzoyl)-5-methoxybenzoate (4-((tert-Butoxycarbonyl)amino)phenyl)boronic acid (915 mg, 3.86 mmol), ethyl 2-bromo-5-methoxybenzoate (500 mg, 1.930 mmol), PEPPSI-IPR catalyst (65.8 mg, 0.096 mmol), and $Cs_2CO_3$ (1886 mg, 5.79 mmol) were placed in a vial. PhCl (10 mL) was added, and the vial was evacuated and backfilled with CO gas (3×). The mixture was heated with stirring at 80° C. under balloon of CO for 20 h. Most of PhCl was removed under reduced pressure, the residue was purified by flash chromatography (0-70% EtOAc/Hex) to afford Intermediate 110A (308 mg, 40% yield) as an amber oil, which solidified upon standing.

MS(ESI) m/z: 400.2 (M+H)⁺; ¹H NMR (500 MHz, DMSO-d₆) δ ppm 9.78 (s, 1H), 7.67-7.57 (m, 2H), 7.48 (d, J=8.4 Hz, 1H), 7.40 (d, J=8.6 Hz, 1H), 7.37 (d, J=2.4 Hz, 1H), 7.26 (dd, J=8.6, 2.6 Hz, 1H), 3.97 (q, J=7.1 Hz, 2H), 3.88 (s, 3H), 1.48 (s, 9H), 0.98 (t, J=7.2 Hz, 3H).

Intermediate 110B: tert-Butyl (4-(6-methoxy-4-oxo-3,4-dihydrophthalazin-1-yl)phenyl)carbamate

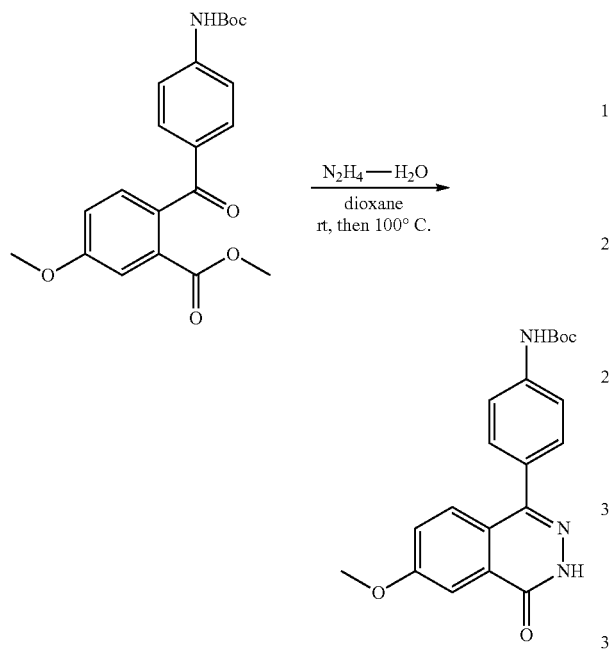

Intermediate 110A (308 mg, 0.799 mmol) was placed in a pressure vial, and dioxane (4 mL), and hydrazine hydrate (0.581 mL, 12.0 mmol) were added sequentially. The reaction mixture was stirred at rt for 15 min, and then at 100° C. for 3 h. The reaction mixture was diluted with EtOAc (100 mL), washed with water (3×), brine, and dried (Na₂SO₄). The organic phase was concentrated and the residue was purified by flash chromatography (5-100% EtOAc/Hex) to afford Intermediate 110B (172 mg, 59% yield) as a white solid. MS(ESI) m/z: 368.1 (M+H)⁺; ¹H NMR (400 MHz, DMSO-d₆) δ ppm 12.69 (s, 1H), 9.56 (s, 1H), 7.71 (d, J=2.9 Hz, 1H), 7.66 (d, J=8.8 Hz, 1H), 7.61 (d, J=8.6 Hz, 2H), 7.49-7.42 (m, 3H), 3.95 (s, 3H), 1.50 (s, 9H).

Intermediate 110

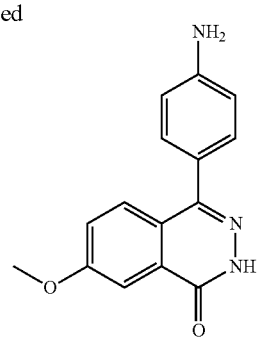

Intermediate 110B (172 mg, 0.468 mmol) was dissolved in TFA (2 mL), and the reaction mixture was stirred at rt for 15 min. TFA was removed under reduced pressure, the residue triturated with Et₂O to give Intermediate 110 (171 mg, 96% yield) as an off-white solid. MS(ESI) m/z: 268.1 (M+H)⁺; ¹H NMR (400 MHz, DMSO-d₆) δ ppm 12.65 (s, 1H), 7.71 (d, J=2.6 Hz, 1H), 7.68 (d, J=9.0 Hz, 1H), 7.46 (dd, J=9.0, 2.9 Hz, 1H), 7.38 (d, J=8.6 Hz, 2H), 6.95 (d, J=8.4 Hz, 2H), 3.95 (s, 3H).

Intermediate 111: N-(4-(3-(Dicyclopropylmethyl)-4-oxo-3,4-dihydrophthalazin-1-yl)phenyl)-1H-pyrazole-4-carboxamide

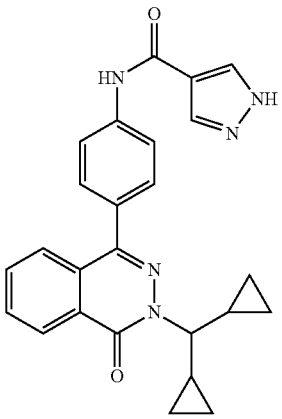 [SMILES: O=C(Nc1ccc(-c2nn(C(C3CC3)C3CC3)c(=O)c3ccccc23)cc1)c1cn[nH]c1]

Intermediate 111A: 4-(4-Bromophenyl)-2-(dicyclopropylmethyl)phthalazin-1(2H)-one

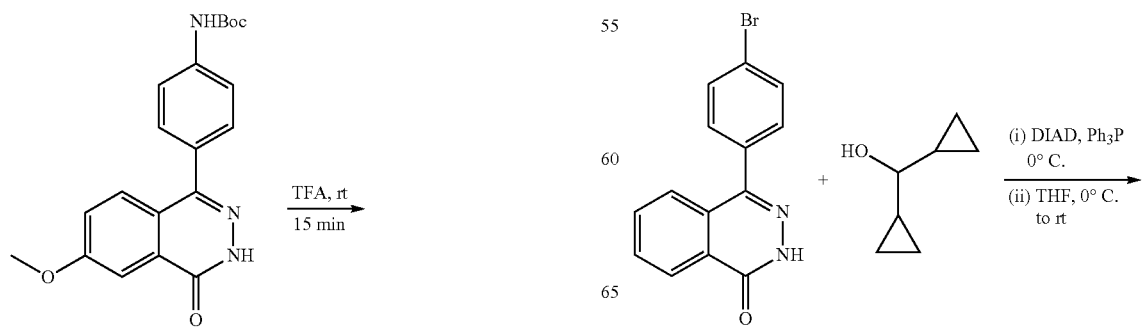

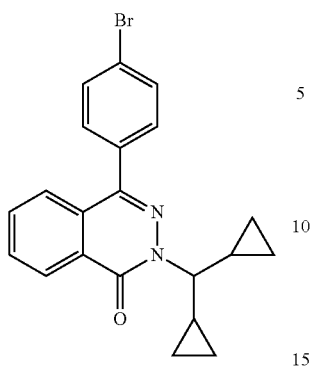
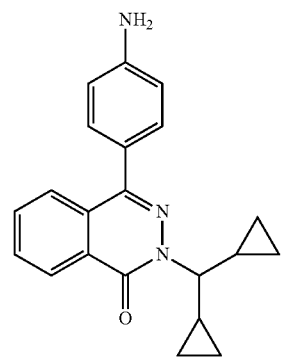

Ph₃P (4.35 g, 16.60 mmol) was dissolved in dry THF (40 mL), and the stirred reaction mixture was cooled to 0° C. Afterwards, DIAD (3.23 mL, 16.60 mmol) was added dropwise over 5 min, and the reaction mixture was stirred at 0° C. for 15 min (thick suspension formed). Then, a suspension of 4-(4-bromophenyl)phthalazin-1(2H)-one (2.000 g, 6.64 mmol) and dicyclopropylmethanol (0.979 mL, 8.30 mmol) in dry THF (20 mL) was added, and the reaction mixture was allowed to reach rt, and stirred at rt for 16 h. The reaction mixture was quenched with MeOH (5 mL), diluted with EtOAc (250 mL). Then CELITE® was added, the solvent was removed under reduced pressure and the residue was purified flash chromatography (EtOAc/hexane) to afford 1.396 g (53.2%) of Intermediate 111A as a white solid. MS(ESI) m/z: 395.1 (M+H)⁺; ¹H NMR (400 MHz, DMSO-d₆) δ ppm 8.56-8.47 (m, 1H), 7.85-7.72 (m, 3H), 7.71-7.63 (m, 2H), 7.59-7.48 (m, 2H), 3.81 (t, J=9.2 Hz, 1H), 1.63-1.56 (m, 2H), 0.75-0.63 (m, 2H), 0.57-0.46 (m, 2H), 0.43-0.30 (m, 4H).

The following reaction was carried out behind the blast shield. Intermediate 111A (1.396 g, 3.53 mmol), L-Proline (0.529 g, 4.59 mmol), and cuprous oxide (0.505 g, 3.53 mmol) were placed into a round-bottom flask, and DMSO (20 mL) was added. The reaction mixture was degassed with stirring (3× vacuum/Ar), and sodium azide (0.459 g, 7.06 mmol) was added. The reaction mixture was degassed again (2× vacuum/Ar), and stirred under Ar at 100° C. for 3 h. The reaction mixture was cooled to rt, was quenched with NH₄Cl (std. aq, 10 mL), diluted with EtOAc (500 mL) and water (200 mL). Organic phase was separated, washed with Na₂CO₃ (aq. std., 2×50 mL), water (1×100 mL), brine (1×50 mL), dried (Na₂SO₄) and filtered. EtOAc was removed under reduced pressure and the residue was purified by flash chromatography (EtOAc/hexane) to afford Intermediate 111B (0.742 g, 63.4% yield) as an off-white solid. MS(ESI) m/z: 332.1 (M+H)⁺; ¹H NMR (400 MHz, DMSO-d₆) δ ppm 8.34 (dd, J=8.1, 1.3 Hz, 1H), 7.97-7.81 (m, 3H), 7.34 (d, J=8.4 Hz, 2H), 6.72 (d, J=8.6 Hz, 2H), 5.45 (s, 2H), 3.67 (t, J=9.0 Hz, 1H), 1.58-1.45 (m, 2H), 0.70-0.60 (m, 2H), 0.55 (dq, J=9.4, 4.9 Hz, 2H), 0.40-0.29 (m, 2H), 0.18 (dq, J=9.4, 4.9 Hz, 2H).

Intermediate 111

Intermediate 111B: 4-(4-Aminophenyl)-2-(dicyclopropylmethyl)phthalazin-1(2H)-one

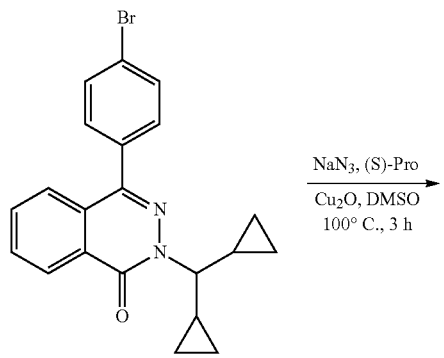
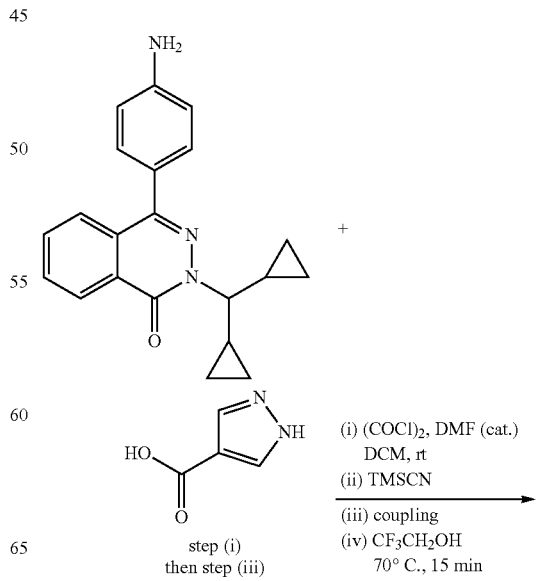

-continued

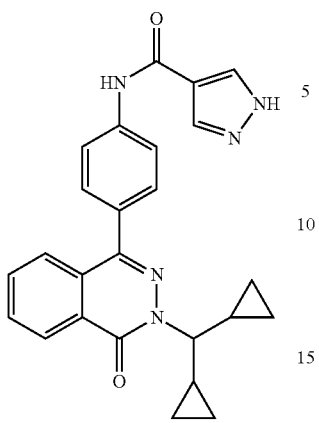

1H-Pyrazole-4-carboxylic acid (0.301 g, 2.69 mmol) was suspended in DCM (20 mL), and a drop a DMF was added. Then, oxalyl chloride (2 M in DCM) (5.60 mL, 11.19 mmol) was added dropwise, and the reaction mixture was stirred for 2 h at rt (reaction mixture became homogeneous). Then, DCM was removed under reduced pressure, and the obtained acid chloride (white solid) was used in the subsequent step. In a separate flask, to a solution of Intermediate 111B (0.742 g, 2.239 mmol) in THF (20 mL), was added Trimethylsilyl cyanide (2.99 mL, 22.39 mmol). The resultant solution was stirred at rt for 10 min, and then was treated with a solution of 1H-pyrazole-4-carboxylic acid chloride obtained as described above in THF (5 mL). The mixture was stirred at 50° C. for 1.5 h. Afterwards, the reaction mixture was concentrated, then trifluoroethanol (10 mL) was added. The mixture was stirred at 70° C. for 15 min, and then concentrated. The obtained reside was purified by flash chromatography (MeOH/DCM) to give 0.781 g (82%) of Intermediate 111. MS(ESI) m/z: 426.1 (M+H)+; 1H NMR (400 MHz, DMSO-d6) δ ppm 13.29 (br. s., 1H), 10.01 (s, 1H), 8.37 (dd, J=7.5, 1.3 Hz, 1H), 8.27 (br. s., 1H), 7.99-7.87 (m, 4H), 7.87-7.81 (m, 1H), 7.66 (d, J=8.6 Hz, 2H), 3.70 (t, J=9.2 Hz, 1H), 1.61-1.47 (m, 2H), 0.72-0.61 (m, 2H), 0.57 (dq, J=9.5, 4.8 Hz, 2H), 0.42-0.31 (m, 2H), 0.20 (dq, J=9.6, 4.9 Hz, 2H)

Intermediate 112:
5-Methyl-1-phenyl-1H-1,2,3-triazole-4-carboxylic Acid

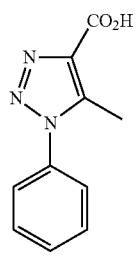

Intermediate 112A: Ethyl 5-methyl-1-phenyl-1H-1,2,3-triazole-4-carboxylate

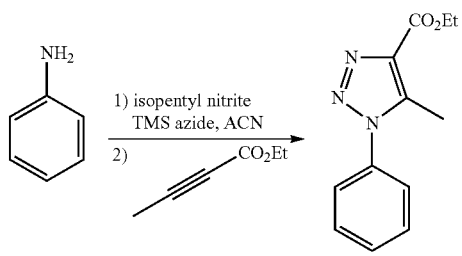

To the solution of aniline (0.33 g, 3.54 mmol) in acetonitrile (6 mL) at 0° C. was added isoamyl nitrite (0.524 mL, 3.90 mmol), followed by azidotrimethylsilane (0.513 mL, 3.90 mmol) dropwise. After 5 min, the cold bath removed, and the reaction was stirred at rt for 10 min, then ethyl but-2-ynoate (0.795 g, 7.09 mmol) added, and the reaction stirred in a sealed tube at 80° C. for 20 h, then cooled to rt. The reaction mixture was concentrated, then the residue was purified via preparative HPLC to afford Intermediate 112A (50 mg, 6% yield). MS(ESI) m/z: 232.0 (M+H)+; 1H NMR (400 MHz, chloroform-d) δ 7.63-7.55 (m, 3H), 7.49-7.41 (m, 2H), 4.47 (q, J=7.0 Hz, 2H), 2.60 (s, 3H), 1.45 (t, J=7.2 Hz, 3H).

Intermediate 112

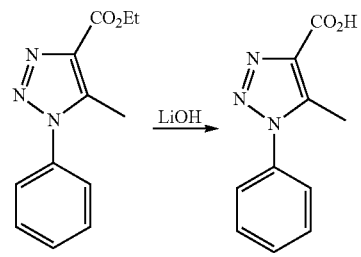

Intermediate 112A (36 mg, 0.16 mmol) was mixed with 1M lithium hydroxide (0.3 mL, 0.3 mmol) in THF (2 mL) and MeOH (2 mL), stirred rt for 2 h. The reaction mixture was concentrated and the residue was purified via preparative HPLC to afford Intermediate 112 (26 mg, 82% yield). MS(ESI) m/z: 204.1 (M+H)+; 1H NMR (400 MHz, methanol-d4) δ 7.70-7.61 (m, 3H), 7.60-7.52 (m, 2H), 2.59-2.54 (m, 3H).

Intermediate 113: 1-(4-Methoxyphenyl)-5-methyl-1H-1,2,3-triazole-4-carboxylic Acid

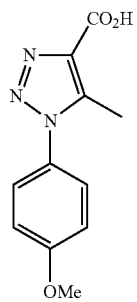 [SMILES: COc1ccc(-n2nnc(C(=O)O)c2C)cc1]

Intermediate 113A: Ethyl 1-(4-methoxyphenyl)-5-methyl-1H-1,2,3-triazole-4-carboxylate Intermediate 113B: Ethyl 1-(4-methoxyphenyl)-4-methyl-1H-1,2,3-triazole-5-carboxylate

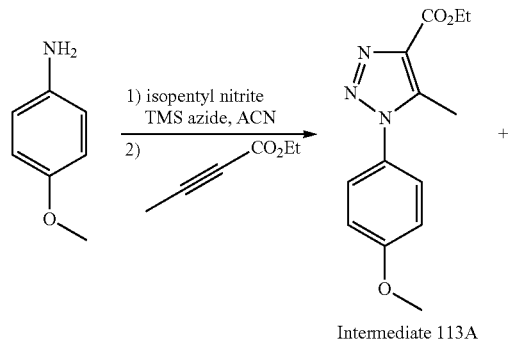

To the solution of 4-methoxyaniline (0.31 g, 2.5 mmol) in acetonitrile (6 mL) at 0° C. was added isoamyl nitrite (0.372 mL, 2.77 mmol), followed by azidotrimethylsilane (0.364 mL, 2.77 mmol) dropwise. After 5 min, the cold bath removed, and the reaction was stirred at rt for 10 min, then ethyl but-2-ynoate (0.564 g, 5.03 mmol) was added, and the reaction stirred in a sealed tube at 80° C. The reaction was stirred at 80° C. for 20 h, then cooled to rt. The reaction mixture was concentrated, then the residue was purified via preparative HPLC to afford Intermediate 113A (60 mg, 9% yield) and Intermediate 113B (22 mg, 3% yield).

Intermediate 113A: MS(ESI) m/z: 262.2 (M+H)$^+$; $^1$H NMR (400 MHz, chloroform-d) δ 7.36-7.30 (m, 2H), 7.06-7.00 (m, 2H), 4.43 (q, J=7.2 Hz, 2H), 3.86 (s, 3H), 2.53 (s, 3H), 1.42 (t, J=7.2 Hz, 3H).

Intermediate 113B: MS(ESI) m/z: 262.2 (M+H)$^+$; $^1$H NMR (400 MHz, chloroform-d) δ 7.37-7.31 (m, 2H), 7.03-6.97 (m, 2H), 4.27 (q, J=7.0 Hz, 2H), 3.87 (s, 3H), 2.62 (s, 3H), 1.25 (t, J=7.2 Hz, 3H).

Intermediate 113

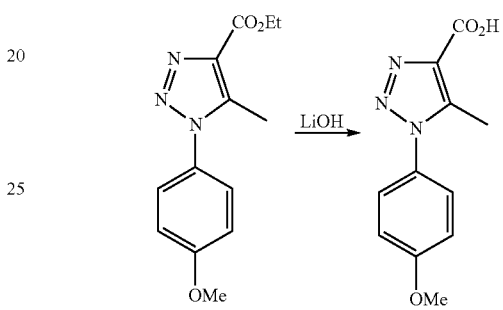

Intermediate 113A (60 mg, 0.23 mmol) was mixed with 1M lithium hydroxide (0.5 mL, 0.5 mmol) in THF (1 mL) and MeOH (1 mL). The reaction mixture was stirred rt for 3 h. The reaction mixture was concentrated and the residue was purified via preparative HPLC to afford Intermediate 113 (48 mg, 90% yield) as a white solid. MS(ESI) m/z: 234.0 (M+H)$^+$; $^1$H NMR (400 MHz, methanol-d$_4$) δ 7.48-7.41 (m, 2H), 7.17-7.11 (m, 2H), 3.88 (s, 3H), 2.52 (s, 3H).

Intermediate 114: 1-(4-Methoxyphenyl)-4-methyl-1H-1,2,3-triazole-5-carboxylic Acid

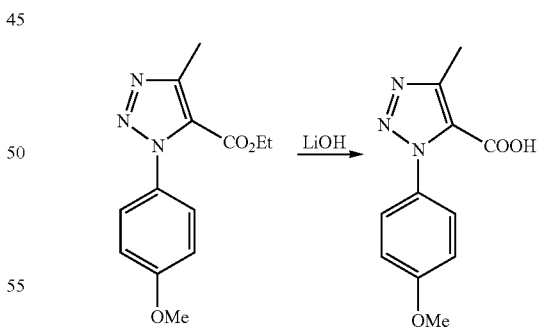

Intermediate 113B (22 mg, 0.084 mmol) was mixed with 1M lithium hydroxide (0.2 mL, 0.2 mmol) in THF (1 mL) and MeOH (1 mL) and was stirred at rt for 2 h. The reaction mixture was concentrated and the residue was acidified with TFA. The mixture was concentrated and the residue was purified by flash chromatography (0-20% MeOH/DCM) to afford Intermediate 114. MS(ESI) m/z: 234.0 (M+H)$^+$; $^1$H NMR (400 MHz, methanol-d$_4$) δ 7.45-7.24 (m, 2H), 7.08-6.90 (m, 2H), 3.87 (s, 3H), 2.58 (s, 3H).

Example 1: 4-(4-(2-(Isoindolin-2-yl)-2-oxoethyl)phenyl)phthalazin-1(2H)-one

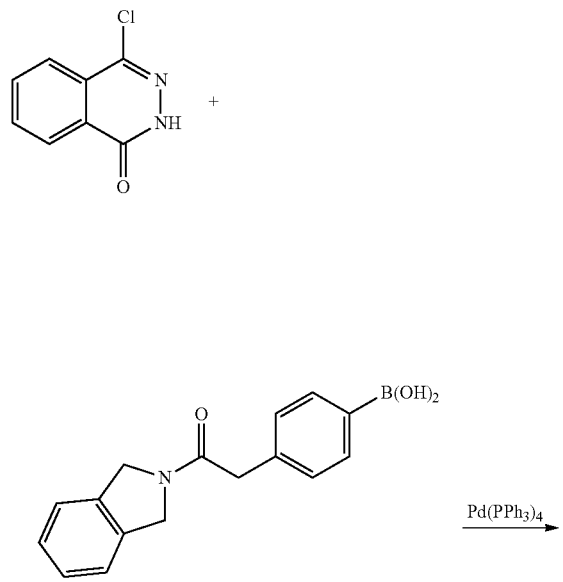

To 4-chlorophthalazin-1(2H)-one (9.9 mg, 0.055 mmol), Intermediate 8 (14 mg, 0.050 mmol) and potassium phosphate (26.4 mg, 0.125 mmol), were added dioxane (3 mL) and water (0.5 mL). The mixture was degassed (evacuated and flushed with Ar (5×)). Pd(PPh$_3$)$_4$ (2.9 mg, 2.5 µmol) was added, then the mixture was degassed (2×). The reaction vial was sealed and heated in a microwave reactor at 150° C. for 25 min. The reaction mixture was concentrated, then was purified by preparative HPLC to afford 4.4 mg (18%) of Example 1. MS(ESI) m/z: 382.20 (M+H)$^+$; $^1$H NMR (500 MHz, DMSO-d$_6$) δ 12.82 (s, 1H), 8.42-8.29 (m, 1H), 7.96-7.84 (m, 2H), 7.77-7.67 (m, 1H), 7.61-7.52 (m, 2H), 7.52-7.43 (m, 2H), 7.41-7.36 (m, 2H), 7.36-7.27 (m, 2H), 4.98 (s, 2H), 4.70 (s, 2H), 3.89 (s, 2H); Analytical HPLC RT=1.51 min (Method E), 1.52 min (Method F).

Example 2: 4-(4-(2-(5-Fluoroisoindolin-2-yl)-2-oxoethyl)phenyl)phthalazin-1 (2H)-one

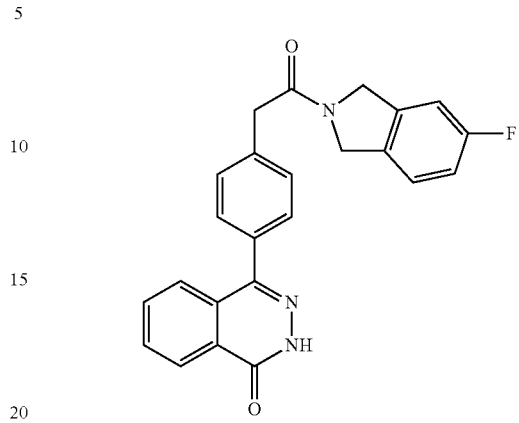

According a method similar to the preparation of Example 1, substitution of isoindoline with 5-fluoroisoindoline afforded Example 2. MS(ESI) m/z: 400.1 (M+H)$^+$; $^1$H NMR (500 MHz, DMSO-d$_6$) δ 12.82 (s, 1H), 8.38-8.31 (m, 1H), 7.93-7.86 (m, 2H), 7.74-7.69 (m, 1H), 7.66-7.36 (m, 5H), 7.23 (d, J=9.1 Hz, 1H), 7.18-7.10 (m, 1H), 4.95 (d, J=16.8 Hz, 2H), 4.68 (d, J=16.8 Hz, 2H), 3.87 (s, 2H); Analytical HPLC RT=1.53 min (Method E), 1.52 min (Method F).

Example 3: 4-(4-(2-(5-Methoxyisoindolin-2-yl)-2-oxoethyl)phenyl)phthalazin-1(2H)-one

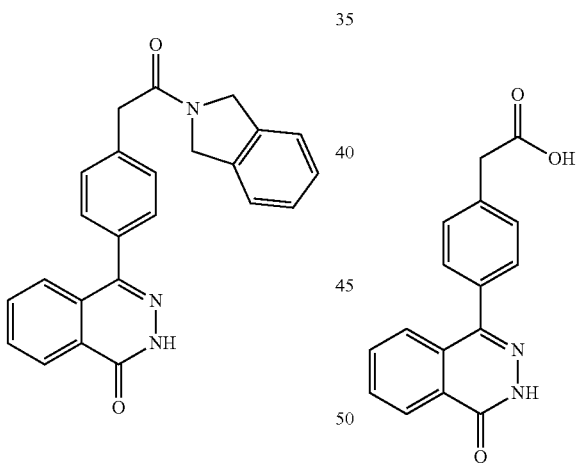

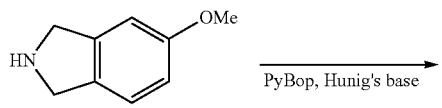

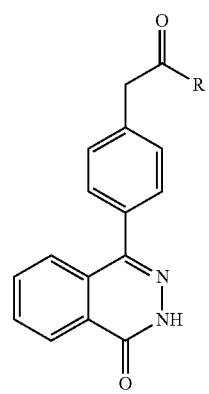

To a solution of Intermediate 1 (25 mg, 0.089 mmol) in DMF (3 mL), was added 5-methoxyisoindoline (20 mg, 0.134 mmol), PyBOP (69.6 mg, 0.134 mmol), and DIEA (0.078 mL, 0.446 mmol). The mixture was stirred at rt for 2 h, then was purified by preparative HPLC to afford 28.1 mg (59%) of Example 3. MS(ESI) m/z: 412.2 (M+H)$^+$; $^1$H NMR (500 MHz, DMSO-d$_6$) δ 12.82 (s, 1H), 8.36-8.31 (m, 1H), 7.93-7.86 (m, 2H), 7.73-7.68 (m, 1H), 7.55 (d, J=7.7 Hz, 2H), 7.46 (d, J=8.0 Hz, 2H), 7.26 (dd, J=8.3, 4.4 Hz, 1H), 6.95 (d, J=11.6 Hz, 1H), 6.88 (dd, J=8.4, 1.8 Hz, 1H), 4.95-4.86 (m, 2H), 4.69-4.59 (m, 2H), 3.87 (s, 2H), 3.75 (s, 3H); Analytical HPLC RT=1.61 min (Method E), 1.61 min (Method F).

The following Examples in Table 1 were made by using the same procedure as shown in Example 3. Intermediate 1 was coupled with the appropriate amine. Various coupling reagents could be used other than the one described in Example 3 such as BOP, PyBop, EDC/HOBt or HATU.

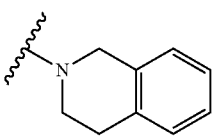 [SMILES: *N1CCc2ccccc2C1]

TABLE 1

| Example | R | Name | LCMS (M + H)$^+$ | HPLC Method, RT (min.) | $^1$H NMR |
|---|---|---|---|---|---|
| 4 | 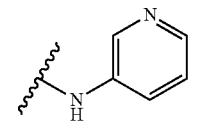 | 4-{4-[2-[2-oxo-2-(1,2,3,4-tetrahydroisoquinolin-2-yl)ethyl]phenyl}-1,2-dihydrophthalazin-1-one | 396.1 | E: 1.56 F: 1.55 | (500 MHz, DMSO-d$_6$) δ 12.92-12.70 (m, 1H), 8.34 (dd, J = 5.4, 2.1 Hz, 1H), 7.97-7.84 (m, 2H), 7.75-7.56 (m, 1H), 7.56-7.47 (m, 2H), 7.47-7.34 (m, 2H), 7.25-7.05 (m, 4H), 4.77 (s, 1H), 4.66 (s, 1H), 3.97-3.84 (m, 2H), 3.79 (t, J = 5.9 Hz, 1H), 3.72 (t, J = 5.9 Hz, 1H), 2.79 (t, J = 5.9 Hz, 2H) |
| 5 | 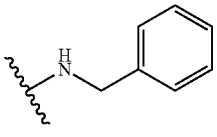 [SMILES: *NCc1ccccc1] | 2-[4-(4-oxo-3,4-dihydrophthalazin-1-yl)phenyl]-N-(pyridin-3-yl)acetamide | 357.1 | E: 0.95 F: 1.13 | (500 MHz, DMSO-d$_6$) δ 12.83 (s, 1H), 10.69 (s, 1H), 8.92 (br. s., 1H), 8.41-8.30 (m, 2H), 8.19 (d, J = 8.5 Hz, 1H), 7.94-7.83 (m, 2H), 7.75-7.66 (m, 1H), 7.60-7.55 (m, 2H), 7.55 (d, J = 3.6 Hz, 1H), 7.54-7.50 (m, 2H), 3.83 (s, 2H) |
| 6 | 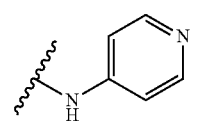 [SMILES: *Nc1ccncc1] | N-benzyl-2-[4-(4-oxo-3,4-dihydrophthalazin-1-yl)phenyl]acetamide | 370.1 | E: 1.50 F: 1.50 | (500 MHz, DMSO-d$_6$) δ 12.82 (s, 1H), 8.62 (t, J = 5.5 Hz, 1H), 8.34 (dd, J = 6.3, 2.8 Hz, 1H), 7.95-7.83 (m, 2H), 7.78-7.63 (m, 1H), 7.57-7.51 (m, J = 8.0 Hz, 2H), 7.49-7.40 (m, J = 8.0 Hz, 2H), 7.36-7.29 (m, 2H), 7.29-7.22 (m, 3H), 4.31 (d, J = 6.1 Hz, 2H), 3.60 (s, 2H) |
| 7 |  | 2-[4-(4-oxo-3,4-dihydrophthalazin-1-yl)phenyl]-N-(pyridin-4-yl)acetamide | 357.1 | E: 0.98 F: 1.13 | (500 MHz, DMSO-d$_6$) δ 12.84 (s, 1H), 11.39 (s, 1H), 8.65 (d, J = 6.3 Hz, 2H), 8.45-8.29 (m, 1H), 7.97 (d, J = 6.6 Hz, 2H), 7.93-7.84 (m, 2H), 7.80-7.65 (m, 1H), 7.63-7.55 (m, J = 8.0 Hz, 2H), 7.55-7.43 (m, J = 8.0 Hz, 2H), 3.93 (s, 2H) |

TABLE 1-continued

| Example | R | Name | LCMS (M + H)+ | HPLC Method, RT (min.) | $^1$H NMR |
|---|---|---|---|---|---|
| 8 | (N-methyl-N-benzyl group structure) | N-benzyl-N-methyl-2-[4-(4-oxo-3,4-dihydrophthalazin-1-yl)phenyl]acetamide | 384.1 | E: 1.54 F: 1.53 | (500 MHz, DMSO-$d_6$) δ 12.83 (br. s., 1H), 8.41-8.29 (m, 1H), 7.96-7.85 (m, 2H), 7.73-7.63 (m, 1H), 7.60-7.14 (m, 9H), 4.81-4.50 (m, 2H), 3.95-3.82 (m, 2H), 3.10-2.80 (m, 3H) |
| 9 | (benzimidazol-2-ylamino structure) | N-(1H-1,3-benzodiazol-2-yl)-2-[4-(4-oxo-3,4-dihydrophthalazin-1-yl)phenyl]acetamide | 396.2 | E: 1.09 F: 1.34 | $^1$H NMR (500 MHz, DMSO-$d_6$) δ 12.83 (s, 1H), 12.03 (br. s., 1H), 8.37-8.29 (m, 1H), 7.93-7.85 (m, 2H), 7.72-7.66 (m, 1H), 7.61-7.53 (m, 4H), 7.47 (dd, J = 5.8, 3.3 Hz, 2H), 7.14 (dd, J = 5.5, 3.0 Hz, 2H), 3.93 (s, 2H) |
| 10 | (benzoxazol-2-ylamino structure) | N-(1,3-benzoxazol-2-yl)-2-[4-(4-oxo-3,4-dihydrophthalazin-1-yl)phenyl]acetamide | 397.1 | E: 1.29 F: 1.31 | $^1$H NMR (500 MHz, DMSO-$d_6$) δ 12.82 (s, 1H), 8.34 (dd, J = 6.2, 2.9 Hz, 1H), 7.94-7.83 (m, 2H), 7.76-7.67 (m, 1H), 7.58-7.45 (m, 5H), 7.26-7.20 (m, 1H), 7.20-7.15 (m, 1H), 3.87 (br. s., 2H) |
| 11 | (4-phenylpiperidin-1-yl structure) | 4-{4-[2-oxo-2-(4-phenylpiperidin-1-yl)ethyl]phenyl}-1,2-dihydrophthalazin-1-one | 424.4 | C: 2.63 D: 3.80 | $^1$H NMR (500 MHz, DMSO-$d_6$) δ 12.84 (br. s., 1H), 8.34 (d, J = 6.1 Hz, 1H), 7.88 (br. s., 2H), 7.68 (d, J = 6.7 Hz, 1H), 7.55 (d, J = 7.9 Hz, 2H), 7.44 (d, J = 7.6 Hz, 2H), 7.32-7.23 (m, 2H), 7.20 (d, J = 6.7 Hz, 3H), 4.58 (d, J = 11.3 Hz, 1H), 4.13 (d, J = 12.8 Hz, 1H), 3.87 (br. s., 2H), 3.13 (t, J = 13.0 Hz, 1H), 2.82-2.71 (m, 1H), 2.66 (t, J = 12.4 Hz, 1H), 1.77 (t, J = 14.5 Hz, 2H), 1.51-1.34 (m, 2H) |
| 12 | (4-benzylpiperazin-1-yl structure) | 4-{4-[2-(4-benzylpiperazin-1-yl)-2-oxoethyl]phenyl}-1,2-dihydrophthalazin-1-one | 439.4 | C: 2.41 D: 3.63 | $^1$H NMR (500 MHz, DMSO-$d_6$) δ 12.84 (br. s., 1H), 8.34 (br. s., 1H), 7.89 (d, J = 3.1 Hz, 2H), 7.69 (d, J = 6.4 Hz, 1H), 7.52 (d, J = 7.3 Hz, 2H), 7.39 (d, J = 7.9 Hz, 2H), 7.35-7.19 (m, 5H), 3.81 (br. s., 2H), 3.57-3.45 (m, 6H), 2.31 (br. s., 4H) |
| 13 | ((2S)-2-(methoxymethyl)pyrrolidin-1-yl structure) | 4-(4-{2-[(2S)-2-(methoxymethyl)pyrrolidin-1-yl]-2-oxoethyl}phenyl)-1,2-dihydrophthalazin-1-one | 378.4 | C: 2.13 D: 3.24 | $^1$H NMR (500 MHz, DMSO-$d_6$) δ 12.84 (br. s., 1H), 8.34 (d, J = 6.1 Hz, 1H), 7.90 (br. s., 2H), 7.70 (d, J = 6.4 Hz, 1H), 7.52 (d, J = 6.1 Hz, 2H), 7.40 (d, J = 7.0 Hz, 2H), 4.08 (br. s., 1H), 3.78-3.68 (m, 2H), 3.23 (br. s., 3H), 2.00-1.76 (m, 5H) |
| 14 | (cyclopropylmethylamino structure) | N-(cyclopropylmethyl)-2-[4-(4-oxo-3,4-dihydrophthalazin-1-yl)phenyl]acetamide | 334.3 | C: 1.94 D: 3.05 | $^1$H NMR (400 MHz, CD$_3$OD/CDCl$_3$ (1:1)) δ 8.43 (dt, J = 4.3, 2.4 Hz, 1H), 7.84-7.64 (m, 3H), 7.55-7.46 (m, 2H), 7.42 (d, J = 8.0 Hz, 2H), 3.59 (s, 2H), 3.05 (d, J = 7.0 Hz, 2H), 0.98-0.81 (m, 1H), 0.50-0.36 (m, 2H), 0.19-0.07 (m, 2H) |
| 15 | (4-(pyrimidin-2-yl)piperazin-1-yl structure) | 4-(4-{2-oxo-2-[4-(pyrimidin-2-yl)piperazin-1-yl]ethyl}phenyl)-1,2-dihydrophthalazin-1-one | 427.4 | C: 2.10 D: 3.26 | $^1$H NMR (500 MHz, DMSO-$d_6$) δ 12.83 (br. s., 1H), 8.44-8.28 (m, 3H), 7.89 (d, J = 3.7 Hz, 2H), 7.69 (br. s., 1H), 7.54 (d, J = 7.3 Hz, 2H), 7.43 (d, J = 7.6 Hz, 2H), 6.70-6.62 (m, 1H), 3.89 (br. s., 2H), 3.72 (br. s., 4H), 3.65 (br. s., 2H), 3.59 (br. s., 2H) |

TABLE 1-continued

| Example | R | Name | LCMS (M + H)+ | HPLC Method, RT (min.) | 1H NMR |
|---|---|---|---|---|---|
| 16 | piperazine-N-(4-methoxyphenyl) | 4-(4-{2-[4-(4-methoxyphenyl)piperazin-1-yl]-2-oxoethyl}phenyl)-1,2-dihydrophthalazin-1-one | 455.4 | C: 2.23<br>D: 3.47 | $^1$H NMR (500 MHz, DMSO-$d_6$) δ 12.83 (br. s., 1H), 8.33 (br. s., 1H), 7.88 (br. s., 2H), 7.68 (br. s., 1H), 7.53 (d, J = 7.9 Hz, 2H), 7.42 (d, J = 7.6 Hz, 2H), 6.95-6.85 (m, 2H), 6.82 (d, J = 8.5 Hz, 2H), 3.88 (br. s., 2H), 3.68 (br. s., 4H), 3.64 (br. s., 2H), 2.96 (br. s., 4H) |
| 17 | 4-benzylpiperidine | 4-{4-[2-(4-benzylpiperidin-1-yl)-2-oxoethyl]phenyl}-1,2-dihydrophthalazin-1-one | 438.4 | C: 2.77<br>D: 4.04 | $^1$H NMR (500 MHz, DMSO-$d_6$) δ 12.84 (br. s., 1H), 8.34 (br. s., 1H), 7.90 (d, J = 3.7 Hz, 2H), 7.69 (d, J = 5.8 Hz, 1H), 7.52 (d, J = 7.9 Hz, 2H), 7.39 (d, J = 7.6 Hz, 2H), 7.30-7.21 (m, 2H), 7.21-7.10 (m, 3H), 4.38 (d, J = 13.1 Hz, 1H), 3.98 (d, J = 11.6 Hz, 1H), 3.80 (br. s., 2H), 2.96 (t, J = 12.4 Hz, 1H), 1.75 (br. s., 1H), 1.56 (br. s., 2H), 0.99 (t, J = 10.2 Hz, 2H) |
| 18 | (1S,2R)-2-phenylcyclopropylamine | 2-[4-(4-oxo-3,4-dihydrophthalazin-1-yl)phenyl]-N-[(1S,2R)-2-phenylcyclopropyl]acetamide | 396.4 | C: 2.35<br>D: 3.56 | $^1$H NMR (500 MHz, DMSO-$d_6$) δ 12.84 (br. s., 1H), 8.49 (br. s., 1H), 8.34 (br. s., 1H), 7.90 (d, J = 3.7 Hz, 2H), 7.71 (d, J = 5.5 Hz, 1H), 7.54 (d, J = 7.6 Hz, 2H), 7.44 (d, J = 7.3 Hz, 2H), 7.29-7.21 (m, 2H), 7.19-7.06 (m, 3H), 3.52 (br. s., 2H), 2.85 (br.s., 1H), 1.97 (br. s., 1H), 1.18 (d, J = 5.8 Hz, 2H) |
| 19 | cyclobutylamine | N-cyclobutyl-2-[4-(4-oxo-3,4-dihydrophthalazin-1-yl)phenyl]acetamide | 334.3 | C: 1.95<br>D: 3.11 | $^1$H NMR (500 MHz, DMSO-$d_6$) δ 12.83 (br. s., 1H), 8.40 (d, J = 6.1 Hz, 1H), 8.33 (br. s., 1H), 7.89 (d, J = 3.4 Hz, 2H), 7.69 (d, J = 6.7 Hz, 1H), 7.51 (d, J = 7.6 Hz, 2H), 7.41 (d, J = 7.9 Hz, 2H), 4.25-4.11 (m, 1H), 3.46 (s, 2H), 2.22-2.11 (m, 2H), 1.96-1.83 (m, 2H), 1.70-1.55 (m, 2H) |
| 20 | anilino | 2-[4-(4-oxo-3,4-dihydrophthalazin-1-yl)phenyl]-N-phenylacetamide | 356.3 | C: 2.21<br>D: 3.36 | $^1$H NMR (500 MHz, DMSO-$d_6$) δ 12.83 (br. s., 1H), 10.25 (br. s., 1H), 8.33 (br. s., 1H), 7.88 (d, J = 4.0 Hz, 2H), 7.70 (br. s., 1H), 7.62 (d, J = 7.6 Hz, 2H), 7.59-7.46 (m, 4H), 7.34-7.25 (m, 2H), 7.09-6.99 (m, 1H), 3.76 (br. s., 2H) |
| 21 | 1,3-benzothiazol-6-ylamino | N-(1,3-benzothiazol-6-yl)-2-[4-(4-oxo-3,4-dihydrophthalazin-1-yl)phenyl]acetamide | 413.4 | C: 1.96<br>D: 3.20 | $^1$H NMR (500 MHz, DMSO-$d_6$) δ 12.85 (br. s., 1H), 10.65 (br. s., 1H), 9.26 (br. s., 1H), 8.58 (br. s., 1H), 8.33 (br. s., 1H), 8.02 (d, J = 8.9 Hz, 1H), 7.89 (br. s., 2H), 7.71 (br. s., 1H), 7.65 (d, J = 9.5 Hz, 1H), 7.55 (br. s., 4H), 3.82 (br. s., 2H) |
| 22 | N-methylanilino | N-methyl-2-[4-(4-oxo-3,4-dihydrophthalazin-1-yl)phenyl]-N-phenylacetamide | 370.3 | C: 2.25<br>D: 3.52 | $^1$H NMR (500 MHz, DMSO-$d_6$) δ 12.83 (br. s., 1H), 8.33 (d, J = 6.7 Hz, 1H), 7.89 (br. s., 2H), 7.73-7.62 (m, J = 7.3 Hz, 1H), 7.54 (d, J = 7.3 Hz, 1H), 7.47 (br. s., 3H), 7.39 (d, J = 7.9 Hz, 4H), 7.20 (br. s., 1H), 3.51 (br. s., 2H), 3.21 (br. s., 3H) |

TABLE 1-continued

| Example | R | Name | LCMS (M + H)+ | HPLC Method, RT (min.) | 1H NMR |
|---|---|---|---|---|---|
| 23 | (2,3-dihydro-1H-indol-1-yl) | 4-{4-[2-(2,3-dihydro-1H-indol-1-yl)-2-oxoethyl]phenyl}-1,2-dihydrophthalazin-1-one | 382.3 | C: 2.48  D: 3.67 | 1H NMR (500 MHz, DMSO-d6) δ 12.85 (br. s., 1H), 8.34 (d, J = 7.3 Hz, 1H), 8.08 (d, J = 7.6 Hz, 1H), 7.96-7.84 (m, 2H), 7.72 (d, J = 7.3 Hz, 1H), 7.59-7.51 (m, 2H), 7.47 (d, J = 7.0 Hz, 2H), 7.24 (d, J = 6.4 Hz, 1H), 7.18-7.10 (m, 1H), 7.00 (t, J = 6.6 Hz, 1H), 4.26-4.17 (m, 2H), 3.96 (br. s., 2H), 3.20-3.14 (m, J = 9.2 Hz, 2H) |
| 24 | NH-(2,3-dihydro-1,4-benzodioxin-6-yl) | N-(2,3-dihydro-1,4-benzodioxin-6-yl)-2-[4-(4-oxo-3,4-dihydrophthalazin-1-yl)phenyl]acetamide | 414.3 | C: 2.13  D: 3.25 | 1H NMR (500 MHz, DMSO-d6) δ 12.84 (br. s., 1H), 10.09 (br. s., 1H), 8.39-8.27 (m, 1H), 7.89 (d, J = 2.4 Hz, 2H), 7.74-7.65 (m, 1H), 7.58-7.51 (m, 2H), 7.49 (d, J = 6.7 Hz, 2H), 7.26 (br. s., 1H), 6.99 (d, J = 6.4 Hz, 1H), 6.78 (d, J = 8.9 Hz, 1H), 4.20 (d, J = 6.4 Hz, 4H), 3.70 (br. s., 2H) |
| 25 | 5-[(4-methylpiperazin-1-yl)methyl]-2,3-dihydro-1H-isoindol-2-yl | 4-[4-(2-{5-[(4-methylpiperazin-1-yl)methyl]-2,3-dihydro-1H-isoindol-2-yl}-2-oxoethyl(phenyl]-1,2-dihydrophthalazin-1-one | 494.3 | E: 0.94  F: 1.15 | 1H NMR (500 MHz, DMSO-d6) δ 12.82 (s, 1H), 8.37-8.30 (m, 1H), 7.93-7.86 (m, 2H), 7.71 (d, J = 7.2 Hz, 1H), 7.55 (d, J = 7.7 Hz, 2H), 7.47 (d, J = 7.7 Hz, 2H), 7.33-7.25 (m, 2H), 7.23 (d, J = 7.7 Hz, 1H), 4.95 (d, J = 7.4 Hz, 2H), 4.67 (d, J = 4.7 Hz, 2H), 3.87 (s, 2H), 3.46 (d, J = 3.3 Hz, 2H), 2.36 (br. s., 8H), 2.17 (br. s., 3H) |
| 26 | NH-(3-methyl-1,2-oxazol-5-yl) | N-(3-methyl-1,2-oxazol-5-yl)-2-[4-(4-oxo-3,4-dihydrophthalazin-1-yl)phenyl]acetamide | 361.2 | C: 2.06  D: 3.11 | 1H NMR (500 MHz, DMSO-d6) δ 12.84 (br. s., 1H), 8.33 (br. s., 1H), 7.89 (br. s., 2H), 7.69 (br. s., 1H), 7.56 (d, J = 7.3 Hz, 2H), 7.48 (d, J = 4.9 Hz, 2H), 6.12 (br. s., 1H), 3.82 (br. s., 2H), 2.17 (br. s., 3H) |
| 27 | NH-(5-methyl-1,2-oxazol-3-yl) | N-(5-methyl-1,2-oxazol-3-yl)-2-[4-(4-oxo-3,4-dihydrophthalazin-1-yl)phenyl]acetamide | 361.2 | C: 2.06  D: 3.08 | 1H NMR (500 MHz, DMSO-d6) δ 12.84 (br. s., 1H), 11.21 (br. s., 1H), 8.33 (br. s., 1H), 7.89 (d, J = 3.1 Hz, 2H), 7.70 (br. s., 1H), 7.55 (d, J = 7.3 Hz, 2H), 7.49 (d, J = 7.0 Hz, 2H), 6.62 (br. s., 1H), 3.78 (br. s., 2H), 2.36 (br. s., 3H) |
| 28 | NH-(1,3-thiazol-2-yl) | 2-[4-(4-oxo-3,4-dihydrophthalazin-1-yl)phenyl]-N-(1,3-thiazol-2-yl)acetamide | 363.2 | C: 2.07  D: 3.13 | 1H NMR (400MHz, DMSO-d6) δ 12.86 (br. s., 1H), 8.36-8.30 (m, 1H), 7.93-7.86 (m, 2H), 7.73-7.69 (m, 1H), 7.58-7.53 (m, 2H), 7.53-7.48 (m, 2H), 7.42 (d, J = 3.5 Hz, 1H), 7.09 (br. s., 1H), 3.83 (s, 2H) |
| 29 | NH-(1,3,4-thiadiazol-2-yl) | 2-[4-(4-oxo-3,4-dihydrophthalazin-1-yl)phenyl]-N-(1,3,4-thiadiazol-2-yl)acetamide | 364.2 | C: 1.84  D: 2.87 | 1H NMR (400MHz, DMSO-d6) δ 12.85 (s, 1H), 9.11 (s, 1H), 8.37-8.30 (m, 1H), 7.95-7.85 (m, 2H), 7.74-7.68 (m, 1H), 7.59-7.53 (m, 2H), 7.53-7.48 (m, 2H), 3.92 (s, 2H) |
| 30 | NH-(6-chloropyridazin-3-yl) | N-(6-chloropyridazin-3-yl)-2-[4-(4-oxo-3,4-dihydrophthalazin-1-yl)phenyl]acetamide | 392.2 | C: 2.12  D: 3.18 | 1H NMR (400 MHz, DMSO-d6) δ 12.86 (br. s., 1H), 11.67 (br. s., 1H), 8.40 (d, J = 9.5 Hz, 1H), 8.36-8.30 (m, 1H), 7.94-7.85 (m, 3H), 7.74-7.66 (m, 1H), 7.60-7.55 (m, 2H), 7.55-7.49 (m, 2H), 3.92 (s, 2H) |

TABLE 1-continued

| Example | R | Name | LCMS (M + H)+ | HPLC Method, RT (min.) | 1H NMR |
|---|---|---|---|---|---|
| 31 | (N-linked NH to 5-methyl-1,3,4-thiadiazol-2-yl) | N-(5-methyl-1,3,4-thiadiazol-2-yl)-2-[4-(4-oxo-3,4-dihydrophthalazin-1-yl)phenyl]acetamide | 378.2 | C: 1.81 D: 3.07 | 1H NMR (400 MHz, DMSO-d6) δ 12.86 (s, 1H), 12.70 (br. s., 1H), 8.36-8.30 (m, 1H), 7.93-7.85 (m, 2H), 7.75-7.66 (m, 1H), 7.60-7.53 (m, 2H), 7.53-7.46 (m, 2H), 3.92 (s, 2H), 2.60 (s, 3H) |
| 32 | 5-methyl-2,3-dihydro-1H-indol-1-yl | 4-{4-[2-(5-methyl-2,3-dihydro-1H-indol-1-yl)-2-oxoethyl]phenyl}-1,2-dihydrophthalazin-1-one | 396.1 | A: 9.56 B: 9.14 | (500 MHz, DMSO-d6) δ 12.83 (s, 1H), 8.41-8.29 (m, 1H), 7.96 (d, J = 8.3 Hz, 1H), 7.91-7.85 (m, 2H), 7.73-7.68 (m, 1H), 7.62-7.52 (m, J = 8.3 Hz, 2H), 7.48-7.42 (m, J = 8.0 Hz, 2H), 7.05 (s, 1H), 6.95 (d, J = 8.3 Hz, 1H), 4.21 (t, J = 8.5 Hz, 2H), 3.94 (s, 2H), 3.14 (t, J = 8.4 Hz, 2H), 2.25 (s, 3H) |
| 33 | 6-ethoxy-2,3-dihydro-1H-indol-1-yl (OEt) | 4-{4-[2-(6-ethoxy-2,3-dihydro-1H-indol-1-yl)-2-oxoethyl]phenyl}-1,2-dihydrophthalazin-1-one | 426.1 | A: 9.62 B: 9.23 | (500 MHz, DMSO-d6) δ 12.83 (s, 1H), 8.42-8.30 (m, 1H), 7.94-7.84 (m, 2H), 7.80-7.65 (m, 2H), 7.62-7.51 (m, J = 8.0 Hz, 2H), 7.51-7.40 (m, J = 8.3 Hz, 2H), 7.11 (d, J = 8.0 Hz, 1H), 6.56 (dd, J = 8.0, 2.5 Hz, 1H), 4.24 (t, J = 8.3 Hz, 2H), 4.02-3.89 (m, 4H), 3.09 (t, J = 8.3 Hz, 3H), 1.30 (t, J = 7.0 Hz, 3H) |
| 34 | 1,2,3,4-tetrahydroquinolin-1-yl | 4-{4-[2-oxo-2-(1,2,3,4-tetrahydroquinolin-1-yl)ethyl]phenyl}-1,2-dihydrophthalazin-1-one | 396.1 | E: 1.70 F: 1.73 | (500 MHz, DMSO-d6) δ 12.81 (s, 1H), 8.37-8.29 (m, 1H), 7.95-7.87 (m, 2H), 7.66 (d, J = 7.7 Hz, 1H), 7.49 (d, J = 7.7 Hz, 3H), 7.33 (br. s., 2H), 7.19 (d, J = 6.9 Hz, 2H), 7.13 (d, J = 7.2 Hz, 1H), 3.99 (s, 2H), 3.75 (t, J = 6.2 Hz, 2H), 2.66 (br. s., 2H), 1.86 (quin, J = 6.5 Hz, 2H) |
| 35 | 6-(trifluoromethyl)-2,3-dihydro-1H-indol-1-yl (CF3) | 4-(4-{2-oxo-2-[6-(trifluoromethyl)-2,3-dihydro-1H-indol-1-yl]ethyl}phenyl)-1,2-dihydrophthalazin-1-one | 450.2 | E: 1.91 F: 1.96 | (500 MHz, DMSO-d6) δ 12.83 (s, 1H), 8.42-8.30 (m, 2H), 7.98-7.84 (m, 2H), 7.80-7.67 (m, 1H), 7.57 (d, J = 8.0 Hz, 2H), 7.48 (d, J = 8.3 Hz, 3H), 7.37 (d, J = 7.7 Hz, 1H), 4.32 (t, J = 8.5 Hz, 2H), 4.01 (s, 2H), 3.29-3.24 (m, 2H) |
| 39 | 3,3-dimethyl-2,3-dihydro-1H-indol-1-yl | 4-{4-[2-(3,3-dimethyl-2,3-dihydro-1H-indol-1-yl)-2-oxoethyl]phenyl}-1,2-dihydrophthalazin-1-one | 410.15 | E: 1.88 F: 1.89 | (500 MHz, DMSO-d6) δ 12.85 (br. s., 1H), 8.38-8.32 (m, 1H), 8.06 (d, J = 8.4 Hz, 1H), 7.93-7.86 (m, 2H), 7.76-7.68 (m, 1H), 7.61-7.53 (m, J = 8.4 Hz, 2H), 7.50-7.44 (m, J = 7.9 Hz, 2H), 7.27 (d, J = 7.4 Hz, 1H), 7.17 (t, J = 7.4 Hz, 1H), 7.08-7.00 (m, 1H), 3.98 (d, J = 8.9 Hz, 4H), 1.31 (s, 6H) |
| 40 | 2-methyl-2,3-dihydro-1H-indol-1-yl | 4-{4-[2-(2-methyl-2,3-dihydro-1H-indol-1-yl)-2-oxoethyl]phenyl}-1,2-dihydrophthalazin-1-one | 396.15 | E: 1.75 F: 1.77 | (500 MHz, CD3OD) δ 8.47-8.41 (m, 1H), 8.10 (d, J = 8.4 Hz, 1H), 7.88-7.77 (m, 3H), 7.63-7.55 (m, 3H), 7.49 (d, J = 7.4 Hz, 2H), 7.25-7.17 (m, 2H), 7.06 (t, J = 7.4 Hz, 1H), 4.05 (d, J = 15.4 Hz, 1H), 3.95 (d, J = 15.9 Hz, 1H), 3.43 (dd, J = 15.6, 8.7 Hz, 1H), 2.72 (d, J = 15.4 Hz, 1H), 1.38 (d, J = 5.9 Hz, 3H), 1.29 (br. s., 1H) |
| 41 | 6-methoxy-2,3-dihydro-1H-indol-1-yl (OMe) | 4-{4-[2-(6-methoxy-2,3-dihydro-1H-indol-1-yl)-2-oxoethyl]phenyl}-1,2-dihydrophthalazin-1-one | 412.0 | A: 8.50 B: 7.65 | (500 MHz, DMSO-d6) δ 12.83 (s, 1H), 8.45-8.27 (m, 1H), 7.94-7.85 (m, 2H), 7.79-7.67 (m, 2H), 7.63-7.53 (m, J = 8.0 Hz, 2H), 7.52-7.43 (m, J = 8.0 Hz, 2H), 7.13 (d, J = 8.3 Hz, 1H), 6.58 (dd, J = 8.3, 2.2 Hz, 1H), 4.25 (t, J = 8.4 Hz, 2H), 3.96 (s, 2H), 3.70 (s, 3H), 3.10 (t, J = 8.4 Hz, 2H) |

Example 36: 2-(2-Fluoro-4-(4,4,5,5-tetramethyl-1,3,2-dioxaborolan-2-yl)phenyl)-1-(isoindolin-2-yl)ethanone

Example 37: 4-(2-Fluoro-4-(2-(isoindolin-2-yl)-2-oxoethyl)phenyl)phthalazin-1(2H)-one

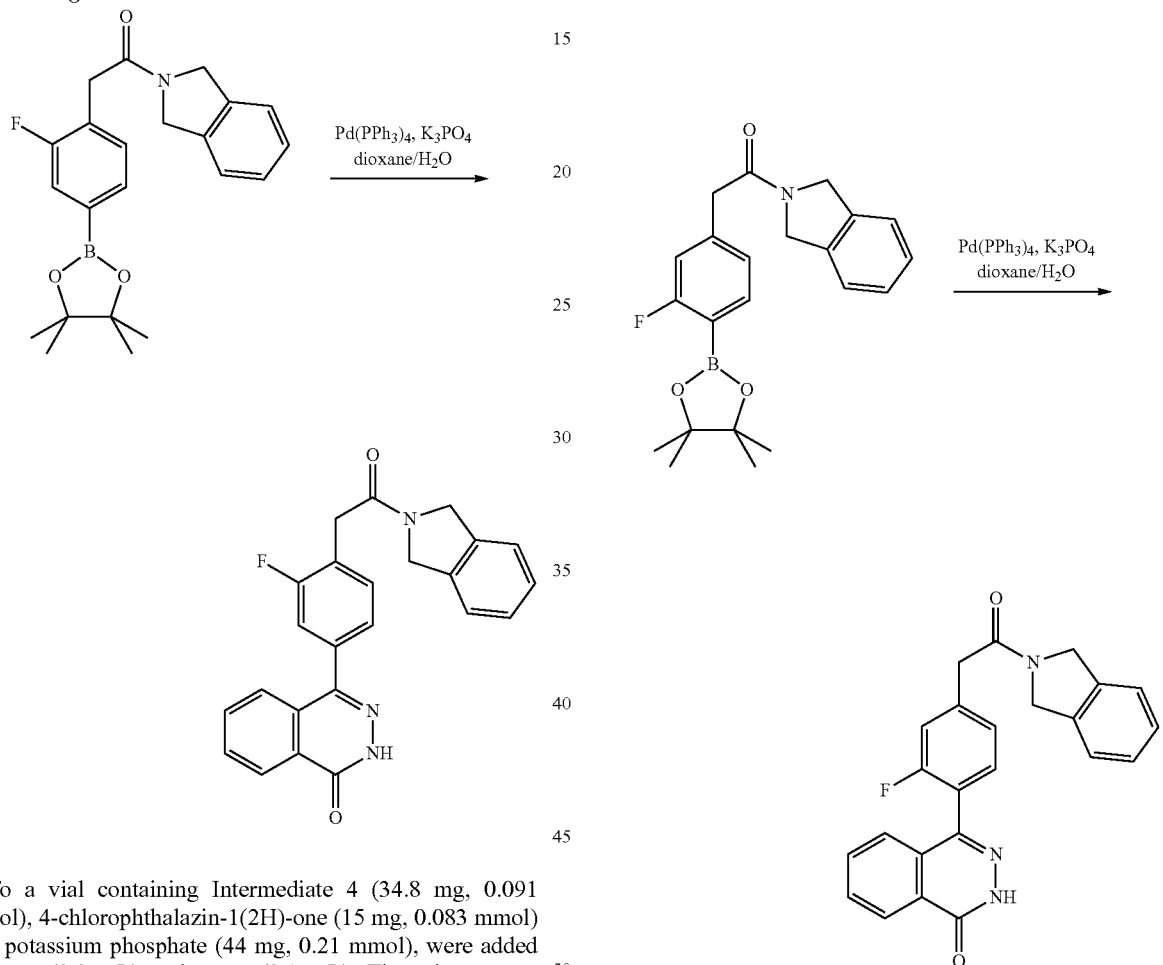

To a vial containing Intermediate 4 (34.8 mg, 0.091 mmol), 4-chlorophthalazin-1(2H)-one (15 mg, 0.083 mmol) and potassium phosphate (44 mg, 0.21 mmol), were added dioxane (0.9 mL) and water (0.1 mL). The mixture was degassed (evacuated and flushed with Ar (3×)). To this mixture was added Pd(Ph₃P)₄ (4.8 mg, 4.2 mol). The mixture was degassed (3×), then the vial was sealed. The vial was heated in a microwave reactor at 150° C. for 25 min. The mixture was concentrated, then was diluted with 4 mL 1:1 DMSO/MeOH. TFA (0.1 mL) was added, then the suspension was filtered and the solid collected. The solid was washed with H₂O (~5 mL), then MeOH (~5 mL), sucked dry and dried in vacuo to afford 34.8 mg (42%) of Example 36 as a white solid. MS(ESI) m/z: 400.0 (M+H)⁺; ¹H NMR (500 MHz, DMSO-d₆) δ 12.89 (s, 1H), 8.38-8.32 (m, 1H), 7.92 (quind, J=7.1, 1.7 Hz, 2H), 7.76-7.71 (m, 1H), 7.51 (t, J=7.8 Hz, 1H), 7.43 (dd, J=10.5, 1.4 Hz, 1H), 7.41-7.37 (m, 3H), 7.35-7.30 (m, 2H), 5.02 (s, 2H), 4.71 (s, 2H), 3.92 (s, 2H); HPLC RT=7.96 min (Method A), 8.02 min (Method B).

To a vial containing Intermediate 5 (34.8 mg, 0.091 mmol), 4-chlorophthalazin-1(2H)-one (15 mg, 0.083 mmol) and potassium phosphate (44.1 mg, 0.208 mmol), were added dioxane (0.9 mL) and water (0.1 mL). The mixture was degassed (evacuated and flushed with Ar (3×)). To this mixture was added Pd(Ph₃P)₄ (4.8 mg, 4.15 mol). The mixture was degassed (3×), then the vial was sealed. The vial was heated in a microwave reactor at 150° C. for 25 min. The reaction mixture separated into two phases upon cooling. The organic phase was collected and was purified by preparative HPLC to afford 11.7 mg (35%) of Example 37. MS(ESI) m/z: 400.2 (M+H)⁺; ¹H NMR (500 MHz, DMSO-d₆) δ 12.94 (br. s., 1H), 8.37-8.29 (m, 1H), 7.92-7.86 (m, 2H), 7.65-7.49 (m, 4H), 7.45-7.28 (m, 4H), 4.99 (s, 2H), 4.71 (s, 2H), 3.93 (s, 2H); HPLC RT=1.56 min (Method E), 1.52 min (Method F).

Example 38: 4-(4-(2-(Isoindolin-2-yl)-2-oxoethyl)phenyl)isoquinolin-1(2H)-one

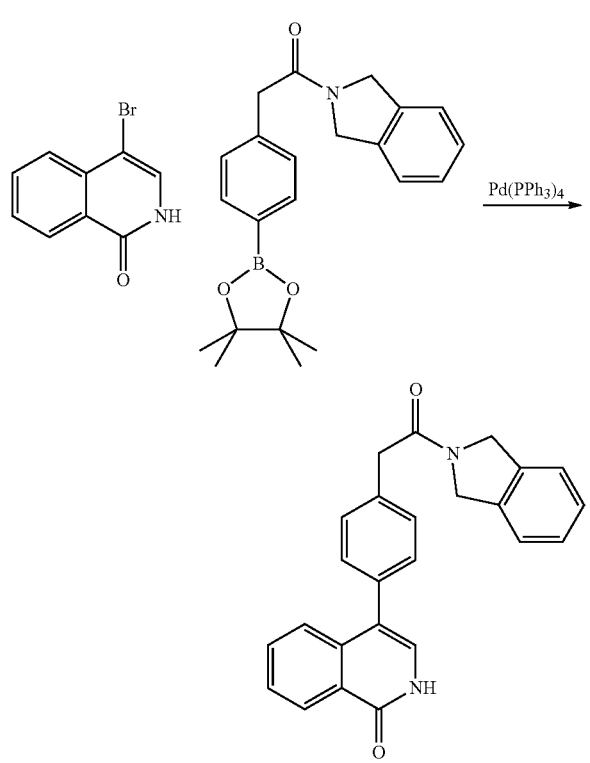

According to the procedure for the preparation of Example 36, coupling of Intermediate 6 (30 mg, 0.13 mmol) and Intermediate 9 (51 mg, 0.14 mmol) afforded 17 mg (33%) of Example 38. MS(ESI) m/z: 381.1 (M+H)+; 1H NMR (500 MHz, DMSO-d6) δ 11.43 (d, J=5.8 Hz, 1H), 8.29 (dd, J=8.1, 1.2 Hz, 1H), 7.69 (td, J=7.7, 1.4 Hz, 1H), 7.61-7.51 (m, 2H), 7.44-7.35 (m, 6H), 7.33-7.28 (m, 2H), 7.08 (s, 1H), 4.97 (s, 2H), 4.69 (s, 2H), 3.84 (s, 2H); HPLC RT=8.20 min (Method A), 7.53 min (Method B).

Example 42: 4-(4-(1-(Indolin-1-yl)-1-oxopropan-2-yl)phenyl)phthalazin-1(2H)-one

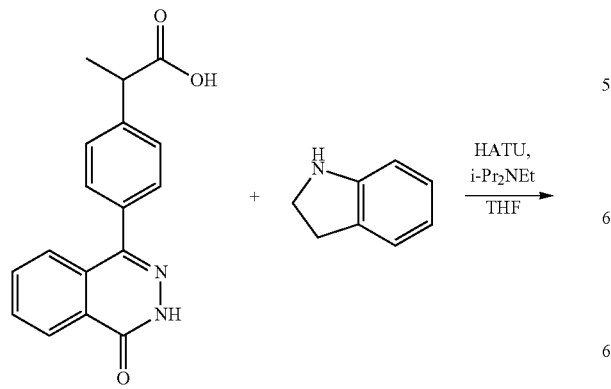

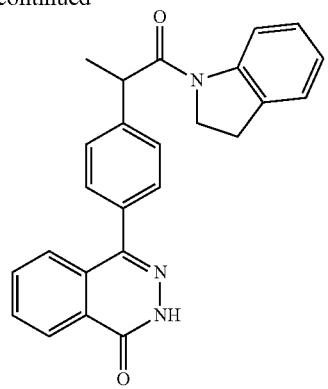

According to the procedure for the preparation of Example 3, coupling of Intermediate 11 (13 mg, 0.044 mmol) and indoline (7.9 mg, 0.066 mmol) using HATU afforded 8.2 mg (46%) of Example 42. MS(ESI) m/z: 396.15 (M+H)+; 1H NMR (500 MHz, DMSO-d6) δ 12.85 (s, 1H), 8.38-8.30 (m, 1H), 8.18 (d, J=8.4 Hz, 1H), 7.92-7.84 (m, 2H), 7.74-7.68 (m, 1H), 7.62-7.55 (m, J=8.4 Hz, 2H), 7.55-7.49 (m, J=8.4 Hz, 2H), 7.20 (d, J=7.4 Hz, 1H), 7.16 (t, J=7.7 Hz, 1H), 7.02-6.94 (m, 1H), 4.37 (td, J=10.4, 6.4 Hz, 1H), 4.23 (q, J=6.4 Hz, 1H), 3.91-3.75 (m, 1H), 3.16-3.00 (m, 2H), 1.46 (d, J=6.4 Hz, 3H); HPLC RT=1.77 min (Method E), 1.75 min (Method F).

Example 43: 4-(4-(1-(Isoindolin-2-yl)-1-oxopropan-2-yl)phenyl)phthalazin-1(2H)-one

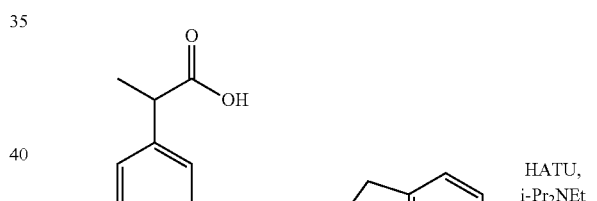

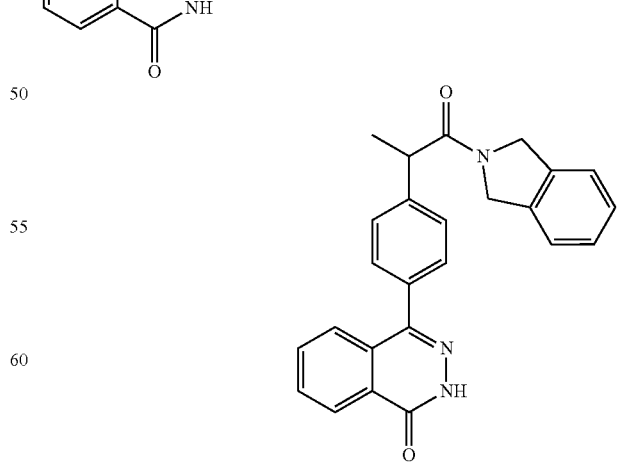

According to the procedure for the preparation of Example 3, coupling of Intermediate 11 (13 mg, 0.044 mmol) and isoindoline (7.9 mg, 0.066 mmol) using HATU afforded 9.0 mg (52%) of Example 43. MS(ESI) m/z: 396.15 (M+H)+; 1H NMR (500 MHz, 1:1 CD3OD/CDCl3) δ 8.49-8.43 (m, 1H), 7.90-7.83 (m, 2H), 7.83-7.78 (m, 1H), 7.61-7.58 (m, 2H), 7.57-7.52 (m, 2H), 7.35-7.23 (m, 4H), 5.04 (d, J=13.9 Hz, 1H), 4.92-4.85 (m, 1H), 4.83-4.77 (m, 1H), 4.66 (d, J=13.9 Hz, 1H), 4.09 (q, J=6.9 Hz, 1H), 1.58 (d, J=6.9 Hz, 3H).

Example 44: N-(4-(4-Oxo-3,4-dihydrophthalazin-1-yl)phenyl)-2,3-dihydro-1H-indene-2-carboxamide

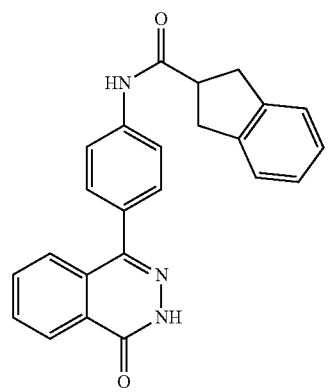 [SMILES: O=C(Nc1ccc(-c2n[nH]c(=O)c3ccccc23)cc1)C1Cc2ccccc2C1]

Example 44A: N-(4-Bromophenyl)-2,3-dihydro-1H-indene-2-carboxamide

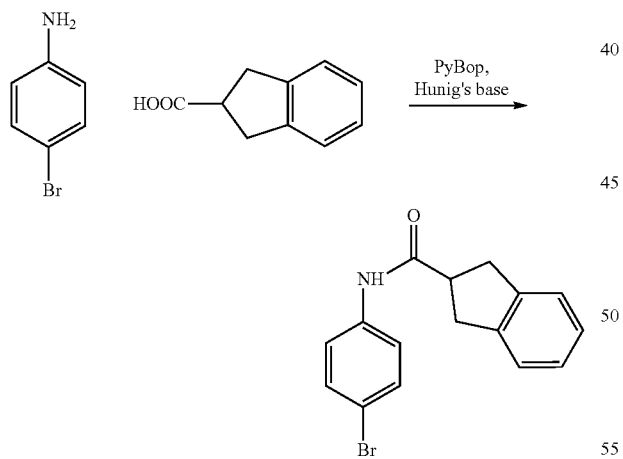

To a solution of 2,3-dihydro-1H-indene-2-carboxylic acid (141 mg, 0.872 mmol) in DMF (3 mL), were added 4-bromoaniline (150 mg, 0.872 mmol), PyBOP (499 mg, 0.959 mmol), and DIEA (0.457 mL, 2.62 mmol). The mixture was stirred at rt for 16 h. The reaction mixture was concentrated and the residue was dissolved in EtOAc, washed with 10% LiCl, 1N HCl and brine. The crude product was purified via flash chromatography to afford 90 mg (33%) of Example 44A. MS(ESI) m/z: 316.0 (M+H)+.

Example 44B: N-(4-(4,4,5,5-Tetramethyl-1,3,2-dioxaborolan-2-yl)phenyl)-2,3-dihydro-1H-indene-2-carboxamide

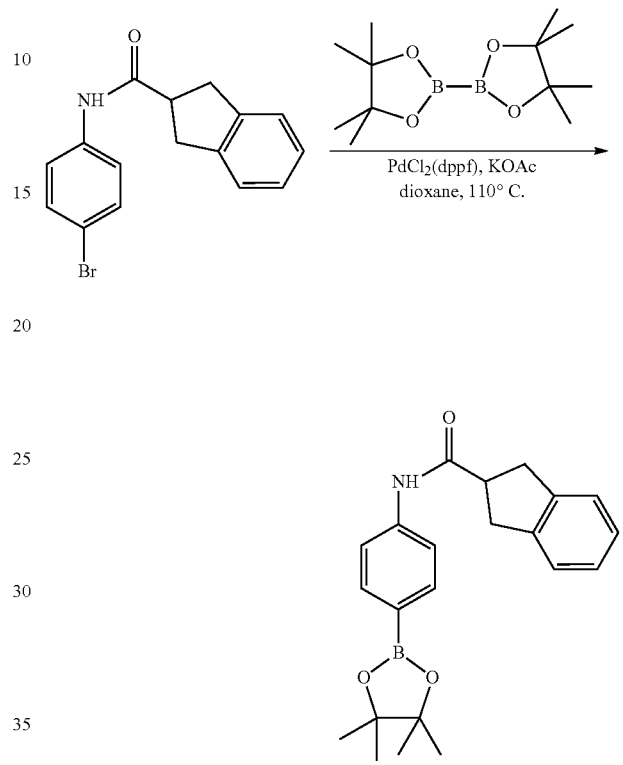

A mixture of Example 44A (62 mg, 0.20 mmol), bis(pinacolato)diboron (74.7 mg, 0.294 mmol), and potassium acetate (57.7 mg, 0.588 mmol) in dioxane (3 mL) was degassed (3× vacuum/Ar). PdCl2(dppf) CH2Cl2 adduct (4.3 mg, 5.9 mol) was added. The reaction mixture was degassed again (3× vacuum/Ar), sealed in a vial and heated at 110° C. for 2 h. The reaction mixture was filtered and concentrated to afford 40 mg (56%) of Example 44B, which was used as is in the following step. MS(ESI) m/z: 364.2 (M+H)+.

Example 44

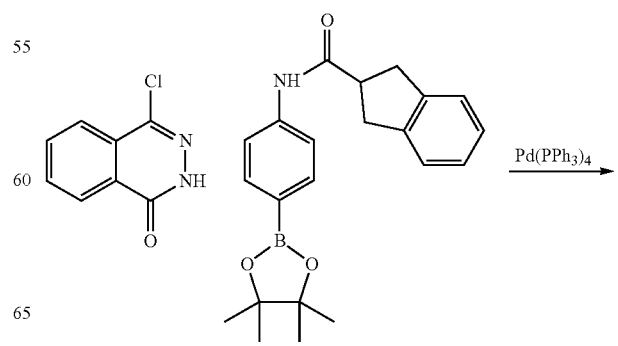

-continued

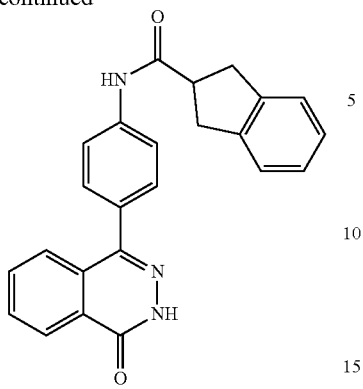

To 4-chlorophthalazin-1(2H)-one (28.3 mg, 0.157 mmol), Example 44B (40 mg, 0.11 mmol) and potassium phosphate (76 mg, 0.36 mmol), were added dioxane (3 mL) and water (0.5 mL). The mixture was degassed (evacuated and flushed with Ar (5×)). Pd(PPh$_3$)$_4$ (8.2 mg, 7.1 mol) was added, then the mixture was degassed (2×). The reaction vial was sealed and heated in a microwave reactor at 150° C. for 25 min. The reaction mixture was concentrated, then was purified by preparative HPLC to yield 17.1 mg (24%) of Example 44. MS(ESI) m/z: 382.1 (M+H)$^+$; $^1$H NMR (500 MHz, DMSO-d$_6$) δ 12.79 (s, 1H), 10.26 (s, 1H), 8.38-8.31 (m, 1H), 7.93-7.85 (m, 2H), 7.84-7.79 (m, J=8.5 Hz, 2H), 7.76-7.69 (m, 1H), 7.59-7.50 (m, J=8.5 Hz, 2H), 7.24 (dd, J=5.1, 3.4 Hz, 2H), 7.15 (dd, J=5.4, 3.2 Hz, 2H), 3.46 (t, J=8.5 Hz, 1H), 3.21 (dd, J=8.4, 3.2 Hz, 4H); HPLC RT=1.67 min (Method E), 1.66 min (Method F).

Example 45: N-(4-(4-Oxo-3,4-dihydrophthalazin-1-yl)phenyl)-2-(pyridin-4-yl)thiazole-4-carboxamide

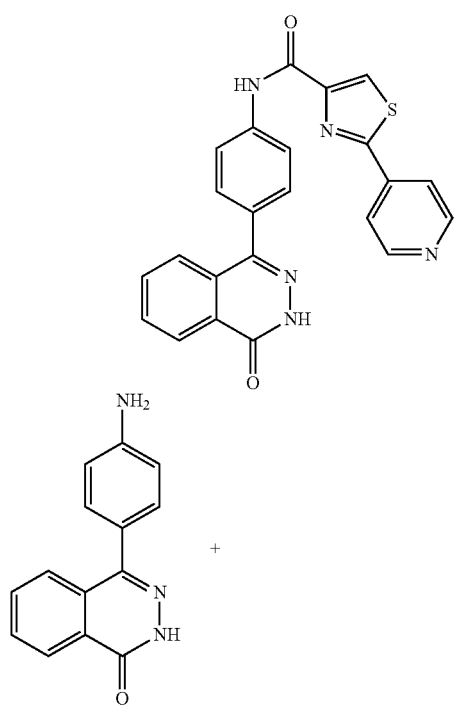

-continued

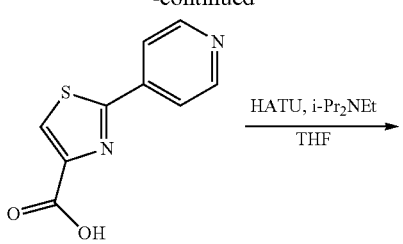

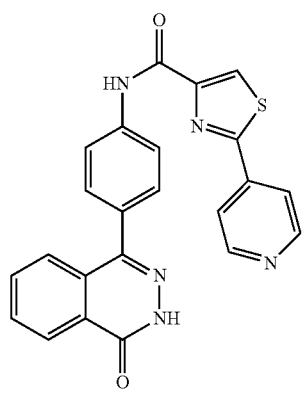

To a mixture of Intermediate 3 (25 mg, 0.105 mmol), 2-(pyridin-4-yl)thiazole-4-carboxylic acid (44 mg, 0.21 mmol), and HATU (60 mg, 0.16 mmol) in THF (1 mL), were added DIEA (0.046 mL, 0.26 mmol) and DMF (1 mL). The mixture was stirred at rt for 2 h, then was concentrated. The crude product was purified via preparative HPLC to afford 25 mg (36%) of Example 45. MS(ESI) m/z: 426.0 (M+H)$^+$; $^1$H NMR (500 MHz, DMSO-d$_6$) δ 12.84 (s, 1H), 10.53 (s, 1H), 8.86 (d, J=4.1 Hz, 2H), 8.73 (s, 1H), 8.44-8.32 (m, 1H), 8.25 (d, J=6.1 Hz, 2H), 8.12-8.02 (m, 2H), 7.97-7.86 (m, 2H), 7.82-7.76 (m, 1H), 7.68-7.60 (m, 2H); HPLC RT=5.13 min (Method A), 5.69 min (Method B).

The following Examples in Table 2 were made by using the same procedure as shown in Example 45. Intermediate 3 was coupled with the appropriate carboxylic acid. Various coupling reagents could be used other than the one described in Example 45, such as BOP, PyBop, EDC/HOBt or T3P.

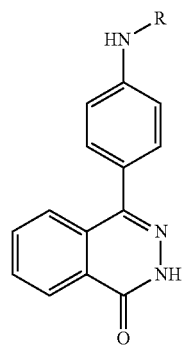

TABLE 2

| Example | R | Name | LCMS (M + H)+ | HPLC Method, RT (min.) | 1H NMR |
|---|---|---|---|---|---|
| 46 | 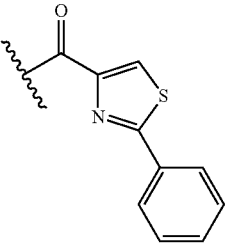 [SMILES: *C(=O)c1csc(-c2ccccc2)n1] | N-[4-(4-oxo-3,4-dihydrophthalazin-1-yl)phenyl]-2-phenyl-1,3-thiazole-4-carboxamide | 425.1 | E: 1.83 F: 1.88 | (500 MHz, DMSO-d6) δ 12.83 (br. s., 1H), 10.44 (br. s., 1H), 8.58-8.51 (m, 1H), 8.35 (dd, J = 7.6, 1.2 Hz, 1H), 8.18 (dd, J = 7.6, 2.1 Hz, 2H), 8.11-8.04 (m, J = 8.5 Hz, 2H), 8.00-7.86 (m, 2H), 7.78 (d, J = 7.4 Hz, 1H), 7.66-7.61 (m, J = 8.5 Hz, 2H), 7.61-7.55 (m, 3H) |
| 47 | 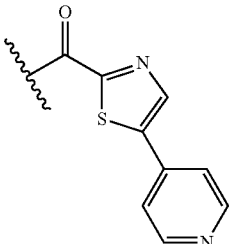 | N-[4-(4-oxo-3,4-dihydrophthalazin-1-yl)phenyl]-5-(pyridin-4-yl)-1,3-thiazole-2-carboxamide | 426.0 | E: 1.11 F: 1.52 | (500 MHz, DMSO-d6) δ 12.85 (s, 1H), 10.91 (s, 1H), 8.96 (s, 1H), 8.82 (d, J = 5.8 Hz, 2H), 8.40-8.33 (m, 1H), 8.30 (d, J = 5.8 Hz, 2H), 8.09-8.01 (m, J = 8.5 Hz, 2H), 7.96-7.87 (m, 2H), 7.77 (d, J = 7.4 Hz, 1H), 7.71-7.63 (m, J = 8.5 Hz, 2H) |
| 48 | 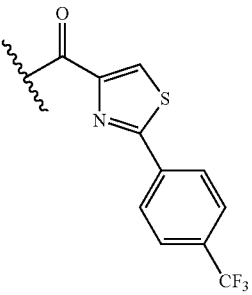 [SMILES: *C(=O)c1csc(-c2ccc(C(F)(F)F)cc2)n1] | N-[4-(4-oxo-3,4-dihydrophthalazin-1-yl)phenyl]-2-[4-(trifluoromethyl)phenyl]-1,3-thiazole-4-carboxamide | 493.2 | E: 1.98 F: 1.99 | (500 MHz, DMSO-d6) δ 12.83 (s, 1H), 10.52 (s, 1H), 8.64 (s, 1H), 8.41 (d, J = 8.3 Hz, 2H), 8.38-8.32 (m, 1H), 8.10-8.03 (m, J = 8.5 Hz, 2H), 7.98-7.86 (m, 4H), 7.81-7.74 (m, 1H), 7.67-7.56 (m, J = 8.5 Hz, 2H) |
| 49 | 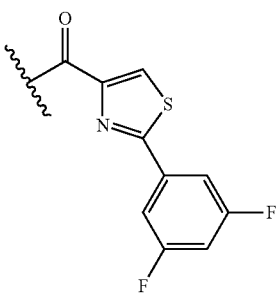 [SMILES: *C(=O)c1csc(-c2cc(F)cc(F)c2)n1] | 2-(3,5-difluorophenyl)-N-[4-(4-oxo-3,4-dihydrophthalazin-1-yl)phenyl]-1,3-thiazole-4-carboxamide | 461.2 | E: 1.87 F: 1.88 | 1H NMR (500 MHz, DMSO-d6) δ 12.83 (s, 1H), 10.51 (s, 1H), 8.77-8.68 (m, 1H), 8.63 (s, 1H), 8.35 (dd, J = 7.6, 1.2 Hz, 1H), 8.13-8.02 (m, J = 8.5 Hz, 2H), 7.98-7.85 (m, 2H), 7.81-7.74 (m, 1H), 7.65-7.61 (m, J = 8.5 Hz, 2H), 7.58 (ddd, J = 11.6, 9.2, 2.3 Hz, 1H), 7.45-7.34 (m, 1H) |
| 50 | 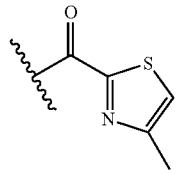 [SMILES: *C(=O)c1nc(C)cs1] | 4-methyl-N-[4-(4-oxo-3,4-dihydrophthalazin-1-yl)phenyl]-1,3-thiazole-2-carboxamide | 363.2 | E: 1.46 F: 1.47 | (500 MHz, DMSO-d6) δ 12.82 (s, 1H), 10.91 (s, 1H), 8.34 (dd, J = 7.6, 1.5 Hz, 1H), 8.10-8.00 (m, J = 8.8 Hz, 2H), 7.91 (td, J = 7.4, 1.4 Hz, 2H), 7.78-7.70 (m, 2H), 7.63-7.53 (m, J = 8.5 Hz, 2H), 2.53 (s, 3H) |
| 51 | 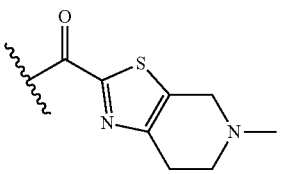 [SMILES: *C(=O)c1nc2c(s1)CN(C)CC2] | 5-methyl-N-[4-(4-oxo-3,4-dihydrophthalazin-1-yl)phenyl]-4H,5H,6H,7H-[1,3]thiazolo[5,4-c]pyridine-2-carboxamide | 418.2 | E: 0.98 F: 1.31 | (500 MHz, DMSO-d6) δ 12.82 (s, 1H), 10.92 (s, 1H), 8.34 (d, J = 7.2 Hz, 1H), 8.08-8.00 (m, J = 8.5 Hz, 2H), 7.96-7.84 (m, 2H), 7.74 (d, J = 7.7 Hz, 1H), 7.63-7.54 (m, J = 8.5 Hz, 2H), 3.72 (s, 2H), 2.97-2.92 (m, 2H), 2.83-2.76 (m, 2H), 2.42 (s, 3H) |

TABLE 2-continued

| Example | R | Name | LCMS (M + H)+ | HPLC Method, RT (min.) | 1H NMR |
|---|---|---|---|---|---|
| 52 | 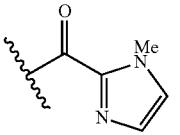 | 1-methyl-N-[4-(4-oxo-3,4-dihydrophthalazin-1-yl)phenyl]-1H-imidazole-2-carboxamide | 346.2 | E: 1.03<br>F: 1.26 | (500 MHz, DMSO-d$_6$) δ 12.81 (s, 1H), 10.55 (s, 1H), 8.38-8.29 (m, 1H), 8.06-7.98 (m, J = 8.5 Hz, 2H), 7.94-7.86 (m, 2H), 7.75 (d, J = 7.4 Hz, 1H), 7.62-7.53 (m, J = 8.5 Hz, 2H), 7.47 (s, 1H), 7.11 (s, 1H), 4.02 (s, 3H) |
| 53 | 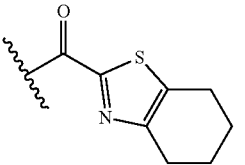 [SMILES: *C(=O)c1nc2c(s1)CCCC2] | N-[4-(4-oxo-3,4-dihydrophthalazin-1-yl)phenyl]-4,5,6,7-tetrahydro-1,3-benzothiazole-2-carboxamide | 403.15 | E: 1.70<br>F: 1.71 | (500 MHz, DMSO-d$_6$) δ 12.82 (s, 1H), 10.85 (s, 1H), 8.34 (dd, J = 7.6, 1.2 Hz, 1H), 8.07-8.01 (m, J = 8.5 Hz, 2H), 7.96-7.85 (m, 2H), 7.74 (d, J = 7.4 Hz, 1H), 7.63-7.53 (m, J = 8.5 Hz, 2H), 2.87 (dt, J = 15.7, 5.8 Hz, 4H), 1.91-1.77 (m, 4H) |
| 54 | 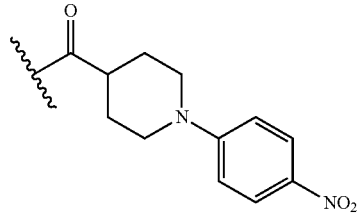 [SMILES: *C(=O)C1CCN(c2ccc([N+](=O)[O-])cc2)CC1] | 1-(4-nitrophenyl)-N-[4-(4-oxo-3,4-dihydrophthalazin-1-yl)phenyl]piperidine-4-carboxamide | 470.25 | E: 1.61<br>F: 1.62 | (500 MHz, DMSO-d$_6$) δ 12.78 (s, 1H), 10.05 (s, 1H), 8.35-8.31 (m, 1H), 7.89 (td, J = 4.6, 1.8 Hz, 2H), 7.79-7.75 (m, J = 8.5 Hz, 2H), 7.75-7.68 (m, 1H), 7.55-7.47 (m, J = 8.5 Hz, 2H), 7.37-7.29 (m, 4H), 7.27-7.20 (m, 1H), 3.48 (s, 2H), 2.96-2.84 (m, 2H), 2.41-2.29 (m, 1H), 1.98 (t, J = 11.1 Hz, 2H), 1.84-1.75 (m, 2H), 1.75-1.64 (m, 2H) |
| 55 | 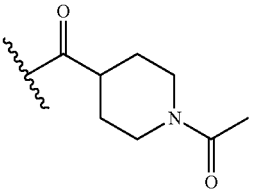 [SMILES: *C(=O)C1CCN(C(C)=O)CC1] | 1-acetyl-N-[4-(4-oxo-3,4-dihydrophthalazin-1-yl)phenyl]piperidine-4-carboxamide | 391.2 | E: 1.06<br>F: 1.07 | (500 MHz, DMSO-d$_6$) δ 12.78 (s, 1H), 10.13 (s, 1H), 8.35-8.30 (m, 1H), 7.96-7.86 (m, 2H), 7.82-7.75 (m, J = 8.5 Hz, 2H), 7.72 (d, J = 8.5 Hz, 1H), 7.56-7.47 (m, J = 8.5 Hz, 2H), 4.42 (d, J = 13.2 Hz, 1H), 3.89 (d, J = 12.1 Hz, 1H), 3.09 (t, J = 12.0 Hz, 1H), 2.66-2.58 (m, 2H), 1.84 (t, J = 13.1 Hz, 2H), 1.69-1.57 (m, 1H), 1.53-1.39 (m, 1H) |
| 56 | 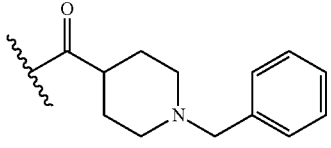 [SMILES: *C(=O)C1CCN(Cc2ccccc2)CC1] | 1-benzyl-N-[4-(4-oxo-3,4-dihydrophthalazin-1-yl)phenyl]piperidine-4-carboxamide | 439.3 | E: 1.05<br>F: 1.15 | (500 MHz, DMSO-d$_6$) δ 12.78 (s, 1H), 10.05 (s, 1H), 8.35-8.31 (m, 1H), 7.89 (td, J = 4.6, 1.8 Hz, 2H), 7.79-7.75 (m, J = 8.5 Hz, H), 7.75-7.68 (m, 1H), 7.55-7.47 (m, J = 8.5 Hz, 2H), 7.37-7.29 (m, 4H), 7.27-7.20 (m, 1H), 3.48 (s, 2H), 2.96-2.84 (m, 2H), 2.41-2.29 (m, 1H), 1.98 (t, J = 11.1 Hz, 2H), 1.84-1.75 (m, 2H), 1.75-1.64 (m, 2H) |
| 57 | 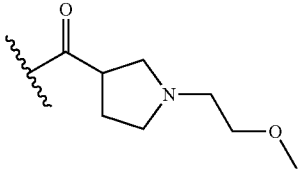 [SMILES: *C(=O)C1CCN(CCOC)C1] | 1-(2-methoxyethyl)-N-[4-(4-oxo-3,4-dihydrophthalazin-1-yl)phenyl]pyrrolidine-3-carboxamide | 393.2 | E: 1.01<br>F: 0.99 | (500 MHz, DMSO-d$_6$) δ 10.14 (br. s., 1H), 8.33 (d, J = 7.4 Hz, 1H), 7.94-7.86 (m, 2H), 7.80-7.74 (m, J = 8.3 Hz, 2H), 7.72 (d, J = 7.2 Hz, 1H), 7.57-7.46 (m, J = 8.3 Hz, 2H), 3.45 (t, J = 5.5 Hz, 3H), 3.26 (s, 3H), 3.12-3.03 (m, 1H), 2.96 (br. s., 1H), 2.73 (br. s., 1H), 2.63 (br. s., 3H), 2.01 (d, J = 6.9 Hz, 2H) |
| 58 | 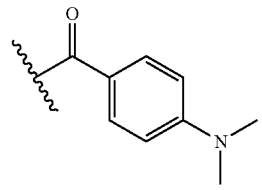 [SMILES: *C(=O)c1ccc(N(C)C)cc1] | 4-(dimethylamino)-N-[4-(4-oxo-3,4-dihydrophthalazin-1-yl)phenyl]benzamide | 385.3 | E: 1.38<br>F: 1.59 | (500 MHz, DMSO-d$_6$) δ 12.80 (s, 1H), 10.07 (s, 1H), 8.34 (d, J = 8.0 Hz, 1H), 7.97-7.86 (m, 6H), 7.76 (d, J = 7.7 Hz, 1H), 7.55 (d, J = 8.3 Hz, 2H), 6.78 (d, J = 8.8 Hz, 2H), 3.01 (s, 6H) |

TABLE 2-continued

| Example | R | Name | LCMS (M + H)+ | HPLC Method, RT (min.) | 1H NMR |
|---|---|---|---|---|---|
| 59 | 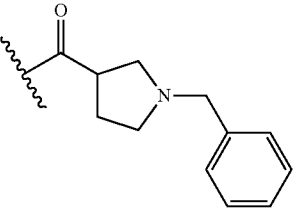 [SMILES: *C(=O)C1CCN(Cc2ccccc2)C1] | 1-benzyl-N-[4-(4-oxo-3,4-dihydrophthalazin-1-yl)phenyl]pyrrolidine-3-carboxamide | 425.25 | E: 1.16 F: 1.26 | (500 MHz, DMSO-d6) δ 12.79 (s, 1H), 10.11 (br. s., 1H), 8.39-8.29 (m, 1H), 7.93-7.86 (m, 2H), 7.79-7.73 (m, J = 8.5 Hz, 2H), 7.72-7.67 (m, 1H), 7.54-7.48 (m, J = 8.5 Hz, 2H), 7.40-7.31 (m, 4H), 7.28 (br. s., 1H), 3.67 (br. s., 2H), 3.14 (br. s., 1H), 2.96 (br. s., 1H), 2.82-2.69 (m, 2H), 2.59 (br. s., 1H), 2.07 (br. s., 2H) |
| 60 | 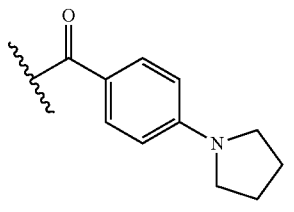 [SMILES: *C(=O)c1ccc(N2CCCC2)cc1] | N-[4-(4-oxo-3,4-dihydrophthalazin-1-yl)phenyl]-4-(pyrrolidin-1-yl)benzamide | 411.2 | E: 1.76 F: 1.74 | (500 MHz, DMSO-d6) δ 12.80 (s, 1H), 10.03 (s, 1H), 8.34 (d, J = 7.7 Hz, 1H), 7.97 (s, 2H), 7.93-7.86 (m, 4H), 7.77 (d, J = 7.7 Hz, 1H), 7.55 (d, J = 8.3 Hz, 2H), 6.62 (d, J = 8.5 Hz, 2H), 1.99 (br. s., 4H) |
| 61 | 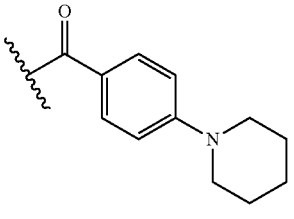 [SMILES: *C(=O)c1ccc(N2CCCCC2)cc1] | N-[4-(4-oxo-3,4-dihydrophthalazin-1-yl)phenyl]-4-(piperidin-1-yl)benzamide | 425.25 | E: 1.23 F: 1.83 | (500 MHz, DMSO-d6) δ 10.11 (s, 1H), 8.34 (d, J = 7.7 Hz, 1H), 7.99-7.86 (m, 6H), 7.76 (d, J = 7.4 Hz, 1H), 7.56 (d, J = 8.3 Hz, 2H), 7.01 (d, J = 8.8 Hz, 2H), 3.34 (br. s., 4H), 1.60 (br. s., 6H) |
| 62 | 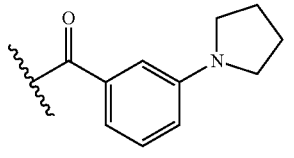 [SMILES: *C(=O)c1cccc(N2CCCC2)c1] | N-[4-(4-oxo-3,4-dihydrophthalazin-1-yl)phenyl]-3-(pyrrolidin-1-yl)benzamide | 411.2 | E: 1.55 F: 1.80 | 1H NMR (500 MHz, DMSO-d6) δ 12.81 (s, 1H), 10.31 (s, 1H), 8.38-8.32 (m, 1H), 7.97 (d, J = 8.5 Hz, 2H), 7.94-7.85 (m, 2H), 7.76 (d, J = 8.3 Hz, 1H), 7.58 (d, J = 8.5 Hz, 2H), 7.36-7.27 (m, 1H), 7.19 (d, J = 7.4 Hz, 1H), 7.07 (s, 1H), 6.75 (dd, J = 8.0, 1.7 Hz, 1H), 3.31 (br. s., 4H), 1.99 (t, J = 6.2 Hz, 4H) |
| 63 | 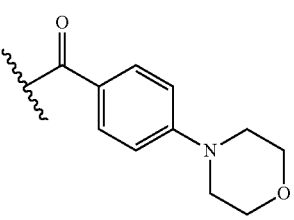 [SMILES: *C(=O)c1ccc(N2CCOCC2)cc1] | 4-(morpholin-4-yl)-N-[4-(4-oxo-3,4-dihydrophthalazin-1-yl)phenyl]benzamide | 427.25 | E: 1.42 F: 1.46 | (500 MHz, DMSO-d6) δ 12.81 (br. s., 1H), 10.18 (s, 1H), 8.34 (d, J = 7.7 Hz, 1H), 8.06-7.86 (m, 6H), 7.80-7.73 (m, 1H), 7.56 (d, J = 8.5 Hz, 2H), 7.05 (d, J = 8.8 Hz, 2H), 3.82-3.71 (m, 4H), 3.29-3.22 (m, 4H) |
| 64 | 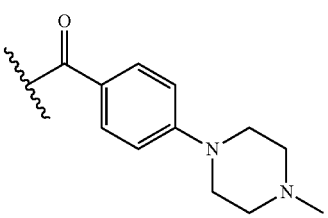 [SMILES: *C(=O)c1ccc(N2CCN(C)CC2)cc1] | 4-(4-methylpiperazin-1-yl)-N-[4-(4-oxo-3,4-dihydrophthalazin-1-yl)phenyl]benzamide | 440.25 | E: 1.06 F: 1.18 | 1H NMR (500 MHz, DMSO-d6) δ 12.80 (s, 1H), 10.14 (s, 1H), 8.34 (d, J = 7.4 Hz, 1H), 7.96 (d, J = 8.3 Hz, 2H), 7.94-7.86 (m, 4H), 7.76 (d, J = 7.7 Hz, 1H), 7.56 (d, J = 8.0 Hz, 2H), 7.04 (d, J = 8.3 Hz, 2H), 2.46 (br. s., 4H), 2.23 (s, 3H) |
| 65 | 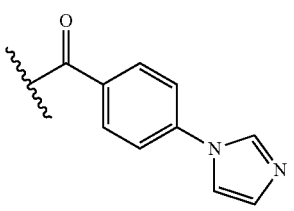 [SMILES: *C(=O)c1ccc(-n2ccnc2)cc1] | 4-(1H-imidazol-1-yl)-N-[4-(4-oxo-3,4-dihydrophthalazin-1-yl)phenyl]benzamide | 408.2 | E: 1.05 F: 1.29 | 1H NMR (500 MHz, DMSO-d6) δ 12.83 (s, 1H), 10.55 (s, 1H), 8.38 (s, 1H), 8.35 (d, J = 8.0 Hz, 1H), 8.22 (s, 1H), 8.00-7.86 (m, 7H), 7.76 (d, J = 7.7 Hz, 1H), 7.71 (t, J = 8.0 Hz, 1H), 7.62 (d, J = 8.5 Hz, 2H), 7.17 (s, 1H) |

TABLE 2-continued

| Example | R | Name | LCMS (M + H)+ | HPLC Method, RT (min.) | 1H NMR |
|---|---|---|---|---|---|
| 66 | (3-dimethylamino-benzoyl group) | 3-(dimethylamino)-N-[4-(4-oxo-3,4-dihydrophthalazin-1-yl)phenyl]benzamide | 385.1 | E: 1.16<br>F: 1.64 | (500 MHz, DMSO-$d_6$) δ 12.84 (br. s., 1H), 10.35 (s, 1H), 8.40-8.31 (m, 1H), 8.00-7.86 (m, 4H), 7.76 (d, J = 7.4 Hz, 1H), 7.59 (d, J = 8.4 Hz, 2H), 7.38-7.32 (m, 1H), 7.28-7.23 (m, 2H), 6.95 (dd, J = 8.2, 2.2 Hz, 1H), 2.98 (s, 6H) |
| 67 | (benzoyl group) | N-[4-(4-oxo-3,4-dihydrophthalazin-1-yl)phenyl]benzamide | 342.2 | E: 1.47<br>F: 1.47 | (500 MHz, DMSO-$d_6$) δ 12.84 (s, 1H), 10.48 (s, 1H), 8.35 (dd, J = 7.7, 1.2 Hz, 1H), 8.04-7.96 (m, 4H), 7.95-7.88 (m, 2H), 7.80-7.73 (m, 1H), 7.65-7.52 (m, 5H) |

Example 68:
4-(4-Oxo-3,4-dihydrophthalazin-1-yl)phenyl isoindoline-2-carboxylate

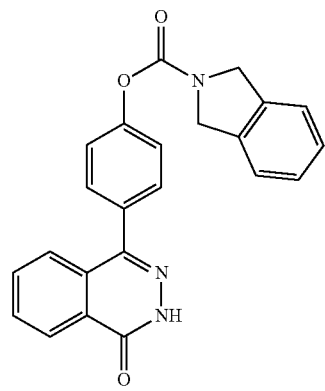 [SMILES: O=C(Oc1ccc(-c2n[nH]c(=O)c3ccccc23)cc1)N1Cc2ccccc2C1]

Example 68A: 4-Bromophenyl isoindoline-2-carboxylate

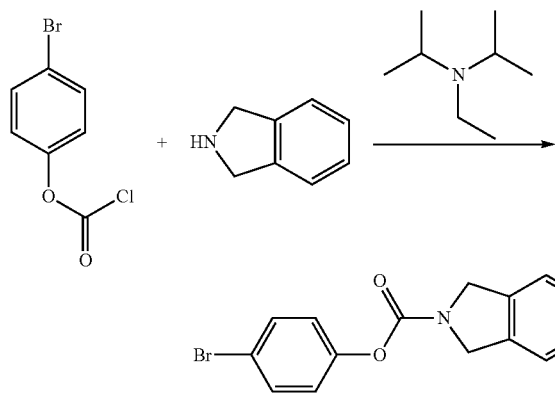

To a solution of isoindoline (167 mg, 1.401 mmol) and DIEA (0.445 mL, 2.55 mmol) in CH$_2$Cl$_2$ (3 mL), was added 4-bromophenyl carbonochloridate (300 mg, 1.274 mmol). The mixture was stirred at rt for 1 h, then was quenched with water. The mixture was diluted with EtOAc (100 mL), then was washed with 1N HCl, sat Na$_2$CO$_3$ and brine, dried over Na$_2$SO$_4$, and concentrated. The crude product was purified via flash chromatography to afford 310 mg (76%) of Example 68A. MS(ESI) m/z: 318.0 (M+H)+; 1H NMR (500 MHz, CDCl$_3$) δ 7.53-7.48 (m, 2H), 7.36-7.29 (m, 4H), 7.13-7.07 (m, 2H), 4.94 (s, 2H), 4.84 (s, 2H).

Example 68B:
(4-((Isoindoline-2-carbonyl)oxy)phenyl)boronic Acid

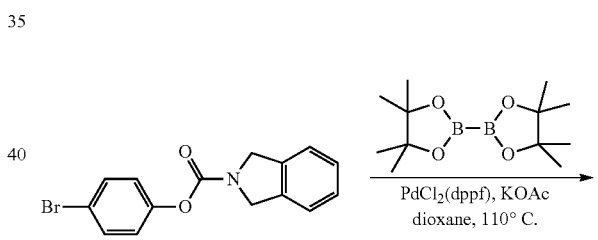

A mixture of Example 68A (100 mg, 0.314 mmol), bis(pinacolato)diboron (104 mg, 0.409 mmol), and potassium acetate (93 mg, 0.943 mmol) in dioxane (3 mL) was degassed (3× vacuum/Ar). PdCl$_2$(dppf) CH$_2$Cl$_2$ adduct (6.90 mg, 9.43 µmol) was added, then the reaction mixture was degassed again (3× vacuum/Ar), sealed in a vial and heated at 110° C. for 2 h. The reaction was concentrated and purified via preparative HPLC to afford 75 mg (84%) of Example 68B. MS(ESI) m/z: 284.1 (M+H)+; 1H NMR (400 MHz, CD$_3$OD) δ 7.83-7.76 (m, 1H), 7.68 (d, J=8.1 Hz, 1H), 7.40-7.28 (m, 4H), 7.24-7.10 (m, 2H), 4.95 (s, 2H), 4.78 (s, 2H).

Example 68

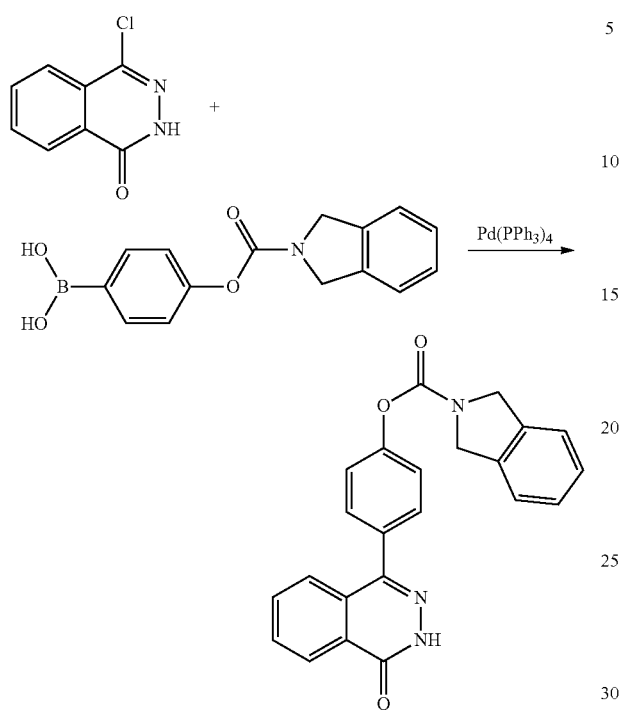

To 4-chlorophthalazin-1(2H)-one (18.24 mg, 0.101 mmol), Example 68B (26 mg, 0.092 mmol) and potassium phosphate (48.7 mg, 0.230 mmol), were added dioxane (3 mL) and water (0.5 mL). The mixture was degassed (evacuated and flushed with Ar (5×)). Pd(PPh$_3$)$_4$ (5.31 mg, 4.59 mol) was added, then the mixture was degassed (2×). The reaction vial was sealed and heated in a microwave reactor at 150° C. for 25 min. The crude product was purified by preparative HPLC to afford 9 mg (20%) of Example 68. MS(ESI) m/z: 384.2 (M+H)$^+$; $^1$H NMR (500 MHz, DMSO-d$_6$) δ 12.86 (s, 1H), 8.45-8.29 (m, 1H), 7.92 (qd, J=7.3, 5.8 Hz, 2H), 7.75-7.69 (m, 1H), 7.67-7.59 (m, 2H), 7.46-7.37 (m, 4H), 7.36-7.28 (m, 2H), 4.96 (s, 2H), 4.76 (s, 2H); HPLC RT=1.77 min (Method E), 1.78 min (Method F).

Example 69: 4-(4-Oxo-3,4-dihydrophthalazin-1-yl)phenyl 3-phenylpyrrolidine-1-carboxylate

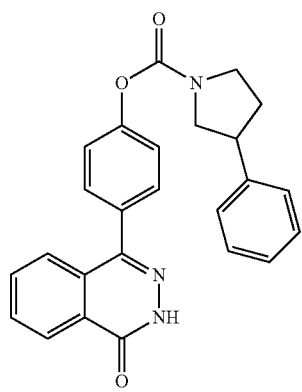 [SMILES: O=C(Oc1ccc(-c2n[nH]c(=O)c3ccccc23)cc1)N1CCC(c2ccccc2)C1]

Example 69A: 4-Bromophenyl 3-phenylpyrrolidine-1-carboxylate

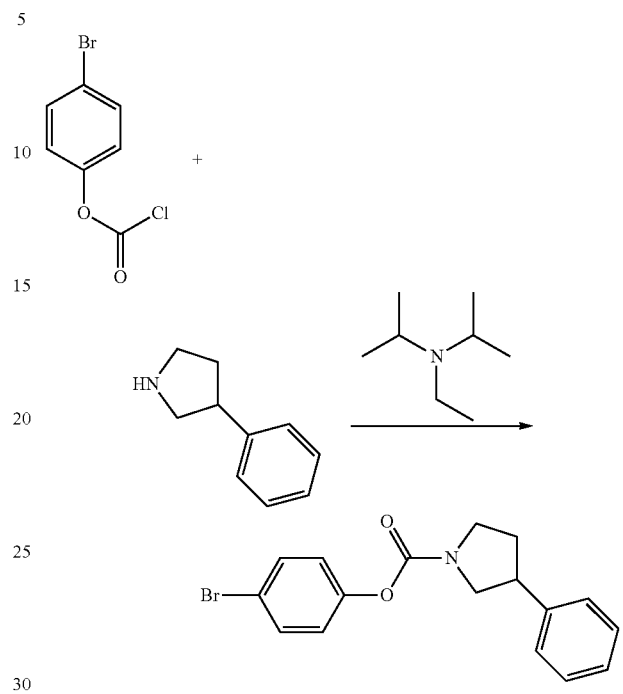

To a mixture of 3-phenylpyrrolidine (141 mg, 0.956 mmol) and DIEA (0.223 mL, 1.274 mmol) in CH$_2$Cl$_2$ (3 mL) at 0° C., was added 4-bromophenyl carbonochloridate (150 mg, 0.637 mmol). The mixture was stirred at rt for 1 h. The reaction mixture was quenched with water and EtOAc (100 mL) was added. The organic phase was washed with 1N HCl, sat Na$_2$CO$_3$ and brine, dried over Na$_2$SO$_4$, concentrated and purified flash chromatography to afford 210 mg (95%) of Example 69A. MS(ESI) m/z: 345.9 (M+H)$^+$; $^1$H NMR (500 MHz, CDCl$_3$) δ 7.56-7.44 (m, 2H), 7.40-7.34 (m, 2H), 7.31-7.26 (m, 3H), 7.09-6.99 (m, 2H), 4.12-3.94 (m, 1H), 3.89-3.73 (m, 1H), 3.64 (td, J=10.2, 6.7 Hz, 1H), 3.60-3.40 (m, 3H), 2.36 (ddtd, J=18.5, 12.4, 6.3, 2.6 Hz, 1H), 2.18-2.01 (m, 1H).

Example 69B: 4-(4,4,5,5-Tetramethyl-1,3,2-dioxaborolan-2-yl)phenyl 3-phenylpyrrolidine-1-carboxylate

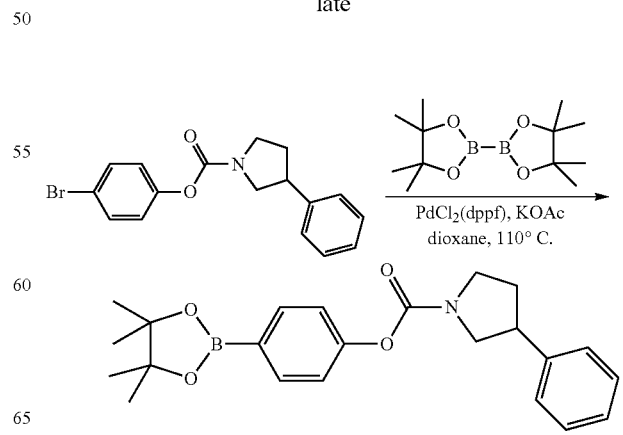

To a mixture of Example 69A (210 mg, 0.607 mmol), bis(pinacolato)diboron (185 mg, 0.728 mmol), and potassium acetate (179 mg, 1.820 mmol) in dioxane (5 mL), was added PdCl$_2$(dppf) CH$_2$Cl$_2$ adduct (13.31 mg, 0.018 mmol). The reaction mixture was degassed (3× vacuum/Ar), sealed in a vial and heated at 110° C. for 2 h. The reaction mixture was diluted with water and extracted with EtOAc. The organic phase was concentrated, then purified via flash chromatography (EtOAc/hexanes) to afford 220 mg (92%) of Example 69B. MS(ESI) m/z: 394.2 (M+H)$^+$; $^1$H NMR (500 MHz, CDCl$_3$) δ 7.86 (dd, J=7.8, 3.7 Hz, 2H), 7.42-7.35 (m, 2H), 7.33-7.26 (m, 3H), 7.22 (t, J=7.0 Hz, 2H), 4.13-3.99 (m, 1H), 3.92-3.77 (m, 1H), 3.72-3.41 (m, 3H), 2.38 (t, J=13.1 Hz, 1H), 2.19-2.07 (m, 1H), 1.37 (s, 12H).

Example 69

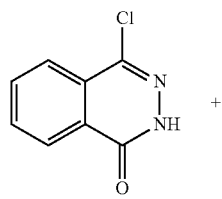

+

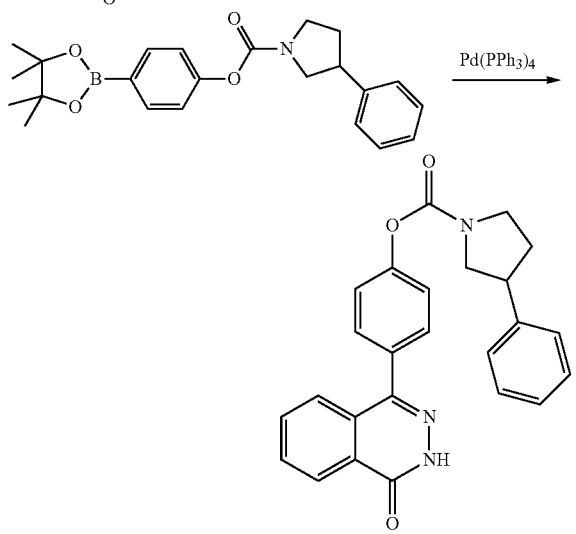

To a 4-cholorophthalazin-1(2H)-one (28 mg, 0.16 mmol), Example 69B (79 mg, 0.20 mmol) and potassium phosphate (82 mg, 0.39 mmol), were added dioxane (3 mL) and water (0.33 mL). The mixture was degassed (evacuated and flushed with Ar (5×)). Pd(PPh$_3$)$_4$ (9.0 mg, 7.8 µmol) was added, then the mixture was degassed (2×). The reaction vial was sealed and heated in a microwave reactor at 150° C. for 35 min. The reaction mixture was concentrated, then was purified by preparative HPLC to afford 8.2 mg (10%) of the Example 69. MS(ESI) m/z: 412.2 (M+H)$^+$; $^1$H NMR (500 MHz, DMSO-d$_6$) δ 12.85 (s, 1H), 8.35 (d, J=7.4 Hz, 1H), 7.99-7.86 (m, 2H), 7.70 (d, J=7.4 Hz, 1H), 7.62 (dd, J=8.5, 3.9 Hz, 2H), 7.44-7.30 (m, 6H), 7.29-7.19 (m, 1H), 4.13-3.97 (m, 1H), 3.97-3.76 (m, 1H), 3.72-3.59 (m, 1H), 3.55-3.42 (m, 2H), 2.42-2.26 (m, 1H), 2.17-1.99 (m, 1H); HPLC RT=1.73 min (Method E), 1.74 min (Method F).

Example 70: 4-(4-Oxo-3,4-dihydrophthalazin-1-yl) phenyl 5-methoxyisoindoline-2-carboxylate

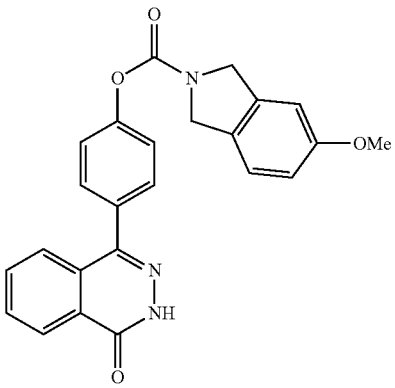 [SMILES: COc1ccc2c(c1)CN(C(=O)Oc1ccc(-c3n[nH]c(=O)c4ccccc34)cc1)C2]

Example 70A: 4-Bromophenyl 5-methoxyisoindoline-2-carboxylate

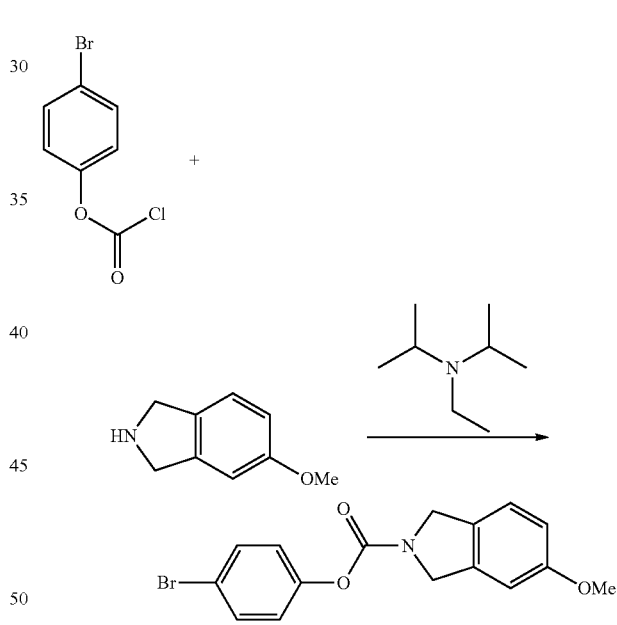

To a solution of a 5-methoxyisoindoline (80 mg, 0.54 mmol) and DIEA (0.18 mL, 1.02 mmol) in CH$_2$Cl$_2$ (3 mL) at 0° C., was added 4-bromophenyl carbonochloridate (120 mg, 0.51 mmol). The reaction mixture was stirred rt for 1 h, then was quenched with water. The mixture was diluted with EtOAc (100 mL). The organic phase was washed with 1N HCl, sat. Na$_2$CO$_3$ and brine, dried over Na$_2$SO$_4$, and concentrated. The crude product was purified via flash chromatography to afford 112 mg (63%) of Example 70A. MS(ESI) m/z: 348.0 (M+H)$^+$; $^1$H NMR (500 MHz, CDCl$_3$) δ 7.55-7.45 (m, 2H), 7.19 (dd, J=12.2, 8.4 Hz, 1H), 7.13-7.03 (m, 2H), 6.88 (dd, J=8.4, 2.3 Hz, 1H), 6.82 (dd, J=10.5, 1.9 Hz, 1H), 4.87 (d, J=16.2 Hz, 2H), 4.78 (d, J=17.1 Hz, 2H), 3.83 (s, 3H).

Example 70B: 4-(4,4,5,5-Tetramethyl-1,3,2-dioxaborolan-2-yl)phenyl 5-methoxyisoindoline-2-carboxylate

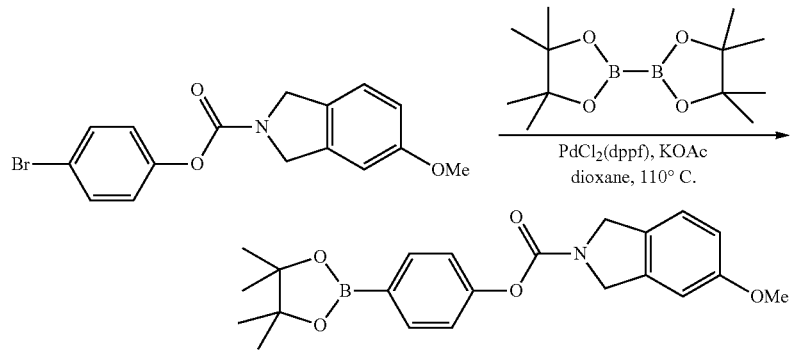

To a mixture of Example 70A (112 mg, 0.322 mmol), bis(pinacolato)diboron (98 mg, 0.39 mmol), and potassium acetate (95 mg, 0.97 mmol) in dioxane (10 mL), was added PdCl$_2$(dppf) CH$_2$Cl$_2$ adduct (7.1 mg, 9.7 mol). The reaction mixture was degassed (3× vacuum/Ar), sealed in a vial and heated at 110° C. for 2 h. The reaction was diluted with water and extracted with EtOAc. The organic phase was concentrated and the residue was purified via flash chromatography to afford 100 mg (79%) of Example 70B. MS(ESI) m/z: 396.2 (M+H)$^+$; $^1$H NMR (500 MHz, CDCl$_3$) δ 7.85 (d, J=8.3 Hz, 2H), 7.25-7.15 (m, 3H), 6.92-6.80 (m, 2H), 4.89 (d, J=16.5 Hz, 2H), 4.79 (d, J=18.2 Hz, 2H), 3.83 (s, 3H), 1.44-1.32 (m, 12H).

Example 70

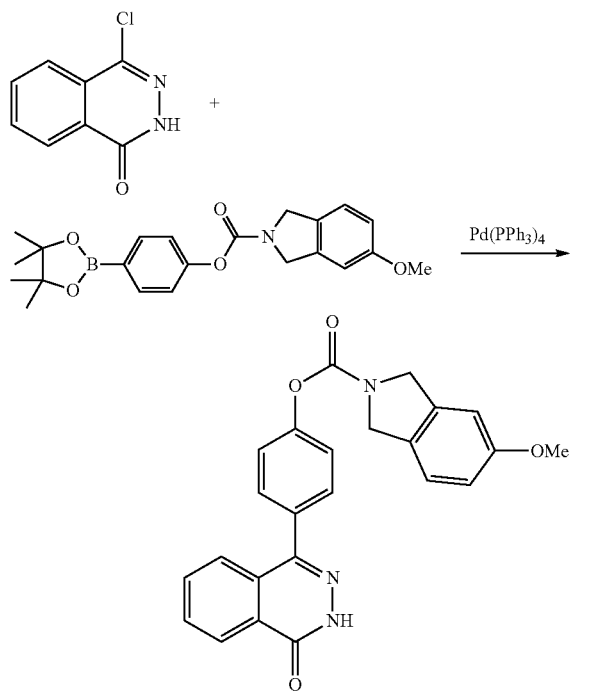

To 4-chlorophthalazin-1(2H)-one (13 mg, 0.072 mmol), Example 70B (29.9 mg, 0.076 mmol) and potassium phosphate (38.2 mg, 0.180 mmol), were added dioxane (3 mL) and water (0.33 mL). The mixture was degassed (evacuated and flushed with Ar (5×)). Pd(PPh$_3$)$_4$ (4.2 mg, 3.6 mol) was added, then the mixture was degassed (2×). The reaction vial was sealed and heated in a microwave reactor at 150° C. for 25 min. The reaction mixture was concentrated, then was purified via preparative HPLC to afford 9 mg (23%) of Example 70. MS(ESI) m/z: 414.1 (M+H)$^+$; $^1$H NMR (500 MHz, DMSO-d$_6$) δ 12.86 (s, 1H), 8.35 (dd, J=7.6, 1.2 Hz, 1H), 7.98-7.88 (m, 2H), 7.76-7.70 (m, 1H), 7.68-7.61 (m, J=8.5 Hz, 2H), 7.43-7.36 (m, J=8.5 Hz, 2H), 7.30 (d, J=8.3 Hz, 1H), 6.99 (br. s., 1H), 6.91 (d, J=8.3 Hz, 1H), 4.92 (s, 1H), 4.87 (s, 1H), 4.72 (s, 1H), 4.68 (s, 1H), 3.81-3.72 (m, 3H); HPLC RT=9.48 min (Method A), 8.98 min (Method B).

Example 71: 4-(4-Oxo-3,4-dihydrophthalazin-1-yl)phenyl 5-fluoroisoindoline-2-carboxylate

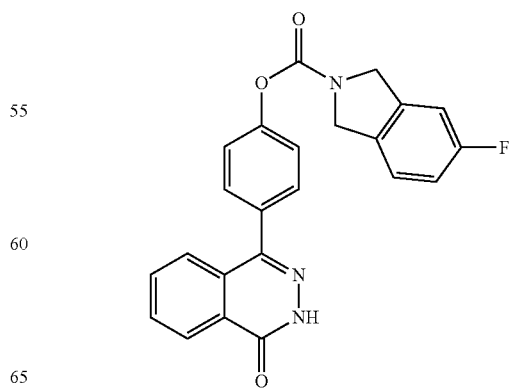

Example 71A: 4-Bromophenyl 5-fluoroisoindoline-2-carboxylate

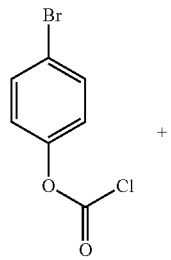

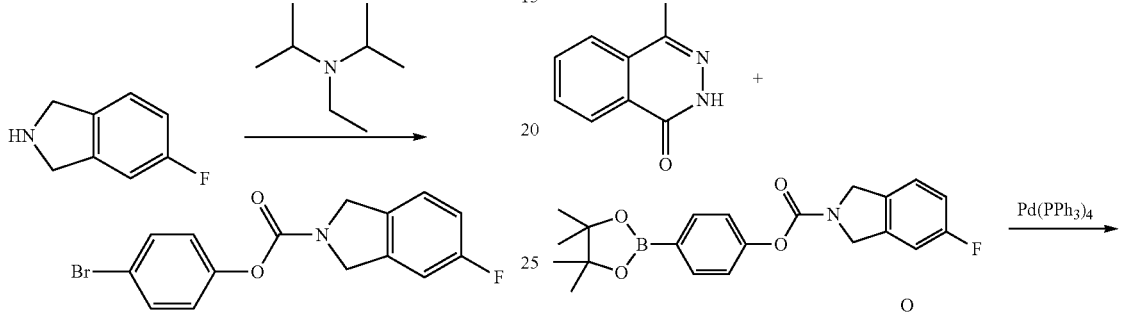

To a mixture of 5-fluoroisoindoline (141 mg, 1.03 mmol) and DIEA (0.326 mL, 1.87 mmol) in CH$_2$Cl$_2$ (3 mL) at 0° C., was added 4-bromophenyl carbonochloridate (220 mg, 0.934 mmol). The mixture was stirred at rt for 1 h, then was quenched with water. The mixture was diluted with EtOAc (100 mL), then was washed with 1N HCl, sat Na$_2$CO$_3$ and brine, dried over Na$_2$SO$_4$, and concentrated. The crude product was purified via flash chromatography (EtOAc/hexanes) to afford 190 mg (61%) of Example 71A. MS(ESI) m/z: 414.1 (M+H)$^+$; $^1$H NMR (500 MHz, CDCl$_3$) δ 7.56-7.46 (m, 2H), 7.34-7.21 (m, 1H), 7.16-7.07 (m, 2H), 7.05-6.97 (m, 2H), 4.92 (d, J=14.0 Hz, 2H), 4.82 (d, J=14.0 Hz, 2H).

Example 71B: 4-(4,4,5,5-Tetramethyl-1,3,2-dioxaborolan-2-yl)phenyl 5-fluoroisoindoline-2-carboxylate

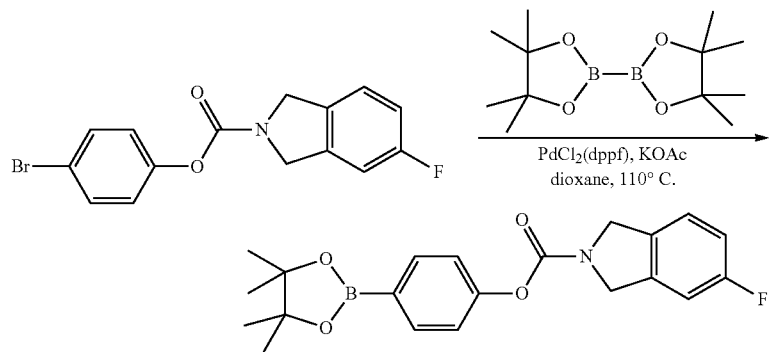

To a mixture of Example 71A (182 mg, 0.541 mmol), bis(pinacolato)diboron (165 mg, 0.65 mmol), and potassium acetate (159 mg, 1.62 mmol) in dioxane (4 mL), was added PdCl$_2$(dppf) CH$_2$Cl$_2$ adduct (11.9 mg, 0.016 mmol). The reaction mixture was degassed (3× vacuum/Ar), sealed in a vial and heated at 110° C. for 2 h. The reaction mixture was partitioned between EtOAc and H$_2$O. The organic phase was concentrated and the residue was purified via flash chromatography to afford 150 mg (72%) of Example 71B. MS(ESI) m/z: 384.2 (M+H)$^+$; $^1$H NMR (500 MHz, CDCl$_3$) δ 7.88-7.83 (m, 2H), 7.28-7.19 (m, 3H), 7.09-6.95 (m, 2H), 4.93 (d, J=14.3 Hz, 2H), 4.82 (d, J=14.0 Hz, 2H), 1.43-1.34 (m, 12H).

Example 71

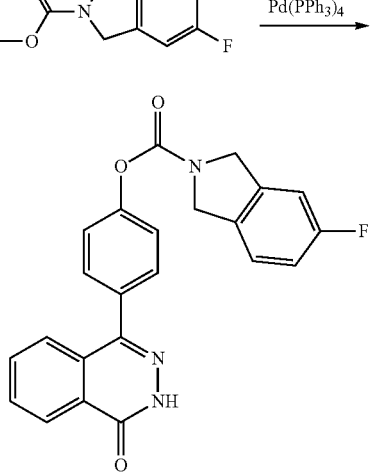

To 4-chlorophthalazin-1(2H)-one (20 mg, 0.11 mmol), Example 71B (44.6 mg, 0.116 mmol) and potassium phosphate (58.8 mg, 0.277 mmol), were added dioxane (3 mL) and water (0.33 mL). The mixture was degassed (evacuated and flushed with Ar (5×)). Pd(PPh$_3$)$_4$ (6.4 mg, 5.5 mol) was added, then the mixture was degassed (2×). The reaction vial was sealed and heated in a microwave reactor at 150° C. for 25 min. The reaction mixture was concentrated and the residue purified via preparative HPLC to afford 5 mg (8%) of Example 71. MS(ESI) m/z: 402.1 (M+H)+; 1H NMR (500 MHz, DMSO-d6) δ 12.86 (s, 1H), 8.39-8.32 (m, 1H), 7.95-7.89 (m, 2H), 7.75-7.69 (m, 1H), 7.66-7.60 (m, 2H), 7.44-7.35 (m, 4H), 7.29-7.15 (m, 4H), 4.94 (d, J=17.3 Hz, 2H), 4.74 (d, J=17.1 Hz, 2H); HPLC RT=9.62 min (Method A), 9.15 min (Method B).

Example 72: 4-(4-Oxo-3,4-dihydrophthalazin-1-yl)phenyl 5-((4-methylpiperazin-1-yl)methyl)isoindoline-2-carboxylate, 2 TFA

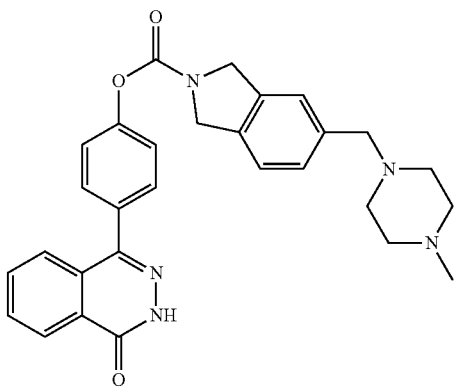 [SMILES: CN1CCN(Cc2ccc3c(c2)CN(C(=O)Oc2ccc(-c4n[nH]c(=O)c5ccccc45)cc2)C3)CC1]

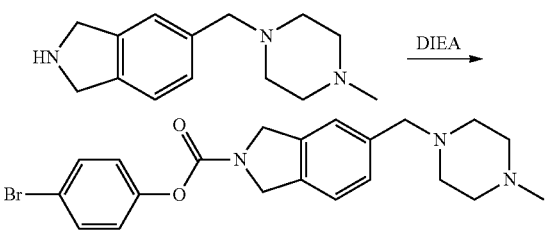

To a solution of Intermediate 2 (196 mg, 0.849 mmol) and DIEA (0.297 mL, 1.70 mmol) in CH$_2$Cl$_2$ (3 mL) at 0° C., was added 4-bromophenyl carbonochloridate (200 mg, 0.849 mmol). The mixture was stirred at rt for 1 h. The reaction mixture was quenched with water and diluted with EtOAc (100 mL). The organic phase was washed with 1N HCl, sat Na$_2$CO$_3$ and brine, dried over Na$_2$SO$_4$ and concentrated. The crude product was purified by flash chromatography, followed by preparative HPLC to afford 280 mg (50%) of Example 72A. MS(ESI) m/z: 430.1 (M+H)+; 1H NMR (500 MHz, CD$_3$OD) δ 7.60-7.51 (m, 2H), 7.49-7.38 (m, 3H), 7.21-7.10 (m, 2H), 4.96 (s, 2H), 4.79 (s, 2H), 4.15 (s, 2H), 3.49 (br. s., 4H), 3.30-3.19 (m, 4H), 2.94 (s, 3H).

Example 72B: 4-(4,4,5,5-Tetramethyl-1,3,2-dioxaborolan-2-yl)phenyl 5-((4-methylpiperazin-1-yl)methyl)isoindoline-2-carboxylate

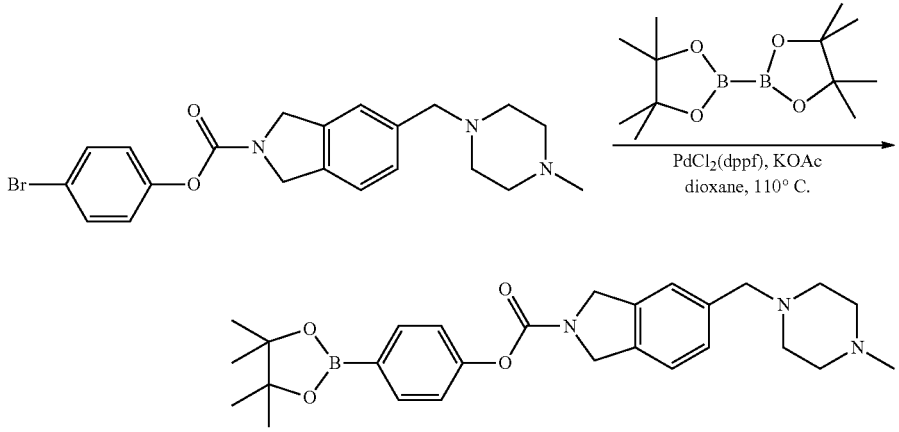

Example 72A: 4-Bromophenyl 5-((4-methylpiperazin-1-yl)methyl)isoindoline-2-carboxylate, 2 TFA

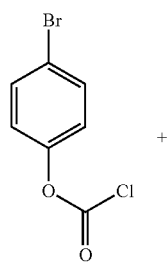

To a mixture of Example 72A (70 mg, 0.106 mmol), bis(pinacolato)diboron (32.4 mg, 0.128 mmol), and potassium acetate (31.3 mg, 0.319 mmol) in dioxane (10 mL), was added PdCl$_2$(dppf) CH$_2$Cl$_2$ adduct (2.3 mg, 3.2 μmol). The reaction mixture was degassed (3× vacuum/Ar), sealed in a vial and heated at 110° C. for 2 h. The reaction was quenched with water, then extracted with EtOAc. The organic phase was concentrated to afford 80 mg of Example 72B, which was used as is in the following step without further purification. MS(ESI) m/z: 478.4 (M+H)+.

Example 72

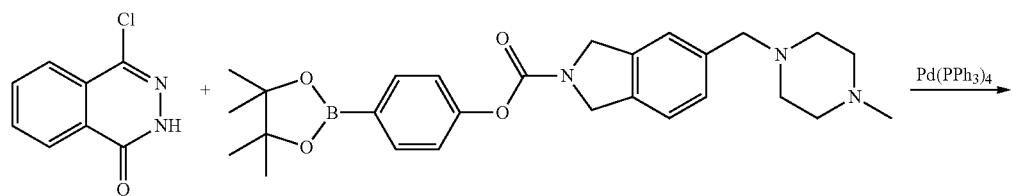

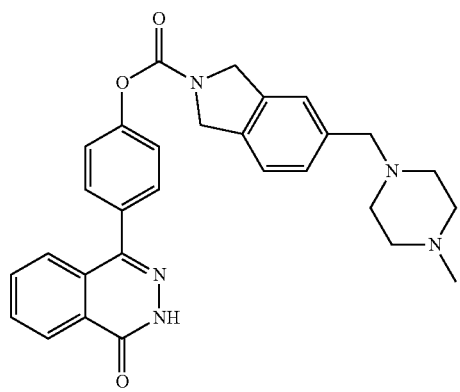

To a vial containing 4-chlorophthalazin-1(2H)-one (22 mg, 0.12 mmol), Example 72B (80 mg, 0.106 mmol) and potassium phosphate (64.6 mg, 0.305 mmol), were added dioxane (3 mL) and water (0.33 mL). The mixture was degassed (evacuated and flushed with Ar (5×)). Pd(PPh$_3$)$_4$ (7.0 mg, 6.1 mol) was added, then the mixture was degassed (2×). The reaction vial was sealed and heated in a microwave reactor at 150° C. for 25 min. The reaction mixture was concentrated and purified via preparative HPLC to afford 22 mg (25%) of Example 72. MS(ESI) m/z: 496.2 (M+H)$^+$; $^1$H NMR (500 MHz, DMSO-d$_6$) δ 12.86 (s, 1H), 8.43-8.31 (m, 1H), 8.02-7.86 (m, 2H), 7.71 (d, J=7.7 Hz, 1H), 7.65 (d, J=8.8 Hz, 2H), 7.47-7.34 (m, 4H), 7.30 (d, J=7.4 Hz, 1H), 4.95 (s, 2H), 4.76 (br. s., 2H), 3.65 (br. s., 2H), 2.99 (br. s., 4H), 2.77 (br. s., 3H), 2.36 (br. s., 2H); HPLC RT=4.32 min (Method A), 5.17 min (Method B).

Example 73: 4-(4-((5-Phenyloxazol-2-yl)amino)phenyl)phthalazin-1 (2H)-one

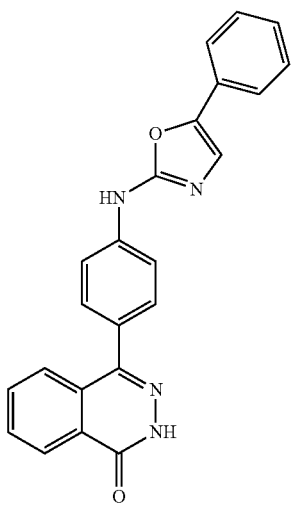 [SMILES: O=c1[nH]nc(-c2ccc(Nc3ncc(-c4ccccc4)o3)cc2)c2ccccc12]

Example 73A: N-(4-Bromophenyl)-5-phenyloxazol-2-amine

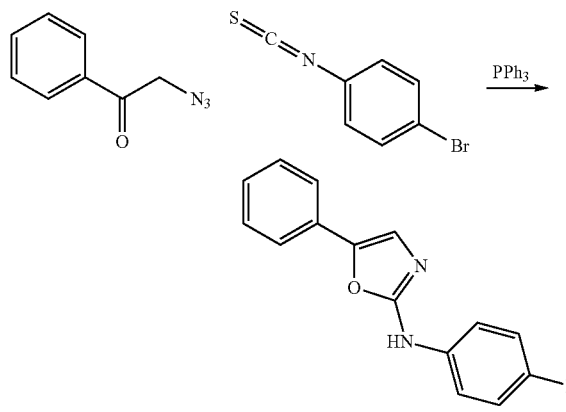

To a solution of 2-azido-1-phenylethanone (*Angew. Chem. Int. Ed.*, 46:4489-4491 (2007)) (126 mg, 0.782 mmol) and 1-bromo-4-isothiocyanatobenzene (167 mg, 0.782 mmol) in dioxane (4 mL) at 80° C., was added triphenylphosphine (205 mg, 0.782 mmol). The mixture was stirred at 85° C. for 30 min, then was cooled to rt. The reaction mixture was concentrated. The solid was recrystallized from hot CH$_3$Cl (~5 mL). The precipitate was suspended in EtOAc (~3 mL), filtered and collected to afford 134 mg (54%) of Example 73A as a white solid. MS(ESI) m/z: 315.0 (M+H)$^+$; $^1$H NMR (400 MHz, CD$_3$OD) δ 7.62-7.57 (m, 2H), 7.51-7.46 (m, 2H), 7.46-7.41 (m, 2H), 7.39 (t, J=7.7 Hz, 2H), 7.26 (dt, J=7.4, 1.3 Hz, 1H), 7.24 (s, 1H).

Example 73B: 5-Phenyl-N-(4-(4,4,5,5-tetramethyl-1,3,2-dioxaborolan-2-yl)phenyl)oxazol-2-amine

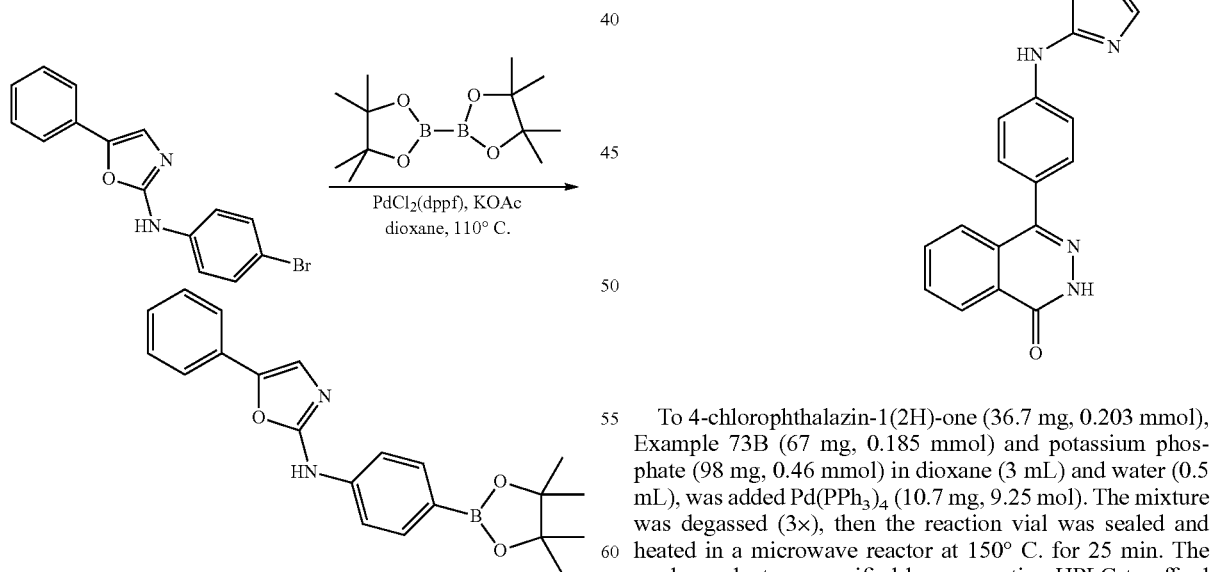

To a vial containing Example 73A (136 mg, 0.432 mmol), bis(pinacolato)diboron (164 mg, 0.647 mmol) and potassium acetate (127 mg, 1.30 mmol), was added dioxane (2 mL). The mixture was degassed (evacuated and flushed with Ar (3×)). PdCl$_2$(dppf) CH$_2$Cl$_2$ adduct (17.6 mg, 0.022 mmol) was added, then the mixture was degassed (2×), then was sealed. The mixture was stirred at 110° C. for 2 h. The reaction mixture was diluted with EtOAc. The organic phase was washed with H$_2$O and brine, dried (Na$_2$SO$_4$) and concentrated. The crude product was purified by flash chromatography (gradient from 0 to 50% ethyl acetate/hexanes) to afford 122 mg (78%) of Example 73B as a white solid. MS(ESI) m/z: 363.1 (M+H)$^+$; $^1$H NMR (400 MHz, CDCl$_3$) δ 7.81 (d, J=8.8 Hz, 2H), 7.55 (dd, J=8.3, 1.2 Hz, 2H), 7.49 (d, J=8.8 Hz, 2H), 7.43 (s, 1H), 7.42-7.36 (m, 2H), 7.29-7.23 (m, 1H), 7.18 (s, 1H), 1.35 (s, 12H).

Example 73

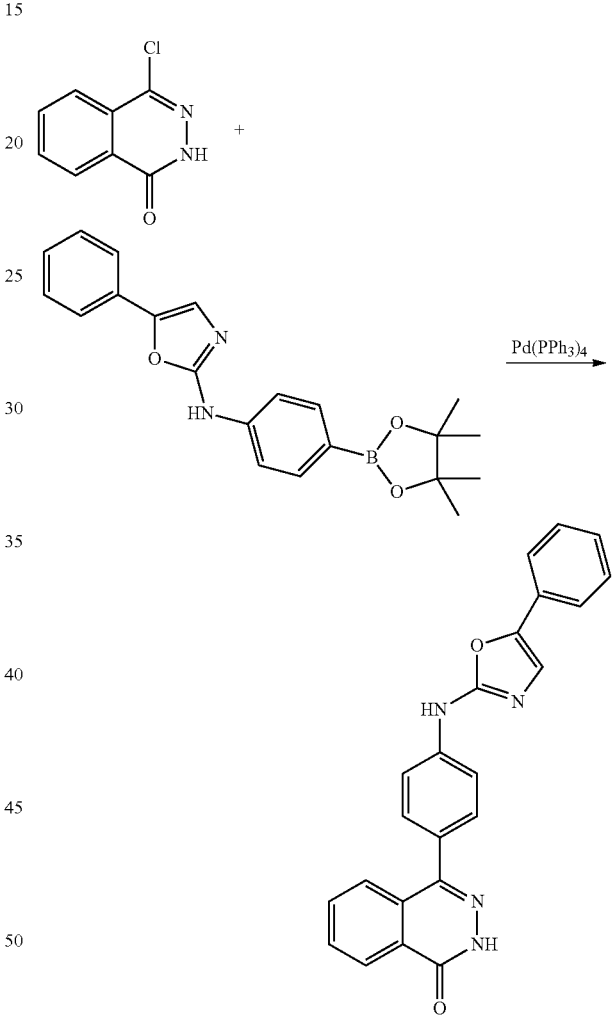

To 4-chlorophthalazin-1(2H)-one (36.7 mg, 0.203 mmol), Example 73B (67 mg, 0.185 mmol) and potassium phosphate (98 mg, 0.46 mmol) in dioxane (3 mL) and water (0.5 mL), was added Pd(PPh$_3$)$_4$ (10.7 mg, 9.25 mol). The mixture was degassed (3×), then the reaction vial was sealed and heated in a microwave reactor at 150° C. for 25 min. The crude product was purified by preparative HPLC to afford 9.7 mg (11%) of Example 73. MS(ESI) m/z: 381.1 (M+H)$^+$; $^1$H NMR (500 MHz, DMSO-d$_6$) δ 12.78 (s, 1H), 10.60 (s, 1H), 8.40-8.30 (m, 1H), 7.96-7.87 (m, 2H), 7.84-7.73 (m, 3H), 7.62 (d, J=7.7 Hz, 2H), 7.57 (d, J=8.5 Hz, 2H), 7.51 (s, 1H), 7.45 (t, J=7.7 Hz, 2H), 7.33-7.24 (m, 1H); HPLC RT=8.99 min (Method A), 8.46 min (Method B).

Example 74: 4-(4-((4-Phenylthiazol-2-yl)amino)phenyl)phthalazin-1(2H)-one

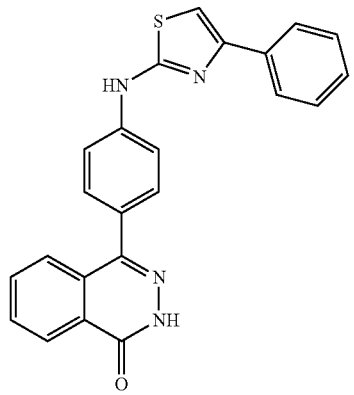 [SMILES: O=c1[nH]nc(-c2ccc(Nc3nc(-c4ccccc4)cs3)cc2)c2ccccc12]

Example 74A:
N-(4-Bromophenyl)-4-phenylthiazol-2-amine

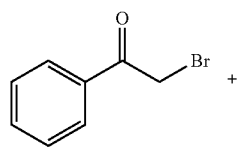

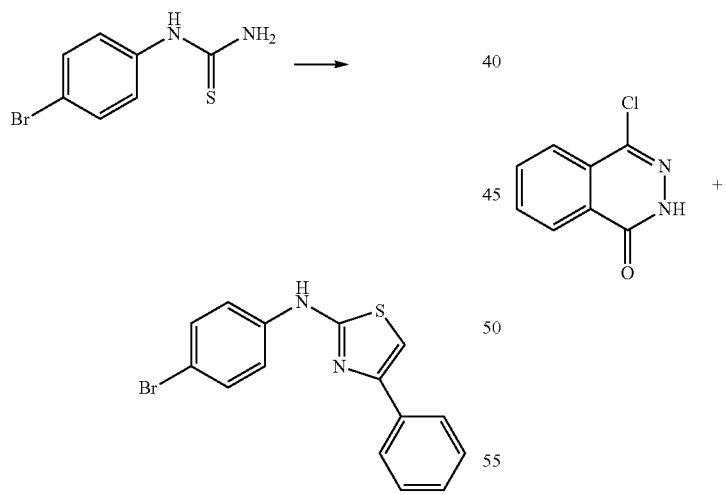

2-Bromo-1-phenylethanone (105 mg, 0.528 mmol) and 1-(4-bromophenyl)thiourea (122 mg, 0.528 mmol) were mixed in glycerol (5 mL) and stirred at 90° C. for 2 h. The reaction mixture was partitioned between EtOAc and water. The organic phase was concentrated and purified via flash chromatography (EtOAc/hexanes) to afford 165 mg (94%) of Example 74A. MS(ESI) m/z: 331.0 (M+H)$^+$; $^1$H NMR (500 MHz, CDCl$_3$) δ 7.87-7.82 (m, 2H), 7.44-7.38 (m, 4H), 7.36-7.31 (m, 1H), 7.29-7.22 (m, 2H), 6.84 (s, 1H).

Example 74B: 4-Phenyl-N-(4-(4,4,5,5-tetramethyl-1,3,2-dioxaborolan-2-yl)phenyl)thiazol-2-amine

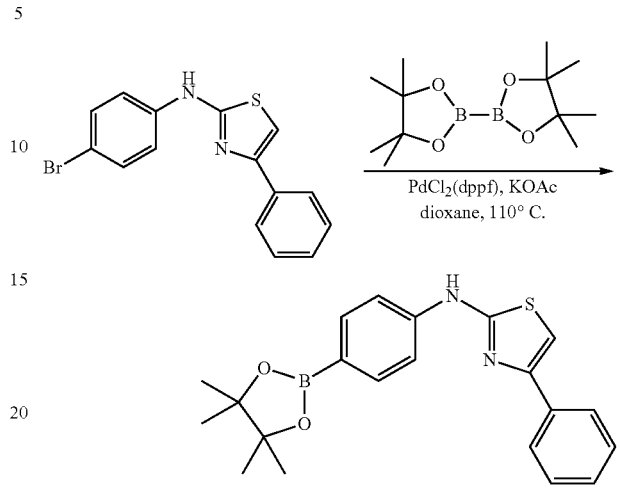

To a mixture of Example 74A (160 mg, 0.483 mmol), bis(pinacolato)diboron (147 mg, 0.580 mmol), and potassium acetate (142 mg, 1.45 mmol) in dioxane (10 mL), was added PdCl$_2$(dppf) CH$_2$Cl$_2$ adduct (10.6 mg, 0.014 mmol). The reaction mixture was degassed (3× vacuum/Ar), sealed in a vial and heated at 110° C. for 2 h. The reaction was diluted with water and extracted with EtOAc. The organic phase was concentrated and the product purified via flash chromatography to afford 130 mg (71%) of Example 74B. MS(ESI) m/z: 379.0 (M+H)$^+$.

Example 74

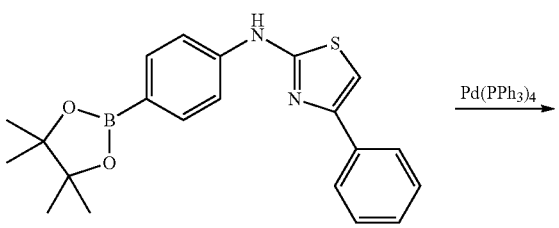

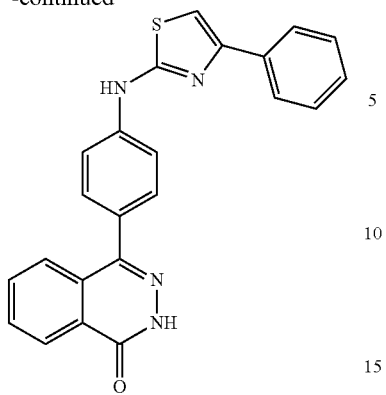

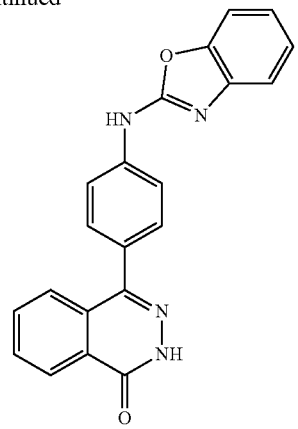

To 4-chlorophthalazin-1(2H)-one (18 mg, 0.10 mmol), Example 74B (45.2 mg, 0.120 mmol) and potassium phosphate (53 mg, 0.25 mmol), were added dioxane (3 mL) and water (0.33 mL). The mixture was degassed (evacuated and flushed with Ar (5×)). Pd(PPh$_3$)$_4$ (5.8 mg, 5.0 μmol) was added, then the mixture was degassed (2×). The reaction vial was sealed and heated in a microwave reactor at 150° C. for 35 min. The reaction mixture was concentrated, then was purified by preparative HPLC to afford 2.0 mg (3.9%) of Example 74. MS(ESI) m/z: 397.0 (M+H)$^+$; $^1$H NMR (500 MHz, DMSO-d$_6$) δ 12.78 (s, 1H), 10.53 (s, 1H), 8.39-8.31 (m, 1H), 8.01-7.86 (m, 6H), 7.81 (d, J=7.4 Hz, 1H), 7.59 (d, J=8.5 Hz, 2H), 7.48-7.38 (m, 3H), 7.37-7.30 (m, 1H); HPLC RT=1.85 min (Method E), 1.90 min (Method F).

Intermediate 3 (35 mg, 0.100 mmol), 2-chlorobenzo[d]oxazole (0.015 mL, 0.130 mmol), and DIEA (0.087 mL, 0.498 mmol) were dissolved in NMP (1 mL) and the reaction mixture was heated in a capped vial at 150° C. for 18 h. The reaction mixture was purified by preparative HPLC to afford 5.0 mg (14%) of Example 75. MS(ESI) m/z: 355.05 (M+H)$^+$; $^1$H NMR (500 MHz, DMSO-d$_6$) δ 12.83 (s, 1H), 10.90 (br. s., 1H), 8.39-8.30 (m, 1H), 7.94 (d, J=8.4 Hz, 2H), 7.93-7.87 (m, 2H), 7.80-7.76 (m, 1H), 7.63 (d, J=8.4 Hz, 2H), 7.51 (dd, J=16.6, 7.7 Hz, 2H), 7.28-7.22 (m, 1H), 7.19-7.14 (m, 1H); HPLC RT=1.58 min (Method E), 1.64 min (Method F).

Example 75: 4-(4-(Benzo[d]oxazol-2-ylamino)phenyl)phthalazin-1(2H)-one

Example 76: N-(4-(4-Oxo-3,4-dihydrophthalazin-1-yl)phenyl)indoline-1-carboxamide

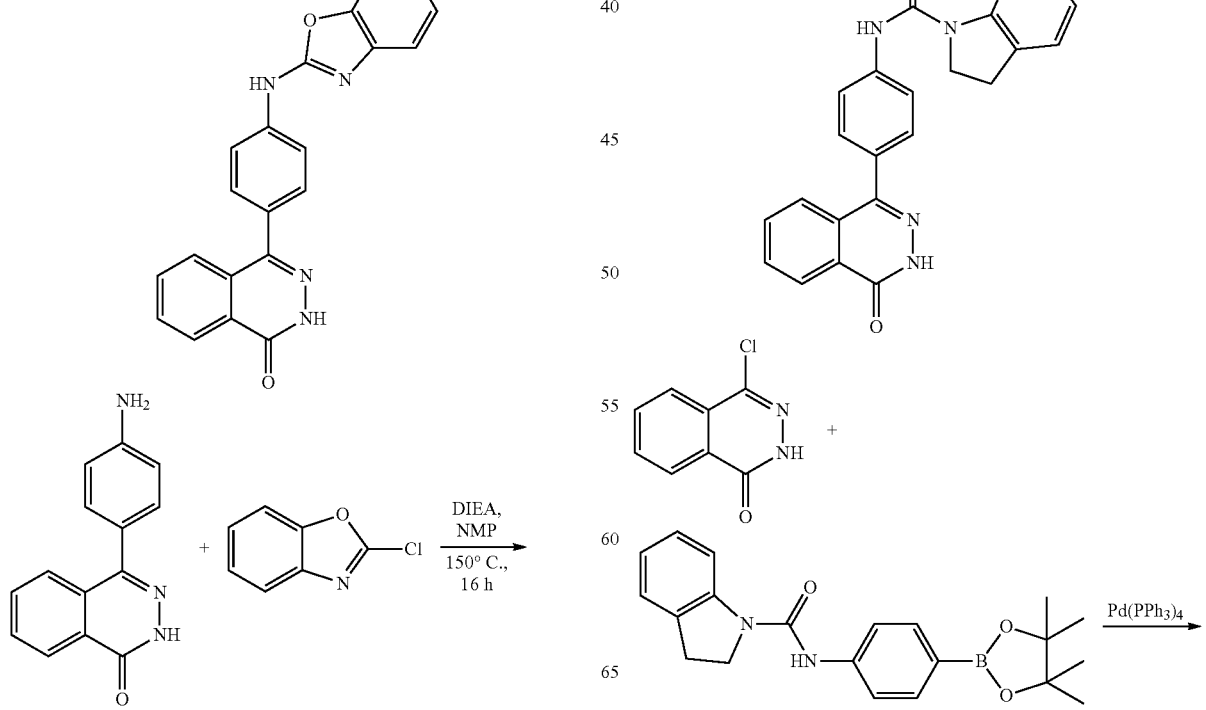

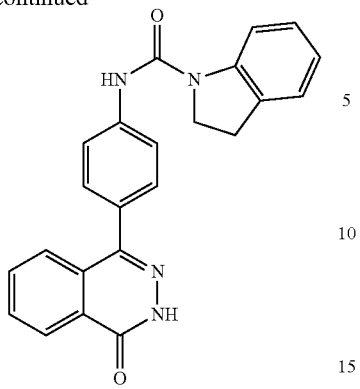

To 4-chlorophthalazin-1(2H)-one (29 mg, 0.16 mmol), Intermediate 10 and potassium phosphate (85 mg, 0.40 mmol), were added dioxane (3 mL) and water (0.33 mL). The mixture was degassed (evacuated and flushed with Ar (5×)). Pd(PPh$_3$)$_4$ (9.28 mg, 8.03 mol) was added, then the mixture was degassed (2×). The reaction vial was sealed and heated in a microwave reactor at 150° C. for 30 min. The reaction mixture was concentrated and purified via preparative HPLC to afford 6.1 mg (9.4%) of Example 76. MS(ESI) m/z: 383.1 (M+H)$^+$; $^1$H NMR (500 MHz, DMSO-d$_6$) δ 12.81 (s, 1H), 8.74 (s, 1H), 8.34 (dd, J=7.7, 1.2 Hz, 1H), 8.00-7.85 (m, 3H), 7.76 (d, J=8.9 Hz, 3H), 7.53 (d, J=8.4 Hz, 2H), 7.22 (d, J=7.4 Hz, 1H), 7.14 (t, J=7.7 Hz, 1H), 6.92 (t, J=7.4 Hz, 1H), 4.18 (t, J=8.7 Hz, 2H), 3.20 (t, J=8.7 Hz, 2H); HPLC RT=1.65 min (Method E), 1.66 min (Method F).

Example 77: N-(4-(1-Oxo-1,2-dihydroisoquinolin-4-yl)phenyl)indoline-1-carboxamide According to the procedure for the preparation of Example 76, coupling of Intermediate 6 (28 mg, 0.125 mmol) and Intermediate 10 (54.6 mg, 0.150 mmol) afforded 7.5 mg (16%) of Example 77. MS(ESI) m/z: 382.1 (M+H)$^+$; $^1$H NMR (500 MHz, DMSO-d$_6$) δ 11.41 (br. s., 1H), 8.63 (s, 1H), 8.30 (d, J=8.0 Hz, 1H), 7.89 (d, J=8.3 Hz, 1H), 7.75-7.66 (m, 3H), 7.59-7.51 (m, 2H), 7.35 (d, J=8.3 Hz, 2H), 7.21 (d, J=7.4 Hz, 1H), 7.13 (t, J=7.7 Hz, 1H), 7.07 (s, 1H), 6.91 (t, J=7.3 Hz, 1H), 4.17 (t, J=8.5 Hz, 2H), 3.20 (t, J=8.3 Hz, 2H); HPLC RT=1.77 min (Method E), 1.73 min (Method F).

Example 78: 4-{4-[(Quinazolin-2-yl)amino]phenyl}-1,2-dihydrophthalazin-1-one, TFA

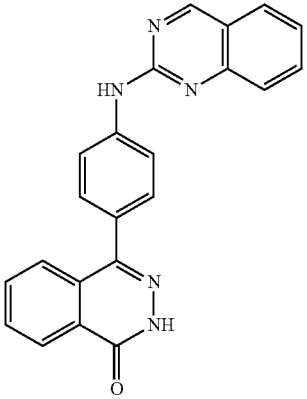

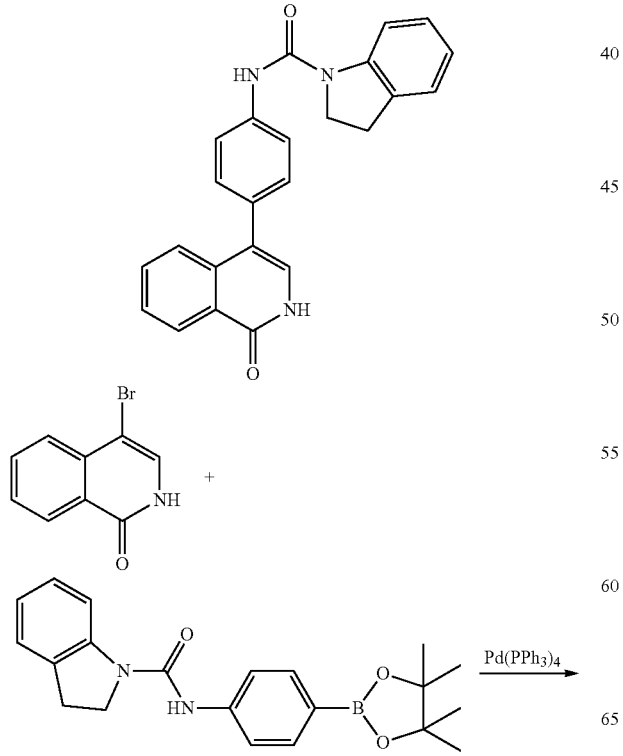

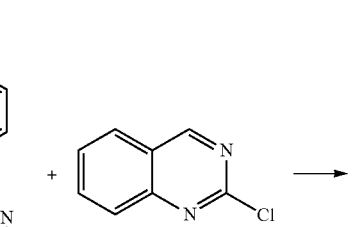

-continued

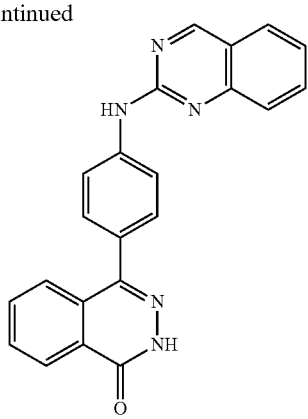

According to the procedure for the preparation of Example 75, Intermediate 3 (35 mg, 0.100 mmol) was reacted with 2-chloroquinazoline at 150° C. for 40 h to afford 4.1 mg (8.6%) of Example 78. MS(ESI) m/z: 366.2 (M+H)$^+$; $^1$H-NMR: (500 MHz, DMSO-d$_6$) δ ppm 12.78 (s, 1H), 10.14 (s, 1H), 9.37 (s, 1H), 8.38-8.31 (m, 1H), 8.19 (d, J=8.5 Hz, 2H), 7.96 (d, J=7.7 Hz, 1H), 7.93-7.87 (m, 2H), 7.84-7.78 (m, 2H), 7.72 (d, J=8.3 Hz, 1H), 7.57 (d, J=8.5 Hz, 2H), 7.42 (t, J=7.3 Hz, 1H); HPLC RT=1.45 min (Method E), 1.70 min (Method F).

Example 79: 4-(4-(Quinazolin-2-ylamino)phenyl)phthalazin-1(2H)-one, TFA

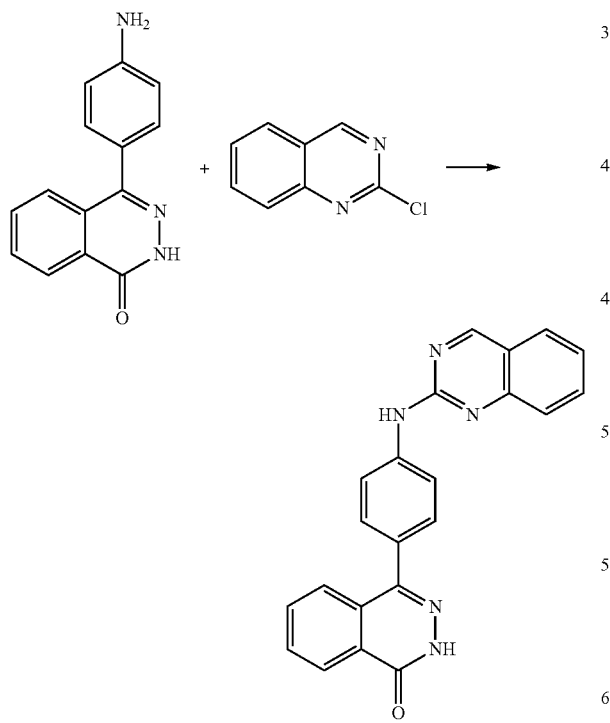

According to the procedure for the preparation of Example 76, coupling of 4-chlorophthalazin-1(2H)-one (25 mg, 0.14 mmol) and Intermediate 12 (60.0 mg, 0.152 mmol) afforded 2.5 mg (4.3%) of Example 79. MS(ESI) m/z: 413.2 (M+H)$^+$; $^1$H NMR (500 MHz, DMSO-d$_6$) δ 12.79 (br. s., 1H), 8.72 (s, 1H), 8.38-8.30 (m, 1H), 8.01-7.86 (m, 2H), 7.76 (d, J=8.5 Hz, 3H), 7.60-7.49 (m, 3H), 7.09 (d, J=8.3 Hz, 1H), 6.49 (dd, J=8.3, 2.5 Hz, 1H), 4.19 (t, J=8.7 Hz, 2H), 3.72 (s, 3H), 3.12 (t, J=8.5 Hz, 2H); HPLC RT=1.67 min (Method E), 1.67 min (Method F).

Example 80: 6-Methoxy-N-(4-(1-oxo-1,2-dihydroisoquinolin-4-yl)phenyl)indoline-1-carboxamide

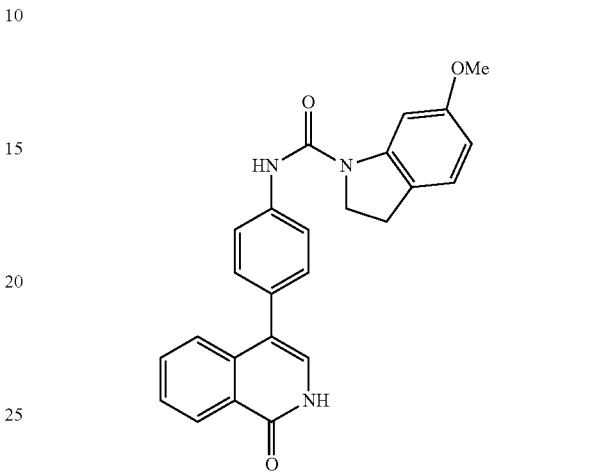

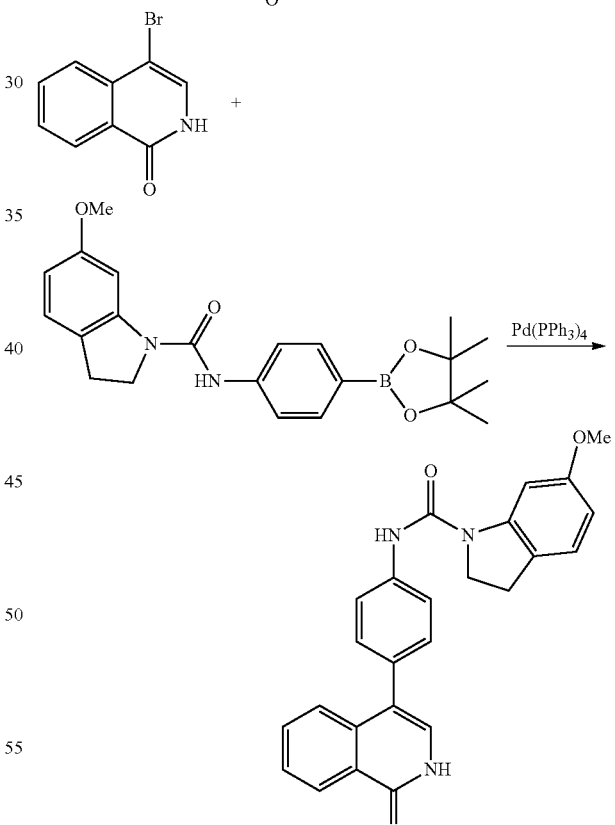

According to the procedure for the preparation of Example 76, coupling of Intermediate 6 (29 mg, 0.129 mmol) and Intermediate 12 (61.2 mg, 0.155 mmol) afforded 5.9 mg (11%) of Example 80. MS(ESI) m/z: 412.2 (M+H)$^+$; $^1$H NMR (500 MHz, DMSO-d$_6$) δ 11.42 (br. s., 1H), 8.63 (s, 1H), 8.30 (d, J=8.0 Hz, 1H), 7.75-7.66 (m, 3H), 7.60-7.51 (m, 3H), 7.35 (d, J=8.5 Hz, 2H), 7.11-7.03 (m, 2H), 6.48 (dd, J=8.1, 2.3 Hz, 1H), 4.18 (t, J=8.5 Hz, 2H), 3.72 (s, 3H), 3.11 (t, J=8.5 Hz, 2H); HPLC RT=1.47 min (Method E), 1.48 min (Method F).

Example 81: (R)—N-(2,3-Dihydro-1H-inden-1-yl)-2-(4-(4-oxo-3,4-dihydrophthalazin-1-yl)phenyl)acetamide

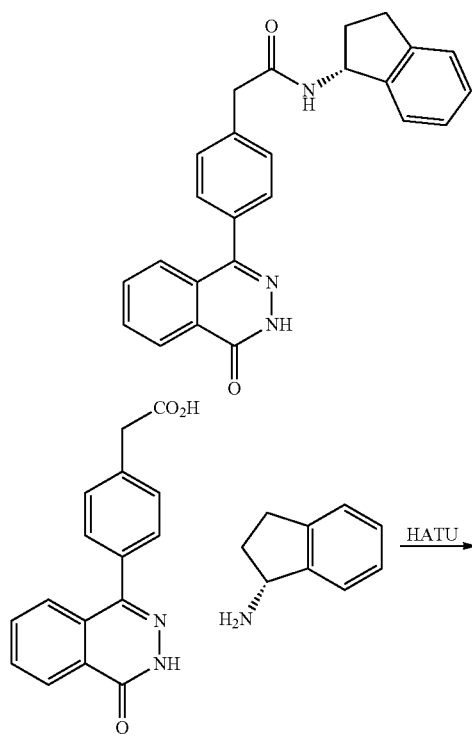

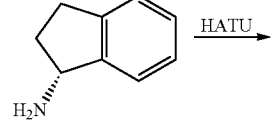

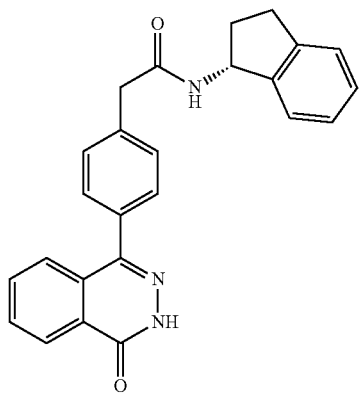

According to the procedure for the preparation of Example 3, coupling of Intermediate 1 (25 mg, 0.089 mmol) with (R)-2,3-dihydro-1H-inden-1-amine (14.3 mg, 0.107 mmol) afforded 13.7 mg (38%) of Example 81. MS(ESI) m/z: 396.2 (M+H)$^+$; $^1$H NMR (500 MHz, DMSO-d$_6$) δ 12.83 (s, 1H), 8.53 (d, J=8.3 Hz, 1H), 8.38-8.32 (m, 1H), 7.94-7.85 (m, 2H), 7.74-7.68 (m, 1H), 7.58-7.52 (m, 2H), 7.50-7.45 (m, 2H), 7.29-7.24 (m, 1H), 7.24-7.14 (m, 3H), 5.29 (q, J=7.8 Hz, 1H), 3.64-3.54 (m, 2H), 2.99-2.90 (m, 1H), 2.86-2.76 (m, 1H), 2.46-2.37 (m, 1H), 1.81 (dq, J=12.7, 8.4 Hz, 1H); HPLC RT=1.58 min (Method E), 1.60 min (Method F).

Example 82: (S)—N-(2,3-Dihydro-1H-inden-1-yl)-2-(4-(4-oxo-3,4-dihydrophthalazin-1-yl)phenyl)acetamide

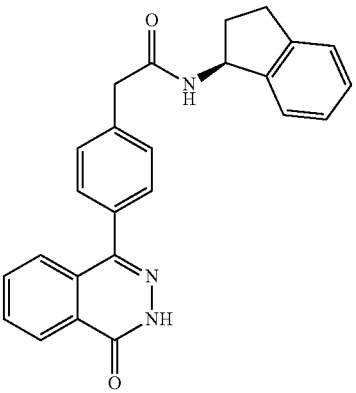

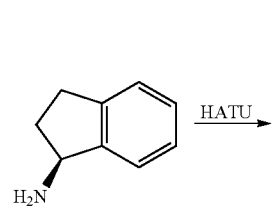

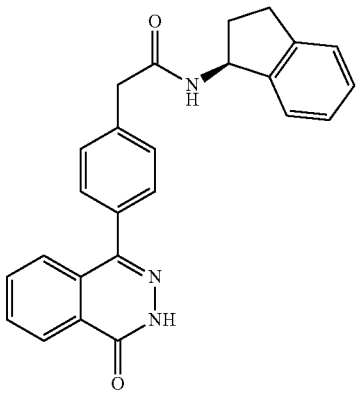

According to the procedure for the preparation of Example 3, coupling of Intermediate 1 (25 mg, 0.089 mmol) with (S)-2,3-dihydro-1H-inden-1-amine (14.3 mg, 0.107 mmol) afforded 19.7 mg (56%) of Example 82. MS(ESI) m/z: 396.2 (M+H)$^+$; 1H NMR (500 MHz, DMSO-d$_6$) δ 12.83 (s, 1H), 8.53 (d, J=8.3 Hz, 1H), 8.38-8.31 (m, 1H), 7.94-7.86 (m, 2H), 7.75-7.68 (m, 1H), 7.58-7.52 (m, 2H), 7.50-7.45 (m, 2H), 7.28-7.24 (m, 1H), 7.24-7.14 (m, 3H), 5.29 (q, J=7.9 Hz, 1H), 3.65-3.54 (m, 2H), 2.99-2.91 (m, 1H), 2.81 (dt, J=16.0, 8.3 Hz, 1H), 2.46-2.37 (m, 1H), 1.81 (dq, J=12.5, 8.4 Hz, 1H); HPLC RT=1.63 min (Method E), 1.63 min (Method F).

Example 83: 4-(4-(2-(6-(Benzyloxy)indolin-1-yl)-2-oxoethyl)phenyl)phthalazin-1(2H)-one

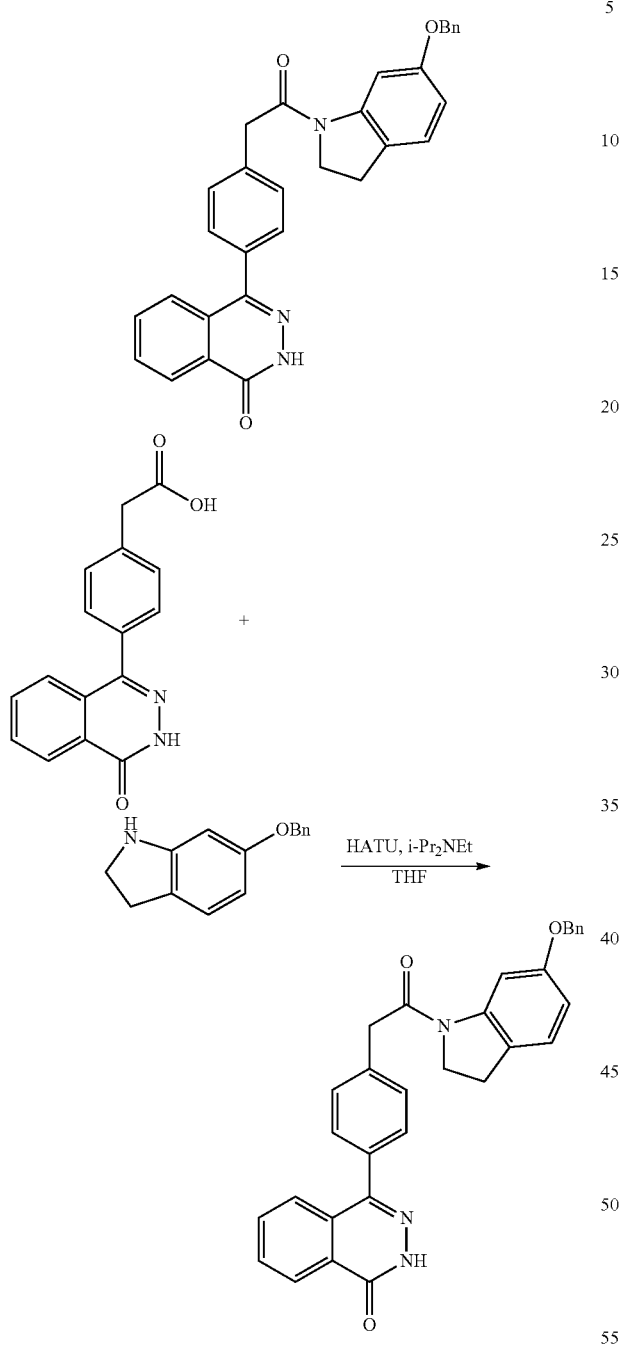

According to the procedure for the preparation of Example 3, coupling of Intermediate 1 (56 mg, 0.20 mmol) with 6-(benzyloxy)indoline (71.2 mg, 0.21 mmol) afforded 38 mg (38%) of Example 83. MS(ESI) m/z: 488.1 (M+H)$^+$; $^1$H NMR (500 MHz, DMSO-d$_6$) δ 12.83 (s, 1H), 8.40-8.30 (m, 1H), 7.99-7.81 (m, 3H), 7.76-7.69 (m, 1H), 7.60-7.53 (m, 2H), 7.50-7.44 (m, J=8.0 Hz, 2H), 7.44-7.40 (m, 2H), 7.39-7.34 (m, 2H), 7.34-7.26 (m, 1H), 7.12 (d, J=8.3 Hz, 1H), 6.66 (dd, J=8.1, 2.3 Hz, 1H), 5.05 (s, 2H), 4.24 (t, J=8.5 Hz, 2H), 3.96 (s, 2H), 3.10 (t, J=8.3 Hz, 2H); HPLC RT=10.56 min (Method A), 9.34 min (Method B).

Example 84

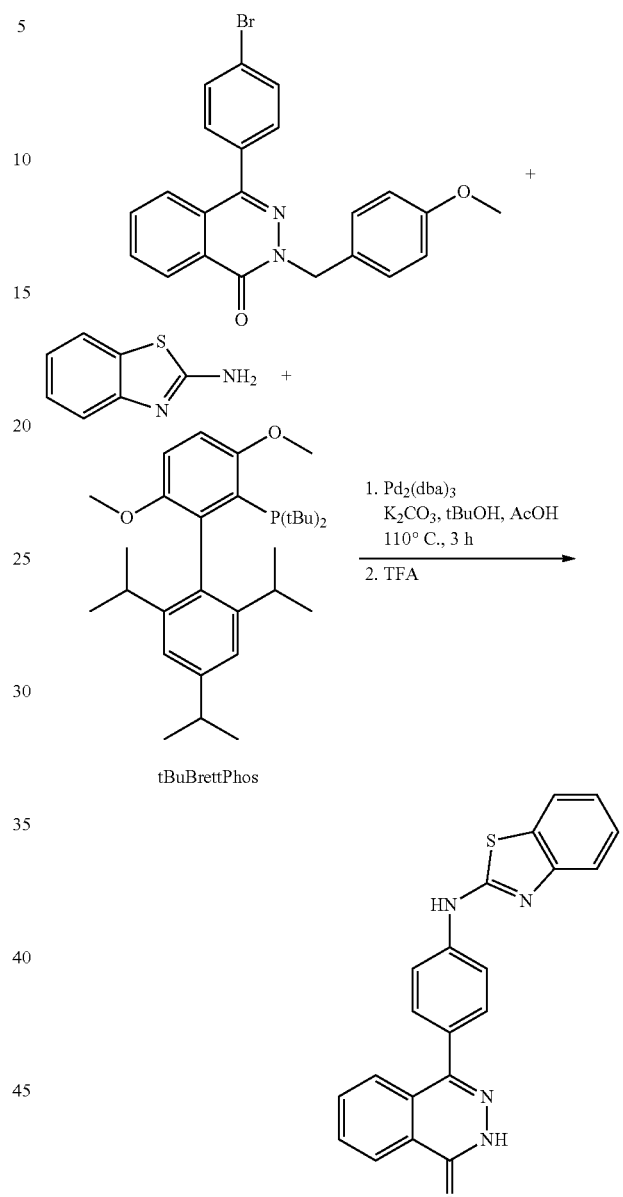

Intermediate 13 (50 mg, 0.12 mmol), benzo[d]thiazol-2-amine (17.8 mg, 0.119 mmol), di-tert-butyl(2',4',6'-triisopropyl-3,6-dimethoxy-[1,1'-biphenyl]-2-yl)phosphine (7.6 mg, 0.016 mmol), Pd$_2$(dba)$_3$ (3.3 mg, 3.6 mol) and K$_2$CO$_3$ (23 mg, 0.17 mmol) were added in a pressure vial. The reaction mixture was degassed (3× vacuum/Ar), and then tBuOH (1 mL) and AcOH (1 drop) were added. The reaction mixture was degassed again, capped, and stirred at 110° C. for 3 h. The reaction mixture was diluted with MeOH/DMSO, filtered and purified by preparative HPLC to afford 4-(4-(benzo[d]thiazol-2-ylamino)phenyl)-2-(4-methoxybenzyl)phthalazin-1(2H)-one (45.9 mg, 79% yield) as a white solid. MS(ESI) m/z: 491.1 (M+H)$^+$; $^1$H NMR (400 MHz, DMSO-d$_6$) δ ppm 10.77 (br. s., 1H), 8.38 (br. s., 1H), 7.99 (d, J=7.9 Hz, 2H), 7.92 (d, J=3.3 Hz, 2H), 7.85 (d, J=7.7 Hz, 2H), 7.69-7.56 (m, 3H), 7.35 (d, J=6.2 Hz, 3H), 7.19 (t, J=7.0 Hz, 1H), 6.90 (d, J=7.9 Hz, 2H), 5.32 (br. s., 2H), 3.71 (s, 3H). The residue was dissolved in TFA (3 mL) and was sealed vial and was heated in a microwave reactor at 150° C. for 30 min. The reaction mixture was evaporated and was purified by preparative HPLC to afford 2.3 mg (6%) of Example 84. MS(ESI) m/z: 371.1 (M+H)$^+$; $^1$H NMR (500 MHz, DMSO-d$_6$) δ ppm 12.80 (s, 1H), 10.72 (s, 1H), 8.35 (d, J=7.4 Hz, 1H), 7.98 (d, J=8.5 Hz, 2H), 7.94-7.89 (m, 2H), 7.85 (d, J=8.0 Hz, 1H), 7.79 (d, J=7.7 Hz, 1H), 7.65 (d, J=8.0 Hz, 1H), 7.61 (d, J=8.5 Hz, 2H), 7.36 (t, J=7.7 Hz, 1H), 7.19 (t, J=7.6 Hz, 1H); HPLC RT=1.68 min (Method E), 1.84 min (Method F).

Example 85: 4-(4-(Phthalazin-1-ylamino)phenyl) phthalazin-1(2H)-one

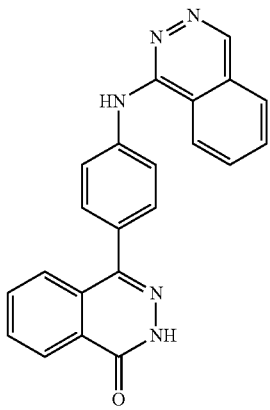 [SMILES: O=c1[nH]nc(-c2ccc(Nc3nncc4ccccc34)cc2)c2ccccc12]

According to the procedure for the preparation of Example 84, Intermediate 13 (50 mg, 0.12 mmol) and 1-chlorophthalazine (25.3 mg, 0.154 mmol) afforded after coupling and deprotection 6.6 mg (40%) of Example 85. MS(ESI) m/z: 366.1 (M+H)$^+$; $^1$H NMR (500 MHz, DMSO-d$_6$) δ ppm 12.81 (s, 1H), 9.39 (s, 1H), 9.20 (s, 1H), 8.65 (d, J=8.0 Hz, 1H), 8.36 (d, J=7.7 Hz, 1H), 8.16 (d, J=8.3 Hz, 2H), 8.09-8.05 (m, 1H), 8.03 (d, J=7.7 Hz, 1H), 8.02-7.97 (m, 1H), 7.96-7.88 (m, 2H), 7.84 (d, J=7.7 Hz, 1H), 7.61 (d, J=8.5 Hz, 2H); HPLC RT=1.07 min (Method E), 1.40 min (Method F).

Example 86: 4-{4-[(5-Methyl-1,3-benzoxazol-2-yl) amino]phenyl}-1,2-dihydrophthalazin-1-one

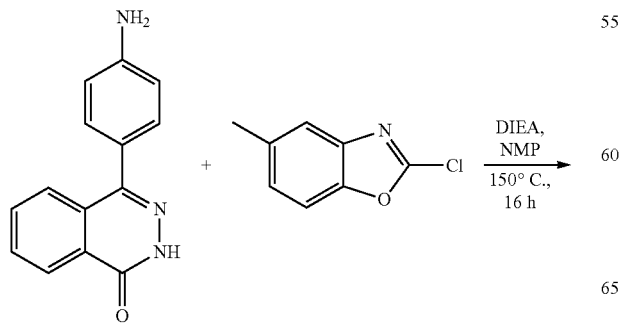

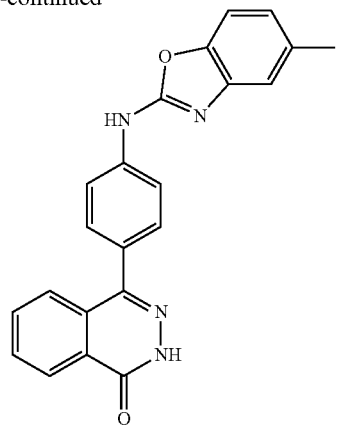

According to the procedure for the preparation of Example 76, coupling of 2-chloro-5-methylbenzo[d]oxazole (25.05 mg, 0.149 mmol) and Intermediate 12 (35 mg, 0.10 mmol) afforded 6.8 mg (18%) of Example 86. MS(ESI) m/z: 469.2 (M+H)$^+$; $^1$H NMR (500 MHz, DMSO-d$_6$) δ 12.80 (br. s., 1H), 8.34 (d, J=7.7 Hz, 1H), 7.97-7.84 (m, 4H), 7.78 (d, J=7.7 Hz, 1H), 7.61 (d, J=8.0 Hz, 2H), 7.38 (d, J=8.0 Hz, 1H), 7.29 (s, 1H), 6.96 (d, J=8.3 Hz, 1H), 2.38 (s, 3H); HPLC RT=1.75 min (Method E), 1.81 min (Method F).

Example 87: 4-(4-((5-Phenyl-1,3,4-thiadiazol-2-yl) amino)phenyl)phthalazin-1(2H)-one

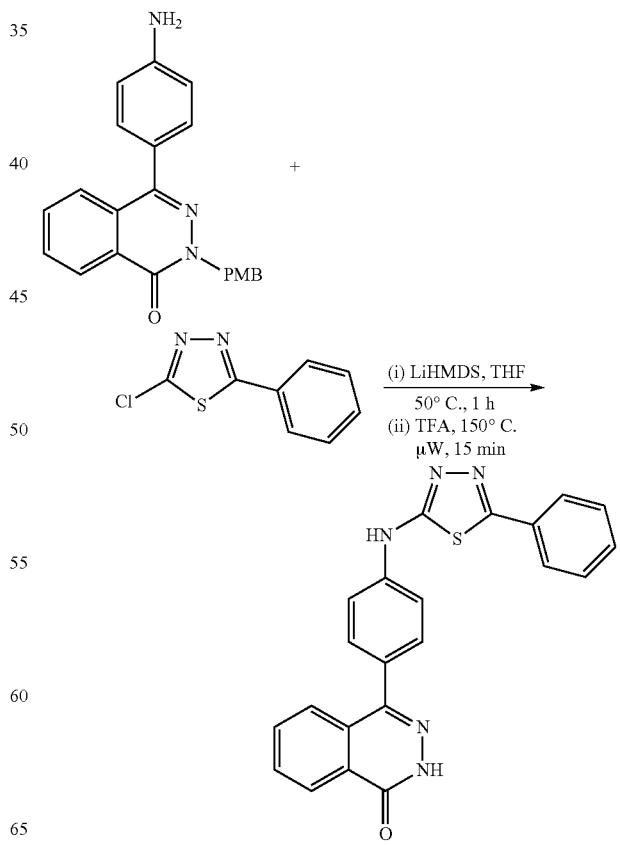

Intermediate 14 (50 mg, 0.14 mmol) and 2-chloro-5-phenyl-1,3,4-thiadiazole (33 mg, 0.17 mmol) were dissolved in dry THF (2 mL). Then, LiHMDS (1 M in THF) (0.364 mL, 0.364 mmol) was added dropwise to the stirred reaction mixture. The reaction mixture was stirred at 50° C. for 1 h. The reaction mixture was cooled to rt, quenched with MeOH (1 mL), and concentrated under reduced pressure. The residue was redissolved in TFA (3 mL), and stirred at 150° C. for 15 min under microwave irradiation. TFA was evaporated, then the residue was purified by prep HPLC to afford 14.1 mg (25%) of Example 87. MS(ESI) m/z: 498.1 (M+H)$^+$; $^1$H NMR (500 MHz, DMSO-d$_6$) δ ppm 12.80 (s, 1H), 10.79 (br. s., 1H), 8.35 (d, J=7.4 Hz, 1H), 7.98-7.87 (m, 4H), 7.85 (d, J=8.0 Hz, 2H), 7.78 (d, J=7.7 Hz, 1H), 7.61 (d, J=8.0 Hz, 2H), 7.56-7.48 (m, 3H); HPLC RT=1.67 min (Method E), 1.68 min (Method F).

Example 88: 4-(4-((5-Phenylthiazol-2-yl)amino)phenyl)phthalazin-1(2H)-one

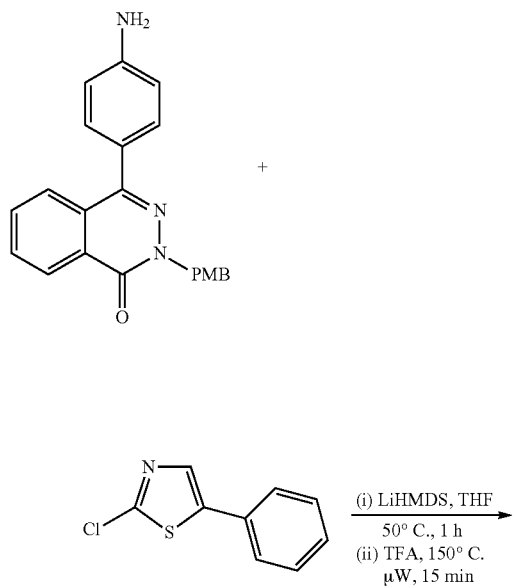

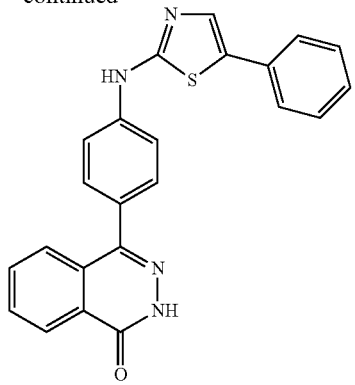

According to the procedure for the preparation of Example 87, coupling of Intermediate 14 (40 mg, 0.112 mmol) and 2-chloro-5-phenylthiazole (26.3 mg, 0.134 mmol) afforded after TFA deprotection and HPLC purification 1.3 mg (3%) on Example 88. MS(ESI) m/z: 397.2 (M+H)$^+$; $^1$H NMR (500 MHz, DMSO-d$_6$) δ ppm 12.78 (br. s., 1H), 10.59 (br. s., 1H), 8.34 (d, J=7.2 Hz, 1H), 7.96-7.87 (m, 2H), 7.85-7.76 (m, 3H), 7.74 (s, 1H), 7.56 (d, J=7.7 Hz, 4H), 7.40 (t, J=7.2 Hz, 2H), 7.31-7.24 (m, 1H); HPLC RT=1.74 min (Method E), 1.95 min (Method F).

The following Examples in Table 3 were made by using the same procedure as shown in Example 45. Intermediate 3 was coupled with the appropriate carboxylic acid. Various coupling reagents could be used other than the one described in Example 45, such as BOP, PyBop, EDC/HOBt or T3P.

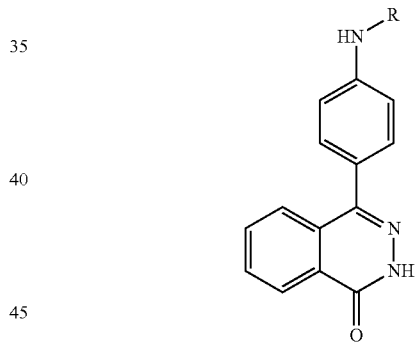

TABLE 3

| Example | R | Name | LCMS (M + H)$^+$ | HPLC Method, RT (min.) | $^1$H NMR |
|---|---|---|---|---|---|
| 89 | ![structure] | N-[4-(4-oxo-3,4-dihydrophthalazin-1-yl)phenyl]imidazo[1,2-a]pyridine-2-carboxamide | 382.1 | A: 5.21 B: 5.58 | $^1$H NMR (500 MHz, DMSO-d$_6$) d 12.82 (s, 1H), 10.58 (s, 1H), 8.69 (d, J = 6.9 Hz, 1H), 8.63 (s, 1H), 8.35 (dd, J = 7.8, 1.5 Hz, 1H), 8.14-8.03 (m, J = 8.5 Hz, 2H), 7.91 (quind, J = 7.6, 1.4 Hz, 2H), 7.81-7.74 (m, 1H), 7.71 (d, J = 9.1 Hz, 1H), 7.64-7.57 (m, J = 8.5 Hz, 2H), 7.49-7.42 (m, 1H), 7.10 (t, J = 6.7 Hz, 1H) |

TABLE 3-continued

| Example | R | Name | LCMS (M + H)+ | HPLC Method, RT (min.) | 1H NMR |
|---|---|---|---|---|---|
| 90 | | 1-methyl-N-[4-(4-oxo-3,4-dihydrophthalazin-1-yl)phenyl]-1H-indole-2-carboxamide | 395.1 | E: 1.77 F: 1.79 | 1H NMR (500 MHz, DMSO-$d_6$) d 12.82 (br. s., 1H), 10.54 (br. s., 1H), 8.39-8.32 (m, 1H), 7.99 (d, J = 8.5 Hz, 2H), 7.97-7.85 (m, 2H), 7.77 (d, J = 7.7 Hz, 1H), 7.72 (d, J = 8.0 Hz, 1H), 7.63-7.54 (m, 3H), 7.38 (s, 1H), 7.34-7.30 (m, 1H), 7.19-7.10 (m, 1H), 4.11-4.00 (m, 3H) |
| 91 | | N-[4-(4-oxo-3,4-dihydrophthalazin-1-yl)phenyl]-2,3-dihydro-1H-indene-1-carboxamide | 382.1 | E: 1.68 F: 1.70 | 1H NMR (500 MHz, DMSO-$d_6$) d 12.79 (s, 1H), 10.47 (s, 1H), 8.37-8.31 (m, 1H), 7.94-7.85 (m, 2H), 7.83 (d, J = 8.5 Hz, 2H), 7.76-7.71 (m, 1H), 7.55 (d, J = 8.5 Hz, 2H), 7.34 (d, J = 6.9 Hz, 1H), 7.28 (d, J = 7.2 Hz, 1H), 7.24-7.14 (m, 2H), 4.17 (t, J = 7.4 Hz, 1H), 3.13-3.03 (m, 1H), 2.97-2.87 (m, 1H), 2.44-2.24 (m, 2H) |
| 92 | | N-[4-(4-oxo-3,4-dihydrophthalazin-1-yl)phenyl]-4-(1H-1,2,4-triazol-1-yl)benzamide | 409.1 | E: 1.33 F: 1.33 | 1H NMR (500 MHz, DMSO-$d_6$) d 12.82 (s, 1H), 10.56 (s, 1H), 9.46 (s, 1H), 8.39-8.28 (m, 2H), 8.24-8.18 (m, J = 8.5 Hz, 2H), 8.11-8.03 (m, J = 8.5 Hz, 2H), 8.03-7.84 (m, 4H), 7.77 (d, J = 8.0 Hz, 1H), 7.61 (d, J = 8.5 Hz, 2H) |
| 93 | | N-[4-(4-oxo-3,4-dihydrophthalazin-1-yl)phenyl]-2,1-benzoxazole-3-carboxamide | 383.0 | A: 8.48 B: 7.27 | 1H NMR (500 MHz, DMSO-$d_6$) d 12.88-12.80 (m, 1H), 11.33 (br. s., 1H), 8.35 (d, J = 7.2 Hz, 1H), 8.14-8.02 (m, 3H), 7.92 (t, J = 7.0 Hz, 2H), 7.84 (d, J = 6.6 Hz, 1H), 7.76 (d, J = 6.3 Hz, 1H), 7.64 (d, J = 5.8 Hz, 2H), 7.56 (t, J = 6.7 Hz, 1H), 7.36 (t, J = 6.2 Hz, 1H) |
| 94 | | 6-(dimethylamino)-N-[4-(4-oxo-3,4-dihydrophthalazin-1-yl)phenyl]-1H-indole-2-carboxamide | 424.2 | E: 1.23 F: 1.74 | 1H NMR (500 MHz, DMSO-$d_6$) d 12.81 (s, 1H), 11.29 (s, 1H), 10.20 (s, 1H), 8.35 (d, J = 7.4 Hz, 1H), 8.05-7.85 (m, 5H), 7.78 (d, J = 8.0 Hz, 1H), 7.59 (d, J = 8.3 Hz, 2H), 7.49 (d, J = 9.1 Hz, 1H), 7.34 (s, 1H), 6.76 (dd, J = 8.8, 1.9 Hz, 1H), 6.65 (s, 1H), 2.93 (s, 6H) |
| 95 | | 2-methyl-N-[4-(4-oxo-3,4-dihydrophthalazin-1-yl)phenyl]imidazo[1,2-a]pyridine-3-carboxamide | 396.1 | E: 1.12 F: 1.37 | 1H NMR (500 MHz, DMSO-$d_6$) d 12.82 (s, 1H), 10.11 (s, 1H), 8.96 (d, J = 6.9 Hz, 1H), 8.35 (d, J = 7.4 Hz, 1H), 7.95-7.86 (m, 4H), 7.78 (d, J = 7.7 Hz, 1H), 7.66-7.58 (m, 3H), 7.47-7.41 (m, 1H), 7.08 (t, J = 6.7 Hz, 1H), 2.68 (s, 3H) |
| 96 | | 5-chloro-1-methyl-N-[4-(4-oxo-3,4-dihydrophthalazin-1-yl)phenyl]-1H-indole-2-carboxamide | 429.1 | E:2.02 F:2.02 | 1H NMR (500 MHz, DMSO-$d_6$) d 12.82 (s, 1H), 10.61 (s, 1H), 8.35 (d, J = 7.7 Hz, 1H), 8.04-7.87 (m, 4H), 7.81 (s, 1H), 7.76 (d, J = 7.7 Hz, 1H), 7.65 (d, J = 8.8 Hz, 1H), 7.61 (d, J = 8.0 Hz, 2H), 7.37-7.28 (m, 2H), 4.04 (s, 3H) |
| 97 | | 5,5-dimethyl-4-oxo-N-[4-(4-oxo-3,4-dihydrophthalazin-1-yl)phenyl]-4,5,6,7-tetrahydro-1H-indole-3-carboxamide | 427.2 | | 1H NMR (500 MHz, DMSO-$d_6$) Shift 12.82 (d, J = 5.8 Hz, 2H), 12.11 (br. s., 1H), 8.34 (d, J = 6.1 Hz, 1H), 7.97-7.50 (m, 8H), 2.89 (d, J = 4.3 Hz, 2H), 1.99 (br. s., 2H), 1.21 (br. s., 6H) |

TABLE 3-continued

| Example | R | Name | LCMS (M + H)+ | HPLC Method, RT (min.) | ¹H NMR |
|---|---|---|---|---|---|
| 98 | (1-methyl-1H-indazol-3-yl carbonyl) | 1-methyl-N-[4-(4-oxo-3,4-dihydrophthalazin-1-yl)phenyl]-1H-indazole-3-carboxamide | 396.2 | | ¹H NMR (500 MHz, DMSO-d₆) Shift 12.83 (s, 1H), 10.58 (s, 1H), 8.35 (d, J = 7.6 Hz, 1H), 8.26 (d, J = 8.2 Hz, 1H), 8.10 (d, J = 8.5 Hz, 2H), 7.98-7.86 (m, 2H), 7.79 (dd, J = 18.6, 8.2 Hz, 2H), 7.59 (d, J = 8.2 Hz, 2H), 7.53 (t, J = 7.8 Hz, 1H), 7.35 (t, J = 7.3 Hz, 1H), 4.23 (s, 3H) |
| 99 | (1-benzyl-1H-indazol-3-yl carbonyl) | 1-benzyl-N-[4-(4-oxo-3,4-dihydrophthalazin-1-yl)phenyl]-1H-indazole-3-carboxamide | 472.2 | | ¹H NMR (500 MHz, DMSO-d₆) Shift 12.83 (s, 1H), 10.61 (s, 1H), 8.35 (d, J = 7.6 Hz, 1H), 8.28 (d, J = 8.2 Hz, 1H), 8.10 (d, J = 8.2 Hz, 2H), 7.98-7.87 (m, 2H), 7.82 (d, J = 8.5 Hz, 1H), 7.77 (d, J = 7.0 Hz, 1H), 7.60 (d, J = 8.2 Hz, 2H), 7.50 (t, J = 7.6 Hz, 1H), 7.41-7.22 (m, 6H), 5.86 (s, 2H) |
| 100 | (5-ethoxy-2-methyl-1-benzofuran-3-yl carbonyl) | 5-ethoxy-2-methyl-N-[4-(4-oxo-3,4-dihydrophthalazin-1-yl)phenyl]-1-benzofuran-3-carboxamide | 440.2 | | ¹H NMR (500 MHz, DMSO-d₆) Shift 12.83 (s, 1H), 10.29 (s, 1H), 8.35 (d, J = 7.0 Hz, 1H), 7.97-7.84 (m, 4H), 7.77 (d, J = 7.6 Hz, 1H), 7.60 (d, J = 8.2 Hz, 2H), 7.50 (d, J = 8.9 Hz, 1H), 7.20 (s, 1H), 6.92 (d, J = 8.5 Hz, 1H), 4.07 (q, J = 7.0 Hz, 2H), 2.67 (s, 3H), 1.35 (t, J = 6.7 Hz, 3H) |
| 101 | (5-methyl-1H-indol-2-yl carbonyl) | 5-methyl-N-[4-(4-oxo-3,4-dihydrophthalazin-1-yl)phenyl]-1H-indole-2-carboxamide | 395.1 | | ¹H NMR (500 MHz, DMSO-d₆) Shift 12.83 (s, 1H), 11.68 (br. s., 1H), 10.38 (s, 1H), 8.35 (d, J = 7.6 Hz, 1H), 8.00 (d, J = 7.6 Hz, 2H), 7.96-7.84 (m, 3H), 7.78 (d, J = 7.3 Hz, 1H), 7.61 (d, J = 7.3 Hz, 2H), 7.47 (s, 1H), 7.42-7.33 (m, 2H), 7.07 (d, J = 8.5 Hz, 1H), 2.39 (s, 3H) |
| 102 | (pyrazolo[1,5-a]pyrimidin-2-yl carbonyl) | N-[4-(4-oxo-3,4-dihydrophthalazin-1-yl)phenyl]pyrazolo[1,5-a]pyrimidine-2-carboxamide | 441.2 | | ¹H NMR (500 MHz, DMSO-d₆) Shift 12.83 (s, 1H), 10.73 (s, 1H), 9.20 (d, J = 6.7 Hz, 1H), 8.74-8.66 (m, 1H), 8.35 (d, J = 7.6 Hz, 1H), 8.07 (d, J = 8.5 Hz, 2H), 7.97-7.87 (m, 2H), 7.76 (d, J = 7.9 Hz, 1H), 7.61 (d, J = 8.2 Hz, 2H), 7.27 (s, 1H), 7.25 (dd, J = 7.0, 4.0 Hz, 1H) |
| 103 | (pyrazolo[1,5-a]pyridin-3-yl carbonyl) | N-[4-(4-oxo-3,4-dihydrophthalazin-1-yl)phenyl]pyrazolo[1,5-a]pyridine-3-carboxamide | 382.0 | A: 7.05 B: 6.25 | ¹H NMR (400 MHz, DMSO-d₆) δ 12.81 (s, 1H), 10.15 (s, 1H), 8.91-8.81 (m, 2H), 8.43-8.27 (m, 2H), 8.05-7.87 (m, 4H), 7.78 (d, J = 7.5 Hz, 1H), 7.65-7.53 (m, 3H), 7.14 (t, J = 6.8 Hz, 1H), 6.59-6.45 (m, 1H) |
| 104 | (imidazo[1,2-a]pyridin-3-yl carbonyl) | N-[4-(4-oxo-3,4-dihydrophthalazin-1-yl)phenyl]imidazo[1,2-a]pyridine-3-carboxamide | | | ¹H NMR (500 MHz, DMSO-d₆) Shift 12.84 (s, 1H), 10.42 (s, 1H), 9.50 (d, J = 6.7 Hz, 1H), 8.64 (s, 1H), 8.35 (d, J = 7.6 Hz, 1H), 7.98-7.84 (m, 4H), 7.78 (t, J = 7.5 Hz, 2H), 7.61 (d, J = 8.5 Hz, 2H), 7.57-7.50 (m, 1H), 7.21 (t, J = 6.7 Hz, 1H) |
| 105 | (5-(benzyloxy)-2-methyl-1-benzofuran-3-yl carbonyl) | 5-(benzyloxy)-2-methyl-N-[4-(4-oxo-3,4-dihydrophthalazin-1-yl)phenyl]-1-benzofuran-3-carboxamide | 502.1 | C: 3.04 D: 4.07 | ¹H NMR (500 MHz, DMSO-d₆) Shift 12.84 (s, 1H), 10.29 (s, 1H), 8.35 (d, J = 7.9 Hz, 1H), 7.97-7.84 (m, 4H), 7.76 (d, J = 7.6 Hz, 1H), 7.60 (d, J = 8.2 Hz, 2H), 7.52 (d, J = 8.9 Hz, 1H), 7.47 (d, J = 7.6 Hz, 2H), 7.39 (t, J = 7.3 Hz, 2H), 7.35-7.27 (m, 2H), 7.01 (d, J = 8.9 Hz, 1H), 5.15 (s, 2H), 2.66 (s, 3H) |

TABLE 3-continued

| Example | R | Name | LCMS (M + H)+ | HPLC Method, RT (min.) | $^1$H NMR |
|---|---|---|---|---|---|
| 106 | (2,3-dihydro-1-benzofuran with 5-OH, attached via C=O at 2-position) | 5-hydroxy-N-[4-(4-oxo-3,4-dihydrophthalazin-1-yl)phenyl]-2,3-dihydro-1-benzofuran-2-carboxamide | 400.2 | C: 1.90 D: 2.96 | $^1$H NMR (500 MHz, DMSO-$d_6$) Shift 12.81 (s, 1H), 10.29 (s, 1H), 8.91 (br. s., 1H), 8.51-8.25 (m, 1H), 7.94-7.80 (m, 4H), 7.75-7.65 (m, 1H), 7.55 (d, J = 8.5 Hz, 2H), 6.75-6.62 (m, 2H), 6.53 (d, J = 6.1 Hz, 1H), 5.28 (dd, J = 9.8, 6.7 Hz, 1H), 3.55-3.41 (m, 1H) |
| 107 | (1-ethyl-1H-indole attached via C=O at 3-position) | 1-ethyl-N-[4-(4-oxo-3,4-dihydrophthalazin-1-yl)phenyl]-1H-indole-2-carboxamide | 409.2 | C: 2.81 D: 3.95 | $^1$H NMR (500 MHz, DMSO-$d_6$) Shift 12.83 (s, 1H), 10.54 (s, 1H), 8.35 (d, J = 7.0 Hz, 1H), 7.99 (d, J = 8.5 Hz, 2H), 7.93-7.87 (m, 2H), 7.80-7.67 (m, 2H), 7.65-7.53 (m, 3H), 7.38 (s, 1H), 7.32 (t, J = 7.8 Hz, 1H), 7.15 (t, J = 7.5 Hz, 1H), 4.62 (d, J = 7.0 Hz, 2H), 1.34 (t, J = 7.0 Hz, 3H) |
| 108 | (4-oxo-5-(propan-2-yl)-3H,4H-pyrrolo[2,1-f][1,2,4]triazine attached via C=O at 6-position) | 4-oxo-N-[4-(4-oxo-3,4-dihydrophthalazin-1-yl)phenyl]-5-(propan-2-yl)-3H,4H-pyrrolo[2,1-f][1,2,4]triazine-6-carboxamide | 441.2 | C: 2.08 D: 3.31 | $^1$H NMR (500 MHz, DMSO-$d_6$) Shift 12.82 (s, 1H), 11.64 (br. s., 1H), 10.21 (s, 1H), 8.34 (d, J = 8.2 Hz, 1H), 8.10 (s, 1H), 7.93-7.84 (m, 5H), 7.76 (d, J = 7.3 Hz, 1H), 7.57 (d, J = 8.2 Hz, 2H), 4.13-4.00 (m, 1H), 1.36 (d, J = 7.0 Hz, 6H) |
| 109 | (4-oxo-4,5,6,7-tetrahydro-1H-indazole attached via C=O at 3-position) | 4-oxo-N-[4-(4-oxo-3,4-dihydrophthalazin-1-yl)phenyl]-4,5,6,7-tetrahydro-1H-indazole-3-carboxamide | 400.3 | C: 2.01 D: 3.40 | $^1$H NMR (500 MHz, DMSO-$d_6$) Shift 12.84 (s, 1H), 12.60 (br. s., 1H), 8.34 (d, J = 6.7 Hz, 1H), 7.96-7.86 (m, 4H), 7.77 (d, J = 7.6 Hz, 1H), 7.65 (d, J = 7.3 Hz, 2H), 2.92 (br. s., 2H), 2.67 (br. s., 2H), 2.16-2.07 (m, 2H) |
| 110 | (1H-pyrazolo[3,4-b]pyridine attached via C=O at 3-position) | N-[4-(4-oxo-3,4-dihydrophthalazin-1-yl)phenyl]-1H-pyrazolo[3,4-b]pyridine-3-carboxamide | 383.2 | C: 1.73 D: 3.01 | $^1$H NMR (500 MHz, DMSO-$d_6$) Shift 12.83 (s, 1H), 10.78 (s, 1H), 9.51 (s, 1H), 8.45 (d, J = 5.8 Hz, 1H), 8.35 (d, J = 7.6 Hz, 1H), 8.11 (d, J = 8.2 Hz, 2H), 7.96-7.87 (m, 3H), 7.77 (d, J = 7.3 Hz, 1H), 7.69 (d, J = 6.1 Hz, 1H), 7.61 (d, J = 8.2 Hz, 2H) |
| 111 | (6-methyl-4-oxo-4H,5H,6H,7H-furo[2,3-c]pyridine attached via C=O at 3-position) | 6-methyl-4-oxo-N-[4-(4-oxo-3,4-dihydrophthalazin-1-yl)phenyl]-4H,5H,6H,7H-furo[2,3-c]pyridine-3-carboxamide | 415.1 | | |
| 112 | ([1,2,4]triazolo[1,5-a]pyrimidine attached via C=O at 2-position) | N-[4-(4-oxo-3,4-dihydrophthalazin-1-yl)phenyl]-[1,2,4]triazolo[1,5-a]pyrimidine-2-carboxamide | 384.2 | | $^1$H NMR (400 MHz, methanol-$d_4$) Shift 13.64 (br. s., 1H), 11.90 (s, 1H), 10.34 (dd, J = 6.8, 2.0 Hz, 1H), 9.86 (dd, J = 4.3, 2.0 Hz, 1H), 9.20-9.11 (m, 1H), 8.92 (d, J = 8.5 Hz, 2H), 8.77-8.67 (m, 2H), 8.60-8.54 (m, 1H), 8.47-8.40 (m, 2H), 8.35 (dd, J = 6.8, 4.3 Hz, 1H) |
| 113 | (pyrazolo[1,5-a]pyrimidine attached via C=O at 3-position) | N-[4-(4-oxo-3,4-dihydrophthalazin-1-yl)phenyl]pyrazolo[1,5-a]pyrimidine-3-carboxamide | 383.1 | | $^1$H NMR (400 MHz, methanol-$d_4$) Shift 13.62 (s, 1H), 10.97 (s, 1H), 10.20 (dd, J = 6.9, 1.6 Hz, 1H), 9.75 (dd, J = 4.1, 1.6 Hz, 1H), 9.57 (s, 1H), 9.18-9.14 (m, 1H), 8.76-8.68 (m, 4H), 8.61-8.56 (m, 1H), 8.43 (d, J = 8.5 Hz, 2H), 8.17 (dd, J = 7.0, 4.0 Hz, 1H) |

TABLE 3-continued

| Example | R | Name | LCMS (M + H)+ | HPLC Method, RT (min.) | ¹H NMR |
|---|---|---|---|---|---|
| 114 | | 5-chloro-N-[4-(4-oxo-3,4-dihydrophthalazin-1-yl)phenyl]-1H-indazole-3-carboxamide | | | ¹H NMR (400 MHz, methanol-$d_4$) Shift 13.64 (br. s., 1H), 11.36 (br. s., 1H), 9.19-9.13 (m, 1H), 8.99 (d, J = 1.8 Hz, 1H), 8.90 (d, J = 8.8 Hz, 2H), 8.72 (quind, J = 7.4, 1.5 Hz, 2H), 8.62-8.53 (m, 2H), 8.39 (d, J = 8.5 Hz, 2H), 8.19 (dd, J = 8.8, 1.8 Hz, 1H) |
| 115 | | N-[4-(4-oxo-3,4-dihydrophthalazin-1-yl)phenyl]-1,3-benzothiazole-2-carboxamide | 399.1 | | ¹H NMR (400 MHz, methanol-$d_4$) Shift 13.64 (s, 1H), 12.14 (s, 1H), 9.19-9.14 (m, 1H), 9.12-9.04 (m, 2H), 8.96-8.90 (m, 2H), 8.78-8.68 (m, 2H), 8.59-8.55 (m, 1H), 8.53-8.41 (m, 5H) |
| 116 | | 2-methyl-N-[4-(4-oxo-3,4-dihydrophthalazin-1-yl)phenyl]-4,5,6,7-tetrahydro-2H-indazole-3-carboxamide | 400.2 | | ¹H NMR (400 MHz, methanol-$d_4$) Shift 13.62 (br. s., 1H), 10.99 (s, 1H), 9.20-9.10 (m, 1H), 8.75-8.65 (m, 3H), 8.58-8.53 (m, 1H), 8.47-8.32 (m, 3H), 4.71 (s, 3H), 3.52 (t, J = 5.8 Hz, 2H), 3.39 (t, J = 5.9 Hz, 2H), 2.63-2.45 (m, 4H) |
| 117 | | 4-methoxy-N-[4-(4-oxo-3,4-dihydrophthalazin-1-yl)phenyl]-1H-indole-3-carboxamide | 411.2 | C: 2.30 D: 3.56 | ¹H NMR (400 MHz, DMSO-$d_6$) Shift 12.81 (br. s., 1H), 10.84 (s, 1H), 8.39-8.32 (m, 1H), 8.07 (s, 1H), 7.97-7.87 (m, 4H), 7.81-7.77 (m, 1H), 7.60 (d, J = 8.5 Hz, 2H), 7.23-7.16 (m, 2H), 6.88-6.82 (m, 1H), 4.15 (s, 3H) |
| 118 | | N-[4-(4-oxo-3,4-dihydrophthalazin-1-yl)phenyl]-1,2-benzoxazole-3-carboxamide | 383.2 | C: 2.58 D: 3.82 | ¹H NMR (400 MHz, DMSO-$d_6$) Shift 12.83 (br. s., 1H), 11.24 (br. s., 1H), 8.38-8.33 (m, 1H), 8.19 (d, J = 8.0 Hz, 1H), 8.06 (d, J = 8.8 Hz, 2H), 7.97-7.87 (m, 3H), 7.83-7.73 (m, 2H), 7.67-7.62 (m, 2H), 7.60-7.54 (m, 1H) |
| 119 | | 5-chloro-N-[4-(4-oxo-3,4-dihydrophthalazin-1-yl)phenyl]-1H-pyrrolo[2,3-b]pyridine-2-carboxamide | 416.1 | C: 2.30 D: 3.61 | |
| 120 | | 5-fluoro-N-[4-(4-oxo-3,4-dihydrophthalazin-1-yl)phenyl]-1H-pyrrolo[2,3-b]pyridine-3-carboxamide | 398.2 | C: 2.04 D: 3.43 | ¹H NMR (400 MHz, DMSO-$d_6$) Shift 12.80 (br. s., 1H), 10.09 (s, 1H), 8.60 (s, 1H), 8.37-8.30 (m, 2H), 8.26 (dd, J = 9.4, 2.9 Hz, 1H), 7.99-7.86 (m, 5H), 7.81-7.75 (m, 1H), 7.58 (d, J = 8.5 Hz, 2H) |
| 121 | | 6-methyl-N-[4-(4-oxo-3,4-dihydrophthalazin-1-yl)phenyl]imidazo[1,2-a]pyrazine-2-carboxamide | 397.1 | | |

TABLE 3-continued

| Example | R | Name | LCMS (M + H)+ | HPLC Method, RT (min.) | 1H NMR |
|---|---|---|---|---|---|
| 122 | | 1-methyl-N-[4-(4-oxo-3,4-dihydrophthalazin-1-yl)phenyl]-1H-indole-3-carboxamide | 395.2 | | |
| 123 | | 5-methoxy-N-[4-(4-oxo-3,4-dihydrophthalazin-1-yl)phenyl]-1H-indazole-3-carboxamide | 412.2 | C: 2.23 D: 3.50 | 1H NMR (400 MHz, DMSO-d6) Shift 12.80 (s, 1H), 10.47 (s, 1H), 8.35 (d, J = 6.8 Hz, 1H), 8.10 (d, J = 8.8 Hz, 2H), 7.96-7.86 (m, 2H), 7.78 (d, J = 9.0 Hz, 1H), 7.64 (s, 1H), 7.61-7.55 (m, 3H), 7.12 (d, J = 9.3 Hz, 1H), 3.85 (s, 3H) |
| 124 | | 8-chloro-N-[4-(4-oxo-3,4-dihydrophthalazin-1-yl)phenyl]imidazo[1,2-a]pyrazine-2-carboxamide | 415.2 | C: 2.03 D: 3.25 | 1H NMR (400 MHz, DMSO-d6) Shift 12.82 (br. s., 1H), 10.58 (br. s., 1H), 8.84 (s, 1H), 8.71 (d, J = 4.5 Hz, 1H), 8.38-8.33 (m, 1H), 8.08 (d, J = 8.8 Hz, 2H), 7.92 (qd, J = 7.2, 5.5 Hz, 2H), 7.86 (d, J = 4.5 Hz, 1H), 7.79-7.74 (m, 1H), 7.61 (d, J = 8.5 Hz, 2H) |
| 125 | | 5-methoxy-N-[4-(4-oxo-3,4-dihydrophthalazin-1-yl)phenyl]-1H-indole-2-carboxamide | 411.3 | C: 2.41 D: 3.63 | 1H NMR (500 MHz, DMSO-d6) Shift 12.83 (br. s., 1H), 11.68 (br. s., 1H), 10.39 (br. s., 1H), 8.35 (d, J = 7.6 Hz, 1H), 8.00 (d, J = 8.5 Hz, 2H), 7.96-7.86 (m, 2H), 7.78 (d, J = 7.6 Hz, 1H), 7.61 (d, J = 8.5 Hz, 2H), 7.42-7.34 (m, 2H), 7.16 (s, 1H), 6.90 (dd, J = 8.7, 1.4 Hz, 1H), 3.79 (s, 3H) |
| 126 | | 7-methyl-N-[4-(4-oxo-3,4-dihydrophthalazin-1-yl)phenyl]imidazo[1,2-a]pyridine-2-carboxamide | 396.3 | C: 2.30 D: 3.50 | 1H NMR (500 MHz, DMSO-d6) Shift 12.82 (s, 1H), 10.48 (s, 1H), 8.52 (d, J = 7.3 Hz, 1H), 8.48 (s, 1H), 8.34 (d, J = 7.3 Hz, 1H), 8.10 (d, J = 8.5 Hz, 2H), 7.98-7.86 (m, 2H), 7.76 (d, J = 7.9 Hz, 1H), 7.57 (d, J = 8.2 Hz, 2H), 7.44 (s, 1H), 6.89 (d, J = 7.0 Hz, 1H), 2.40 (s, 3H) |
| 127 | | 6-methoxy-1-methyl-N-[4-(4-oxo-3,4-dihydrophthalazin-1-yl)phenyl]-1H-indole-2-carboxamide | 425.2 | C: 2.71 D: 3.82 | 1H NMR (500 MHz, DMSO-d6) Shift 12.83 (s, 1H), 10.40 (s, 1H), 8.38-8.31 (m, 1H), 7.97 (d, J = 8.5 Hz, 2H), 7.95-7.86 (m, 2H), 7.77 (d, J = 7.3 Hz, 1H), 7.62-7.54 (m, 3H), 7.34 (s, 1H), 7.07 (s, 1H), 6.80 (dd, J = 8.9, 2.1 Hz, 1H), 4.01 (s, 3H), 3.86 (s, 3H) |
| 128 | | N-[4-(4-oxo-3,4-dihydrophthalazin-1-yl)phenyl]-6-(propan-2-yloxy)-1H-indole-2-carboxamide | 439.3 | C: 2.75 D: 3.89 | 1H NMR (500 MHz, DMSO-d6) Shift 12.83 (s, 1H), 11.54 (br. s., 1H), 10.31 (s, 1H), 8.35 (d, J = 7.9 Hz, 1H), 8.00 (d, J = 8.5 Hz, 2H), 7.96-7.86 (m, 3H), 7.78 (d, J = 7.3 Hz, 1H), 7.60 (d, J = 8.5 Hz, 2H), 7.56 (d, J = 8.5 Hz, 1H), 7.41 (s, 1H), 6.93 (s, 1H), 6.72 (dd, J = 8.5, 1.8 Hz, 1H), 4.58 (dt, J = 12.2, 6.1 Hz, 1H), 1.30 (d, J = 6.1 Hz, 6H) |

TABLE 3-continued

| Example | R | Name | LCMS (M + H)+ | HPLC Method, RT (min.) | $^1$H NMR |
|---|---|---|---|---|---|
| 129 | | 7-methoxy-N-[4-(4-oxo-3,4-dihydrophthalazin-1-yl)phenyl]-1H-indole-2-carboxamide | 411.3 | C: 2.54 D: 3.73 | $^1$H NMR (500 MHz, DMSO-d$_6$) Shift 12.84 (s, 1H), 11.66 (s, 1H), 10.36 (s, 1H), 8.39-8.32 (m, 1H), 7.98 (d, J = 8.5 Hz, 2H), 7.94-7.86 (m, 2H), 7.78 (d, J = 7.3 Hz, 1H), 7.62 (d, J = 8.5 Hz, 2H), 7.34 (s, 1H), 7.26 (d, J = 8.2 Hz, 1H), 7.03 (t, J = 7.9 Hz, 1H), 6.81 (d, J = 7.6 Hz, 1H), 3.96 (s, 3H) |
| 130 | | 5-ethoxy-1-methyl-N-[4-(4-oxo-3,4-dihydrophthalazin-1-yl)phenyl]-1H-indole-2-carboxamide | 439.2 | C: 2.70 D: 3.90 | $^1$H NMR (500 MHz, DMSO-d$_6$) Shift 12.84 (s, 1H), 10.49 (s, 1H), 8.40-8.29 (m, 1H), 7.98 (d, J = 8.5 Hz, 2H), 7.94-7.86 (m, 2H), 7.80-7.74 (m, 1H), 7.59 (d, J = 8.5 Hz, 2H), 7.49 (d, J = 9.2 Hz, 1H), 7.27 (s, 1H), 7.17 (d, J = 2.1 Hz, 1H), 6.97 (dd, J = 8.9, 2.4 Hz, 1H), 4.05 (q, J = 6.9 Hz, 2H), 4.01 (s, 3H), 1.36 (t, J = 6.9 Hz, 3H) |
| 131 | | 2-methyl-N-[4-(4-oxo-3,4-dihydrophthalazin-1-yl)phenyl]-2H-indazole-3-carboxamide | 396.2 | C: 2.16 D: 3.47 | $^1$H NMR (500 MHz, DMSO-d$_6$) Shift 12.85 (br. s., 1H), 10.86 (br. s., 1H), 8.35 (d, J = 7.9 Hz, 1H), 8.00-7.84 (m, 5H), 7.76 (t, J = 8.2 Hz, 2H), 7.63 (d, J = 8.2 Hz, 2H), 7.38 (t, J = 7.5 Hz, 1H), 7.28 (t, J = 7.2 Hz, 1H), 4.38 (s, 3H) |
| 132 | | N-[4-(4-oxo-3,4-dihydrophthalazin-1-yl)phenyl]-1-(propan-2-yl)-1H-indazole-3-carboxamide | 424.3 | C: 2.93 D: 4.06 | $^1$H NMR (500 MHz, DMSO-d$_6$) Shift 12.84 (s, 1H), 10.29 (s, 1H), 8.35 (d, J = 8.5 Hz, 1H), 8.25 (d, J = 8.2 Hz, 1H), 8.08 (d, J = 8.5 Hz, 2H), 7.98-7.83 (m, 3H), 7.79 (d, J = 7.6 Hz, 1H), 7.61 (d, J = 8.5 Hz, 2H), 7.50 (t, J = 7.5 Hz, 1H), 7.34 (t, J = 7.5 Hz, 1H), 5.16 (quin, J = 6.6 Hz, 1H), 1.62 (d, J = 6.4 Hz, 6H) |
| 133 | | N-[4-(4-oxo-3,4-dihydrophthalazin-1-yl)phenyl]imidazo[1,2-a]pyrazine-2-carboxamide | 383.1 | C: 1.90 D: 3.05 | $^1$H NMR (500 MHz, DMSO-d$_6$) Shift 12.83 (s, 1H), 10.77 (s, 1H), 9.23 (s, 1H), 8.72 (s, 1H), 8.70-8.64 (m, 1H), 8.34 (d, J = 7.9 Hz, 1H), 8.11 (d, J = 8.5 Hz, 2H), 8.03 (d, J = 4.9 Hz, 1H), 7.95-7.86 (m, 2H), 7.76 (d, J = 7.3 Hz, 1H), 7.59 (d, J = 8.2 Hz, 2H) |
| 134 | | N-[4-(4-oxo-3,4-dihydrophthalazin-1-yl)phenyl]-5H,6H,7H,8H-imidazo[1,2-a]pyridine-2-carboxamide | 386.2 | C: 1.93 D: 3.21 | $^1$H NMR (500 MHz, DMSO-d$_6$) Shift 12.80 (s, 1H), 9.99 (s, 1H), 8.34 (d, J = 6.7 Hz, 1H), 8.03 (d, J = 8.5 Hz, 2H), 7.94-7.84 (m, 2H), 7.78-7.67 (m, 2H), 7.53 (d, J = 8.5 Hz, 2H), 4.09-3.96 (m, 2H), 2.82 (t, J = 6.0 Hz, 2H), 2.01-1.81 (m, 4H) |
| 135 | | N-[4-(4-oxo-3,4-dihydrophthalazin-1-yl)phenyl]-1H-pyrrolo[2,3-b]pyridine-3-carboxamide | 382.2 | C: 2.03 D: 3.24 | $^1$H NMR (400 MHz, DMSO-d$_6$) Shift 12.79 (br. s., 1H), 10.03 (s, 1H), 8.53 (dd, J = 7.9, 1.6 Hz, 1H), 8.49 (s, 1H), 8.39-8.30 (m, 2H), 8.00-7.86 (m, 4H), 7.81-7.76 (m, 1H), 7.62-7.54 (m, 2H), 7.24 (dd, J = 8.0, 4.8 Hz, 1H) |

TABLE 3-continued

| Example | R | Name | LCMS (M + H)+ | HPLC Method, RT (min.) | ¹H NMR |
|---|---|---|---|---|---|
| 136 | (structure) | 1-benzyl-N-[4-(4-oxo-3,4-dihydrophthalazin-1-yl)phenyl]-1H-indole-2-carboxamide | 471.4 | C: 3.12<br>D: 4.22 | ¹H NMR (400 MHz, DMSO-d₆) Shift 12.81 (br. s., 1H), 10.60 (s, 1H), 8.39-8.29 (m, 1H), 7.99-7.93 (m, 2H), 7.93-7.85 (m, 2H), 7.82-7.71 (m, 2H), 7.58 (d, J = 8.8 Hz, 3H), 7.47 (s, 1H), 7.34-7.23 (m, 3H), 7.23-7.08 (m, 4H), 5.91 (s, 2H) |
| 137 | (structure) | 1-(2-hydroxy-2-methylpropyl)-N-[4-(4-oxo-3,4-dihydrophthalazin-1-yl)phenyl]-1H-indazole-3-carboxamide | 454.2 | E: 1.64<br>F: 1.60 | ¹H NMR (500 MHz, DMSO-d₆) d 12.85 (s, 1H), 10.44 (s, 1H), 8.35 (d, J = 7.7 Hz, 1H), 8.23 (d, J = 8.0 Hz, 1H), 8.08 (d, J = 8.0 Hz, 2H), 7.92 (t, J = 8.8 Hz, 2H), 7.87 (d, J = 8.8 Hz, 1H), 7.78 (d, J = 7.7 Hz, 1H), 7.60 (d, J = 8.0 Hz, 2H), 7.48 (t, J = 7.6 Hz, 1H), 7.32 (t, J = 7.3 Hz, 1H), 4.79 (s, 1H), 4.49 (s, 2H), 1.19 (s, 6H) |
| 138 | (structure) | 1-(2-hydroxy-2-methylpropyl)-N-[4-(4-oxo-3,4-dihydrophthalazin-1-yl)phenyl]-1H-indole-3-carboxamide | 453.2 | E: 1.65<br>F: 1.66 | ¹H NMR (500 MHz, DMSO-d₆) d 12.83 (br. s., 1H), 10.01 (br. s., 1H), 8.38 (br. s., 1H), 8.35 (d, J = 7.4 Hz, 1H), 8.24 (d, J = 6.9 Hz, 1H), 7.97 (d, J = 8.0 Hz, 2H), 7.95-7.86 (m, 2H), 7.80 (d, J = 6.9 Hz, 1H), 7.66 (d, J = 8.0 Hz, 1H), 7.57 (d, J = 7.7 Hz, 2H), 7.28-7.12 (m, 2H), 4.85 (br. s., 1H), 4.17 (br. s., 2H), 1.15 (br. s., 6H) |
| 139 | (structure) | 2,7-dimethyl-N-[4-(4-oxo-3,4-dihydrophthalazin-1-yl)phenyl]imidazo[1,2-a]pyridine-3-carboxamide | 410.2 | E: 1.09<br>F: 1.43 | |
| 140 | (structure) | 2-ethyl-N-[4-(4-oxo-3,4-dihydrophthalazin-1-yl)phenyl]imidazo[1,2-a]pyrimidine-3-carboxamide | 411.2 | E: 1.15<br>F: 1.46 | ¹H NMR (500 MHz, DMSO-d₆) d 12.83 (s, 1H), 10.33 (s, 1H), 9.25 (dd, J = 6.9, 1.9 Hz, 1H), 8.67 (dd, J = 4.1, 1.9 Hz, 1H), 8.38-8.33 (m, 1H), 7.97-7.87 (m, 4H), 7.79-7.75 (m, 1H), 7.62 (d, J = 8.5 Hz, 2H), 7.22 (dd, J = 6.7, 4.3 Hz, 1H), 3.11 (q, J = 7.5 Hz, 2H), 1.33 (t, J = 7.6 Hz, 3H) |
| 141 | (structure) | 6-methoxy-N-[4-(4-oxo-3,4-dihydrophthalazin-1-yl)phenyl]pyrazolo[1,5-a]pyridine-3-carboxamide | 412.1 | E: 1.41<br>F: 1.41 | ¹H NMR (500 MHz, DMSO-d₆) d 12.81 (s, 1H), 10.11 (s, 1H), 8.74 (s, 1H), 8.55 (d, J = 1.9 Hz, 1H), 8.35 (dd, J = 7.7, 1.4 Hz, 1H), 8.18 (d, J = 9.6 Hz, 1H), 7.96 (d, J = 8.5 Hz, 2H), 7.91 (ddd, J = 9.6, 7.6, 1.5 Hz, 2H), 7.81-7.76 (m, 1H), 7.58 (d, J = 8.5 Hz, 2H), 7.36 (dd, J = 9.6, 2.2 Hz, 1H), 3.88 (s, 3H) |
| 142 | (structure) | 1-[2-(dimethylamino)ethyl]-N-[4-(4-oxo-3,4-dihydrophthalazin-1-yl)phenyl]-1H-indazole-3-carboxamide | 453.2 | E: 1.37<br>F: 1.41 | ¹H NMR (500 MHz, DMSO-d₆) d 12.84 (s, 1H), 10.42 (s, 1H), 9.44 (br. s., 1H), 8.36 (d, J = 7.4 Hz, 1H), 8.29 (d, J = 8.0 Hz, 1H), 8.06 (d, J = 8.5 Hz, 2H), 7.96-7.89 (m, 3H), 7.77 (d, J = 8.0 Hz, 1H), 7.67-7.55 (m, 3H), 7.41 (t, J = 7.6 Hz, 1H), 4.96 (br. s., 2H), 3.77 (br. s., 2H), 3.02-2.85 (m, 6H) |

TABLE 3-continued

| Example | R | Name | LCMS (M + H)+ | HPLC Method, RT (min.) | 1H NMR |
|---|---|---|---|---|---|
| 143 | 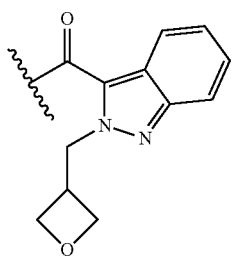 [SMILES: *C(=O)c1c2ccccc2nn1CC1COC1] | 2-(oxetan-3-ylmethyl)-N-[4-(4-oxo-3,4-dihydrophthalazin-1-yl)phenyl]-2H-indazole-3-carboxamide | 452.2 | E: 1.14 F: 1.14 | 1H NMR (500 MHz, DMSO-d6) d 12.87 (s, 1H), 11.37 (s, 1H), 8.39-8.35 (m, 1H), 8.31 (d, J = 8.5 Hz, 1H), 8.06 (d, J = 8.8 Hz, 1H), 8.02-7.89 (m, 5H), 7.74 (d, J = 7.7 Hz, 1H), 7.70 (d, J = 8.5 Hz, 3H), 5.23-5.15 (m, 2H), 4.97-4.88 (m, 2H), 4.70 (dd, J = 11.3, 5.0 Hz, 1H), 3.73 (br. s., 2H), 3.68-3.58 (m, 1H) |
| 144 | 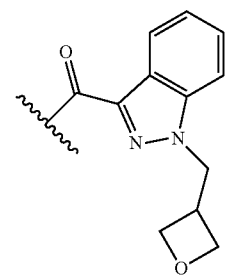 [SMILES: *C(=O)c1nn(CC2COC2)c2ccccc12] | 1-(oxetan-3-ylmethyl)-N-(4-(4-oxo-3,4-dihydrophthalazin-1-yl)phenyl)-1H-indazole-3-carboxamide | 452.1 | E: 1.15 F: 1.14 | 1H NMR (500 MHz, DMSO-d6) d 12.82 (s, 1H), 10.40 (s, 1H), 8.35 (d, J = 7.7 Hz, 1H), 8.25 (d, J = 8.0 Hz, 1H), 8.15-8.05 (m, J = 8.3 Hz, 2H), 7.97-7.88 (m, 3H), 7.78 (d, J = 8.0 Hz, 1H), 7.64-7.58 (m, J = 8.5 Hz, 2H), 7.53 (t, J = 7.7 Hz, 1H), 7.35 (t, J = 7.4 Hz, 1H), 4.89 (d, J = 7.2 Hz, 2H), 4.78-4.67 (m, 2H), 4.55 (t, J = 6.1 Hz, 2H), 3.68-3.56 (m, 1H) |
| 145 | 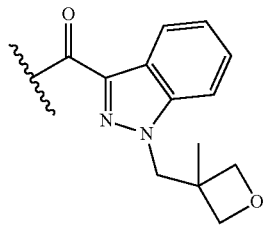 [SMILES: *C(=O)c1nn(CC2(C)COC2)c2ccccc12] | 1-[(3-methyloxetan-3-yl)methyl]-N-[4-(4-oxo-3,4-dihydrophthalazin-1-yl)phenyl]-1H-indazole-3-carboxamide | 466.2 | E: 1.63 F: 1.62 | 1H NMR (500 MHz, DMSO-d6) d 12.82 (s, 1H), 10.36 (s, 1H), 8.35 (d, J = 7.4 Hz, 1H), 8.26 (d, J = 8.3 Hz, 1H), 8.13-8.02 (m, J = 8.0 Hz, 2H), 8.00-7.85 (m, 3H), 7.77 (d, J = 7.7 Hz, 1H), 7.63-7.58 (m, J = 8.0 Hz, 2H), 7.53 (t, J = 7.6 Hz, 1H), 7.35 (t, J = 7.4 Hz, 1H), 4.80 (br. s., 4H), 4.33 (d, J = 5.8 Hz, 2H), 1.20 (s, 3H) |
| 146 | 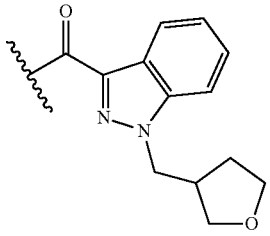 [SMILES: *C(=O)c1nn(CC2CCOC2)c2ccccc12] | N-[4-(4-oxo-3,4-dihydrophthalazin-1-yl)phenyl]-1-(oxolan-3-ylmethyl)-1H-indazole-3-carboxamide | 466.2 | E: 1.63 F: 1.64 | 1H NMR (500 MHz, DMSO-d6) d 12.82 (s, 1H), 10.46 (s, 1H), 8.35 (d, J = 7.4 Hz, 1H), 8.26 (d, J = 8.0 Hz, 1H), 8.13-8.04 (m, J = 7.7 Hz, 2H), 7.96-7.87 (m, 3H), 7.78 (d, J = 7.7 Hz, 1H), 7.67-7.57 (m, J = 8.0 Hz, 2H), 7.53 (t, J = 7.7 Hz, 1H), 7.35 (t, J = 7.3 Hz, 1H), 4.57 (d, J = 7.4 Hz, 2H), 3.86 (d, J = 7.2 Hz, 1H), 3.74-3.64 (m, 2H), 3.59 (br. s., 1H), 3.05-2.94 (m, 1H), 1.95 (dd, J = 11.8, 7.2 Hz, 1H), 1.72 (dd, J = 12.2, 6.5 Hz, 1H) |
| 147 | 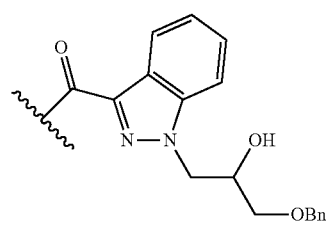 [SMILES: *C(=O)c1nn(CC(O)COCc2ccccc2)c2ccccc12] | 1-[3-(benzyloxy)-2-hydroxypropyl]-N-[4-(4-oxo-3,4-dihydrophthalazin-1-yl)phenyl]-1H-indazole-3-carboxamide | 546.2 | E: 1.95 F: 1.95 | 1H NMR (500 MHz, DMSO-d6) d 12.82 (s, 1H), 10.48 (s, 1H), 8.39-8.33 (m, 1H), 8.25 (d, J = 8.0 Hz, 1H), 8.10-8.05 (m, 2H), 7.98-7.87 (m, 2H), 7.83-7.74 (m, 2H), 7.62-7.58 (m, 2H), 7.48 (ddd, J = 8.3, 7.1, 0.8 Hz, 1H), 7.39-7.35 (m, 4H), 7.35-7.32 (m, 1H), 7.32-7.27 (m, 1H), 5.24 (d, J = 5.5 Hz, 1H), 4.71-4.61 (m, 1H), 4.59-4.51 (m, 3H), 4.31-4.21 (m, 1H), 3.51 (d, J = 5.5 Hz, 2H) |

TABLE 3-continued

| Example | R | Name | LCMS (M + H)+ | HPLC Method, RT (min.) | $^1$H NMR |
|---|---|---|---|---|---|
| 148 | (1-(oxolan-2-ylmethyl)-1H-indazole-3-carbonyl) | N-[4-(4-oxo-3,4-dihydrophthalazin-1-yl)phenyl]-1-(oxolan-2-ylmethyl)-1H-indazole-3-carboxamide | 466.3 | E: 1.84 F: 1.83 | $^1$H NMR (500 MHz, DMSO-$d_6$) d 12.82 (s, 1H), 10.49 (s, 1H), 8.37-8.34 (m, 1H), 8.25 (d, J = 8.3 Hz, 1H), 8.12-8.07 (m, 2H), 7.97-7.88 (m, 2H), 7.84 (d, J = 8.5 Hz, 1H), 7.80-7.76 (m, 1H), 7.63-7.57 (m, 2H), 7.50 (ddd, J = 8.4, 7.0, 1.1 Hz, 1H), 7.33 (td, J = 7.5, 0.7 Hz, 1H), 4.62 (d, J = 5.8 Hz, 2H), 4.40 (t, J = 6.3 Hz, 1H), 3.81-3.72 (m, 1H), 3.62 (dt, J = 8.2, 6.8 Hz, 1H), 2.12-1.92 (m, 1H), 1.88-1.79 (m, 2H), 1.78-1.68 (m, 1H) |
| 149 | (1-(2,3-dihydroxypropyl)-1H-indazole-3-carbonyl) | 1-(2,3-dihydroxypropyl)-N-[4-(4-oxo-3,4-dihydrophthalazin-1-yl)phenyl]-1H-indazole-3-carboxamide | 456.2 | E: 1.40 F: 1.38 | $^1$H NMR (500 MHz, DMSO-$d_6$) d 12.82 (s, 1H), 10.49 (s, 1H), 8.38-8.33 (m, 1H), 8.25 (d, J = 8.3 Hz, 1H), 8.12-8.09 (m, 1H), 8.09-8.07 (m, 1H), 7.97-7.89 (m, 2H), 7.82-7.76 (m, 2H), 7.62-7.58 (m, 2H), 7.49 (ddd, J = 8.4, 7.0, 1.1 Hz, 1H), 7.35-7.30 (m, 1H), 5.04 (d, J = 5.2 Hz, 1H), 4.86 (t, J = 5.6 Hz, 1H), 4.66 (dd, J = 14.2, 3.7 Hz, 1H), 4.48 (dd, J = 14.2, 8.1 Hz, 1H), 4.13-4.03 (m, 1H), 3.53-3.40 (m, 2H) |
| 150 | (1-(oxan-4-ylmethyl)-1H-indazole-3-carbonyl) | 1-(oxan-4-ylmethyl)-N-[4-(4-oxo-3,4-dihydrophthalazin-1-yl)phenyl]-1H-indazole-3-carboxamide | 480.0 | E: 1.80 F: 1.79 | $^1$H NMR (500 MHz, DMSO-$d_6$) d 12.82 (s, 1H), 10.47 (s, 1H), 8.35 (dd, J = 7.6, 1.2 Hz, 1H), 8.25 (d, J = 8.3 Hz, 1H), 8.15-8.05 (m, J = 8.5 Hz, 2H), 7.94-7.84 (m, 3H), 7.82-7.74 (m, 1H), 7.63-7.56 (m, J = 8.5 Hz, 2H), 7.55-7.47 (m, 1H), 7.34 (t, J = 7.4 Hz, 1H), 4.48 (d, J = 7.2 Hz, 2H), 3.88-3.76 (m, 2H), 3.29-3.18 (m, 2H), 2.37-2.21 (m, 1H), 1.50-1.26 (m, 4H) |
| 151 | (1-(2-methoxyethyl)-1H-indazole-3-carbonyl) | 1-(2-methoxyethyl)-N-[4-(4-oxo-3,4-dihydrophthalazin-1-yl)phenyl]-1H-indazole-3-carboxamide | 440.2 | E: 1.73 F: 1.73 | $^1$H NMR (500 MHz, DMSO-$d_6$) d 12.82 (s, 1H), 10.49 (s, 1H), 8.35 (dd, J = 7.8, 1.2 Hz, 1H), 8.25 (d, J = 8.3 Hz, 1H), 8.13-8.06 (m, 2H), 7.95-7.88 (m, 2H), 7.84 (d, J = 8.5 Hz, 1H), 7.78 (dd, J = 7.8, 1.0 Hz, 1H), 7.64-7.58 (m, 2H), 7.50 (ddd, J = 8.4, 7.2, 1.0 Hz, 1H), 7.34 (t, J = 7.6 Hz, 1H), 4.75 (t, J = 5.4 Hz, 2H), 3.88 (t, J = 5.2 Hz, 2H), 3.23 (s, 3H) |
| 152 | (1-(oxetan-2-ylmethyl)-1H-indazole-3-carbonyl) | 1-(oxetan-2-ylmethyl)-N-[4-(4-oxo-3,4-dihydrophthalazin-1-yl)phenyl]-1H-indazole-3-carboxamide | 452.2 | E: 1.61 F: 1.61 | $^1$H NMR (500 MHz, DMSO-$d_6$) d 12.82 (s, 1H), 10.50 (s, 1H), 8.35 (dd, J = 7.6, 1.2 Hz, 1H), 8.25 (d, J = 8.3 Hz, 1H), 8.14-8.05 (m, J = 8.5 Hz, 2H), 7.97-7.88 (m, 3H), 7.80-7.74 (m, 1H), 7.64-7.57 (m, J = 8.5 Hz, 2H), 7.50 (dd, J = 8.5, 1.1 Hz, 1H), 7.34 (t, J = 7.4 Hz, 1H), 5.33-5.15 (m, 1H), 4.90 (dd, J = 14.9, 6.3 Hz, 1H), 4.80 (dd, J = 14.9, 3.9 Hz, 1H), 4.48 (ddd, J = 8.4, 7.0, 5.8 Hz, 1H), 4.30 (dt, J = 9.0, 5.9 Hz, 1H), 2.78-2.72 (m, 1H), 2.60-2.54 (m, 1H) |
| 153 | (1-(2-hydroxypropyl)-1H-indazole-3-carbonyl) | 1-(2-hydroxypropyl)-N-[4-(4-oxo-3,4-dihydrophthalazin-1-yl)phenyl]-1H-indazole-3-carboxamide | 440.2 | E: 1.55 F: 1.55 | $^1$H NMR (500 MHz, DMSO-$d_6$) d 12.85 (s, 1H), 10.51 (s, 1H), 8.35 (dd, J = 7.8, 1.2 Hz, 1H), 8.24 (d, J = 8.3 Hz, 1H), 8.12-8.06 (m, J = 8.5 Hz, 2H), 7.97-7.87 (m, 2H), 7.83 (d, J = 8.5 Hz, 1H), 7.79-7.75 (m, 1H), 7.62-7.57 (m, J = 8.5 Hz, 2H), 7.53-7.46 (m, 1H), 7.32 (t, J = 7.4 Hz, 1H), 5.02 (d, J = 5.0 Hz, 1H), 4.47 (d, J = 6.1 Hz, 2H), 4.32-4.19 (m, 1H), 1.16 (d, J = 6.3 Hz, 3H) |

TABLE 3-continued

| Example | R | Name | LCMS (M + H)+ | HPLC Method, RT (min.) | 1H NMR |
|---|---|---|---|---|---|
| 154 | | 1-[2-(2-methoxyethoxy)ethyl]-N-[4-(4-oxo-3,4-dihydrophthalazin-1-yl)phenyl]-1H-indazole-3-carboxamide | 484.3 | E: 1.66 F: 1.66 | 1H NMR (500 MHz, DMSO-$d_6$) d 12.85 (s, 1H), 10.54 (s, 1H), 8.35 (dd, J = 7.8, 1.2 Hz, 1H), 8.25 (d, J = 8.3 Hz, 1H), 8.14-8.06 (m, J = 8.5 Hz, 2H), 8.00-7.89 (m, 2H), 7.86 (d, J = 8.5 Hz, 1H), 7.83-7.75 (m, 1H), 7.65-7.58 (m, J = 8.5 Hz, 2H), 7.51 (t, J = 7.7 Hz, 1H), 7.34 (t, J = 7.4 Hz, 1H), 4.75 (t, J = 5.4 Hz, 2H), 3.96 (t, J = 5.4 Hz, 2H), 3.51 (dd, J = 5.6, 3.7 Hz, 2H), 3.13 (s, 3H) |
| 155 | | 1-(2-hydroxyethyl)-N-[4-(4-oxo-3,4-dihydrophthalazin-1-yl)phenyl]-1H-indazole-3-carboxamide | 426.2 | E: 1.43 F: 1.42 | 1H NMR (500 MHz, DMSO-$d_6$) d 12.85 (s, 1H), 10.53 (s, 1H), 8.35 (dd, J = 7.7, 1.4 Hz, 1H), 8.25 (d, J = 8.3 Hz, 1H), 8.13-8.07 (m, J = 8.5 Hz, 2H), 7.97-7.88 (m, 2H), 7.82 (d, J = 8.5 Hz, 1H), 7.80-7.76 (m, 1H), 7.62-7.58 (m, J = 8.5 Hz, 2H), 7.52-7.47 (m, 1H), 7.33 (t, J = 7.4 Hz, 1H), 4.98 (t, J = 5.5 Hz, 1H), 4.62 (t, J = 5.4 Hz, 2H), 3.94 (q, J = 5.5 Hz, 2H) |
| 156 | | 1-[2-(oxan-4-yl)ethyl]-N-[4-(4-oxo-3,4-dihydrophthalazin-1-yl)phenyl]-1H-indazole-3-carboxamide | 494.3 | E: 1.96 F: 1.92 | 1H NMR (500 MHz, DMSO-$d_6$) d 12.85 (s, 1H), 10.50 (s, 1H), 8.38-8.33 (m, 1H), 8.26 (d, J = 8.3 Hz, 1H), 8.12-8.07 (m, J = 8.5 Hz, 2H), 7.97-7.89 (m, 2H), 7.85 (d, J = 8.5 Hz, 1H), 7.78 (d, J = 7.4 Hz, 1H), 7.63-7.57 (m, J = 8.5 Hz, 2H), 7.52 (t, J = 7.7 Hz, 1H), 7.34 (t, J = 7.6 Hz, 1H), 4.62 (t, J = 7.4 Hz, 2H), 3.83 (dd, J = 11.3, 3.0 Hz, 2H), 3.25 (t, J = 11.0 Hz, 2H), 1.96-1.87 (m, 2H), 1.67 (d, J = 12.9 Hz, 2H), 1.53 (ddt, J = 14.4, 7.2, 3.8 Hz, 1H), 1.26 (qd, J = 12.2, 4.5 Hz, 2H) |
| 157 | | 1-[2-(benzyloxy)ethyl]-N-[4-(4-oxo-3,4-dihydrophthalazin-1-yl)phenyl]-1H-indazole-3-carboxamide | 516.3 | E: 2.08 F: 2.11 | 1H NMR (500 MHz, DMSO-$d_6$) d 12.85 (s, 1H), 10.53 (s, 1H), 8.37-8.33 (m, 1H), 8.26 (d, J = 8.0 Hz, 1H), 8.12-8.07 (m, J = 8.5 Hz, 2H), 7.96-7.84 (m, 3H), 7.78 (d, J = 7.7 Hz, 1H), 7.64-7.58 (m, J = 8.5 Hz, 2H), 7.50 (t, J = 7.7 Hz, 1H), 7.34 (t, J = 7.6 Hz, 1H), 7.27-7.19 (m, 3H), 7.15-7.10 (m, 2H), 4.81 (t, J = 5.1 Hz, 2H), 4.47 (s, 2H), 3.97 (t, J = 5.2 Hz, 2H) |
| 158 | | 6-fluoro-1-(2-hydroxy-2-methylpropyl)-N-[4-(4-oxo-3,4-dihydrophthalazin-1-yl)phenyl]-1H-indazole-3-carboxamide | 472.2 | E: 1.65 F: 1.66 | 1H NMR (500 MHz, DMSO-$d_6$) d 12.85 (s, 1H), 10.49 (s, 1H), 8.35 (dd, J = 7.7, 1.4 Hz, 1H), 8.23 (dd, J = 8.8, 5.5 Hz, 1H), 8.09-8.05 (m, J = 8.8 Hz, 2H), 7.97-7.89 (m, 2H), 7.80-7.76 (m, 1H), 7.73 (dd, J = 9.9, 1.9 Hz, 1H), 7.63-7.58 (m, J = 8.8 Hz, 2H), 7.21 (td, J = 9.1, 1.9 Hz, 1H), 4.45 (s, 2H), 1.19 (s, 6H) |
| 159 | | 6-fluoro-1-(oxetan-3-ylmethyl)-N-[4-(4-oxo-3,4-dihydrophthalazin-1-yl)phenyl]-1H-indazole-3-carboxamide | 470.3 | E: 1.74 F: 1.71 | 1H NMR (500 MHz, DMSO-$d_6$) d 12.85 (s, 1H), 10.48 (s, 1H), 8.41-8.31 (m, 1H), 8.24 (dd, J = 8.9, 5.4 Hz, 1H), 8.15-8.01 (m, J = 8.5 Hz, 2H), 8.01-7.85 (m, 3H), 7.77 (d, J = 7.7 Hz, 1H), 7.66-7.52 (m, J = 8.5 Hz, 2H), 7.24 (td, J = 9.1, 1.9 Hz, 1H), 4.85 (d, J = 7.4 Hz, 2H), 4.69 (dd, J = 7.7, 6.3 Hz, 2H), 4.54 (t, J = 6.2 Hz, 2H), 3.71-3.54 (m, 1H) |

TABLE 3-continued

| Example | R | Name | LCMS (M + H)+ | HPLC Method, RT (min.) | 1H NMR |
|---|---|---|---|---|---|
| 160 | 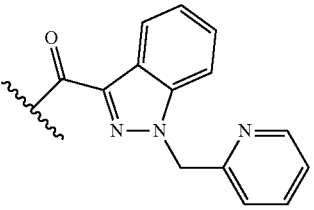 [SMILES: *C(=O)c1nn(Cc2ccccn2)c2ccccc12] | N-[4-(4-oxo-3,4-dihydrophthalazin-1-yl)phenyl]-1-(pyridin-2-ylmethyl)-1H-indazole-3-carboxamide | 473.3 | A: 10.97 B: 10.36 | 1H NMR (400 MHz, DMSO-$d_6$) d 12.82 (s, 1H), 10.59 (s, 1H), 8.62-8.49 (m, 1H), 8.42-8.23 (m, 2H), 8.14-8.04 (m, 2H), 7.94-7.88 (m, 2H), 7.84-7.73 (m, 3H), 7.61-7.56 (m, 2H), 7.50 (ddd, J = 8.4, 7.0, 1.1 Hz, 1H), 7.38-7.31 (m, 2H), 7.16 (d, J = 7.9 Hz, 1H), 5.97 (s, 2H) |
| 161 | 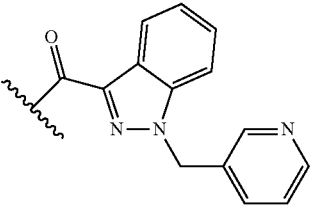 [SMILES: *C(=O)c1nn(Cc2cccnc2)c2ccccc12] | N-[4-(4-oxo-3,4-dihydrophthalazin-1-yl)phenyl]-1-(pyridin-3-ylmethyl)-1H-indazole-3-carboxamide | 473.3 | A: 8.60 B: 9.15 | 1H NMR (500 MHz, DMSO-$d_6$) d 12.82 (s, 1H), 10.57 (s, 1H), 8.77 (d, J = 4.1 Hz, 1H), 8.62 (br. s., 1H), 8.42-8.33 (m, 1H), 8.28 (d, J = 8.0 Hz, 1H), 8.09 (d, J = 8.8 Hz, 2H), 7.98-7.89 (m, 3H), 7.89-7.83 (m, 1H), 7.82-7.74 (m, 1H), 7.60 (d, J = 8.5 Hz, 2H), 7.56-7.49 (m, 2H), 7.37 (t, J = 7.6 Hz, 1H), 5.94 (s, 2H) |
| 162 | 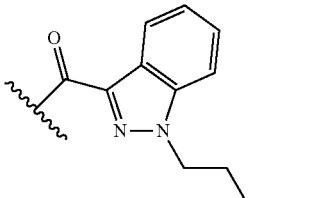 | 1-[3-(benzyloxy)propyl]-N-[4-(4-oxo-3,4-dihydrophthalazin-1-yl)phenyl]-1H-indazole-3-carboxamide | 530.3 | E: 2.15 F: 2.14 | 1H NMR (500 MHz, DMSO-$d_6$) d 12.84 (s, 1H), 10.52 (s, 1H), 8.35 (d, J = 7.7 Hz, 1H), 8.26 (d, J = 8.3 Hz, 1H), 8.12-8.07 (m, J = 8.3 Hz, 2H), 7.97-7.87 (m, 2H), 7.79 (t, J = 9.5 Hz, 2H), 7.62-7.56 (m, J = 8.5 Hz, 2H), 7.50 (t, J = 7.7 Hz, 1H), 7.37-7.27 (m, 6H), 4.67 (t, J = 6.9 Hz, 2H), 4.44 (s, 2H), 3.45 (t, J = 5.9 Hz, 2H), 2.24 (t, J = 6.5 Hz, 2H) |
| 163 | 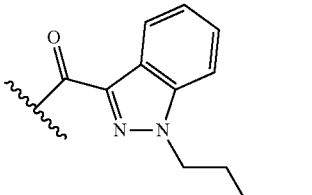 | 1-(3-methoxypropyl)-N-[4-(4-oxo-3,4-dihydrophthalazin-1-yl)phenyl]-1H-indazole-3-carboxamide | 454.2 | E: 1.78 F: 1.77 | 1H NMR (500 MHz, DMSO-$d_6$) d 12.84 (s, 1H), 10.53 (s, 1H), 8.35 (d, J = 7.7 Hz, 1H), 8.26 (d, J = 8.3 Hz, 1H), 8.13-8.06 (m, J = 8.5 Hz, 2H), 7.98-7.89 (m, 2H), 7.79 (t, J = 9.1 Hz, 2H), 7.64-7.57 (m, J = 8.3 Hz, 2H), 7.51 (d, J = 8.0 Hz, 1H), 7.34 (t, J = 7.4 Hz, 1H), 4.63 (t, J = 6.9 Hz, 2H), 3.32-3.29 (m, 2H), 3.22 (s, 3H), 2.18 (t, J = 6.5 Hz, 2H) |
| 164 | 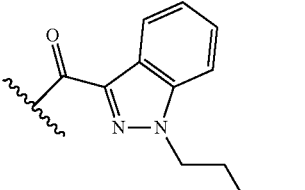 | 1-(3-hydroxypropyl)-N-[4-(4-oxo-3,4-dihydrophthalazin-1-yl)phenyl]-1H-indazole-3-carboxamide | 440.3 | E: 1.48 F: 1.48 | 1H NMR (500 MHz, DMSO-$d_6$) d 12.84 (s, 1H), 10.52 (s, 1H), 8.35 (d, J = 7.7 Hz, 1H), 8.25 (d, J = 8.3 Hz, 1H), 8.15-8.08 (m, J = 8.3 Hz, 2H), 7.96-7.86 (m, 2H), 7.82 (d, J = 8.5 Hz, 1H), 7.78 (d, J = 7.7 Hz, 1H), 7.62-7.57 (m, J = 8.3 Hz, 2H), 7.51 (t, J = 7.6 Hz, 1H), 7.34 (t, J = 7.6 Hz, 1H), 4.70 (t, J = 5.0 Hz, 1H), 4.64 (t, J = 7.0 Hz, 2H), 3.45 (q, J = 5.8 Hz, 2H), 2.09 (t, J = 6.6 Hz, 2H) |
| 165 | 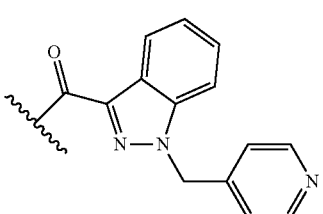 | N-[4-(4-oxo-3,4-dihydrophthalazin-1-yl)phenyl]-1-(pyridin-4-ylmethyl)-1H-indazole-3-carboxamide | 473.3 | E: 1.20 F: 1.58 | 1H NMR (500 MHz, DMSO-$d_6$) d 12.85 (s, 1H), 10.65 (s, 1H), 8.65 (d, J = 5.2 Hz, 2H), 8.32 (d, J = 8.0 Hz, 1H), 8.35 (d, J = 7.4 Hz, 1H), 8.16-8.03 (m, J = 8.3 Hz, 2H), 7.98-7.89 (m, 2H), 7.84 (d, J = 8.5 Hz, 1H), 7.77 (d, J = 7.7 Hz, 1H), 7.64-7.58 (m, J = 8.3 Hz, 2H), 7.54 (t, J = 7.7 Hz, 1H), 7.43-7.35 (m, 3H), 6.04 (s, 2H) |

TABLE 3-continued

| Example | R | Name | LCMS (M + H)+ | HPLC Method, RT (min.) | ¹H NMR |
|---|---|---|---|---|---|
| 166 | (pyrrolo[3,2-c]pyridin-3-yl carbonyl) | N-[4-(4-oxo-3,4-dihydrophthalazin-1-yl)phenyl]-1H-pyrrolo[3,2-c]pyridine-3-carboxamide | 382.2 | E: 0.96  F: 1.03 | ¹H NMR (500 MHz, DMSO-$d_6$) d 13.18 (br. s., 1H), 12.86 (s, 1H), 10.46 (s, 1H), 9.58 (br. s., 1H), 8.81 (s, 1H), 8.52 (d, J = 6.1 Hz, 1H), 8.35 (d, J = 8.0 Hz, 1H), 8.05 (d, J = 6.3 Hz, 1H), 8.01-7.97 (m, J = 8.3 Hz, 2H), 7.96-7.87 (m, 2H), 7.78 (d, J = 7.7 Hz, 1H), 7.66-7.60 (m, J = 8.3 Hz, 2H), 6.57 (br. s., 1H) |
| 167 | (5-fluoro-1-(2-hydroxy-2-methylpropyl)indazol-3-ylcarbonyl) | 5-fluoro-1-(2-hydroxy-2-methylpropyl)-N-[4-(4-oxo-3,4-dihydrophthalazin-1-yl)phenyl]-1H-indazole-3-carboxamide | 472.2 | E: 1.63  F: 1.64 | ¹H NMR (500 MHz, DMSO-$d_6$) d 12.85 (s, 1H), 10.49 (s, 1H), 8.35 (d, J = 7.7 Hz, 1H), 8.12-8.05 (m, J = 8.3 Hz, 2H), 7.99-7.90 (m, 3H), 7.86 (d, J = 8.5 Hz, 1H), 7.77 (d, J = 7.7 Hz, 1H), 7.63-7.57 (m, J = 8.3 Hz, 2H), 7.41 (t, J = 9.1 Hz, 1H), 4.81 (s, 1H), 4.49 (s, 2H), 1.19 (s, 6H) |
| 168 | (1-(oxan-2-ylmethyl)indazol-3-ylcarbonyl) | 1-(oxan-2-ylmethyl)-N-[4-(4-oxo-3,4-dihydrophthalazin-1-yl)phenyl]-1H-indazole-3-carboxamide | 480.2 | E: 2.04  F: 2.04 | ¹H NMR (500 MHz, DMSO-$d_6$) d 12.85 (s, 1H), 10.53 (s, 1H), 8.35 (d, J = 7.4 Hz, 1H), 8.24 (d, J = 8.3 Hz, 1H), 8.14-8.08 (m, J = 8.0 Hz, 2H), 7.97-7.87 (m, 2H), 7.87-7.73 (m, 2H), 7.66-7.57 (m, J = 8.0 Hz, 2H), 7.49 (t, J = 7.8 Hz, 1H), 7.33 (t, J = 7.4 Hz, 1H), 4.69-4.57 (m, 1H), 4.57-4.47 (m, 1H), 3.98-3.84 (m, 2H), 3.79 (d, J = 11.0 Hz, 1H), 3.29-3.18 (m, 1H), 1.88-1.76 (m, 1H), 1.65 (d, J = 12.4 Hz, 1H), 1.50-1.29 (m, 4H) |
| 169 | (1-(2-hydroxy-2-methylpropyl)pyrrolo[2,3-b]pyridin-3-ylcarbonyl) | 1-(2-hydroxy-2-methylpropyl)-N-[4-(4-oxo-3,4-dihydrophthalazin-1-yl)phenyl]-1H-pyrrolo[2,3-b]pyridine-3-carboxamide | 454.2 | E: 1.41  F: 1.46 | ¹H NMR (500 MHz, DMSO-$d_6$) d 12.84 (s, 1H), 10.18 (s, 1H), 8.61 (s, 1H), 8.56 (d, J = 7.7 Hz, 1H), 8.38-8.32 (m, 2H), 8.02-7.95 (m, J = 8.0 Hz, 2H), 7.95-7.85 (m, 2H), 7.79 (d, J = 7.7 Hz, 1H), 7.63-7.55 (m, J = 8.0 Hz, 2H), 7.33-7.23 (m, 1H), 4.30 (s, 2H), 1.11 (s, 6H) |
| 170 | (1-[(oxolan-3-yl)methyl]indazol-3-ylcarbonyl), enantiomer 1 | N-[4-(4-oxo-3,4-dihydrophthalazin-1-yl)phenyl]-1-[3-ylmethyl]-1H-indazole-3-carboxamide | 466.3 | E: 1.80  F: 1.80 | ¹H NMR (500 MHz, DMSO-$d_6$) d 12.82 (br. s., 1H), 10.46 (br. s., 1H), 8.35 (d, J = 6.6 Hz, 1H), 8.26 (d, J = 7.4 Hz, 1H), 8.11-8.04 (m, J = 7.7 Hz, 2H), 7.98-7.86 (m, 3H), 7.78 (d, J = 7.2 Hz, 1H), 7.62-7.57 (m, J = 8.0 Hz, 2H), 7.53 (br. s., 1H), 7.35 (br. s., 1H), 4.57 (d, J = 6.3 Hz, 2H), 3.88-3.80 (m, 1H), 3.72-3.64 (m, 2H), 3.60-3.53 (m, 1H), 2.96 (br. s., 1H), 1.94 (br. s., 1H), 1.72 (br. s., 1H) |

TABLE 3-continued

| Example | R | Name | LCMS (M + H)+ | HPLC Method, RT (min.) | 1H NMR |
|---|---|---|---|---|---|
| 171 | (structure: indazole-3-carbonyl with N1-(oxolan-3-ylmethyl); enantiomer 2) | N-[4-(4-oxo-3,4-dihydrophthalazin-1-yl)phenyl]-1-[oxolan-3-ylmethyl]-1H-indazole-3-carboxamide | 466.3 | E: 1.80 F: 1.80 | 1H NMR (500 MHz, DMSO-$d_6$) d 12.82 (br. s., 1H), 10.46 (br. s., 1H), 8.35 (d, J = 6.9 Hz, 1H), 8.26 (d, J = 7.7 Hz, 1H), 8.12-8.03 (m, J = 7.7 Hz, 2H), 7.98-7.84 (m, 3H), 7.78 (d, J = 6.9 Hz, 1H), 7.65-7.57 (m, J = 7.7 Hz, 2H), 7.56-7.46 (m, 1H), 7.39-7.27 (m, 1H), 4.57 (d, J = 6.6 Hz, 2H), 3.88-3.80 (m, 1H), 3.73-3.64 (m, 2H), 3.63-3.54 (m, 1H), 2.96 (br. s., 1H), 1.94 (br. s., 1H), 1.72 (br. s., 1H) |
| 172 | (structure: pyrazolo[1,5-a]pyridine-3-carbonyl with 6-(2-hydroxy-2-methylpropoxy)) | 6-(2-hydroxy-2-methylpropoxy)-N-[4-(4-oxo-3,4-dihydrophthalazin-1-yl)phenyl]pyrazolo[1,5-a]pyridine-3-carboxamide | 470.1 | E: 1.44 F: 1.44 | 1H NMR (500 MHz, DMSO-$d_6$) d 12.84 (br. s., 1H), 10.12 (br. s., 1H), 8.74 (br. s., 1H), 8.55 (br. s., 1H), 8.35 (d, J = 7.2 Hz, 1H), 8.19 (d, J = 9.6 Hz, 1H), 7.99-7.86 (m, 4H), 7.78 (d, J = 7.4 Hz, 1H), 7.59 (d, J = 8.0 Hz, 2H), 7.38 (d, J = 9.6 Hz, 1H), 4.74 (br. s., 1H), 4.12 (br. s., 1H), 3.83 (br. s., 2H), 3.16 (br. s., 2H), 1.23 (br. s., 6H) |
| 173 | (structure: 5-fluoro-indazole-3-carbonyl with N1-(oxolan-3-ylmethyl)) | 5-fluoro-N-[4-(4-oxo-3,4-dihydrophthalazin-1-yl)phenyl]-1-(oxolan-3-ylmethyl)-1H-indazole-3-carboxamide | 484.2 | E: 1.81 F: 1.81 | 1H NMR (500 MHz, DMSO-$d_6$) d 12.82 (br. s., 1H), 10.50 (br. s., 1H), 8.35 (br. s., 1H), 8.07 (d, J = 6.6 Hz, 2H), 8.03-7.94 (m, 1H), 7.90 (br. s., 3H), 7.78 (br. s., 1H), 7.60 (d, J = 6.6 Hz, 2H), 7.53-7.39 (m, 1H), 4.58 (br. s., 2H), 3.85 (br. s., 1H), 3.69 (d, J = 8.0 Hz, 2H), 3.57 (br. s., 1H), 2.94 (br. s., 1H), 1.95 (br. s., 1H), 1.71 (br. s., 1H) |
| 174 | (structure: 6-fluoro-indazole-3-carbonyl with N1-(oxolan-3-ylmethyl)) | 6-fluoro-N-[4-(4-oxo-3,4-dihydrophthalazin-1-yl)phenyl]-1-(oxolan-3-ylmethyl)-1H-indazole-3-carboxamide | 484.3 | E: 1.83 F: 1.83 | 1H NMR (500 MHz, DMSO-$d_6$) d 12.82 (br. s., 1H), 10.50 (br. s., 1H), 8.34 (br. s., 1H), 8.26 (br. s., 1H), 8.07 (d, J = 7.2 Hz, 2H), 7.91 (br. s., 2H), 7.83 (d, J = 9.9 Hz, 1H), 7.78 (br. s., 1H), 7.60 (d, J = 6.9 Hz, 2H), 7.24 (t, J = 8.5 Hz, 1H), 4.53 (br. s., 2H), 3.85 (br. s., 1H), 3.75-3.63 (m, 2H), 3.57 (br. s., 1H), 2.94 (br. s., 1H), 1.94 (br. s., 1H), 1.71 (br. s., 1H) |
| 175 | (structure: pyrazolo[1,5-a]pyridine-3-carbonyl with 6-(2-methoxyethoxy)) | 6-(2-methoxyethoxy)-N-[4-(4-oxo-3,4-dihydrophthalazin-1-yl)phenyl]pyrazolo[1,5-a]pyridine-3-carboxamide | 456.2 | E: 1.45 F: 1.45 | 1H NMR (500 MHz, DMSO-$d_6$) d 12.81 (br. s., 1H), 10.11 (br. s., 1H), 8.74 (br. s., 1H), 8.57 (br. s., 1H), 8.35 (br. s., 1H), 8.18 (d, J = 9.4 Hz, 1H), 7.98-7.88 (m, 4H), 7.79 (br. s., 1H), 7.58 (d, J = 5.2 Hz, 2H), 7.37 (d, J = 9.6 Hz, 1H), 4.21 (br. s., 2H), 3.71 (br. s., 2H) |
| 176 | (structure: pyrazolo[1,5-a]pyridine-3-carbonyl with 6-[2-(pyrrolidin-1-yl)ethoxy]) | N-[4-(4-oxo-3,4-dihydrophthalazin-1-yl)phenyl]-6-[2-(pyrrolidin-1-yl)ethoxy]pyrazolo[1,5-a]pyridine-3-carboxamide | 495.3 | E: 1.05 F: 1.05 | 1H NMR (500 MHz, DMSO-$d_6$) d 12.81 (s, 1H), 10.12 (s, 1H), 8.75 (s, 1H), 8.63 (s, 1H), 8.35 (dd, J = 7.6, 1.5 Hz, 1H), 8.21 (d, J = 9.6 Hz, 1H), 8.02-7.90 (m, 3H), 7.79-7.74 (m, 1H), 7.59 (d, J = 8.5 Hz, 2H), 7.39 (dd, J = 9.6, 1.9 Hz, 1H), 4.28 (br. s., 2H), 2.89 (s, 4H), 1.82 (br. s., 4H) |

TABLE 3-continued

| Example | R | Name | LCMS (M + H)+ | HPLC Method, RT (min.) | 1H NMR |
|---|---|---|---|---|---|
| 177 | | 6-[2-(dimethylamino)ethoxy]-N-[4-(4-oxo-3,4-dihydrophthalazin-1-yl)phenyl]pyrazolo[1,5-a]pyridine-3-carboxamide | 469.2 | E: 1.04 F: 1.05 | $^1$H NMR (500 MHz, DMSO-$d_6$) d 12.82 (s, 1H), 10.14 (s, 1H), 8.78 (s, 1H), 8.70 (d, J = 1.7 Hz, 1H), 8.40-8.32 (m, 1H), 8.24 (d, J = 9.6 Hz, 1H), 8.00-7.87 (m, 4H), 7.77 (d, J = 7.7 Hz, 1H), 7.59 (d, J = 8.5 Hz, 2H), 7.41 (dd, J = 9.5, 2.1 Hz, 1H), 4.45 (t, J = 5.0 Hz, 2H), 3.57 (t, J = 4.7 Hz, 2H), 2.96-2.87 (m, 6H) |
| 178 | | 5-fluoro-1-(2-methylprop-1-en-1-yl)-N-[4-(4-oxo-3,4-dihydrophthalazin-1-yl)phenyl]-1H-indazole-3-carboxamide | 454.2 | E: 1.71 F: 1.71 | $^1$H NMR (500 MHz, DMSO-$d_6$) d 12.84 (s, 1H), 10.79 (s, 1H), 8.35 (dd, J = 7.8, 1.5 Hz, 1H), 7.97-7.85 (m, 5H), 7.79-7.74 (m, 1H), 7.63 (d, J = 8.5 Hz, 2H), 7.56 (dd, J = 9.5, 2.3 Hz, 1H), 7.33 (td, J = 9.3, 2.3 Hz, 1H), 7.29-7.24 (m, 1H), 1.97-1.86 (m, 3H), 1.79 (d, J = 1.1 Hz, 3H) |
| 179 | | 6-fluoro-1-(2-methylprop-1-en-1-yl)-N-[4-(4-oxo-3,4-dihydrophthalazin-1-yl)phenyl]-1H-indazole-3-carboxamide | 454.2 | E: 1.71 F: 1.71 | $^1$H NMR (500 MHz, DMSO-$d_6$) d 12.84 (s, 1H), 10.92 (s, 1H), 8.39-8.31 (m, 1H), 7.96-7.88 (m, 5H), 7.79-7.72 (m, 1H), 7.66-7.59 (m, 2H), 7.54 (dd, J = 10.2, 1.9 Hz, 1H), 7.27-7.23 (m, 1H), 7.21-7.15 (m, 1H), 1.92 (d, J = 1.4 Hz, 3H), 1.80 (d, J = 1.4 Hz, 3H) |
| 180 | | 6-fluoro-5-methoxy-N-[4-(4-oxo-3,4-dihydrophthalazin-1-yl)phenyl]-1-benzofuran-2-carboxamide | 430.1 | E: 1.61 F: 1.61 | $^1$H NMR (500 MHz, DMSO-$d_6$) d 12.83 (s, 1H), 10.71 (s, 1H), 8.40-8.31 (m, 1H), 8.06-7.96 (m, J = 8.5 Hz, 2H), 7.95-7.87 (m, 2H), 7.79 (s, 1H), 7.77-7.70 (m, 2H), 7.63-7.58 (m, J = 8.8 Hz, 2H), 7.56 (d, J = 8.8 Hz, 1H), 3.92 (s, 3H) |
| 181 | | 5-(2-hydroxy-2-methylpropoxy)-N-[4-(4-oxo-3,4-dihydrophthalazin-1-yl)phenyl]pyrazolo[1,5-a]pyridine-3-carboxamide | 470.1 | A: 6.62 B: 5.93 | $^1$H NMR (400 MHz, DMSO-$d_6$) d 12.81 (s, 1H), 10.03 (s, 1H), 8.75 (s, 1H), 8.69 (d, J = 7.5 Hz, 1H), 8.38-8.30 (m, 1H), 8.02-7.86 (m, 4H), 7.81-7.75 (m, 1H), 7.65-7.53 (m, 3H), 6.82 (dd, J = 7.5, 2.6 Hz, 1H), 1.25 (s, 6H) |
| 182 | | 5-methoxy-N-[4-(4-oxo-3,4-dihydrophthalazin-1-yl)phenyl]pyrazolo[1,5-a]pyridine-3-carboxamide | 412.1 | E: 1.30 F: 1.37 | $^1$H NMR (500 MHz, DMSO-$d_6$) d 10.08 (s, 1H), 8.71 (s, 1H), 8.64 (d, J = 7.6 Hz, 1H), 8.33 (d, J = 7.3 Hz, 1H), 7.96-7.86 (m, 4H), 7.76 (d, J = 7.9 Hz, 1H), 7.64-7.52 (m, 3H), 6.90-6.74 (m, 1H), 3.70-3.57 (m, 3H) |

TABLE 3-continued

| Example | R | Name | LCMS (M + H)+ | HPLC Method, RT (min.) | 1H NMR |
|---|---|---|---|---|---|
| 183 | (pyrrolidinylethoxy-pyrazolopyridine carbonyl structure) | N-[4-(4-oxo-3,4-dihydrophthalazin-1-yl)phenyl]-5-[2-(pyrrolidin-1-yl)ethoxy]pyrazolo[1,5-a]pyridine-3-carboxamide | 495.2 | E: 1.08<br>F: 1.07 | 1H NMR (500 MHz, DMSO-d6) d 10.08 (br. s., 1H), 8.71 (br. s., 1H), 8.64 (d, J = 7.3 Hz, 1H), 8.33 (d, J = 6.7 Hz, 1H), 7.98-7.83 (m, 4H), 7.75 (d, J = 7.0 Hz, 1H), 7.63-7.52 (m, 3H), 6.79 (d, J = 4.9 Hz, 1H), 4.20 (br. s., 2H), 3.65-3.42 (m, 4H), 2.87 (d, J = 4.6 Hz, 2H), 1.86 (br. s., 1H), 1.68 (br. s., 4H) |
| 184 | (methoxyethoxy-pyrazolopyridine carbonyl structure) | 5-(2-methoxyethoxy)-N-[4-(4-oxo-3,4-dihydrophthalazin-1-yl)phenyl]pyrazolo[1,5-a]pyridine-3-carboxamide | 456.1 | E: 1.37<br>F: 1.35 | 1H NMR (500 MHz, DMSO-d6) d 12.82 (s, 1H), 10.07 (s, 1H), 8.71 (s, 1H), 8.65 (d, J = 7.3 Hz, 1H), 8.33 (d, J = 7.3 Hz, 1H), 8.03-7.83 (m, 4H), 7.76 (d, J = 7.3 Hz, 1H), 7.63-7.47 (m, 3H), 6.80 (d, J = 7.3 Hz, 1H), 4.22 (br. s., 2H), 3.72 (br. s., 1H), 3.62 (br. s., 1H), 3.58 (d, J = 7.6 Hz, 3H) |
| 185 | (hydroxypropoxy-pyrazolopyridine carbonyl structure) | 5-(2-hydroxypropoxy)-N-[4-(4-oxo-3,4-dihydrophthalazin-1-yl)phenyl]pyrazolo[1,5-a]pyridine-3-carboxamide | 456.2 | E: 1.26<br>F: 1.26 | 1H NMR (500 MHz, DMSO-d6) d 12.84 (s, 1H), 10.07 (s, 1H), 8.80-8.60 (m, 2H), 8.34 (d, J = 7.4 Hz, 1H), 7.97-7.87 (m, 4H), 7.77 (d, J = 7.7 Hz, 1H), 7.67-7.52 (m, 3H), 6.86-6.75 (m, 1H), 4.11-3.91 (m, 2H), 3.67-3.41 (m, 1H), 1.39-1.14 (m, 3H) |
| 186 | (hydroxyethoxy-pyrazolopyridine carbonyl structure) | 5-(2-hydroxyethoxy)-N-[4-(4-oxo-3,4-dihydrophthalazin-1-yl)phenyl]pyrazolo[1,5-a]pyridine-3-carboxamide | 412.2 | E: 1.15<br>F: 1.15 | 1H NMR (500 MHz, DMSO-d6) d 12.83 (s, 1H), 10.05 (s, 1H), 8.75 (s, 1H), 8.70 (d, J = 7.4 Hz, 1H), 8.35 (d, J = 7.4 Hz, 1H), 8.03-7.84 (m, 4H), 7.78 (d, J = 7.7 Hz, 1H), 7.64-7.50 (m, 3H), 6.81 (dd, J = 7.4, 2.7 Hz, 1H), 4.14 (t, J = 4.7 Hz, 2H), 3.79 (d, J = 4.4 Hz, 2H) |
| 187 | (morpholinoethoxy-pyrazolopyridine carbonyl structure) | 5-[2-(morpholin-4-yl)ethoxy]-N-[4-(4-oxo-3,4-dihydrophthalazin-1-yl)phenyl]pyrazolo[1,5-a]pyridine-3-carboxamide | 511.1 | E: 1.30<br>F: 1.06 | 1H NMR (500 MHz, DMSO-d6) d 10.10 (s, 1H), 8.76 (s, 1H), 8.69 (d, J = 7.4 Hz, 1H), 8.35 (d, J = 7.4 Hz, 1H), 8.02-7.87 (m, 4H), 7.78 (d, J = 7.7 Hz, 1H), 7.63 (br. s., 1H), 7.57 (d, J = 8.1 Hz, 2H), 6.81 (d, J = 5.0 Hz, 1H), 4.23 (t, J = 5.2 Hz, 2H), 2.82-2.73 (m, 2H) |
| 188 | (6-morpholinoethoxy-pyrazolopyridine carbonyl structure) | 6-[2-(morpholin-4-yl)ethoxy]-N-[4-(4-oxo-3,4-dihydrophthalazin-1-yl)phenyl]pyrazolo[1,5-a]pyridine-3-carboxamide | 511.1 | E: 1.34<br>F: 1.07 | 1H NMR (500 MHz, DMSO-d6) d 10.13 (br. s., 1H), 8.74 (br. s., 1H), 8.58 (br. s., 1H), 8.35 (d, J = 7.7 Hz, 1H), 8.17 (d, J = 9.8 Hz, 1H), 7.99-7.87 (m, 4H), 7.78 (d, J = 7.7 Hz, 1H), 7.58 (d, J = 7.7 Hz, 2H), 7.37 (d, J = 9.8 Hz, 1H), 4.19 (br. s., 2H), 3.59 (br. s., 4H), 2.73 (d, J = 5.0 Hz, 2H) |

TABLE 3-continued

| Example | R | Name | LCMS (M + H)+ | HPLC Method, RT (min.) | ¹H NMR |
|---|---|---|---|---|---|
| 189 | (5-methyl-1-phenyl-1H-pyrazole-4-carbonyl) | 5-methyl-N-[4-(4-oxo-3,4-dihydrophthalazin-1-yl)phenyl]-1-phenyl-1H-pyrazole-4-carboxamide | 422.2 | E: 1.51 F: 1.51 | (500 MHz, DMSO-$d_6$) δ ppm 12.84 (s, 1H), 10.10 (s, 1H), 8.51-8.26 (m, 2H), 8.01-7.87 (m, 4H), 7.76 (d, J = 7.7 Hz, 1H), 7.64-7.42 (m, 7H), 2.57 (s, 3H) |
| 190 | (1-phenyl-5-(trifluoromethyl)-1H-pyrazole-4-carbonyl) | N-[4-(4-oxo-3,4-dihydrophthalazin-1-yl)phenyl]-1-phenyl-5-(trifluoromethyl)-1H-pyrazole-4-carboxamide | 476.3 | E: 1.67 F: 1.67 | (500 MHz, DMSO-$d_6$) δ ppm 12.85 (s, 1H), 10.78 (s, 1H), 8.35 (br. s., 2H), 7.89 (d, J = 8.1 Hz, 4H), 7.75 (d, J = 7.1 Hz, 1H), 7.67-7.59 (m, 5H), 7.56 (br. s., 2H) |
| 191 | (1-phenyl-1H-pyrazole-4-carbonyl) | N-[4-(4-oxo-3,4-dihydrophthalazin-1-yl)phenyl]-1-phenyl-1H-pyrazole-4-carboxamide | 408.3 | E: 1.48 F: 1.47 | (500 MHz, DMSO-$d_6$) δ ppm 12.85 (s, 1H), 10.23 (s, 1H), 9.14 (s, 1H), 8.55-8.17 (m, 2H), 7.92 (dd, J = 13.6, 8.2 Hz, 6H), 7.77 (d, J = 7.4 Hz, 1H), 7.60 (d, J = 8.4 Hz, 2H), 7.56 (t, J = 7.9 Hz, 2H), 7.44-7.30 (m, 1H) |
| 192 | (1-methyl-5-phenyl-1H-pyrazole-4-carbonyl) | 1-methyl-N-[4-(4-oxo-3,4-dihydrophthalazin-1-yl)phenyl]-5-phenyl-1H-pyrazole-4-carboxamide | 422.3 | E: 1.38 F: 1.38 | (500 MHz, DMSO-$d_6$) δ ppm 12.81 (s, 1H), 9.97 (s, 1H), 8.33 (d, J = 7.1 Hz, 1H), 8.19 (s, 1H), 7.94 (s, 1H), 7.92-7.84 (m, 2H), 7.79 (d, J = 8.4 Hz, 2H), 7.72 (d, J = 7.4 Hz, 1H), 7.56-7.43 (m, 6H), 3.71 (s, 3H) |
| 193 | (3-(3-chloro-2-fluorophenyl)-4,5-dihydroisoxazole-5-carbonyl) | 3-(3-chloro-2-fluorophenyl)-N-[4-(4-oxo-3,4-dihydrophthalazin-1-yl)phenyl]-4,5-dihydro-1,2-oxazole-5-carboxamide | 463.2 | E: 1.69 F: 1.70 | ¹H NMR (500 MHz, DMSO-$d_6$) d 12.83 (s, 1H), 10.57 (s, 1H), 8.33 (d, J = 7.1 Hz, 1H), 7.93-7.80 (m, 4H), 7.80-7.67 (m, 3H), 7.57 (d, J = 8.4 Hz, 2H), 7.34 (t, J = 7.9 Hz, 1H), 5.42-5.32 (m, 1H), 3.81 (d, J = 10.4 Hz, 2H), 3.39 (d, J = 5.7 Hz, 1H) |
| 194 | (5-(2-hydroxy-3-methoxypropoxy)pyrazolo[1,5-a]pyridine-3-carbonyl) | 5-(2-hydroxy-3-methoxypropoxy)-N-[4-(4-oxo-3,4-dihydrophthalazin-1-yl)phenyl]pyrazolo[1,5-a]pyridine-3-carboxamide | 486.1 | A: 5.99 B: 5.45 | ¹H NMR (500 MHz, DMSO-$d_6$) d 12.81 (s, 1H), 10.04 (s, 1H), 8.75 (s, 1H), 8.69 (d, J = 7.4 Hz, 1H), 8.36-8.33 (m, 1H), 8.01-7.86 (m, 4H), 7.78 (dd, J = 7.7, 0.8 Hz, 1H), 7.63-7.56 (m, 3H), 6.81 (dd, J = 7.4, 2.8 Hz, 1H), 4.15-4.09 (m, 1H), 4.05-3.99 (m, 2H), 3.48-3.41 (m, 2H), 3.35-3.30 (m, 3H) |
| 195 | (1-(3-methylphenyl)-1H-imidazole-4-carbonyl) | 1-(3-methylphenyl)-N-[4-(4-oxo-3,4-dihydrophthalazin-1-yl)phenyl]-1H-imidazole-4-carboxamide | 422.1 | A: 8.34 B: 7.46 | ¹H NMR (500 MHz, DMSO-$d_6$) d 12.81 (s, 1H), 10.20 (s, 1H), 8.45 (s, 1H), 8.48 (s, 1H), 8.35 (d, J = 7.2 Hz, 1H), 8.06 (d, J = 8.8 Hz, 2H), 7.96-7.87 (m, 2H), 7.77 (d, J = 8.0 Hz, 1H), 7.66 (s, 1H), 7.61-7.54 (m, 3H), 7.44 (s, 1H), 7.26 (d, J = 7.7 Hz, 1H), 6.51 (s, 1H), 2.41 (s, 3H) |
| 196 | (3-phenyl-4,5-dihydroisoxazole-5-carbonyl) | N-[4-(4-oxo-3,4-dihydrophthalazin-1-yl)phenyl]-3-phenyl-4,5-dihydro-1,2-oxazole-5-carboxamide | 411.2 | E: 1.56 F: 1.58 | ¹H NMR (500 MHz, DMSO-$d_6$) d 12.82 (s, 1H), 10.50 (s, 1H), 8.36-8.25 (m, 1H), 7.96-7.82 (m, 4H), 7.77-7.66 (m, 3H), 7.55 (d, J = 8.2 Hz, 2H), 7.52-7.41 (m, 3H), 5.32 (dd, J = 10.4, 7.9 Hz, 1H), 3.79-3.68 (m, 2H) |

TABLE 3-continued

| Example | R | Name | LCMS (M + H)+ | HPLC Method, RT (min.) | $^1$H NMR |
|---|---|---|---|---|---|
| 197 | | 1-(2-methoxyphenyl)-N-[4-(4-oxo-3,4-dihydrophthalazin-1-yl)phenyl]-1H-pyrazole-4-carboxamide | 438.3 | E: 1.51 F: 1.51 | (500 MHz, DMSO-d$_6$) δ ppm 12.85 (s, 1H), 10.21 (s, 1H), 8.83 (s, 1H), 8.34 (d, J = 7.1 Hz, 1H), 8.29 (s, 1H), 7.97-7.85 (m, 4H), 7.76 (d, J = 7.7 Hz, 1H), 7.67 (d, J = 7.1 Hz, 1H), 7.59 (d, J = 8.4 Hz, 2H), 7.47-7.39 (m, 1H), 7.30 (d, J = 8.4 Hz, 1H), 7.13 (t, J = 7.6 Hz, 1H), 3.91 (s, 3H) |
| 198 | | 1-(3-chlorophenyl)-N-[4-(4-oxo-3,4-dihydrophthalazin-1-yl)phenyl]-1H-pyrazole-4-carboxamide | 442.2 | E: 1.75 F: 1.75 | (500 MHz, DMSO-d$_6$) δ ppm 12.85 (s, 1H), 10.24 (s, 1H), 9.20 (s, 1H), 8.39 (s, 1H), 8.34 (d, J = 7.4 Hz, 1H), 8.01 (br. s., 1H), 7.96-7.87 (m, 5H), 7.77 (d, J = 7.4 Hz, 1H), 7.63-7.55 (m, 3H), 7.46 (d, J = 8.1 Hz, 1H) |
| 199 | | 5-chloro-N-[4-(4-oxo-3,4-dihydrophthalazin-1-yl)phenyl]-1-phenyl-1H-pyrazole-4-carboxamide | 442.2 | E: 1.62 F: 1.62 | (500 MHz, DMSO-d$_6$) δ ppm 12.85 (s, 1H), 10.31 (s, 1H), 8.47 (s, 1H), 8.35 (d, J = 7.1 Hz, 1H), 7.98-7.84 (m, 4H), 7.76 (d, J = 7.4 Hz, 1H), 7.67-7.54 (m, 7H) |
| 200 | | 1-benzyl-N-[4-(4-oxo-3,4-dihydrophthalazin-1-yl)phenyl]-1H-pyrazole-4-carboxamide | 422.2 | E: 1.44 F: 1.44 | (500 MHz, DMSO-d$_6$) δ ppm 12.83 (s, 1H), 10.07 (s, 1H), 8.48 (s, 1H), 8.34 (d, J = 7.4 Hz, 1H), 8.10 (s, 1H), 7.97-7.84 (m, 4H), 7.75 (d, J = 7.7 Hz, 1H), 7.56 (d, J = 8.4 Hz, 2H), 7.42-7.35 (m, 2H), 7.34-7.27 (m, 3H), 5.40 (s, 2H) |
| 201 | | 5-(adamantan-1-yl)-1-methyl-N-[4-(4-oxo-3,4-dihydrophthalazin-1-yl)phenyl]-1H-pyrazole-3-carboxamide | 480.3 | E: 2.20 F: 2.21 | (500 MHz, DMSO-d$_6$) δ ppm 12.83 (s, 1H), 10.16 (s, 1H), 8.34 (d, J = 7.7 Hz, 1H), 7.97 (d, J = 8.4 Hz, 2H), 7.94-7.85 (m, 2H), 7.75 (d, J = 7.4 Hz, 1H), 7.55 (d, J = 8.4 Hz, 2H), 6.56 (s, 1H), 4.08 (s, 3H), 2.06 (br. s., 3H), 2.00 (br. s., 6H), 1.84-1.65 (m, 6H) |
| 202 | | 1-(3-chloro-2-fluorophenyl)-5-methyl-N-[4-(4-oxo-3,4-dihydrophthalazin-1-yl)phenyl]-1H-pyrazole-4-carboxamide | 474.2 | E: 1.72 F: 1.72 | (500 MHz, DMSO-d$_6$) δ ppm 12.84 (s, 1H), 10.15 (s, 1H), 8.42 (s, 1H), 8.34 (d, J = 7.1 Hz, 1H), 7.98-7.87 (m, 4H), 7.84 (t, J = 7.1 Hz, 1H), 7.76 (d, J = 7.4 Hz, 1H), 7.64 (t, J = 6.9 Hz, 1H), 7.58 (d, J = 8.1 Hz, 2H), 7.46 (t, J = 7.9 Hz, 1H), 2.45 (s, 3H) |
| 203 | | 1-(3-methoxyphenyl)-N-[4-(4-oxo-3,4-dihydrophthalazin-1-yl)phenyl]-1H-pyrazole-4-carboxamide | 438.2 | E: 1.56 F: 1.64 | (500 MHz, DMSO-d$_6$) δ ppm 10.31 (s, 1H), 8.69 (d, J = 2.5 Hz, 1H), 8.39-8.32 (m, 1H), 7.98-7.88 (m, 5H), 7.83 (dd, J = 4.8, 3.4 Hz, 2H), 7.77 (d, J = 7.4 Hz, 1H), 7.66 (d, J = 1.7 Hz, 1H), 7.62-7.56 (m, 2H), 6.64-6.59 (m, 1H), 4.05 (s, 3H) |

TABLE 3-continued

| Example | R | Name | LCMS (M + H)+ | HPLC Method, RT (min.) | 1H NMR |
|---|---|---|---|---|---|
| 204 | (pyrazole with N-ethyl, acyl at 3-position) | 1-ethyl-N-[4-(4-oxo-3,4-dihydrophthalazin-1-yl)phenyl]-1H-pyrazole-3-carboxamide | 360.2 | E: 1.34<br>F: 1.36 | (500 MHz, DMSO-d$_6$) δ ppm 12.82 (s, 1H), 10.17 (s, 1H), 8.35-8.31 (m, 1H), 7.97 (d, J = 8.5 Hz, 2H), 7.94-7.86 (m, 3H), 7.74 (d, J = 7.0 Hz, 1H), 7.55 (d, J = 8.5 Hz, 2H), 6.80 (d, J = 2.4 Hz, 1H), 4.26 (q, J = 7.2 Hz, 2H), 1.44 (t, J = 7.3 Hz, 3H) |
| 205 | (1,5-dimethylpyrazole, acyl at 3) | 1,5-dimethyl-N-[4-(4-oxo-3,4-dihydrophthalazin-1-yl)phenyl]-1H-pyrazole-3-carboxamide | 360.2 | E: 1.30<br>F: 1.32 | (500 MHz, DMSO-d$_6$) δ ppm 12.81 (s, 1H), 10.12 (s, 1H), 8.33 (d, J = 7.0 Hz, 1H), 7.96 (d, J = 8.2 Hz, 2H), 7.90 (quin, J = 6.9 Hz, 2H), 7.74 (d, J = 7.6 Hz, 1H), 7.54 (d, J = 8.5 Hz, 2H), 6.59 (s, 1H), 3.84 (s, 3H), 2.31 (s, 3H) |
| 206 | (5-tert-butyl-1-methylpyrazole, acyl at 3) | 5-tert-butyl-1-methyl-N-[4-(4-oxo-3,4-dihydrophthalazin-1-yl)phenyl]-1H-pyrazole-3-carboxamide | 402.2 | E: 1.68<br>F: 1.72 | (500 MHz, DMSO-d$_6$) δ ppm 12.82 (s, 1H), 10.12 (s, 1H), 8.33 (d, J = 7.0 Hz, 1H), 7.99-7.85 (m, 4H), 7.74 (d, J = 7.3 Hz, 1H), 7.54 (d, J = 8.5 Hz, 2H), 6.59 (s, 1H), 4.03 (s, 3H), 1.36 (s, 9H) |
| 207 | (1-methyl-5-phenylpyrazole, acyl at 3) | 1-methyl-N-[4-(4-oxo-3,4-dihydrophthalazin-1-yl)phenyl]-5-phenyl-1H-pyrazole-3-carboxamide | 422.2 | E: 1.70<br>F: 1.75 | (500 MHz, DMSO-d$_6$) δ ppm 12.83 (s, 1H), 10.31 (s, 1H), 8.34 (d, J = 7.9 Hz, 1H), 7.99 (d, J = 8.5 Hz, 2H), 7.94-7.85 (m, 2H), 7.75 (d, J = 7.6 Hz, 1H), 7.64-7.58 (m, 2H), 7.58-7.51 (m, 4H), 7.52-7.44 (m, 1H), 6.95 (s, 1H), 3.97 (s, 3H) |
| 208 | (1-benzyl-5-methylpyrazole, acyl at 3) | 1-benzyl-5-methyl-N-[4-(4-oxo-3,4-dihydrophthalazin-1-yl)phenyl]-1H-pyrazole-3-carboxamide | 436.2 | E: 1.73<br>F: 1.76 | (500 MHz, DMSO-d$_6$) δ ppm 12.82 (s, 1H), 10.18 (s, 1H), 8.36-8.31 (m, 1H), 7.97 (d, J = 8.5 Hz, 2H), 7.94-7.85 (m, 2H), 7.74 (d, J = 7.3 Hz, 1H), 7.54 (d, J = 8.5 Hz, 2H), 7.40-7.33 (m, 2H), 7.32-7.25 (m, 1H), 7.17 (d, J = 7.3 Hz, 2H), 6.67 (s, 1H), 5.44 (s, 2H), 2.25 (s, 3H) |
| 209 | (1-(3-methylphenyl)-2-oxopyrrolidine, acyl at 3) | 1-(3-methylphenyl)-2-oxo-N-[4-(4-oxo-3,4-dihydrophthalazin-1-yl)phenyl]pyrrolidine-3-carboxamide | 439.2 | E: 1.63<br>F: 1.66 | 1H NMR (500 MHz, DMSO-d$_6$) d 12.82 (s, 1H), 10.52 (s, 1H), 8.47-8.30 (m, 1H), 7.94-7.86 (m, 2H), 7.83-7.78 (m, J = 8.2 Hz, 2H), 7.72 (d, J = 7.3 Hz, 1H), 7.59-7.52 (m, J = 8.5 Hz, 2H), 7.49-7.43 (m, 2H), 7.27 (t, J = 7.8 Hz, 1H), 6.99 (d, J = 7.3 Hz, 1H), 3.95-3.86 (m, 2H), 3.80 (t, J = 8.7 Hz, 1H), 2.48-2.35 (m, 2H), 2.31 (s, 3H) |
| 210 | (1-(4-methylphenyl)-5-oxopyrrolidine, acyl at 3) | 1-(4-methylphenyl)-5-oxo-N-[4-(4-oxo-3,4-dihydrophthalazin-1-yl)phenyl]pyrrolidine-3-carboxamide | 439.2 | E: 1.49<br>F: 1.50 | 1H NMR (500 MHz, DMSO-d$_6$) d 12.81 (s, 1H), 10.44 (s, 1H), 8.43-8.25 (m, 1H), 7.95-7.84 (m, 2H), 7.80-7.74 (m, J = 8.2 Hz, 2H), 7.70 (d, J = 7.0 Hz, 1H), 7.53 (t, J = 8.4 Hz, 4H), 7.24-7.15 (m, J = 8.2 Hz, 2H), 4.09 (t, J = 9.3 Hz, 1H), 3.98 (dd, J = 9.8, 6.1 Hz, 1H), 2.89-2.68 (m, 3H), 2.27 (s, 3H) |

TABLE 3-continued

| Example | R | Name | LCMS (M + H)+ | HPLC Method, RT (min.) | $^1$H NMR |
|---|---|---|---|---|---|
| 211 | | 1-(3-chloro-2-fluorophenyl)-5-oxo-N-[4-(4-oxo-3,4-dihydrophthalazin-1-yl)phenyl]pyrrolidine-3-carboxamide | 477.2 | E: 1.48 F: 1.49 | $^1$H NMR (500 MHz, DMSO-d$_6$) d 12.82 (s, 1H), 10.44 (s, 1H), 8.40-8.26 (m, 1H), 7.94-7.86 (m, 2H), 7.78 (d, J = 8.5 Hz, 2H), 7.70 (d, J = 7.3 Hz, 1H), 7.59-7.51 (m, 3H), 7.46 (t, J = 6.9 Hz, 1H), 7.28 (t, J = 8.4 Hz, 2H), 4.12-4.03 (m, 1H), 4.00-3.91 (m, 1H), 2.85-2.63 (m, 3H) |
| 212 | | 1-methyl-N-[4-(4-oxo-3,4-dihydrophthalazin-1-yl)phenyl]-1H-pyrazole-4-carboxamide | 346.2 | E: 1.09 F: 1.10 | (500 MHz, DMSO-d$_6$) δ ppm 12.82 (s, 1H), 10.06 (s, 1H), 8.35-8.32 (m, 1H), 8.31 (s, 1H), 8.04 (s, 1H), 7.93-7.83 (m, 4H), 7.74 (d, J = 7.3 Hz, 1H), 7.55 (d, J = 8.5 Hz, 2H), 3.89 (s, 3H) |
| 213 | | 5-methyl-N-[4-(4-oxo-3,4-dihydrophthalazin-1-yl)phenyl]-1-phenyl-1H-pyrazole-3-carboxamide | 422.2 | E: 1.73 F: 1.77 | (500 MHz, DMSO-d$_6$) δ ppm 12.83 (s, 1H), 10.24 (s, 1H), 8.35-8.29 (m, 1H), 7.96 (d, J = 8.5 Hz, 2H), 7.94-7.83 (m, 2H), 7.74 (d, J = 7.3 Hz, 1H), 7.65-7.61 (m, 2H), 7.60-7.54 (m, 4H), 7.53-7.48 (m, 1H), 6.82 (s, 1H), 2.35 (s, 3H) |
| 214 | | 5-methyl-1-(2-methylphenyl)-N-[4-(4-oxo-3,4-dihydrophthalazin-1-yl)phenyl]-1H-pyrazole-4-carboxamide | 436.2 | E: 1.64 F: 1.67 | (500 MHz, DMSO-d$_6$) δ ppm 12.83 (s, 1H), 10.09 (s, 1H), 8.38-8.31 (m, 2H), 7.98-7.84 (m, 4H), 7.75 (d, J = 7.6 Hz, 1H), 7.56 (d, J = 8.5 Hz, 2H), 7.49-7.42 (m, 2H), 7.39 (t, J = 6.9 Hz, 1H), 7.31 (d, J = 7.6 Hz, 1H), 3.61 (s, 3H), 2.31 (s, 3H) |
| 215 | | 2-oxo-N-[4-(4-oxo-3,4-dihydrophthalazin-1-yl)phenyl]-1-phenylpyrrolidine-3-carboxamide | 425.1 | E: 1.50 F: 1.52 | $^1$H NMR (500 MHz, DMSO-d$_6$) d 12.82 (s, 1H), 10.53 (s, 1H), 8.35-8.30 (m, 1H), 7.94-7.86 (m, 2H), 7.81 (d, J = 8.5 Hz, 2H), 7.72 (d, J = 7.0 Hz, 1H), 7.69-7.62 (m, J = 7.9 Hz, 2H), 7.59-7.52 (m, J = 8.5 Hz, 2H), 7.40 (t, J = 7.9 Hz, 2H), 7.17 (t, J = 7.3 Hz, 1H), 4.01-3.88 (m, 2H), 3.84-3.77 (m, 1H), 2.48-2.32 (m, 2H) |
| 216 | | 1-(2-methoxyphenyl)-2-oxo-N-[4-(4-oxo-3,4-dihydrophthalazin-1-yl)phenyl]pyrrolidine-3-carboxamide | 455.1 | E: 1.43 F: 1.45 | $^1$H NMR (500 MHz, DMSO-d$_6$) d 12.82 (s, 1H), 10.48 (s, 1H), 8.45-8.25 (m, 1H), 7.93-7.86 (m, 2H), 7.81 (d, J = 8.5 Hz, 2H), 7.74-7.70 (m, 1H), 7.55 (d, J = 8.5 Hz, 2H), 7.36-7.29 (m, 1H), 7.22 (dd, J = 7.6, 1.2 Hz, 1H), 7.11 (d, J = 8.2 Hz, 1H), 6.98 (t, J = 7.6 Hz, 1H), 3.79 (s, 3H), 3.73-3.67 (m, 2H), 2.41-2.31 (m, 1H) |
| 217 | | 5-oxo-N-[4-(4-oxo-3,4-dihydrophthalazin-1-yl)phenyl]-1-phenylpyrrolidine-3-carboxamide | 425 | E: 1.93 F: 1.97 | $^1$H NMR (500 MHz, DMSO-d$_6$) d 12.82 (s, 1H), 10.46 (s, 1H), 8.33 (d, J = 7.6 Hz, 1H), 7.93-7.86 (m, 2H), 7.78 (d, J = 7.9 Hz, 2H), 7.70 (d, J = 7.3 Hz, 1H), 7.68-7.62 (m, J = 8.5 Hz, 2H), 7.57-7.51 (m, J = 8.2 Hz, 2H), 7.38 (t, J = 7.6 Hz, 2H), 7.15 (t, J = 7.3 Hz, 1H), 4.13 (t, J = 9.2 Hz, 1H), 4.01 (dd, J = 9.8, 5.8 Hz, 1H), 2.95-2.82 (m, 2H), 2.82-2.75 (m, 1H) |

TABLE 3-continued

| Example | R | Name | LCMS (M + H)+ | HPLC Method, RT (min.) | 1H NMR |
|---|---|---|---|---|---|
| 218 | 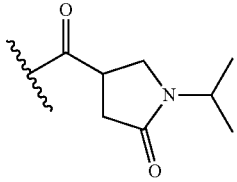 [SMILES: *C(=O)C1CC(=O)N(C(C)C)C1] | 5-oxo-N-[4-(4-oxo-3,4-dihydrophthalazin-1-yl)phenyl]-1-(propan-2-yl)pyrrolidine-3-carboxamide | 391.1 | E: 1.63<br>F: 1.66 | 1H NMR (500 MHz, DMSO-d6) d 10.35 (s, 1H), 8.41-8.26 (m, 1H), 8.02-7.82 (m, 2H), 7.80-7.66 (m, 3H), 7.53 (d, J = 8.5 Hz, 2H), 4.14 (dt, J = 13.7, 6.8 Hz, 1H), 3.62 (s, 2H), 3.43 (dd, J = 9.8, 6.1 Hz, 1H), 3.32 (t, J = 7.2 Hz, 1H), 2.62-2.53 (m, 1H), 1.07 (d, J = 7.0 Hz, 3H), 1.08 (d, J = 7.0 Hz, 3H) |
| 219 | 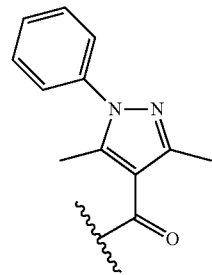 [SMILES: *C(=O)c1c(C)nn(-c2ccccc2)c1C] | 3,5-dimethyl-N-[4-(4-oxo-3,4-dihydrophthalazin-1-yl)phenyl]-1-phenyl-1H-pyrazole-4-carboxamide | 436.3 | E: 1.44<br>F: 1.53 | (500 MHz, DMSO-d6) δ ppm 12.83 (s, 1H), 10.08 (s, 1H), 8.34 (d, J = 6.7 Hz, 1H), 7.96-7.89 (m, 2H), 7.89-7.83 (m, 2H), 7.87 (d, J = 8.4 Hz, 2H), 7.76 (d, J = 7.1 Hz, 1H), 7.61-7.53 (m, 3H), 7.53-7.43 (m, 2H), 2.43 (s, 3H), 2.38 (s, 3H) |
| 220 | 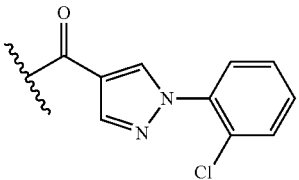 [SMILES: *C(=O)c1cnn(-c2ccccc2Cl)c1] | 1-(2-chlorophenyl)-N-[4-(4-oxo-3,4-dihydrophthalazin-1-yl)phenyl]-1H-pyrazole-4-carboxamide | 442.1 | E: 1.59<br>F: 1.61 | (500 MHz, DMSO-d6) δ ppm 12.82 (s, 1H), 10.19 (s, 1H), 8.81 (s, 1H), 8.38-8.32 (m, 2H), 7.95-7.91 (m, 3H), 7.90-7.87 (m, 1H), 7.80-7.73 (m, 2H), 7.71-7.67 (m, 1H), 7.60 (d, J = 8.5 Hz, 2H), 7.58-7.54 (m, 2H) |
| 221 | 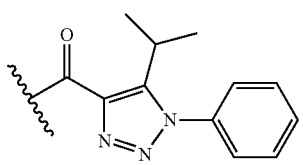 [SMILES: *C(=O)c1nnn(-c2ccccc2)c1C(C)C] | N-[4-(4-oxo-3,4-dihydrophthalazin-1-yl)phenyl]-1-phenyl-5-(propan-2-yl)-1H-1,2,3-triazole-4-carboxamide | 451.3 | E: 1.84<br>F: 1.84 | 1H NMR (500 MHz, DMSO-d6) d 12.85 (s, 1H), 10.76 (s, 1H), 8.35 (d, J = 7.4 Hz, 1H), 8.05 (d, J = 8.4 Hz, 2H), 7.98-7.85 (m, 2H), 7.76 (d, J = 7.7 Hz, 1H), 7.69 (d, J = 3.7 Hz, 3H), 7.59 (d, J = 8.1 Hz, 4H), 3.26-3.18 (m, 1H), 1.33 (d, J = 7.1 Hz, 6H) |
| 222 | 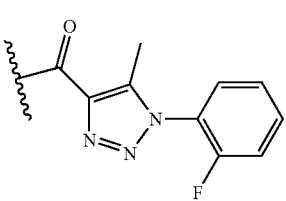 [SMILES: *C(=O)c1nnn(-c2ccccc2F)c1C] | 1-(2-fluorophenyl)-5-methyl-N-[4-(4-oxo-3,4-dihydrophthalazin-1-yl)phenyl]-1H-1,2,3-triazole-4-carboxamide | 441.2 | E: 1.66<br>F: 1.66 | 1H NMR (500 MHz, DMSO-d6) d 12.84 (s, 1H), 10.80 (s, 1H), 8.34 (d, J = 7.4 Hz, 1H), 8.11-8.02 (m, J = 8.4 Hz, 2H), 7.98-7.87 (m, 2H), 7.83-7.72 (m, 3H), 7.64 (t, J = 9.1 Hz, 1H), 7.60-7.56 (m, J = 8.4 Hz, 2H), 7.52 (t, J = 7.6 Hz, 1H), 3.46-3.34 (m, 1H) |
| 223 | 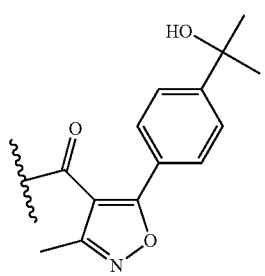 [SMILES: *C(=O)c1c(C)noc1-c1ccc(C(C)(C)O)cc1] | 5-[4-(2-hydroxypropan-2-yl)phenyl]-3-methyl-N-[4-(4-oxo-3,4-dihydrophthalazin-1-yl)phenyl]-1,2-oxazole-4-carboxamide | 481.2 | E: 1.47<br>F: 1.42 | 1H NMR (500 MHz, DMSO-d6) d 8.35 (d, J = 6.7 Hz, 1H), 7.91 (t, J = 5.7 Hz, 2H), 7.84 (d, J = 8.4 Hz, 2H), 7.81-7.72 (m, 3H), 7.61 (d, J = 8.4 Hz, 2H), 7.64 (d, J = 8.4 Hz, 3H), 2.39 (s, 3H), 1.43 (s, 6H) |

TABLE 3-continued

| Example | R | Name | LCMS (M + H)+ | HPLC Method, RT (min.) | ¹H NMR |
|---|---|---|---|---|---|
| 224 | | 5-[4-(hydroxymethyl)phenyl]-3-methyl-N-[4-(4-oxo-3,4-dihydrophthalazin-1-yl)phenyl]-1,2-oxazole-4-carboxamide | 453.2 | E: 1.33 F: 1.36 | ¹H NMR (500 MHz, DMSO-d₆) d 10.76 (s, 1H), 8.40-8.30 (m, 1H), 7.95-7.88 (m, 2H), 7.86-7.73 (m, 5H), 7.60 (d, J = 8.5 Hz, 2H), 7.50 (d, J = 8.3 Hz, 2H), 5.33 (br. s., 1H), 4.56 (d, J = 4.4 Hz, 2H), 2.40 (s, 3H) |
| 225 | | 1-(3-chlorophenyl)-5-ethyl-N-[4-(4-oxo-3,4-dihydrophthalazin-1-yl)phenyl]-1H-1,2,3-triazole-4-carboxamide | 470.3 | E: 1.61 F: 1.61 | ¹H NMR (500 MHz, DMSO-d₆) d 12.82 (s, 1H), 10.79 (s, 1H), 8.35 (d, J = 7.6 Hz, 1H), 8.11-8.04 (m, J = 8.2 Hz, 2H), 7.96-7.85 (m, 3H), 7.79-7.69 (m, 3H), 7.68-7.64 (m, 1H), 7.61-7.55 (m, J = 8.5 Hz, 2H), 3.03 (q, J = 7.3 Hz, 2H), 1.09 (t, J = 7.5 Hz, 3H) |
| 226 | | N-[4-(4-oxo-3,4-dihydrophthalazin-1-yl)phenyl]-1-phenyl-1H-pyrazole-3-carboxamide | 408.1 | E: 1.58 F: 1.67 | (500 MHz, DMSO-d₆) δ ppm 12.85 (s, 1H), 10.38 (s, 1H), 8.68 (d, J = 2.4 Hz, 1H), 8.35 (d, J = 7.7 Hz, 1H), 8.04 (dd, J = 8.1, 4.4 Hz, 4H), 7.97-7.86 (m, 2H), 7.77 (d, J = 7.7 Hz, 1H), 7.64-7.52 (m, 4H), 7.42 (t, J = 7.4 Hz, 1H), 7.08 (d, J = 2.4 Hz, 1H) |
| 227 | | 1-methyl-N-[4-(4-oxo-3,4-dihydrophthalazin-1-yl)phenyl]-1H-pyrazole-3-carboxamide | 346.1 | E: 1.07 F: 1.07 | (500 MHz, DMSO-d₆) δ ppm 12.83 (s, 1H), 10.27 (s, 1H), 8.34 (d, J = 7.4 Hz, 1H), 8.00 (d, J = 8.4 Hz, 2H), 7.96-7.83 (m, 3H), 7.75 (d, J = 7.4 Hz, 1H), 7.55 (d, J = 8.4 Hz, 2H), 6.80 (d, J = 2.0 Hz, 1H), 3.98 (s, 3H) |
| 228 | | 3-methyl-N-[4-(4-oxo-3,4-dihydrophthalazin-1-yl)phenyl]-1-phenyl-1H-pyrazole-4-carboxamide | 422.2 | E: 1.66 F: 1.66 | (500 MHz, DMSO-d₆) δ ppm 12.84 (s, 1H), 10.09 (s, 1H), 9.11 (s, 1H), 8.34 (d, J = 8.4 Hz, 1H), 7.97-7.86 (m, 4H), 7.82 (d, J = 8.1 Hz, 2H), 7.76 (d, J = 7.7 Hz, 1H), 7.61-7.51 (m, 4H), 7.41-7.33 (m, 1H) |
| 229 | | 1-methyl-N-[4-(4-oxo-3,4-dihydrophthalazin-1-yl)phenyl]-5-propyl-1H-pyrazole-3-carboxamide | 388.1 | E: 1.49 F: 1.49 | (500 MHz, DMSO-d₆) δ ppm 12.82 (s, 1H), 10.18 (s, 1H), 8.34 (d, J = 7.1 Hz, 1H), 7.99 (d, J = 8.4 Hz, 2H), 7.95-7.84 (m, 2H), 7.75 (d, J = 7.1 Hz, 1H), 7.54 (d, J = 8.4 Hz, 2H), 6.60 (s, 1H), 3.87 (s, 3H), 2.65 (t, J = 7.6 Hz, 2H), 1.65 (sxt, J = 7.4 Hz, 2H), 0.97 (t, J = 7.2 Hz, 3H) |
| 230 | | N-[4-(4-oxo-3,4-dihydrophthalazin-1-yl)phenyl]-2-phenyl-1H-imidazole-4-carboxamide | 408.2 | E: 1.23 F: 1.49 | ¹H NMR (500 MHz, DMSO-d₆) d 12.82 (s, 1H), 10.05 (s, 1H), 8.34 (d, J = 7.6 Hz, 1H), 8.14-8.06 (m, J = 7.6 Hz, 2H), 8.04-7.97 (m, 3H), 7.96-7.87 (m, 2H), 7.77 (d, J = 7.9 Hz, 1H), 7.61-7.54 (m, J = 8.2 Hz, 2H), 7.52 (t, J = 7.5 Hz, 2H), 7.44 (t, J = 7.3 Hz, 1H) |

TABLE 3-continued

| Example | R | Name | LCMS (M + H)+ | HPLC Method, RT (min.) | 1H NMR |
|---|---|---|---|---|---|
| 231 | | N-[4-(4-oxo-3,4-dihydrophthalazin-1-yl)phenyl]-1-phenyl-5-propyl-1H-1,2,3-triazole-4-carboxamide | 451.1 | E: 1.93 F: 1.95 | 1H NMR (500 MHz, DMSO-d$_6$) d 12.83 (s, 1H), 10.73 (s, 1H), 8.35 (d, J = 7.0 Hz, 1H), 8.10-8.00 (m, J = 8.2 Hz, 2H), 7.96-7.86 (m, 2H), 7.76 (d, J = 7.9 Hz, 1H), 7.71-7.65 (m, 3H), 7.64-7.61 (m, 2H), 7.60-7.54 (m, J = 8.5 Hz, 2H), 3.00 (t, J = 7.5 Hz, 2H), 1.54-1.42 (m, 2H), 0.76 (t, J = 7.3 Hz, 3H) |
| 232 | | 5-methyl-N-[4-(4-oxo-3,4-dihydrophthalazin-1-yl)phenyl]-1-[3-(trifluoromethyl)phenyl]-1H-1,2,3-triazole-4-carboxamide | 491.1 | E: 1.92 F: 1.91 | 1H NMR (500 MHz, DMSO-d$_6$) d 12.82 (s, 1H), 10.79 (s, 1H), 8.39-8.33 (m, 1H), 8.14 (s, 1H), 8.10-8.02 (m, 4H), 7.96-7.87 (m, 3H), 7.80-7.73 (m, 1H), 7.59 (d, J = 8.5 Hz, 2H) |
| 233 | | 1-ethyl-N-[4-(4-oxo-3,4-dihydrophthalazin-1-yl)phenyl]-1H-imidazole-5-carboxamide | 360.2 | E: 1.04 F: 1.18 | 1H NMR (500 MHz, DMSO-d$_6$) d 12.82 (s, 1H), 10.27 (s, 1H), 8.34 (d, J = 7.3 Hz, 1H), 7.99-7.83 (m, 6H), 7.74 (d, J = 7.6 Hz, 1H), 7.57 (d, J = 8.2 Hz, 2H), 4.36 (q, J = 6.9 Hz, 2H), 1.34 (t, J = 7.2 Hz, 3H) |
| 234 | | N-(1-tert-butyl-3-{[4-(4-oxo-3,4-dihydrophthalazin-1-yl)phenyl]carbamoyl}-1H-pyrazol-4-yl)pyridine-4-carboxamide | 508.2 | E: 1.41 F: 1.71 | 1H-NMR: (500 MHz, DMSO-d$_6$) δ ppm 12.87 (s, 1H), 10.59 (s, 1H), 10.28 (s, 1H), 8.81 (d, J = 5.4 Hz, 2H), 8.44 (s, 1H), 8.34 (d, J = 8.1 Hz, 1H), 7.98 (d, J = 8.4 Hz, 2H), 7.95-7.86 (m, 2H), 7.80 (d, J = 5.7 Hz, 2H), 7.74 (d, J = 7.7 Hz, 1H), 7.59 (d, J = 8.4 Hz, 2H), 1.63 (s, 9H) |
| 235 | | 1-tert-butyl-5-methyl-N-[4-(4-oxo-3,4-dihydrophthalazin-1-yl)phenyl]-1H-pyrazole-3-carboxamide | 402.2 | E: 1.67 F: 1.68 | 1H-NMR: (500 MHz, DMSO-d$_6$) δ ppm 12.84 (s, 1H), 9.86 (s, 1H), 7.98-7.85 (m, 4H), 7.75 (d, J = 7.7 Hz, 1H), 7.55 (d, J = 8.4 Hz, 2H), 6.61 (s, 1H), 2.47 (s, 3H), 1.63 (s, 9H) |
| 236 | | N-[4-(4-oxo-3,4-dihydrophthalazin-1-yl)phenyl]-1-phenyl-1H-pyrazole-5-carboxamide | 408.2 | E: 1:48 F: 1.44 | 1H-NMR: (500 MHz, DMSO-d$_6$) δ ppm 12.85 (s, 1H), 10.81 (s, 1H), 8.40-8.25 (m, 1H), 7.94-7.85 (m, 2H), 7.83-7.76 (m, 3H), 7.70 (d, J = 8.4 Hz, 1H), 7.54 (d, J = 8.4 Hz, 2H), 7.50-7.36 (m, 5H), 7.07 (s, 1H) |
| 237 | | N-[4-(4-oxo-3,4-dihydrophthalazin-1-yl)phenyl]-5-(pyridin-2-yl)-1H-1,2,4-triazole-3-carboxamide | 410.2 | E: 1.01 F: 1.11 | 1H NMR (500 MHz, DMSO-d$_6$) d 12.86 (s, 1H), 8.78 (d, J = 4.0 Hz, 1H), 8.36 (d, J = 7.1 Hz, 1H), 8.24 (d, J = 8.1 Hz, 1H), 8.12-8.03 (m, 3H), 7.97-7.88 (m, 2H), 7.78 (d, J = 7.4 Hz, 1H), 7.62 (d, J = 8.4 Hz, 3H) |

TABLE 3-continued

| Example | R | Name | LCMS (M + H)+ | HPLC Method, RT (min.) | 1H NMR |
|---|---|---|---|---|---|
| 238 | 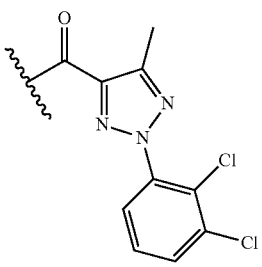 [SMILES: *C(=O)c1nn(-c2cccc(Cl)c2Cl)nc1C] | 2-(2,3-dichlorophenyl)-5-methyl-N-[4-(4-oxo-3,4-dihydrophthalazin-1-yl)phenyl]-2H-1,2,3-triazole-4-carboxamide | 491.2 | E: 2.07 F: 1.97 | 1H NMR (500 MHz, DMSO-$d_6$) d 10.72 (s, 1H), 8.34 (d, J = 7.1 Hz, 1H), 8.02-7.97 (m, J = 8.4 Hz, 2H), 7.95 (d, J = 8.4 Hz, 1H), 7.93-7.88 (m, 2H), 7.84 (d, J = 8.1 Hz, 1H), 7.74 (d, J = 7.1 Hz, 1H), 7.64 (t, J = 8.1 Hz, 1H), 7.60-7.56 (m, J = 8.8 Hz, 2H), 3.89 (s, 1H), 2.64-2.57 (m, 3H) |
| 239 | 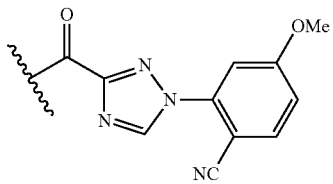 [SMILES: *C(=O)c1ncn(-c2cc(OC)ccc2C#N)n1] | 1-(2-cyano-5-methoxyphenyl)-N-[4-(4-oxo-3,4-dihydrophthalazin-1-yl)phenyl]-1H-1,2,4-triazole-3-carboxamide | 464.2 | E: 1.38 F: 1.30 | 1H NMR (500 MHz, DMSO-$d_6$) d 9.39 (s, 1H), 8.34 (d, J = 7.1 Hz, 1H), 8.03 (d, J = 8.4 Hz, 2H), 8.06 (d, J = 8.8 Hz, 1H), 7.97-7.88 (m, 2H), 7.75 (d, J = 7.4 Hz, 1H), 7.64-7.55 (m, 3H), 7.33 (dd, J = 8.8, 2.4 Hz, 1H), 3.95 (s, 3H) |
| 240 | 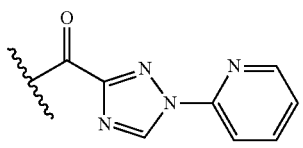 [SMILES: *C(=O)c1ncn(-c2ccccn2)n1] | N-[4-(4-oxo-3,4-dihydrophthalazin-1-yl)phenyl]-1-(pyridin-2-yl)-1H-1,2,4-triazole-3-carboxamide | 410.3 | E: 1.08 F: 1.10 | 1H NMR (500 MHz, DMSO-$d_6$) d 12.85 (s, 1H), 8.76 (d, J = 4.4 Hz, 1H), 8.35 (d, J = 7.1 Hz, 1H), 8.23 (d, J = 7.7 Hz, 1H), 8.05 (d, J = 8.8 Hz, 3H), 7.97-7.87 (m, 2H), 7.77 (d, J = 7.4 Hz, 1H), 7.61 (d, J = 8.4 Hz, 3H), 3.90 (s, 1H) |
| 241 | 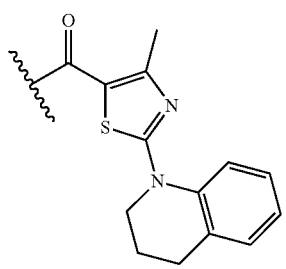 [SMILES: *C(=O)c1sc(N2CCCc3ccccc32)nc1C] | 4-methyl-N-[4-(4-oxo-3,4-dihydrophthalazin-1-yl)phenyl]-2-(1,2,3,4-tetrahydroquinolin-1-yl)-1,3-thiazole-5-carboxamide | 494.1 | E: 1.85 F: 2.00 | 1H NMR (500 MHz, DMSO-$d_6$) d 12.80 (br. s., 1H), 9.89 (br. s., 1H), 8.38-8.30 (m, 1H), 7.95-7.88 (m, 3H), 7.84-7.79 (m, J = 8.5 Hz, 2H), 7.76-7.71 (m, 1H), 7.60-7.51 (m, J = 8.5 Hz, 2H), 7.30-7.20 (m, 2H), 7.13-7.06 (m, 1H), 3.98-3.88 (m, 2H), 2.79 (t, J = 6.3 Hz, 2H), 2.54 (s, 3H), 1.96 (quin, J = 6.2 Hz, 2H) |
| 242 | 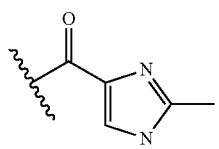 [SMILES: *C(=O)c1c[nH]c(C)n1] | 2-methyl-N-[4-(4-oxo-3,4-dihydrophthalazin-1-yl)phenyl]-1H-imidazole-4-carboxamide | 346.2 | E: 1.07 F: 0.92 | 1H NMR (500 MHz, DMSO-$d_6$) d 12.80 (s, 1H), 10.00 (br. s., 1H), 8.34 (d, J = 7.6 Hz, 1H), 8.03-7.97 (m, J = 8.2 Hz, 2H), 7.94-7.86 (m, 2H), 7.78-7.73 (m, 2H), 7.58-7.49 (m, J = 8.2 Hz, 2H), 2.38 (s, 3H) |
| 243 | 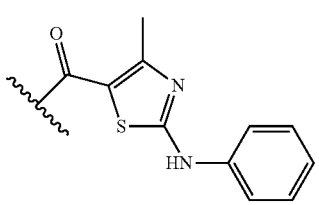 [SMILES: *C(=O)c1sc(Nc2ccccc2)nc1C] | 4-methyl-N-[4-(4-oxo-3,4-dihydrophthalazin-1-yl)phenyl]-2-(phenylamino)-1,3-thiazole-5-carboxamide | 454.2 | E: 1.85 F: 2.00 | 1H NMR (500 MHz, DMSO-$d_6$) d 9.93 (s, 1H), 8.34 (d, J = 7.9 Hz, 1H), 7.99-7.88 (m, 3H), 7.82 (d, J = 8.2 Hz, 2H), 7.74 (d, J = 7.9 Hz, 1H), 7.64-7.60 (m, J = 8.2 Hz, 2H), 7.58-7.53 (m, J = 8.2 Hz, 2H), 7.35 (t, J = 7.6 Hz, 2H), 7.25 (br. s., 2H), 7.15 (br. s., 2H), 7.05 (br. s., 2H), 2.06 (s, 3H) |

Example 244: 3-(Dimethylamino)-N-[4-(1-oxo-1,2-dihydroisoquinolin-4-yl)phenyl]benzamide, TFA

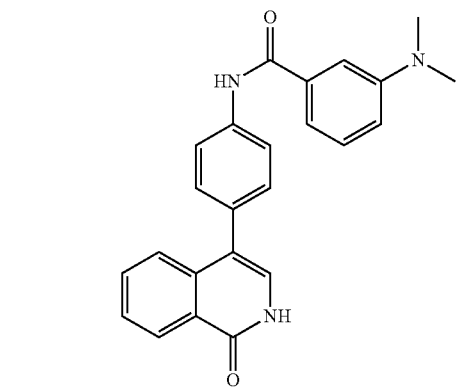

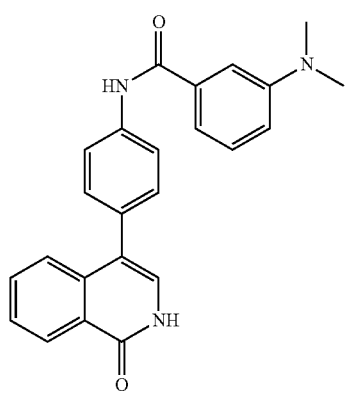

Intermediate 66 (15 mg, 0.043 mmol), 3-(dimethylamino) benzoic acid (14 mg, 0.086 mmol), and HATU (24 mg, 0.064 mmol) were dissolved in DMF (1 mL). DIEA (0.037 mL, 0.21 mmol) was added, then the mixture was stirred at rt for 24 h. The mixture was concentrated, then was purified by prep HPLC to afford Example 244 (9 mg, 41% yield). MS(ESI) m/z: 384.1 (M+H)$^+$; $^1$H NMR (500 MHz, DMSO-d$_6$) δ 11.43 (d, J=5.8 Hz, 1H), 10.24 (s, 1H), 8.30 (dd, J=8.0, 0.8 Hz, 1H), 7.97-7.86 (m, 2H), 7.77-7.68 (m, 1H), 7.60-7.52 (m, 2H), 7.49-7.39 (m, 2H), 7.36-7.31 (m, 1H), 7.29-7.20 (m, 2H), 7.09 (d, J=5.8 Hz, 1H), 6.99-6.91 (m, 1H), 2.98 (s, 6H); HPLC RT=5.63 min (Method A), 5.22 min (Method B).

Example 245: 4-(Dimethylamino)-N-(4-(1-oxo-1,2-dihydroisoquinolin-4-yl)phenyl)benzamide, formate Salt

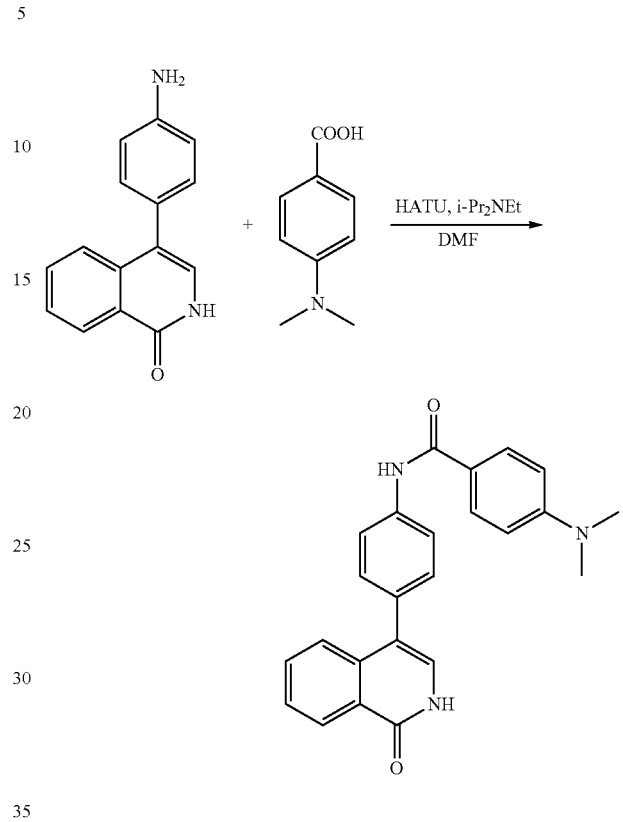

According to the procedure for the preparation of Example 244, coupling of Intermediate 66 (15 mg, 0.043 mmol) and 4-(dimethylamino)benzoic acid (14.15 mg, 0.086 mmol) afforded Example 245 (2.1 mg, 11% yield). MS(ESI) m/z: 384.2 (M+H)$^+$; $^1$H NMR (500 MHz, DMSO-d$_6$) δ 11.42 (d, J=4.4 Hz, 1H), 9.98 (s, 1H), 8.30 (d, J=8.0 Hz, 1H), 7.89 (d, J=8.5 Hz, 4H), 7.71 (t, J=7.6 Hz, 1H), 7.59-7.49 (m, 2H), 7.38 (d, J=7.7 Hz, 2H), 7.08 (d, J=5.0 Hz, 1H), 6.78 (d, J=8.0 Hz, 2H), 3.01 (s, 6H); HPLC RT=1.51 min (Method E), 1.71 min (Method F).

Example 246: N-(4-(1-Oxo-1,2-dihydroisoquinolin-4-yl)phenyl)-4,5,6,7-tetrahydrobenzo[d]thiazole-2-carboxamide

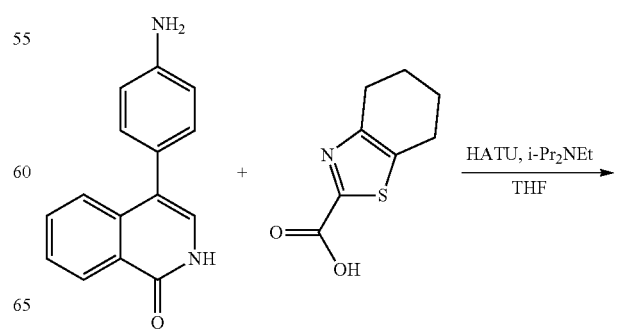

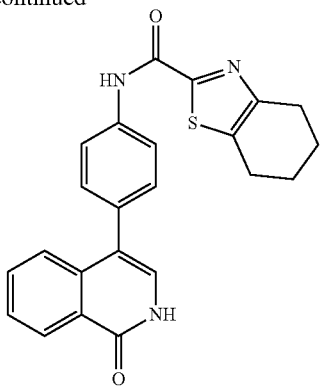

According to the procedure for the preparation of Example 244, coupling of Intermediate 66 (15 mg, 0.043 mmol) and 4,5,6,7-tetrahydrobenzo[d]thiazole-2-carboxylic acid (12 mg, 0.064 mmol) afforded Example 246 (7.9 mg, 46% yield). MS(ESI) m/z: 402.1 (M+H)+; $^1$H NMR (500 MHz, DMSO-$d_6$) δ 11.51 (br. s., 1H), 10.86 (br. s., 1H), 8.29 (d, J=7.2 Hz, 1H), 8.02-7.94 (m, 2H), 7.71 (br. s., 1H), 7.58-7.51 (m, 2H), 7.47-7.37 (m, J=7.7 Hz, 2H), 7.10 (br. s., 1H), 2.95-2.81 (m, 4H), 1.85 (br. s., 4H); HPLC RT=2.02 min (Method E), 2.02 min (Method F).

Example 247: N-(4-(1-Oxo-1,2-dihydroisoquinolin-4-yl)phenyl)benzo[c]isoxazole-3-carboxamide

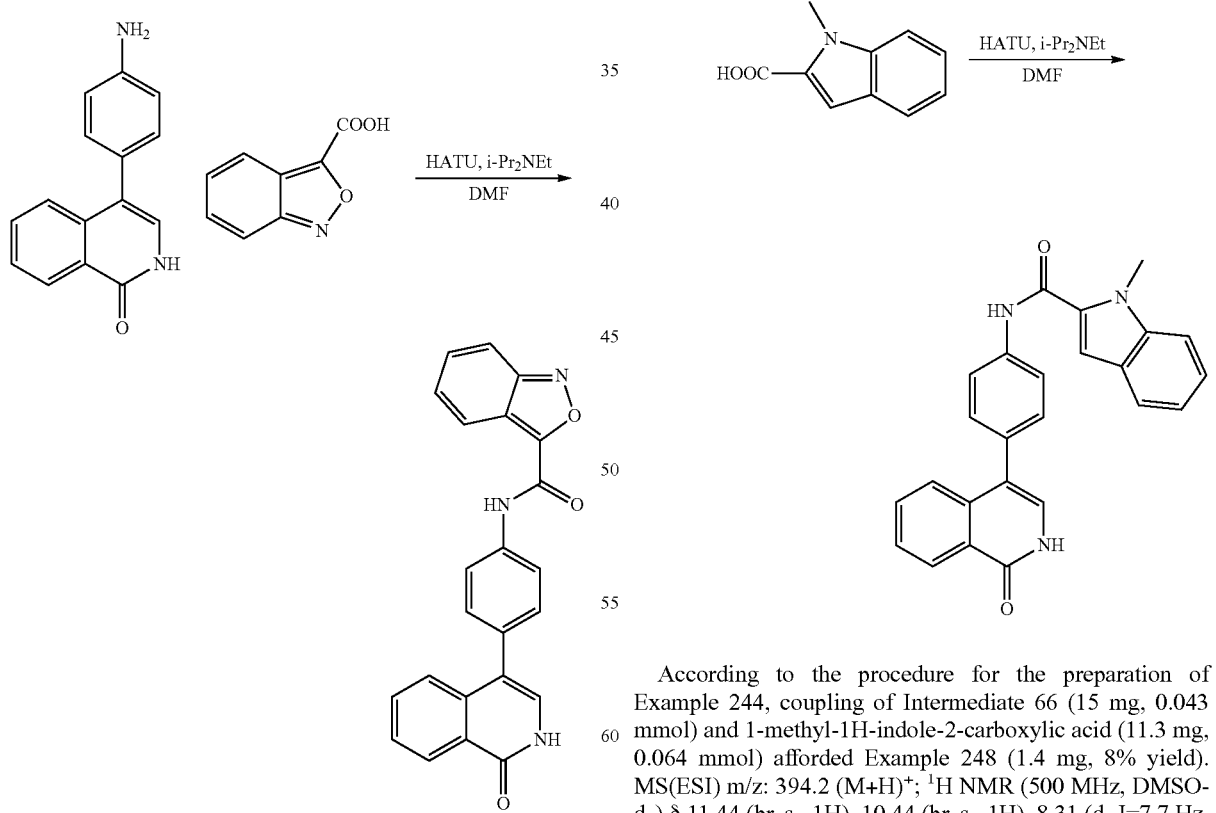

According to the procedure for the preparation of Example 244, coupling of Intermediate 66 (15 mg, 0.043 mmol) and benzo[c]isoxazole-3-carboxylic acid (10.5 mg, 0.064 mmol) afforded Example 247 (4 mg, 19% yield). MS(ESI) m/z: 382.0 (M+H)+; $^1$H NMR (500 MHz, DMSO-$d_6$) δ 11.46 (br. s., 1H), 11.25 (br. s., 1H), 8.31 (d, J=8.0 Hz, 1H), 8.05 (d, J=8.8 Hz, 1H), 8.00 (d, J=6.9 Hz, 2H), 7.83 (d, J=9.1 Hz, 1H), 7.72 (br. s., 1H), 7.56 (d, J=7.2 Hz, 3H), 7.47 (d, J=6.9 Hz, 2H), 7.39-7.31 (m, 1H), 7.13 (d, J=5.5 Hz, 1H); HPLC RT=8.83 min (Method A), 7.54 min (Method B).

Example 248: 1-Methyl-N-(4-(1-oxo-1,2-dihydroisoquinolin-4-yl)phenyl)-1H-indole-2-carboxamide

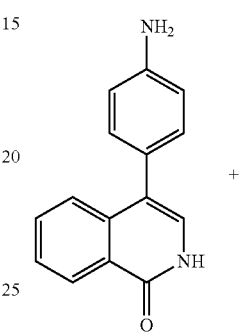

+

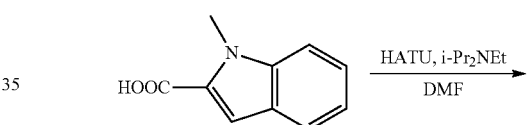

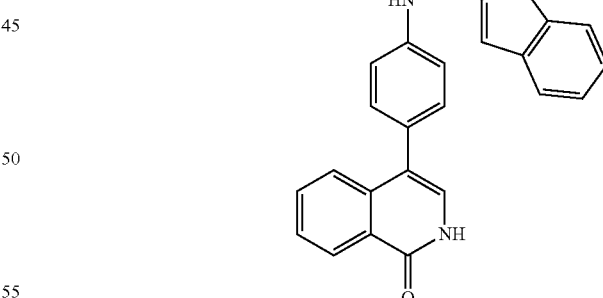

According to the procedure for the preparation of Example 244, coupling of Intermediate 66 (15 mg, 0.043 mmol) and 1-methyl-1H-indole-2-carboxylic acid (11.3 mg, 0.064 mmol) afforded Example 248 (1.4 mg, 8% yield). MS(ESI) m/z: 394.2 (M+H)+; $^1$H NMR (500 MHz, DMSO-$d_6$) δ 11.44 (br. s., 1H), 10.44 (br. s., 1H), 8.31 (d, J=7.7 Hz, 1H), 7.92-7.88 (m, J=7.7 Hz, 2H), 7.71 (br. s., 2H), 7.51 (m, 3H), 7.48-7.40 (m, J=7.7 Hz, 2H), 7.37-7.29 (m, 2H), 7.15 (t, J=7.0 Hz, 1H), 7.10 (br. s., 1H), 4.04 (br. s., 3H); HPLC RT=1.96 min (Method E), 1.94 min (Method F).

Example 249: N-(4-(1-Oxo-1,2-dihydroisoquinolin-4-yl)phenyl)-4-(piperidin-1-yl)benzamide

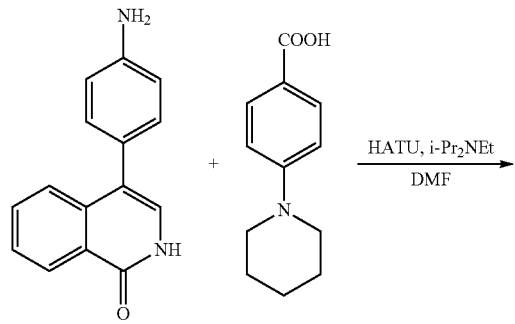

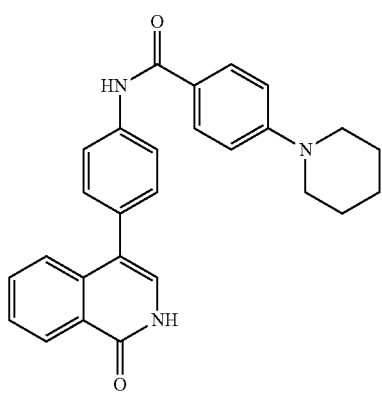

According to the procedure for the preparation of Example 244, coupling of Intermediate 66 (15 mg, 0.043 mmol) and 4-(piperidin-1-yl)benzoic acid (12 mg, 0.059 mmol) afforded Example 249 (4.8 mg, 26% yield). MS(ESI) m/z: 424.2 (M+H)$^+$; $^1$H NMR (500 MHz, DMSO-d$_6$) δ 11.43 (br. s., 1H), 10.03 (br. s., 1H), 8.30 (d, J=7.7 Hz, 1H), 7.93-7.85 (m, 4H), 7.75-7.67 (m, 1H), 7.58-7.49 (m, 2H), 7.38 (d, J=8.0 Hz, 2H), 7.08 (s, 1H), 7.00 (d, J=8.3 Hz, 2H), 1.60 (br. s., 6H); HPLC RT=1.39 min (Method E), 1.97 min (Method F).

Example 250: 4-Morpholino-N-(4-(1-oxo-1,2-dihydroisoquinolin-4-yl)phenyl)benzamide

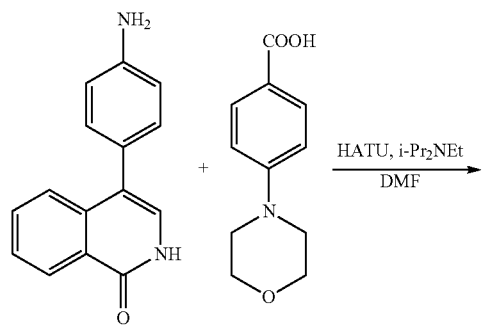

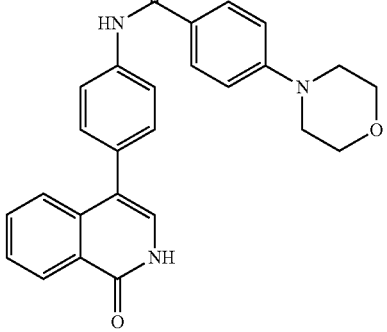

According to the procedure for the preparation of Example 244, coupling of Intermediate 66 (13 mg, 0.037 mmol) and 4-morpholinobenzoic acid (11.54 mg, 0.056 mmol) afforded Example 250 (3.7 mg, 22% yield). MS(ESI) m/z: 422.2 (M+H)$^+$; $^1$H NMR (500 MHz, DMSO-d$_6$) δ 11.41 (br. s., 1H), 10.08 (br. s., 1H), 8.30 (d, J=8.0 Hz, 1H), 8.02-7.86 (m, 4H), 7.71 (t, J=7.4 Hz, 1H), 7.60-7.52 (m, 2H), 7.39 (d, J=8.0 Hz, 2H), 7.11-7.02 (m, 3H), 3.76 (br. s., 4H), 3.27 (br. s., 4H); HPLC RT=1.51 min (Method E), 1.51 min (Method F).

Example 251: N-(4-(1-Oxo-1,2-dihydroisoquinolin-4-yl)phenyl)-4-(pyrrolidin-1-yl)benzamide

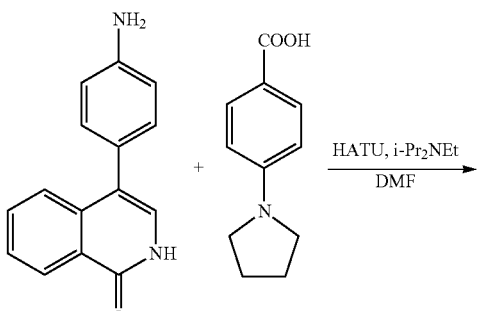

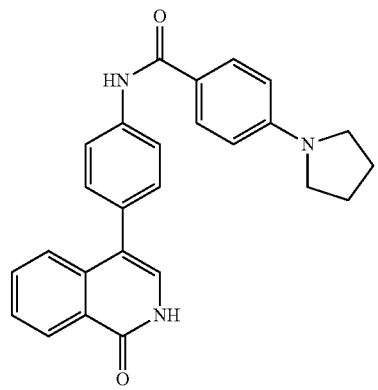

According to the procedure for the preparation of Example 244, coupling of Intermediate 66 (13 mg, 0.037 mmol) and 4-(pyrrolidin-1-yl)benzoic acid (10.65 mg, 0.056 mmol) afforded Example 251 (0.4 mg, 3% yield). MS(ESI) m/z: 410.2 (M+H)$^+$; $^1$H NMR (500 MHz, DMSO-d$_6$) δ 9.95 (br. s., 1H), 8.30 (d, J=7.7 Hz, 1H), 7.89 (d, J=7.7 Hz, 4H), 7.76-7.67 (m, 1H), 7.59-7.51 (m, 2H), 7.37 (d, J=8.0 Hz, 2H), 7.08 (s, 1H), 6.61 (d, J=8.3 Hz, 2H), 3.90 (s, 1H), 1.99 (br. s., 4H); HPLC RT=1.92 min (Method E), 1.91 min (Method F).

Example 252: 4-(4-(2-(5-Methoxy-7-methylindolin-1-yl)-2-oxoethyl)phenyl)phthalazin-1(2H)-one

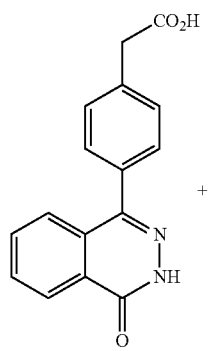

+

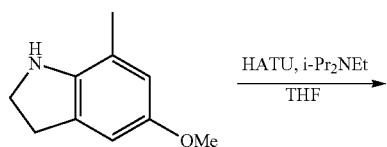

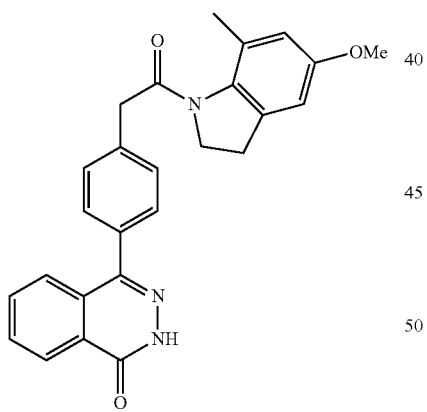

Intermediate 1 (15 mg, 0.038 mmol), 5-methoxy-7-methylindoline (9.3 mg, 0.057 mmol), and HATU (21.8 mg, 0.057 mmol) were dissolved in DMF (1 mL). The this mixture was added DIEA (0.017 mL, 0.095 mmol). The mixture was stirred at rt overnight, then was concentrated. The residue was purified by prep HPLC to afford Example 252 (11 mg, 65% yield). MS(ESI) m/z: 426.2 (M+H)+; 1H NMR (500 MHz, DMSO-d6) δ 12.83 (s, 1H), 8.34 (d, J=6.9 Hz, 1H), 7.98-7.85 (m, 2H), 7.71 (d, J=6.6 Hz, 1H), 7.63-7.54 (m, J=7.4 Hz, 2H), 7.50-7.42 (m, J=7.4 Hz, 2H), 6.72 (br. s., 1H), 6.57 (br. s., 1H), 4.12 (t, J=7.0 Hz, 2H), 4.00 (br. s., 2H), 3.71 (s, 3H), 2.97 (t, J=6.9 Hz, 2H), 2.13 (s, 3H); HPLC RT=1.77 min (Method E), 1.76 min (Method F).

Example 253: 4-(4-(2-(7-Bromo-5-(trifluoromethoxy)indolin-1-yl)-2-oxoethyl)phenyl)phthalazin-1(2H)-one

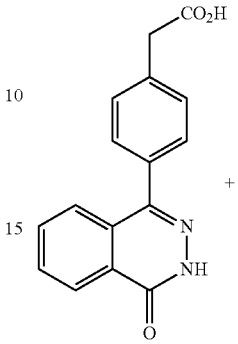

+

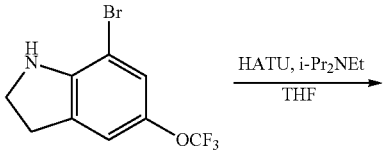

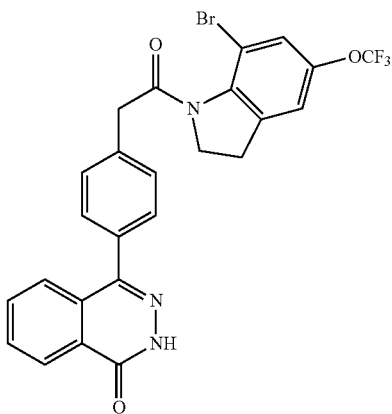

According to the procedure for the preparation of Example 252, coupling of Intermediate 1 (15 mg, 0.038 mmol) and 7-bromo-5-(trifluoromethoxy)indoline, HCl (18.2 mg, 0.057 mmol) afforded Example 253 (11 mg, 54% yield). MS(ESI) m/z: 544.1 (M+H)+; 1H NMR (500 MHz, DMSO-d6) δ 12.83 (s, 1H), 8.34 (d, J=6.9 Hz, 1H), 8.00-7.82 (m, 2H), 7.71 (d, J=6.9 Hz, 1H), 7.61-7.53 (m, 2H), 7.51-7.43 (m, 3H), 7.40 (br. s., 1H), 4.22 (t, J=7.3 Hz, 2H), 4.06 (s, 2H), 3.15 (t, J=7.2 Hz, 2H); HPLC RT=2.08 min (Method E), 2.06 min (Method F).

Example 254: 4-(4-(2-(6-Ethoxyindolin-1-yl)-2-oxoethyl)phenyl)isoquinolin-1(2H)-one

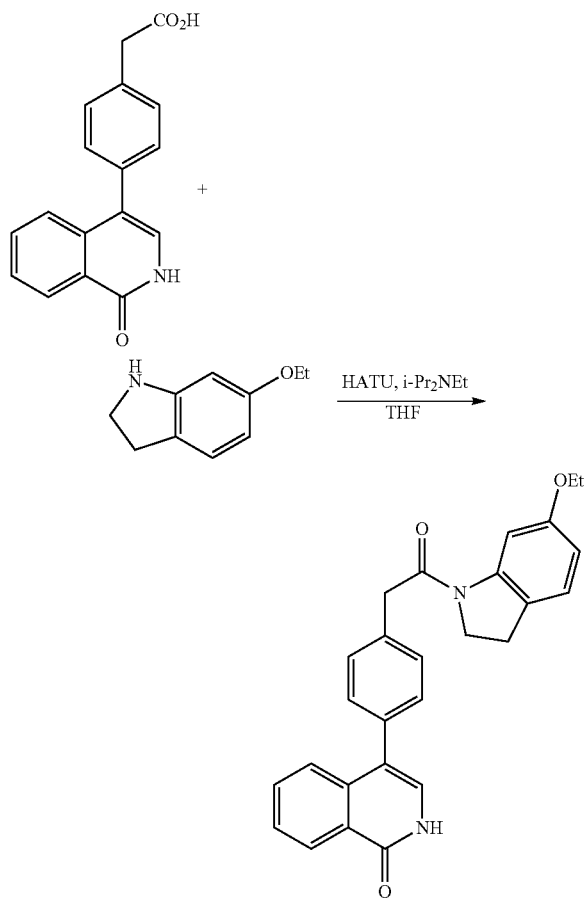

According to the procedure for the preparation of Example 252, coupling of Intermediate 67 (12 mg, 0.043 mmol) and 6-ethoxyinoline (0.430 mL, 0.086 mmol) afforded Example 254 (10.5 mg, 55% yield). MS(ESI) m/z: 425.2 (M+H)+; 1H NMR (500 MHz, DMSO-d6) δ 11.44 (br. s., 1H), 8.30 (d, J=7.7 Hz, 1H), 7.75 (br. s., 1H), 7.73-7.66 (m, 1H), 7.54 (d, J=7.7 Hz, 2H), 7.40 (s, 4H), 7.13-7.05 (m, 2H), 6.55 (d, J=8.0 Hz, 1H), 4.23 (t, J=7.8 Hz, 2H), 3.95 (q, J=6.6 Hz, 2H), 3.91 (br. s., 2H), 3.08 (t, J=8.0 Hz, 2H), 1.29 (t, J=6.7 Hz, 3H); HPLC RT=1.95 min (Method E), 1.95 min (Method F).

Example 255: 4-(4-(2-(Isoindolin-2-yl)-2-oxoethyl)phenyl)-6,7-dimethoxyisoquinolin-1(2H)-one

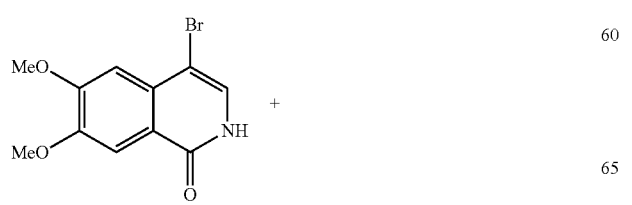

-continued

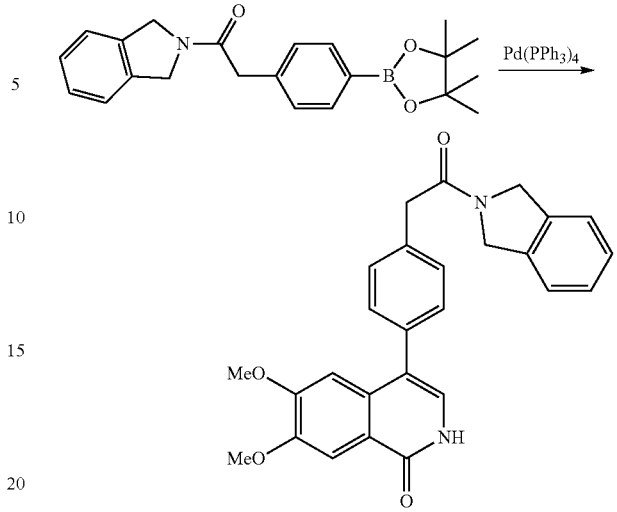

To Intermediate 68 (20 mg, 0.070 mmol), Intermediate 9 (25.6 mg, 0.070 mmol) and K3PO4 (37.4 mg, 0.176 mmol), were added dioxane (3 mL) and water (0.333 mL). The mixture was degassed (evacuated and flushed with Ar (5×)). Pd(PPh3)4 (4.1 mg, 3.5 mol) was added, then the mixture was degassed (2×). The reaction vial was sealed and heated in a microwave reactor at 150° C. for 25 min. The reaction mixture was concentrated then was purified by prep HPLC to afford Example 255 (7.5 mg, 24% yield). MS(ESI) m/z: 441.2 (M+H)+; 1H NMR (500 MHz, DMSO-d6) δ 11.30 (br. s., 1H), 7.68 (s, 1H), 7.50-7.33 (m, 6H), 7.31 (br. s., 2H), 6.98 (br. s., 2H), 4.96 (br. s., 2H), 4.69 (br. s., 2H), 3.95-3.86 (m, 3H), 3.84 (br. s., 2H), 3.72 (s, 3H); HPLC RT=1.62 min (Method E), 1.62 min (Method F).

Example 256: 4-(2-Fluoro-4-(2-(isoindolin-2-yl)-2-oxoethyl)phenyl)isoquinolin-1(2H)-one

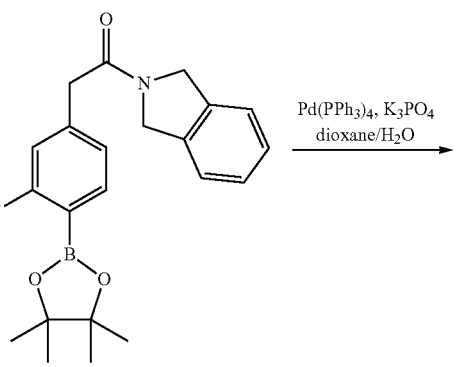

311
-continued

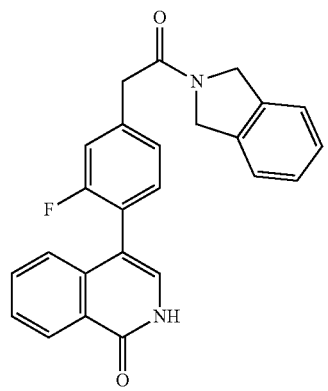

According to the procedure for the preparation of Example 255, coupling of Intermediate 5 (37 mg, 0.098 mmol) and 4-bromoisoquinolin-1(2H)-one (20 mg, 0.089 mmol) afforded Example 256 (6.6 mg, 18% yield). MS(ESI) m/z: 339.2 (M+H)+; $^1$H NMR (500 MHz, DMSO-$d_6$) δ 11.50 (br. s., 1H), 8.28 (d, J=8.0 Hz, 1H), 7.69 (t, J=7.4 Hz, 1H), 7.53 (t, J=7.3 Hz, 1H), 7.37 (d, J=4.4 Hz, 3H), 7.34-7.20 (m, 5H), 7.16 (br. s., 1H), 4.98 (br. s., 2H), 4.70 (br. s., 2H), 3.88 (br. s., 2H); HPLC RT=1.72 min (Method E), 1.70 min (Method F).

Example 257: N-(4-(6,7-Dimethoxy-1-oxo-1,2-dihydroisoquinolin-4-yl)phenyl)-6-methoxyindoline-1-carboxamide

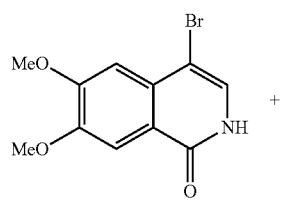

+

312
-continued

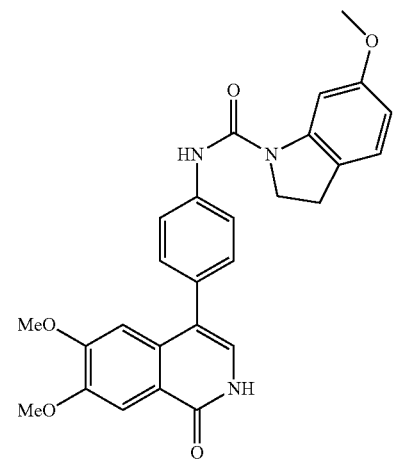

According to the procedure for the preparation of Example 255, coupling of Intermediate 12 (33 mg, 0.084 mmol) and Intermediate 68 (20 mg, 0.070 mmol) afforded Example 257 (8.9 mg, 27% yield). MS(ESI) m/z: 472.1 (M+H)+; $^1$H NMR (500 MHz, DMSO-$d_6$) δ 11.28 (br. s., 1H), 8.61 (br. s., 1H), 7.95 (br. s., 1H), 7.74-7.66 (m, 3H), 7.55 (br. s., 1H), 7.40 (d, J=8.0 Hz, 2H), 7.08 (d, J=7.7 Hz, 1H), 7.03-6.93 (m, 2H), 6.48 (d, J=8.0 Hz, 1H), 4.17 (t, J=8.1 Hz, 2H), 3.89 (s, 3H), 3.74 (s, 3H), 3.71 (s, 3H), 3.11 (t, J=8.3 Hz, 2H); HPLC RT=1.71 min (Method E), 1.70 min (Method F).

Example 258: 4-(4-(2-(6-Isopropoxyindolin-1-yl)-2-oxoethyl)phenyl)phthalazin-1(2H)-one

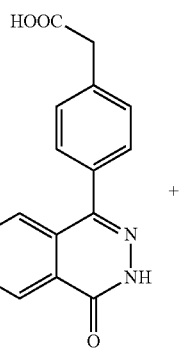

+

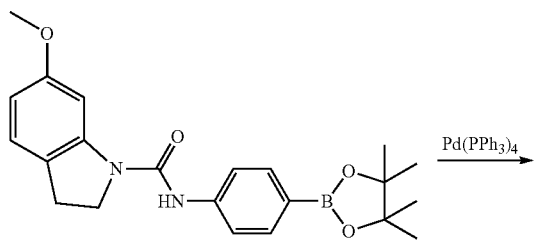

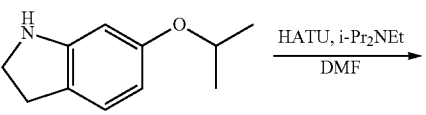

313
-continued

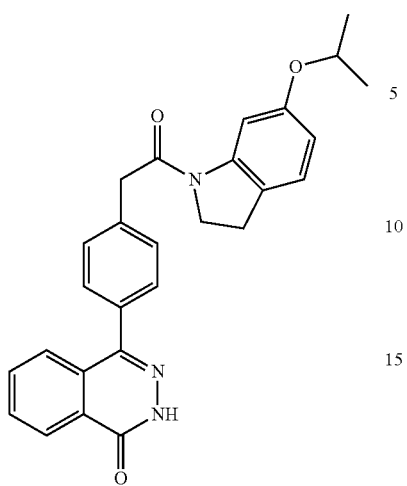

To a solution of Intermediate 1 (12 mg, 0.043 mmol), Intermediate 69 (12.5 mg, 0.043 mmol), and HATU (24.4 mg, 0.064 mmol) in DMF (1 mL), was add DIEA (0.037 mL, 0.21 mmol). The mixture was stirred rt for 16 h, then the mixture was purified via prep HPLC to afford Example 258 (13 mg; 69% yield) as white solid. MS(ESI) m/z: 440.1 (M+H)+; $^1$H NMR (500 MHz, DMSO-d$_6$) δ 12.86 (br. s., 1H), 8.40-8.32 (m, 1H), 7.90 (br. s., 2H), 7.74 (br. s., 2H), 7.60-7.53 (m, 2H), 7.48-7.42 (m, 2H), 7.10 (d, J=7.2 Hz, 1H), 6.55 (d, J=7.7 Hz, 1H), 4.48 (d, J=5.2 Hz, 1H), 4.28-4.17 (m, 2H), 3.96 (br. s., 2H), 3.09 (br. s., 2H), 1.23 (br. s., 6H); HPLC RT=1.93 min (Method E), 191 min (Method F).

Example 259: 4-(4-(2-(Indolin-1-yl)-2-oxoethyl)-2-methylphenyl)phthalazin-1(2H)-one

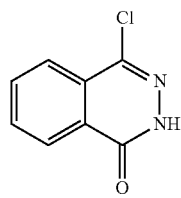

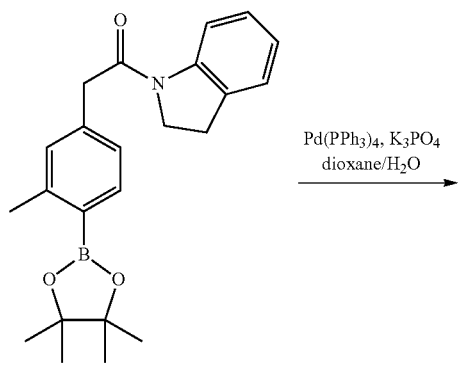

314
-continued

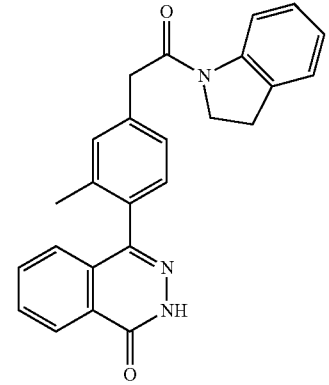

According to the procedure for the preparation of Example 76, coupling of 4-chlorophthalazin-1(2H)-one (15 mg, 0.083 mmol) and Intermediate 71 (34.5 mg, 0.091 mmol), afforded 1.8 mg (5.5%) of Example 259. MS(ESI) m/z: 396.2 (M+H)+; $^1$H NMR (500 MHz, DMSO-d$_6$) δ 12.82 (br. s., 1H), 8.33 (d, J=3.3 Hz, 1H), 8.09 (d, J=8.0 Hz, 1H), 7.87 (d, J=3.3 Hz, 2H), 7.34-7.21 (m, 5H), 7.15 (br. s., 1H), 7.00 (br. s., 1H), 4.23 (t, J=7.8 Hz, 2H), 3.92 (br. s., 2H), 3.19 (br. s., 2H), 2.07 (br. s., 3H); HPLC RT=1.96 min (Method E), 1.99 min (Method F).

Example 260: 4-(4-(2-(Isoindolin-2-yl)-2-oxoethyl)-2-methylphenyl)phthalazin-1(2H)-one

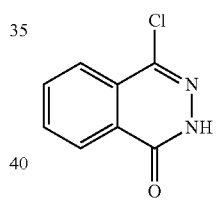

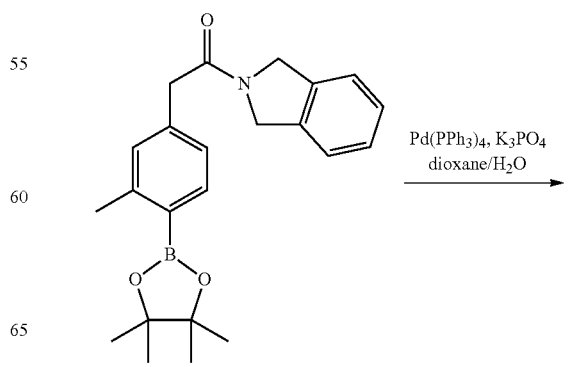

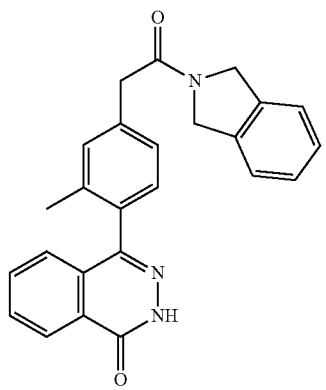
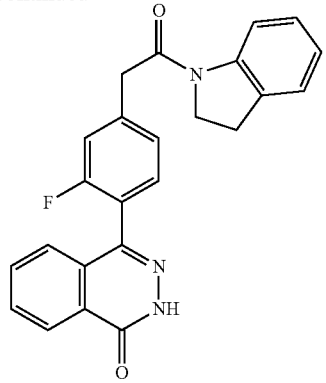

According to the procedure for the preparation of Example 76, coupling of 4-chlorophthalazin-1(2H)-one (15 mg, 0.083 mmol) and Intermediate 70 (34.5 mg, 0.091 mmol), afforded 10.4 mg (32%) of Example 260. MS(ESI) m/z: 396.2 (M+H)+; $^1$H NMR (500 MHz, DMSO-$d_6$) δ 12.82 (s, 1H), 8.35-8.29 (m, 1H), 7.90-7.81 (m, 2H), 7.41-7.34 (m, 2H), 7.34-7.29 (m, 3H), 7.27 (s, 2H), 7.24-7.20 (m, 1H), 4.98 (s, 2H), 4.70 (s, 2H), 3.84 (s, 2H), 2.07 (s, 3H); HPLC RT=1.70 min (Method E), 1.73 min (Method F).

According to the procedure for the preparation of Example 76, coupling of 4-chlorophthalazin-1(2H)-one (15 mg, 0.083 mmol) and Intermediate 72 (34.8 mg, 0.091 mmol), afforded 10.6 mg (31%) of Example 261. MS(ESI) m/z: 400.2 (M+H)+; $^1$H NMR (500 MHz, DMSO-$d_6$) δ 12.98 (br. s., 1H), 8.36-8.30 (m, 1H), 8.08 (d, J=8.3 Hz, 1H), 7.93-7.86 (m, 2H), 7.53 (t, J=7.7 Hz, 1H), 7.47-7.41 (m, 1H), 7.36 (d, J=11.0 Hz, 1H), 7.32 (d, J=7.7 Hz, 1H), 7.26 (d, J=7.2 Hz, 1H), 7.16 (t, J=7.7 Hz, 1H), 7.05-6.97 (m, 1H), 4.24 (t, J=8.5 Hz, 2H), 4.01 (s, 2H), 3.20 (t, J=8.4 Hz, 2H); HPLC RT=1.81 min (Method E), 1.83 min (Method F).

Example 261: 4-(2-Fluoro-4-(2-(indolin-1-yl)-2-oxoethyl)phenyl)phthalazin-1(2H)-one Example 262: 4-{4-[2-(2,3-Dihydro-1H-isoindol-2-yl)-2-oxoethyl]phenyl}-6-methoxy-1,2-dihydroisoquinolin-1-one

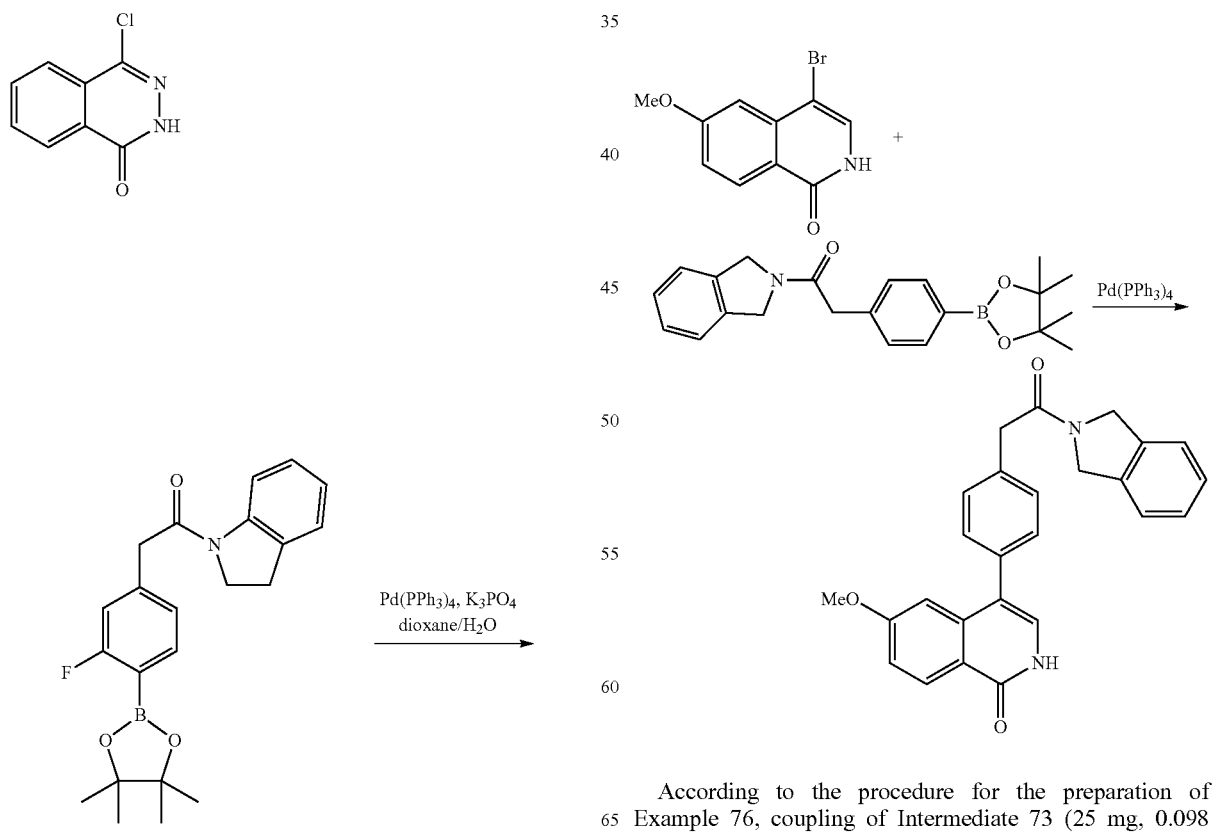

According to the procedure for the preparation of Example 76, coupling of Intermediate 73 (25 mg, 0.098 mmol) and Intermediate 9 (35.7 mg, 0.098 mmol), afforded 14.4 mg (35%) of Example 262. MS(ESI) m/z: 411.2

(M+H)⁺; ¹H NMR (500 MHz, DMSO-d₆) δ 11.30 (br. s., 1H), 8.22 (d, J=8.8 Hz, 1H), 7.41 (s, 4H), 7.38-7.34 (m, 2H), 7.32-7.28 (m, 2H), 7.14 (dd, J=8.8, 2.5 Hz, 1H), 7.06 (s, 1H), 6.92 (d, J=2.5 Hz, 1H), 4.96 (s, 2H), 4.69 (s, 2H), 3.84 (s, 2H), 3.75 (s, 3H); HPLC RT=1.61 min (Method E), 1.62 min (Method F).

Example 263: 4-(4-(2-(Isoindolin-2-yl)-2-oxoethyl)-2-methylphenyl)isoquinolin-1(2H)-one Example 264: 4-(4-(2-(Indolin-1-yl)-2-oxoethyl)-2-methylphenyl)isoquinolin-1(2H)-one

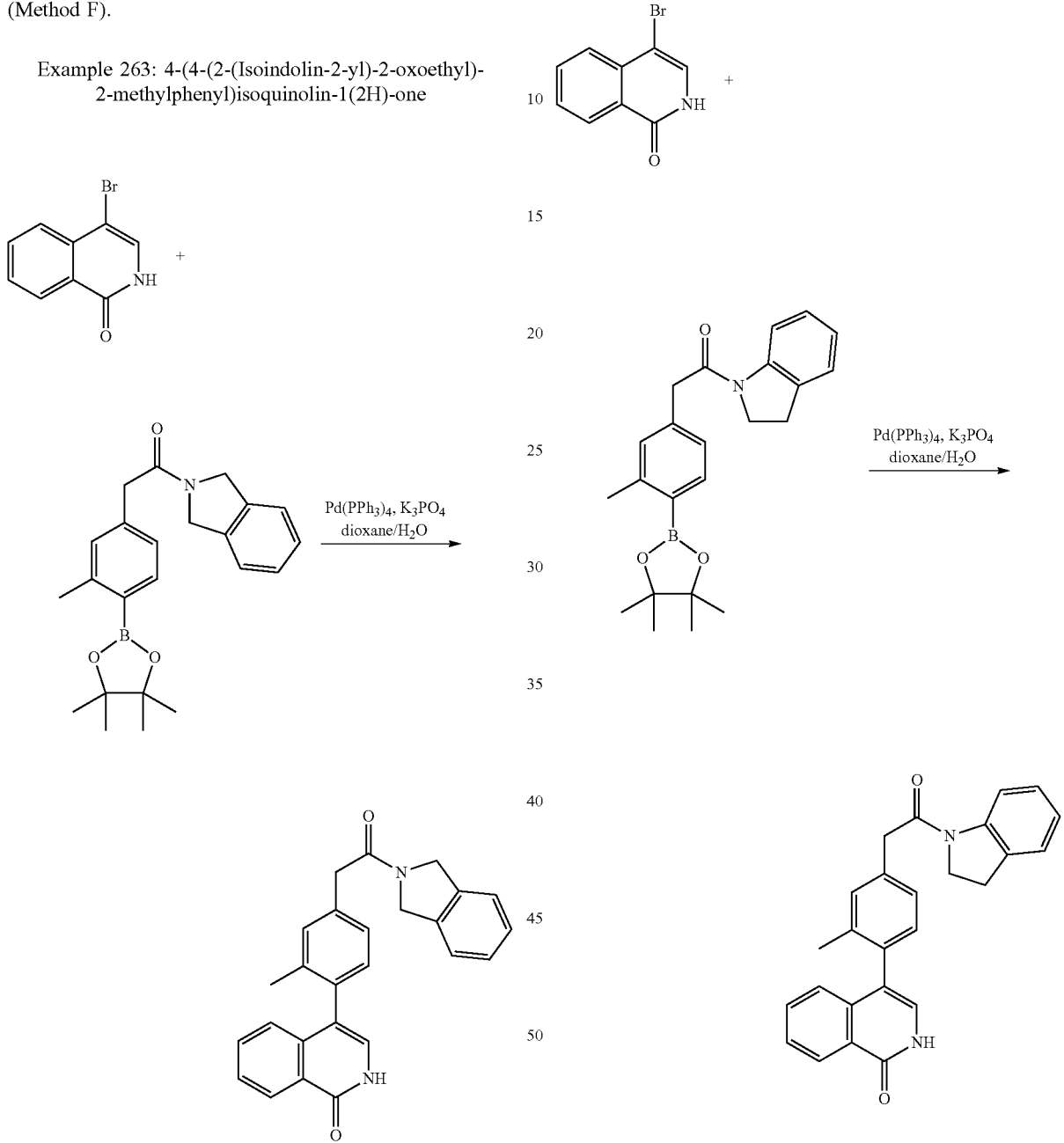

According to the procedure for the preparation of Example 255, coupling of Intermediate 70 (32.8 mg, 0.087 mmol) and 4-bromoisoquinolin-1(2H)-one (15 mg, 0.067 mmol) afforded Example 263 (2.1 mg, 8% yield). MS(ESI) m/z: 395.3 (M+H)⁺; ¹H NMR (500 MHz, DMSO-d₆) δ 11.40 (d, J=5.8 Hz, 1H), 8.27 (dd, J=8.0, 1.1 Hz, 1H), 7.64 (ddd, J=8.3, 7.0, 1.5 Hz, 1H), 7.53-7.48 (m, 1H), 7.40-7.34 (m, 2H), 7.34-7.29 (m, 2H), 7.28 (s, 1H), 7.24-7.19 (m, 1H), 7.18-7.14 (m, 1H), 7.03-6.97 (m, 2H), 4.97 (s, 2H), 4.69 (s, 2H), 3.80 (s, 2H), 2.03 (s, 3H); HPLC RT=1.68 min (Method E), 1.67 min (Method F).

According to the procedure for the preparation of Example 255, coupling of Intermediate 71 (32.8 mg, 0.087 mmol) and 4-bromoisoquinolin-1(2H)-one (15 mg, 0.067 mmol) afforded Example 264 (1.7 mg, 6% yield). MS(ESI) m/z: 395.3 (M+H)⁺; ¹H NMR (500 MHz, DMSO-d₆) δ 11.41 (d, J=4.4 Hz, 1H), 8.28 (dd, J=8.0, 1.1 Hz, 1H), 8.09 (d, J=8.0 Hz, 1H), 7.64 (td, J=7.6, 1.5 Hz, 1H), 7.54-7.47 (m, 1H), 7.28 (s, 1H), 7.25 (d, J=7.4 Hz, 1H), 7.23-7.20 (m, 1H), 7.19-7.16 (m, 1H), 7.16-7.13 (m, 1H), 7.01 (d, J=7.4 Hz, 3H), 4.23 (t, J=8.7 Hz, 2H), 3.88 (s, 2H), 3.18 (t, J=8.5 Hz, 2H), 2.04 (s, 3H); HPLC RT=1.81 min (Method E), 1.80 min (Method F).

Example 265: 4-(4-(2-(6-(2-Hydroxy-2-methyl-propoxy)indolin-1-yl)-2-oxoethyl)phenyl)phthalazin-1(2H)-one

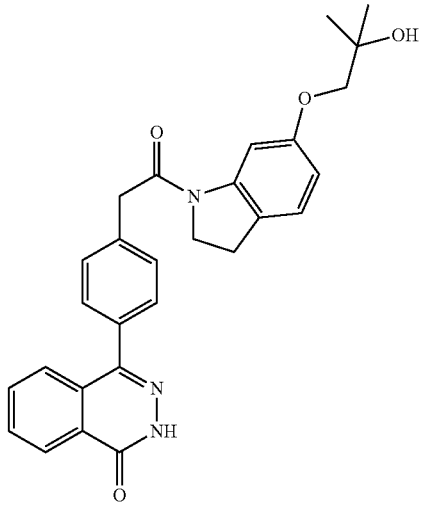 [SMILES: CC(C)(O)COc1ccc2c(c1)N(C(=O)Cc1ccc(-c3n[nH]c(=O)c4ccccc34)cc1)CC2]

According to the procedure for the preparation of Example 258, coupling of Intermediate 1 (10 mg, 0.036 mmol), Intermediate 74 (11.5 mg, 0.036 mmol) afforded Example 265 (13.2 mg, 0.028 mmol, 78% yield). MS(ESI) m/z: 470.2 (M+H)$^+$; $^1$H NMR (500 MHz, DMSO-d$_6$) δ 12.86 (s, 1H), 8.39-8.30 (m, 1H), 7.93-7.88 (m, 2H), 7.76 (d, J=2.5 Hz, 1H), 7.73-7.68 (m, 1H), 7.60-7.54 (m, J=8.3 Hz, 2H), 7.50-7.43 (m, J=8.3 Hz, 2H), 7.11 (d, J=8.3 Hz, 1H), 6.57 (dd, J=8.3, 2.5 Hz, 1H), 4.61 (s, 1H), 4.24 (t, J=8.5 Hz, 2H), 3.96 (s, 2H), 3.63 (s, 2H), 3.10 (t, J=8.4 Hz, 2H), 1.18 (s, 6H); HPLC RT=1.61 min (Method E), 1.61 min (Method F).

Example 266: N-(4-(6-Methoxy-1-oxo-1,2-dihydroisoquinolin-4-yl)phenyl)indoline-1-carboxamide

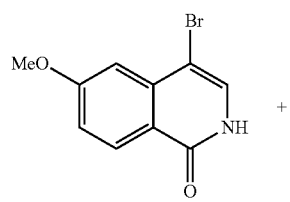

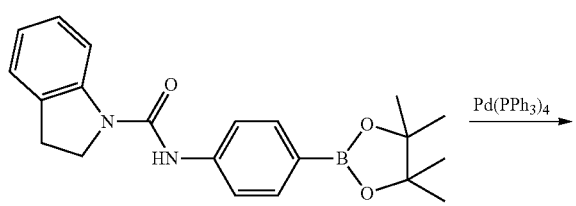

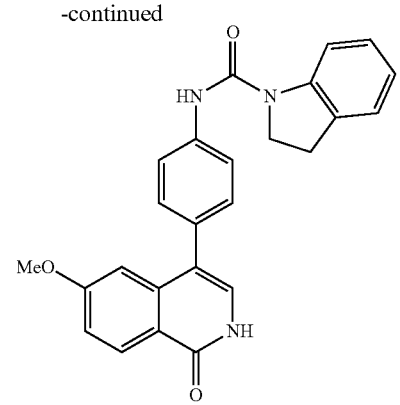

According to the procedure for the preparation of Example 76, coupling of Intermediate 73 (18 mg, 0.071 mmol) and Intermediate 10 (28.4 mg, 0.078 mmol) afforded 5.3 mg (17%) of Example 266. MS(ESI) m/z: 412.2 (M+H)$^+$; $^1$H NMR (500 MHz, DMSO-d$_6$) δ 11.28 (d, J=6.1 Hz, 1H), 8.64 (s, 1H), 8.22 (d, J=8.8 Hz, 1H), 7.89 (d, J=8.0 Hz, 1H), 7.70-7.65 (m, 2H), 7.41-7.35 (m, 2H), 7.21 (d, J=7.2 Hz, 1H), 7.17-7.11 (m, 2H), 7.05 (d, J=6.1 Hz, 1H), 6.94 (d, J=2.5 Hz, 1H), 6.93-6.88 (m, 1H), 4.16 (t, J=8.8 Hz, 2H), 3.77 (s, 3H), 3.19 (t, J=8.5 Hz, 2H); HPLC RT=1.71 min (Method E), 1.71 min (Method F).

Example 267: 4-(6-Methoxy-1-oxo-1,2-dihydroisoquinolin-4-yl)phenyl 5-methoxyisoindoline-2-carboxylate

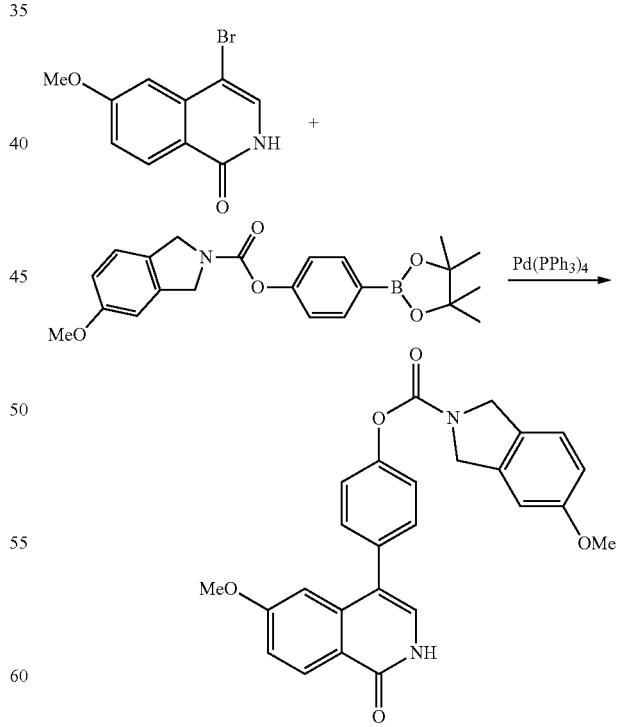

According to the procedure for the preparation of Example 76, coupling of Intermediate 73 (18 mg, 0.071 mmol) and Example 70B (28 mg, 0.071 mmol) afforded 11.9 mg (36%) of Example 267. MS(ESI) m/z: 443.2 (M+H)$^+$; $^1$H NMR (500 MHz, DMSO-$d_6$) δ 11.33 (br. s., 1H), 8.23 (d, J=8.8 Hz, 1H), 7.54-7.44 (m, 2H), 7.35-7.26 (m, 3H), 7.15 (dd, J=8.8, 2.5 Hz, 1H), 7.14-7.08 (m, 1H), 6.98 (s, 1H), 6.94-6.86 (m, 2H), 4.89 (s, 1H), 4.85 (s, 1H), 4.71 (s, 1H), 4.66 (s, 1H), 3.77 (d, J=2.2 Hz, 6H); HPLC RT=1.86 min (Method E), 1.86 min (Method F).

Example 268: 6-Methoxy-N-(4-(6-methoxy-1-oxo-1,2-dihydroisoquinolin-4-yl)phenyl)indoline-1-carboxamide

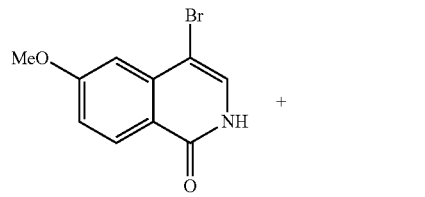

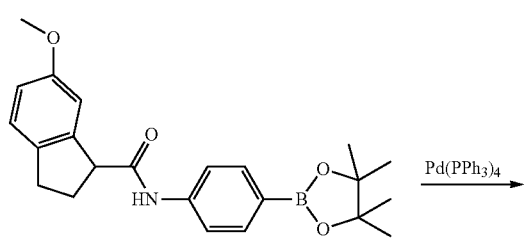

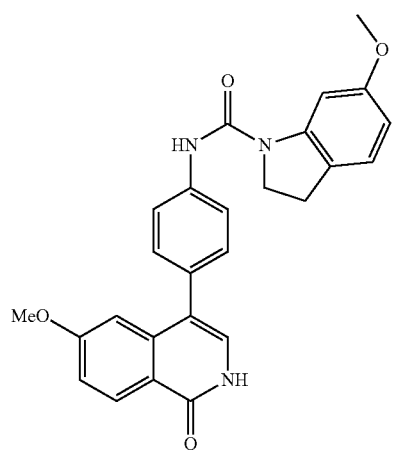

According to the procedure for the preparation of Example 76, coupling of Intermediate 73 (25 mg, 0.098 mmol) and Intermediate 12 (42.7 mg, 0.108 mmol) afforded 3.9 mg (9%) of Example 268. MS(ESI) m/z: 442.2 (M+H)$^+$; $^1$H NMR (500 MHz, DMSO-$d_6$) δ 8.64 (s, 1H), 8.22 (d, J=8.8 Hz, 1H), 7.74-7.65 (m, J=8.8 Hz, 2H), 7.55 (d, J=2.5 Hz, 1H), 7.42-7.34 (m, J=8.5 Hz, 2H), 7.14 (dd, J=8.8, 2.5 Hz, 1H), 7.09 (d, J=8.0 Hz, 1H), 7.04 (d, J=6.1 Hz, 1H), 6.94 (d, J=2.5 Hz, 1H), 6.48 (dd, J=8.3, 2.5 Hz, 1H), 4.17 (t, J=8.5 Hz, 2H), 3.77 (s, 3H), 3.71 (s, 3H), 3.11 (t, J=8.5 Hz, 2H); HPLC RT=1.71 min (Method E), 1.71 min (Method F).

Example 269: 4-(6-Methoxy-1-oxo-1,2-dihydroisoquinolin-4-yl)phenyl isoindoline-2-carboxylate

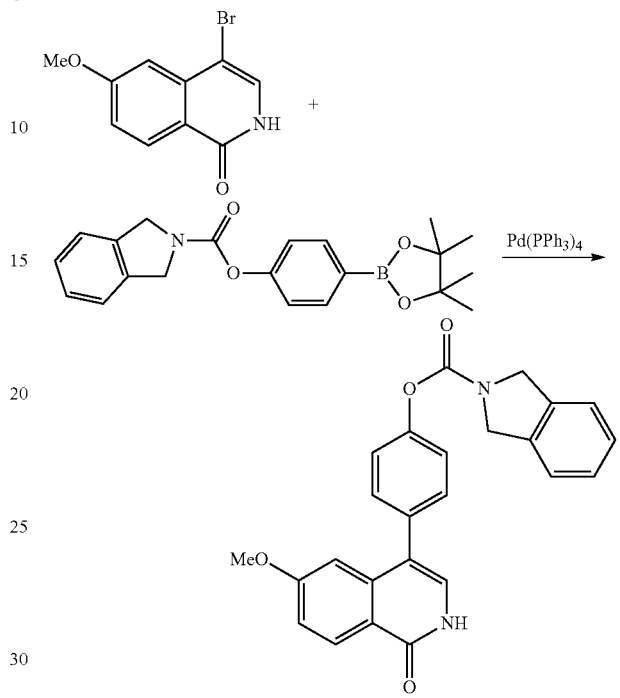

According to the procedure for the preparation of Example 76, coupling of Intermediate 73 (18 mg, 0.071 mmol) and Example 68B (25.9 mg, 0.071 mmol) afforded 7.1 mg (23%) of Example 269. MS(ESI) m/z: 413.2 (M+H)$^+$; $^1$H NMR (500 MHz, DMSO-$d_6$) δ 11.34 (d, J=5.5 Hz, 1H), 8.23 (d, J=9.1 Hz, 1H), 7.53-7.45 (m, 2H), 7.44-7.38 (m, 2H), 7.36-7.33 (m, 3H), 7.16 (dd, J=8.8, 2.5 Hz, 1H), 7.10 (d, J=5.8 Hz, 1H), 6.90 (d, J=2.5 Hz, 1H), 4.94 (s, 2H), 4.75 (s, 2H), 3.77 (s, 3H); HPLC RT=1.88 min (Method E), 1.88 min (Method F).

The following Examples in Table 4 were made by using the same procedure as shown in Example 3. Intermediate 1 was coupled with the appropriate amine. Various coupling reagents could be used other than the one described in Example 3 such as BOP, PyBop, EDC/HOBt or HATU.

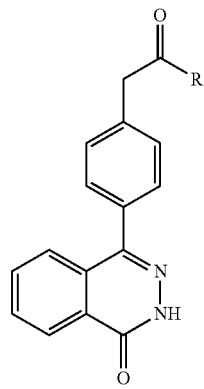

TABLE 4

| Example | R | IUPAC name | LCMS (M + H)+ | HPLC Method, RT (min.) | 1H NMR |
|---|---|---|---|---|---|
| 270 | (indoline with 6-(pyridin-3-ylmethoxy) substituent) | 4-(4-{2-oxo-2-[6-(pyridin-3-ylmethoxy)-2,3-dihydro-1H-indol-1-yl]ethyl}phenyl)-1,2-dihydrophthalazin-1-one | 489.2 | E: 1.33  F: 1.65 | 1H NMR (500 MHz, DMSO-d6) d 12.86 (s, 1H), 8.77 (s, 1H), 8.65 (d, J = 4.4 Hz, 1H), 8.38-8.31 (m, 1H), 8.11 (d, J = 8.0 Hz, 1H), 7.92-7.82 (m, 3H), 7.75-7.69 (m, 1H), 7.64 (dd, J = 7.7, 5.2 Hz, 1H), 7.59-7.54 (m, J = 8.3 Hz, 2H), 7.50-7.43 (m, J = 8.0 Hz, 2H), 7.15 (d, J = 8.0 Hz, 1H), 6.69 (dd, J = 8.3, 2.5 Hz, 1H), 5.17 (s, 2H), 4.25 (t, J = 8.4 Hz, 2H), 3.11 (t, J = 8.4 Hz, 2H) |
| 271 | (indoline with 6-(pyridin-2-ylmethoxy) substituent) | 4-(4-{2-oxo-2-[6-(pyridin-2-ylmethoxy)-2,3-dihydro-1H-indol-1-yl]ethyl}phenyl)-1,2-dihydrophthalazin-1-one | 489.2 | E: 1.33  F: 1.70 | 1H NMR (500 MHz, DMSO-d6) d 12.86 (s, 1H), 8.57 (d, J = 4.7 Hz, 1H), 8.40-8.28 (m, 1H), 7.98-7.82 (m, 4H), 7.73 (d, J = 8.0 Hz, 1H), 7.56 (d, J = 8.0 Hz, 2H), 7.50-7.44 (m, 2H), 7.38-7.31 (m, 1H), 7.13 (d, J = 8.0 Hz, 1H), 6.66 (dd, J = 8.1, 2.1 Hz, 1H), 5.13 (s, 2H), 4.24 (t, J = 8.4 Hz, 2H), 3.96 (s, 2H), 3.10 (t, J = 8.3 Hz, 2H) |
| 272 | (indoline with 6-(pyridin-4-ylmethoxy) substituent) | 4-(4-{2-oxo-2-[6-(pyridin-4-ylmethoxy)-2,3-dihydro-1H-indol-1-yl]ethyl}phenyl)-1,2-dihydrophthalazin-1-one | 489.2 | E: 1.30  F: 1.64 | 1H NMR (500 MHz, DMSO-d6) d 12.86 (s, 1H), 8.55 (d, J = 5.8 Hz, 2H), 8.39-8.27 (m, 1H), 7.95-7.88 (m, 2H), 7.76-7.67 (m, 1H), 7.60-7.54 (m, J = 8.3 Hz, 2H), 7.51-7.44 (m, J = 8.0 Hz, 2H), 7.41 (d, J = 5.5 Hz, 2H), 7.14 (d, J = 8.3 Hz, 1H), 6.66 (dd, J = 8.3, 2.5 Hz, 1H), 5.14 (s, 2H), 4.25 (t, J = 8.5 Hz, 2H), 3.96 (s, 2H), 3.10 (t, J = 8.3 Hz, 2H) |
| 273 | (ketone with 4-phenyl connected to 5-isopropoxy indoline) | 4-(4-{2-oxo-2-[5-(propan-2-yloxy)-2,3-dihydro-1H-indol-1-yl]ethyl}phenyl)-1,2-dihydrophthalazin-1-one | 440.1 | A: 9.77  B: 9.24 | 1H NMR (500 MHz, DMSO-d6) d 12.82 (s, 1H), 8.40-8.31 (m, 1H), 7.97 (d, J = 8.8 Hz, 1H), 7.94-7.86 (m, 2H), 7.78-7.69 (m, 1H), 7.60-7.52 (m, J = 8.0 Hz, 2H), 7.51-7.45 (m, J = 8.3 Hz, 2H), 6.83 (s, 1H), 6.69 (dd, J = 8.8, 2.5 Hz, 1H), 4.56-4.45 (m, 1H), 4.20 (t, J = 8.4 Hz, 2H), 3.93 (s, 2H), 3.20-3.07 (m, 4H), 1.29-1.19 (m, 6H) |
| 274 | (indoline with 6-[(3R)-oxolan-3-yloxy]) | 4-[4-(2-oxo-2-{6-[(3R)-oxolan-3-yloxy]-2,3-dihydro-1H-indol-1-yl}ethyl)phenyl]-1,2-dihydrophthalazin-1-one | 468.2 | E: 1.64  F: 1.64 | 1H NMR (500 MHz, DMSO-d6) d 12.86 (s, 1H), 8.38-8.30 (m, 1H), 7.93-7.85 (m, 2H), 7.79-7.69 (m, 2H), 7.63-7.52 (m, J = 8.0 Hz, 2H), 7.52-7.42 (m, J = 8.0 Hz, 2H), 7.13 (d, J = 8.0 Hz, 1H), 6.64-6.50 (m, 1H), 4.93 (br. s., 1H), 4.24 (t, J = 8.4 Hz, 2H), 3.96 (s, 2H), 3.86-3.78 (m, 2H), 3.78-3.70 (m, 2H), 3.10 (t, J = 8.3 Hz, 2H), 2.16 (dd, J = 13.8, 6.1 Hz, 1H), 2.02-1.83 (m, 1H) |
| 275 | (indoline with 6-[(3S)-oxolan-3-yloxy]) | 4-[4-(2-oxo-2-(6-[(3S)-oxolan-3-yloxy]-2,3-dihydro-1H-indol-1-yl}ethyl)phenyl]-1,2-dihydrophthalazin-1-one | 468.2 | E: 1.64  F: 1.61 | 1H NMR (500 MHz, DMSO-d6) d 12.86 (s, 1H), 8.38-8.30 (m, 1H), 7.92-7.87 (m, 2H), 7.77-7.69 (m, 2H), 7.61-7.52 (m, J = 8.0 Hz, 2H), 7.51-7.42 (m, J = 8.0 Hz, 2H), 7.13 (d, J = 8.3 Hz, 1H), 6.58-6.51 (m, 1H), 4.93 (br. s., 1H), 4.24 (t, J = 8.4 Hz, 2H), 3.96 (s, 2H), 3.88-3.79 (m, 2H), 3.78-3.70 (m, 2H), 3.10 (t, J = 8.4 Hz, 2H), 2.22-2.12 (m, 1H), 2.00-1.89 (m, 1H) |
| 276 | (tetrahydrobenzoxazol-3-yl amino) | 2-[4-(4-oxo-3,4-dihydrophthalazin-1-yl)phenyl]-N-(4,5,6,7-tetrahydro-1,2-benzoxazol-3-yl)acetamide | 401.2 | E: 1.44  F: 1.44 | 1H NMR (500 MHz, DMSO-d6) d 12.86 (s, 1H), 11.08 (br. s., 1H), 8.34 (d, J = 7.2 Hz, 1H), 7.94-7.87 (m, 2H), 7.70 (d, J = 7.7 Hz, 1H), 7.59-7.54 (m, J = 7.7 Hz, 2H), 7.51-7.44 (m, J = 7.7 Hz, 2H), 3.79 (s, 2H), 2.65-2.57 (m, 2H), 2.44-2.32 (m, 2H), 1.69 (d, J = 5.8 Hz, 2H), 1.65-1.55 (m, 2H) |
| 277 | (indoline with 6-{[(3R)-1-methylpyrrolidin-3-yl]oxy}) | 4-{4-[2-(6-{[(3R)-1-methylpyrrolidin-3-yl]oxy}-2,3-dihydro-1H-indol-1-yl)-2-oxoethyl]phenyl}-1,2-dihydrophthalazin-1-one | 481.2 | E: 1.40  F: 1.40 | 1H NMR (500 MHz, DMSO-d6) d 12.86 (br. s., 1H), 8.34 (d, J = 6.9 Hz, 1H), 7.93-7.87 (m, 2H), 7.76-7.69 (m, 2H), 7.59-7.55 (m, J = 7.4 Hz, 2H), 7.49-7.41 (m, J = 7.4 Hz, 2H), 7.11 (d, J = 8.3 Hz, 1H), 6.51 (d, J = 8.0 Hz, 1H), 4.75 (br. s., 1H), 4.24 (t, J = 8.3 Hz, 2H), 3.96 (s, 2H), 3.09 (t, J = 8.1 Hz, 2H), 2.76-2.70 (m, 1H), 2.62 (d, J = 7.4 Hz, 1H), 2.56 (d, J = 10.2 Hz, 1H), 2.40-2.29 (m, 1H), 2.27-2.16 (m, 4H), 1.90 (s, 1H), 1.79-1.69 (m, 1H) |
| 278 | (5-tert-butyl-isoxazol-3-yl amino) | N-(5-tert-butyl-1,2-oxazol-3-yl)-2-[4-(4-oxo-3,4-dihydrophthalazin-1-yl)phenyl]acetamide | 403.2 | E: 1.70  F: 1.74 | 1H NMR (500 MHz, DMSO-d6) d 12.85 (s, 1H), 11.29 (br. s., 1H), 8.43-8.28 (m, 1H), 7.89 (dd, J = 4.8, 3.4 Hz, 2H), 7.69 (d, J = 7.4 Hz, 1H), 7.59-7.53 (m, J = 7.4 Hz, 2H), 7.53-7.43 (m, J = 7.7 Hz, 2H), 6.60 (s, 1H), 3.90 (s, 1H), 3.78 (s, 2H), 1.28 (s, 9H) |

TABLE 4-continued

| Example | R | IUPAC name | LCMS (M + H)+ | HPLC Method, RT (min.) | 1H NMR |
|---|---|---|---|---|---|
| 279 | (indoline with 6-O-CH2CH2-N(CH3)2) | 4-[4-(2-{6-[2-(dimethylamino)ethoxy]-2,3-dihydro-1H-indol-1-yl}-2-oxoethyl)phenyl]-1,2-dihydrophthalazin-1-one | 469.1 | E: 1.27 F: 1.27 | 1H NMR (500 MHz, DMSO-d6) d 12.86 (s, 1H), 8.34 (d, J = 6.9 Hz, 1H), 7.90 (d, J = 3.6 Hz, 2H), 7.81-7.69 (m, 2H), 7.61-7.51 (m, J = 7.4 Hz, 2H), 7.50-7.38 (m, J = 7.4 Hz, 2H), 7.12 (d, J = 8.3 Hz, 1H), 6.58 (d, J = 8.0 Hz, 1H), 4.24 (t, J = 8.3 Hz, 2H), 4.07-3.95 (m, 4H), 3.10 (t, J = 8.1 Hz, 2H), 2.62 (br. s., 2H), 2.22 (s, 6H) |
| 280 | (NH-dimethylisoxazole) | N-(dimethyl-1,2-oxazol-3-yl)-2-[4-(4-oxo-3,4-dihydrophthalazin-1-yl)phenyl]acetamide | 375.2 | E: 1.29 F: 1.30 | 1H NMR (500 MHz, DMSO-d6) d 12.86 (br. s., 1H), 10.51 (br. s., 1H), 8.34 (d, J = 7.2 Hz, 1H), 8.02-7.81 (m, 3H), 7.70 (d, J = 6.9 Hz, 1H), 7.61-7.54 (m, J = 7.4 Hz, 2H), 7.53-7.44 (m, J = 7.4 Hz, 2H), 3.80 (s, 2H), 2.30 (s, 3H), 1.78 (s, 3H) |
| 281 | (indoline with 6-O-(3S)-1-methylpyrrolidin-3-yl) | 4-{4-[2-(6-{[(3S)-1-methylpyrrolidin-3-yl]oxy}-2,3-dihydro-1H-indol-1-yl)-2-oxoethyl]phenyl}-1,2-dihydrophthalazin-1-one | 481.2 | E: 1.31 F: 1.34 | 1H NMR (500 MHz, DMSO-d6) d 12.86 (s, 1H), 8.34 (d, J = 6.9 Hz, 1H), 7.96-7.84 (m, 2H), 7.79-7.69 (m, 2H), 7.66-7.54 (m, J = 7.7 Hz, 2H), 7.51-7.42 (m, J = 7.7 Hz, 2H), 7.11 (d, J = 8.0 Hz, 1H), 6.52 (d, J = 8.0 Hz, 1H), 4.76 (br. s., 1H), 4.24 (t, J = 8.3 Hz, 2H), 3.96 (s, 2H), 3.09 (t, J = 8.3 Hz, 2H), 2.78-2.72 (m, 1H), 2.65 (d, J = 6.9 Hz, 1H), 2.59 (d, J = 10.2 Hz, 1H), 2.39-2.34 (m, 1H), 2.30-2.20 (m, 4H), 1.79-1.69 (m, 1H) |
| 282 | (indoline with 6-O-(1-methylpiperidin-4-yl)) | 4-[4-(2-{6-[(1-methylpiperidin-4-yl)oxy]-2,3-dihydro-1H-indol-1-yl}-2-oxoethyl)phenyl]-1,2-dihydrophthalazin-1-one | 495.1 | E: 1.35 F: 1.35 | 1H NMR (500 MHz, DMSO-d6) d 12.87 (s, 1H), 9.46 (br. s., 1H), 8.35 (d, J = 6.3 Hz, 1H), 7.95 (s, 1H), 7.91 (d, J = 3.6 Hz, 2H), 7.83 (br. s., 1H), 7.72 (br. s., 1H), 7.63-7.53 (m, J = 7.7 Hz, 2H), 7.50-7.42 (m, J = 7.4 Hz, 2H), 7.19-7.09 (m, 1H), 6.72-6.61 (m, 1H), 4.25 (t, J = 8.0 Hz, 2H), 3.97 (br. s., 2H), 3.31 (d, J = 12.1 Hz, 2H), 3.20-3.04 (m, 4H), 2.89 (s, 2H), 2.82 (br. s., 2H), 2.77 (br. s., 1H), 2.73 (s, 2H), 2.55 (br. s., 1H), 2.20 (d, J = 13.2 Hz, 1H), 2.09-2.00 (m, 1H), 1.99-1.88 (m, 1H), 1.70 (q, J = 12.1 Hz, 1H) |
| 283 | (indoline with 6-O-CH2-CO2Me) | methyl 2-[(1-{2-[4-(4-oxo-3,4-dihydrophthalazin-1-yl)phenyl]acetyl}-2,3-dihydro-1H-indol-6-yl)oxy]acetate | 470.1 | A: 8.46 B: 8.47 | 1H NMR (500 MHz, DMSO-d6) d 12.83 (s, 1H), 8.39-8.32 (m, 1H), 7.95-7.86 (m, 2H), 7.77-7.70 (m, 2H), 7.61-7.53 (m, J = 8.3 Hz, 2H), 7.51-7.44 (m, J = 8.3 Hz, 2H), 7.13 (d, J = 8.0 Hz, 1H), 6.57 (dd, J = 8.3, 2.5 Hz, 1H), 4.72 (s, 2H), 4.25 (t, J = 8.5 Hz, 2H), 3.96 (s, 2H), 3.76-3.59 (m, 3H), 3.10 (t, J = 8.3 Hz, 2H) |
| 284 | (indoline with 6-O-CH2-oxetan-3-yl) | 4-(4-{2-[6-(oxetan-3-ylmethoxy)-2,3-dihydro-1H-indol-1-yl]-2-oxoethyl}phenyl)-1,2-dihydrophthalazin-1-one | 468.2 | E: 1.61 F: 1.61 | 1H NMR (500 MHz, DMSO-d6) d 12.86 (br. s., 1H), 8.34 (d, J = 6.1 Hz, 1H), 7.90 (br. s., 2H), 7.78 (br. s., 1H), 7.72 (d, J = 6.6 Hz, 1H), 7.56 (d, J = 6.9 Hz, 2H), 7.46 (d, J = 7.2 Hz, 2H), 7.13 (d, J = 7.2 Hz, 1H), 6.60 (d, J = 7.7 Hz, 1H), 4.68 (br. s., 2H), 4.40 (br. s., 2H), 4.25 (t, J = 7.6 Hz, 2H), 4.13 (d, J = 5.2 Hz, 2H), 3.97 (br. s., 2H), 3.10 (t, J = 7.3 Hz, 2H), 1.23 (br. s., 1H) |
| 285 | (6-nitroindoline) | 4-{4-[2-(6-nitro-2,3-dihydro-1H-indol-1-yl)-2-oxoethyl]phenyl}-1,2-dihydrophthalazin-1-one | 427.1 | E: 1.70 F: 1.65 | 1H NMR (500 MHz, DMSO-d6) d 12.86 (br. s., 1H), 8.84 (br. s., 1H), 8.39-8.30 (m, 1H), 8.02-7.87 (m, 3H), 7.73 (br. s., 1H), 7.57 (d, J = 7.2 Hz, 2H), 7.54-7.45 (m, 3H), 4.36 (t, J = 8.0 Hz, 2H), 4.03 (br. s., 2H) |
| 286 | (indoline with 6-O-CH2CH2-pyrrolidin-1-yl) | 4-[4-(2-oxo-2-{6-[2-(pyrrolidin-1-yl)ethoxy]-2,3-dihydro-1H-indol-1-yl}ethyl)phenyl]-1,2-dihydrophthalazin-1-one | 495.2 | E: 1.27 F: 1.31 | 1H NMR (500 MHz, DMSO-d6) d 12.83 (s, 1H), 8.41-8.28 (m, 1H), 7.94-7.84 (m, 2H), 7.78-7.68 (m, 2H), 7.63-7.51 (m, J = 8.3 Hz, 2H), 7.49-7.41 (m, J = 8.0 Hz, 2H), 7.11 (d, J = 8.3 Hz, 1H), 6.58 (dd, J = 8.3, 2.5 Hz, 1H), 4.24 (t, J = 8.4 Hz, 2H), 4.07-3.92 (m, 4H), 3.10 (t, J = 8.4 Hz, 2H), 2.81-2.69 (m, 2H), 1.66 (dt, J = 6.7, 3.1 Hz, 4H) |
| 291 | (indoline with 6-CONMe2) | N,N-dimethyl-1-{2-[4-(4-oxo-3,4-dihydrophthalazin-1-yl)phenyl]acetyl}-2,3-dihydro-1H-indole-6-carboxamide | 453.2 | E: 1.53 F: 1.50 | 1H NMR (500 MHz, DMSO-d6) d 12.86 (br .s., 1H), 8.34 (d, J = 6.3 Hz, 1H), 8.09 (br. s., 1H), 7.91-7.85 (m, 2H), 7.72 (d, J = 6.6 Hz, 1H), 7.62-7.53 (m, J = 7.2 Hz, 2H), 7.50-7.41 (m, J = 7.2 Hz, 2H), 7.30 (d, J = 7.2 Hz, 1H), 7.03 (d, J = 7.4 Hz, 1H), 4.33-4.21 (m, 2H), 3.98 (br. s., 2H), 3.22 (t, J = 8.1 Hz, 2H), 2.96 (br. s., 3H), 2.89 (br. s., 3H) |

TABLE 4-continued

| Example | R | IUPAC name | LCMS (M + H)⁺ | HPLC Method, RT (min.) | ¹H NMR |
|---|---|---|---|---|---|
| 292 | | 4-(4-{2-[6-(4-methylpiperazine-1-carbonyl)-2,3-dihydro-1H-indol-1-yl]-2-oxoethyl}phenyl)-1,2-dihydrophthalazin-1-one | 508.3 | E: 1.33 F: 1.44 | ¹H NMR (500 MHz, DMSO-$d_6$) d 12.86 (br. s., 1H), 8.34 (d, J = 6.3 Hz, 1H), 8.08 (br. s., 1H), 7.90 (br. s., 2H), 7.72 (d, J = 6.1 Hz, 1H), 7.60-7.53 (m, J = 7.4 Hz, 2H), 7.51-7.45 (m, J = 7.4 Hz, 2H), 7.31 (d, J = 7.4 Hz, 1H), 7.01 (d, J = 7.2 Hz, 1H), 4.27 (t, J = 7.8 Hz, 2H), 4.04-3.94 (m, 2H), 3.58 (br. s., 2H), 3.22 (t, J = 7.8 Hz, 2H), 2.32 (br. s., 2H), 2.24 (br. s., 2H), 2.17 (br. s., 3H) |
| 293 | | 4-(4-{2-[6-(morpholine-4-carbonyl)-2,3-dihydro-1H-indol-1-yl]-2-oxoethyl}phenyl)-1,2-dihydrophthalazin-1-one | 495.2 | E: 1.35 F: 1.35 | ¹H NMR (500 MHz, DMSO-$d_6$) d 12.83 (s, 1H), 8.37-8.30 (m, 1H), 8.11 (s, 1H), 7.92-7.86 (m, 2H), 7.74-7.69 (m, 1H), 7.59-7.54 (m, J = 8.3 Hz, 2H), 7.51-7.44 (m, J = 8.0 Hz, 2H), 7.31 (d, J = 7.4 Hz, 1H), 7.04 (dd, J = 7.7, 1.4 Hz, 1H), 4.27 (t, J = 8.5 Hz, 2H), 4.04-3.93 (m, 2H), 3.57 (br. s., 6H), 3.22 (t, J = 8.4 Hz, 2H) |
| 294 | | 4-(4-{2-[5-(4-hydroxypiperidine-1-carbonyl)-2,3-dihydro-1H-indol-1-yl]-2-oxoethyl}phenyl)-1,2-dihydrophthalazin-1-one | 509.2 | E: 1.21 F: 1.27 | ¹H NMR (500 MHz, DMSO-$d_6$) d 12.83 (s, 1H), 8.38-8.31 (m, 1H), 8.09 (d, J = 8.3 Hz, 1H), 7.94-7.86 (m, 2H), 7.76-7.69 (m, 1H), 7.60-7.54 (m, J = 8.3 Hz, 2H), 7.50-7.44 (m, J = 8.0 Hz, 2H), 7.27 (s, 1H), 7.19 (d, J = 8.3 Hz, 1H), 4.76 (d, J = 4.1 Hz, 1H), 4.26 (t, J = 8.5 Hz, 2H), 3.99 (s, 2H), 3.90 (s, 2H), 3.72 (ddt, J = 12.1. 8.1, 3.8 Hz, 1H), 3.25-3.10 (m, 4H), 1.73 (br. s., 2H), 1.34 (br. s., 2H) |
| 295 | | 4-(4-{2-[6-(4-hydroxypiperidine-1-carbonyl)-2,3-dihydro-1H-indol-1-yl]-2-oxoethyl}phenyl)-1,2-dihydrophthalazin-1-one | 509.2 | E: 1.32 F: 1.32 | ¹H NMR (500 MHz, DMSO-$d_6$) d 12.83 (s, 1H), 8.40-8.31 (m, 1H), 8.08 (s, 1H), 7.92-7.86 (m, 2H), 7.75-7.69 (m, 1H), 7.59-7.53 (m, J = 8.0 Hz, 2H), 7.53-7.45 (m, J = 8.0 Hz, 2H), 7.30 (d, J = 7.7 Hz, 1H), 7.00 (dd, J = 7.4, 1.1 Hz, 1H), 4.75 (d, J = 4.1 Hz, 1H), 4.27 (t, J = 8.4 Hz, 2H), 4.05-3.91 (m, 3H), 3.71 (td, J = 8.0, 4.1 Hz, 1H), 3.51 (s, 1H), 3.22 (t, J = 8.5 Hz, 2H), 3.13 (br. s., 2H), 1.75 (br. s., 1H), 1.68 (br. s., 1H), 1.40 (br. s., 1H), 1.35-1.23 (m, 7H) |
| 296 | | 4-(4-{2-[5-(morpholine-4-carbonyl)-2,3-dihydro-1H-indol-1-yl]-2-oxoethyl}phenyl)-1,2-dihydrophthalazin-1-one | 495.2 | E: 1.38 F: 1.38 | ¹H NMR (500 MHz, DMSO-$d_6$) d 12.83 (s, 1H), 8.37-8.29 (m, 1H), 8.10 (d, J = 8.0 Hz, 1H), 7.93-7.86 (m, 2H), 7.75-7.70 (m, 1H), 7.61-7.54 (m, J = 8.0 Hz, 2H), 7.50-7.45 (m, J = 8.0 Hz, 2H), 7.31 (s, 1H), 7.23 (d, J = 8.3 Hz, 1H), 4.27 (t, J = 8.4 Hz, 2H), 3.99 (s, 2H), 3.59 (br. s., 4H), 3.48 (br. s., 4H), 3.21 (t, J = 8.3 Hz, 2H) |

Example 287: 4-(2-Fluoro-4-(2-(indolin-1-yl)-2-oxoethyl)phenyl)isoquinolin-1(2H)-one

Example 288: 4-(4-(2-(6-(2-Hydroxy-2-methyl-propoxy)indolin-1-yl)-2-oxoethyl)phenyl)isoquinolin-1(2H)-one

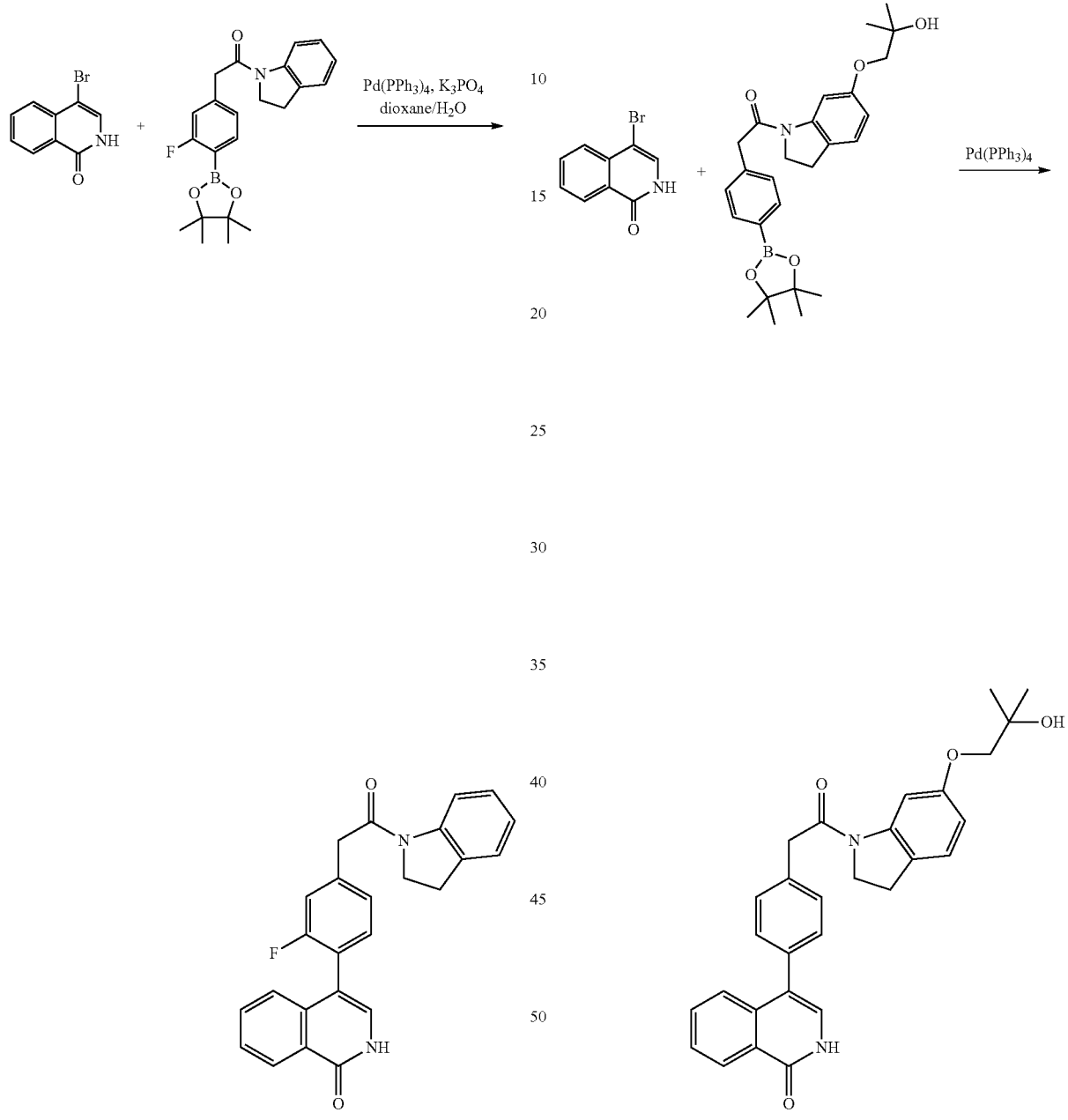

According to the procedure for the preparation of Example 76, coupling of Intermediate 6 (15 mg, 0.067 mmol) and Intermediate 72 (33.2 mg, 0.087 mmol), afforded 10.6 mg (31%) of Example 287. MS(ESI) m/z: 399.2 (M+H)$^+$; $^1$H NMR (500 MHz, DMSO-d$_6$) δ 11.55 (br. s., 1H), 8.28 (dd, J=8.1, 1.0 Hz, 1H), 8.08 (d, J=8.0 Hz, 1H), 7.69 (ddd, J=8.3, 7.1, 1.4 Hz, 1H), 7.58-7.50 (m, 1H), 7.40 (t, J=7.8 Hz, 1H), 7.32-7.27 (m, 1H), 7.27-7.20 (m, 3H), 7.19-7.12 (m, 2H), 7.04-6.97 (m, 1H), 4.23 (t, J=8.5 Hz, 2H), 3.97 (s, 2H), 3.19 (t, J=8.5 Hz, 2H); HPLC RT=1.76 min (Method E), 1.76 min (Method F).

According to the procedure for the preparation of Example 76, coupling of Intermediate 6 (20 mg, 0.089 mmol) and Intermediate 87 (40.3 mg, 0.089 mmol), afforded 11.9 mg (28%) of Example 287. MS(ESI) m/z: 469.3 (M+H)$^+$; $^1$H NMR (500 MHz, DMSO-d$_6$) δ 11.47 (d, J=5.5 Hz, 1H), 8.33-8.27 (m, 1H), 7.76 (d, J=1.9 Hz, 1H), 7.73-7.67 (m, 1H), 7.58-7.51 (m, 2H), 7.40 (s, 4H), 7.13-7.06 (m, 2H), 6.57 (dd, J=8.1, 2.3 Hz, 1H), 4.62 (s, 1H), 4.23 (t, J=8.5 Hz, 2H), 3.91 (d, J=7.2 Hz, 2H), 3.63 (s, 2H), 3.09 (t, J=8.4 Hz, 2H), 1.18 (s, 6H); HPLC RT=1.70 min (Method E), 1.69 min (Method F).

Example 289: 4-(4-(2-(6-(2-Hydroxy-2-methyl-propoxy)indolin-1-yl)-2-oxoethyl)phenyl)-6-methoxyisoquinolin-1(2H)-one

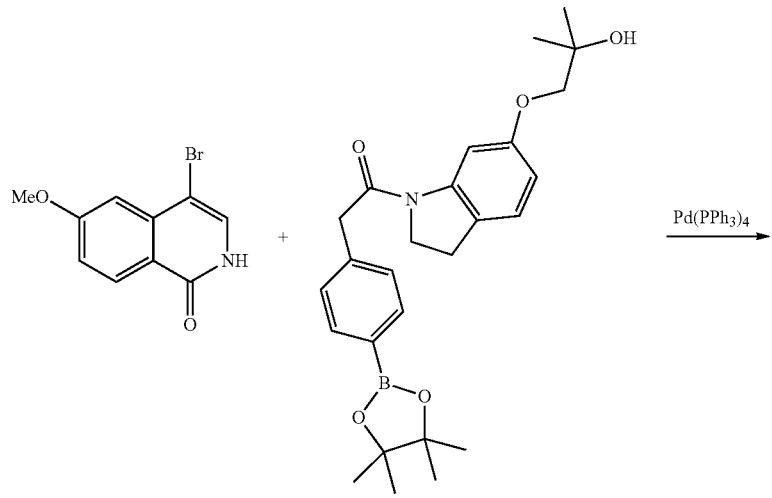

According to the procedure for the preparation of Example 76, coupling of Intermediate 73 (22 mg, 0.087 mmol) and Intermediate 87 (39.1 mg, 0.087 mmol) afforded 12.4 mg (29%) of Example 289. MS(ESI) m/z: 499.3 (M+H)$^+$; $^1$H NMR (500 MHz, DMSO-d$_6$) δ 11.30 (d, J=5.8 Hz, 1H), 8.23 (d, J=9.1 Hz, 1H), 7.76 (d, J=1.9 Hz, 1H), 7.48-7.37 (m, 4H), 7.23-7.09 (m, 2H), 7.06 (d, J=5.5 Hz, 1H), 6.94 (d, J=2.2 Hz, 1H), 6.57 (dd, J=8.1, 2.3 Hz, 1H), 4.61 (s, 1H), 4.23 (t, J=8.4 Hz, 2H), 3.92 (s, 2H), 3.77 (s, 3H), 3.63 (s, 2H), 3.09 (t, J=8.4 Hz, 2H), 1.17 (s, 6H); HPLC RT=1.70 min (Method E), 1.70 min (Method F).

333

Example 290: 2-((1-(2-(4-(4-Oxo-3,4-dihydrophthalazin-1-yl)phenyl)acetyl)indolin-6-yl)oxy) acetic Acid

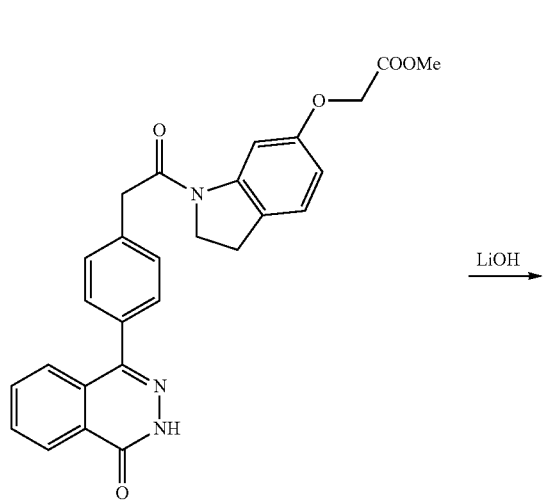

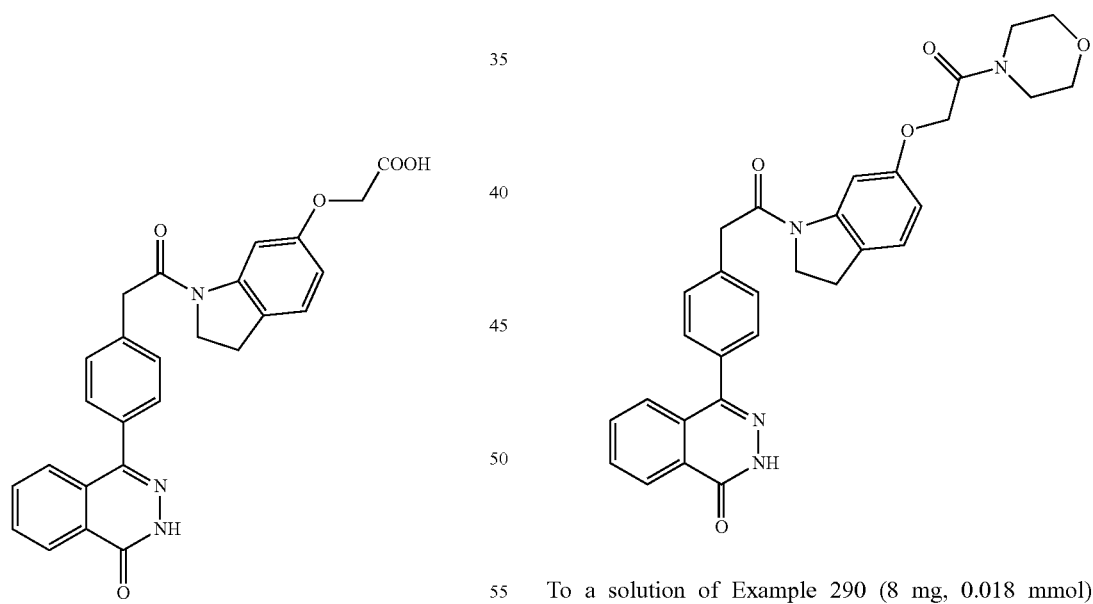

A mixture of Example 283 (32 mg, 0.068 mmol) and 1M lithium hydroxide (0.2 mL, 0.200 mmol) in THF (2 mL) was stirred rt for 2 h. The mixture was concentrated, then was purified by prep HPLC to afford Example 290 (28 mg, 90% yield). MS(ESI) m/z: 456.0 (M+H)+; $^1$H NMR (500 MHz, methanol-$d_4$) δ 8.50-8.44 (m, 1H), 7.96-7.84 (m, 4H), 7.63-7.58 (m, 2H), 7.57-7.52 (m, 2H), 7.11 (d, J=8.3 Hz, 1H), 6.64 (dd, J=8.3, 2.5 Hz, 1H), 4.62 (s, 2H), 4.27 (t, J=8.4 Hz, 2H), 4.00 (s, 2H), 3.16 (t, J=8.3 Hz, 2H); HPLC RT=7.44 min (Method A), 7.57 min (Method B).

334

Example 297: 4-(4-(2-(6-(2-Morpholino-2-oxoethoxy)indolin-1-yl)-2-oxoethyl)phenyl)phthalazin-1 (2H)-one

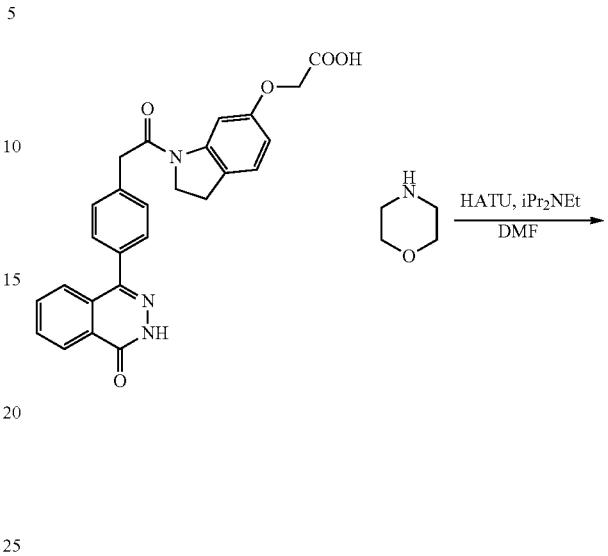

To a solution of Example 290 (8 mg, 0.018 mmol), morpholine (3.06 mg, 0.035 mmol), and HATU (10.02 mg, 0.026 mmol) in DMF (1 mL), was add DIEA (0.015 mL, 0.088 mmol). The mixture was stirred rt for 1 h, then was purified by prep HPLC to afford Example 297 (6.1 mg, 64% yield). MS(ESI) m/z: 525.3 (M+H)+; $^1$H NMR (500 MHz, DMSO-$d_6$) δ 12.86 (br. s., 1H), 8.34 (d, J=6.1 Hz, 1H), 7.90 (br. s., 2H), 7.73 (br. s., 2H), 7.56 (d, J=6.6 Hz, 2H), 7.46 (d, J=6.9 Hz, 2H), 7.12 (d, J=5.8 Hz, 1H), 6.57 (d, J=8.0 Hz, 1H), 4.75 (br. s., 2H), 4.24 (t, J=7.4 Hz, 2H), 3.96 (br. s., 2H), 3.59 (br. s., 2H), 3.55 (br. s., 2H), 3.44 (d, J=11.8 Hz, 4H), 3.10 (t, J=7.6 Hz, 2H); HPLC RT=1.45 min (Method E), 1.45 min (Method F).

Example 298: 2-((1-(2-(4-(4-Oxo-3,4-dihydrophthalazin-1-yl)phenyl)acetyl)indolin-6-yl)oxy)acetamide

Example 299: 4-(4-(2-(6-(2-(4-Methylpiperazin-1-yl)-2-oxoethoxy)indolin-1-yl)-2-oxoethyl)phenyl)phthalazin-1(2H)-one

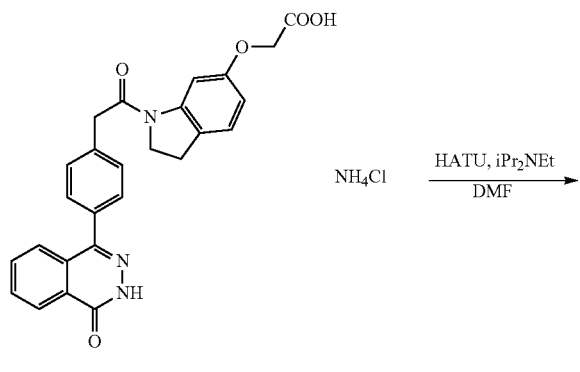

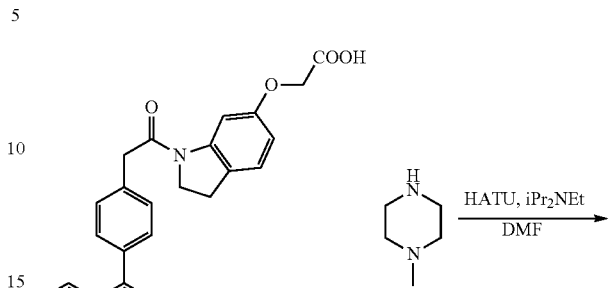

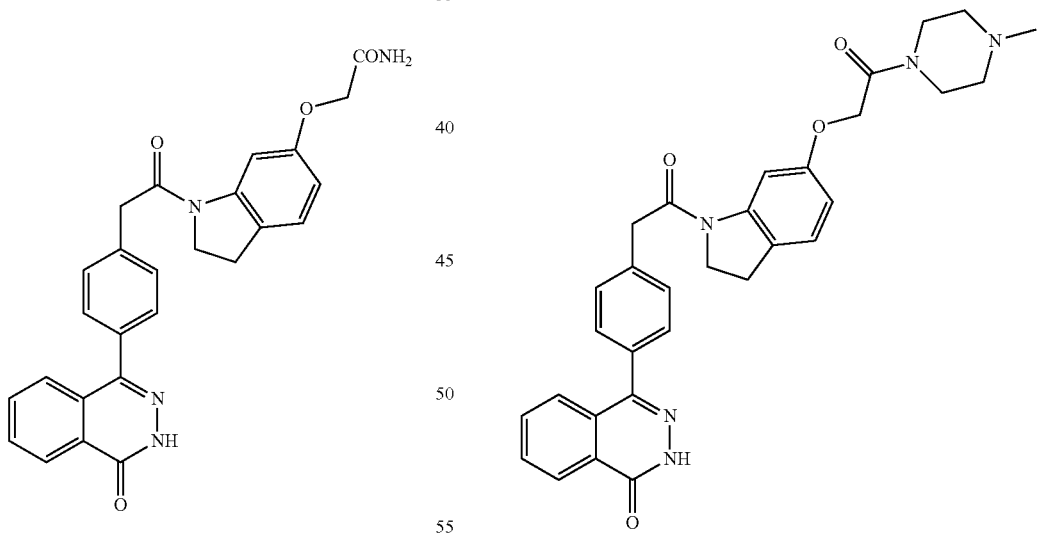

According to the procedure for the preparation of Example 297, coupling of Example 290 (8 mg, 0.018 mmol) and ammonium chloride (1.9 mg, 0.035 mmol) afforded Example 298 (5.1 mg, 63% yield). MS(ESI) m/z: 455.2 (M+H)$^+$; $^1$H NMR (500 MHz, DMSO-d$_6$) δ 12.86 (br. s., 1H), 8.34 (d, J=6.3 Hz, 1H), 7.90 (br. s., 2H), 7.79 (br. s., 1H), 7.73 (d, J=6.6 Hz, 1H), 7.56 (d, J=7.4 Hz, 2H), 7.53-7.45 (m, 3H), 7.35 (br. s., 1H), 7.13 (d, J=6.3 Hz, 1H), 6.65-6.55 (m, 1H), 4.35 (br. s., 2H), 4.24 (t, J=7.8 Hz, 2H), 3.96 (br. s., 2H), 3.10 (t, J=7.8 Hz, 2H); HPLC RT=1.48 min (Method E), 1.49 min (Method F).

According to the procedure for the preparation of Example 297, coupling of Example 290 (8 mg, 0.018 mmol) and 1-methylpiperazine (4.40 mg, 0.044 mmol) afforded Example 299 (1.2 mg, 9% yield). MS(ESI) m/z: 538.4 (M+H)$^+$; $^1$H NMR (500 MHz, DMSO-d$_6$) δ 12.87 (br. s., 1H), 9.98 (br. s., 1H), 8.40-8.29 (m, 1H), 7.91 (br. s., 2H), 7.76-7.67 (m, 2H), 7.57 (d, J=6.9 Hz, 2H), 7.46 (d, J=6.9 Hz, 2H), 7.19-7.09 (m, 1H), 6.59 (d, J=7.7 Hz, 1H), 4.87 (br. s., 1H), 4.79 (br. s., 1H), 4.39 (br. s., 1H), 4.26 (br. s., 2H), 4.06 (br. s., 1H), 3.98 (br. s., 2H), 3.17-3.04 (m, 3H), 2.65 (br. s., 3H); HPLC RT=1.30 min (Method E), 1.30 min (Method F).

Example 300: 4-(Dimethylamino)-N-(1-(2-(4-(4-oxo-3,4-dihydrophthalazin-1-yl)phenyl)acetyl)indolin-6-yl)benzamide

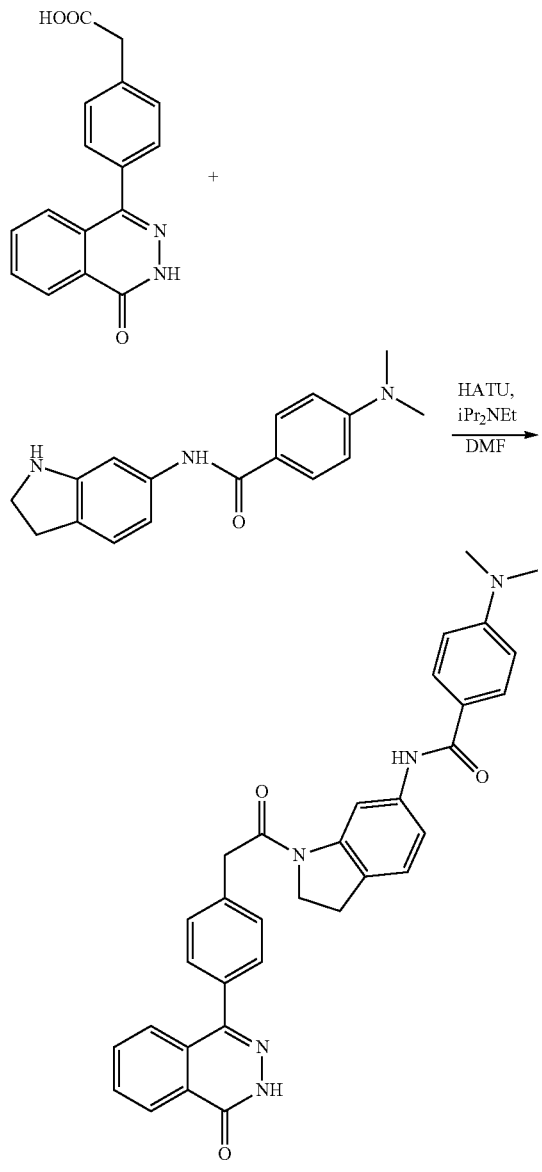

According to the procedure for the preparation of Example 3, coupling of Intermediate 1 (11 mg, 0.039 mmol), and Intermediate 95 (22 mg, 0.043 mmol) afforded Example 300 (8.6 mg, 40% yield). MS(ESI) m/z: 544.3 (M+H)$^+$; $^1$H NMR (500 MHz, DMSO-d$_6$) δ 12.84 (s, 1H), 9.81 (s, 1H), 8.38-8.31 (m, 1H), 8.01 (d, J=8.5 Hz, 1H), 7.92-7.81 (m, 4H), 7.76-7.69 (m, 2H), 7.57 (d, J=8.0 Hz, 2H), 7.48 (d, J=8.0 Hz, 3H), 6.75 (d, J=9.1 Hz, 2H), 4.24 (t, J=8.5 Hz, 2H), 3.96 (s, 2H), 3.19 (t, J=8.4 Hz, 2H), 2.99 (s, 6H); HPLC RT=1.55 min (Method E), 1.70 min (Method F).

The following Examples in Table 5 were made by using the same procedure as shown in Example 45. Intermediate 94 was coupled with the appropriate carboxylic acid. Various coupling reagents could be used other than the one described in Example 45, such as BOP, PyBop, EDC/HOBt or T3P.

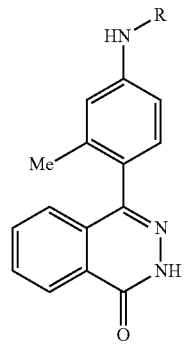

| Example | R | IUPAC name | LCMS (M + H)$^+$ | HPLC Method, RT (min.) | $^1$H NMR |
|---|---|---|---|---|---|
| 301 | ![structure] | 1-(2-hydroxy-2-methylpropyl)-N-[3-methyl-4-(4-oxo-3,4-dihydrophthalazin-1-yl)phenyl]-1H-indazole-3-carboxamide | 468.2 | E: 1.64 F: 1.67 | $^1$H NMR (500 MHz, DMSO-d$_6$) d 12.79 (s, 1H), 10.27 (s, 1H), 8.38-8.30 (m, 1H), 8.24 (d, J = 8.3 Hz, 1H), 7.94 (d, J = 1.7 Hz, 1H), 7.90-7.83 (m, 4H), 7.48 (td, J = 7.7, 0.8 Hz, 1H), 7.36-7.25 (m, 3H), 4.77 (s, 1H), 4.48 (s, 2H), 2.11 (s, 3H), 1.20 (s, 6H) |

-continued

| Example | R | IUPAC name | LCMS (M + H)+ | HPLC Method, RT (min.) | 1H NMR |
|---|---|---|---|---|---|
| 302 | | 1-(2-hydroxy-2-methylpropyl)-N-[3-methyl-4-(4-oxo-3,4-dihydrophthalazin-1-yl)phenyl]-1H-indole-3-carboxamide | 467.1 | A: 7.85 B: 7.05 | 1H NMR (400 MHz, methanol-$d_4$) d 8.48-8.41 (m, 1H), 8.23 (d, J = 7.5 Hz, 1H), 8.15 (s, 1H), 7.93-7.83 (m, 2H), 7.76 (d, J = 1.8 Hz, 1H), 7.71 (dd, J = 8.3, 2.1 Hz, 1H), 7.56 (d, J = 8.1 Hz, 1H), 7.47-7.40 (m, 1H), 7.34-7.24 (m, 2H), 7.24-7.18 (m, 1H), 4.23 (s, 2H), 2.16 (s, 3H), 1.25 (s, 6H) |
| 303 | | 1-[2-(dimethylamino)ethyl]-N-[3-methyl-4-(4-oxo-3,4-dihydrophthalazin-1-yl)phenyl]-1H-indazole-3-carboxamide | 467.3 | E: 1.33 F: 1.53 | 1H NMR (500 MHz, DMSO-$d_6$) d 12.80 (s, 1H), 10.29 (s, 1H), 9.39 (br. s., 1H), 8.38-8.33 (m, 1H), 8.29 (d, J = 8.0 Hz, 1H), 7.95-7.80 (m, 5H), 7.59 (t, J = 7.7 Hz, 1H), 7.41 (d, J = 7.7 Hz, 1H), 7.35 (d, J = 8.3 Hz, 1H), 7.32-7.25 (m, 1H), 4.96 (t, J = 5.9 Hz, 2H), 3.80 (br. s., 2H), 2.95 (br. s., 6H), 2.12 (s, 3H) |
| 304 | | 2-[2-(dimethylamino)ethyl]-N-[3-methyl-4-(4-oxo-3,4-dihydrophthalazin-1-yl)phenyl]-2H-indazole-3-carboxamide | 467.2 | E: 1.31 F: 1.45 | 1H NMR (500 MHz, DMSO-$d_6$) d 12.80 (s, 1H), 10.93 (s, 1H), 8.41-8.31 (m, 1H), 7.91-7.81 (m, 4H), 7.80-7.71 (m, 2H), 7.45-7.35 (m, 2H), 7.32-7.24 (m, 2H), 4.84 (t, J = 6.2 Hz, 2H), 2.83 (t, J = 6.3 Hz, 2H), 2.17 (s, 6H), 2.11 (s, 3H) |
| 305 | | N-[3-methyl-4-(4-oxo-3,4-dihydrophthalazin-1-yl)phenyl]-2-(oxetan-3-ylmethyl)-2H-indazole-3-carboxamide | 466.2 | E: 1.09 F: 1.08 | 1H NMR (500 MHz, DMSO-$d_6$) d 12.84 (s, 1H), 11.28 (s, 1H), 8.38-8.33 (m, 1H), 8.31 (d, J = 8.5 Hz, 1H), 8.06 (d, J = 8.8 Hz, 1H), 8.00-7.93 (m, 1H), 7.92-7.86 (m, 2H), 7.84 (s, 1H), 7.81 (d, J = 8.3 Hz, 1H), 7.70 (t, J = 7.7 Hz, 1H), 7.43 (d, J = 8.3 Hz, 1H), 7.27 (d, J = 8.3 Hz, 1H), 5.16 (dd, J = 13.3, 8.1 Hz, 2H), 5.01-4.87 (m, 2H), 4.70 (dd, J = 11.3, 4.7 Hz, 1H), 3.73 (br. s., 2H), 3.67-3.59 (m, 1H), 2.14 (s, 3H) |
| 306 | | N-[3-methyl-4-(4-oxo-3,4-dihydrophthalazin-1-yl)phenyl]-2,1-benzoxazole-3-carboxamide | 397.1 | E: 1.68 F: 1.68 | 1H NMR (500 MHz, DMSO-$d_6$) d 12.81 (s, 1H), 11.23 (s, 1H), 8.40-8.28 (m, 1H), 8.05 (d, J = 8.8 Hz, 1H), 7.96 (s, 1H), 7.90-7.81 (m, 4H), 7.55 (dd, J = 9.2, 6.5 Hz, 1H), 7.40-7.32 (m, 2H), 7.31-7.25 (m, 1H), 2.11 (s, 3H) |

-continued

| Example | R | IUPAC name | LCMS (M + H)+ | HPLC Method, RT (min.) | 1H NMR |
|---|---|---|---|---|---|
| 307 | | benzyl 4-[(3-{[3-methyl-4-(4-oxo-3,4-dihydrophthalazin-1-yl)phenyl]carbamoyl}-1H-indazol-1-yl)methyl]piperidine-1-carboxylate | 672.2 | A: 11.59 B: 9.87 | 1H NMR (400 MHz, DMSO-$d_6$) d 12.79 (s, 1H), 10.34 (s, 1H), 8.37-8.31 (m, 1H), 8.25 (d, J = 8.1 Hz, 1H), 7.96 (d, J = 2.0 Hz, 1H), 7.92-7.82 (m, 4H), 7.51 (ddd, J = 8.4, 7.0, 1.1 Hz, 1H), 7.41-7.23 (m, 7H), 5.06 (s, 2H), 4.48 (d, J = 7.0 Hz, 2H), 4.02 (d, J = 13.0 Hz, 2H), 2.78 (br. s., 2H), 2.36-2.19 (m, 1H), 2.16-2.03 (m, 3H), 1.51 (d, J = 11.0 Hz, 2H), 1.26 (qd, J = 12.4, 4.1 Hz, 2H) |
| 308 | | 5-fluoro-N-[3-methyl-4-(4-oxo-3,4-dihydrophthalazin-1-yl)phenyl]-1H-pyrrolo[2,3-b]pyridine-3-carboxamide | 414.2 | E: 1.44 F: 1.44 | 1H NMR (500 MHz, DMSO-$d_6$) d 12.78 (s, 1H), 12.48 (br. s., 1H), 9.98 (s, 1H), 8.58 (d, J = 2.5 Hz, 1H), 8.33 (br. s., 2H), 8.26 (dd, J = 9.4, 2.8 Hz, 1H), 7.95 (s, 1H), 7.90-7.84 (m, 2H), 7.81 (s, 1H), 7.76 (d, J = 8.3 Hz, 1H), 7.30-7.25 (m, 1H), 2.10 (s, 3H) |
| 309 | | 7-methoxy-N-[3-methyl-4-(4-oxo-3,4-dihydrophthalazin-1-yl)phenyl]-1H-indole-2-carboxamide | 425.2 | E: 1.72 F: 1.73 | 1H NMR (500 MHz, DMSO-$d_6$) d 12.79 (s, 1H), 11.62 (s, 1H), 10.26 (s, 1H), 8.40-8.21 (m, 1H), 7.90-7.84 (m, 2H), 7.84-7.76 (m, 2H), 7.38-7.23 (m, 4H), 7.03 (t, J = 7.8 Hz, 1H), 6.81 (d, J = 7.7 Hz, 1H), 3.97 (s, 3H), 3.90 (s, 1H), 2.11 (s, 3H) |
| 310 | | N-[3-methyl-4-(4-oxo-3,4-dihydrophthalazin-1-yl)phenyl]pyrazolo[1,5-a]pyridine-3-carboxamide | 396.2 | E: 1.45 F: 1.45 | 1H NMR (500 MHz, DMSO-$d_6$) d 12.78 (s, 1H), 10.06 (s, 1H), 8.90-8.81 (m, 2H), 8.38-8.27 (m, 2H), 7.91-7.85 (m, 2H), 7.82 (s, 1H), 7.78 (d, J = 8.3 Hz, 1H), 7.60-7.52 (m, 1H), 7.30 (d, J = 8.0 Hz, 2H), 7.14 (t, J = 6.9 Hz, 1H), 3.90 (s, 1H), 2.10 (s, 3H) |
| 311 | | 2-methyl-N-[3-methyl-4-(4-oxo-3,4-dihydrophthalazin-1-yl)phenyl]imidazo[1,2-a]pyridine-3-carboxamide | 410.2 | E: 1.08 F: 1.40 | 1H NMR (500 MHz, DMSO-$d_6$) d 12.79 (s, 1H), 10.02 (s, 1H), 8.96 (d, J = 6.9 Hz, 1H), 8.33 (d, J = 4.7 Hz, 1H), 7.91-7.84 (m, 2H), 7.76 (s, 1H), 7.71 (d, J = 8.3 Hz, 1H), 7.64 (d, J = 8.8 Hz, 1H), 7.45 (d, J = 7.4 Hz, 1H), 7.36-7.26 (m, 2H), 7.11-7.06 (m, 1H), 2.68 (s, 3H), 2.10 (s, 3H) |
| 312 | | N-[3-methyl-4-(4-oxo-3,4-dihydrophthalazin-1-yl)phenyl]imidazo[1,2-a]pyridine-3-carboxamide | 396.2 | E: 1.09 F: 1.14 | 1H NMR (500 MHz, DMSO-$d_6$) d 12.79 (s, 1H), 10.31 (s, 1H), 9.51 (d, J = 7.2 Hz, 1H), 8.64 (s, 1H), 8.39-8.29 (m, 1H), 7.87 (dd, J = 4.8, 2.6 Hz, 2H), 7.83-7.73 (m, 3H), 7.54 (t, J = 7.8 Hz, 1H), 7.37-7.26 (m, 2H), 7.20 (t, J = 6.7 Hz, 1H), 2.11 (s, 3H) |
| 313 | | N-[3-methyl-4-(4-oxo-3,4-dihydrophthalazin-1-yl)phenyl]-1-(oxan-4-ylmethyl)-1H-indazole-3-carboxamide | 494.2 | E: 1.86 F: 1.90 | 1H NMR (500 MHz, DMSO-$d_6$) d 12.79 (s, 1H), 10.34 (s, 1H), 8.37-8.30 (m, 1H), 8.25 (d, J = 8.0 Hz, 1H), 7.97 (s, 1H), 7.93-7.85 (m, 4H), 7.51 (t, J = 7.4 Hz, 1H), 7.40-7.26 (m, 3H), 4.48 (d, J = 6.9 Hz, 2H), 3.84 (d, J = 10.7 Hz, 2H), 3.29-3.18 (m, 2H), 2.37-2.24 (m, 1H), 2.10 (s, 3H), 1.40 (br. s., 4H) |

-continued

| Example | R | IUPAC name | LCMS (M + H)+ | HPLC Method, RT (min.) | 1H NMR |
|---|---|---|---|---|---|
| 314 | | N-[3-methyl-4-(4-oxo-3,4-dihydrophthalazin-1-yl)phenyl]-1-[(3-methyloxetan-3-yl)methyl]-1H-indazole-3-carboxamide | 480.3 | E: 1.68 F: 1.67 | 1H NMR (500 MHz, DMSO-$d_6$) d 12.79 (br. s., 1H), 10.23 (br. s., 1H), 8.34 (d, J = 4.4 Hz, 1H), 8.26 (d, J = 8.3 Hz, 1H), 7.93 (br. s., 1H), 7.91-7.82 (m, 4H), 7.53 (t, J = 7.2 Hz, 1H), 7.41-7.27 (m, 3H), 4.80 (br. s., 4H), 4.33 (d, J = 5.0 Hz, 2H), 3.90 (s, 1H), 2.11 (br. s., 3H), 1.20 (br. s., 3H) |
| 325 | | N-[3-methyl-4-(4-oxo-3,4-dihydrophthalazin-1-yl)phenyl]-6-[2-(pyrrolidin-1-yl)ethoxy]pyrazolo[1,5-a]pyridine-3-carboxamide | 509.2 | E: 1.18 F: 1.14 | 1H NMR (500 MHz, DMSO-$d_6$) d 12.79 (s, 1H), 10.06 (s, 1H), 8.76 (s, 1H), 8.65 (s, 1H), 8.40-8.30 (m, 1H), 8.23 (d, J = 9.8 Hz, 1H), 7.91-7.85 (m, 2H), 7.83-7.73 (m, 2H), 7.41 (d, J = 9.5 Hz, 1H), 7.32-7.22 (m, 2H), 4.35 (br. s., 2H), 2.09 (s, 3H), 1.90 (br. s., 4H) |

The following Examples in Table 6 were made by using the same procedure as shown in Example 45. Intermediate 96 was coupled with the appropriate carboxylic acid. Various coupling reagents could be used other than the one described in Example 45, such as BOP, PyBop, EDC/HOBt or T3P.

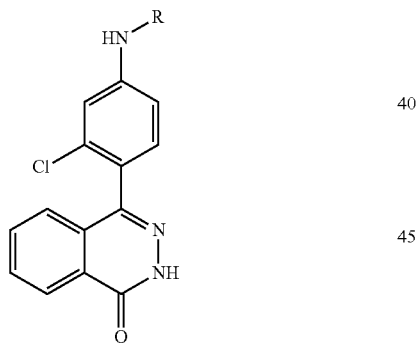

TABLE 6

| Example | R | IUPAC name | LCMS (M + H)+ | HPLC Method, RT (min.) | 1H NMR |
|---|---|---|---|---|---|
| 315 | | N-[3-chloro-4-(4-oxo-3,4-dihydrophthalazin-1-yl)phenyl]-1-(2-hydroxy-2-methylpropyl)-1H-indazole-3-carboxamide | 488.2 | E: 1.78 F: 1.78 | 1H NMR (500 MHz, DMSO-$d_6$) d 12.89 (br. s., 1H), 10.62 (s, 1H), 8.40-8.30 (m, 2H), 8.24 (d, J = 8.3 Hz, 1H), 8.04 (d, J = 8.5 Hz, 1H), 7.92-7.85 (m, 3H), 7.55 (d, J = 8.3 Hz, 1H), 7.49 (t, J = 7.7 Hz, 1H), 7.37-7.28 (m, 2H), 4.77 (br. s., 1H), 4.49 (s, 2H), 1.20 (s, 6H) |

TABLE 6-continued

| Example | R | IUPAC name | LCMS (M + H)+ | HPLC Method, RT (min.) | 1H NMR |
|---|---|---|---|---|---|
| 316 | | tert-butyl 3-[(3-{[3-chloro-4-(4-oxo-3,4-dihydrophthalazin-1-yl)phenyl]carbamoyl}-1H-indazol-1-yl)methyl]azetidine-1-carboxylate | 585.2 | A: 11.7 B: 9.80 | 1H NMR (400 MHz, methanol-$d_4$) d 8.48-8.41 (m, 1H), 8.37-8.29 (m, 1H), 8.25 (t, J = 2.0 Hz, 1H), 7.97-7.84 (m, 3H), 7.76 (d, J = 8.6 Hz, 1H), 7.62-7.49 (m, 2H), 7.47-7.41 (m, 1H), 7.41-7.32 (m, 1H), 4.79 (d, J = 7.0 Hz, 2H), 4.07 (t, J = 8.5 Hz, 2H), 3.91 (dd, J = 8.8, 5.3 Hz, 2H), 1.41 (s, 9H) |
| 317 | | N-[3-chloro-4-(4-oxo-3,4-dihydrophthalazin-1-yl)phenyl]imidazo[1,2-a]pyridine-3-carboxamide | 416.1 | E: 1.15 F: 1.46 | 1H NMR (500 MHz, DMSO-$d_6$) d 12.89 (s, 1H), 10.55 (s, 1H), 9.51 (d, J = 6.9 Hz, 1H), 8.68 (s, 1H), 8.41-8.26 (m, 1H), 8.18 (s, 1H), 7.93-7.86 (m, 3H), 7.83 (d, J = 9.1 Hz, 1H), 7.65-7.54 (m, 2H), 7.36-7.29 (m, 1H), 7.26 (t, J = 6.9 Hz, 1H) |
| 318 | | N-[3-chloro-4-(4-oxo-3,4-dihydrophthalazin-1-yl)phenyl]-1-(oxan-4-ylmethyl)-1H-indazole-3-carboxamide | 514.2 | E: 1.94 F: 1.95 | 1H NMR (500 MHz, DMSO-$d_6$) d 12.89 (s, 1H), 10.68 (s, 1H), 8.33 (br. s., 2H), 8.26 (d, J = 8.3 Hz, 1H), 8.05 (d, J = 8.3 Hz, 1H), 7.92-7.85 (m, 3H), 7.59-7.49 (m, 2H), 7.40-7.28 (m, 2H), 4.49 (d, J = 6.9 Hz, 2H), 3.90 (s, 1H), 3.84 (d, J = 11.0 Hz, 2H), 3.29-3.20 (m, 2H), 2.34-2.23 (m, 1H), 1.40 (br. s., 4H) |
| 319 | | N-[3-chloro-4-(4-oxo-3,4-dihydrophthalazin-1-yl)phenyl]-1-(oxolan-3-ylmethyl)-1H-indazole-3-carboxamide | 500.2 | E: 1.77 F: 1.77 | 1H NMR (500 MHz, DMSO-$d_6$) d 12.89 (s, 1H), 10.66 (s, 1H), 8.39-8.30 (m, 2H), 8.26 (d, J = 8.0 Hz, 1H), 8.05 (d, J = 8.3 Hz, 1H), 7.94-7.85 (m, 3H), 7.62-7.51 (m, 2H), 7.37 (t, J = 7.4 Hz, 1H), 7.33-7.28 (m, 1H), 4.58 (d, J = 7.2 Hz, 2H), 3.92-3.81 (m, 1H), 3.69 (q, J = 8.1 Hz, 2H), 3.64-3.57 (m, 1H), 3.03-2.92 (m, 1H), 1.95 (dd, J = 12.5, 7.0 Hz, 1H), 1.72 (dd, J = 12.4, 6.3 Hz, 1H) |
| 320 | | N-[3-chloro-4-(4-oxo-3,4-dihydrophthalazin-1-yl)phenyl]-1-[(3-methyloxetan-3-yl)methyl]-1H-indazole-3-carboxamide | 500.2 | E: 1.77 F: 1.76 | 1H NMR (500 MHz, DMSO-$d_6$) d 12.89 (br. s., 1H), 10.55 (br. s., 1H), 8.38-8.31 (m, 1H), 8.30 (s, 1H), 8.26 (d, J = 8.0 Hz, 1H), 8.04 (d, J = 8.3 Hz, 1H), 7.94-7.86 (m, 3H), 7.60-7.50 (m, 2H), 7.36 (t, J = 7.6 Hz, 1H), 7.33-7.28 (m, 1H), 4.86-4.77 (m, 4H), 4.37-4.28 (m, 2H), 1.20 (s, 3H) |

Example 321: 1-((1-(4-Hydroxybutyl)piperidin-4-yl)methyl)-N-(3-methyl-4-(4-oxo-3,4-dihydrophthalazin-1-yl)phenyl)-1H-indazole-3-carboxamide

Example 322: 1-((1-(4-Hydroxybutyl)piperidin-4-yl)methyl)-N-(4-(4-oxo-3,4-dihydrophthalazin-1-yl)phenyl)-1H-indazole-3-carboxamide

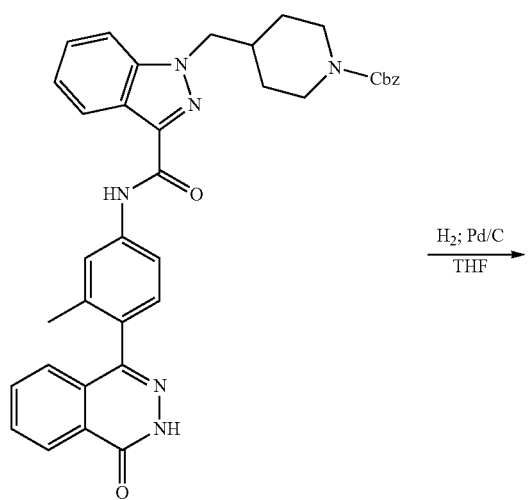

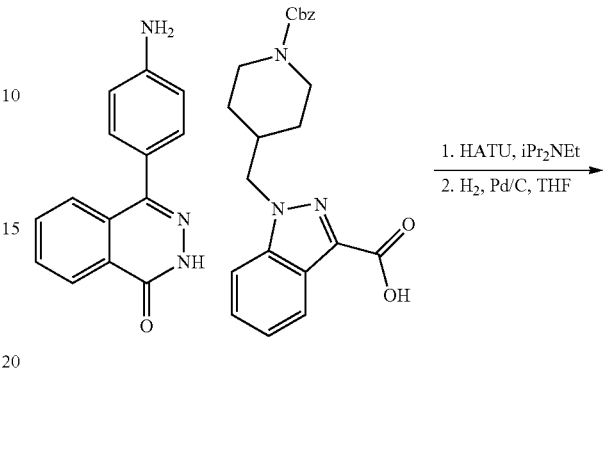

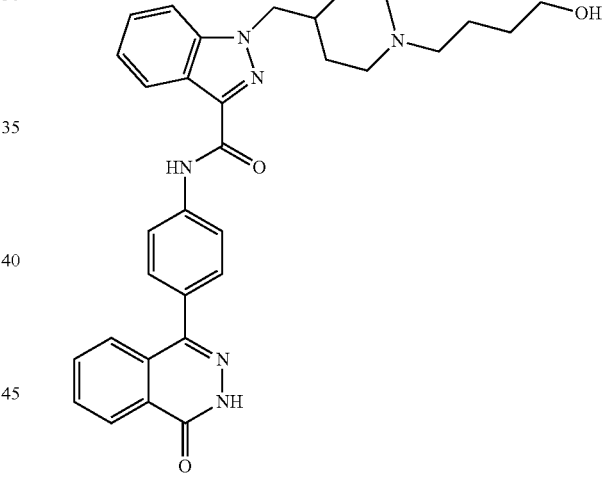

To a degassed solution of Example 307 (24 mg, 0.038 mmol) in THF (2 mL), was added 10% Pd/C (5 mg). The mixture was stirred under H₂ (balloon). The mixture was filtered, then was purified by prep HPLC to afford Example 321 (20 mg, 0.034 mmol, 88% yield). MS(ESI) m/z: 565.3 (M+H)$^+$; $^1$H NMR (400 MHz, methanol-$d_4$) δ 8.48-8.43 (m, 1H), 8.33 (d, J=8.1 Hz, 1H), 7.91-7.86 (m, 2H), 7.85-7.82 (m, 1H), 7.80 (dd, J=8.3, 1.9 Hz, 1H), 7.73 (d, J=8.6 Hz, 1H), 7.58-7.51 (m, 1H), 7.45-7.40 (m, 1H), 7.39-7.32 (m, 2H), 4.60-4.52 (m, 2H), 3.66-3.56 (m, 2H), 3.41 (d, J=13.0 Hz, 1H), 3.18-3.07 (m, 1H), 3.05-2.89 (m, 2H), 2.48 (ddt, J=11.2, 7.5, 3.9 Hz, 1H), 2.22-2.14 (m, 3H), 2.03-1.75 (m, 4H), 1.74-1.51 (m, 4H); HPLC RT=5.67 min (Method A), 6.19 min (Method B).

Intermediate 3 (23.7 mg, 0.051 mmol) was coupled with Intermediate 21 (20 mg, 0.051 mmol) according to the procedure for Example 45 to afford after prep HPLC the amide product (21 mg, 67% yield). MS(ESI) m/z: 613.2 (M+H)$^+$. The residue (21 mg) was dissolved in THF (2 mL). To this mixture was added 10% Pd/C (5 mg). The mixture was stirred under H₂ (balloon) for 16 h. The mixture was filtered and purified by prep HPLC to afford Example 322 (15 mg, 79% yield). MS(ESI) m/z: 551.2 (M+H)$^+$; $^1$H NMR (400 MHz, methanol-$d_4$) δ 8.46-8.42 (m, 1H), 8.32 (d, J=8.1 Hz, 1H), 8.01-7.95 (m, 2H), 7.92-7.83 (m, 3H), 7.74-7.69 (m, 1H), 7.66-7.61 (m, 2H), 7.52 (td, J=7.7, 0.9 Hz, 1H), 7.37-7.31 (m, 1H), 4.54 (dd, J=6.7, 3.2 Hz, 2H), 3.63-3.55 (m, 2H), 3.41 (d, J=13.0 Hz, 1H), 3.18-3.05 (m, 2H), 3.05-2.87 (m, 2H), 2.55-2.37 (m, 1H), 1.93 (d, J=14.7 Hz, 2H), 1.89-1.76 (m, 2H), 1.75-1.53 (m, 3H); HPLC RT=5.53 min (Method A), 6.33 min (Method B).

Example 323: N-(4-(6-Methoxy-1-oxo-1,2-dihydroisoquinolin-4-yl)-3-methylphenyl)indoline-1-carboxamide

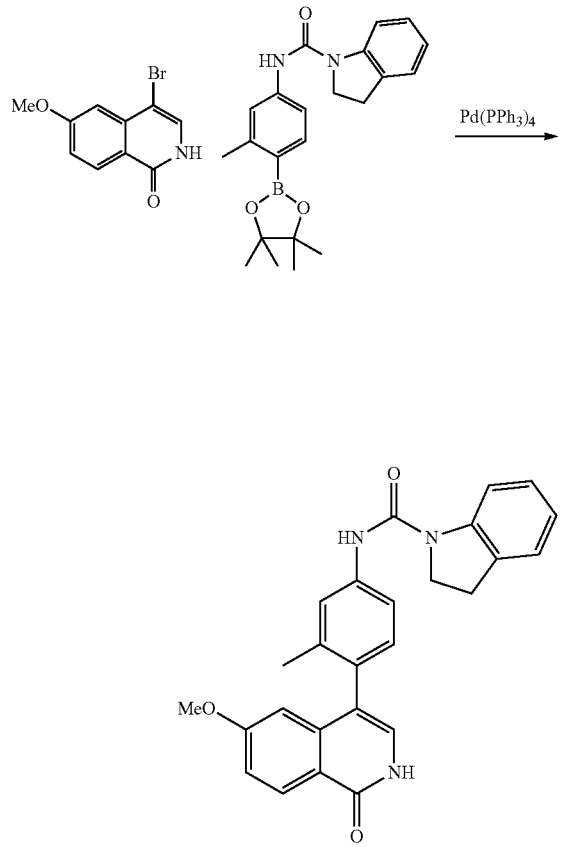

According to the procedure for the preparation of Example 76, coupling of Intermediate 73 (10 mg, 0.039 mmol) and Intermediate 97 (14.9 mg, 0.039 mmol), afforded 2.7 mg (15%) of Example 323. MS(ESI) m/z: 426.2 (M+H)$^+$; $^1$H NMR (500 MHz, DMSO-d$_6$) δ 11.19 (d, J=5.8 Hz, 1H), 8.55 (s, 1H), 8.21 (d, J=8.8 Hz, 1H), 7.89 (d, J=8.3 Hz, 1H), 7.57 (s, 1H), 7.51 (d, J=8.0 Hz, 2H), 7.21 (d, J=7.2 Hz, 1H), 7.12 (t, J=7.0 Hz, 3H), 6.96 (d, J=5.8 Hz, 1H), 6.91-6.85 (m, 1H), 6.39 (s, 1H), 4.15 (t, J=8.7 Hz, 2H), 3.70 (s, 3H), 3.19 (t, J=8.5 Hz, 2H), 2.06 (s, 3H); HPLC RT=1.77 min (Method E), 1.78 min (Method F).

Example 324: N-(3-Methyl-4-(4-oxo-3,4-dihydrophthalazin-1-yl)phenyl)indoline-1-carboxamide

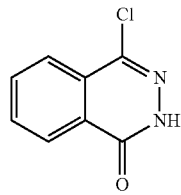

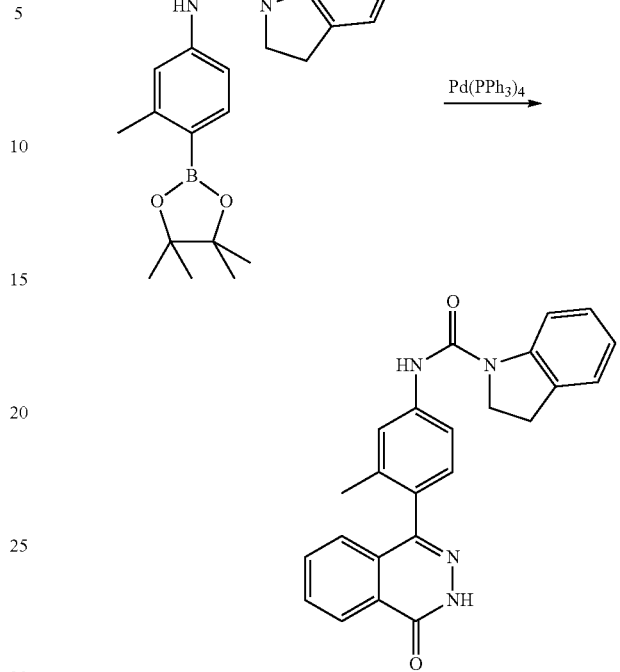

According to the procedure for the preparation of Example 76, coupling of 4-chlorophthalazin-1(2H)-one (20 mg, 0.11 mmol) and Intermediate 97 (46 mg, 0.12 mmol), afforded 4.4 mg (10%) of Example 324. MS(ESI) m/z: 397.2 (M+H)$^+$; $^1$H NMR (500 MHz, DMSO-d$_6$) δ 12.76 (s, 1H), 8.63 (s, 1H), 8.37-8.28 (m, 1H), 7.93-7.83 (m, 3H), 7.61 (s, 1H), 7.57 (d, J=8.3 Hz, 1H), 7.33-7.27 (m, 1H), 7.21 (d, J=7.4 Hz, 1H), 7.24 (d, J=8.5 Hz, 1H), 7.14 (t, J=7.7 Hz, 1H), 6.92 (t, J=7.3 Hz, 1H), 4.17 (t, J=8.4 Hz, 2H), 3.20 (t, J=8.5 Hz, 2H), 2.07 (s, 3H); HPLC RT=1.73 min (Method E), 1.73 min (Method F).

Example 326: 1-(Azetidin-3-ylmethyl)-N-(3-methyl-4-(4-oxo-3,4-dihydrophthalazin-1-yl)phenyl)-1H-indazole-3-carboxamide, TFA

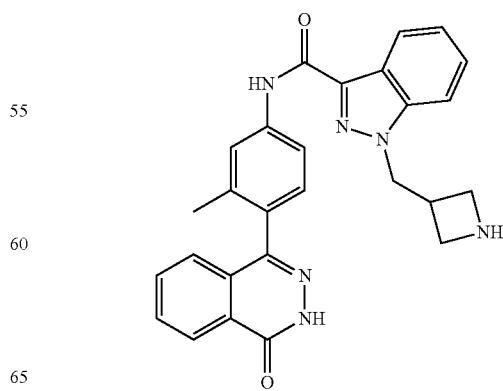

Example 326A: tert-Butyl 3-((3-((3-methyl-4-(4-oxo-3,4-dihydrophthalazin-1-yl)phenyl)carbamoyl)-1H-indazol-1-yl)methyl)azetidine-1-carboxylate

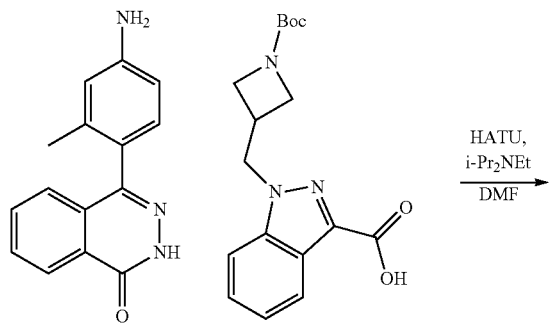

To a solution of Intermediate 94 (55 mg, 0.12 mmol), Intermediate 33 (38 mg, 0.12 mmol), and HATU (45.8 mg, 0.12 mmol) in DMF (1 mL), was added DIEA (0.1 mL, 0.57 mmol). The mixture was stirred at rt for 4 h, then was concentrated. The residue was purified via preparative HPLC to afford Example 326A (45 mg, 70% yield). MS(ESI) m/z: 565.3 (M+H)$^+$.

Example 326

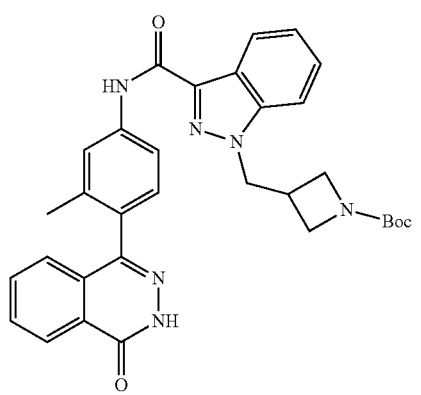

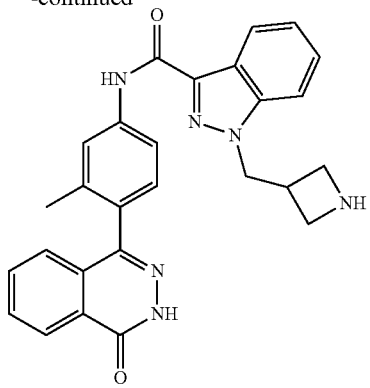

Example 326A (30 mg, 0.053 mmol) was stirred with TFA (0.5 ml) in DCM (1 ml) for 10 min, then was concentrated. The residue was purified by prep HPLC to afford Example 326 (30 mg, 97% yield). MS(ESI) m/z: 465.0 (M+H)$^+$; $^1$H NMR (400 MHz, methanol-d$_4$) δ 8.53-8.42 (m, 1H), 8.35 (dt, J=8.2, 1.0 Hz, 1H), 7.94-7.86 (m, 2H), 7.85-7.82 (m, 1H), 7.80 (dd, J=8.4, 1.8 Hz, 1H), 7.74 (d, J=8.6 Hz, 1H), 7.56 (ddd, J=8.4, 7.0, 1.1 Hz, 1H), 7.45-7.39 (m, 1H), 7.39-7.33 (m, 2H), 4.82-4.79 (m, 2H), 4.27-4.12 (m, 4H), 3.76-3.61 (m, 1H), 2.19 (s, 3H); HPLC RT=5.38 min (Method A), 5.98 min (Method B).

Example 327: 1-(Azetidin-3-ylmethyl)-N-[3-chloro-4-(4-oxo-3,4-dihydrophthalazin-1-yl)phenyl]-1H-indazole-3-carboxamide, TFA

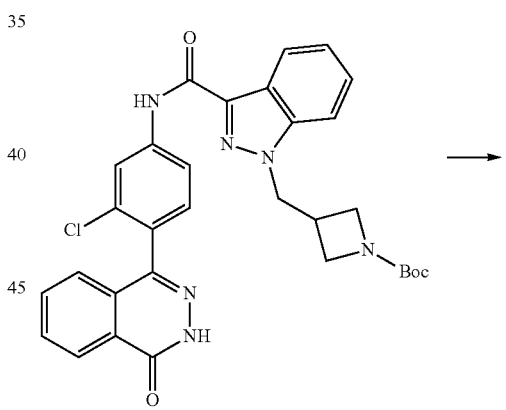

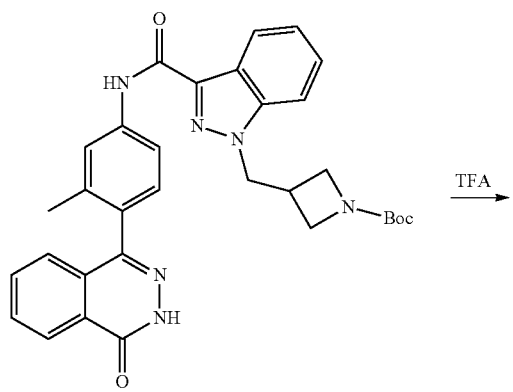

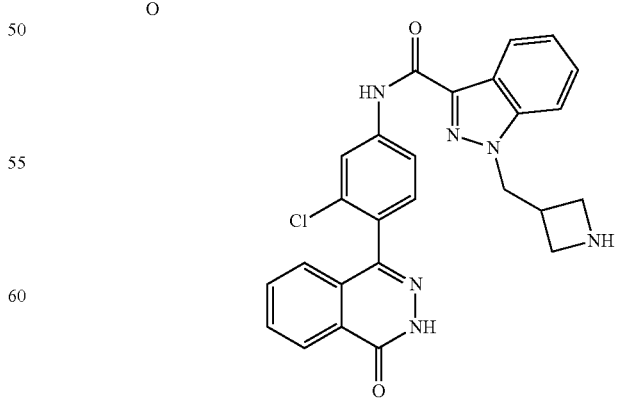

Example 316 (24 mg, 0.041 mmol) stirred with TFA (0.5 ml) and DCM (2 ml) for 10 min, then was concentrated. The residue was purified via preparative HPLC to afford Example 327 (20 mg, 81% yield). MS(ESI) m/z: 485.1 (M+H)+; $^1$H NMR (400 MHz, methanol-$d_4$) δ 8.49-8.40 (m, 1H), 8.39-8.31 (m, 1H), 8.24-8.17 (m, 1H), 7.96-7.85 (m, 3H), 7.74 (d, J=8.6 Hz, 1H), 7.61-7.48 (m, 2H), 7.46-7.35 (m, 2H), 4.83-4.81 (m, 2H), 4.31-4.10 (m, 4H), 3.67 (t, J=7.8 Hz, 1H); HPLC RT=5.83 min (Method A), 6.83 min (Method B).

Example 328: 2-(3-{[4-(4-Oxo-3,4-dihydrophthalazin-1-yl)phenyl]carbamoyl}-1H-indazol-1-yl)acetic Acid

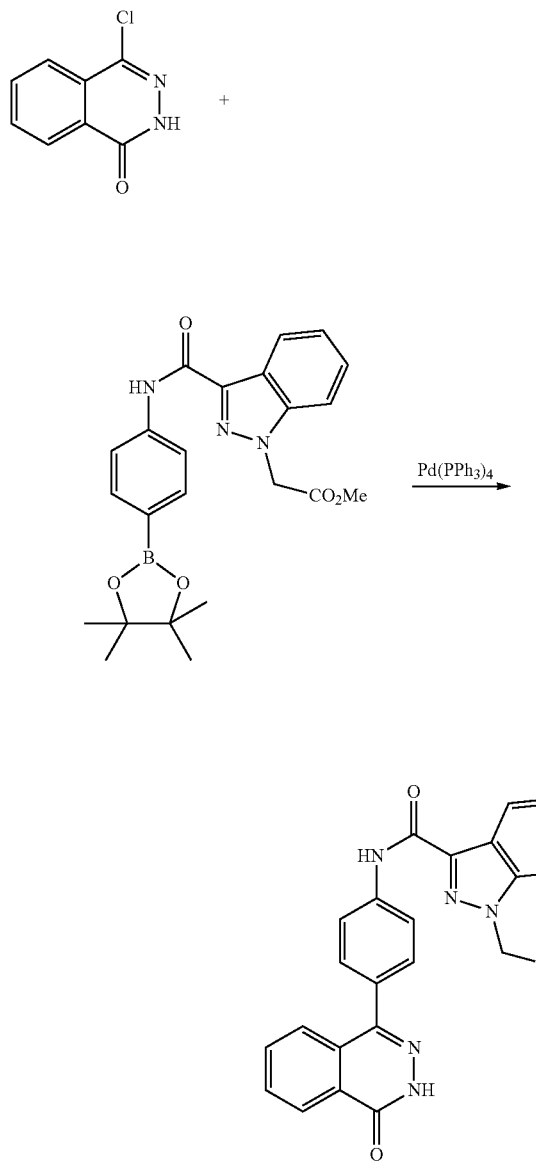

To 4-chlorophthalazin-1(2H)-one (40.8 mg, 0.226 mmol), Intermediate 98 (82 mg, 0.188 mmol) and phosphoric acid, potassium salt (100 mg, 0.47 mmol), were added dioxane (5 mL) and water (0.56 mL). The mixture was degassed (evacuated and flushed with Ar (5×)). Pd(PPh$_3$)$_4$ (10.9 mg, 9.42 mol) was added, then the mixture was degassed (2×). The reaction vial was sealed and heated in a microwave reactor at 150° C. for 25 min. The product was purified by prep HPLC to afford Example 328 (20 mg, 24% yield). MS(ESI) m/z: 440.1 (M+H)+; $^1$H NMR (400 MHz, DMSO-$d_6$) δ 12.82 (s, 1H), 10.60 (s, 1H), 8.40-8.32 (m, 1H), 8.28 (d, J=8.1 Hz, 1H), 8.15-8.06 (m, J=8.6 Hz, 2H), 7.97-7.87 (m, 2H), 7.82 (d, J=8.6 Hz, 1H), 7.79-7.74 (m, 1H), 7.63-7.56 (m, J=8.6 Hz, 2H), 7.53 (td, J=7.7, 1.1 Hz, 1H), 7.36 (t, J=7.6 Hz, 1H), 5.46 (s, 2H); HPLC RT=7.28 min (Method A), 6.64 min (Method B).

Example 329: 1-((1-Acetylazetidin-3-yl)methyl)-N-(3-chloro-4-(4-oxo-3,4-dihydrophthalazin-1-yl)phenyl)-1H-indazole-3-carboxamide

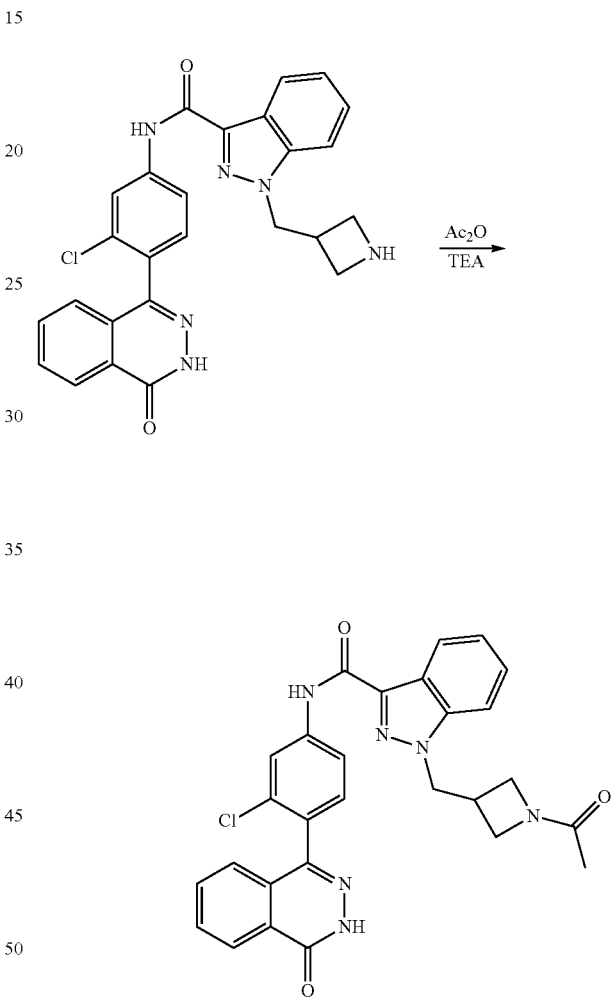

Example 327 (10 mg, 0.021 mmol) was mixed with acetic anhydride (3.2 mg, 0.031 mmol) and TEA (4.17 mg, 0.041 mmol) in CH$_2$Cl$_2$ (1 mL) and stirred at rt o/n. The reaction mixture was concentrated, then was purified by prep HPLC to afford Example 329 (9.6 mg, 87% yield). MS(ESI) m/z: 527.2 (M+H)+; $^1$H NMR (500 MHz, DMSO-$d_6$) δ 12.89 (s, 1H), 10.62 (br. s., 1H), 8.38-8.31 (m, 2H), 8.26 (d, J=8.3 Hz, 1H), 8.04 (d, J=8.3 Hz, 1H), 7.98-7.92 (m, 1H), 7.92-7.85 (m, 2H), 7.60-7.50 (m, 2H), 7.37 (t, J=7.2 Hz, 1H), 7.35-7.28 (m, 1H), 7.20 (s, 1H), 7.10 (s, 1H), 7.00 (s, 1H), 4.83 (br. s., 2H), 4.21 (t, J=8.3 Hz, 1H), 4.05 (br. s., 1H), 3.96-3.86 (m, 1H), 3.79 (br. s., 1H), 3.25 (br. s., 2H), 2.55 (br. s., 2H), 1.74 (s, 3H); HPLC RT=1.55 min (Method E), 1.55 min (Method F).

Example 330: N-(3-Methyl-4-(4-oxo-3,4-dihydrophthalazin-1-yl)phenyl)-1-((1-methylazetidin-3-yl)methyl)-1H-indazole-3-carboxamide

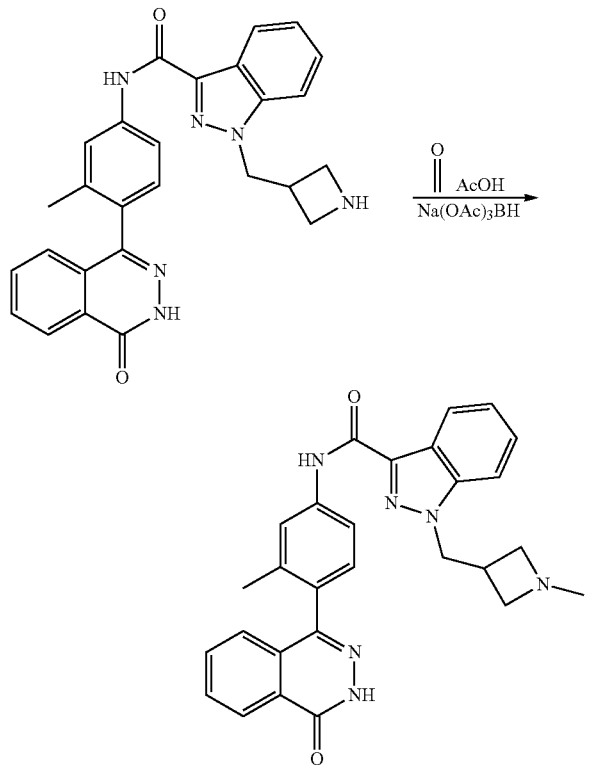

To a solution of Example 326 (10 mg, 0.017 mmol) in CH$_2$Cl$_2$ (1 mL), were added TEA (1.7 mg, 0.017 mmol), followed by formaldehyde (2.8 mg, 0.035 mmol), acetic acid (5.2 mg, 0.086 mmol), and Na(OAc)$_3$BH (7.3 mg, 0.035 mmol). The mixture was stirred rt for 16 h, then was concentrated and purified by prep HPLC to afford Example 330 (3.8 mg, 46% yield). MS(ESI) m/z: 479.2 (M+H)$^+$; $^1$H NMR (500 MHz, DMSO-d$_6$) δ 12.79 (s, 1H), 10.30 (s, 1H), 8.34 (d, J=4.7 Hz, 1H), 8.25 (d, J=7.7 Hz, 1H), 7.92-7.77 (m, 4H), 7.52 (t, J=7.4 Hz, 1H), 7.39-7.21 (m, 3H), 4.76 (d, J=6.9 Hz, 2H), 3.14 (br. s., 4H), 3.05-2.96 (m, 1H), 2.25 (br. s., 3H), 2.10 (s, 3H); HPLC RT=1.35 min (Method E), 1.35 min (Method F).

Example 331: 3-(3-((4-(4-Pxo-3,4-dihydrophthalazin-1-yl)phenyl)carbamoyl)-1H-indazol-1-yl)propanoic acid

Example 332: Methyl 3-(3-((4-(4-oxo-3,4-dihydrophthalazin-1-yl)phenyl)carbamoyl)-1H-indazol-1-yl)propanoate

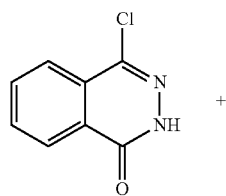

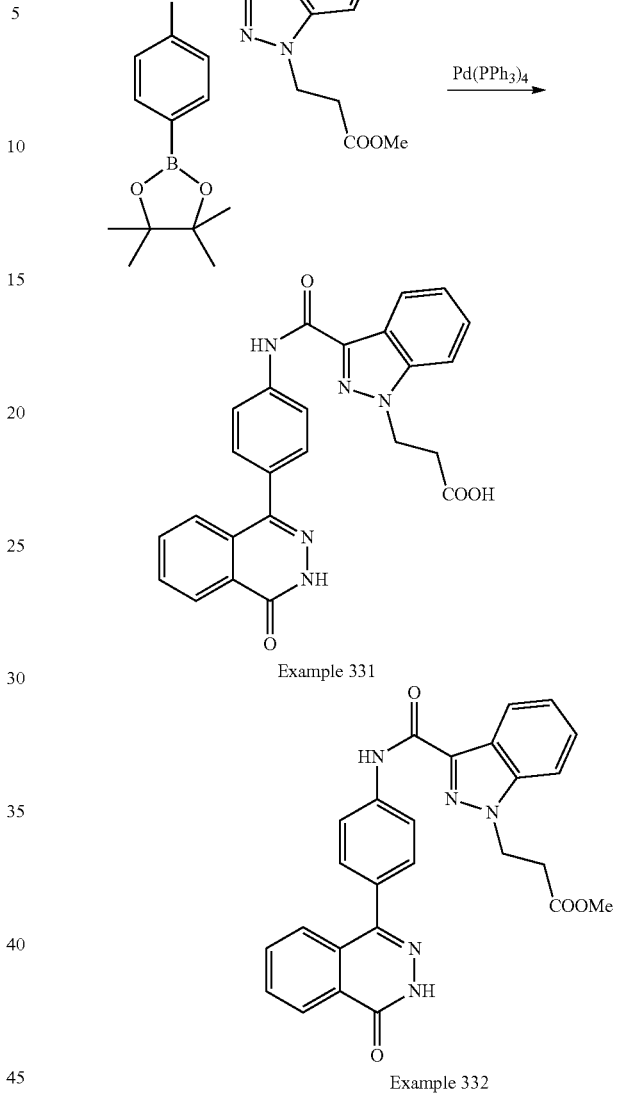

Example 331

Example 332

According to the procedure for the preparation of Example 76, coupling of 4-chlorophthalazin-1(2H)-one (40.7 mg, 0.225 mmol) and Intermediate 99 (92 mg, 0.205 mmol), afforded Example 331 (8 mg, 8.5% yield) and Example 332 (42 mg, 43% yield).

Example 331: MS(ESI) m/z: 454.2 (M+H)$^+$; $^1$H NMR (500 MHz, DMSO-d$_6$) δ 12.82 (s, 1H), 12.45 (br. s., 1H), 10.45 (s, 1H), 8.41-8.31 (m, 1H), 8.24 (d, J=8.3 Hz, 1H), 8.13-8.05 (m, 2H), 8.00-7.83 (m, 3H), 7.82-7.73 (m, 1H), 7.65-7.57 (m, 2H), 7.52 (ddd, J=8.4, 7.0, 1.1 Hz, 1H), 7.39-7.29 (m, 1H), 4.77 (t, J=6.7 Hz, 2H), 3.04 (t, J=6.9 Hz, 2H)); HPLC RT=7.51 min (Method A), 6.78 min (Method B).

Example 332: MS(ESI) m/z: 468.2 (M+H)$^+$; $^1$H NMR (500 MHz, DMSO-d$_6$) δ 12.82 (s, 1H), 10.45 (s, 1H), 8.42-8.28 (m, 1H), 8.26-8.20 (m, 1H), 8.12-8.03 (m, 2H), 7.97-7.83 (m, 3H), 7.83-7.73 (m, 1H), 7.67-7.59 (m, 2H), 7.53 (ddd, J=8.5, 7.1, 1.0 Hz, 1H), 7.41-7.28 (m, 1H), 4.81 (t, J=6.7 Hz, 2H), 3.58 (s, 3H), 3.13 (t, J=6.7 Hz, 2H); HPLC RT=8.90 min (Method A), 7.84 min (Method B).

Example 333: 1-(3-Hydroxy-3-methylbutyl)-N-(4-(4-oxo-3,4-dihydrophthalazin-1-yl)phenyl)-1H-indazole-3-carboxamide

Example 334: 1-(2-((2-Hydroxy-2-methylpropyl)amino)-2-oxoethyl)-N-(4-(4-oxo-3,4-dihydrophthalazin-1-yl)phenyl)-1H-indazole-3-carboxamide

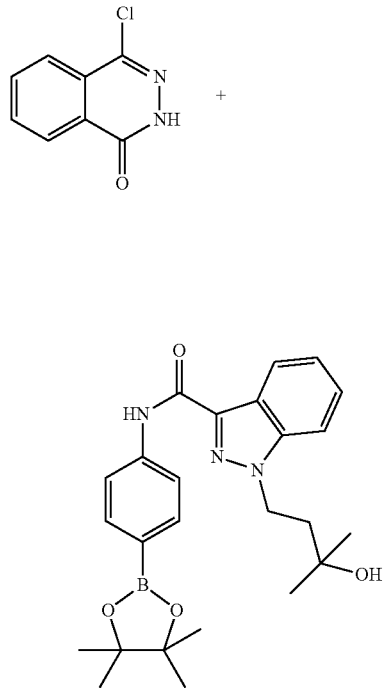

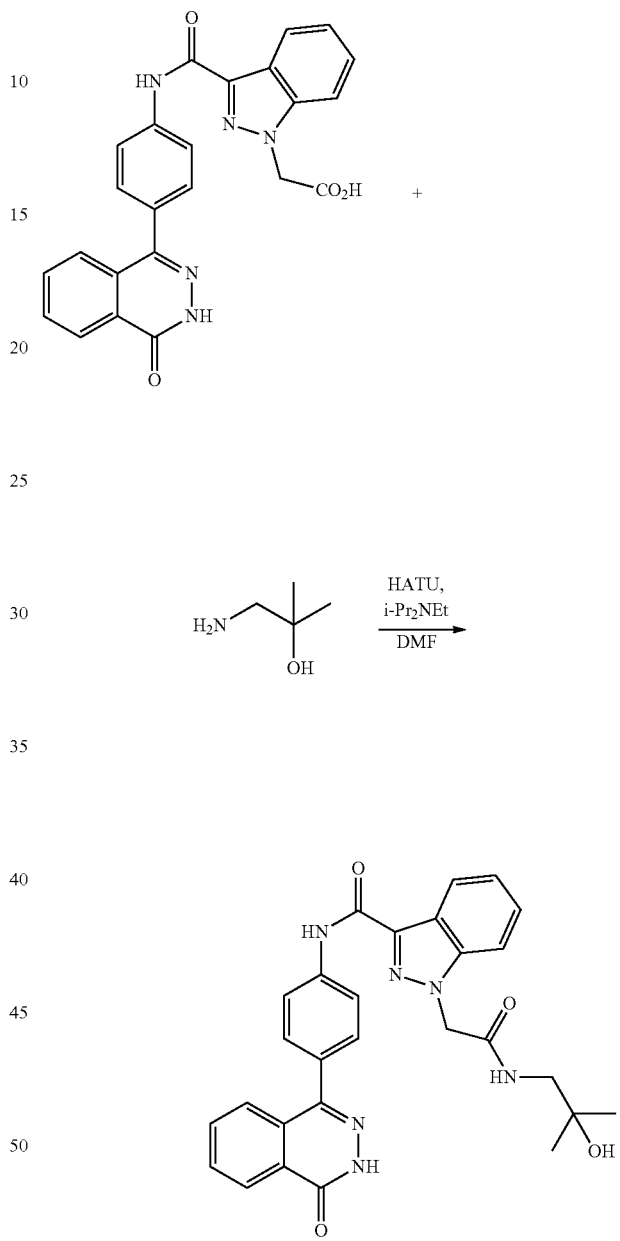

According to the procedure for the preparation of Example 76, coupling of 4-chlorophthalazin-1(2H)-one (22.6 mg, 0.113 mmol) and Intermediate 100 (51 mg, 0.125 mmol), afforded Example 333 (5.2 mg, 9.7% yield). MS(ESI) m/z: 468.3 (M+H)$^+$; $^1$H NMR (500 MHz, DMSO-d$_6$) δ 12.82 (s, 1H), 10.48 (s, 1H), 8.35 (dd, J=7.7, 1.4 Hz, 1H), 8.26 (d, J=8.3 Hz, 1H), 8.09 (d, J=8.5 Hz, 2H), 7.97-7.90 (m, 2H), 7.81-7.74 (m, 2H), 7.60 (s, 1H), 7.57-7.48 (m, 1H), 7.34 (t, J=7.6 Hz, 1H), 4.69-4.63 (m, 2H), 4.57 (br. s., 1H), 2.55 (t, J=5.0 Hz, 1H), 2.09-2.00 (m, 2H), 1.21 (s, 6H); HPLC RT=1.68 min (Method E), 1.68 min (Method F).

To Example 328 (8 mg, 0.018 mmol), 1-amino-2-methylpropan-2-ol (3.3 mg, 0.036 mmol), and HATU (7.6 mg, 0.020 mmol) in DMF (1 mL), was added DIEA (0.016 mL, 0.091 mmol). The mixture was stirred at rt for 16 h, then was purified by prep HPLC to afford Example 334 (6 mg, 64% yield). MS(ESI) m/z: 511.3 (M+H)$^+$; $^1$H NMR (500 MHz, DMSO-d$_6$) δ 12.82 (s, 1H), 10.55 (s, 1H), 8.39-8.34 (m, 1H), 8.27 (d, J=8.0 Hz, 1H), 8.18 (t, J=6.1 Hz, 1H), 8.12-8.03 (m, 2H), 7.98-7.86 (m, 2H), 7.83-7.76 (m, 1H), 7.73 (d, J=8.5 Hz, 1H), 7.63-7.56 (m, 2H), 7.51 (ddd, J=8.4, 7.0, 1.1 Hz, 1H), 7.42-7.32 (m, 1H), 5.36 (s, 2H), 3.10 (d, J=6.1 Hz, 2H), 1.10 (s, 6H); HPLC RT=1.42 min (Method E), 1.41 min (Method F).

Example 335: 1-(2-(((1-Hydroxycyclobutyl)methyl)amino)-2-oxoethyl)-N-(4-(4-oxo-3,4-dihydrophthalazin-1-yl)phenyl)-1H-indazole-3-carboxamide

Example 336: 1-(3-((2-Hydroxy-2-methylpropyl)amino)-3-oxopropyl)-N-(4-(4-oxo-3,4-dihydrophthalazin-1-yl)phenyl)-1H-indazole-3-carboxamide

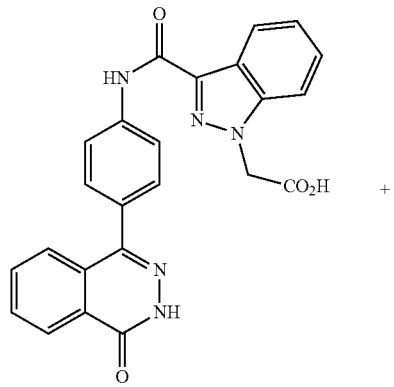
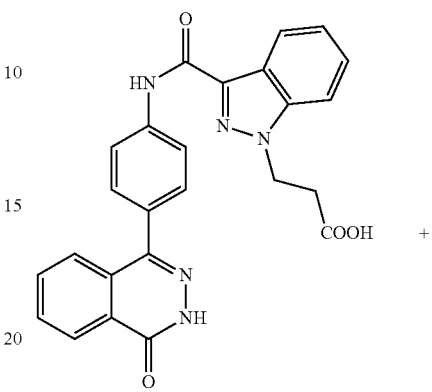

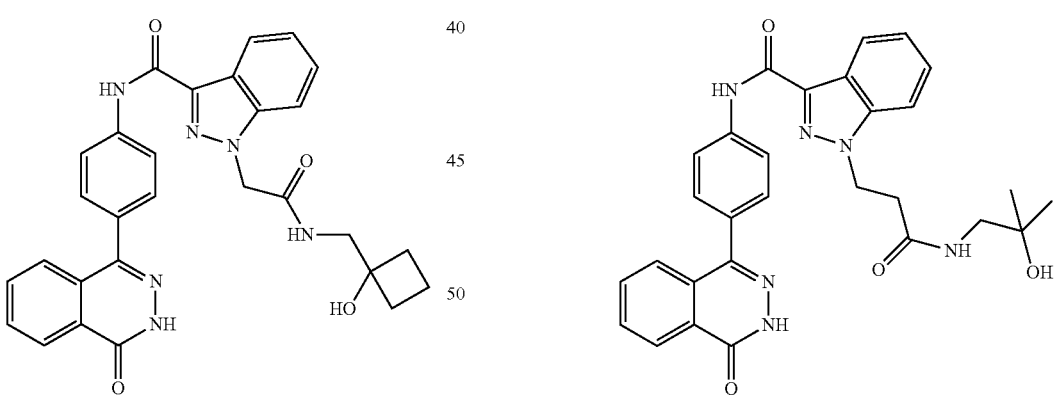

According to the procedure for the preparation of Example 334, coupling of Example 328 (8 mg, 0.018 mmol) and 1-(aminomethyl)cyclobutanol (3.7 mg, 0.036 mmol) afforded Example 335 (2.7 mg, 26% yield). MS(ESI) m/z: 523.3 (M+H)$^+$; $^1$H NMR (500 MHz, DMSO-$d_6$) δ 12.81 (s, 1H), 10.57 (s, 1H), 8.41-8.32 (m, 1H), 8.29-8.21 (m, 2H), 8.14-8.06 (m, 2H), 7.98-7.86 (m, 3H), 7.78 (dd, J=7.8, 1.0 Hz, 1H), 7.75-7.71 (m, 1H), 7.63-7.55 (m, 2H), 7.53-7.47 (m, 1H), 7.40-7.31 (m, 1H), 5.36 (s, 2H), 3.90 (s, 1H), 3.26 (d, J=5.8 Hz, 2H), 2.00-1.86 (m, 4H), 1.70-1.55 (m, 1H), 1.42 (dt, J=11.2, 9.0 Hz, 1H); HPLC RT=1.47 min (Method E), 1.46 min (Method F).

According to the procedure for the preparation of Example 334, coupling of Example 331 (9 mg, 0.02 mmol) and 1-amino-2-methylpropan-2-ol (3.5 mg, 0.040 mmol) afforded Example 336 (7.4 mg, 65% yield). MS(ESI) m/z: 525.2 (M+H)$^+$; $^1$H NMR (500 MHz, DMSO-$d_6$) δ 12.82 (s, 1H), 10.44 (s, 1H), 8.35 (dd, J=7.8, 1.2 Hz, 1H), 8.23 (d, J=8.3 Hz, 1H), 8.12-8.05 (m, J=8.5 Hz, 2H), 7.98-7.84 (m, 3H), 7.82 (d, J=8.5 Hz, 2H), 7.78 (dd, J=7.8, 1.0 Hz, 1H), 7.63-7.58 (m, J=8.5 Hz, 2H), 7.53-7.47 (m, 1H), 7.33 (t, J=7.4 Hz, 1H), 4.79 (t, J=6.7 Hz, 2H), 2.98 (d, J=6.1 Hz, 2H), 2.93-2.86 (m, 2H), 0.92 (s, 6H); HPLC RT=1.46 min (Method E), 1.46 min (Method F).

Example 337: 1-(3-Morpholino-3-oxopropyl)-N-(4-(4-oxo-3,4-dihydrophthalazin-1-yl)phenyl)-1H-indazole-3-carboxamide

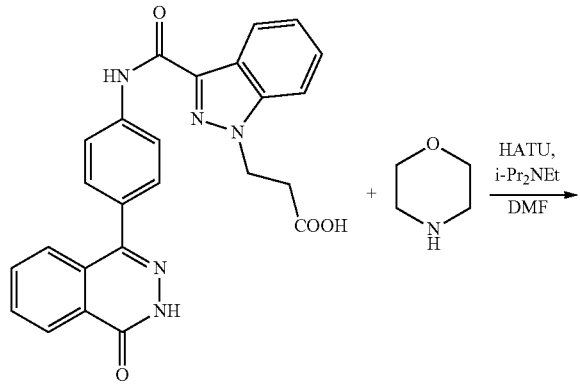

Example 338: 1-(Azetidin-3-ylmethyl)-N-(4-(4-oxo-3,4-dihydrophthalazin-1-yl)phenyl)-1H-indazole-3-carboxamide

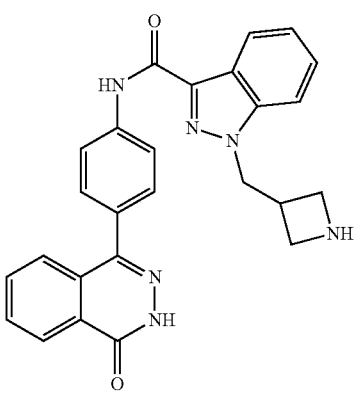 [SMILES: O=C(Nc1ccc(-c2n[nH]c(=O)c3ccccc23)cc1)c1nn(CC2CNC2)c2ccccc12]

According to the procedure for the preparation of Example 326, coupling of Intermediate 3 and Intermediate 33, followed by TFA deprotection afforded Example 338. MS(ESI) m/z: 451.1 (M+H)$^+$; $^1$H NMR (500 MHz, DMSO-d$_6$) δ 12.83 (s, 1H), 10.40 (s, 1H), 8.68 (br. s., 1H), 8.52 (br. s., 1H), 8.40-8.34 (m, 1H), 8.29-8.23 (m, 1H), 8.09-8.03 (m, 2H), 7.97-7.85 (m, 3H), 7.80-7.72 (m, 1H), 7.67-7.60 (m, 2H), 7.57 (ddd, J=8.4, 7.0, 1.1 Hz, 1H), 7.41-7.35 (m, 1H), 4.81 (d, J=6.9 Hz, 2H), 4.14-4.02 (m, 2H), 3.99-3.87 (m, 2H); HPLC RT=5.09 min (Method A), 5.73 min (Method B).

Example 339: 1-((1-Acetylazetidin-3-yl)methyl)-N-(4-(4-oxo-3,4-dihydrophthalazin-1-yl)phenyl)-1H-indazole-3-carboxamide

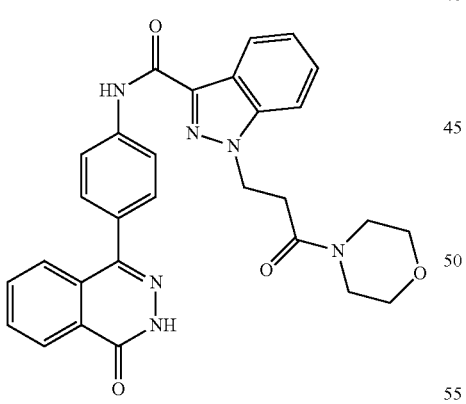

According to the procedure for the preparation of Example 334, coupling of Example 331 (9 mg, 0.02 mmol) and morpholine (3.5 mg, 0.040 mmol) afforded Example 337 (7.3 mg, 70% yield). MS(ESI) m/z: 523.2 (M+H)$^+$; $^1$H NMR 12.82 (s, 1H), 10.46 (s, 1H), 8.40-8.30 (m, 1H), 8.24 (d, J=8.3 Hz, 1H), 8.13-8.05 (m, 2H), 7.98-7.83 (m, 3H), 7.81-7.73 (m, 1H), 7.62-7.58 (m, 2H), 7.51 (ddd, J=8.3, 7.1, 0.8 Hz, 1H), 7.34 (t, J=7.6 Hz, 1H), 4.80 (t, J=7.0 Hz, 2H), 3.52-3.37 (m, 8H), 3.09 (t, J=6.9 Hz, 2H); HPLC RT=1.55 min (Method E), 1.51 min (Method F).

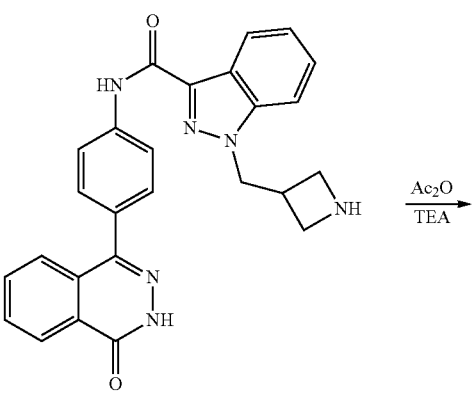

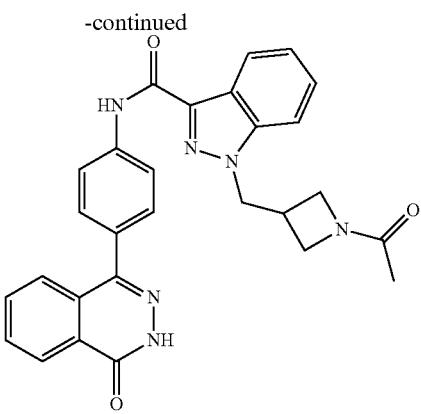

According to the procedure for the preparation of Example 329, acylation of Example 338 (9 mg, 0.016 mmol) with acetic anhydride afforded Example 339 (5.0 mg, 63% yield). MS(ESI) m/z: 493.3 (M+H)+; 1H NMR (500 MHz, DMSO-d6) δ 12.85 (s, 1H), 10.46 (s, 1H), 8.35 (d, J=7.7 Hz, 1H), 8.25 (d, J=8.0 Hz, 1H), 8.11-8.06 (m, J=8.3 Hz, 2H), 7.97-7.90 (m, 3H), 7.78 (d, J=7.7 Hz, 1H), 7.64-7.58 (m, J=8.5 Hz, 2H), 7.54 (t, J=7.7 Hz, 1H), 7.36 (t, J=7.4 Hz, 1H), 4.83 (dd, J=6.9, 4.7 Hz, 2H), 4.21 (t, J=8.4 Hz, 1H), 4.05 (dd, J=8.1, 5.6 Hz, 1H), 3.97-3.89 (m, 2H), 3.79 (dd, J=9.4, 5.5 Hz, 1H), 3.30-3.19 (m, 1H), 1.74 (s, 3H); HPLC RT=1.48 min (Method E), 1.47 min (Method F).

Example 340: 1-((1-Methylazetidin-3-yl)methyl)-N-(4-(4-oxo-3,4-dihydrophthalazin-1-yl)phenyl)-1H-indazole-3-carboxamide

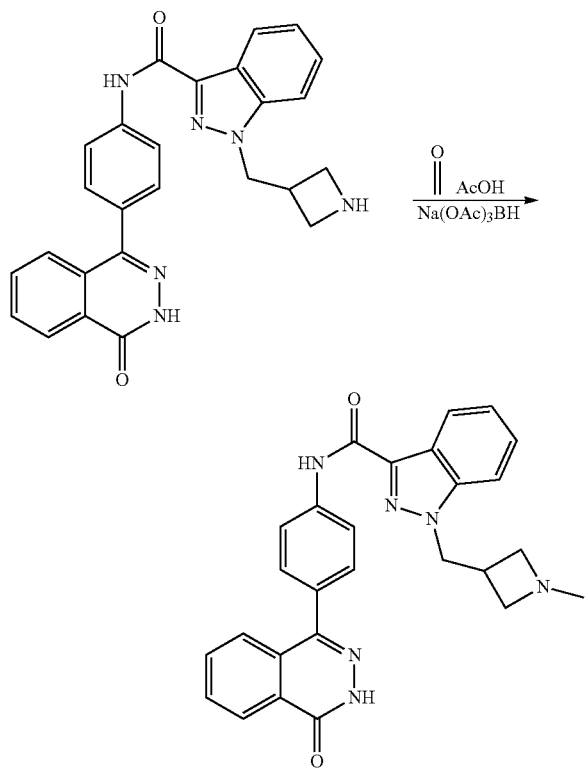

According to the procedure for the preparation of Example 330, reductive amination of Example 339 (12 mg, 0.021 mmol) afforded Example 340 (9.1 mg, 90% yield). MS(ESI) m/z: 465.2 (M+H)+; 1H NMR (500 MHz, DMSO-d6) δ 12.86 (s, 1H), 10.41 (d, J=13.5 Hz, 1H), 9.82 (br. s., 1H), 8.36 (d, J=7.7 Hz, 1H), 8.30-8.24 (m, 1H), 8.11-8.03 (m, J=8.3 Hz, 2H), 7.98-7.87 (m, 3H), 7.77 (d, J=7.7 Hz, 1H), 7.65-7.60 (m, J=8.3 Hz, 2H), 7.57 (t, J=7.6 Hz, 1H), 7.38 (t, J=7.4 Hz, 1H), 4.84 (t, J=7.3 Hz, 2H), 4.31 (d, J=5.5 Hz, 1H), 4.27-4.14 (m, 1H), 4.03 (d, J=6.9 Hz, 2H), 2.85 (dd, J=16.4, 4.5 Hz, 3H); HPLC RT=1.33 min (Method E), 1.36 min (Method F).

Example 341: Methyl 3-((3-((4-(4-oxo-3,4-dihydrophthalazin-1-yl)phenyl)carbamoyl)-1H-indazol-1-yl)methyl)azetidine-1-carboxylate

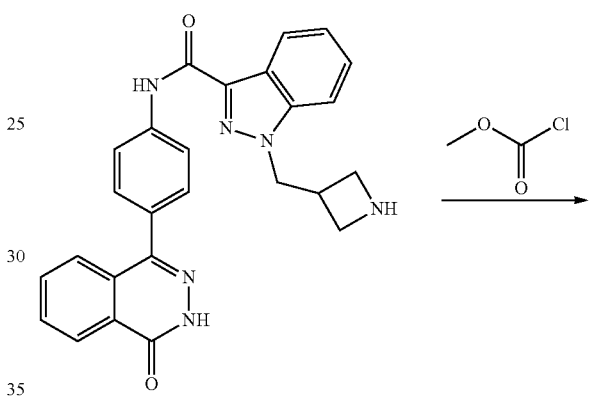

According to the procedure for the preparation of Example 329, acylation of Example 338 (8 mg, 0.014 mmol) with methyl chloroformate afforded Example 341 (5.1 mg, 67% yield). MS(ESI) m/z: 509.3 (M+H)+; 1H NMR (500 MHz, DMSO-d6) δ 12.85 (s, 1H), 10.46 (s, 1H), 8.35 (d, J=7.7 Hz, 1H), 8.25 (d, J=8.0 Hz, 1H), 8.12-8.04 (m, J=8.0 Hz, 2H), 7.97-7.88 (m, 3H), 7.78 (d, J=7.7 Hz, 1H), 7.63-7.59 (m, J=8.0 Hz, 2H), 7.53 (t, J=7.7 Hz, 1H), 7.35 (t, J=7.6 Hz, 1H), 4.82 (d, J=7.2 Hz, 2H), 4.01 (br. s., 2H), 3.93-3.84 (m, 2H), 3.54 (s, 3H), 3.27-3.14 (m, 1H); HPLC RT=1.74 min (Method E), 1.74 min (Method F).

Example 342: N-(4-(4-Oxo-3,4-dihydrophthalazin-1-yl)phenyl)-1-(piperidin-4-ylmethyl)-1H-indazole-3-carboxamide, TFA Example 343: 1-((1-Acetylpiperidin-4-yl)methyl)-N-(4-(4-oxo-3,4-dihydrophthalazin-1-yl)phenyl)-1H-indazole-3-carboxamide

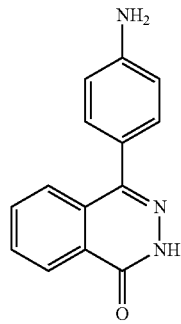

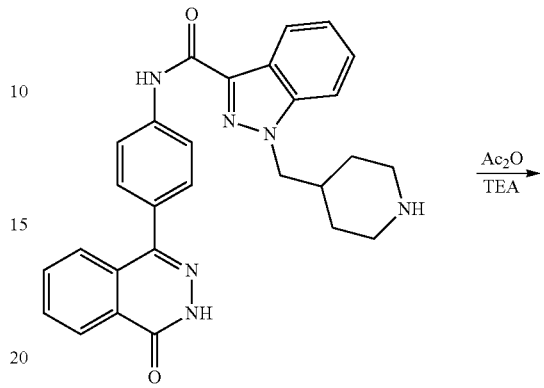

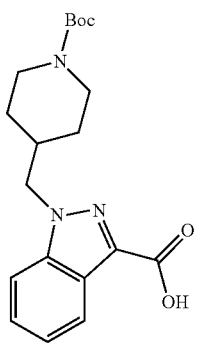

1. HATU, i-Pr$_2$NEt
2. TFA

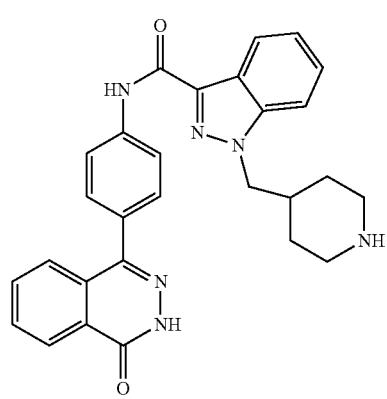

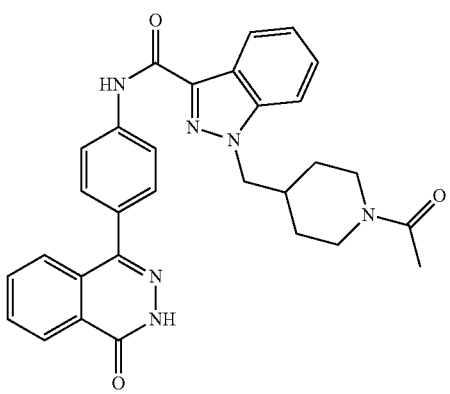

According to the procedure for the preparation of Example 45, coupling of Intermediate 3 (95 mg, 0.20 mmol) and Intermediate 101 (88 mg, 0.245 mmol), afforded after TFA deprotection Example 342 (78 mg, 79% yield). MS(ESI) m/z: 479.4 (M+H)$^+$; $^1$H NMR (500 MHz, DMSO-d$_6$) δ 12.83 (s, 1H), 10.49 (s, 1H), 8.48 (d, J=9.9 Hz, 1H), 8.38-8.34 (m, 1H), 8.27 (d, J=8.0 Hz, 1H), 8.15 (d, J=11.3 Hz, 1H), 8.11-8.07 (m, 2H), 7.94-7.88 (m, 3H), 7.79-7.74 (m, 1H), 7.64-7.59 (m, 2H), 7.54 (ddd, J=8.4, 7.0, 1.1 Hz, 1H), 7.39-7.33 (m, 1H), 4.55 (d, J=6.6 Hz, 2H), 3.27 (d, J=12.4 Hz, 2H), 2.93-2.80 (m, 2H), 2.39-2.27 (m, 1H), 1.71 (d, J=13.8 Hz, 2H), 1.54-1.39 (m, 2H); HPLC RT=8.74 min (Method A), 9.34 min (Method B).

According to the procedure for the preparation of Example 329, acylation of Example 342 (12 mg, 0.020 mmol) with acetic anhydride afforded Example 343 (8.9 mg, 84% yield). MS(ESI) m/z: 521.3 (M+H)$^+$; $^1$H NMR (500 MHz, DMSO-d$_6$) δ 12.85 (s, 1H), 10.52 (s, 1H), 8.35 (d, J=7.4 Hz, 1H), 8.25 (d, J=8.0 Hz, 1H), 8.14-8.04 (m, J=8.0 Hz, 2H), 7.98-7.87 (m, 3H), 7.78 (d, J=7.4 Hz, 1H), 7.62-7.58 (m, J=7.7 Hz, 2H), 7.52 (t, J=7.6 Hz, 1H), 7.34 (t, J=7.2 Hz, 1H), 4.49 (d, J=6.6 Hz, 2H), 4.37 (d, J=12.4 Hz, 1H), 3.80 (d, J=13.5 Hz, 1H), 2.96 (t, J=12.9 Hz, 1H), 2.30 (br. s., 1H), 1.97 (s, 3H), 1.50 (t, J=15.5 Hz, 2H), 1.37-1.25 (m, 1H), 1.18 (d, J=12.1 Hz, 1H); HPLC RT=1.61 min (Method E), 1.61 min (Method F).

Example 344: Methyl 4-((3-((4-(4-oxo-3,4-dihydrophthalazin-1-yl)phenyl)carbamoyl)-1H-indazol-1-yl)methyl)piperidine-1-carboxylate

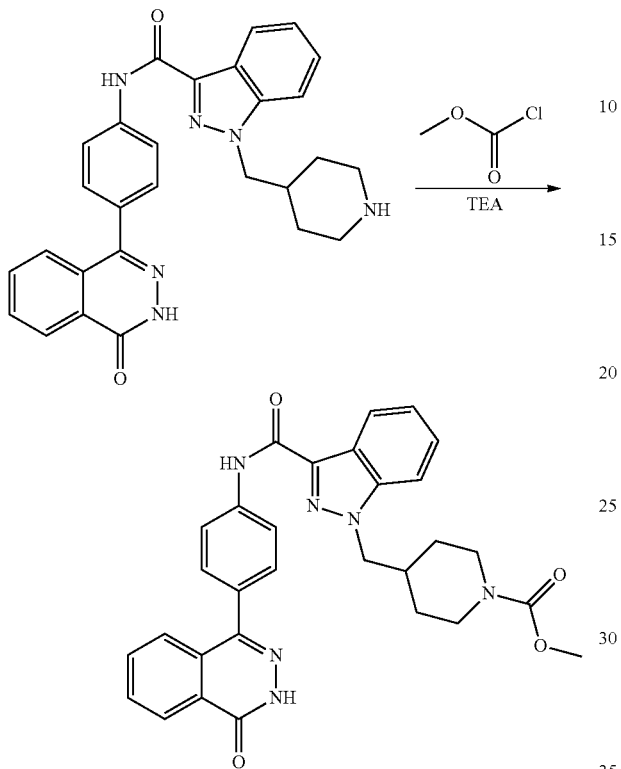

According to the procedure for the preparation of Example 329, acylation of Example 342 (10 mg, 0.017 mmol) with methyl chloroformate afforded Example 344 (4.7 mg, 52% yield). MS(ESI) m/z: 537.3 (M+H)$^+$; $^1$H NMR (500 MHz, DMSO-d$_6$) δ 12.85 (s, 1H), 10.51 (s, 1H), 8.35 (d, J=7.4 Hz, 1H), 8.25 (d, J=8.0 Hz, 1H), 8.12-8.05 (m, J=8.0 Hz, 2H), 7.95-7.87 (m, 3H), 7.78 (d, J=7.7 Hz, 1H), 7.63-7.57 (m, J=7.7 Hz, 2H), 7.51 (t, J=7.6 Hz, 1H), 7.34 (t, J=7.3 Hz, 1H), 4.48 (d, J=6.9 Hz, 2H), 3.96 (br. s., 2H), 3.57 (s, 3H), 2.73 (br. s., 2H), 2.25 (br. s., 1H), 1.47 (br. s., 2H), 1.32-1.19 (m, 2H); HPLC RT=1.83 min (Method E), 1.83 min (Method F).

Example 345: 1-(2-Hydroxy-2-methylpropyl)-N-(3-methoxy-4-(4-oxo-3,4-dihydrophthalazin-1-yl)phenyl)-1H-indazole-3-carboxamide

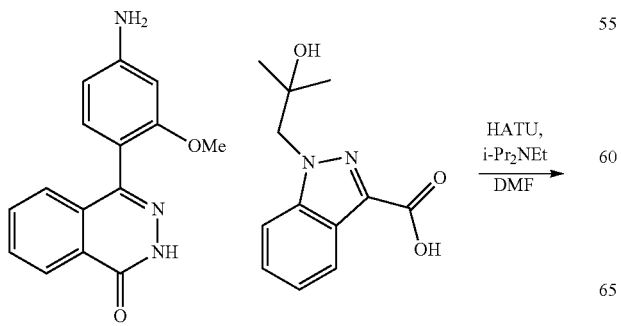

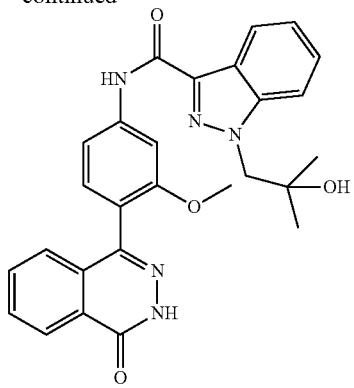

According to the procedure for the preparation of Example 45, coupling of Intermediate 102 (16 mg, 0.042 mmol) and Intermediate 15 (9.8 mg, 0.042 mmol), afforded Example 345 (14.8 mg, 73% yield). MS(ESI) m/z: 484.3 (M+H)$^+$; $^1$H NMR (500 MHz, DMSO-d$_6$) δ 12.75 (br. s., 1H), 10.37 (br. s., 1H), 8.35-8.28 (m, 1H), 8.24 (d, J=7.2 Hz, 1H), 7.90-7.80 (m, 4H), 7.70 (d, J=7.2 Hz, 1H), 7.48 (br. s., 1H), 7.40-7.28 (m, 3H), 4.79 (br. s., 1H), 4.49 (br. s., 2H), 3.72 (br. s., 3H), 1.20 (br. s., 6H); HPLC RT=1.65 min (Method E), 1.66 min (Method F).

Example 346: N-(3-Ethoxy-4-(4-oxo-3,4-dihydrophthalazin-1-yl)phenyl)-1-(2-hydroxy-2-methylpropyl)-1H-indazole-3-carboxamide

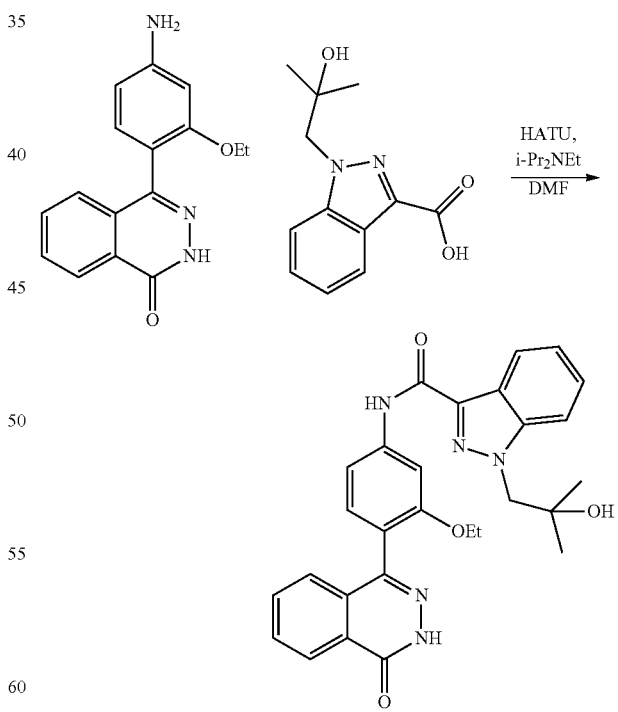

According to the procedure for the preparation of Example 45, coupling of Intermediate 103 (14 mg, 0.050 mmol) and Intermediate 15 (11.7 mg, 0.050 mmol), afforded Example 346 (22.9 mg, 92% yield). MS(ESI) m/z: 498.3 (M+H)$^+$; $^1$H NMR (500 MHz, DMSO-d$_6$) δ 12.74 (br. s., 1H), 10.35 (br. s., 1H), 8.33-8.27 (m, 1H), 8.24 (d, J=7.7 Hz, 1H), 7.92-7.81 (m, 4H), 7.69 (d, J=8.0 Hz, 1H), 7.48 (br. s., 1H), 7.42-7.37 (m, 1H), 7.33 (d, J=7.7 Hz, 2H), 4.77 (br. s., 1H), 4.49 (br. s., 2H), 4.06 (br. s., 2H), 1.20 (br. s., 6H), 1.06 (br. s., 3H); HPLC RT=1.76 min (Method E), 1.76 min (Method F).

Example 347: N-(3-Ethoxy-4-(4-oxo-3,4-dihydrophthalazin-1-yl)phenyl)-1-((tetrahydrofuran-3-yl)methyl)-1H-indazole-3-carboxamide

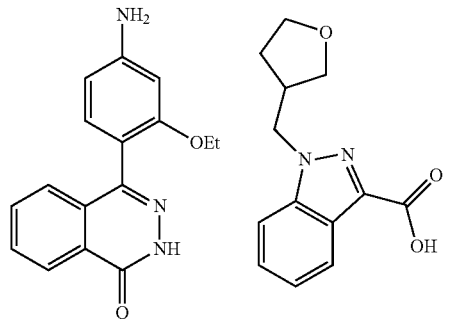

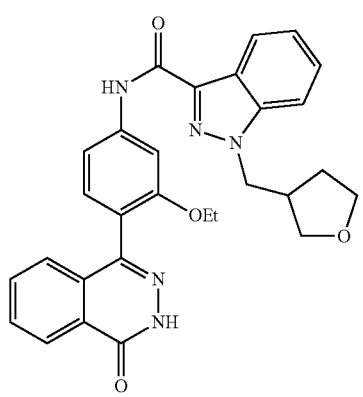

According to the procedure for the preparation of Example 45, coupling of Intermediate 103 (11 mg, 0.039 mmol) and Intermediate 24 (9.6 mg, 0.039 mmol), afforded Example 347 (17.6 mg, 87% yield). MS(ESI) m/z: 510.4 (M+H)+; 1H NMR (500 MHz, DMSO-d6) δ 12.74 (s, 1H), 10.40 (s, 1H), 8.34-8.24 (m, 2H), 7.90 (s, 1H), 7.86-7.82 (m, 3H), 7.71 (dd, J=8.3, 1.7 Hz, 1H), 7.53 (ddd, J=8.3, 7.1, 1.1 Hz, 1H), 7.43-7.29 (m, 3H), 4.58 (d, J=7.7 Hz, 2H), 4.14-4.00 (m, 2H), 3.87-3.81 (m, 1H), 3.72-3.64 (m, 2H), 3.58 (dd, J=8.8, 5.5 Hz, 1H), 2.96 (s, 1H), 1.94 (s, 1H), 1.72 (d, J=7.4 Hz, 1H), 1.06 (t, J=7.0 Hz, 3H); HPLC RT=1.81 min (Method E), 1.81 min (Method F).

Example 348: N-(3-Methoxy-4-(4-oxo-3,4-dihydrophthalazin-1-yl)phenyl)-1-((tetrahydrofuran-3-yl)methyl)-1H-indazole-3-carboxamide

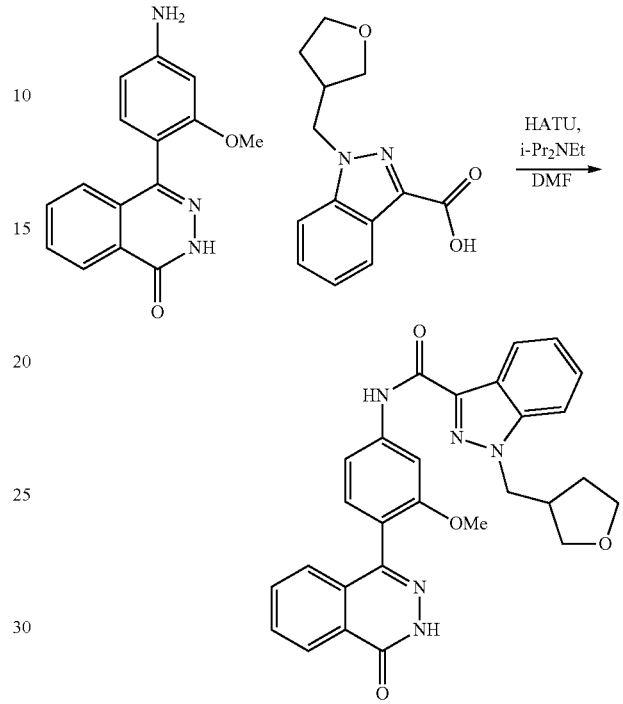

According to the procedure for the preparation of Example 45, coupling of Intermediate 102 (15 mg, 0.039 mmol) and Intermediate 24 (9.7 mg, 0.039 mmol), afforded Example 348 (19.1 mg, 97% yield). MS(ESI) m/z: 496.3 (M+H)+; 1H NMR (500 MHz, DMSO-d6) δ 12.79 (br. s., 1H), 10.48 (br. s., 1H), 8.28 (br. s., 2H), 7.90 (d, J=7.2 Hz, 1H), 7.88-7.81 (m, 3H), 7.73 (br. s., 1H), 7.53 (br. s., 1H), 7.35 (d, J=8.8 Hz, 3H), 4.58 (br. s., 2H), 3.86 (br. s., 1H), 3.72 (br. s., 3H), 3.68 (br. s., 2H), 3.59 (br. s., 1H), 2.96 (br. s., 1H), 1.94 (br. s., 1H), 1.77-1.65 (m, 1H); HPLC RT=1.71 min (Method E), 1.71 min (Method F).

Example 349: Propan-2-yl 4-[(3-{[4-(4-oxo-3,4-dihydrophthalazin-1-yl)phenyl]carbamoyl}-1H-indazol-1-yl)methyl]piperidine-1-carboxylate

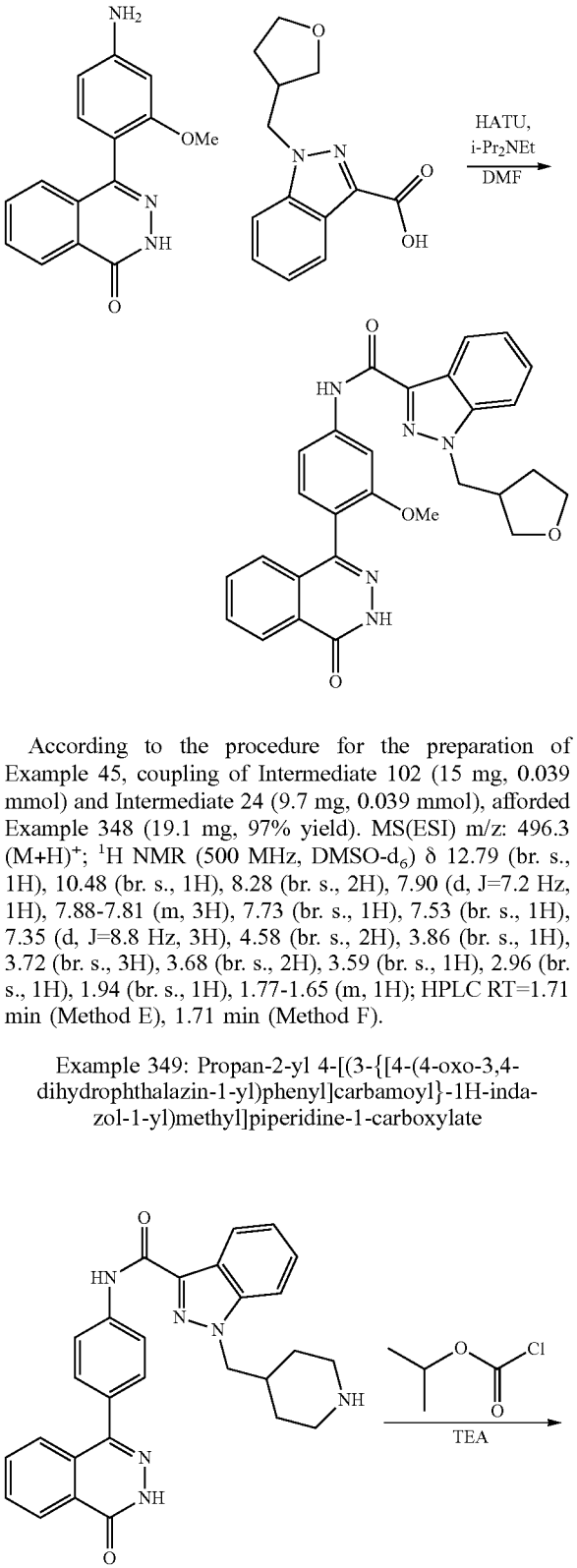

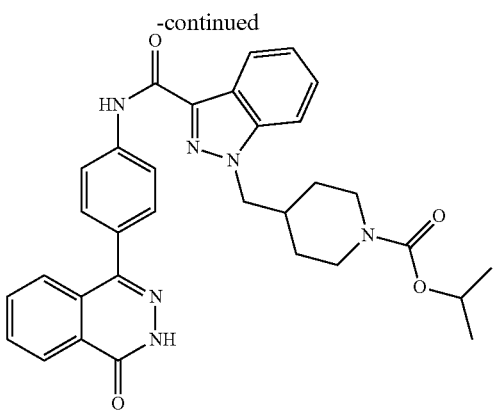

According to the procedure for the preparation of Example 329, acylation of Example 342 (10 mg, 0.017 mmol) with isopropyl chloroformate afforded Example 349 (8 mg, 84% yield). MS(ESI) m/z: 565.2 (M+H)$^+$; $^1$H NMR (500 MHz, DMSO-d$_6$) δ 12.82 (s, 1H), 10.47 (s, 1H), 8.35 (dd, J=7.7, 1.4 Hz, 1H), 8.25 (d, J=8.3 Hz, 1H), 8.13-8.06 (m, J=8.8 Hz, 2H), 7.97-7.85 (m, 3H), 7.81-7.73 (m, 1H), 7.63-7.58 (m, J=8.5 Hz, 2H), 7.55-7.48 (m, 1H), 7.34 (t, J=7.4 Hz, 1H), 4.75 (quin, J=6.2 Hz, 1H), 4.48 (d, J=7.2 Hz, 2H), 4.07-3.93 (m, 2H), 2.82-2.66 (m, 2H), 2.25 (ddd, J=11.1, 7.4, 3.7 Hz, 1H), 1.48 (d, J=11.0 Hz, 2H), 1.30-1.22 (m, 2H), 1.20-1.10 (m, 6H); HPLC RT=2.04 min (Method E), 2.04 min (Method F).

Example 350: 2-Fluoroethyl 4-[(3-{[4-(4-oxo-3,4-dihydrophthalazin-1-yl)phenyl]carbamoyl}-1H-indazol-1-yl)methyl]piperidine-1-carboxylate

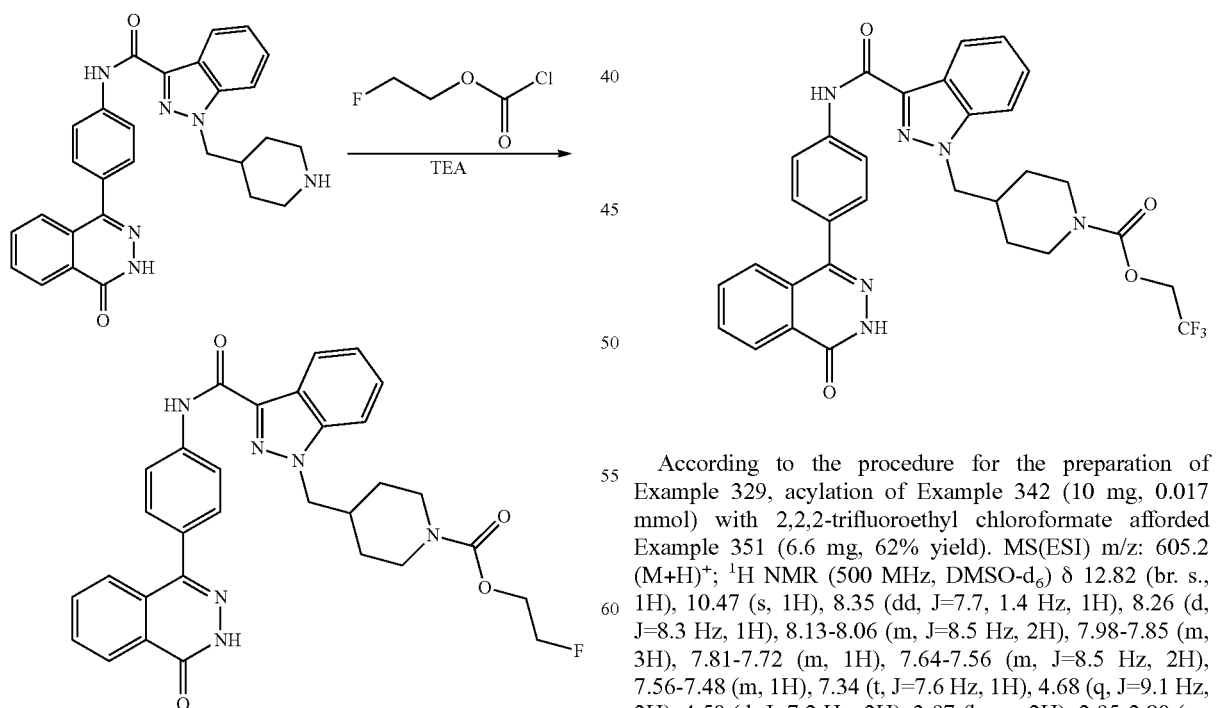

According to the procedure for the preparation of Example 329, acylation of Example 342 (10 mg, 0.017 mmol) with 2-fluoroethyl chloroformate afforded Example 350 (8.5 mg, 86% yield). MS(ESI) m/z: 569.2 (M+H)$^+$; $^1$H NMR (500 MHz, DMSO-d$_6$) δ 12.82 (br. s., 1H), 10.48 (s, 1H), 8.35 (dd, J=7.7, 1.4 Hz, 1H), 8.26 (d, J=8.3 Hz, 1H), 8.12-8.05 (m, J=8.5 Hz, 2H), 7.96-7.84 (m, 3H), 7.77 (d, J=7.7 Hz, 1H), 7.65-7.56 (m, J=8.5 Hz, 2H), 7.55-7.48 (m, 1H), 7.34 (t, J=7.6 Hz, 1H), 4.66-4.61 (m, 1H), 4.55-4.51 (m, 1H), 4.49 (d, J=7.2 Hz, 2H), 4.27-4.23 (m, 1H), 4.23-4.15 (m, 1H), 3.99 (d, J=13.2 Hz, 2H), 2.77 (br. s., 1H), 2.73 (s, 1H), 2.27 (ddd, J=11.1, 7.4, 3.7 Hz, 1H), 1.51 (d, J=11.0 Hz, 2H), 1.27 (qd, J=12.4, 4.1 Hz, 2H); HPLC RT=1.93 min (Method E), 1.95 min (Method F).

Example 351: 2,2,2-Trifluoroethyl 4-[(3-{[4-(4-oxo-3,4-dihydrophthalazin-1-yl)phenyl]carbamoyl}-1H-indazol-1-yl)methyl]piperidine-1-carboxylate

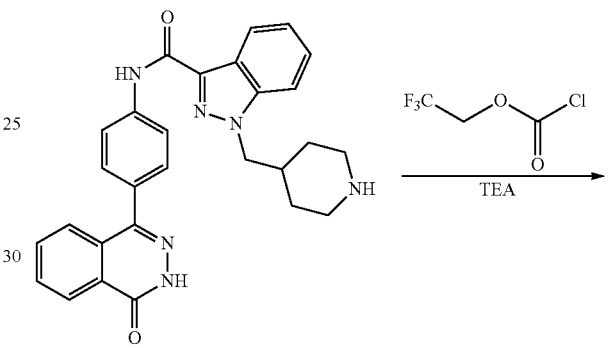

According to the procedure for the preparation of Example 329, acylation of Example 342 (10 mg, 0.017 mmol) with 2,2,2-trifluoroethyl chloroformate afforded Example 351 (6.6 mg, 62% yield). MS(ESI) m/z: 605.2 (M+H)$^+$; $^1$H NMR (500 MHz, DMSO-d$_6$) δ 12.82 (br. s., 1H), 10.47 (s, 1H), 8.35 (dd, J=7.7, 1.4 Hz, 1H), 8.26 (d, J=8.3 Hz, 1H), 8.13-8.06 (m, J=8.5 Hz, 2H), 7.98-7.85 (m, 3H), 7.81-7.72 (m, 1H), 7.64-7.56 (m, J=8.5 Hz, 2H), 7.56-7.48 (m, 1H), 7.34 (t, J=7.6 Hz, 1H), 4.68 (q, J=9.1 Hz, 2H), 4.50 (d, J=7.2 Hz, 2H), 3.97 (br. s., 2H), 2.95-2.80 (m, 2H), 2.29 (ddt, J=11.2, 7.5, 3.9 Hz, 1H), 1.65-1.47 (m, 2H), 1.28 (qd, J=12.3, 4.3 Hz, 2H); HPLC RT=2.02 min (Method E), 2.02 min (Method F).

Example 352: N-(2-Methoxy-4-(4-oxo-3,4-dihydrophthalazin-1-yl)phenyl)-1-((tetrahydrofuran-3-yl)methyl)-1H-indazole-3-carboxamide

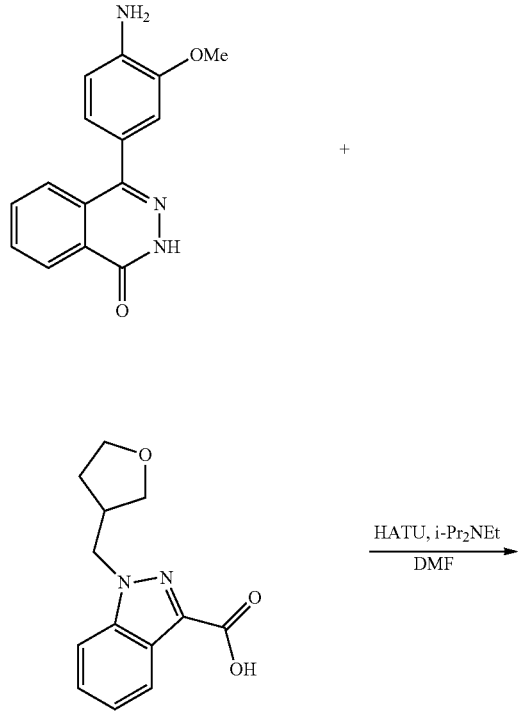

According to the procedure for the preparation of Example 45, coupling of Intermediate 104 (15 mg, 0.056 mmol) and Intermediate 24 (13.8 mg, 0.056 mmol), afforded Example 352 (19.4 mg, 68% yield). MS(ESI) m/z: 496.3 (M+H)$^+$; $^1$H NMR (500 MHz, DMSO-d$_6$) δ 12.84 (s, 1H), 9.58 (s, 1H), 8.55 (d, J=8.3 Hz, 1H), 8.35 (dd, J=7.8, 1.5 Hz, 1H), 8.27 (d, J=8.3 Hz, 1H), 7.95-7.88 (m, 3H), 7.86-7.80 (m, 1H), 7.59-7.51 (m, 1H), 7.38 (t, J=7.4 Hz, 1H), 7.34 (d, J=1.7 Hz, 1H), 7.25 (dd, J=8.1, 1.8 Hz, 1H), 4.65-4.52 (m, 2H), 4.00 (s, 3H), 3.89-3.84 (m, 1H), 3.75 (dd, J=8.5, 6.9 Hz, 1H), 3.72-3.66 (m, 1H), 3.59 (dd, J=8.5, 5.8 Hz, 1H), 2.99-2.86 (m, 1H), 2.05-1.92 (m, 1H), 1.72 (dd, J=12.9, 6.6 Hz, 1H); HPLC RT=1.82 min (Method E), 1.82 min (Method F).

Example 353: 1-(2-Hydroxy-2-methylpropyl)-N-(2-hydroxy-4-(4-oxo-3,4-dihydrophthalazin-1-yl)phenyl)-1H-indazole-3-carboxamide

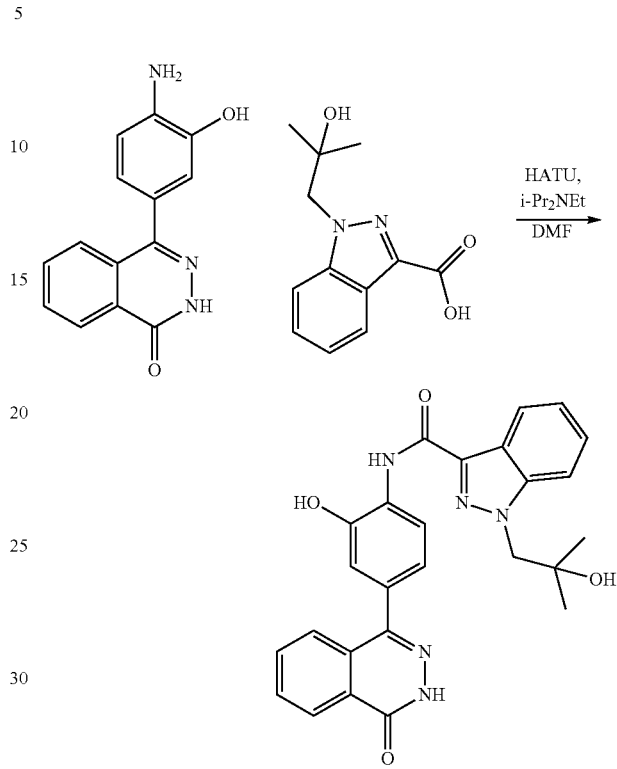

According to the procedure for the preparation of Example 45, coupling of Intermediate 105 (8 mg, 0.032 mmol) and Intermediate 15 (7.4 mg, 0.032 mmol), afforded Example 353 (0.9 mg, 6% yield). MS(ESI) m/z: 470.3 (M+H)$^+$; $^1$H NMR (500 MHz, DMSO-d$_6$) δ 12.80 (s, 1H), 9.59 (s, 1H), 8.53 (d, J=8.3 Hz, 1H), 8.35 (d, J=7.4 Hz, 1H), 8.26 (d, J=8.3 Hz, 1H), 7.98-7.80 (m, 4H), 7.49 (t, J=7.7 Hz, 1H), 7.34 (t, J=7.6 Hz, 1H), 7.22-7.16 (m, 1H), 7.11 (dd, J=8.3, 1.4 Hz, 1H), 4.76 (s, 1H), 4.56-4.43 (m, 2H), 1.28-1.15 (m, 6H); HPLC RT=1.60 min (Method E), 1.56 min (Method F).

Example 354: N-(2-Hydroxy-4-(4-oxo-3,4-dihydrophthalazin-1-yl)phenyl)-1-((tetrahydrofuran-3-yl)methyl)-1H-indazole-3-carboxamide

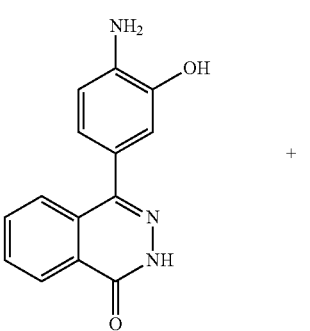

375

-continued

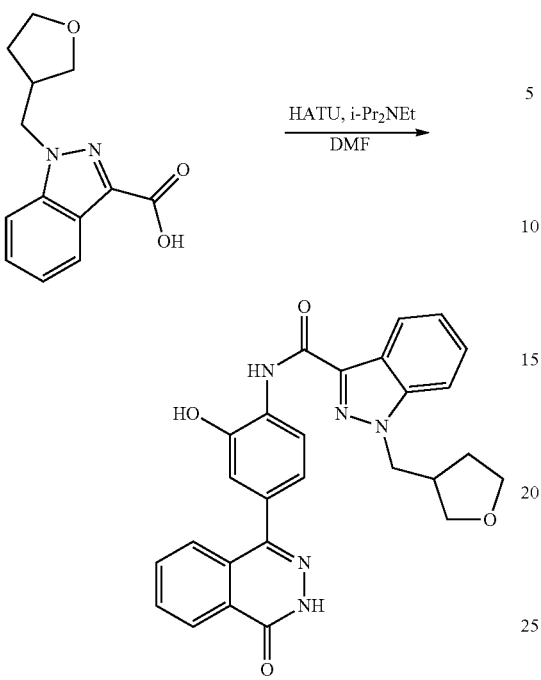

According to the procedure for the preparation of Example 45, coupling of Intermediate 105 (16 mg, 0.063 mmol) and Intermediate 24 (15.6 mg, 0.063 mmol), afforded Example 354 (4 mg, 13% yield). MS(ESI) m/z: 482.4 (M+H)$^+$; $^1$H NMR (400 MHz, DMSO-d$_6$) δ 12.80 (s, 1H), 10.63 (s, 1H), 9.59 (s, 1H), 8.51 (d, J=8.4 Hz, 1H), 8.37-8.32 (m, 1H), 8.31-8.26 (m, 1H), 7.96-7.87 (m, 3H), 7.86-7.80 (m, 1H), 7.54 (ddd, J=8.4, 7.0, 1.1 Hz, 1H), 7.44-7.33 (m, 1H), 7.17 (d, J=1.8 Hz, 1H), 7.12 (dd, J=8.3, 1.9 Hz, 1H), 4.67-4.54 (m, 2H), 3.95-3.82 (m, 1H), 3.75 (dd, J=8.6, 7.0 Hz, 1H), 3.70-3.63 (m, 1H), 3.63-3.50 (m, 1H), 2.96-2.82 (m, 1H), 2.06-1.91 (m, 1H), 1.72 (dt, J=13.5, 6.6 Hz, 1H); HPLC RT=9.20 min (Method A), 8.67 min (Method B).

Example 355: N-(3-(Hydroxymethyl)-4-(4-oxo-3,4-dihydrophthalazin-1-yl)phenyl)-1-((tetrahydrofuran-3-yl)methyl)-1H-indazole-3-carboxamide

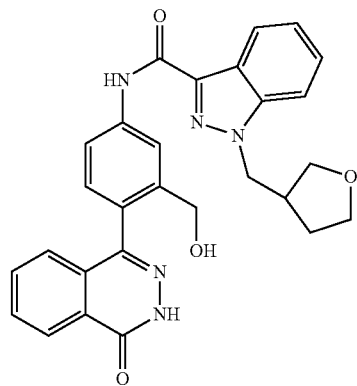

376

Example 355A: Methyl 2-(4-oxo-3,4-dihydrophthalazin-1-yl)-5-(1-(((tetrahydrofuran-3-yl)methyl)-1H-indazole-3-carboxamido)benzoate

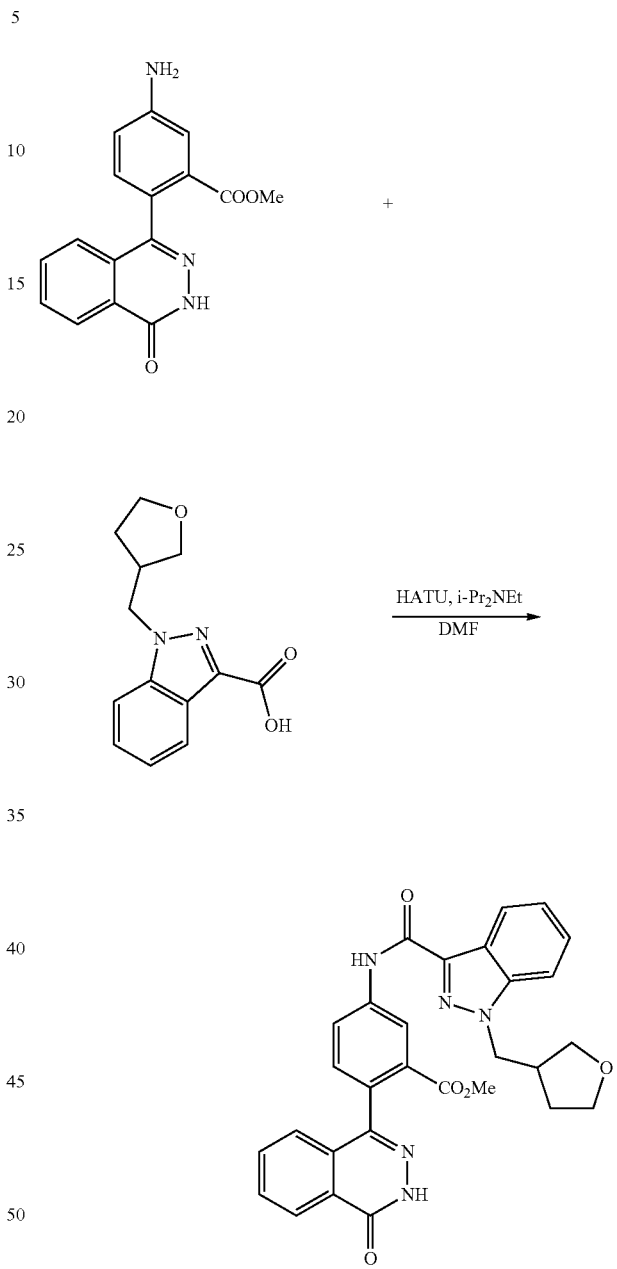

To a mixture of Intermediate 106 (34 mg, 0.12 mmol), Intermediate 24 (28 mg, 0.12 mmol), and HATU (48.2 mg, 0.127 mmol) in DMF (2 mL), was added DIEA (0.100 mL, 0.58 mmol). The reaction mixture was stirred at rt for 16 h, the was concentrated. The residue was purified by preparative HPLC to afford Example 355A (39 mg, 64% yield). MS(ESI) m/z: 524.4 (M+H)$^+$; $^1$H NMR (500 MHz, DMSO-d$_6$) δ 10.71 (s, 1H), 8.70 (d, J=2.2 Hz, 1H), 8.39-8.31 (m, 1H), 8.28 (td, J=5.5, 2.8 Hz, 2H), 7.90 (d, J=8.5 Hz, 1H), 7.88-7.80 (m, 2H), 7.61-7.51 (m, 2H), 7.42-7.34 (m, 1H), 7.32-7.25 (m, 1H), 4.68-4.52 (m, 2H), 3.86 (td, J=8.0, 5.6 Hz, 1H), 3.77-3.63 (m, 2H), 3.63-3.58 (m, 1H), 3.55 (s, 3H), 3.06-2.92 (m, 1H), 2.03-1.87 (m, 1H), 1.78-1.67 (m, 1H).

Example 355

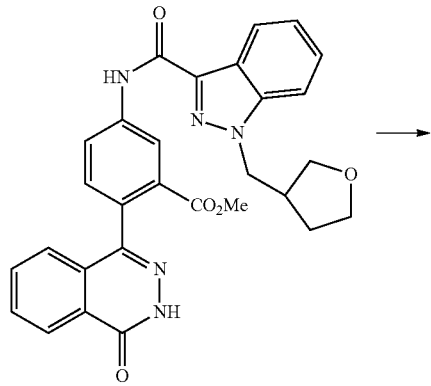

→

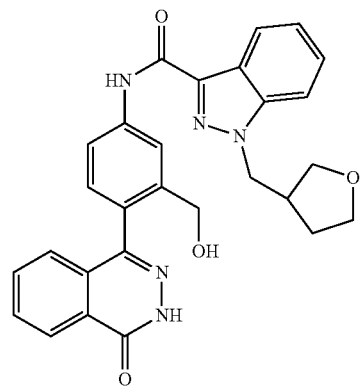 [SMILES: O=C(Nc1ccc(-c2n[nH]c(=O)c3ccccc23)c(CO)c1)c1nn(CC2CCOC2)c2ccccc12]

To a solution of Example 355A (13.2 mg, 0.025 mmol) in THF (1 mL) was added lithium borohydride (2M in THF, 0.684 mL, 1.37 mmol) at room temperature. The reaction mixture was stirred at room temperature for 4 h, then was diluted with MeOH and DMSO and the solution was purified by preparative HPLC to afford Example 355 (7.6 mg, 58% yield). MS(ESI) m/z: 496.1 (M+H)$^+$; $^1$H NMR (500 MHz, DMSO-d$_6$) δ 12.77 (s, 1H), 10.40 (s, 1H), 8.39-8.30 (m, 1H), 8.26 (d, J=8.3 Hz, 1H), 8.22 (d, J=1.9 Hz, 1H), 7.93 (dd, J=8.3, 2.2 Hz, 1H), 7.91-7.83 (m, 3H), 7.55-7.49 (m, 1H), 7.39-7.28 (m, 3H), 4.65-4.52 (m, 2H), 4.35 (br. s., 2H), 3.87-3.81 (m, 1H), 3.73-3.65 (m, 2H), 3.59 (dd, J=8.8, 5.5 Hz, 1H), 3.04-2.93 (m, 1H), 2.04-1.89 (m, 1H), 1.80-1.68 (m, 1H); HPLC RT=1.55 min (Method E), 1.55 min (Method F).

Example 356: 1-((1-Methylpiperidin-4-yl)methyl)-N-(4-(4-oxo-3,4-dihydrophthalazin-1-yl)phenyl)-1H-indazole-3-carboxamide

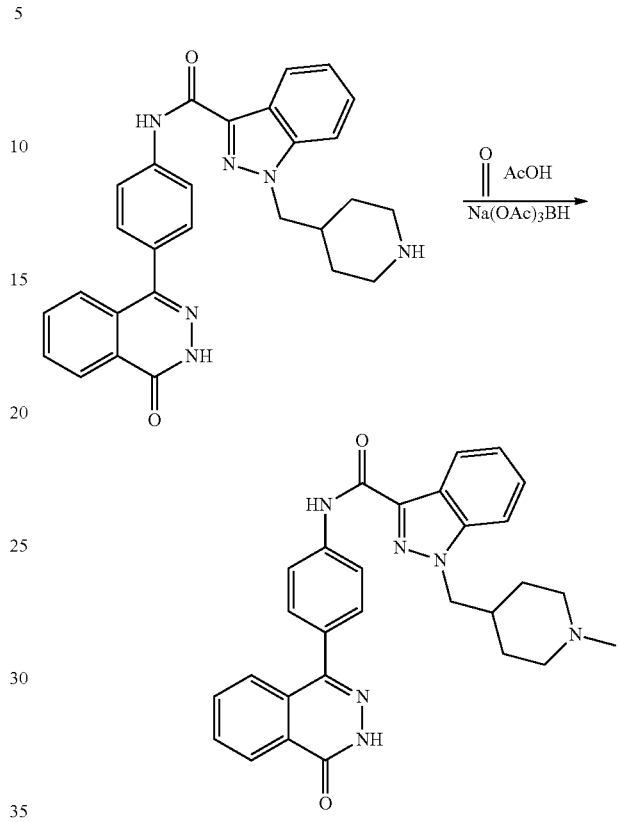

According to the procedure for the preparation of Example 330, reductive amination of Example 342 (12 mg, 0.021 mmol) afforded Example 356 (6.4 mg, 64% yield). MS(ESI) m/z: 493.2 (M+H)$^+$; $^1$H NMR (500 MHz, DMSO-d$_6$) δ 12.82 (s, 1H), 10.47 (s, 1H), 8.42-8.32 (m, 1H), 8.25 (d, J=8.3 Hz, 1H), 8.13-8.05 (m, J=8.5 Hz, 2H), 7.99-7.84 (m, 3H), 7.78 (d, J=8.3 Hz, 1H), 7.65-7.55 (m, J=8.8 Hz, 2H), 7.51 (t, J=7.7 Hz, 1H), 7.34 (t, J=7.4 Hz, 1H), 4.47 (d, J=7.2 Hz, 2H), 2.83-2.66 (m, 2H), 2.14 (s, 3H), 2.05-1.96 (m, 1H), 1.81 (t, J=11.1 Hz, 2H), 1.52-1.30 (m, 4H); HPLC RT=1.30 min (Method E), 1.28 min (Method F).

Example 357: 1-(2-Hydroxy-2-methylpropyl)-N-(2-methoxy-4-(4-oxo-3,4-dihydrophthalazin-1-yl)phenyl)-1H-indazole-3-carboxamide

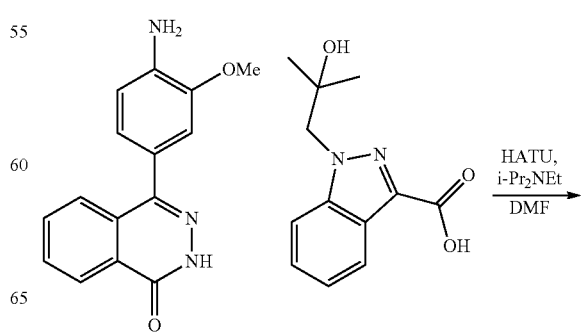

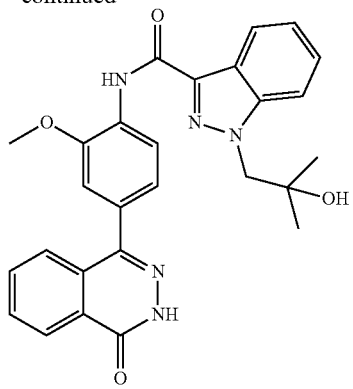

According to the procedure for the preparation of Example 45, coupling of Intermediate 104 (16 mg, 0.060 mmol) and Intermediate 15 (14 mg, 0.060 mmol), afforded Example 357 (6.1 mg, 20% yield). MS(ESI) m/z: 484.3 (M+H)$^+$; $^1$H NMR (500 MHz, DMSO-d$_6$) δ 12.83 (s, 1H), 9.59 (s, 1H), 8.57 (d, J=8.3 Hz, 1H), 8.35 (dd, J=7.7, 1.4 Hz, 1H), 8.25 (d, J=8.0 Hz, 1H), 7.98-7.78 (m, 4H), 7.54-7.46 (m, 1H), 7.39-7.31 (m, 2H), 7.25 (dd, J=8.1, 1.8 Hz, 1H), 4.77 (s, 1H), 4.47 (s, 2H), 3.99 (s, 3H), 1.21 (s, 6H); HPLC RT=1.69 min (Method E), 1.70 min (Method F).

Example 358: N-(2-Fluoro-4-(4-oxo-3,4-dihydrophthalazin-1-yl)phenyl)-1-(2-hydroxy-2-methylpropyl)-1H-indazole-3-carboxamide

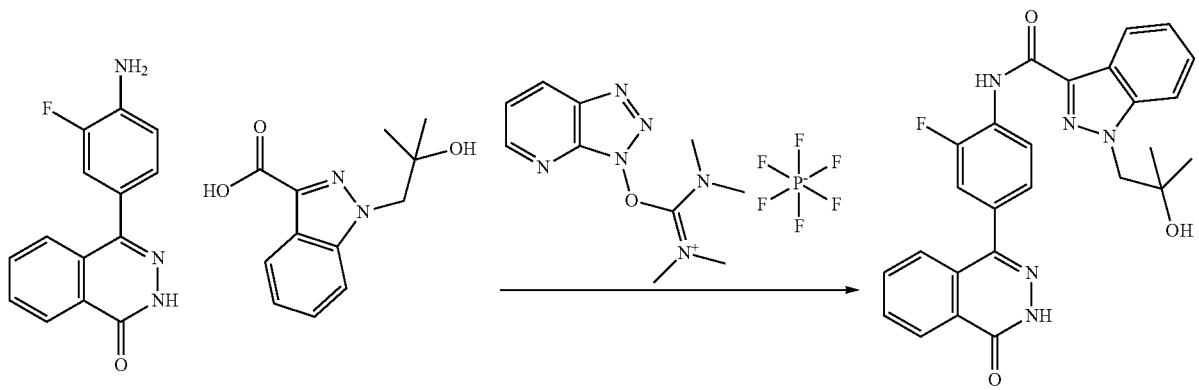 [SMILES: Nc1ccc(-c2n[nH]c(=O)c3ccccc23)cc1F ; CC(C)(O)Cn1nc(C(=O)O)c2ccccc21 ; CN(C)C(On1nnc2cccnc21)=[N+](C)C ; F[P-](F)(F)(F)(F)F ; CC(C)(O)Cn1nc(C(=O)Nc2ccc(-c3n[nH]c(=O)c4ccccc34)cc2F)c2ccccc21]

To a solution of Intermediate 107 (15 mg, 0.041 mmol), Intermediate 15 (10.5 mg, 0.045 mmol) and DIEA (0.035 mL, 0.20 mmol) in DMF (1 mL) at rt, was added HATU (17 mg, 0.045 mmol). The mixture was stirred at rt for 5 days. The reaction mixture was diluted with MeOH (1 mL), then was filtered and purified by prep HPLC to afford Example 358 (6.0 mg, 30% yield). MS(ESI) m/z: 472.2 (M+H)$^+$; $^1$H NMR (500 MHz, DMSO-d$_6$) δ 12.90 (s, 1H), 9.85 (s, 1H), 8.29-8.44 (m, 1H), 8.17-8.29 (m, 2H), 7.89-7.99 (m, 2H), 7.88 (d, J=8.80 Hz, 1H), 7.78 (d, J=7.43 Hz, 1H), 7.60 (dd, J=1.65, 11.28 Hz, 1H), 7.46-7.53 (m, 2H), 7.33 (t, J=7.43 Hz, 1H), 4.48 (s, 2H), 1.20 (s, 6H); HPLC RT=1.67 min (Method E), 1.66 min (Method F).

Example 359: 1-(2-Hydroxyethyl)-N-(3-(hydroxymethyl)-4-(4-oxo-3,4-dihydrophthalazin-1-yl)phenyl)-1H-indazole-3-carboxamide

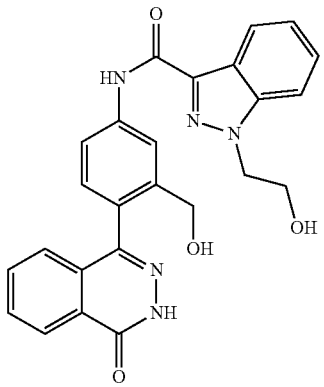 [SMILES: O=C(Nc1ccc(-c2n[nH]c(=O)c3ccccc23)c(CO)c1)c1nn(CCO)c2ccccc12]

According to the procedure of the preparation of Example 355, substituting Intermediate 35 for Intermediate 24 afforded Example 359. MS(ESI) m/z: 456.2 (M+H)+; $^1$H NMR (500 MHz, DMSO-$d_6$) δ 12.80 (s, 1H), 10.45 (s, 1H), 8.36-8.30 (m, 1H), 8.27-8.19 (m, 2H), 7.93-7.84 (m, 3H), 7.81 (d, J=8.4 Hz, 1H), 7.49 (t, J=7.6 Hz, 1H), 7.38-7.28 (m, 3H), 4.61 (t, J=5.0 Hz, 2H), 4.34 (br. s., 2H), 3.94 (d, J=5.4 Hz, 2H); HPLC RT=1.31 min (Method E), 1.31 min (Method F).

Example 360: 1-(2-Hydroxy-2-methylpropyl)-N-(3-(hydroxymethyl)-4-(4-oxo-3,4-dihydrophthalazin-1-yl)phenyl)-1H-indazole-3-carboxamide

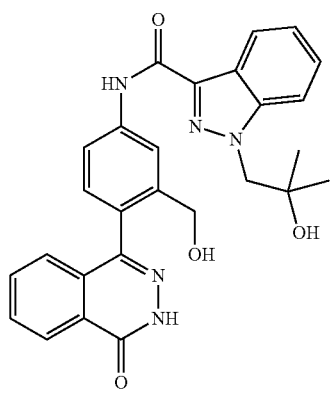 [SMILES: CC(C)(O)Cn1nc(C(=O)Nc2ccc(-c3n[nH]c(=O)c4ccccc34)c(CO)c2)c2ccccc21]

According to the procedure of the preparation of Example 355, substituting Intermediate 15 for Intermediate 24 afforded Example 360. MS(ESI) m/z: 484.2 (M+H)+; $^1$H NMR (500 MHz, DMSO-$d_6$) δ 12.80 (s, 1H), 10.39 (s, 1H), 8.38-8.28 (m, 1H), 8.23 (d, J=8.1 Hz, 1H), 8.18 (s, 1H), 7.99-7.80 (m, 4H), 7.48 (t, J=7.6 Hz, 1H), 7.38-7.20 (m, 3H), 5.17 (t, J=5.4 Hz, 1H), 4.84 (s, 1H), 4.48 (s, 2H), 4.34 (br. s., 2H), 3.89 (s, 1H), 1.19 (s, 6H); HPLC RT=1.39 min (Method E), 1.40 min (Method F).

Example 361: N-(3-(Hydroxymethyl)-4-(4-oxo-3,4-dihydrophthalazin-1-yl)phenyl)-1-(2-(tetrahydro-2H-pyran-4-yl)ethyl)-1H-indazole-3-carboxamide

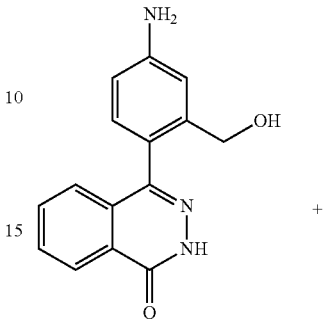

+

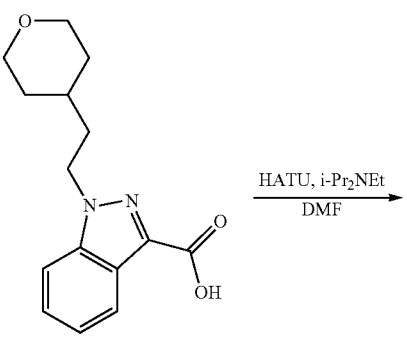

HATU, i-Pr$_2$NEt
DMF

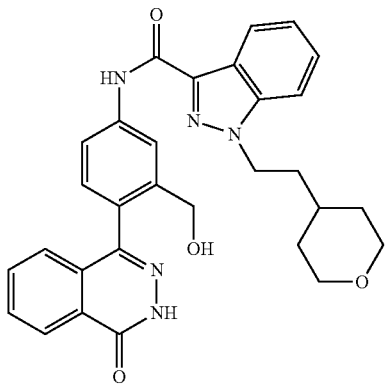

According to the procedure for the preparation of Example 45, coupling of Intermediate 108 (12.5 mg, 0.047 mmol) and Intermediate 15 (14 mg, 0.051 mmol), afforded Example 361 (13.4 mg, 53% yield). MS(ESI) m/z: 484.3 (M+H)+; $^1$H NMR (500 MHz, DMSO-$d_6$) δ 12.77 (s, 1H), 10.40 (s, 1H), 8.34-8.29 (m, 1H), 8.28-8.19 (m, 2H), 7.97-7.80 (m, 4H), 7.52 (td, J=7.7, 1.1 Hz, 1H), 7.40-7.27 (m, 3H), 5.11 (t, J=5.4 Hz, 1H), 4.61 (t, J=7.4 Hz, 2H), 4.34 (br. s., 2H), 3.85-3.79 (m, 2H), 3.29-3.19 (m, 3H), 1.96-1.85 (m, 2H); HPLC RT=1.63 min (Method E), 1.64 min (Method F).

Example 362: N-(3-(Hydroxymethyl)-4-(4-oxo-3,4-dihydrophthalazin-1-yl)phenyl)pyrazolo[1,5-a]pyridine-3-carboxamide

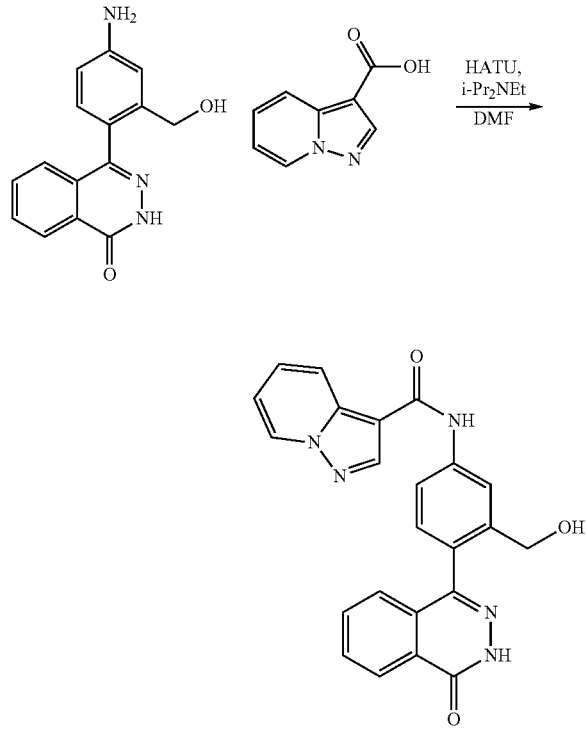

According to the procedure for the preparation of Example 45, coupling of Intermediate 108 (13 mg, 0.049 mmol) and pyrazolo[1,5-a]pyridine-3-carboxylic acid (7.9 mg, 0.049 mmol), afforded Example 362 (4.1 mg, 20% yield). MS(ESI) m/z: 412.2 (M+H)$^+$; $^1$H NMR (500 MHz, DMSO-d$_6$) δ 12.78 (br. s., 1H), 10.16 (br. s., 1H), 8.90-8.77 (m, 2H), 8.43-8.24 (m, 2H), 8.04 (br. s., 1H), 7.96-7.81 (m, 3H), 7.55 (t, J=7.5 Hz, 1H), 7.39-7.26 (m, 2H), 7.14 (t, J=6.4 Hz, 1H), 4.33 (br. s., 2H); HPLC RT=1.28 min (Method E), 1.16 min (Method F).

Example 363: N-(3-(Hydroxymethyl)-4-(4-oxo-3,4-dihydrophthalazin-1-yl)phenyl)-1-methyl-1H-indazole-3-carboxamide

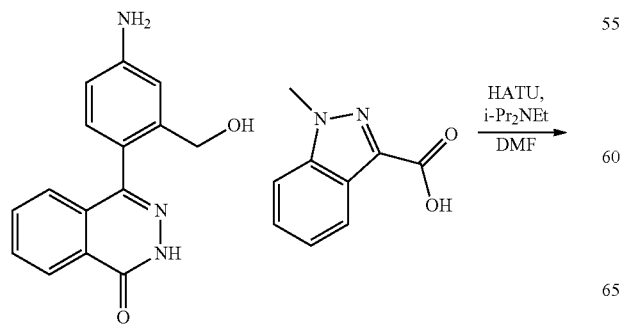

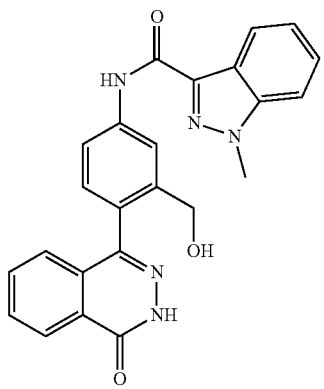

According to the procedure for the preparation of Example 45, coupling of Intermediate 108 (8 mg, 0.030 mmol) and 1-methyl-1H-indazole-3-carboxylic acid (5.3 mg, 0.030 mmol), afforded Example 363 (7 mg, 55% yield). MS(ESI) m/z: 426.2 (M+H)$^+$; $^1$H NMR (500 MHz, DMSO-d$_6$) δ 12.77 (s, 1H), 10.49 (s, 1H), 8.37-8.29 (m, 1H), 8.28-8.20 (m, 2H), 7.92-7.83 (m, 3H), 7.80 (d, J=8.5 Hz, 1H), 7.53 (ddd, J=8.4, 7.0, 1.1 Hz, 1H), 7.41-7.25 (m, 3H), 5.10 (t, J=5.4 Hz, 1H), 4.34 (br. s., 2H), 4.23 (s, 3H); HPLC RT=1.40 min (Method E), 1.41 min (Method F).

Example 364: N-(3-(Hydroxymethyl)-4-(4-oxo-3,4-dihydrophthalazin-1-yl)phenyl)-1-isopropyl-1H-indazole-3-carboxamide

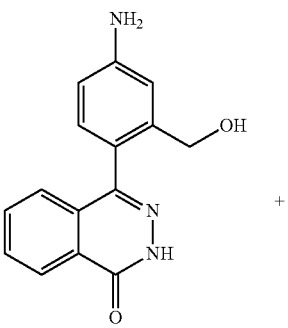

+

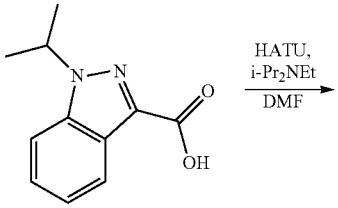

385

-continued

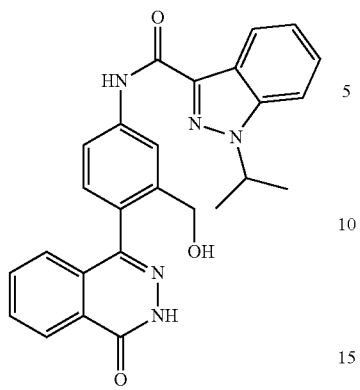

According to the procedure for the preparation of Example 45, coupling of Intermediate 108 (8 mg, 0.030 mmol) and 1-isopropyl-1H-indazole-3-carboxylic acid (6.1 mg, 0.030 mmol), afforded Example 364 (6.9 mg, 51% yield). MS(ESI) m/z: 454.2 (M+H)$^+$; $^1$H NMR (500 MHz, DMSO-d$_6$) δ 12.78 (s, 1H), 10.25 (s, 1H), 8.37-8.30 (m, 1H), 8.25 (d, J=8.0 Hz, 1H), 8.19 (d, J=1.9 Hz, 1H), 8.01-7.92 (m, 1H), 7.91-7.83 (m, 3H), 7.50 (td, J=7.7, 0.8 Hz, 1H), 7.38-7.28 (m, 3H), 5.25-5.06 (m, 2H), 4.35 (br. s., 2H), 1.62 (d, J=6.6 Hz, 6H); HPLC RT=1.81 min (Method E), 1.69 min (Method F).

Example 365: N-(3-(Hydroxymethyl)-4-(4-oxo-3,4-dihydrophthalazin-1-yl)phenyl)imidazo[1,2-a]pyridine-3-carboxamide

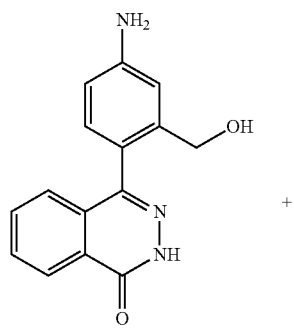

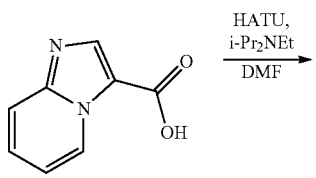

386

-continued

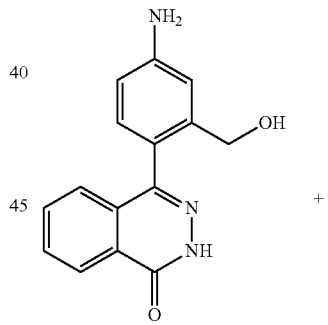

According to the procedure for the preparation of Example 45, coupling of Intermediate 108 (10 mg, 0.037 mmol) and imidazo[1,2-a]pyridine-3-carboxylic acid (6.7 mg, 0.041 mmol), afforded Example 365 (10.7 mg, 68% yield). MS(ESI) m/z: 412.2 (M+H)$^+$; $^1$H NMR (500 MHz, DMSO-d$_6$) δ 9.51 (d, J=7.0 Hz, 1H), 8.66 (s, 1H), 8.41-8.23 (m, 1H), 8.05 (s, 1H), 7.93 (s, 1H), 7.92-7.83 (m, 3H), 7.78 (d, J=8.9 Hz, 1H), 7.54 (t, J=7.8 Hz, 1H), 7.32 (d, J=7.9 Hz, 2H), 7.21 (t, J=6.7 Hz, 1H), 4.34 (br. s., 2H), 3.11 (d, J=7.3 Hz, 1H); HPLC RT=0.95 min (Method E), 1.14 min (Method F).

Example 366: 5-Fluoro-N-(3-(hydroxymethyl)-4-(4-oxo-3,4-dihydrophthalazin-1-yl)phenyl)-1-((tetrahydrofuran-3-yl)methyl)-1H-indazole-3-carboxamide

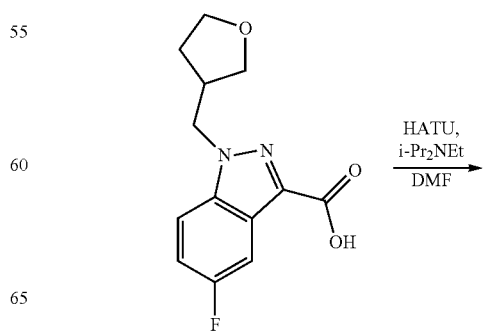

387

-continued

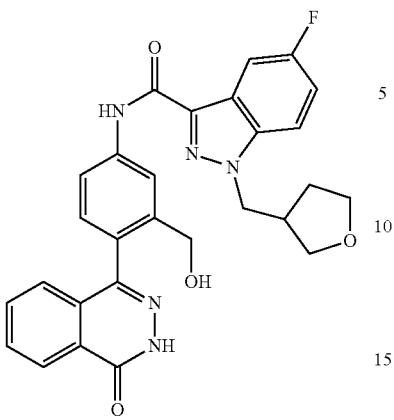

According to the procedure for the preparation of Example 45, coupling of Intermediate 108 (10 mg, 0.037 mmol) and Intermediate 49 (10.9 mg, 0.041 mmol), afforded Example 366 (8.6 mg, 45% yield). MS(ESI) m/z: 514.2 (M+H)$^+$; $^1$H NMR (500 MHz, DMSO-d$_6$) δ 10.43 (s, 1H), 8.32 (d, J=5.2 Hz, 1H), 8.15 (s, 1H), 7.99-7.77 (m, 6H), 7.42 (t, J=9.0 Hz, 1H), 7.36-7.26 (m, 2H), 4.54 (d, J=7.3 Hz, 2H), 4.33 (br. s., 2H), 3.91-3.76 (m, 1H), 3.61-3.51 (m, 1H), 2.99-2.90 (m, 1H), 1.99-1.88 (m, 1H), 1.69 (dq, J=12.7, 6.6 Hz, 1H); HPLC RT=1.52 min (Method E), 1.48 min (Method F).

Example 367: N-(3-(Hydroxymethyl)-4-(4-oxo-3,4-dihydrophthalazin-1-yl)phenyl)-1-((tetrahydrofuran-2-yl)methyl)-1H-indazole-3-carboxamide

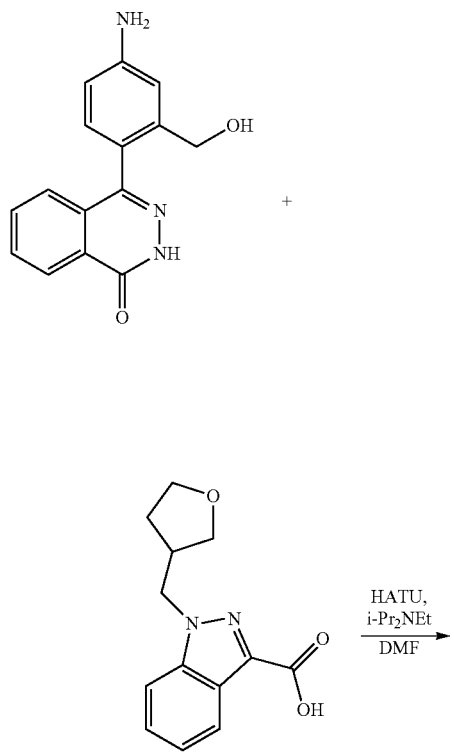

388

-continued

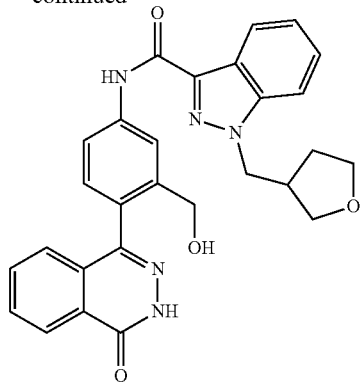

According to the procedure for the preparation of Example 45, coupling of Intermediate 108 (9.5 mg, 0.036 mmol) and Intermediate 109 (9.6 mg, 0.039 mmol), afforded Example 367 (13.7 mg, 74% yield). MS(ESI) m/z: 496.2 (M+H)$^+$; $^1$H NMR (500 MHz, DMSO-d$_6$) δ 10.46 (s, 1H), 8.41-8.30 (m, 1H), 8.29-8.18 (m, 2H), 8.00-7.78 (m, 4H), 7.50 (t, J=7.6 Hz, 1H), 7.38-7.26 (m, 3H), 4.62 (d, J=5.4 Hz, 2H), 4.41 (quin, J=6.1 Hz, 1H), 4.34 (br. s., 2H), 3.73 (q, J=6.8 Hz, 1H), 3.68-3.56 (m, 1H), 3.44-3.33 (m, 1H), 2.08-1.94 (m, 1H), 1.86-1.71 (m, 3H); HPLC RT=1.54 min (Method E), 1.66 min (Method F).

Example 368: 6-Fluoro-N-(3-(hydroxymethyl)-4-(4-oxo-3,4-dihydrophthalazin-1-yl)phenyl)-1-((tetrahydrofuran-3-yl)methyl)-1H-indazole-3-carboxamide

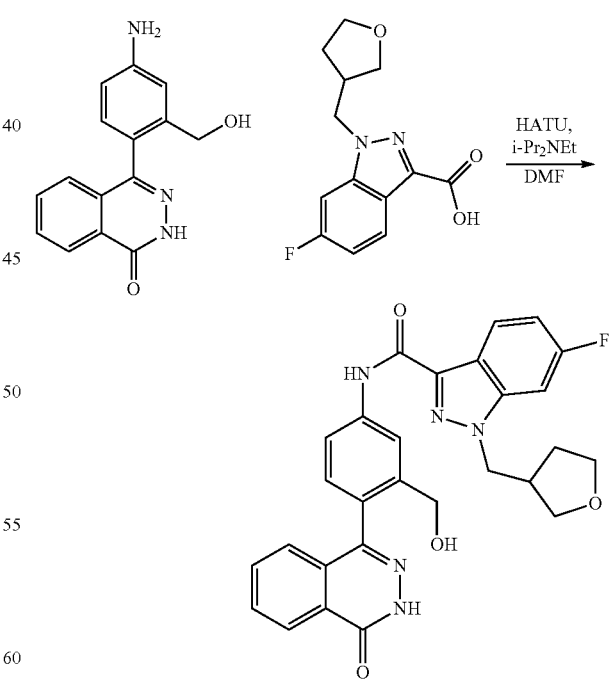

According to the procedure for the preparation of Example 45, coupling of Intermediate 108 (9.5 mg, 0.036 mmol) and Intermediate 50 (10.3 mg, 0.039 mmol), afforded Example 368 (8.6 mg, 47% yield). MS(ESI) m/z: 514.2 (M+H)$^+$; (500 MHz, DMSO-d$_6$) δ 10.47 (s, 1H), 8.39-8.30

(m, 1H), 8.30-8.17 (m, 2H), 7.96-7.77 (m, 4H), 7.39-7.31 (m, 2H), 7.24 (t, J=8.9 Hz, 1H), 4.63-4.49 (m, 2H), 4.34 (br. s., 2H), 3.88-3.80 (m, 1H), 3.76-3.64 (m, 2H), 3.58 (dd, J=8.6, 5.6 Hz, 1H), 2.95 (dt, J=13.7, 6.8 Hz, 1H), 2.07-1.89 (m, 1H), 1.71 (dq, J=12.9, 6.6 Hz, 1H); HPLC RT=1.55 min (Method E), 1.76 min (Method F).

Example 369: 1-(2-Hydroxy-2-methylpropyl)-N-(4-(6-methoxy-4-oxo-3,4-dihydrophthalazin-1-yl)phenyl)-1H-indazole-3-carboxamide

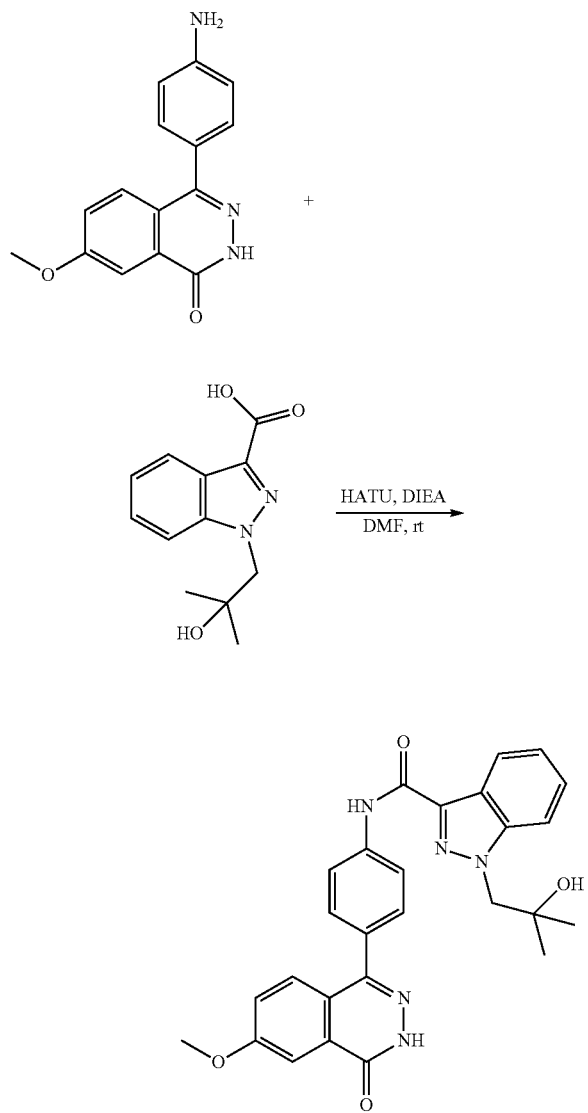

According to the procedure for the preparation of Example 45, coupling of Intermediate 110 (15 mg, 0.039 mmol) and Intermediate 15 (11 mg, 0.047 mmol), afforded Example 369 (0.9 mg, 6% yield). MS(ESI) m/z: 484.2 (M+H)$^+$; $^1$H NMR (500 MHz, DMSO-$d_6$) δ ppm 12.75 (s, 1H), 10.40 (s, 1H), 8.23 (d, J=8.3 Hz, 1H), 8.06 (d, J=8.8 Hz, 2H), 7.86 (d, J=8.8 Hz, 1H), 7.76-7.69 (m, 2H), 7.58 (d, J=8.5 Hz, 2H), 7.53-7.42 (m, 2H), 7.32 (t, J=7.6 Hz, 1H), 4.79 (s, 1H), 4.49 (s, 2H), 3.97 (s, 3H), 1.20 (s, 6H); HPLC RT=1.76 min (Method E), 1.64 min (Method F).

Example 370: N-(4-(6-Methoxy-4-oxo-3,4-dihydrophthalazin-1-yl)phenyl)imidazo[1,2-a]pyridine-2-carboxamide

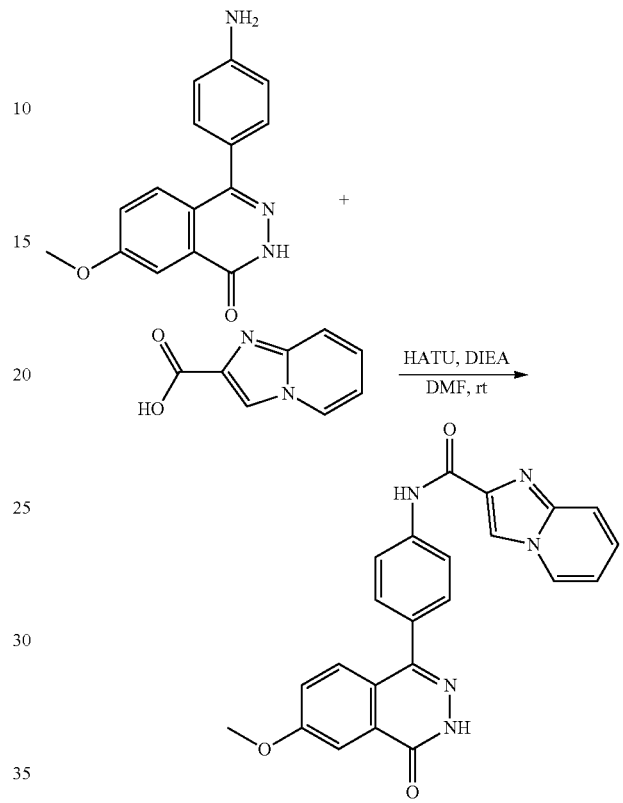

According to the procedure for the preparation of Example 45, coupling of Intermediate 110 (15 mg, 0.039 mmol) and Intermediate 15 (7.7 mg, 0.047 mmol), afforded Example 370 (0.5 mg, 3% yield). MS(ESI) m/z: 412.2 (M+H)$^+$; $^1$H NMR (500 MHz, DMSO-$d_6$) δ ppm 12.74 (s, 1H), 10.51 (s, 1H), 8.64 (d, J=6.6 Hz, 1H), 8.57 (s, 1H), 8.09 (d, J=8.3 Hz, 2H), 7.76-7.64 (m, 3H), 7.56 (d, J=8.5 Hz, 2H), 7.49 (dd, J=9.1, 2.8 Hz, 1H), 7.43-7.36 (m, 1H), 7.04 (t, J=6.7 Hz, 1H), 3.96 (s, 3H); HPLC RT=1.18 min (Method E), 1.37 min (Method F).

Example 371: N-(4-(4-Oxo-3,4-dihydrophthalazin-1-yl)phenyl)spiro[indoline-3,4'-piperidine]-1-carboxamide

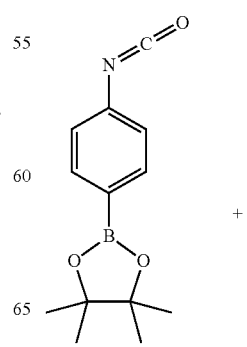

-continued

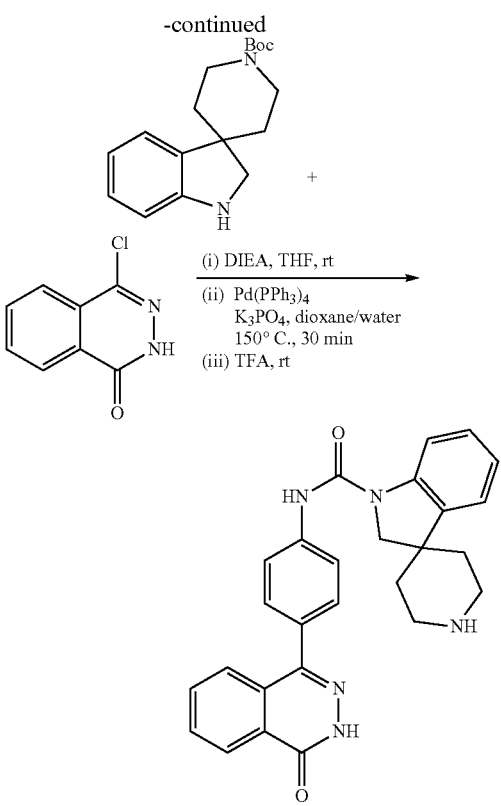

2-(4-Isocyanatophenyl)-4,4,5,5-tetramethyl-1,3,2-dioxaborolane (50 mg, 0.204 mmol) and tert-butyl spiro[indoline-3,4'-piperidine]-1'-carboxylate (58.8 mg, 0.204 mmol) were dissolved in THF (3 mL), and DIEA (0.053 mL, 0.31 mmol) was added. The reaction mixture was stirred at rt for 1 h. THF was removed under reduced pressure. To the obtained residue were added 4-chlorophthalazin-1(2H)-one (18.4 mg, 0.102 mmol) and phosphoric acid, potassium salt (54.1 mg, 0.255 mmol), followed by dioxane (3 mL) and water (0.333 mL). The mixture was degassed (evacuated and flushed with Ar (3×)). Pd(PPh$_3$)$_4$ (11.8 mg, 10.2 mol) was added, then the mixture was degassed (2×). The reaction vial was sealed and heated in a microwave reactor at 150° C. for 30 min. The solvent was removed under reduced pressure, and the residue was treated with TFA (2 mL). The reaction mixture was stirred for 15 min. TFA was removed under reduced pressure. The residue was purified by prep HPLC to afford Example 371 (11.9 mg, 25% yield). MS(ESI) m/z: 452.3 (M+H)$^+$; $^1$H NMR (500 MHz, DMSO-d$_6$) δ ppm 12.83 (s, 1H), 8.90 (br. s., 1H), 8.81 (s, 1H), 8.35 (d, J=7.4 Hz, 1H), 8.02-7.85 (m, 4H), 7.76 (d, J=8.4 Hz, 3H), 7.55 (d, J=8.4 Hz, 2H), 7.23 (t, J=7.7 Hz, 1H), 7.18 (d, J=7.4 Hz, 1H), 7.06-6.95 (m, 1H), 4.18 (s, 2H), 3.48-3.33 (m, 1H), 3.02 (br. s., 2H), 2.11-1.99 (m, 2H), 1.88 (d, J=13.8 Hz, 2H); HPLC RT=1.13 min (Method E), 1.09 min (Method F).

Example 372: N-(4-(4-Oxo-3,4-dihydrophthalazin-1-yl)phenyl)-1-(piperidin-4-yl)-1H-1,2,3-triazole-4-carboxamide

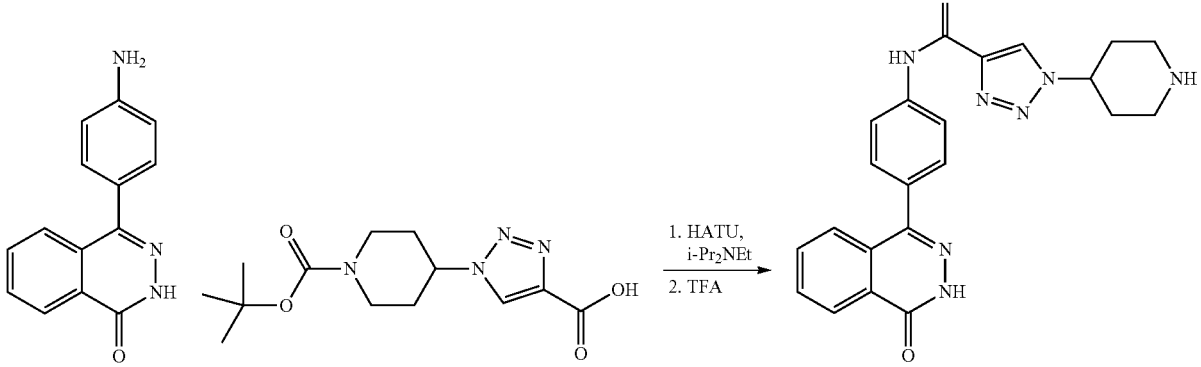

To a mixture of Intermediate 12 (20 mg, 0.084 mmol), 1-(1-(tert-butoxycarbonyl)piperidin-4-yl)-1H-1,2,3-triazole-4-carboxylic acid (25 mg, 0.084 mmol), HATU (38.5 mg, 0.101 mmol) in DMF (1.5 mL), was added DIEA (0.074 mL, 0.42 mmol). The mixture was stirred rt for 16 h, then was concentrated. The residue was stirred with TFA (0.5 mL) in DCM (1 mL) for 30 min, then was concentrated and purified by prep HPLC to afford Example 372 (9.6 mg, 27% yield). MS(ESI) m/z: 416.2 (M+H)$^+$; $^1$H NMR (500 MHz, DMSO-d$_6$) δ 12.88-12.81 (m, 1H), 10.71 (s, 1H), 8.88 (s, 1H), 8.34 (d, J=7.4 Hz, 1H), 8.02 (d, J=8.4 Hz, 2H), 7.95-7.85 (m, 2H), 7.75 (d, J=7.1 Hz, 1H), 7.58 (d, J=8.4 Hz, 2H), 4.94 (br. s., 1H), 3.46 (d, J=12.1 Hz, 1H), 3.18-3.04 (m, 2H), 2.38 (d, J=12.8 Hz, 2H), 2.23 (d, J=10.8 Hz, 2H); HPLC RT=0.78 min (Method E), 0.75 min (Method F).

Example 373: 1-Cyclohexyl-N-(4-(4-oxo-3,4-dihydrophthalazin-1-yl)phenyl)-1H-pyrazole-4-carboxamide, TFA

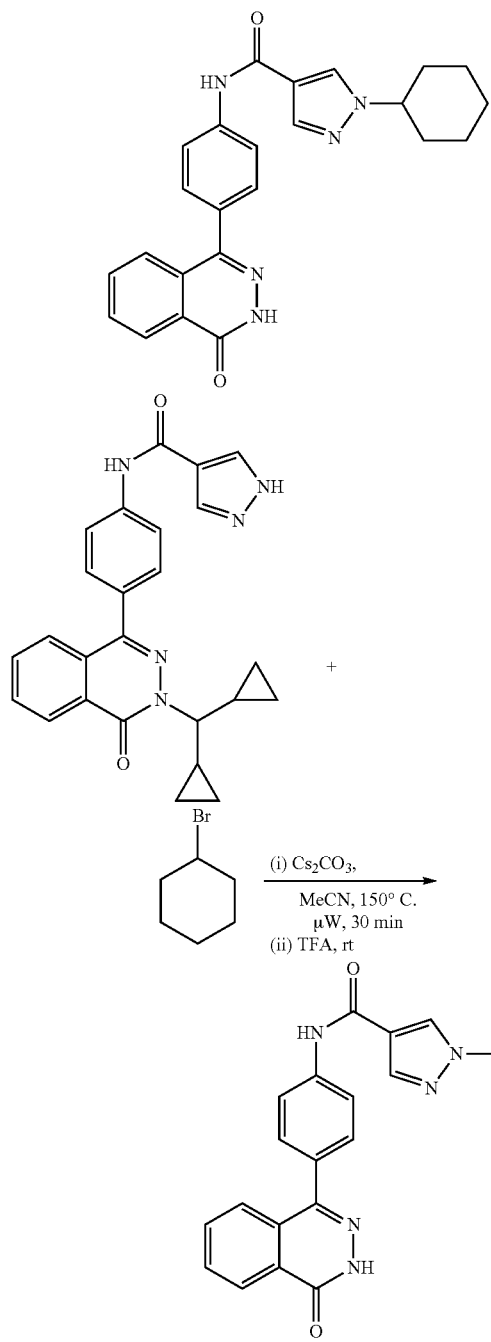

Intermediate 111 (25 mg, 0.059 mmol) was suspended in dry MeCN (1.5 mL), then bromocyclohexane (0.072 mL, 0.588 mmol) was added, followed by cesium carbonate (96 mg, 0.294 mmol) and the reaction mixture was heated under microwave irradiation at 150° C. for 30 min. The reaction mixture was cooled to rt, and most of MeCN was removed under reduced pressure. The obtained residue was treated TFA (2 mL), and the reaction mixture was stirred at rt for 15 min. TFA was removed under reduced pressure. The crude product was purified by preparative HPLC to afford 17.6 mg (57%) of Example 373. MS(ESI) m/z: 414.2 (M+H)$^+$; $^1$H NMR (500 MHz, DMSO-d$_6$) δ ppm 12.81 (s, 1H), 10.01 (s, 1H), 8.40 (s, 1H), 8.36-8.30 (m, 1H), 8.05 (s, 1H), 7.93-7.84 (m, 4H), 7.75 (d, J=7.6 Hz, 1H), 7.56 (d, J=8.5 Hz, 2H), 4.27-4.14 (m, 1H), 2.10-2.00 (m, 2H), 1.82 (d, J=13.4 Hz, 2H), 1.77-1.60 (m, 3H), 1.41 (q, J=12.9 Hz, 2H), 1.22 (q, J=13.0 Hz, 1H); HPLC RT=1.61 min (Method E), 1.62 min (Method F).

Example 374: 1-Cyclopentyl-N-(4-(4-oxo-3,4-dihydrophthalazin-1-yl)phenyl)-1H-pyrazole-4-carboxamide, TFA

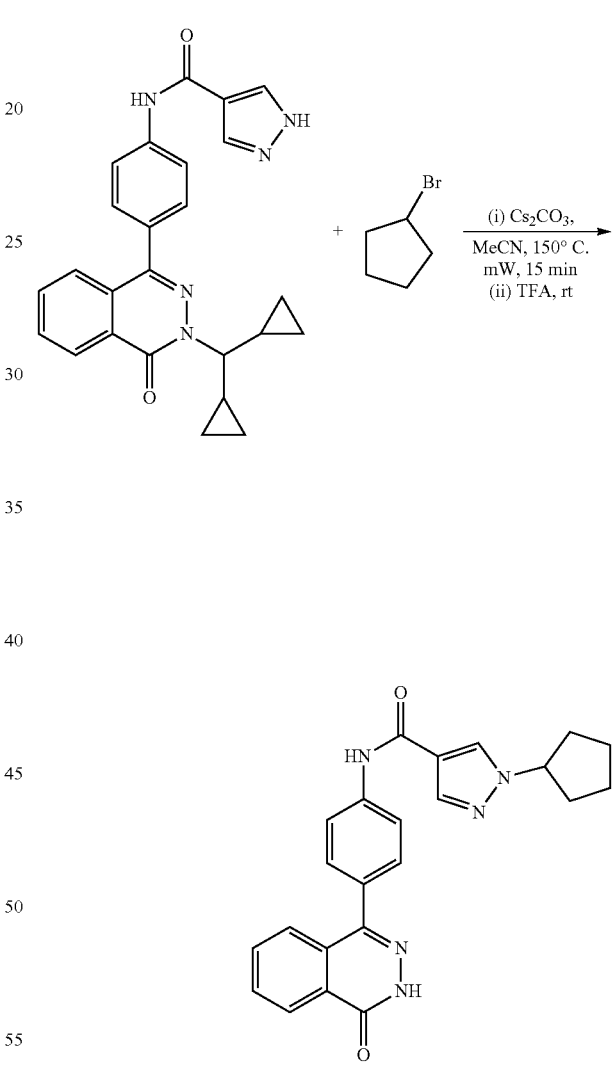

According to the procedure for the preparation of Example 373, substituting bromocyclopentane for bromocyclohexane afforded Example 374. MS(ESI) m/z: 400.1 (M+H)$^+$; $^1$H NMR (500 MHz, DMSO-d$_6$) δ ppm 12.82 (s, 1H), 10.04 (s, 1H), 8.39 (s, 1H), 8.35-8.31 (m, 1H), 8.04 (s, 1H), 7.94-7.88 (m, 2H), 7.86 (d, J=8.5 Hz, 2H), 7.74 (d, J=7.3 Hz, 1H), 7.55 (d, J=8.5 Hz, 2H), 4.74 (quin, J=6.9 Hz, 1H), 2.17-2.05 (m, 2H), 1.91 (dd, J=12.8, 7.0 Hz, 2H), 1.84-1.74 (m, 2H), 1.71-1.60 (m, 2H); HPLC RT=1.50 min (Method E), 1.51 min (Method F).

Example 375: 1-(Cyclopropylmethyl)-N-(4-(4-oxo-3,4-dihydrophthalazin-1-yl)phenyl)-1H-pyrazole-4-carboxamide, TFA Example 376: N-(4-(4-Oxo-3,4-dihydrophthalazin-1-yl)phenyl)-1-(2,2,2-trifluoroethyl)-1H-pyrazole-4-carboxamide, TFA

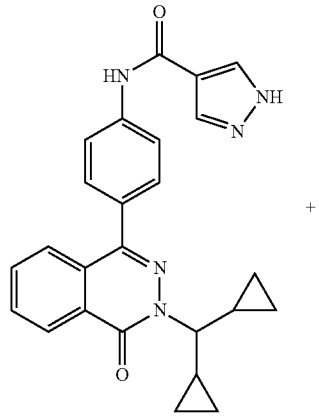

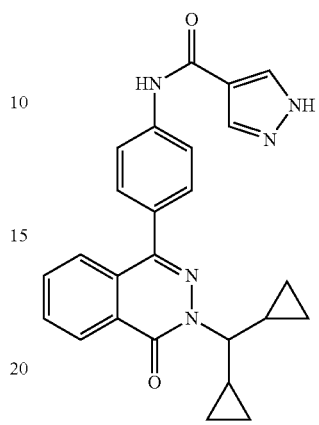

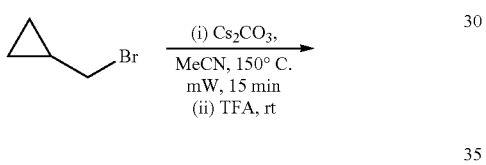

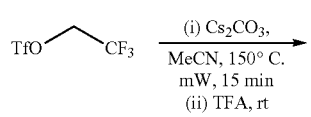

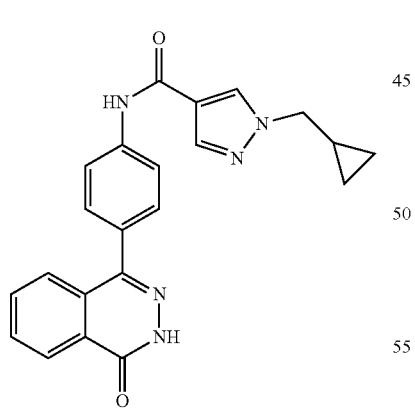

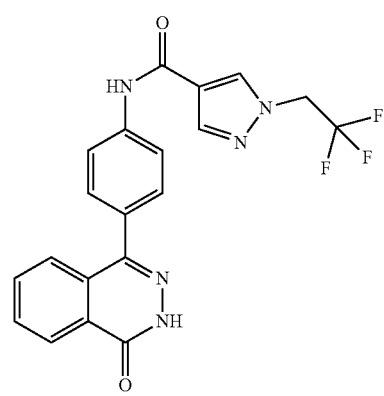

According to the procedure for the preparation of Example 373, substituting (bromomethyl)cyclopropane for bromocyclohexane afforded Example 375. MS(ESI) m/z: 386.2 (M+H)$^+$; $^1$H NMR (500 MHz, DMSO-d$_6$) δ ppm 12.82 (s, 1H), 10.08 (s, 1H), 8.40 (s, 1H), 8.33 (d, J=7.0 Hz, 1H), 8.06 (s, 1H), 7.95-7.82 (m, 4H), 7.74 (d, J=7.3 Hz, 1H), 7.55 (d, J=8.2 Hz, 2H), 4.02 (d, J=7.3 Hz, 2H), 1.32-1.22 (m, 1H), 0.59-0.52 (m, 2H), 0.42-0.34 (m, 2H); HPLC RT=1.36 min (Method E), 1.36 min (Method F).

According to the procedure for the preparation of Example 373, substituting 2,2,2-trifluoroethyl trifluoromethanesulfonate for bromocyclohexane afforded Example 376. MS(ESI) m/z: 386.2 (M+H)$^+$; $^1$H NMR (500 MHz, DMSO-d$_6$) δ ppm 12.83 (s, 1H), 10.23 (s, 1H), 8.50 (s, 1H), 8.33 (d, J=7.3 Hz, 1H), 8.18 (s, 1H), 7.95-7.82 (m, 4H), 7.74 (d, J=7.6 Hz, 1H), 7.56 (d, J=8.2 Hz, 2H), 5.20 (q, J=9.1 Hz, 2H); HPLC RT=1.34 min (Method E), 1.35 min (Method F).

Example 377: 1-(2-Hydroxy-2-methylpropyl)-N-(4-(4-oxo-3,4-dihydrophthalazin-1-yl)phenyl)-1H-pyrazole-4-carboxamide Example 378: N-(4-(4-Oxo-3,4-dihydrophthalazin-1-yl)phenyl)-1-(3,3,3-trifluoro-2-hydroxypropyl)-1H-pyrazole-4-carboxamide

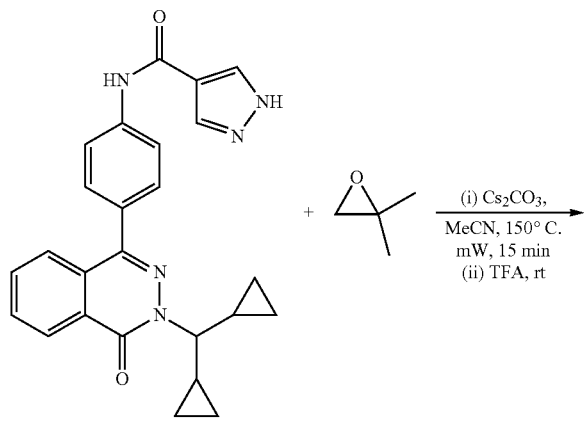

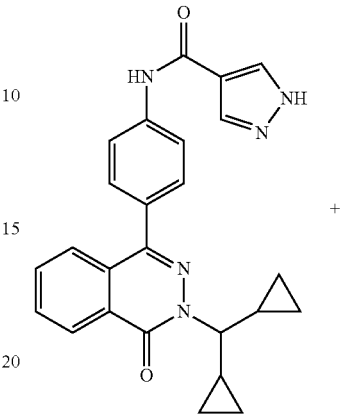

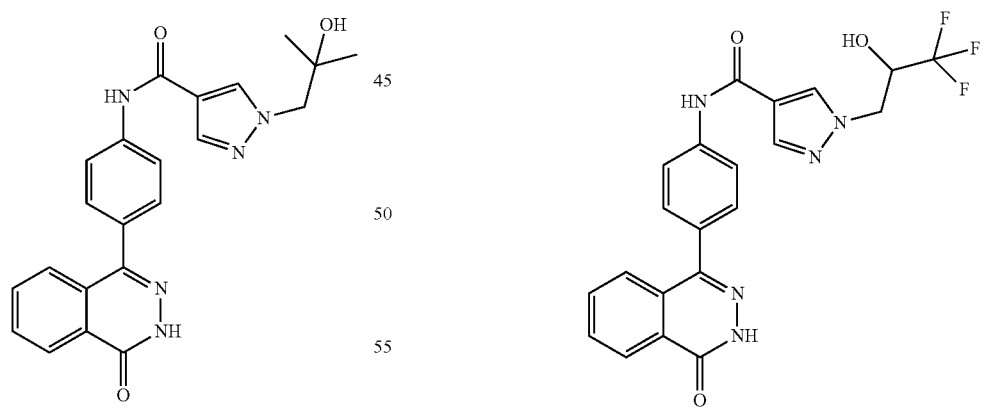

According to the procedure for the preparation of Example 373, substituting 2,2-dimethyloxirane for bromocyclohexane afforded Example 377. MS(ESI) m/z: 404.2 (M+H)⁺; ¹H NMR (500 MHz, DMSO-d₆) δ ppm 12.84 (s, 1H), 10.10 (s, 1H), 8.36-8.28 (m, 2H), 8.05 (s, 1H), 7.95-7.84 (m, 4H), 7.75 (d, J=7.4 Hz, 1H), 7.55 (d, J=8.4 Hz, 2H), 4.91 (s, 1H), 4.07 (s, 2H), 1.08 (s, 6H); HPLC RT=0.98 min (Method E), 0.98 min (Method F).

According to the procedure for the preparation of Example 373, substituting 2-(trifluoromethyl)oxirane for bromocyclohexane afforded Example 378. MS(ESI) m/z: 440.2 (M+H)⁺; ¹H NMR (500 MHz, DMSO-d₆) δ ppm 12.83 (s, 1H), 10.11 (s, 1H), 8.44 (s, 1H), 8.36-8.30 (m, 1H), 8.14 (s, 1H), 7.99-7.84 (m, 5H), 7.75 (d, J=7.4 Hz, 1H), 7.57 (d, J=8.4 Hz, 2H), 4.53-4.40 (m, 2H), 4.39-4.27 (m, 1H); HPLC RT=1.11 min (Method E), 1.11 min (Method F).

Example 379: 1-(2-Hydroxy-3-methoxypropyl)-N-(4-(4-oxo-3,4-dihydrophthalazin-1-yl)phenyl)-1H-pyrazole-4-carboxamide Example 380: N-(4-(4-Oxo-3,4-dihydrophthalazin-1-yl)phenyl)-1-(3,3,3-trifluoro-2-hydroxy-2-(trifluoromethyl)propyl)-1H-pyrazole-4-carboxamide

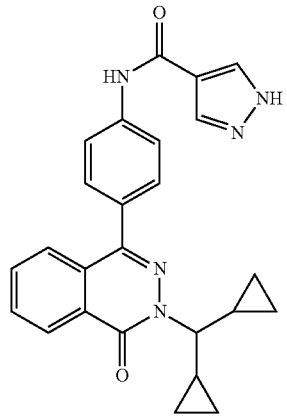

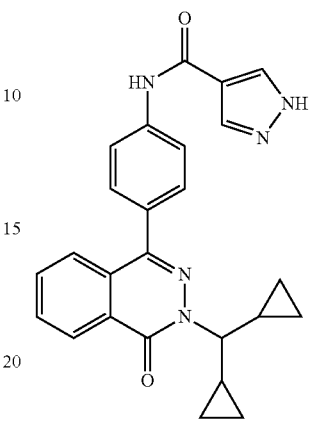

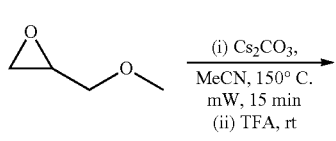

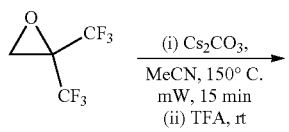

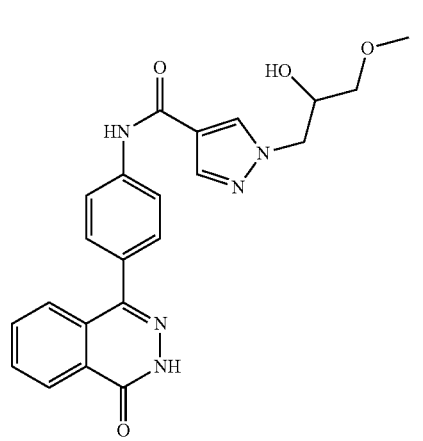

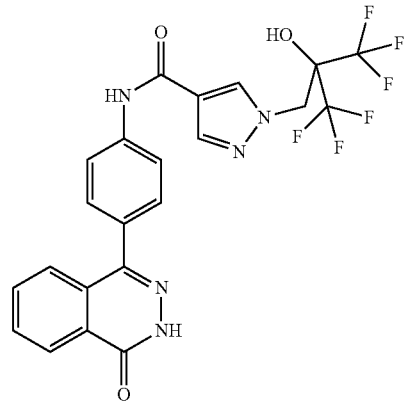

According to the procedure for the preparation of Example 373, substituting 2-(methoxymethyl)oxirane for bromocyclohexane afforded Example 379. MS(ESI) m/z: 420.2 (M+H)$^+$; $^1$H NMR (500 MHz, DMSO-d$_6$) δ ppm 10.07 (s, 1H), 8.38-8.29 (m, 2H), 8.06 (s, 1H), 7.96-7.84 (m, 4H), 7.75 (d, J=7.4 Hz, 1H), 7.56 (d, J=8.4 Hz, 2H), 4.23 (dd, J=13.8, 3.7 Hz, 1H), 4.13-4.04 (m, 1H), 3.98 (br. s., 1H), 3.31-3.25 (m, 5H); HPLC RT=0.91 min (Method E), 1.00 min (Method F).

According to the procedure for the preparation of Example 373, substituting 2,2-bis(trifluoromethyl)oxirane for bromocyclohexane afforded Example 380. MS(ESI) m/z: 512.2 (M+H)$^+$; $^1$H NMR (500 MHz, DMSO-d$_6$) δ ppm 12.83 (s, 1H), 10.17 (s, 1H), 8.40 (s, 1H), 8.33 (d, J=7.3 Hz, 1H), 8.11 (s, 1H), 7.97-7.81 (m, 4H), 7.74 (d, J=7.6 Hz, 1H), 7.56 (d, J=7.9 Hz, 2H), 4.81 (s, 2H); HPLC RT=1.48 min (Method E), 1.50 min (Method F).

Example 381: 1-(tert-Butyl)-N-(4-(4-oxo-3,4-dihydrophthalazin-1-yl)phenyl)-1H-pyrazole-4-carboxamide

Example 382: N-(4-(4-Oxo-3,4-dihydrophthalazin-1-yl)phenyl)-1-propyl-1H-pyrazole-4-carboxamide, TFA

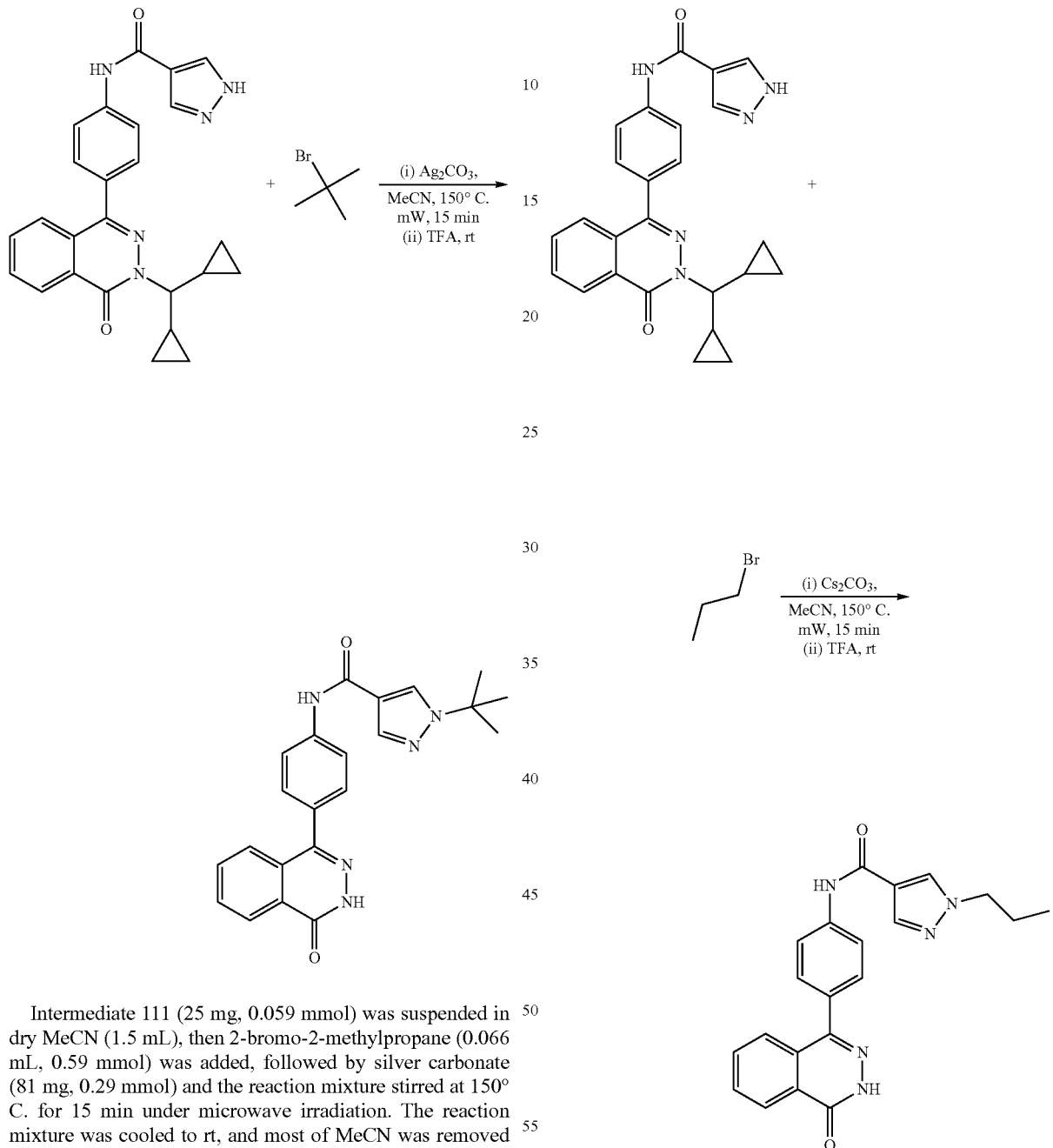

Intermediate 111 (25 mg, 0.059 mmol) was suspended in dry MeCN (1.5 mL), then 2-bromo-2-methylpropane (0.066 mL, 0.59 mmol) was added, followed by silver carbonate (81 mg, 0.29 mmol) and the reaction mixture stirred at 150° C. for 15 min under microwave irradiation. The reaction mixture was cooled to rt, and most of MeCN was removed under reduced pressure. The obtained residue was treated with TFA (2 mL), and the reaction mixture was stirred at rt for 15 min. TFA was removed under reduced pressure, the residue was diluted with DMF (2 mL), filtered and purified by prep HPLC to afford Example 381 (2.6 mg, 11% yield). MS(ESI) m/z: 388.2 (M+H)$^+$; $^1$H NMR (500 MHz, DMSO-$d_6$) δ ppm 12.82 (s, 1H), 10.03 (s, 1H), 8.46 (s, 1H), 8.33 (d, J=7.9 Hz, 1H), 8.05 (s, 1H), 7.95-7.88 (m, 2H), 7.86 (d, J=8.5 Hz, 2H), 7.74 (d, J=7.6 Hz, 1H), 7.55 (d, J=8.5 Hz, 2H), 1.55 (s, 9H); HPLC RT=1.42 min (Method E), 1.44 min (Method F).

According to the procedure for the preparation of Example 373, substituting 1-bromopropane for bromocyclohexane afforded Example 382. MS(ESI) m/z: 374.2 (M+H)$^+$; $^1$H NMR (500 MHz, DMSO-$d_6$) δ ppm 12.82 (s, 1H), 10.09 (s, 1H), 8.32 (s, 2H), 8.05 (s, 1H), 7.94-7.87 (m, 2H), 7.85 (d, J=8.2 Hz, 2H), 7.73 (d, J=7.6 Hz, 1H), 7.54 (d, J=8.2 Hz, 2H), 4.10 (t, J=6.9 Hz, 2H), 1.79 (sxt, J=7.2 Hz, 2H), 0.81 (t, J=7.3 Hz, 3H); HPLC RT=1.30 min (Method E), 1.32 min (Method F).

Example 383: N-(4-(4-Oxo-3,4-dihydrophthalazin-1-yl)phenyl)-1-(2,2,3,3-tetrafluoropropyl)-1H-pyrazole-4-carboxamide, TFA Example 384: N-(4-(4-Oxo-3,4-dihydrophthalazin-1-yl)phenyl)-1-(tetrahydro-2H-pyran-4-yl)-1H-pyrazole-4-carboxamide

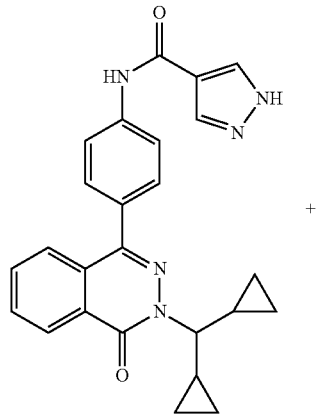

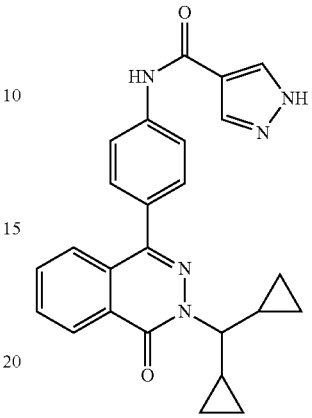

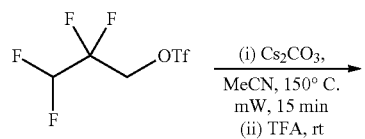

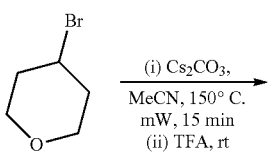

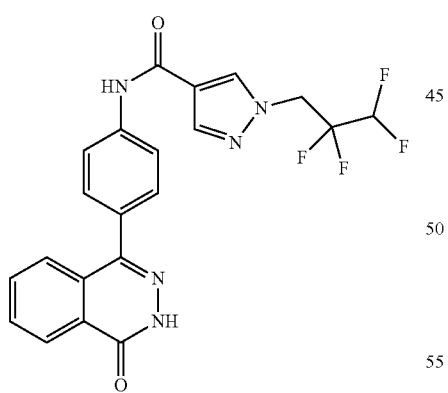

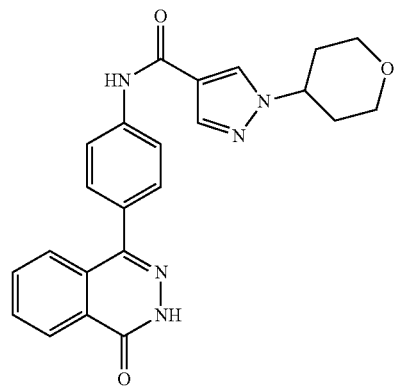

According to the procedure for the preparation of Example 373, substituting 2,2,3,3-tetrafluoropropyl trifluoromethanesulfonate for bromocyclohexane afforded Example 383. MS(ESI) m/z: 446.1 (M+H)$^+$; $^1$H NMR (500 MHz, DMSO-$d_6$) δ ppm 12.83 (s, 1H), 10.22 (s, 1H), 8.46 (s, 1H), 8.33 (d, J=7.6 Hz, 1H), 8.16 (s, 1H), 7.95-7.87 (m, 2H), 7.85 (d, J=8.5 Hz, 2H), 7.73 (d, J=7.6 Hz, 1H), 7.55 (d, J=8.2 Hz, 2H), 6.73-6.25 (m, 1H), 4.99 (t, J=15.0 Hz, 2H); HPLC RT=1.40 min (Method E), 1.40 min (Method F).

According to the procedure for the preparation of Example 373, substituting 4-bromotetrahydro-2H-pyran for bromocyclohexane afforded Example 384. MS(ESI) m/z: 416.2 (M+H)$^+$; $^1$H NMR (500 MHz, DMSO-$d_6$) δ ppm 12.81 (s, 1H), 10.01 (s, 1H), 8.46 (s, 1H), 8.34 (d, J=7.6 Hz, 1H), 8.10 (s, 1H), 7.98-7.85 (m, 4H), 7.76 (d, J=7.6 Hz, 1H), 7.57 (d, J=8.2 Hz, 2H), 4.49 (t, J=11.3 Hz, 1H), 3.98 (d, J=10.1 Hz, 2H), 3.49 (t, J=11.4 Hz, 1H), 2.10-1.89 (m, 4H); HPLC RT=1.22 min (Method E), 1.22 min (Method F).

Example 385: 1-(Cyclopropylmethyl)-N-(4-(4-oxo-3,4-dihydrophthalazin-1-yl)phenyl)-1H-pyrazole-4-carboxamide, TFA

Example 386: 1-(2,2-Difluoroethyl)-N-(4-(4-oxo-3,4-dihydrophthalazin-1-yl)phenyl)-1H-pyrazole-4-carboxamide

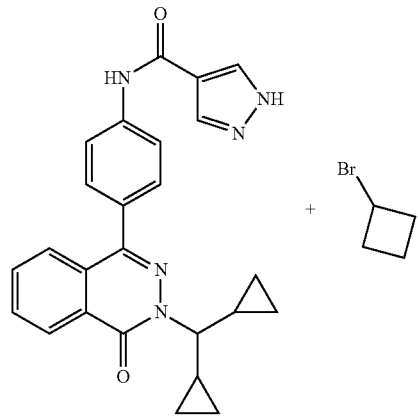

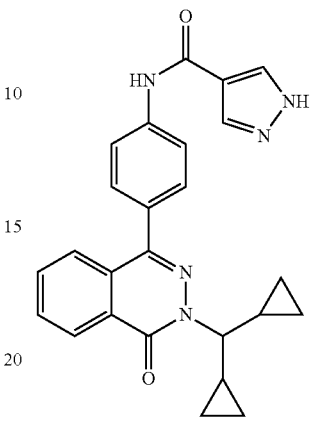

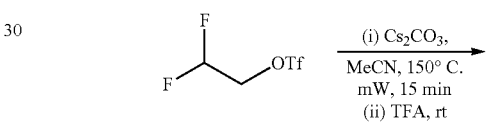

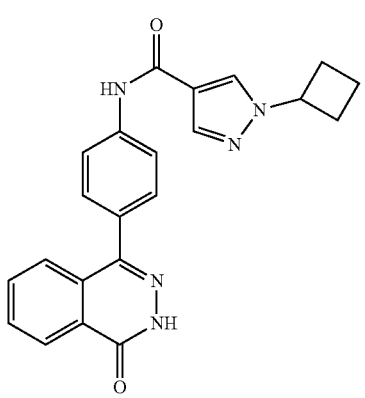

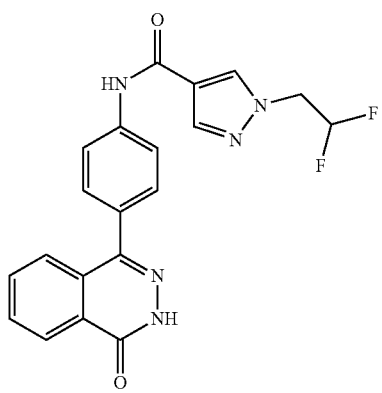

According to the procedure for the preparation of Example 373, substituting bromocyclobutane for bromocyclohexane afforded Example 385. MS(ESI) m/z: 386.2 (M+H)$^+$; $^1$H NMR (500 MHz, DMSO-d$_6$) δ ppm 12.81 (s, 1H), 10.02 (s, 1H), 8.46 (s, 1H), 8.34 (d, J=7.3 Hz, 1H), 8.09 (s, 1H), 7.94-7.84 (m, 4H), 7.75 (d, J=7.6 Hz, 1H), 7.56 (d, J=8.5 Hz, 2H), 4.90 (quin, J=8.3 Hz, 1H), 2.49-2.37 (m, 4H), 1.87-1.76 (m, 2H); HPLC RT=1.39 min (Method E), 1.39 min (Method F).

According to the procedure for the preparation of Example 373, substituting 2,2-difluoroethyl trifluoromethanesulfonate for bromocyclohexane afforded Example 386. MS(ESI) m/z: 396.2 (M+H)$^+$; $^1$H NMR (500 MHz, DMSO-d$_6$) δ ppm 12.83 (s, 1H), 10.14 (s, 1H), 8.46 (s, 1H), 8.34 (d, J=7.1 Hz, 1H), 8.16 (s, 1H), 7.97-7.85 (m, 4H), 7.76 (d, J=7.4 Hz, 1H), 7.57 (d, J=8.8 Hz, 2H), 6.42 (t, J=54.2 Hz, 1H), 4.73 (td, J=15.2, 3.2 Hz, 2H); HPLC RT=1.17 min (Method E), 1.17 min (Method F).

Example 387: 1-(2-Hydroxypropyl)-N-(4-(4-oxo-3,4-dihydrophthalazin-1-yl)phenyl)-1H-pyrazole-4-carboxamide

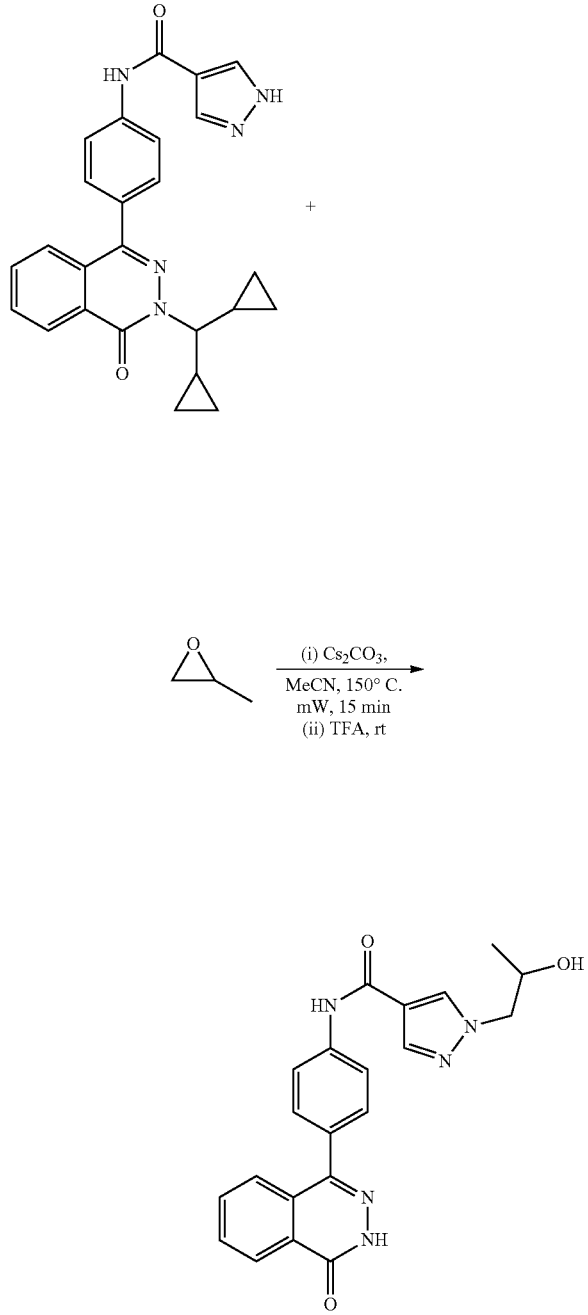

According to the procedure for the preparation of Example 373, substituting 2-methyloxirane for bromocyclohexane afforded Example 387. MS(ESI) m/z: 396.2 (M+H)$^+$; $^1$H NMR (500 MHz, DMSO-d$_6$) δ ppm 12.83 (s, 1H), 10.06 (s, 1H), 8.37-8.31 (m, 2H), 8.06 (s, 1H), 7.95-7.86 (m, 4H), 7.75 (d, J=7.4 Hz, 1H), 7.56 (d, J=8.1 Hz, 2H), 5.06 (d, J=4.7 Hz, 1H), 4.15-4.08 (m, 1H), 4.07-3.95 (m, 2H), 1.07 (d, J=6.1 Hz, 3H); HPLC RT=0.99 min (Method E), 0.99 min (Method F).

Example 388: 1-(4-Chlorophenyl)-N-(4-(4-oxo-3,4-dihydrophthalazin-1-yl)phenyl)-1H-pyrazole-4-carboxamide

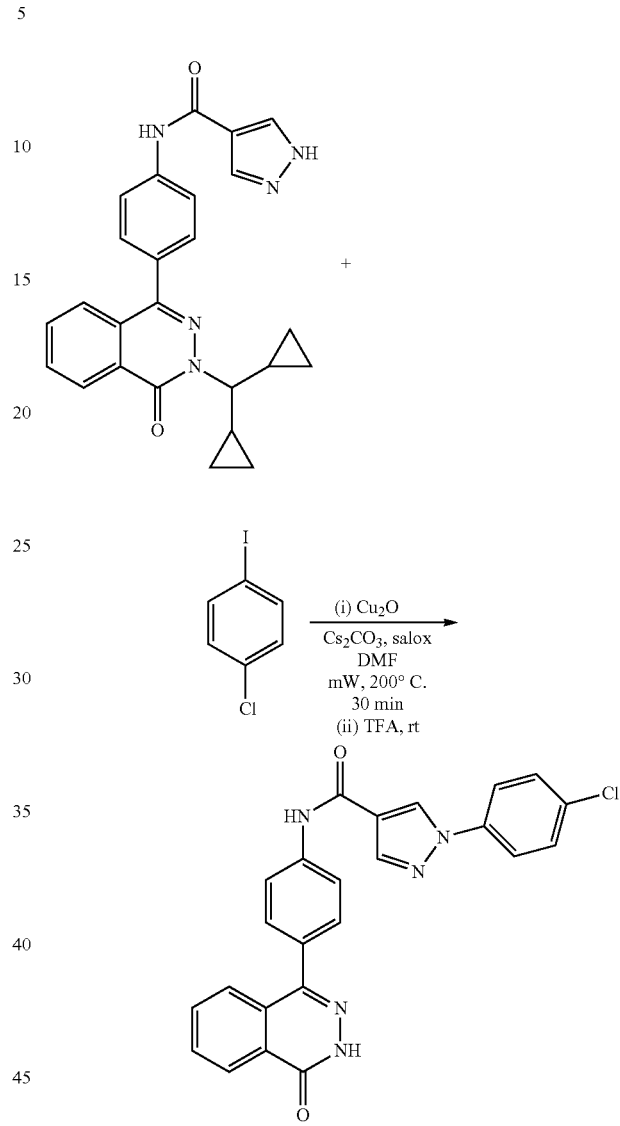

Intermediate 111 (20 mg, 0.047 mmol), 1-chloro-4-iodobenzene (34 mg, 0.141 mmol), salicylaldoxime (6.5 mg, 0.047 mmol) and cesium carbonate (46 mg, 0.14 mmol) were suspended in DMF (1.5 mL). The obtained suspension was degassed (3× vacuum/Ar), then copper(I) oxide (1.7 mg, 0.012 mmol) was added. The reaction mixture was degassed again (2× vacuum/Ar) and was stirred under microwave irradiation at 200° C. for 30 min. The reaction mixture was cooled to rt, and most of DMF was evaporated. The obtained residue was treated TFA (2 mL), and the reaction mixture was stirred at rt for 15 min. TFA was removed under reduced pressure, the residue was purified by prep HPLC to afford Example 388 (2.2 mg, 10% yield). MS(ESI) m/z: 442.2 (M+H)$^+$; $^1$H NMR (500 MHz, DMSO-d$_6$) δ ppm 12.82 (s, 1H), 10.22 (s, 1H), 9.13 (s, 1H), 8.37 (s, 1H), 8.34 (d, J=7.6 Hz, 1H), 8.02-7.84 (m, 6H), 7.76 (d, J=7.6 Hz, 1H), 7.61 (dd, J=13.9, 8.4 Hz, 4H); HPLC RT=1.77 min (Method E), 1.76 min (Method F).

Example 389: 1-(Oxetan-3-yl)-N-(4-(4-oxo-3,4-dihydrophthalazin-1-yl)phenyl)-1H-pyrazole-4-carboxamide Example 390: N-(4-(4-Oxo-3,4-dihydrophthalazin-1-yl)phenyl)-1-(tetrahydrofuran-3-yl)-1H-pyrazole-4-carboxamide

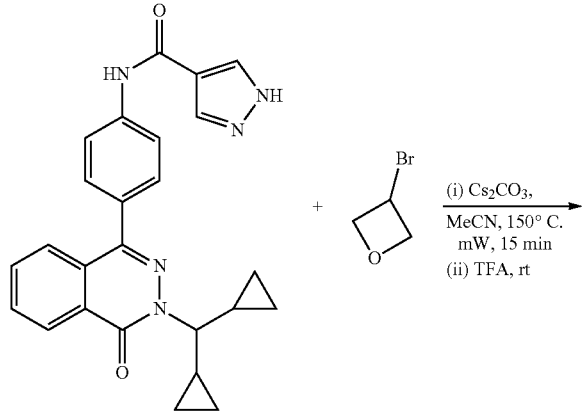

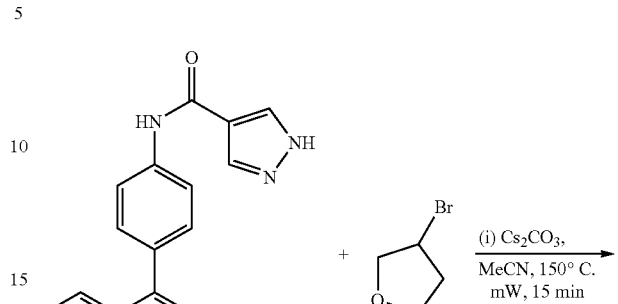

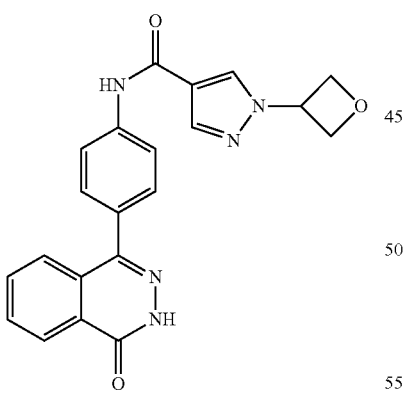

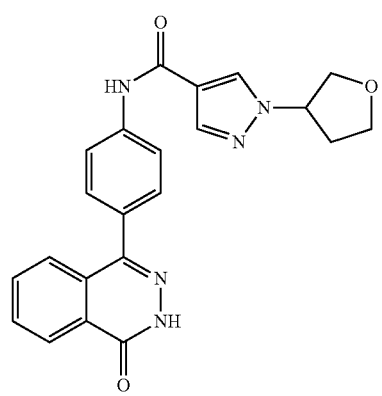

According to the procedure for the preparation of Example 373, substituting 3-bromooxetane for bromocyclohexane afforded Example 389. MS(ESI) m/z: 388.0 (M+H)$^+$; $^1$H NMR (500 MHz, DMSO-d$_6$) δ ppm 12.84 (s, 1H), 10.12 (s, 1H), 8.54 (s, 1H), 8.37-8.30 (m, 1H), 8.21 (s, 1H), 7.96-7.85 (m, 4H), 7.75 (d, J=7.4 Hz, 1H), 7.57 (d, J=8.4 Hz, 2H), 5.65 (quin, J=6.9 Hz, 1H), 5.00-4.93 (m, 2H), 4.93-4.87 (m, 2H); HPLC RT=1.03 min (Method E), 0.94 min (Method F).

According to the procedure for the preparation of Example 373, substituting 3-bromotetrahydrofuran for bromocyclohexane afforded Example 390. MS(ESI) m/z: 402.1 (M+H)$^+$; $^1$H NMR (500 MHz, DMSO-d$_6$) δ ppm 12.83 (s, 1H), 10.07 (s, 1H), 8.45 (s, 1H), 8.34 (d, J=7.1 Hz, 1H), 8.09 (s, 1H), 7.97-7.85 (m, 4H), 7.75 (d, J=7.7 Hz, 1H), 7.57 (d, J=8.1 Hz, 2H), 5.10 (br. s., 1H), 4.06-3.97 (m, 2H), 3.97-3.90 (m, 1H), 3.88-3.78 (m, 1H), 2.48-2.36 (m, 1H), 2.27 (d, J=3.7 Hz, 1H); HPLC RT=1.10 min (Method E), 1.02 min (Method F).

411

Example 391: N-(4-(4-Oxo-3,4-dihydrophthalazin-1-yl)phenyl)-1H-pyrazole-4-carboxamide, TFA

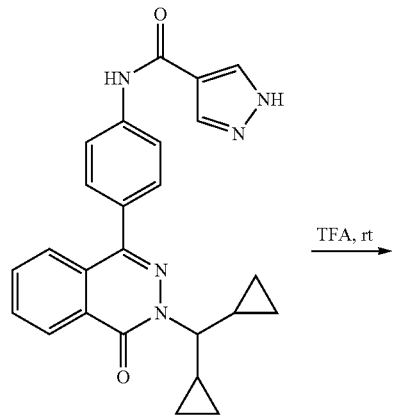

TFA, rt

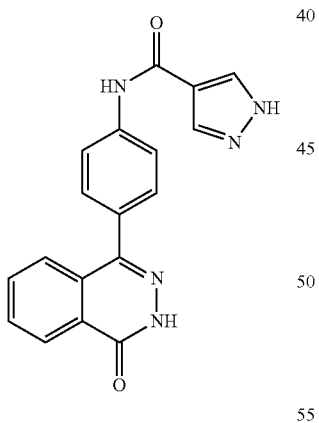

Intermediate 111 (20 mg, 0.047 mmol) was treated with TFA (2 mL). The reaction mixture was stirred at rt for 15 min. TFA was removed under reduced pressure, then the residue was purified by prep HPLC to afford Example 391 (11.6 mg, 53% yield). MS(ESI) m/z: 332.0 (M+H)$^+$; $^1$H NMR (500 MHz, DMSO-d$_6$) δ ppm 12.81 (s, 1H), 10.02 (s, 1H), 8.41 (br. s., 1H), 8.34 (d, J=7.3 Hz, 1H), 8.10 (br. s., 1H), 7.96-7.84 (m, 4H), 7.76 (d, J=7.6 Hz, 1H), 7.56 (d, J=7.9 Hz, 2H); HPLC RT=1.01 min (Method E), 1.01 min (Method F).

412

Example 392: 1-(Bicyclo[2.2.1]heptan-7-yl)-N-(4-(4-oxo-3,4-dihydrophthalazin-1-yl)phenyl)-1H-pyrazole-4-carboxamide

Example 393: 1-((1S,2S,4R)-Bicyclo[2.2.1]heptan-2-yl)-N-(4-(4-oxo-3,4-dihydrophthalazin-1-yl)phenyl)-1H-pyrazole-4-carboxamide

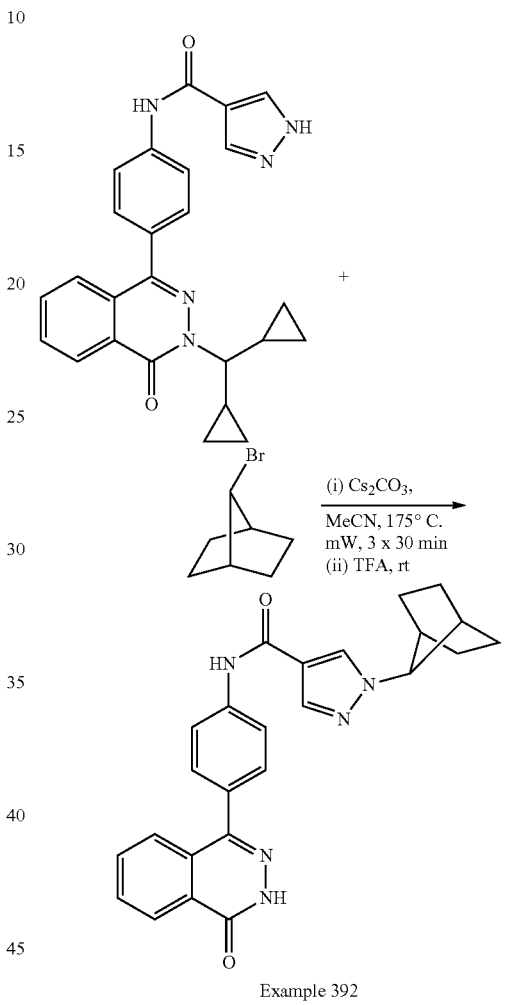

(i) Cs$_2$CO$_3$, MeCN, 175° C. mW, 3 x 30 min
(ii) TFA, rt

Example 392

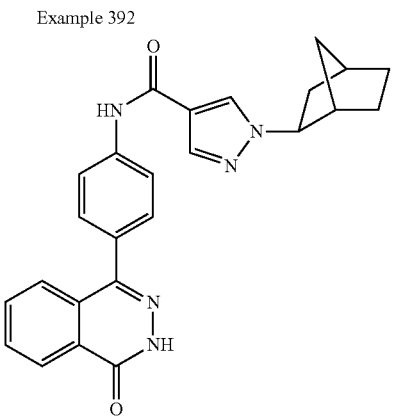

Example 393

Intermediate 111 (20 mg, 0.047 mmol) was suspended in dry MeCN (1.5 mL), then (1R,4S)-7-bromobicyclo[2.2.1]heptane (0.060 mL, 0.470 mmol) was added, followed by cesium carbonate (153 mg, 0.470 mmol) and the reaction mixture was heated under microwave irradiation at 150° C. for 15 min. The reaction mixture was heated at 175° C. for 30 min (3×). The reaction mixture was cooled to rt, and most of MeCN was removed under reduced pressure. The obtained residue was treated TFA (2 mL), and the reaction mixture was stirred at rt for 15 min. TFA was removed under reduced pressure, the residue was purified by prep HPLC to afford Example 392 (7.8 mg, 38% yield) and Example 393 (2.5 mg, 13% yield).

Example 392: MS(ESI) m/z: 426.0 (M+H)+; 1H NMR (500 MHz, DMSO-d6) δ ppm 12.81 (s, 1H), 9.98 (s, 1H), 8.46 (s, 1H), 8.34 (d, J=7.6 Hz, 1H), 8.04 (s, 1H), 7.98-7.87 (m, 4H), 7.76 (d, J=7.3 Hz, 1H), 7.56 (d, J=8.2 Hz, 2H), 4.38-4.29 (m, 1H), 2.47 (br. s., 1H), 2.39 (br. s., 1H), 2.05 (d, J=13.4 Hz, 1H), 1.91-1.83 (m, 1H), 1.75 (d, J=9.8 Hz, 1H), 1.65-1.46 (m, 2H), 1.38-1.30 (m, 1H), 1.21 (d, J=9.2 Hz, 2H); HPLC RT=1.51 min (Method E), 1.52 min (Method F).

Example 393: MS(ESI) m/z: 426.0 (M+H)+; 1H NMR (500 MHz, DMSO-d6) δ ppm 12.81 (br. s., 1H), 9.99 (br. s., 1H), 8.51-8.40 (m, 1H), 8.34 (d, J=7.0 Hz, 1H), 8.07 (br. s., 1H), 7.89 (d, J=7.9 Hz, 4H), 7.76 (d, J=7.0 Hz, 1H), 7.57 (d, J=7.3 Hz, 2H), 4.73 (br. s., 1H), 2.34 (br. s., 1H), 2.08 (d, J=14.3 Hz, 1H), 1.90 (br. s., 1H), 1.78 (br. s., 1H), 1.65-1.47 (m, 2H), 1.46-1.27 (m, 4H); HPLC RT=1.49 min (Method E), 1.49 min (Method F).

Example 394: 5-Methyl-N-(3-methyl-4-(4-oxo-3,4-dihydrophthalazin-1-yl)phenyl)-1-phenyl-1H-pyrazole-4-carboxamide

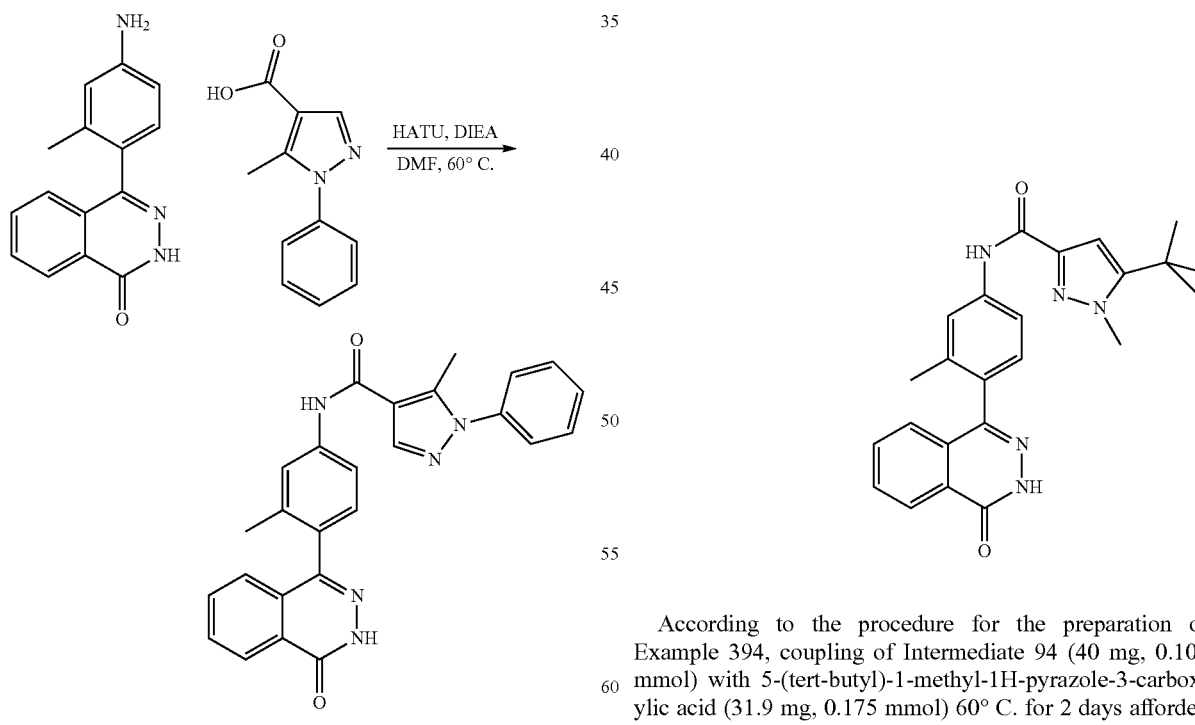

Intermediate 94 (50 mg, 0.137 mmol) was dissolved in dry DMF (2 mL), then 5-methyl-1-phenyl-1H-pyrazole-4-carboxylic acid (55.4 mg, 0.274 mmol) and DIEA (0.143 mL, 0.821 mmol) were added. After stirring for 5 min at rt, HATU (52 mg, 0.137 mmol) was added, and the reaction mixture was stirred at 60° C. for 4 h. The reaction mixture was quenched with MeOH (0.1 mL) was purified by preparative HPLC to afford Example 394 (18 mg, 29% yield) as an off-white solid. MS(ESI) m/z: 436.0 (M+H)+; 1H NMR (400 MHz, DMSO-d6) δ ppm 12.78 (s, 1H), 9.97 (s, 1H), 8.37 (s, 1H), 8.35-8.29 (m, 1H), 7.91-7.84 (m, 2H), 7.79 (d, J=1.8 Hz, 1H), 7.74 (dd, J=8.4, 2.0 Hz, 1H), 7.63-7.54 (m, 4H), 7.54-7.46 (m, 1H), 7.32-7.26 (m, 2H), 2.58 (s, 3H), 2.09 (s, 3H); HPLC RT=8.43 min (Method A), 8.11 min (Method B).

Example 395: 5-(tert-Butyl)-1-methyl-N-(3-methyl-4-(4-oxo-3,4-dihydrophthalazin-1-yl)phenyl)-1H-pyrazole-3-carboxamide

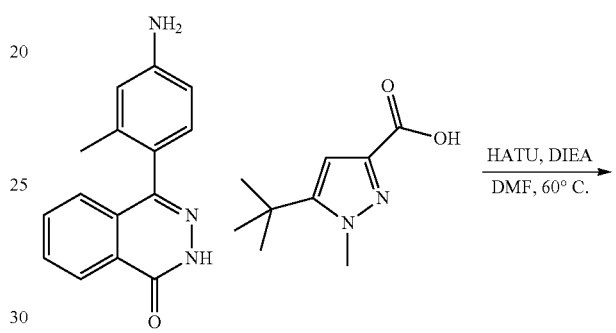

According to the procedure for the preparation of Example 394, coupling of Intermediate 94 (40 mg, 0.109 mmol) with 5-(tert-butyl)-1-methyl-1H-pyrazole-3-carboxylic acid (31.9 mg, 0.175 mmol) 60° C. for 2 days afforded Example 395 (18.2 mg, 39% yield). MS(ESI) m/z: 416.1 (M+H)+; 1H NMR 1H-NMR: (500 MHz, DMSO-d6) δ ppm 12.77 (s, 1H), 10.00 (s, 1H), 8.35-8.29 (m, 1H), 7.91-7.83 (m, 3H), 7.79 (dd, J=8.4, 2.0 Hz, 1H), 7.31-7.24 (m, 2H), 6.59 (s, 1H), 4.05 (s, 3H), 2.07 (s, 3H), 1.39 (s, 9H); HPLC RT=13.24 min (Method A), 11.79 min (Method B).

Example 396: 1-(1,1-Dioxidotetrahydrothiophen-3-yl)-N-(4-(4-oxo-3,4-dihydrophthalazin-1-yl)phenyl)-1H-pyrazole-4-carboxamide, TFA

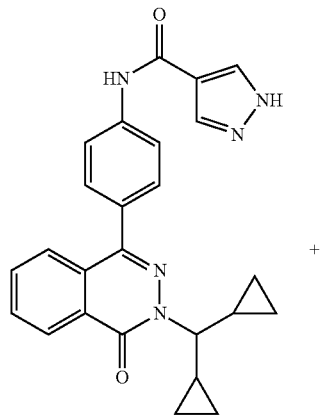

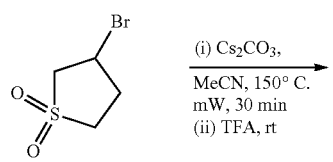

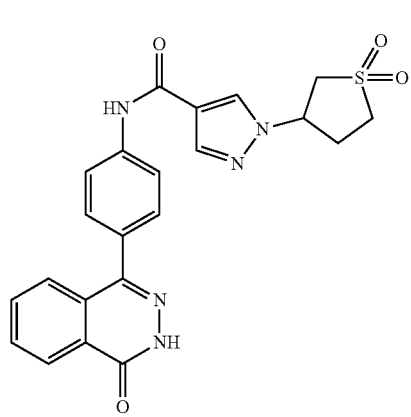

According to the procedure for the preparation of Example 373, substituting 3-bromotetrahydrothiophene 1,1-dioxide for bromocyclohexane afforded Example 396. MS(ESI) m/z: 450.1 (M+H)$^+$; $^1$H NMR (500 MHz, DMSO-d$_6$) δ ppm 12.81 (s, 1H), 10.09 (s, 1H), 8.54 (s, 1H), 8.34 (d, J=7.3 Hz, 1H), 8.19 (s, 1H), 7.98-7.84 (m, 4H), 7.76 (d, J=7.6 Hz, 1H), 7.58 (d, J=7.9 Hz, 2H), 5.35 (t, J=7.3 Hz, 1H), 3.78 (dd, J=13.6, 8.4 Hz, 1H), 3.51 (dd, J=13.9, 7.5 Hz, 1H), 3.49-3.38 (m, 1H), 2.73-2.65 (m, 1H), 2.64-2.55 (m, 1H); HPLC RT=1.13 min (Method E), 1.14 min (Method F).

Example 397: N-(4-(4-Oxo-3,4-dihydrophthalazin-1-yl)phenyl)-1-(pyrrolidin-3-yl)-1H-pyrazole-4-carboxamide

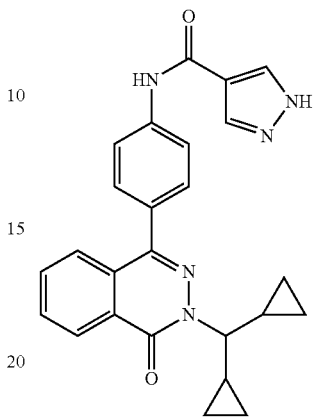

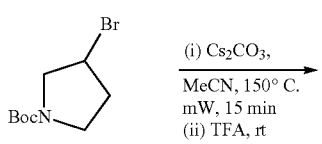

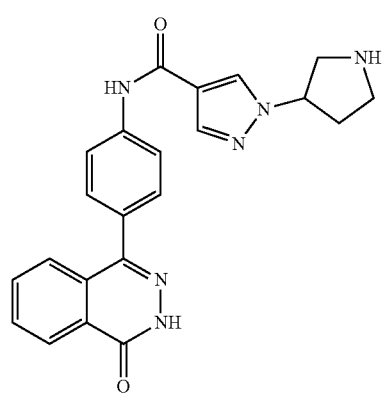

According to the procedure for the preparation of Example 373, substituting tert-butyl 3-bromopyrrolidine-1-carboxylate for bromocyclohexane afforded Example 397. MS(ESI) m/z: 401.3 (M+H)$^+$; $^1$H NMR (500 MHz, DMSO-d$_6$) δ ppm 10.09 (s, 1H), 8.45 (s, 1H), 8.34 (d, J=7.1 Hz, 1H), 8.09 (s, 1H), 7.95-7.83 (m, 5H), 7.74 (d, J=7.4 Hz, 1H), 7.56 (d, J=8.4 Hz, 2H), 4.96 (br. s., 1H), 3.29 (dd, J=12.1, 7.1 Hz, 1H), 3.17-3.06 (m, 2H), 3.03-2.93 (m, 1H), 2.32-2.22 (m, 1H), 2.15-2.01 (m, 1H); HPLC RT=0.85 min (Method E), 0.85 min (Method F).

Example 398: N-(4-(4-Oxo-3,4-dihydrophthalazin-1-yl)phenyl)-1-(3,3,3-trifluoropropyl)-1H-pyrazole-4-carboxamide Example 399: N-(4-(4-Oxo-3,4-dihydrophthalazin-1-yl)phenyl)-1-(3-(pyrrolidin-1-yl)propyl)-1H-pyrazole-4-carboxamide

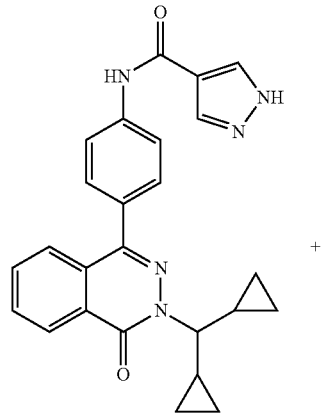 +

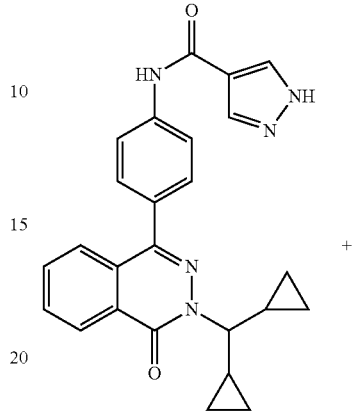 +

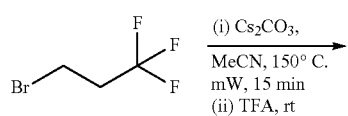

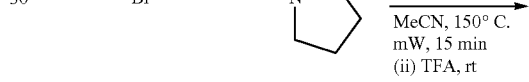

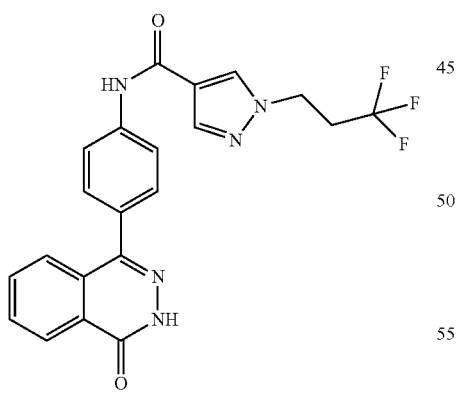

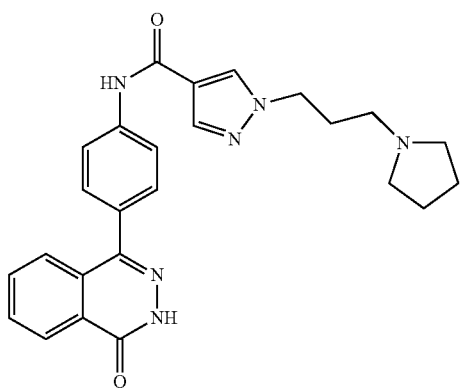

According to the procedure for the preparation of Example 373, substituting 3-bromo-1,1,1-trifluoropropane for bromocyclohexane afforded Example 398. MS(ESI) m/z: 428.2 (M+H)+; 1H NMR (500 MHz, DMSO-d6) δ ppm 12.84 (s, 1H), 10.11 (s, 1H), 8.44 (s, 1H), 8.34 (d, J=7.1 Hz, 1H), 8.13 (s, 1H), 7.95-7.83 (m, 4H), 7.75 (d, J=7.7 Hz, 1H), 7.56 (d, J=8.4 Hz, 2H), 4.46 (t, J=6.6 Hz, 2H), 2.98-2.89 (m, 2H); HPLC RT=1.35 min (Method E), 1.35 min (Method F).

According to the procedure for the preparation of Example 373, substituting 1-(3-bromopropyl)pyrrolidine, HCl for bromocyclohexane afforded Example 399. MS(ESI) m/z: 443.3 (M+H)+; 1H NMR (500 MHz, DMSO-d6) δ ppm 12.83 (s, 1H), 10.02 (s, 1H), 8.39 (s, 1H), 8.34 (d, J=7.1 Hz, 1H), 8.08 (s, 1H), 7.97-7.85 (m, 4H), 7.76 (d, J=8.1 Hz, 1H), 7.57 (d, J=8.4 Hz, 2H), 4.21 (t, J=6.9 Hz, 2H), 2.43 (br. s., 4H), 2.37 (t, J=7.1 Hz, 2H), 1.97 (quin, J=6.9 Hz, 2H), 1.69 (br. s., 4H); HPLC RT=0.91 min (Method E), 0.90 min (Method F).

Example 400: 5-Methyl-N-(4-(4-oxo-3,4-dihydrophthalazin-1-yl)phenyl)-1-phenyl-1H-1,2,3-triazole-4-carboxamide

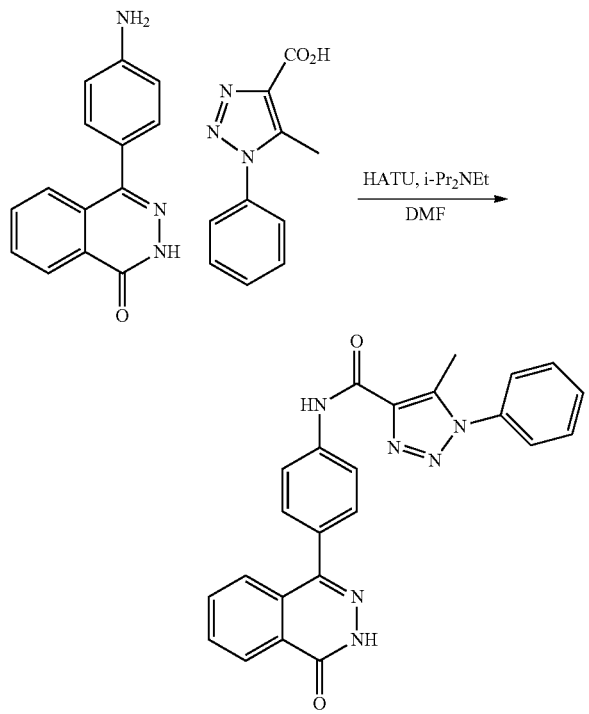

To a mixture of Intermediate 12 (15 mg, 0.043 mmol), Intermediate 112 (9.5 mg, 0.047 mmol), and HATU (18 mg, 0.047 mmol) in DMF (1.5 mL), was added DIEA (0.037 mL, 0.21 mmol). The mixture was stirred rt for 3 h, then 50° C. overnight. The mixture was purified by prep PHLC to afford Example 400 (4.6 mg, 24% yield). MS(ESI) m/z: 423.1 (M+H)$^+$; $^1$H NMR (500 MHz, DMSO-d$_6$) δ 12.82 (s, 1H), 10.73 (s, 1H), 8.35 (d, J=6.7 Hz, 1H), 8.09-8.03 (m, J=7.9 Hz, 2H), 7.97-7.87 (m, 2H), 7.76 (d, J=7.3 Hz, 1H), 7.67 (br. s., 5H), 7.61-7.55 (m, J=7.9 Hz, 2H), 2.60 (s, 3H); HPLC RT=1.70 min (Method E), 1.71 min (Method F).

Example 401: 1-(4-Methoxyphenyl)-5-methyl-N-(4-(4-oxo-3,4-dihydrophthalazin-1-yl)phenyl)-1H-1,2,3-triazole-4-carboxamide

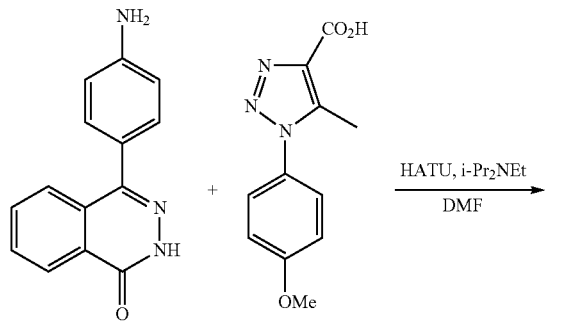

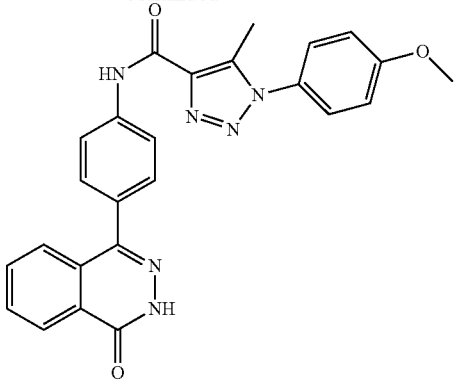

According to the procedure for the preparation of Example 400, coupling of Intermediate 12 (12 mg, 0.034 mmol) and Intermediate 113 (8.8 mg, 0.038 mmol) afforded Example 401 (1.8 mg, 11% yield). MS(ESI) m/z: 453.2 (M+H)$^+$; $^1$H NMR (500 MHz, DMSO-d$_6$) δ 12.82 (s, 1H), 10.70 (s, 1H), 8.34 (d, J=7.6 Hz, 1H), 8.05 (d, J=7.9 Hz, 2H), 7.91 (t, J=7.6 Hz, 2H), 7.76 (d, J=7.9 Hz, 1H), 7.58 (d, J=8.2 Hz, 4H), 7.19 (d, J=8.2 Hz, 2H), 3.86 (s, 3H), 2.56 (s, 3H); HPLC RT=1.69 min (Method E), 1.70 min (Method F).

Example 402: 1-(4-Methoxyphenyl)-4-methyl-N-(4-(4-oxo-3,4-dihydrophthalazin-1-yl)phenyl)-1H-1,2,3-triazole-5-carboxamide

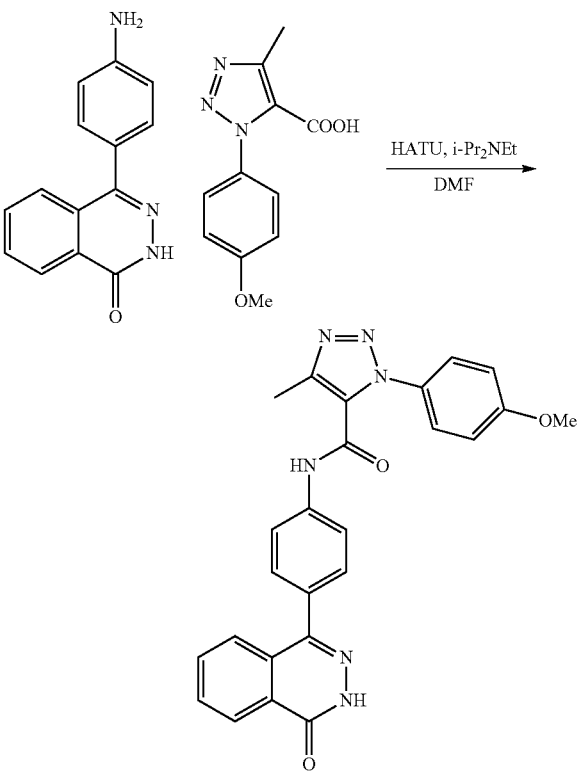

According to the procedure for the preparation of Example 400, coupling of Intermediate 12 (12 mg, 0.034 mmol) and Intermediate 114 (8.8 mg, 0.038 mmol) afforded Example 402 (2.5 mg, 16% yield). MS(ESI) m/z: 453.2

(M+H)⁺; ¹H NMR (500 MHz, DMSO-d₆) δ 12.83 (s, 1H), 10.98 (s, 1H), 8.33 (d, J=7.6 Hz, 1H), 7.89 (d, J=4.3 Hz, 2H), 7.76 (d, J=7.9 Hz, 2H), 7.70 (d, J=7.0 Hz, 1H), 7.58 (d, J=7.9 Hz, 2H), 7.50 (d, J=8.2 Hz, 2H), 7.11 (d, J=8.5 Hz, 2H), 3.80 (s, 3H), 2.45 (s, 3H); HPLC RT=1.44 min (Method E), 1.45 min (Method F).

Example 403: 5-(Difluoromethoxy)-1-methyl-N-(4-(4-oxo-3,4-dihydrophthalazin-1-yl)phenyl)-1H-pyrazole-3-carboxamide

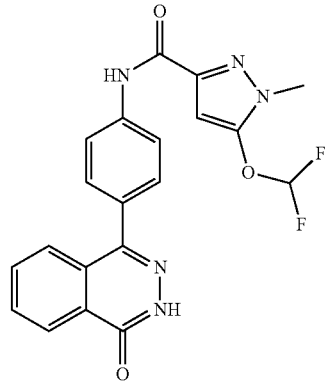

Example 403A: Methyl 5-(difluoromethoxy)-1-methyl-1H-pyrazole-3-carboxylate

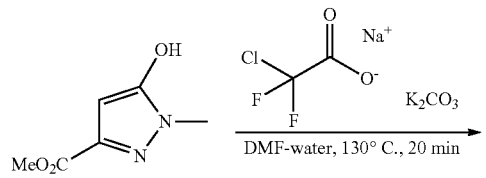

Methyl 5-hydroxy-1-methyl-1H-pyrazole-3-carboxylate (*J. Med. Chem.*, 54:8174 (2011)) (0.35 g, 2.24 mmol), K₂CO₃ (0.62 g, 4.48 mmol), and sodium chlorodifluoroacetate (0.684 g, 4.48 mmol) were dissolved in DMF (10 ml) and water (1 ml). The reaction was heated to 130° C. for 20 min. The reaction was diluted with water (100 mL) and EtOAc (200 mL). The organic phase was separated, washed with water (5×), brine and dried (Na₂SO₄). EtOAc was removed under reduced pressure and the residue was purified by flash chromatography: (40 g) 0-80% EtOAc/Hex. Fractions were combined and concentrated under reduced pressure to give Example 403A (0.373 g, 81% yield) as a colorless syrup. MS(ESI) m/z: 207.0 (M+H)⁺; ¹H-NMR: (400 MHz, CDCl₃) δ ppm 6.44 (t, J=1.0 Hz, 1H), 6.46 (t, J=72.2 Hz, 1H), 3.92 (s, 3H), 3.82 (s, 3H); ¹⁹F-NMR: (376 MHz, CDCl₃) δ ppm −84.02 (s, 2F).

Example 403B: 5-(Difluoromethoxy)-1-methyl-1H-pyrazole-3-carboxylic Acid

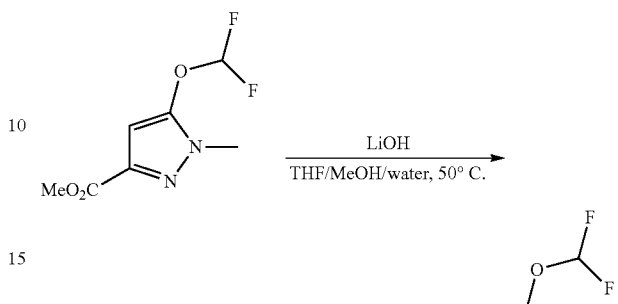

Example 403A (0.373 g, 1.809 mmol) was dissolved in THF (7.5 ml) and MeOH (1.5 ml), then LiOH (1 M in water) (5.43 ml, 5.43 mmol) was added. The reaction was heated to 50° C. for 2 h. The reaction mixture was quenched with TFA (0.418 ml, 5.43 mmol), and concentrated under reduced pressure. The residue was diluted with DMSO/MeOH/water and was purified by preparative HPLC. Fractions were combined and concentrated to afford Example 403B (0.230 g, 66% yield) as a white solid. MS(ESI) m/z: 192.9 (M+H)⁺; ¹H-NMR: (500 MHz, DMSO-d₆) δ ppm 7.30 (t, J=70.4 Hz, 1H), 6.42 (s, 1H), 3.74 (s, 3H); ¹⁹F-NMR: (376 MHz, DMSO-d₆) δ ppm −84.72 (s, 2F)

Example 403

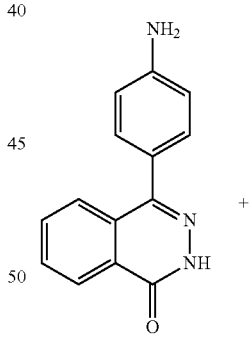

+

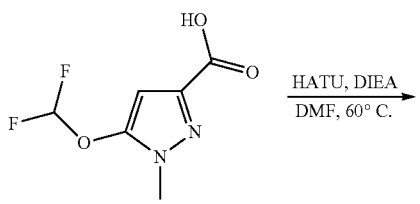

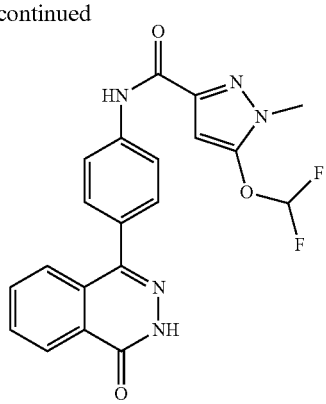

According to the procedure for the preparation of Example 400, coupling of Intermediate 12 (30 mg, 0.064 mmol) and Example 403B (24.8 mg, 0.129 mmol) afforded Example 403 (14.7 mg, 55% yield). MS(ESI) m/z: 412.2 (M+H)$^+$; $^1$H NMR (500 MHz, DMSO-d$_6$)$^1$H-NMR: (500 MHz, DMSO-d$_6$) δ ppm 12.83 (s, 1H), 10.37 (s, 1H), 8.34 (d, J=7.1 Hz, 1H), 7.98 (d, J=8.4 Hz, 2H), 7.93-7.84 (m, 2H), 7.74 (d, J=7.4 Hz, 1H), 7.56 (d, J=8.4 Hz, 2H), 7.52-7.14 (m, 1H), 6.58 (s, 1H), 3.81 (s, 3H); HPLC RT=1.45 min (Method E), 1.45 min (Method F).

Example 404: 1-(3-Methoxyphenyl)-N-(4-(4-oxo-3,4-dihydrophthalazin-1-yl)phenyl)-1H-1,2,3-triazole-4-carboxamide

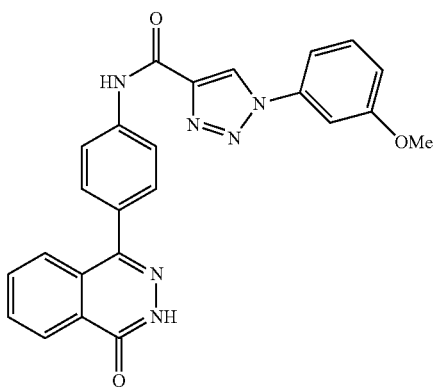

Example 404A: Ethyl 1-(3-methoxyphenyl)-1H-1,2,3-triazole-4-carboxylate

To the solution of 3-methoxyaniline (0.3 g, 2.44 mmol) in acetonitrile (6 mL) at 0° C. was added isoamyl nitrite (0.327 mL, 2.44 mmol), followed by azidotrimethylsilane (0.320 mL, 2.44 mmol) dropwise. After 5 min, the ice bath removed, and the reaction mixture was stirred at rt for 10 min, then ethyl propiolate (0.494 mL, 4.87 mmol) added. The reaction mixture stirred in a sealed tube at 80° C. for 20 h, then was cooled to rt. The reaction mixture was concentrated and the residue was purified by flash chromatography (0-40% EtOAc/Hexanes) to afford Example 404A. MS(ESI) m/z: 248.0 (M+H)$^+$; $^1$H NMR (400 MHz, chloroform-d) δ 8.48 (s, 1H), 7.42-7.32 (m, 1H), 7.28 (t, J=2.2 Hz, 1H), 7.26-7.19 (m, 1H), 6.99-6.88 (m, 1H), 4.38 (q, J=7.0 Hz, 2H), 3.81 (s, 3H), 1.36 (t, J=7.2 Hz, 3H).

Example 404B: 1-(3-Methoxyphenyl)-1H-1,2,3-triazole-4-carboxylic Acid

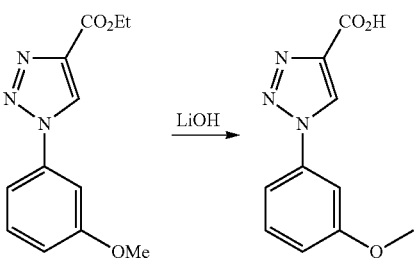 [SMILES: CCOC(=O)c1cn(-c2cccc(OC)c2)nn1 ; "LiOH" ; COc1cccc(-n2cc(C(=O)O)nn2)c1]

Example 404A (120 mg, 0.485 mmol) mixed with 1M lithium hydroxide (1.2 mL, 1.2 mmol) in THF (2 mL) and THF (2 mL). The reaction mixture was stirred at rt for 2 h, then was concentrated. The residue was purified by flash chromatography (0-20% MeOH/DCM) to afford Example 404B (100 mg, 94% yield) as a yellow solid. MS(ESI) m/z: 220.0 (M+H)$^+$; $^1$H NMR (400 MHz, DMSO-d$_6$) δ 9.03 (s, 1H), 7.59-7.43 (m, 3H), 7.08-7.00 (m, 1H), 3.86 (s, 3H).

Example 404

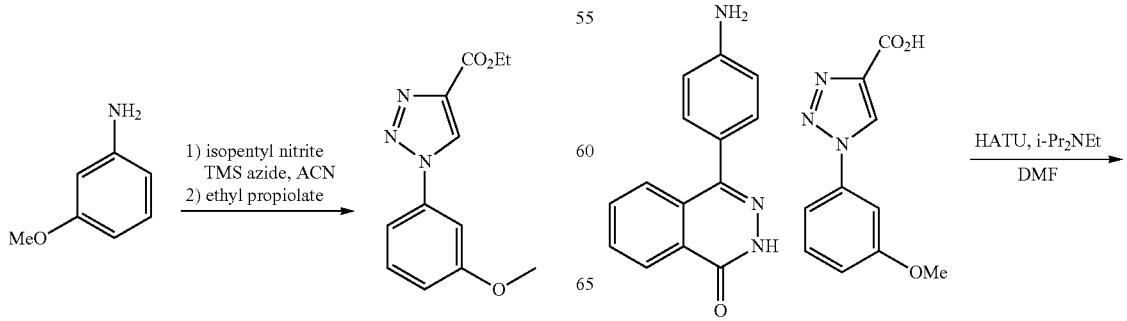

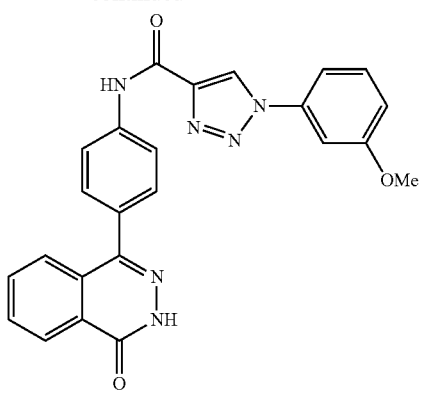

According to the procedure for the preparation of Example 400, coupling of Intermediate 12 (10 mg, 0.028 mmol) and Example 404B (6.9 mg, 0.031 mmol) afforded Example 404 (1.9 mg, 15% yield). MS(ESI) m/z: 439.15 (M+H)$^+$; $^1$H NMR (500 MHz, DMSO-$d_6$) δ 12.90 (s, 1H), 10.88 (s, 1H), 9.59 (s, 1H), 8.42 (d, J=7.6 Hz, 1H), 8.13 (d, J=7.9 Hz, 2H), 7.98 (t, J=7.6 Hz, 2H), 7.83 (d, J=7.3 Hz, 1H), 7.73-7.64 (m, 4H), 7.61 (d, J=7.0 Hz, 1H), 7.19 (d, J=8.2 Hz, 1H), 3.95 (s, 3H); HPLC RT=1.66 min (Method E), 1.66 min (Method F).

Example 405: 1-(2-Methoxyphenyl)-5-methyl-N-(4-(4-oxo-3,4-dihydrophthalazin-1-yl)phenyl)-1H-1,2,3-triazole-4-carboxamide

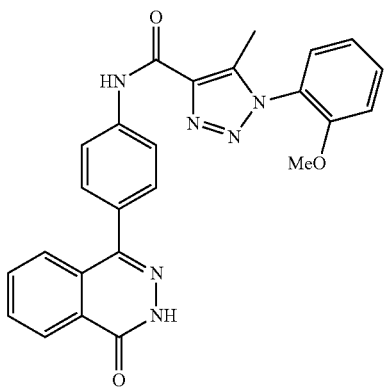 [SMILES: COc1ccccc1-n1nnc(C(=O)Nc2ccc(-c3n[nH]c(=O)c4ccccc34)cc2)c1C]

Example 405A: Ethyl 1-(2-methoxyphenyl)-5-methyl-1H-1,2,3-triazole-4-carboxylate

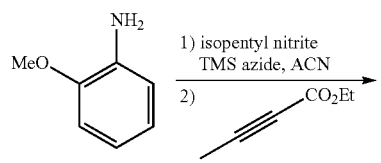

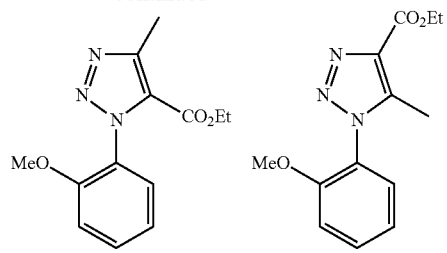

Example 405A

To the solution of 2-methoxyaniline (0.30 g, 2.44 mmol) in acetonitrile (3 mL) at 0° C. was added isoamyl nitrite (0.360 mL, 2.68 mmol), followed by azidotrimethylsilane (0.352 mL, 2.68 mmol) dropwise. After 5 min, the cold bath removed, and the reaction mixture was stirred at rt for 10 min, then ethyl but-2-ynoate (0.546 g, 4.87 mmol) added, and the reaction mixture was stirred in a sealed tube at 80° C. for 20 h, then cooled to rt. The reaction mixture was concentrated and the residue was purified by flash chromatography (0-40% EtOAc/Hexanes) to afford 1st peak at 30% EtOAc and 2nd peak at 35% EtOAc.

1st Peak:

Ethyl 1-(2-methoxyphenyl)-4-methyl-1H-1,2,3-triazole-5-carboxylate (55 mg, 8.6% yield) yellow solid. MS(ESI) m/z: 262.2 (M+H)$^+$; $^1$H NMR (400 MHz, chloroform-d) δ 7.47 (ddd, J=8.3, 7.6, 1.8 Hz, 1H), 7.40 (dd, J=7.7, 1.8 Hz, 1H), 7.08 (td, J=7.6, 1.2 Hz, 1H), 7.01 (dd, J=8.4, 1.1 Hz, 1H), 4.21 (q, J=7.3 Hz, 2H), 3.74 (s, 3H), 2.62 (s, 3H), 1.16 (t, J=7.2 Hz, 3H).

2nd Peak:

Example 405A (0.177 g, 28% yield) yellow solid. MS(ESI) m/z: 262.2 (M+H)$^+$; $^1$H NMR 67.57-7.50 (m, 1H), 7.36 (dd, J=7.8, 1.7 Hz, 1H), 7.16-7.07 (m, 2H), 4.46 (q, J=7.0 Hz, 2H), 3.80 (s, 3H), 2.42 (s, 3H), 1.45 (t, J=7.2 Hz, 3H).

Example 405B: 1-(2-Methoxyphenyl)-5-methyl-1H-1,2,3-triazole-4-carboxylic Acid

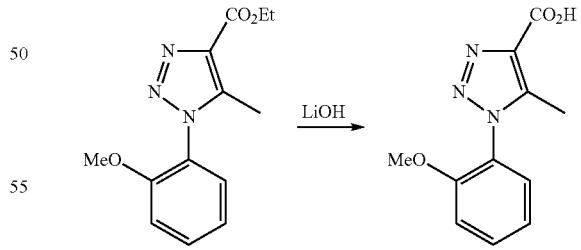

Example 405A (177 mg, 0.677 mmol) stirred with 1M LiOH in THF (2 mL) at rt for 3 h. The reaction mixture was acidified with TFA, then was concentrated. The residue was purified via preparative HPLC to afford Example 405B. MS(ESI) m/z: 234.1 (M+H)$^+$; $^1$H NMR (400 MHz, methanol-$d_4$) δ 7.64-7.57 (m, 1H), 7.40 (dd, J=7.7, 1.5 Hz, 1H), 7.31-7.25 (m, 1H), 7.16 (td, J=7.6, 1.1 Hz, 1H), 3.83 (s, 3H), 2.38 (s, 3H).

Example 405

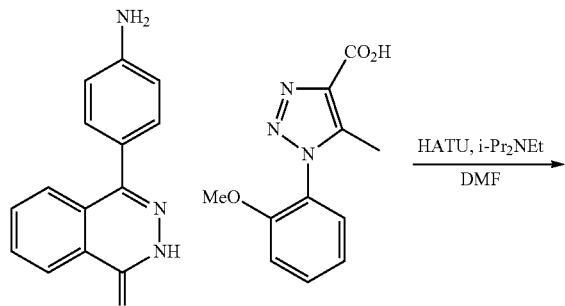

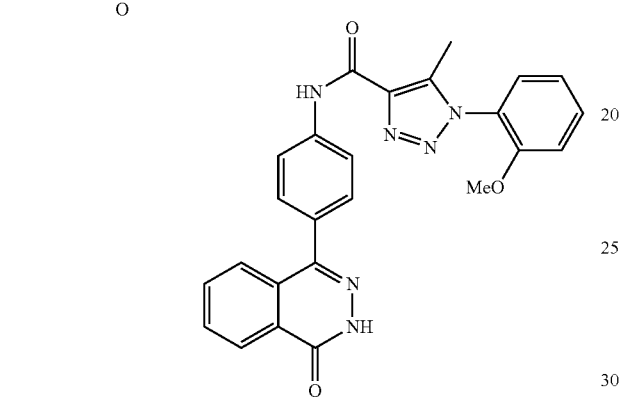

Intermediate 12 (12 mg, 0.051 mmol), Example 405B (13 mg, 0.056 mmol), HATU (21 mg, 0.056 mmol) were mixed in DMF (1.5 mL), add DIEA (0.044 mL, 0.253 mmol), stirred 45° C. for 4 h. The reaction mixture was purified by preparative HPLC to afford Example 405 (7.1 mg, 31% yield). MS(ESI) m/z: 453.2 (M+H)+; $^1$H NMR (500 MHz, DMSO-$d_6$) δ 10.68 (s, 1H), 8.35 (d, J=7.4 Hz, 1H), 8.03 (d, J=8.4 Hz, 2H), 7.95-7.91 (m, 2H), 7.77 (d, J=8.1 Hz, 1H), 7.66 (t, J=7.6 Hz, 1H), 7.59 (d, J=8.4 Hz, 2H), 7.50 (d, J=7.4 Hz, 1H), 7.36 (d, J=8.4 Hz, 1H), 7.21 (t, J=7.6 Hz, 1H), 3.82 (s, 3H), 2.39 (s, 3H); HPLC RT=1.67 min (Method E), 1.58 min (Method F).

Example 406: 1-(2-Methoxyphenyl)-N-(4-(4-oxo-3,4-dihydrophthalazin-1-yl)phenyl)-1H-1,2,3-triazole-4-carboxamide

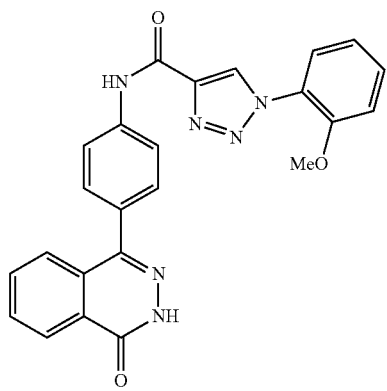 [SMILES: COc1ccccc1-n1cc(C(=O)Nc2ccc(-c3n[nH]c(=O)c4ccccc34)cc2)nn1]

According to the procedure for the preparation of Example 404, substituting 2-methoxyaniline for 3-methoxyaniline afforded Example 406. MS(ESI) m/z: 439.2 (M+H)+; $^1$H NMR (500 MHz, DMSO-$d_6$) δ 12.87 (s, 1H), 10.77 (s, 1H), 9.04 (s, 1H), 8.35 (d, J=7.4 Hz, 1H), 8.02 (d, J=8.4 Hz, 2H), 7.95-7.90 (m, 2H), 7.76 (d, J=7.7 Hz, 1H), 7.69 (d, J=7.7 Hz, 1H), 7.64-7.56 (m, 3H), 7.36 (d, J=8.4 Hz, 1H), 7.19 (t, J=7.7 Hz, 1H), 3.88 (s, 3H); HPLC RT=1.51 min (Method E), 1.51 min (Method F).

Example 407: 3-Cyclopropyl-1-methyl-N-(4-(4-oxo-3,4-dihydrophthalazin-1-yl)phenyl)-1H-pyrazole-5-carboxamide

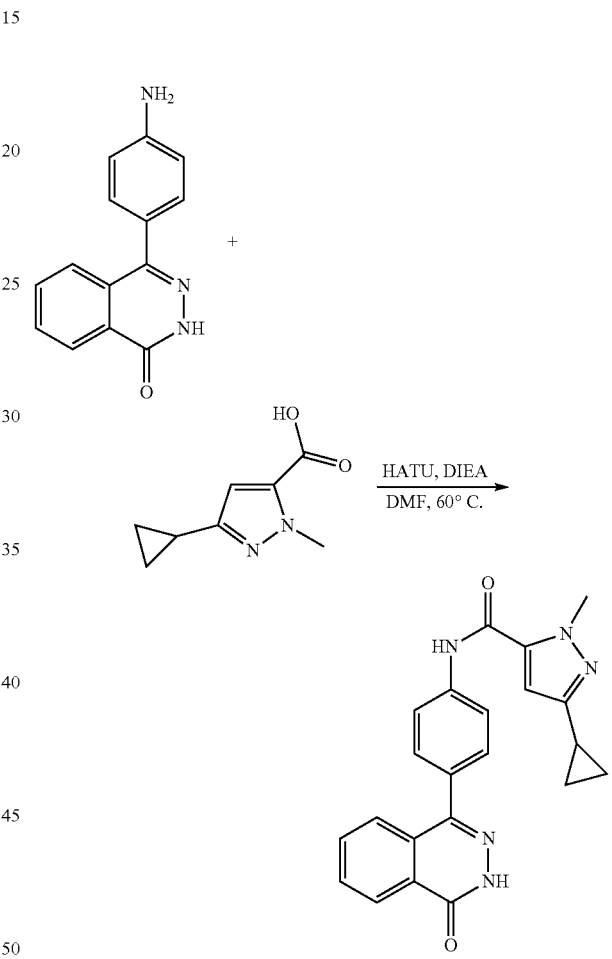

Intermediate 12, 2 TFA (30 mg, 0.064 mmol) was dissolved in dry DMF (1 mL), then 3-cyclopropyl-1-methyl-1H-pyrazole-5-carboxylic acid (21.4 mg, 0.129 mmol) and DIEA (0.068 mL, 0.387 mmol) were added. After stirring for 5 min at rt, HATU (37 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 407 (21.7 mg, 87% yield). MS(ESI) m/z: 386.2 (M+H)+; $^1$H NMR (500 MHz, DMSO-$d_6$) δ 12.85 (s, 1H), 10.33 (s, 1H), 8.34 (d, J=7.1 Hz, 1H), 7.97-7.83 (m, 4H), 7.73 (d, J=7.7 Hz, 1H), 7.58 (d, J=8.4 Hz, 2H), 6.78 (s, 1H), 3.99 (s, 3H), 1.97-1.83 (m, 1H), 0.96-0.82 (m, 2H), 0.67 (d, J=3.7 Hz, 2H); HPLC RT=1.47 min (Method E), 1.48 min (Method F).

Example 408: 1-Methyl-N-(4-(4-oxo-3,4-dihydrophthalazin-1-yl)phenyl)-3-(trifluoromethyl)-1H-pyrazole-5-carboxamide

Example 409: N-(4-(4-Oxo-3,4-dihydrophthalazin-1-yl)phenyl)-1-(2,2,2-trifluoroethyl)-1H-pyrazole-3-carboxamide

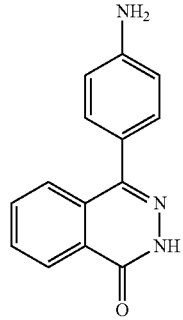

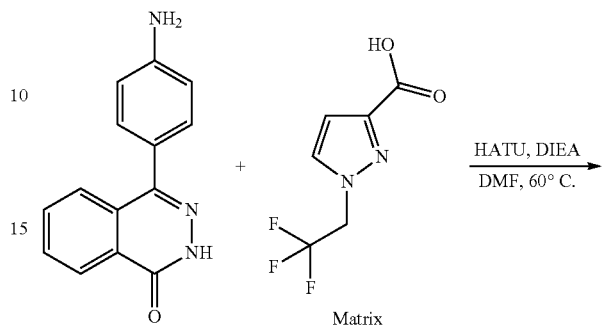

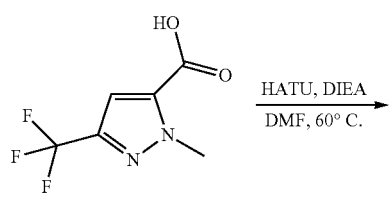

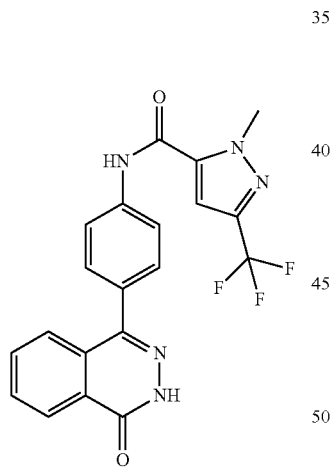

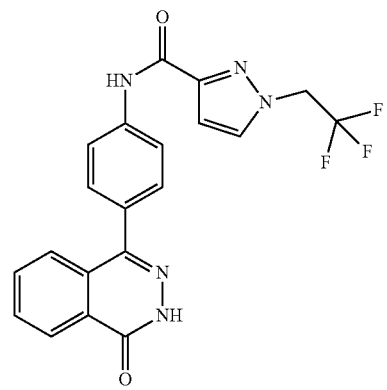

Intermediate 12, 2 TFA (30 mg, 0.064 mmol) was dissolved in dry DMF (1 mL), then 1-methyl-3-(trifluoromethyl)-1H-pyrazole-5-carboxylic acid (25.0 mg, 0.129 mmol) and DIEA (0.068 mL, 0.387 mmol) were added. After stirring for 5 min at rt, HATU (36.8 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 408 (19.6 mg, 73% yield). MS(ESI) m/z: 414.2 (M+H)$^+$; $^1$H NMR (500 MHz, DMSO-d$_6$) δ 12.86 (s, 1H), 10.64 (s, 1H), 8.34 (d, J=7.1 Hz, 1H), 7.98-7.84 (m, 4H), 7.73 (d, J=7.7 Hz, 1H), 7.61 (d, J=8.4 Hz, 2H), 7.54 (s, 1H), 4.18 (s, 3H); HPLC RT=1.68 min (Method E), 1.68 min (Method F).

Intermediate 12, 2 TFA (30 mg, 0.064 mmol) was dissolved in dry DMF (1 mL), then 1-(2,2,2-trifluoroethyl)-1H-pyrazole-3-carboxylic acid (25.0 mg, 0.129 mmol) and DIEA (0.068 mL, 0.387 mmol) were added. After stirring for 5 min at rt, HATU (36.8 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 409 (21.2 mg, 79% yield). MS(ESI) m/z: 414.1 (M+H)$^+$; $^1$H NMR (500 MHz, DMSO-d$_6$) δ 12.82 (s, 1H), 10.32 (s, 1H), 8.34 (d, J=7.3 Hz, 1H), 8.03 (br. s., 1H), 7.98 (d, J=7.6 Hz, 2H), 7.90 (t, J=7.6 Hz, 2H), 7.75 (d, J=7.3 Hz, 1H), 7.57 (d, J=7.9 Hz, 2H), 6.95 (br. s., 1H), 5.28 (q, J=8.5 Hz, 2H); HPLC RT=1.46 min (Method E), 1.47 min (Method F).

431

Example 410: 1-(Difluoromethyl)-N-(4-(4-oxo-3,4-dihydrophthalazin-1-yl)phenyl)-1H-pyrazole-3-carboxamide

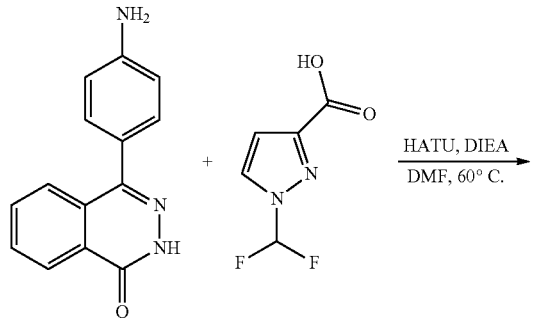

432

Example 411: 1-(2,2-Difluoroethyl)-N-(4-(4-oxo-3,4-dihydrophthalazin-1-yl)phenyl)-1H-pyrazole-5-carboxamide

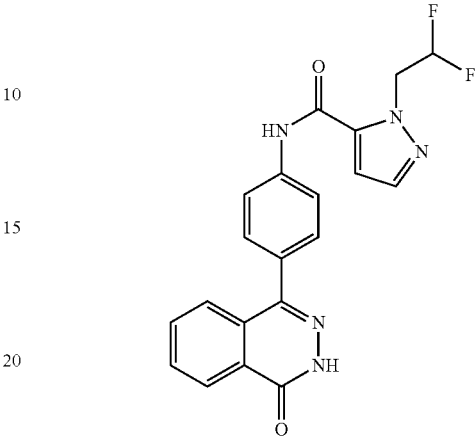

Example 411A: Methyl 1-(2,2-difluoroethyl)-1H-pyrazole-3-carboxylate

Example 411B: Methyl 1-(2,2-difluoroethyl)-1H-pyrazole-5-carboxylate

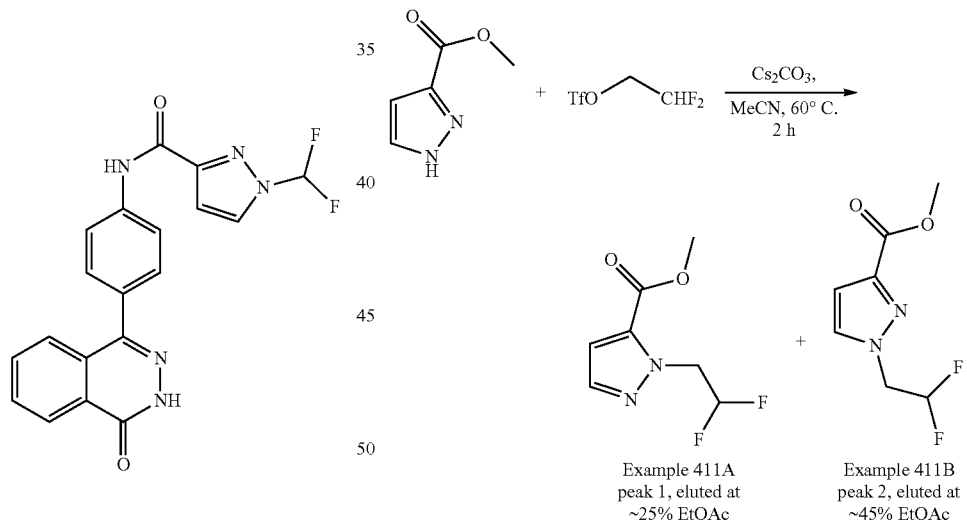

Example 411A peak 1, eluted at ~25% EtOAc

Example 411B peak 2, eluted at ~45% EtOAc

Intermediate 12, 2 TFA (30 mg, 0.064 mmol) was dissolved in dry DMF (1 mL), then 1-(difluoromethyl)-1H-pyrazole-3-carboxylic acid (20.9 mg, 0.129 mmol) and DIEA (0.068 mL, 0.387 mmol) were added. After stirring for 5 min at rt, HATU (36.8 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 410 (16.6 mg, 67% yield). MS(ESI) m/z: 382.2 (M+H)$^+$; $^1$H NMR (500 MHz, DMSO-$d_6$) δ 12.84 (s, 1H), 10.58 (s, 1H), 8.44 (d, J=2.4 Hz, 1H), 8.34 (d, J=7.1 Hz, 1H), 8.09-7.80 (m, 5H), 7.75 (d, J=7.4 Hz, 1H), 7.58 (d, J=8.4 Hz, 2H), 7.06 (d, J=2.0 Hz, 1H); HPLC RT=1.34 min (Method E), 1.25 min (Method F).

Methyl 1H-pyrazole-3-carboxylate (0.500 g, 3.96 mmol) was dissolved in dry MeCN (30 mL), then 2,2-difluoroethyl trifluoromethanesulfonate (0.633 mL, 4.76 mmol) was added, followed by cesium carbonate (1.94 g, 5.95 mmol) and the reaction mixture was stirred at 60° C. for 2 h. The reaction mixture was cooled to rt, diluted with EtOAc. Then CELITE® was added, and solvent was removed under reduced pressure. The residue was purified by flash chromatography (solid loading on CELITE®): 0-60% EtOAc/Hex affording two products.

Example 411A (0.271 g, 1.425 mmol, 35.9% yield) as a colorless syrup: peak 1 eluted at ~25% EtOAc. MS(ESI) m/z: 190.9 (M+H)$^+$; $^1$H-NMR: (400 MHz, CDCl$_3$) δ ppm 7.57 (d, J=2.0 Hz, 1H), 6.89 (d, J=2.0 Hz, 1H), 6.31-5.95 (m, 1H), 4.98 (td, J=13.1, 4.4 Hz, 2H), 3.91 (s, 3H); ¹⁹F-NMR: (376 MHz, CDCl₃) δ ppm −122.87 (s, 2F).

Example 411B: (0.398 g, 2.093 mmol, 52.8% yield) as a colorless syrup: peak 2 eluted at ~45% EtOAc. MS(ESI) m/z: 190.9 (M+H)⁺; ¹H-NMR: (400 MHz, CDCl₃) δ ppm 7.51 (d, J=2.4 Hz, 1H), 6.87 (d, J=2.4 Hz, 1H), 6.29-5.94 (m, 1H), 4.55 (td, J=13.4, 4.3 Hz, 2H), 3.94 (s, 3H); ¹⁹F-NMR: (376 MHz, CDCl₃) δ ppm −122.42 (s, 2F).

Example 411C:
1-(2,2-Difluoroethyl)-1H-pyrazole-5-carboxylic Acid

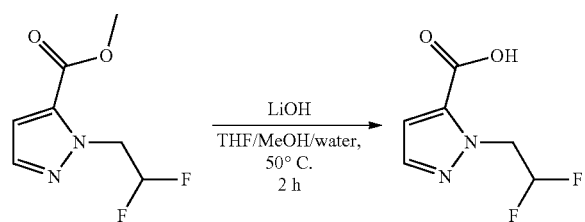

Example 411A (0.398 g, 2.093 mmol) was dissolved in THF (8.7 ml) and MeOH (1.7 ml), then LiOH (1 M in water) (6.28 ml, 6.28 mmol) was added. The reaction was heated to 50° C. for 2 h. The reaction mixture was quenched with TFA (0.484 ml, 6.28 mmol), and concentrated under reduced pressure. The residue was diluted with DMSO/MeOH/water, and was purified by preparative to afford Example 411C (0.173 g, 46.9% yield) as a white solid. MS(ESI) m/z: 176.9 (M+H)⁺; ¹H NMR (400 MHz, DMSO-d₆) δ 13.59 (br. s., 1H), 7.64 (d, J=2.0 Hz, 1H), 6.90 (d, J=2.0 Hz, 1H), 6.60-6.12 (m, 1H), 4.98 (td, J=14.5, 4.0 Hz, 2H).

Example 411

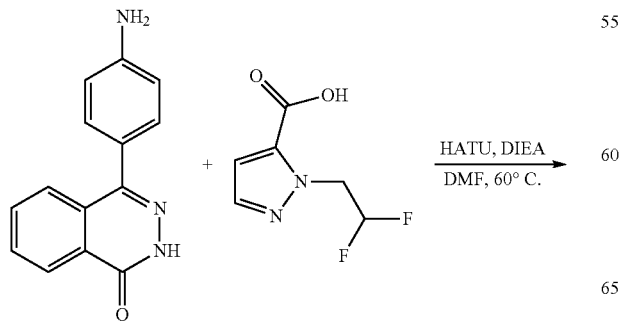

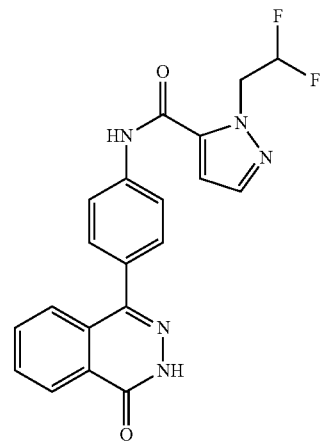 [SMILES: O=C(Nc1ccc(-c2n[nH]c(=O)c3ccccc23)cc1)c1ccnn1CC(F)F]

Intermediate 12, 2 TFA (30 mg, 0.064 mmol) was dissolved in dry DMF (1 mL), then Example 411C (22.7 mg, 0.129 mmol) and DIEA (0.068 mL, 0.387 mmol) were added. After stirring for 5 min at rt, HATU (36.8 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 411 (16.6 mg, 67% yield). MS(ESI) m/z: 396.2 (M+H)⁺; ¹H NMR (500 MHz, DMSO-d₆) δ 12.85 (s, 1H), 10.56 (s, 1H), 8.35 (d, J=7.1 Hz, 1H), 7.98-7.85 (m, 4H), 7.74 (d, J=8.1 Hz, 1H), 7.71 (d, J=1.7 Hz, 1H), 7.61 (d, J=8.4 Hz, 2H), 7.20 (d, J=1.7 Hz, 1H), 6.56-6.25 (m, 1H), 5.03 (td, J=14.6, 3.5 Hz, 2H); HPLC RT=1.38 min (Method E), 1.28 min (Method F).

Example 412: 1-(2,2-Difluoroethyl)-N-(4-(4-oxo-3, 4-dihydrophthalazin-1-yl)phenyl)-1H-pyrazole-3-carboxamide

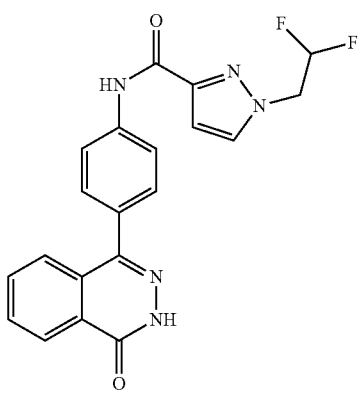 [SMILES: O=C(Nc1ccc(-c2n[nH]c(=O)c3ccccc23)cc1)c1ccn(CC(F)F)n1]

Example 412A:
1-(2,2-Difluoroethyl)-1H-pyrazole-3-carboxylic Acid

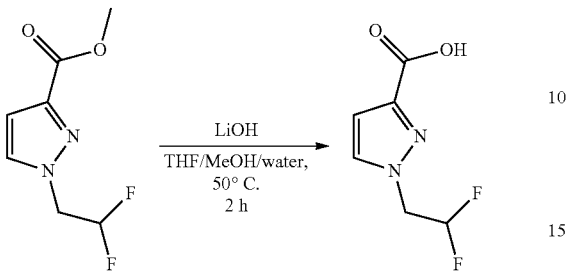

Example 411B (0.271 g, 1.43 mmol) was dissolved in THF (5.9 ml) and MeOH (1.2 ml), then LiOH (1 M in water) (4.28 ml, 4.28 mmol) was added. The reaction was heated to 50° C. for 2 h. The reaction mixture was quenched with TFA (0.329 ml, 4.28 mmol), and concentrated under reduced pressure. The residue was diluted with DMSO/MeOH/water, and was purified by preparative HPLC to afford Example 412A (0.177 g, 71% yield) as a white solid. MS(ESI) m/z: 176.9 (M+H)$^+$; $^1$H NMR (400 MHz, DMSO-d$_6$) δ 12.76 (s, 1H), 7.88 (d, J=2.4 Hz, 1H), 6.75 (d, J=2.4 Hz, 1H), 6.59-6.19 (m, 1H), 4.72 (td, J=15.2, 3.7 Hz, 2H).

Example 412

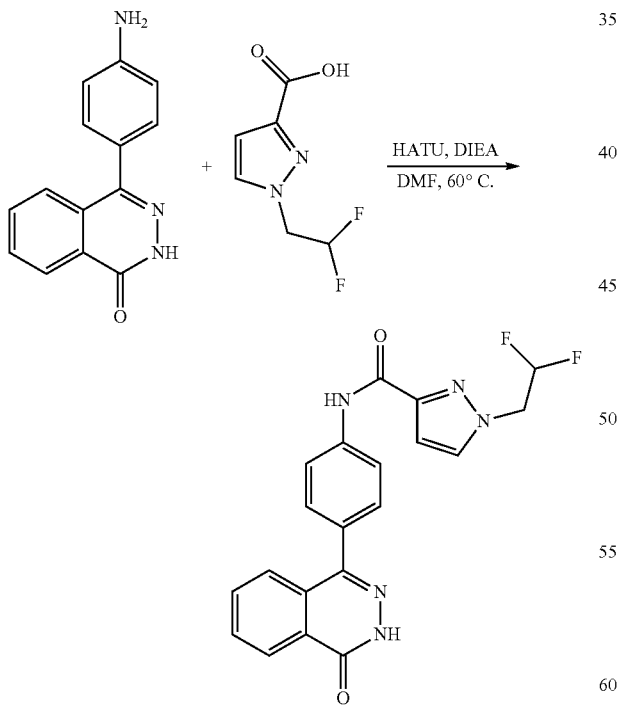

Intermediate 12, 2 TFA (30 mg, 0.064 mmol) was dissolved in dry DMF (1 mL), then Example 412A (22.7 mg, 0.129 mmol) and DIEA (0.068 mL, 0.387 mmol) were added. After stirring for 5 min at rt, HATU (36.8 mg, 0.097 mmol) was added, and the reaction mixture was stirred at 60° C. for 3 h. The reaction mixture was quenched with MeOH (0.1 mL), diluted with DMF, filtered and purified by preparative HPLC to afford Example 412 (23.3 mg, 91% yield). MS(ESI) m/z: 396.2 (M+H)$^+$; $^1$H NMR (500 MHz, DMSO-d$_6$) δ 12.79 (s, 1H), 10.26 (s, 1H), 8.30 (d, J=7.1 Hz, 1H), 7.99-7.81 (m, 5H), 7.71 (d, J=7.7 Hz, 1H), 7.53 (d, J=8.4 Hz, 2H), 6.86 (d, J=2.0 Hz, 1H), 6.58-6.30 (m, 1H), 4.74 (td, J=15.1, 3.2 Hz, 2H); HPLC RT=1.31 min (Method E), 1.31 min (Method F).

What is claimed is:
1. A compound of Formula (I):

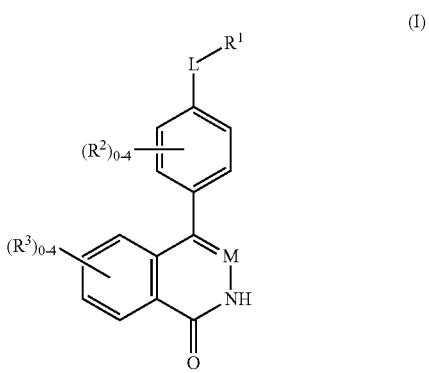

or a stereoisomer, a tautomer, a pharmaceutically acceptable salt thereof, wherein:
M is CR$^{10}$;
L is selected from —CR$^4$R$^4$C(O)—, —OC(O)—, —NR$^6$C(O)—, and —NR$^6$—;
R$^1$ is selected from NR$^5$R$^5$, C$_{3\text{-}10}$ carbocycle and 4- to 15-membered heterocycle comprising carbon atoms and 1-4 heteroatoms selected from N, NR$^8$, O, and S(O)$_p$; wherein said carbocycle and heterocycle are substituted with 1-4 R$^7$;
R$^2$, at each occurrence, is independently selected from halogen, C$_{1\text{-}6}$ alkyl, C$_{1\text{-}4}$ alkoxy, C$_{1\text{-}4}$ alkylthio, C$_{1\text{-}4}$ haloalkyl, —OH, —CH$_2$OH, —OCH$_2$F, —OCHF$_2$, —OCF$_3$, CN, —NH$_2$, —NH(C$_{1\text{-}4}$ alkyl), —N(C$_{1\text{-}4}$ alkyl)$_2$, —CO$_2$H, —CH$_2$CO$_2$H, —CO$_2$(C$_{1\text{-}4}$ alkyl), —CO(C$_{1\text{-}4}$ alkyl), —CH$_2$NH$_2$, —CONH$_2$, —CONH(C$_{1\text{-}4}$ alkyl), —CON(C$_{1\text{-}4}$ alkyl)$_2$, —OCH$_2$CO$_2$H, —NHCO(C$_{1\text{-}4}$ alkyl), —NHCO$_2$(C$_{1\text{-}4}$ alkyl), —NHSO$_2$(C$_{1\text{-}4}$ alkyl), —SO$_2$NH$_2$, —C(=NH)NH$_2$, 3- to 13-membered carbocycle, and 4- to 14-membered heterocycle comprising carbon atoms and 1 to 4 heteroatoms selected from N, O, S, wherein said alkyl, alkoxy, alkylthio, haloalkyl, carbocycle, and heterocycle are substituted with 0-4 R$^9$;
R$^3$, at each occurrence, is independently selected from halogen, C$_{1\text{-}6}$ alkyl, C$_{1\text{-}4}$ alkoxy, C$_{1\text{-}4}$ alkylthio, C$_{1\text{-}4}$ haloalkyl, —CH$_2$OH, —OCH$_2$F, —OCHF$_2$, —OCF$_3$, CN, —NH$_2$, —NH(C$_{1\text{-}4}$ alkyl), —N(C$_{1\text{-}4}$ alkyl)$_2$, —CO$_2$H, —CH$_2$CO$_2$H, —CO$_2$(C$_{1\text{-}4}$ alkyl), —CO(C$_{1\text{-}4}$ alkyl), —CH$_2$NH$_2$, —CONH$_2$, —CONH(C$_{1\text{-}4}$ alkyl), —CON(C$_{1\text{-}4}$ alkyl)$_2$, —OCH$_2$CO$_2$H, —NHCO(C$_{1\text{-}4}$ alkyl), —NHCO$_2$(C$_{1\text{-}4}$ alkyl), —NHSO$_2$(C$_{1\text{-}4}$ alkyl), —SO$_2$NH$_2$, —C(=NH)NH$_2$, 3- to 13-membered carbocycle, and 4- to 14-membered heterocycle comprising carbon atoms and 1 to 4 heteroatoms selected from N, O, S, wherein said alkyl, alkoxy, alkylthio, haloalkyl, carbocycle, and heterocycle are substituted with 0-4 R$^9$;

R⁴, at each occurrence, is independently selected from H, OH, NH₂, CH₂NH₂, C₁₋₄ haloalkyl, OCH₂F, OCHF₂, OCF₃, —NH(C₁₋₄ alkyl), —N(C₁₋₄ alkyl)₂, C₁₋₄ alkoxy, CH₂OH, CH₂O(C₁₋₄ alkyl), CH₂CO₂H, CH₂CO₂(C₁₋₄ alkyl), C₁₋₄ alkyl, 3- to 13-membered carbocycle, and 4- to 14-membered heterocycle comprising carbon atoms and 1 to 4 heteroatoms selected from N, O, S, wherein said alkyl, alkoxy, haloalkyl, carbocycle, and heterocycle are substituted with 0-4 R⁹;

R⁵, at each occurrence, is independently selected from H, C₁₋₄ alkyl, —(CR⁶R⁶)ₙ—C₃₋₁₀ carbocycle and —(CR⁶R⁶)ₙ— 4-10 membered heterocycle comprising carbon atoms and 1-4 heteroatoms selected from N, NR⁸, O, and S(O)ₚ, wherein said alkyl, carbocycle and heterocycle are substituted with 1-4 R⁷;

alternatively, R⁵ and R⁵ are taken together with the nitrogen atom to which they are attached to form 4- to 15-membered heterocycle comprising carbon atoms and 1 to 4 heteroatoms selected from N, O, S, and substituted with 1-4 R⁷;

R⁶, at each occurrence, is independently selected from H and C₁₋₄ alkyl;

R⁷, at each occurrence, is independently selected from H, =O, NO₂, halogen, C₁₋₄ alkyl, C₁₋₄ alkoxy, CN, OH, CF₃, —(CH₂)ₙ—CO₂H, —(CH₂)ₙ—CO₂(C₁₋₄ alkyl), —(CH₂)ₙ—NR⁸R⁸, —NHCO(C₁₋₄ alkyl), —NHCOCF₃, —NHCO₂(C₁₋₄ alkyl), —NHCO₂(CH₂)₂ O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)ₙ—CONR⁸R⁸, —O(CH₂)ₙ-3- to 13-membered carbocycle, —O(CH₂)ₙ-4- to 14-membered heterocycle comprising carbon atoms and 1 to 4 heteroatoms selected from N, O, S, —NHCO-3- to 13-membered carbocycle, —NHCO-4- to 14-membered heterocycle comprising carbon atoms and 1 to 4 heteroatoms selected from N, O, S, —(CH₂)ₙ-3- to 13-membered carbocycle, and —(CH₂)ₙ-4- to 14-membered heterocycle comprising carbon atoms and 1-4 heteroatoms selected from N, NR⁸, O, and S(O)ₚ, wherein said alkyl, alkenyl, alkynyl, alkoxy, carbocycle, and heterocycle are substituted with 0-4 R⁹;

R⁸, at each occurrence, is independently selected from H, C₁₋₄ alkyl, C₂₋₄ alkenyl, C₂₋₄ alkynyl, —(CH₂)ₙ—C(O)C₁₋₄alkyl, —(CH₂)ₙ—C(O)-3- to 13-membered carbocycle, —(CH₂)ₙ—C(O)-4- to 14-membered heterocycle comprising carbon atoms and 1 to 4 heteroatoms selected from N, O, S, —(CH₂)ₙ—C(O)NRᵃRᵃ, —(CH₂)ₙ—C(O)O-alkyl, —(CH₂)ₙ—C(O)O-3- to 13-membered carbocycle, —(CH₂)ₙ—C(O)O-4- to 14-membered heterocycle comprising carbon atoms and 1 to 4 heteroatoms selected from N, O, S, —(CH₂)ₙ—SO₂alkyl, —(CH₂)ₙ SO₂-3- to 13-membered carbocycle, —(CH₂)ₙ—SO₂-4- to 14-membered heterocycle comprising carbon atoms and 1 to 4 heteroatoms selected from N, O, S, —(CH₂)ₙ—SO₂NRᵃRᵃ, —(CH₂)ₙ-3- to 13-membered carbocycle, and —(CH₂)ₙ-4- to 14-membered heterocycle comprising carbon atoms and 1 to 4 heteroatoms selected from N, O, S, wherein said alkyl, carbocycle, and heterocycle are substituted with 0-4 R⁹;

alternatively, R⁸ and R⁸ are taken together with the nitrogen atom to which they are attached to form 4- to 10-membered heterocycle comprising carbon atoms and 1 to 4 heteroatoms selected from N, O, S, and substituted with 0-4 R⁹;

R⁹, at each occurrence, is independently selected from halogen, OH, NO₂, CHF₂, CF₃, C₁₋₄ alkyl, C₁₋₄ alkoxy, CH₂OH, CO(C₁₋₄ alkyl), CO₂H, CO₂(C₁₋₄ alkyl), —(CH₂)ₙNRᵃRᵃ, —(CH₂)ₙCONRᵃRᵃ, —O(CH₂)ₙ-3- to 13-membered carbocycle, —O(CH₂)ₙ-4- to 14-membered heterocycle comprising carbon atoms and 1 to 4 heteroatoms selected from N, O, S, —O(CH₂)ₙNRᵃRᵃ, —(CR¹⁰R¹⁰)ₙ-4-10 membered heterocycle comprising carbon atoms and 1 to 4 heteroatoms selected from N, O, S, wherein said alkyl, alkoxy, carbocycle, and heterocycle are substituted with 0-4 R^b;

R¹⁰ is selected from H and C₁₋₄ alkyl;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form 4- to 10-membered heterocycle comprising carbon atoms and 1 to 4 heteroatoms selected from N, O, S, wherein said alkyl, alkylene, and heterocycle are substituted with 0-4 R^b;

R^b, at each occurrence, is independently selected from =O, OH, halogen, C₁₋₄ alkyl, C₁₋₄ alkoxy, OCF₃, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N(C₁₋₄ alkyl)₂, —C₁₋₄ alkylene-O—P(O)(OH)₂, —NHCO₂(C₁₋₄ alkyl), —Rᶜ, CORᶜ, CO₂Rᶜ, and CONHRᶜ;

Rᶜ, at each occurrence, is independently selected from —(CH₂)ₙ—C₃₋₆ cycloalkyl, —(CH₂)ₙ-phenyl, and —(CH₂)ₙ-5- to 6-membered heterocycle containing carbon atoms and 1-4 heteroatoms selected from the group consisting of: N, NH, N(C₁₋₄ alkyl), O, and S(O)ₚ; wherein each ring moiety is substituted with 0-2 R^d;

R^d, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and 4- to 14-membered heterocycle containing carbon atoms and 1-4 heteroatoms selected from the group consisting of: N, NH, N(C₁₋₄ alkyl), O, and S(O)ₚ;

n, at each occurrence, is independently selected from 0, 1, 2, 3, and 4;

p, at each occurrence, is independently selected from 0, 1, and 2;

provided
when L is NHC(O), R¹ is other than

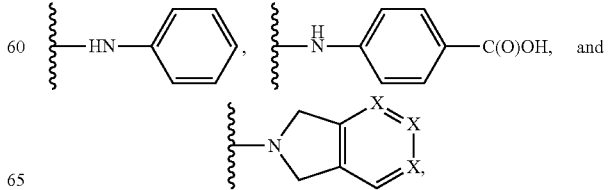

wherein X is N or a substituted or unsubstituted carbon atom;

when L is NR$^6$, R$^1$ is heterocycle substituted with 1-4 R$^7$.

2. The compound of claim 1, wherein:

M is CR$^{10}$;

L is selected from —CR$^4$R$^4$C(O)—, —OC(O)—, and —NR$^6$C(O)—;

R$^1$ is selected from NR$^5$R$^5$, C$_{3-10}$ carbocycle and 4- to 15-membered heterocycle comprising carbon atoms and 1-4 heteroatoms selected from N, NR$^8$, O, and S(O)$_p$; wherein said carbocycle, and heterocycle are substituted with 1-4 R$^7$;

R$^3$, at each occurrence, is independently selected from halogen, C$_{1-6}$ alkyl, C$_{1-4}$ alkoxy;

R$^4$ is H;

R$^5$, at each occurrence, is independently selected from H, C$_{1-4}$ alkyl, —(CR$^6$R$^6$)$_n$—C$_{3-10}$ carbocycle and 4-10 membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form 4- to 15-membered heterocycle substituted with 1-4 R$^7$;

R$^7$, at each occurrence, is independently selected from H, C$_{1-4}$ alkyl, C$_{1-4}$ alkoxy, —NR$^8$R$^8$, —(CH$_2$)$_n$-3- to 13-membered carbocycle, and —(CH$_2$)$_n$-4- to 14-membered heterocycle comprising carbon atoms and 1-4 heteroatoms selected from N, NR$^8$, O, and S(O)$_p$, wherein said alkyl, alkoxy, carbocycle, and heterocycle are substituted with 0-4 R$^9$;

R$^8$, at each occurrence, is independently selected from H and C$_{1-4}$ alkyl;

R$^9$, at each occurrence, is independently selected from halogen, OH, C$_{1-4}$ alkyl, C$_{1-4}$ alkoxy;

R$^{10}$ is selected from H and C$_{1-4}$ alkyl;

n, at each occurrence, is independently selected from 0, 1, 2, 3, and 4; and p, at each occurrence, is independently selected from 0, 1, and 2.

3. The compound of claim 1, having Formula (II):

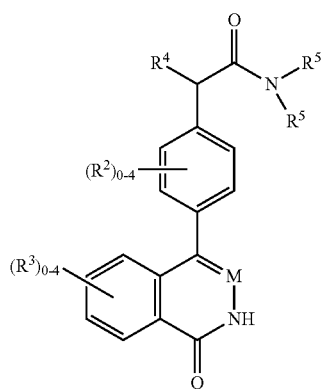

(II)

or a stereoisomer, a tautomer, or a pharmaceutically acceptable salt thereof, wherein:

M is CR$^{10}$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle comprising carbon atoms and 1 to 4 heteroatoms selected from N, O, S, and substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-3- to 13-membered carbocycle, —O (CH$_2$)$_n$-4- to 14-membered heterocycle comprising carbon atoms and 1 to 4 heteroatoms selected from N, O, S, —NHCO-3- to 13-membered carbocycle, —NHCO-4- to 14-membered heterocycle, —(CH$_2$)$_n$-3- to 13-membered carbocycle, and —(CH$_2$)$_n$-4- to 14-membered heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, C(O)-3- to 13-membered carbocycle, C(O)-4- to 14-membered heterocycle comprising carbon atoms and 1 to 4 heteroatoms selected from N, O, S, —(CH$_2$)$_n$ C(O)NR$^a$R$^a$, C(O)O-alkyl, C(O)O-3- to 13-membered carbocycle, C(O)O-4- to 14-membered heterocycle comprising carbon atoms and 1 to 4 heteroatoms selected from N, O, S, SO$_2$alkyl, SO$_2$-3- to 13-membered carbocycle, SO$_2$-4- to 14-membered heterocycle comprising carbon atoms and 1 to 4 heteroatoms selected from N, O, S, SO$_2$NR$^a$R$^a$, —(CH$_2$)$_n$-3- to 13-membered carbocycle, and —(CH$_2$)$_n$-4- to 14-membered heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$—NR$^a$R$^a$, —(CH$_2$)$_n$—CONR$^a$R$^a$, —O(CH$_2$)$_n$-4- to 14-membered heterocycle comprising carbon atoms and 1 to 4 heteroatoms selected from N, O, S, —O(CH$_2$)$_{(2-4)}$NR$^a$R$^a$, —(CR$^{10}$R$^{10}$)$_n$-4-10 membered heterocycle comprising carbon atoms and 1 to 4 heteroatoms selected from N, O, S, wherein said alkyl, alkoxy, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$ (C$_{1-4}$ alkyl), —CONH$_2$, —CONH—C$_{1-4}$ alkylene-CO$_2$ (C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle comprising carbon atoms and 1 to 4 heteroatoms selected from N, O, S, wherein said alkyl, alkylene, and heterocycle are substituted with 0-4 R$^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —CONH—$C_{1-4}$ alkylene-$O(C_{1-4}$ alkyl), —CONH—$C_{1-4}$ alkylene-$N(C_{1-4}$ alkyl$)_2$, —CONH—$C_{1-4}$ alkylene-$N(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and 4- to 14-membered heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2.

4. The compound of claim 3, wherein:

$R^5$ is selected from H, $C_{1-4}$ alkyl, —$(CH_2)_n$—$C_{3-10}$ carbocycle, —$(CH_2)_n$-4-10 membered heterocycle selected from

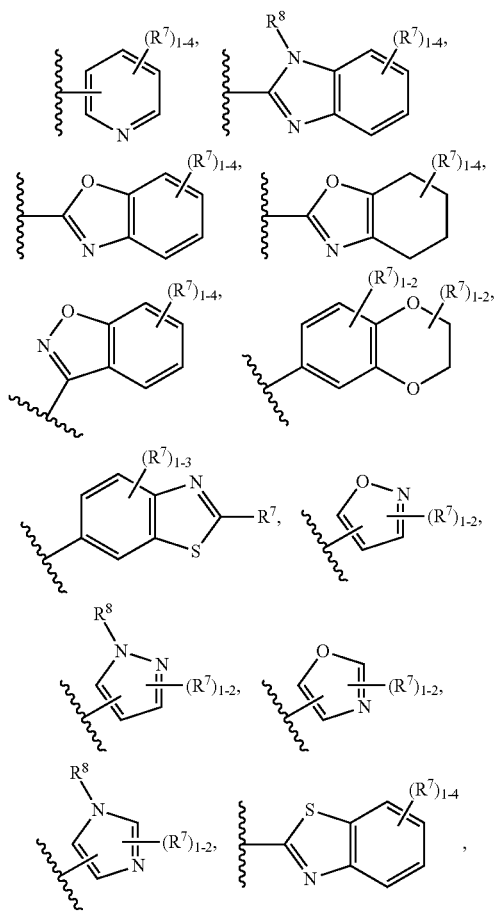

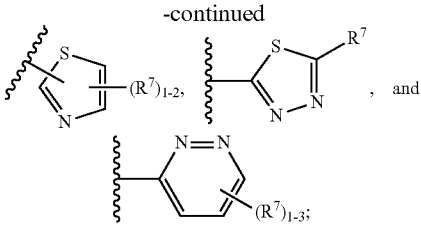

wherein said alkyl, cycloalkyl, aryl are substituted with 1-4 $R^7$.

5. The compound of claim 3, wherein:

$R^5$ and $R^5$ are taken together with the nitrogen atom to which they are attached to for heterocycle selected from

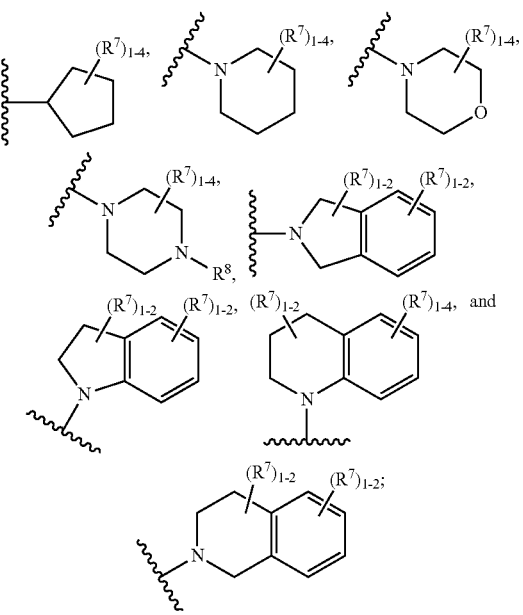

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$CH_2NH_2$, —$NHCO(C_{1-4}$ alkyl), —$NHCOCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl$)_2$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-3- to 13-membered carbocycle, —O $(CH_2)_n$-4- to 14-membered heterocycle comprising carbon atoms and 1 to 4 heteroatoms selected from N, O, S, —NHCO-3- to 13-membered carbocycle, —NHCO-4- to 14-membered heterocycle comprising carbon atoms and 1 to 4 heteroatoms selected from N, O, S, —$(CH_2)_n$-3- to 13-membered carbocycle, and —$(CH_2)_n$-4- to 14-membered heterocycle comprising carbon atoms and 1-4 heteroatoms selected from N, $NR^8$, O, and $S(O)_p$, wherein said alkyl, alkoxy, carbocycle, and heterocycle are substituted with 0-4 $R^9$;

$R^8$, at each occurrence, is independently selected from H, $C_{1-4}$ alkyl, $C(O)C_{1-4}$alkyl, C(O)-3- to 13-membered carbocycle, C(O)-4- to 14-membered heterocycle comprising carbon atoms and 1 to 4 heteroatoms selected from N, O, S, —(CH$_2$)$_n$—C(O)NR$^a$R$^a$, C(O)O-alkyl, C(O)O-3- to 13-membered carbocycle, C(O)O-4- to 14-membered heterocycle comprising carbon atoms and 1 to 4 heteroatoms selected from N, O, S, SO$_2$alkyl, SO$_2$-3- to 13-membered carbocycle, SO$_2$-4- to 14-membered heterocycle comprising carbon atoms and 1 to 4 heteroatoms selected from N, O, S, SO$_2$NR$^a$R$^a$, —(CH$_2$)$_n$-3- to 13-membered carbocycle, and —(CH$_2$)$_n$-4- to 14-membered heterocycle comprising carbon atoms and 1 to 4 heteroatoms selected from N, O, S, wherein said alkyl, carbocycle, and heterocycle are substituted with 0-4 R$^9$;

alternatively, R$^8$ and R$^8$ are taken together with the nitrogen atom to which they are attached to form 4- to 10-membered heterocycle comprising carbon atoms and 1 to 4 heteroatoms selected from N, O, S, and substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$-4- to 14-membered heterocycle, —O(CH$_2$)$_{(2-4)}$NR$^a$R$^a$, —(CR$^{10}$R$^{10}$)$_n$-4-10 membered heterocycle comprising carbon atoms and 1 to 4 heteroatoms selected from N, O, S, wherein said alkyl, alkoxy, carbocycle, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle comprising carbon atoms and 1 to 4 heteroatoms selected from N, O, S, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$; and R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and 4- to 14-membered heterocycle containing carbon atoms and 1-4 heteroatoms selected from the group consisting of: N, NH, N(C$_{1-4}$ alkyl), O, and S(O)$_p$.

6. The compound of claim 1, having Formula (III):

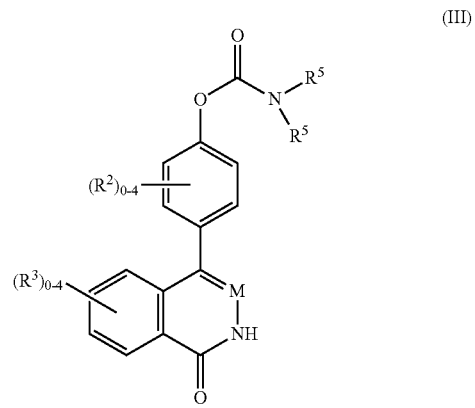

(III)

or a stereoisomer, a tautomer, a pharmaceutically acceptable salt thereof, wherein:

M is CR$^{10}$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle comprising carbon atoms and 1 to 4 heteroatoms selected from N, O, S, and substituted with 1-4 R$^7$;

R$^6$, at each occurrence, is independently selected from H and C$_{1-4}$ alkyl;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-3- to 13-membered carbocycle, —O(CH$_2$)$_n$-4- to 14-membered heterocycle comprising carbon atoms and 1 to 4 heteroatoms selected from N, O, S, —NHCO-3- to 13-membered carbocycle, —NHCO-4- to 14-membered heterocycle comprising carbon atoms and 1 to 4 heteroatoms selected from N, O, S, —(CH$_2$)$_n$-3- to 13-membered carbocycle, and —(CH$_2$)$_n$-4- to 14-membered heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, C(O)-3- to 13-membered carbocycle, C(O)-4- to 14-membered heterocycle comprising carbon atoms and 1 to 4 heteroatoms selected from N, O, S, —(CH$_2$)$_n$—C(O)NR$^a$R$^a$, C(O)O-alkyl, C(O)O-3- to 13-membered carbocycle, C(O)O-4- to 14-membered heterocycle comprising carbon atoms and 1 to 4 heteroatoms selected from N, O, S, $SO_2$alkyl, $SO_2$-3- to 13-membered carbocycle, $SO_2$-4- to 14-membered heterocycle comprising carbon atoms and 1 to 4 heteroatoms selected from N, O, S, $SO_2NR^aR^a$, —$(CH_2)_n$-3- to 13-membered carbocycle, and —$(CH_2)_n$-4- to 14-membered heterocycle comprising carbon atoms and 1 to 4 heteroatoms selected from N, O, S, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_n$ $NR^aR^a$, —$(CH_2)_nCONR^aR^a$, —$O(CH_2)_n$-4- to 14-membered heterocycle comprising carbon atoms and 1 to 4 heteroatoms selected from N, O, S, —$O(CH_2)_{(2-4)}$ $NR^aR^a$, —$(CR^{10}R^{10})_n$-4-10 membered heterocycle comprising carbon atoms and 1 to 4 heteroatoms selected from N, O, S, wherein said alkyl, alkoxy, carbocycle, and heterocycle are substituted with 0-4 $R^b$;

n, at each occurrence, is independently selected from 0, 1, 2, 3, and 4; and p, at each occurrence, is independently selected from 0, 1, and 2.

7. The compound of claim 1, wherein:

L is —$NR^6$—;

$R^1$ is heteroaryl substituted with 1-4 $R^7$;

$R^7$, at each occurrence, is independently selected from H, halogen, $C_{1-4}$ alkyl, $C_{1-4}$ alkoxy, CN, OH, —$(CH_2)_n$-3- to 13-membered carbocycle, and —$(CH_2)_n$-4- to 14-membered heterocycle comprising carbon atoms and 1 to 4 heteroatoms selected from N, O, S, wherein said alkyl, alkoxy, carbocycle, and heterocycle are substituted with 0-4 $R^9$.

8. The compound of claim 7, wherein:

L is —$NR^6$—; and $R^1$ is selected from

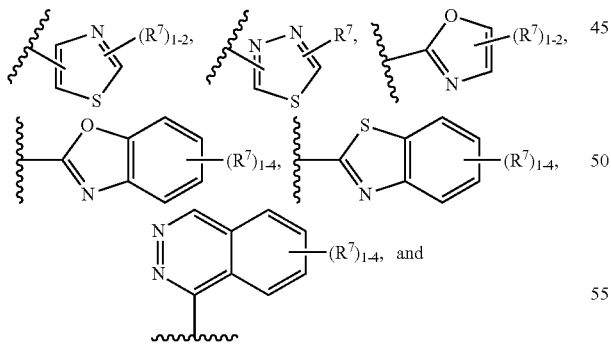

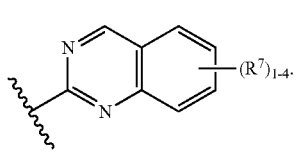

9. The compound of claim 2, having Formula (IV):

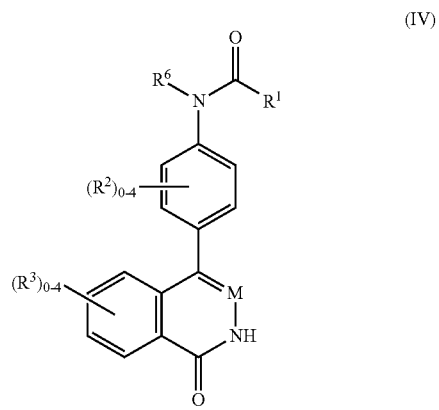

or a stereoisomer, a tautomer, a pharmaceutically acceptable salt thereof, wherein:

$R^1$ is selected from $NR^5R^5$, $C_{3-10}$ carbocycle, and 5- to 10-membered heterocycle comprising carbon atoms and 1 to 4 heteroatoms selected from N, O, S, wherein said carbocycle and heterocycle are substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle comprising carbon atoms and 1 to 4 heteroatoms selected from N, O, S, and substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2$ $O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-3- to 13-membered carbocycle, —$O(CH_2)_n$-4- to 14-membered heterocycle comprising carbon atoms and 1 to 4 heteroatoms selected from N, O, S, —NHCO-3- to 13-membered carbocycle, —NHCO-4- to 14-membered heterocycle comprising carbon atoms and 1 to 4 heteroatoms selected from N, O, S, —$(CH_2)_n$-3- to 13-membered carbocycle, and —$(CH_2)_n$-4- to 14-membered heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-4}$ alkyl, $C_{2-4}$ alkenyl, $C(O)C_{1-4}$alkyl, C(O)-3- to 13-membered carbocycle, C(O)-4- to 14-membered heterocycle comprising carbon atoms and 1 to 4 heteroatoms selected from N, O, S, —$(CH_2)_n$—C(O)

NR$^a$R$^a$, C(O)O-alkyl, C(O)O-3- to 13-membered carbocycle, C(O)O-4- to 14-membered heterocycle, SO$_2$alkyl, SO$_2$-3- to 13-membered carbocycle, SO$_2$-4- to 14-membered heterocycle comprising carbon atoms and 1 to 4 heteroatoms selected from N, O, S, SO$_2$NR$^a$R$^a$, —(CH$_2$)$_n$-3- to 13-membered carbocycle, and —(CH$_2$)$_n$-3- to 13-membered heterocycle comprising carbon atoms and 1 to 4 heteroatoms selected from N, O, S, wherein said alkyl, alkenyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$-4- to 14-membered heterocycle comprising carbon atoms and 1 to 4 heteroatoms selected from N, O, S, —O(CH$_2$)$_{(2-4)}$NR$^a$R$^a$, —(CR$^{10}$R$^{10}$)$_n$— 4-10 membered heterocycle comprising carbon atoms and 1 to 4 heteroatoms selected from N, O, S, wherein said alkyl, alkoxy, and heterocycle are substituted with 0-4 R$^b$;

n, at each occurrence, is independently selected from 0, 1, 2, 3, and 4;

p, at each occurrence, is independently selected from 0, 1, and 2.

10. The compound of claim 9, wherein:

R$^1$ is selected from

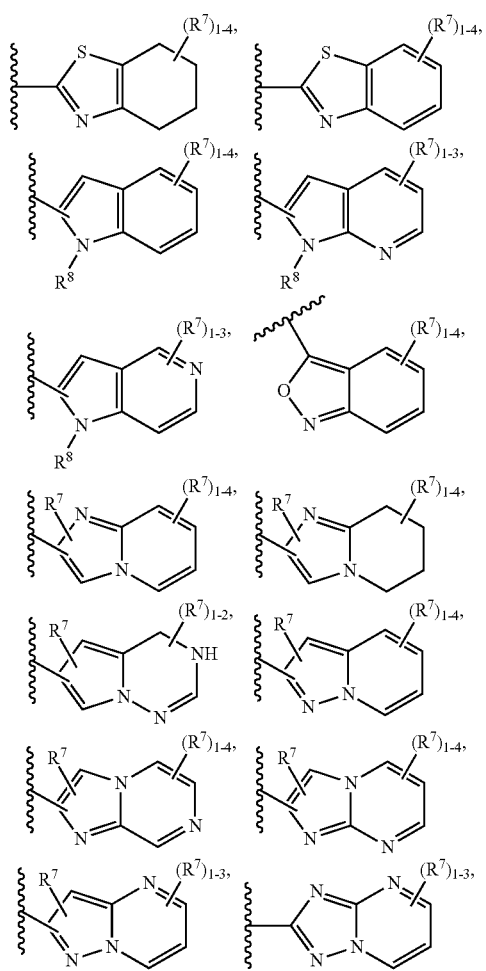
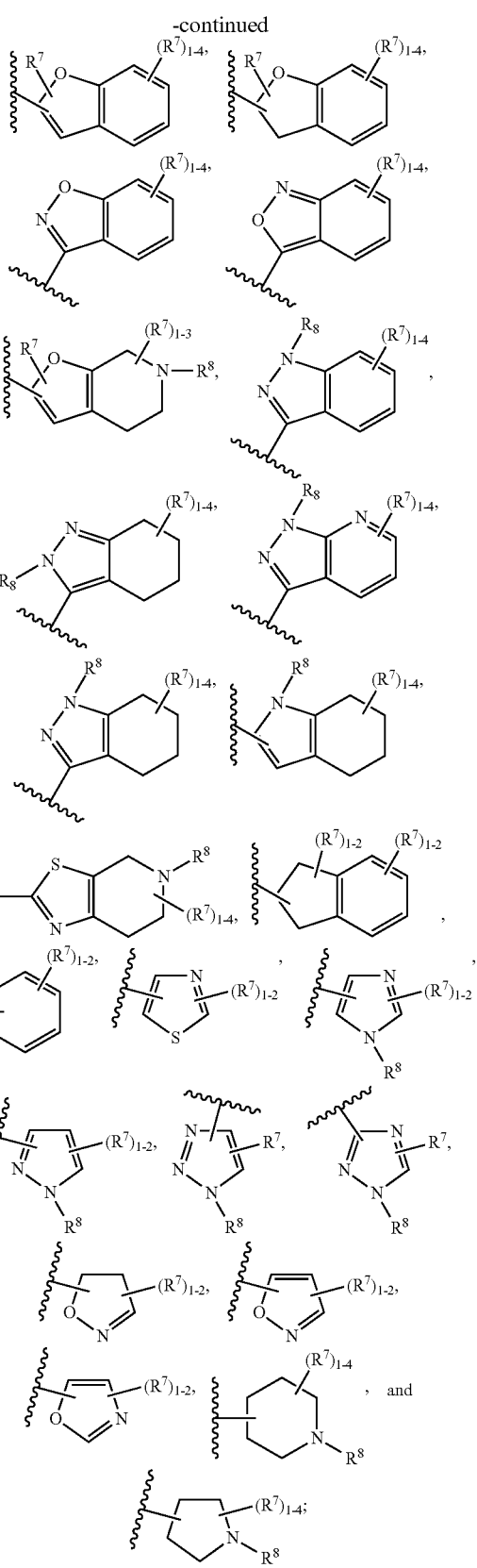

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-3- to 13-membered carbocycle, —O(CH$_2$)$_n$-4- to 14-membered heterocycle comprising carbon atoms and 1 to 4 heteroatoms selected from N, O, S, —NHCO-3- to 13-membered carbocycle, —NHCO-4- to 14-membered heterocycle comprising carbon atoms and 1 to 4 heteroatoms selected from N, O, S, —(CH$_2$)$_n$-3- to 13-membered carbocycle, and —(CH$_2$)$_n$-4- to 14-membered heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, C(O)-3- to 13-membered carbocycle, C(O)-4- to 14-membered heterocycle comprising carbon atoms and 1 to 4 heteroatoms selected from N, O, S, —(CH$_2$)$_n$—C(O)NR$^a$R$^a$, C(O)O-alkyl, C(O)O-3- to 13-membered carbocycle, C(O)O-4- to 14-membered heterocycle, SO$_2$alkyl, SO$_2$-3- to 13-membered carbocycle, SO$_2$-4- to 14-membered heterocycle comprising carbon atoms and 1 to 4 heteroatoms selected from N, O, S, SO$_2$NR$^a$R$^a$, —(CH$_2$)$_n$-3- to 13-membered carbocycle, and —(CH$_2$)$_n$-4- to 14-membered heterocycle comprising carbon atoms and 1 to 4 heteroatoms selected from N, O, S, wherein said alkyl, carbocycle, and heterocycle are substituted with 0-4 R$^9$;

alternatively, R$^8$ and R$^8$ are taken together with the nitrogen atom to which they are attached to form 4- to 10-membered heterocycle comprising carbon atoms and 1 to 4 heteroatoms selected from N, O, S, and substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$-4- to 14-membered heterocycle comprising carbon atoms and 1 to 4 heteroatoms selected from N, O, S, —O(CH$_2$)$_{(2-4)}$NR$^a$R$^a$, —(CR$^{10}$R$^{10}$)$_n$-4-10 membered heterocycle comprising carbon atoms and 1 to 4 heteroatoms selected from N, O, S, wherein said alkyl, alkoxy, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle comprising carbon atoms and 1 to 4 heteroatoms selected from N, O, S, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$; and R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and 4- to 14-membered heterocycle containing carbon atoms and 1-4 heteroatoms selected from the group consisting of: N, NH, N(C$_{1-4}$ alkyl), O, and S(O)$_p$.

11. The compound of claim 9, wherein:

R$^1$ is NR$^5$R$^5$;

R$^5$ and R$^5$ are taken together with the nitrogen atom to which they are attached to form 4- to 10-membered heterocycle comprising carbon atoms and 1 to 4 heteroatoms selected from N, O, S and substituted with 1-4 R$^7$;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-3- to 13-membered carbocycle, —O(CH$_2$)$_n$-3- to 13-membered carbocycle, —O(CH$_2$)$_n$-4- to 14-membered heterocycle comprising carbon atoms and 1 to 4 heteroatoms selected from N, O, S, and —(CH$_2$)$_n$— 4- to 14-membered heterocycle comprising carbon atoms and 1-4 heteroatoms selected from N, NR$^8$, O, and S(O)$_p$, wherein said alkyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, C(O)-3- to 13-membered carbocycle, C(O)-4- to 14-membered heterocycle, —(CH$_2$)$_n$—C(O)NR$^a$R$^a$, C(O)O-alkyl, C(O)O-3- to 13-membered carbocycle, C(O)O-4- to 14-membered heterocycle comprising carbon atoms and 1 to 4 heteroatoms selected from N, O, S, SO$_2$alkyl, SO$_2$-3- to 13-membered carbocycle, SO$_2$-4- to 14-membered heterocycle comprising carbon atoms and 1 to 4 heteroatoms selected from N, O, S, SO$_2$NR$^a$R$^a$, —(CH$_2$)$_n$-cycloalkyl, —(CH$_2$)$_n$-phenyl, and —(CH$_2$)$_n$-4- to 14-membered heterocycle comprising carbon atoms and 1 to 4 heteroatoms selected from N, O, S, wherein said alkyl, carbocycle, and heterocycle are substituted with 0-4 R$^9$; and R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle comprising carbon atoms and 1 to 4 heteroatoms selected from N, O, S, wherein said alkyl, alkoxy, and heterocycle are substituted with 0-4 R$^b$.

12. The compound of claim 1 selected from
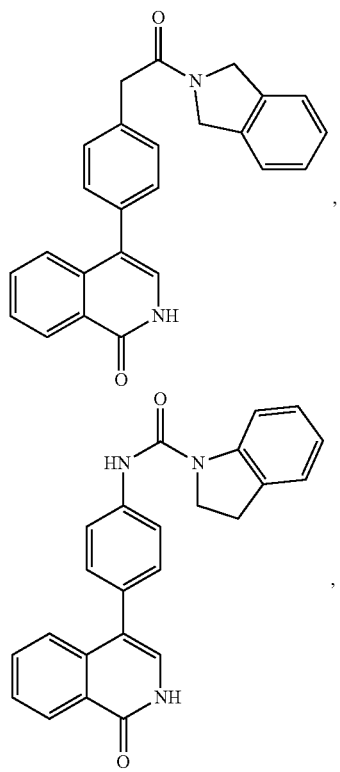
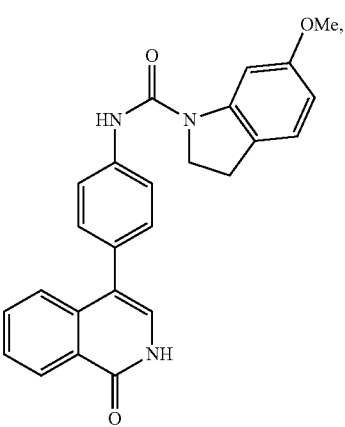
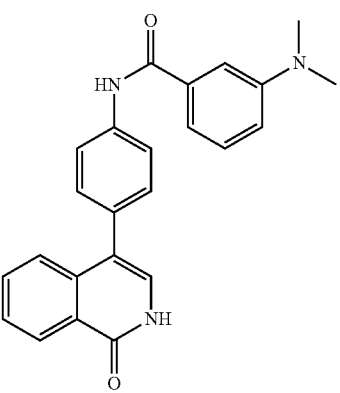
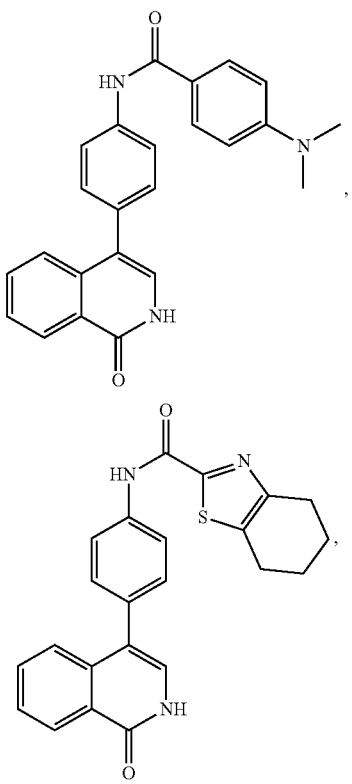
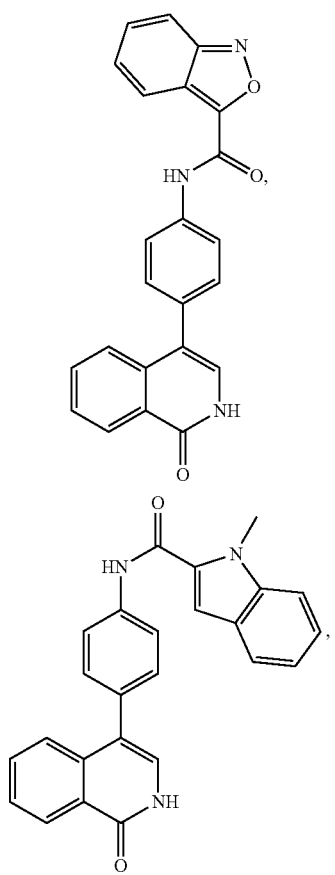

453
-continued
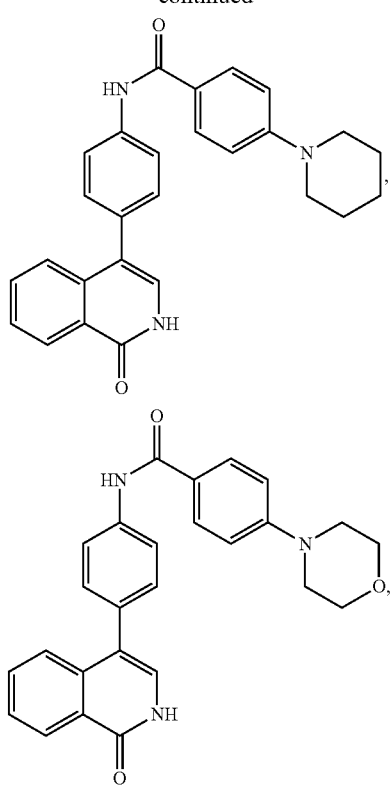
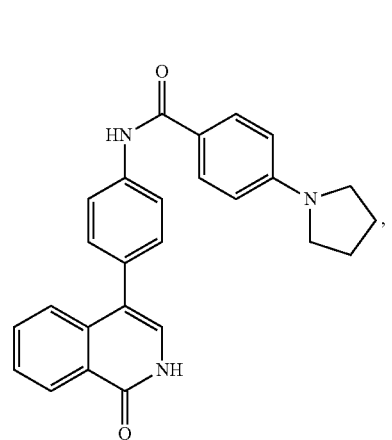
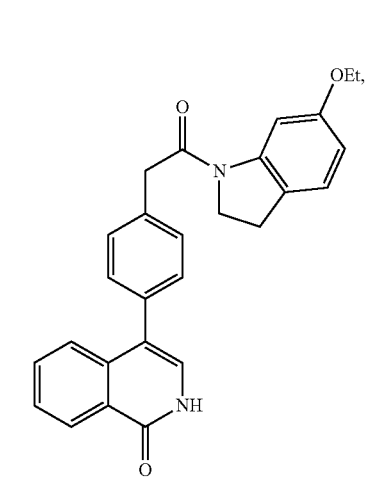
454
-continued
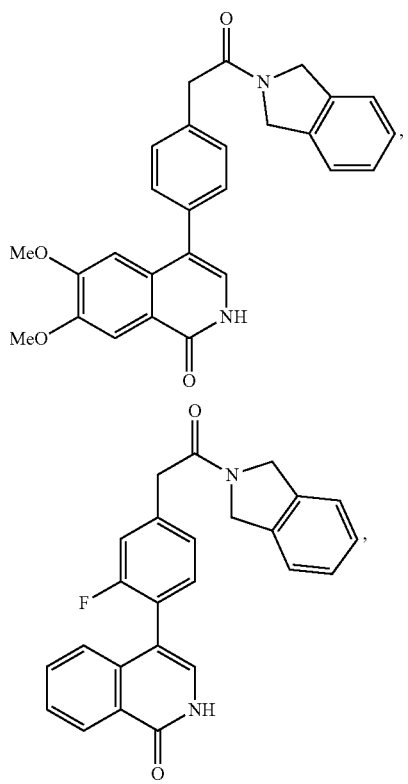
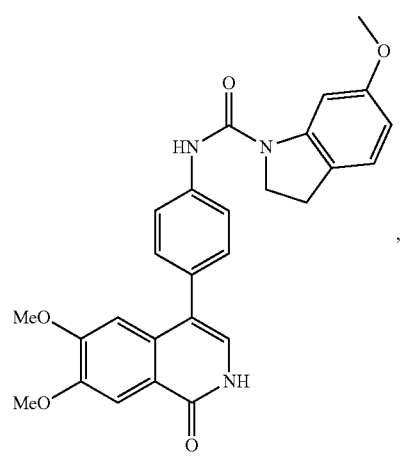
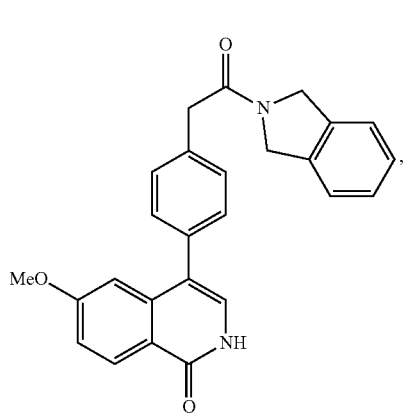

455
-continued
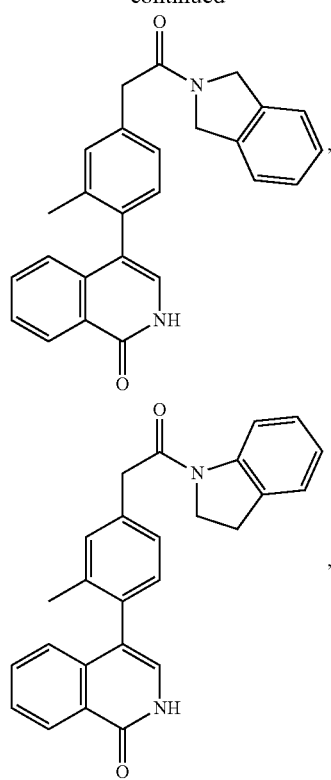
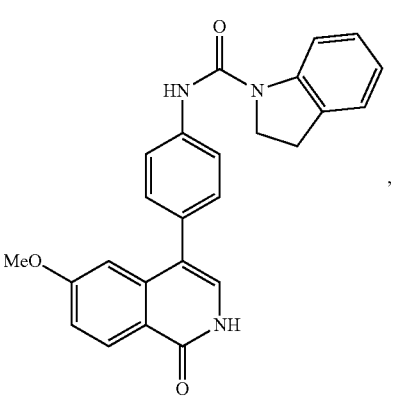
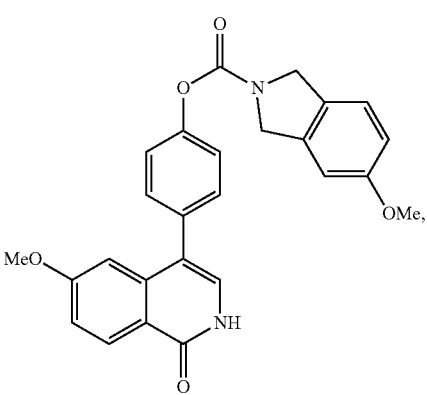
456
-continued
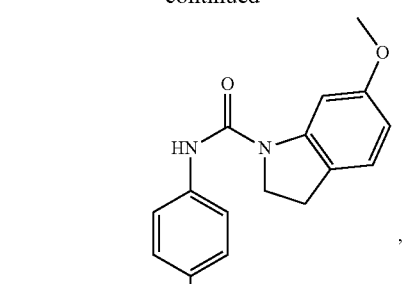
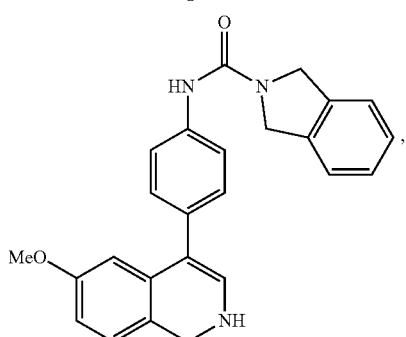
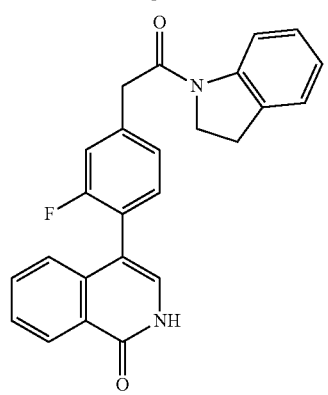
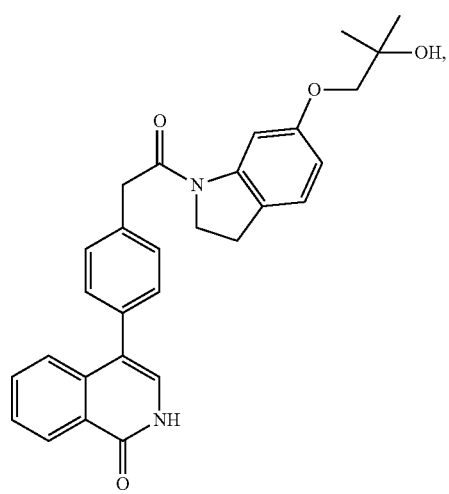

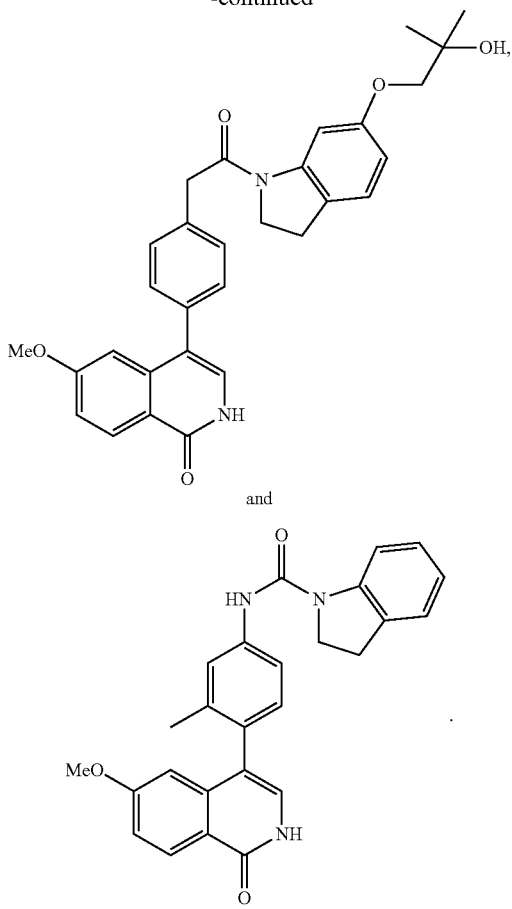

13. A pharmaceutical composition comprising one or more compounds according to claim 1 and a pharmaceutically acceptable carrier or diluent.

14. A method for the treatment of angina, atherosclerosis, stroke, cerebrovascular disease, heart failure, coronary artery disease, myocardial infarction, peripheral vascular disease, stenosis, vasospasm, hypertension or pulmonary hypertension.

15. The method of claim 14, wherein said smooth muscle related disorder is selected from the group consisting of glaucoma, erectile dysfunction, and bronchial asthma.

16. The method of claim 14, wherein said autoimmune disorder is selected from the group consisting of rheumatoid arthritis, systemic lupus erythematosus, multiple sclerosis, irritable bowel syndrome, and systemic sclerosis.

17. A method for inhibiting Rho kinase activity, comprising (a) providing target cells and a composition comprising a compound described in claim 1; and (b) exposing said target cells to said composition under conditions such that said composition binds to said target cells so as to inhibit Rho kinase activity within said target cells.

* * * * *